US012441754B2

(12) United States Patent
Zetterberg

(10) Patent No.: US 12,441,754 B2
(45) Date of Patent: *Oct. 14, 2025

(54) GALACTOSIDE INHIBITOR OF GALECTINS

(71) Applicant: GALECTO BIOTECH AB, Copenhagen (DK)

(72) Inventor: Fredrik Zetterberg, Askim (SE)

(73) Assignee: GALECTO BIOTECH AB, Copenhagen (DK)

( * ) Notice: Subject to any disclaimer, the term of this patent is extended or adjusted under 35 U.S.C. 154(b) by 784 days.

This patent is subject to a terminal disclaimer.

(21) Appl. No.: 17/624,383

(22) PCT Filed: Jul. 3, 2020

(86) PCT No.: PCT/EP2020/068809

§ 371 (c)(1),
(2) Date: Jan. 3, 2022

(87) PCT Pub. No.: WO2021/001528

PCT Pub. Date: Jan. 7, 2021

(65) Prior Publication Data

US 2023/0014870 A1 Jan. 19, 2023

(30) Foreign Application Priority Data

Jul. 3, 2019 (EP) .................................... 19184144

(51) Int. Cl.
*C07H 19/056* (2006.01)

(52) U.S. Cl.
CPC .................................. *C07H 19/056* (2013.01)

(58) Field of Classification Search
CPC ......... C07H 19/056; A61P 11/00; A61P 35/00
USPC ............................................................ 514/43
See application file for complete search history.

(56) References Cited

U.S. PATENT DOCUMENTS 10,988,502 B2 * 4/2021 Zetterberg ................ A61P 9/10
11,046,725 B2 * 6/2021 Zetterberg .............. A61P 11/00
11,377,464 B2 * 7/2022 Brimert ...................... A61P 9/10
11,447,517 B2 * 9/2022 Zetterberg ............. C07H 15/26
11,827,666 B2 * 11/2023 Zetterberg ........... C07H 19/056
11,939,349 B2 * 3/2024 Zetterberg ........... C07H 19/056

FOREIGN PATENT DOCUMENTS

WO WO 2018/011093 A1 * 1/2018 ........... C07H 19/056
WO 2019137971 A1 7/2019

OTHER PUBLICATIONS

International Search Report and Written Opinion issued on Oct. 21, 2020 in corresponding International Application No. PCT/EP2020/068809; 9 pages.

* cited by examiner

*Primary Examiner* — Ganapathy Krishnan
(74) *Attorney, Agent, or Firm* — Maier & Maier, PLLC

(57) ABSTRACT

The present invention relates to a D-galactopyranose compound of formula (1)

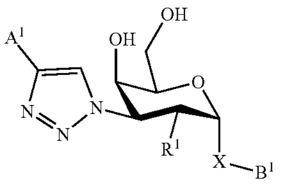

wherein the pyranose ring is α-D-galactopyranose, and these compounds are high affinity galectin-1 and/or galectin 3 inhibitors for use in treatment of inflammation; fibrosis; scarring; keloid formation; aberrant scar formation; surgical adhesions; septic shock; cancer; metastasising cancers; autoimmune diseases, metabolic disorders; heart disease; heart failure; pathological angiogenesis; eye diseases; atherosclerosis; metabolic diseases; diabetes type I; diabetes type II; insulin resistance; Diastolic heart failure; asthma; liver disorders.

17 Claims, No Drawings

GALACTOSIDE INHIBITOR OF GALECTINS

TECHNICAL FIELD

The present invention relates to novel compounds, the use of said compounds as medicament and for the manufacture of a medicament for the treatment of cancers; fibrosis; scarring; keloid formation; aberrant scar formation; surgical adhesions; pathological angiogenesis; eye diseases; HIV-1 diseases; inflammation or transplant rejection in mammals. The invention also relates to pharmaceutical compositions comprising said novel compounds.

BACKGROUND ART

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytosolic sites, or secreted (induced or constitutively) by a non-classical (non-ER-Golgi) pathway (as first shown for galectin-1 (Cooper and Barondes, 1991)), with as yet unknown mechanism, but possibly similar to the export of e.g. IL-1 (Leffler et al., 2004; Arthur et al., 2015). Galectins can also function in all these compartments; for galectin-1, solid evidence published in well respected journals support roles in RNA splicing in the nucleus, activation of H-RAS in the cytosol, accumulation around disrupted vesicles, and a variety of extracellular effects on cell signaling and adhesion (Elola et al. 2015, Aits et al., 2015, Blanchard et al., 2016). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectinor galectin inhibitors.

Galectin-1, the first discovered and second most studied galectin, is expressed in all tissues with a certain preference but not exclusive for cells of mesenchymal orgin like fibroblasts and lymphocytes. It is involved in the regulation of cell growth, adhesion, signaling, differentiation, development, immune system and host-pathogen interactions (Blanchard et al., 2016). Expression profiles of galectin-1 in the various stages of cancer progression and its role in the tumor microenvironment have been thoroughly reviewed.

Galectin-1 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Galectin-1 in Immunity and Inflammation

Galectin-1 has been found mainly to have an immunosuppressive and anti-inflammatory role (Elola et al., 2015), although in some cases it may also be proinflammatory. Galectin-1 binds specific glycosylation pattern on T-helper cells to selectively induce apoptosis in activated Th1 and Th17 cells. (Perillo et. al., 1995) (Toscano, M. A. et al., 2007). The immunosuppressive effect of galectin-1 has suggested that galectin-1 itself, might be a potential treatment for autoimmune and other inflammatory conditions. Conversly, inhibiting its immunosuppressive effect in e.g. cancer has also been proposed as a treatment, as described below.

Galectin-1 in Angiogenesis.

Like galectin-3, galectin-1 has been shown promote angiogenesis under certain circumstances (Hockl et al., 2016) in a way involving its carbohydrate bining-activity. Particularly interesting is the observation that it might promote tumor angiogenesis by a pathway parallel to VEGF. Hence, inhibiting galectin-1 may be anti-angiogenic when inhibition based on anti-VEGF fails. The discovery that the anti-angiogenic peptide Anginex (and related compounds) binds to galectin-1 suggested another mechanism for galectin-1 in angiogenesis, but the details remain unclear; Anginex is described as inhibiting galectin-1 activity in some reports, but as enhancing its carbohydrate binding-activities in another.

Galectin-1 in Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-ß receptor (Partridge et al., 2004), which in turn regulates alternative macrophage differentiation into M2 macrophages and myofibroblast activation. Galectin-1 has also been suggested to a play a role in fibrosis, including by TGF-ß related mechanism, but the evidence is less clear than for galectin-3.

Hence, also galectin-1 is a good candidate for being an endogenous enhancer of TGF-ß signaling and myofibroblast activation (Kathiriya et al), and galectin-1 inhibitors may be also be useful in treating fibrosis and adverse tissue remodeling.

Galectin-1 in Cancer.

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment—reviewed in (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Melero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Thus drugs targeting galectin-1 activities in cancer such as suppressing immunity or enhancing angiogenesis may become useful anti-cancer treatments.

Known Inhibitors

Natural Ligands

Solid phase binding assays and inhibition assays have identified a number of saccharides and glycoconjugates with the ability to bind galectins (reviewed by Leffler, 2001, Leffler et al., 2004). All galectins bind lactose with a $K_d$ of about 0.1-1 mM. The affinity of D-galactose is 50-100 times lower. N-Acetyllactosamine and related disaccharides bind about as well as lactose, but for certain galectins, they can bind either worse or up to 10 times better. Galactose (10 mM) (Tejler et. al. 2009) and Lactose (190 μM) (van Hattum, 2013) both have low affinity to Galectin-1.

The above-described natural saccharides that have been identified as galectin-1 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

A patent review covering galectin-1 inhibitors and their potential as therapeutics were recently published. (Blanchard 2016). The small molecule monosaccharides covered in this review have been reported as having galectin-1 affinity which is at best similar to lactose. Disaccharides on the other hand, in particular thiodigalactosides (TDG), has been reported to have high affinity towards galectin-1. (T. Delaine, 2016, ChemBioChem 10.1002/cbic.201600285)

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. Chlorinconjugated lactose have been reported to have high affinity (0.54 μM) as measured in an Elisa assay. (Pandey et. al. 2002, in EP1256586 (A1)). A chemically modified form of citrus pectin (Platt and Raz, 1992) that inhibits galectin-3 shows anti-tumor activity in vivo (Pienta et al., 1995; Nangia-Makker et al., 2002). Cluster molecules having up to four lactose moieties showed a strong multivalency effect when binding to galectin-3, but not to galectin-1 and galectin-5 (Vrasidas et al., 2003).

Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (Andre et al., 1999) and glycopolymers (Pohl et al., 1999; David et al., 2004), made polyvalent in lactose-residues, have been described as galectin-3 inhibitors with marginally improved potency as compared to lactose. Multivalent lactose derivatives have been shown to have a pronounced cluster effect towards galectin-1 (Tejler et. al., 2006). In addition, these compounds were selective over other galectins. Peptide based compounds such as Anginex and non-peptidic topomimetics (Dings et. al. 2012) have been reported to be allosteric galectin-1 inhibitors. The aforementioned synthetic compounds that have been identified as galectin-1 ligands are not suitable for use as active components in pharmaceutical compositions, because they are hydrophilic in nature and are not readily absorbed from the gastrointestinal tract following oral administration. In addition the aforementioned compounds have moderate affinity and selectivity.

Natural oligosaccharides, glycoclusters, glycodendrimers, peptides, non-peptidic topomimetics and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 μM, which is a 20-fold improvement in comparison with the natural N-acetyllactosamine disaccharide (Sörme et al., 2002; Sörme et al., 2003b, 2005). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2; T. Delaine, 2016, ChemBioChem 10.1002/cbic.201600285) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

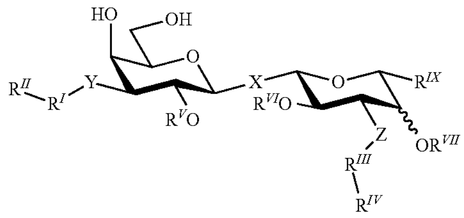

as described in WO/2005/113568, and

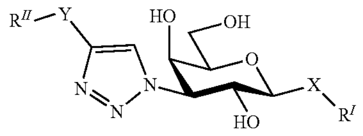

as described in WO/2005/113569, in which $R^I$ can be a D-galactose.

In recently published (T. Delaine, 2016, ChemBioChem 10.1002/cbic.201600285) is disclosed a

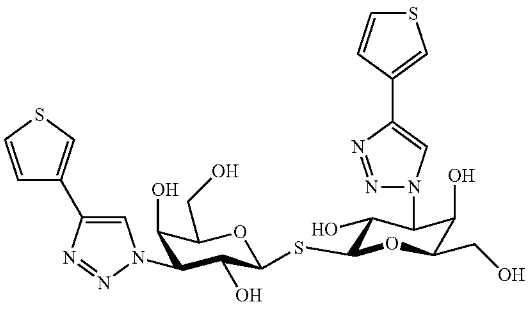

TDG substituted with a thiophene triazole substituent in the C3 and C3' positions with high affinity (<10 nM) to Galectin-1.

In recently published US20140099319, WO2014067986 and T. Delaine, 2016, ChemBioChem 10.1002/cbic.201600285, is disclosed a compound

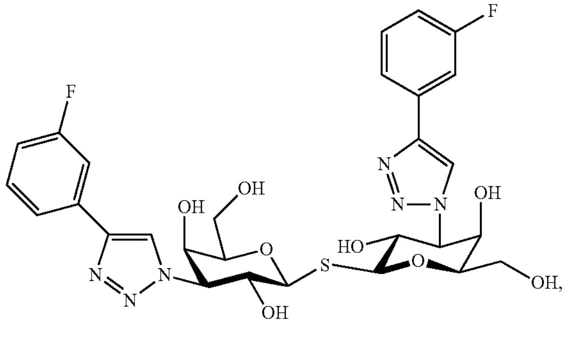

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 μM towards galectin 3 and 190 μM towards galectin 1. (Giguere, D et. al. 2011, 2008, 2006).

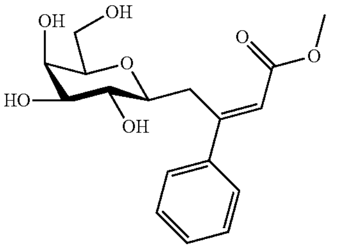

Gal-1 313μM
Gal-3 > 5000

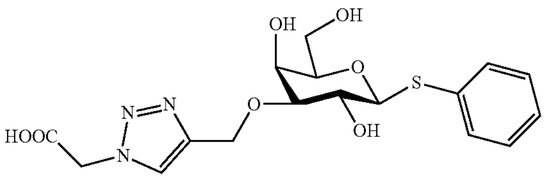

Gal-1 1.25 mM
Gal-3 5 mM

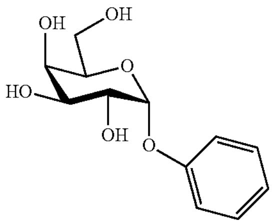

lower affinity than lactose
towards Galectin 1 and 3

There is no disclosure or mentioning of corresponding alpha-anomers having affinity towards galectin-1 or galectin-3 better than lactose.

SUMMARY OF THE INVENTION

The compounds of the present invention are novel α-D-galactopyranose compounds that unexpectedly have shown high affinity for galectin-1 and some compounds in addition have high affinity for galectin-3 as well and are considered novel potent drug candidates. Some compounds have good systemic uptake in in vitro and in vivo ADME studies and are suitable for oral treatment of diseases and disorders disclosed herein.

In broad aspect the present invention concerns A D-galactopyranose compound of formula (1)

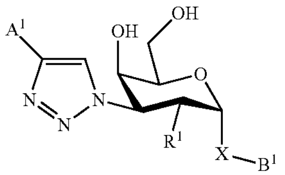

wherein the pyranose ring is α-D-galactopyranose, $A^1$ is selected from the group consisting of

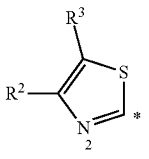 and 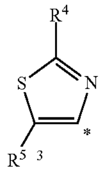

wherein the asterix * indicates the carbon atom of the heteroaromatic ring that is covalently attached to the triazole group of formula (1);

wherein $R^2$ is selected from the group consisting of hydrogen, $C_{1-6}$ alkyl, OH and halogen;

$R^3$ is selected from the group consisting of hydrogen, $C_{1-6}$ alkyl and halogen;

$R^4$ is selected from the group consisting of OH, halogen and amino;

$R^5$ is selected from the group consisting of hydrogen, $C_{1-6}$ alkyl and halogen;

X is selected from S, SO, $SO_2$, O, C═O, and $CR^{2a}R^{3a}$ wherein $R^{2a}$ and $R^{3a}$ are independently selected from hydrogen, OH, or halogen;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{4a}$—CONH— wherein $R^{4a}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{5a}$—CONH— wherein $R^{5a}$ is selected from $C_{1-3}$ alkyl and cyclopropyl; b) an aryl, such as phenyl or naphthyl, optionally substituted with a group selected from a halogen; a spiro heterocycle, such as N-(2-oxa)-6-azaspiro[3.3]heptanyl; $C_2$-alkynyl; $C_2$-alkynyl; CN; —COOH; $COOC_{1-4}$ alkyl; —$CONR^6R^7$, wherein $R^6$ and $R^7$ are independently selected from H, $C_{1-3}$ alkyl, cyclopropyl, and iso-propyl, or $R^6$ and $R^7$ together with the nitrogen form a heterocycloalkyl; $C_{1-3}$ alkyl, optionally substituted with a F; cyclopropyl, optionally substituted with a F; isopropyl, optionally substituted with a F; $SC_{1-3}$ alkyl, optionally substituted with a F; $OC_{1-3}$ alkyl, optionally substituted with a F; O-cyclopropyl, optionally substituted with a F; O-isopropyl, optionally substituted with a F; $NR^8R^9$, wherein $R^8$ and $R^9$ are independently selected from H, $C_{1-3}$ alkyl and isopropyl; OH; and $R^{10}$—CONH— wherein $R^{10}$ is selected from $C_{1-3}$ alkyl and cyclopropyl; an aryl; and a heterocycle c) a $C_{5-7}$ cycloalkyl, optionally substituted with a substituent selected from a halogen, $C_2$-alkynyl, CN, methyl optionally substituted with a F, $OCH_3$ optionally substituted with a F, $OCH_2CH_3$ optionally substituted with a F, OH, and $R^{11}$—CONH— wherein $R^{11}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; $COOC_{1-4}$ alkyl; —$CONR^{12}R^{13}$, wherein $R^{12}$ and $R^{13}$ are independently selected from H, $C_{1-3}$ alkyl, cyclopropyl, and iso-propyl or $R^{12}$ and $R^{13}$ together with the nitrogen form a heterocycloalkyl; $C_{1-3}$ alkyl, optionally substituted with a F; cyclopropyl, optionally substituted with a F; isopropyl, optionally substituted with a F; $SC_{1-3}$ alkyl, optionally substituted with a F; $OC_{1-3}$ alkyl, optionally substituted with a F; O-cyclopropyl, optionally substituted with a F; O-isopropyl, optionally substituted with a F; $SC_{1-3}$ alkyl, optionally substituted with a F; $NR^{14}R^{15}$, wherein $R^{14}$ and $R^{15}$ are independently selected from H, $C_{1-3}$ alkyl and isopropyl; OH; an aryl; a heterocycle; and $R^{16}$—CONH— wherein $R^{16}$ is selected from $C_{1-3}$ alkyl and cyclopropyl; e) a $C_{1-6}$ alkyl or branched $C_{3-6}$ alkyl; f) $C_{2-6}$ alkynyl $R^1$ is selected from the group consisting of a) H, b) OH, c) $OC_{1-6}$ alkyl optionally substituted with one or more halogen, phenyl, phenyl substituted with one or more groups selected form OH and halogen, CN, $OR^{17}$, $NR^{18}R^{19}$, and $CONH_2$, wherein $R^{17}$ is selected from the group consisting of H, CN, a halogen, methyl optionally substituted with a F, $OCH_3$ optionally substituted with a F, $OCH_2CH_3$ optionally substituted with a F, OH, and $R^{20}$—CONH— wherein $R^{20}$ is selected from $C_{1-3}$ alkyl and cyclopropyl, $R^{18}$ is selected from the group consisting of H, CN, a halogen, methyl optionally substituted with a F, $OCH_3$ optionally substituted with a F, $OCH_2CH_3$ optionally substituted with a F, OH, and $R^{21}$—CONH— wherein $R^{21}$ is selected from $C_{1-3}$ alkyl and cyclopropyl, and $R^{19}$ is selected from the group consisting of H, CN, a halogen, methyl optionally substituted with a F, $OCH_3$ optionally substituted with a F, $OCH_2CH_3$ optionally substituted with a F, OH, and $R^{22}$—CONH— wherein $R^{22}$ is selected from $C_{1-3}$ alkyl and cyclopropyl, d) branched $OC_{3-6}$ alkyl optionally substituted with one or more halogen, CN, $OR^{23}$, $NR^{24}R^{25}$, and $CONH_2$, wherein $R^{23}$ is selected from the group consisting of H, CN, a halogen, methyl optionally substituted with a F, $OCH_3$ optionally substituted with a F, $OCH_2CH_3$ optionally substituted with a F, OH, and $R^{26}$—CONH— wherein $R^{26}$ is selected from $C_{1-3}$ alkyl and cyclopropyl, $R^{24}$ is selected from the group consisting of H, CN, a halogen, methyl optionally substituted with a F, $OCH_3$ optionally substituted with a F, $OCH_2CH_3$ optionally substituted with a F, OH, and $R^{27}$—CONH— wherein $R^{27}$ is selected from $C_{1-3}$ alkyl and cyclopropyl, and $R^{25}$ is selected from the group consisting of H, CN, a halogen, methyl optionally substituted with a F, $OCH_3$ optionally substituted with a F, $OCH_2CH_3$ optionally substituted with a F, OH, and $R^{28}$—CONH— wherein $R^{28}$ is selected from $C_{1-3}$ alkyl and cyclopropyl, and e) cyclic $OC_{3-6}$ alkyl optionally substituted with one or more halogen, CN, $OR^{29}$, $NR^{30}R^{31}$, and $CONH_2$, wherein $R^{29}$ is selected from the group consisting of H, CN, a halogen, methyl optionally substituted with a F, $OCH_3$ optionally substituted with a F, $OCH_2CH_3$ optionally substituted with a F, OH, and $R^{32}$—CONH— wherein $R^{32}$ is selected from $C_{1-3}$ alkyl and cyclopropyl, $R^{30}$ is selected from the group consisting of H, CN, a halogen, methyl optionally substituted with a F, $OCH_3$ optionally substituted with a F, $OCH_2CH_3$ optionally substituted with a F, OH, and $R^{33}$—CONH— wherein $R^{33}$ is selected from $C_{1-3}$ alkyl and cyclopropyl, and $R^{31}$ is selected from the group consisting of H, CN, a halogen, methyl optionally substituted with a F, $OCH_3$ optionally substituted with a F, $OCH_2CH_3$ optionally substituted with a F, OH, and $R^{34}$—CONH— wherein $R^{34}$ is selected from $C_{1-3}$ alkyl and cyclopropyl; or a pharmaceutically acceptable salt or solvate thereof.

In a further aspect the present invention concerns a D-galactopyranose compound of formula (1)

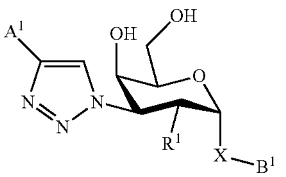

wherein the pyranose ring is α-D-galactopyranose, $A^1$ is selected from the group consisting of

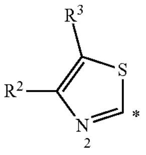

and

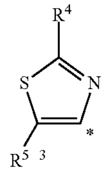

wherein the asterix * indicates the carbon atom of the heteroaromatic ring that is covalently attached to the triazole group of formula (1);

wherein $R^2$ is selected from the group consisting of hydrogen, $C_{1-6}$ alkyl, OH and halogen;

$R^3$ is selected from the group consisting of hydrogen, $C_{1-6}$ alkyl and halogen;

$R^4$ is selected from the group consisting of OH, halogen and amino;

$R^5$ is selected from the group consisting of hydrogen, $C_{1-6}$ alkyl and halogen;

X is selected from S, SO, $SO_2$, O, C═O, and $CR^{2a}R^{3a}$ wherein $R^{2a}$ and $R^{3a}$ are independently selected from hydrogen, OH, or halogen;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{4a}$—CONH— wherein $R^{4a}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{5a}$—CONH— wherein $R^{5a}$ is selected from $C_{1-3}$ alkyl and cyclopropyl; b) an aryl, such as phenyl or naphthyl, optionally substituted with a group selected from a halogen; CN; —COOH; —$CONR^6R^7$, wherein $R^6$ and $R^7$ are independently selected from H, $C_{1-3}$ alkyl, cyclopropyl, and iso-propyl, or $R^6$ and $R^7$ together with the nitrogen form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^8R^9$, wherein $R^8$ and $R^9$ are independently selected from H, $C_{1-3}$ alkyl and isopropyl; OH; a heterocycle; and $R^{10}$—CONH— wherein $R^{10}$ is selected from $C_{1-3}$ alkyl and cyclopropyl; c) a $C_{5-7}$ cycloalkyl, optionally substituted with a substituent selected from a halogen, $C_2$-alkynyl, CN, methyl optionally substituted with a F, $OCH_3$ optionally substituted with a F, $OCH_2CH_3$ optionally substituted with a F, OH, and $R^{11}$—CONH— wherein $R^{11}$ is selected from $C_{1-3}$ alkyl and cyclopropyl; and d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; —$CONR^{12}R^{13}$, wherein $R^{12}$ and $R^{13}$ are independently selected from H, $C_{1-3}$ alkyl, cyclopropyl, and iso-propyl or $R^{12}$ and $R^{13}$ together with the nitrogen form a heterocycloalkyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{14}R^{15}$, wherein $R^{14}$ and $R^{15}$ are independently selected from H, $C_{1-3}$ alkyl and isopropyl; OH; a heterocycle; and $R^{16}$—CONH— wherein $R^{16}$ is selected from $C_{1-3}$ alkyl and cyclopropyl; e) a $C_{1-6}$ alkyl or branched $C_{3-6}$ alkyl; f) $C_{2-6}$ alkynyl, $R^1$ is selected from the group consisting of a) H, b) OH, c) $OC_{1-6}$ alkyl optionally substituted with one or more halogen, phenyl, phenyl substituted with one or more groups selected form OH and halogen, CN, $OR^{17}$, $NR^{18}R^{19}$, and $CONH_2$, wherein $R^{17}$ is selected from the group consisting of H, CN, a halogen, methyl optionally substituted with a F, $OCH_3$ optionally substituted with a F, $OCH_2CH_3$ optionally substituted with a F, OH, and $R^{20}$—CONH— wherein $R^{20}$ is selected from $C_{1-3}$ alkyl and cyclopropyl, $R^{18}$ is selected from the group consisting of H, CN, a halogen, methyl optionally substituted with a F, $OCH_3$ optionally substituted with a F, $OCH_2CH_3$ optionally substituted with a F, OH, and $R^{21}$—CONH— wherein $R^{21}$ is selected from $C_{1-3}$ alkyl and cyclopropyl, and $R^{19}$ is selected from the group consisting of H, CN, a halogen, methyl optionally substituted with a F, $OCH_3$ optionally substituted with a F, $OCH_2CH_3$ optionally substituted with a F, OH, and $R^{22}$—CONH— wherein $R^{22}$ is selected from $C_{1-3}$ alkyl and cyclopropyl, d) branched $OC_{3-6}$ alkyl optionally substituted with one or more halogen, CN, $OR^{23}$, $NR^{24}R^{25}$, and $CONH_2$, wherein $R^{23}$ is selected from the group consisting of H, CN, a halogen, methyl optionally substituted with a F, $OCH_3$ optionally substituted with a F, $OCH_2CH_3$ optionally substituted with a F, OH, and $R^{26}$—CONH— wherein $R^{26}$ is selected from $C_{1-3}$ alkyl and cyclopropyl, $R^{24}$ is selected from the group consisting of H, CN, a halogen, methyl optionally substituted with a F, $OCH_3$ optionally substituted with a F, $OCH_2CH_3$ optionally substituted with a F, OH, and $R^{27}$—CONH— wherein $R^{27}$ is selected from $C_{1-3}$ alkyl and cyclopropyl, and $R^{25}$ is selected from the group consisting of H, CN, a halogen, methyl optionally substituted with a F, $OCH_3$ optionally substituted with a F, $OCH_2CH_3$ optionally substituted with a F, OH, and $R^{28}$—CONH— wherein $R^{28}$ is selected from $C_{1-3}$ alkyl and cyclopropyl, and e) cyclic $OC_{3-6}$ alkyl optionally substituted with one or more halogen, CN, $OR^{29}$, $NR^{30}R^{31}$, and $CONH_2$, wherein $R^{29}$ is selected from the group consisting of H, CN, a halogen, methyl optionally substituted with a F, $OCH_3$ optionally substituted with a F, $OCH_2CH_3$ optionally substituted with a F, OH, and $R^{32}$—CONH— wherein $R^{32}$ is selected from $C_{1-3}$ alkyl and cyclopropyl, $R^{30}$ is selected from the group consisting of H, CN, a halogen, methyl optionally substituted with a F, $OCH_3$ optionally substituted with a F, $OCH_2CH_3$ optionally substituted with a F, OH, and $R^{33}$—CONH— wherein $R^{33}$ is selected from $C_{1-3}$ alkyl and cyclopropyl, and $R^{31}$ is selected from the group consisting of H, CN, a halogen, methyl optionally substituted with a F, $OCH_3$ optionally substituted with a F, $OCH_2CH_3$ optionally substituted with a F, OH, and $R^{34}$—CONH— wherein $R^{34}$ is selected from $C_{1-3}$ alkyl and cyclopropyl; or a pharmaceutically acceptable salt or solvate thereof.

In one embodiment $B^1$ is selected from d) a heterocycle, such as heteroaryl or heterocycloalkyl, optionally substituted with a group selected from a halogen; a spiro heterocycle, such as N-(2-oxa)-6-azaspiro[3.3]heptanyl; $C_2$-alkynyl; CN; —COOH; —$CONR^{12}R^{13}$, wherein $R^{12}$ and $R^{13}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{14}R^{15}$, wherein $R^{14}$ and $R^{15}$ are independently selected from H, $C_{1-3}$ alkyl and isopropyl; OH; heterocycle; and $R^{16}$—CONH— wherein $R^{16}$ is selected from $C_{1-3}$ alkyl and cyclopropyl.

In one embodiment $A^1$ is selected from formula 2 wherein $R^2$ is selected from the group consisting of hydrogen, methyl, OH and halogen; and $R^3$ is selected from the group consisting of hydrogen, $C_{1-6}$ alkyl and halogen. In a preferred embodiment $R^2$ is hydrogen, methyl or halogen, and $R^3$ is H. Depending on conditions such as acidic or basic the OH group may be on the oxo tautomer form. In another preferred embodiment $R^2$ is halogen, and $R^3$ is hydrogen. In a further embodiment $R^2$ is a halogen, such as Cl; and $R^3$ is selected from the group consisting of $C_{1-6}$ alkyl, such as methyl, and halogen, such as Cl.

In a still further embodiment $A^1$ is selected from formula 3 wherein $R^4$ is selected from the group consisting of OH, halogen and amino; and $R^5$ is selected from the group consisting of hydrogen, $C_{1-6}$ alkyl and halogen. In a preferred embodiment $R^4$ is OH and $R^5$ is hydrogen. In another preferred embodiment $R^4$ is amino and $R^5$ is hydrogen. In a further preferred embodiment $R^4$ is halogen and $R^5$ is hydrogen.

In a preferred embodiment $A^1$ is

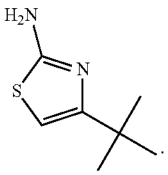

In a further embodiment $A^1$ is

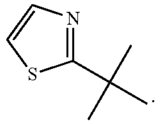

In another preferred embodiment $A^1$ is

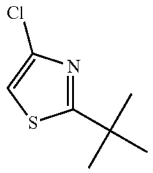

and $R^1$ is selected from the group consisting of a), c), d) and e) of the aspect above.

In a still further preferred embodiment $A^1$ is

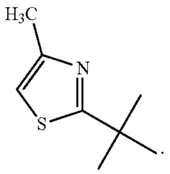

In a further preferred embodiment $A^1$ is

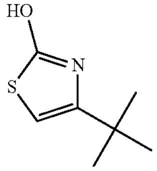

and $R^1$ is selected from the group consisting of a), c), d) and e) of the aspect above.

In a still further preferred embodiment $A^1$ is

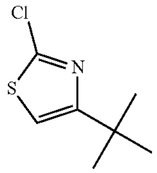

and $R^1$ is selected from the group consisting of a), c), d) and e) of the aspect above.

In a further embodiment $A^1$ is

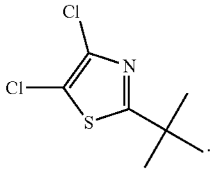

In a still further embodiment $A^1$ is

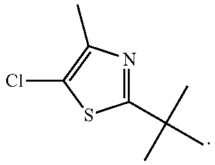

In a further embodiment X is selected from S, SO, $SO_2$, and O, such as S, SO, and $SO_2$, preferably S.

In a still further embodiment $R^1$ is selected from H, OH, $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen. In a more preferred embodiment $R^1$ is selected from H, $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen. In a still more preferred embodiment $R^1$ is selected from $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen.

In another embodiment $R^1$ is selected from H, OH, $OCH_3$, and $OC_{1-6}$ alkyl optionally substituted with one or more halogen; such as H, OH, $OCH_3$, and $OCH_2CF_3$.

In a further embodiment $B^1$ is selected from a heteroaryl, optionally substituted with a group selected from a halogen; $C_2$-alkynyl; CN; methyl optionally substituted with a F; and a heteroaryl. In a further embodiment B1 is selected from a heteroaryl, optionally substituted with a group selected from a halogen; CN; methyl optionally substituted with a F; and a heteroaryl. Preferably, B1 is selected from a pyridinyl, optionally substituted with a group selected from a Cl; Br; CN; ethynyl; methyl; $CF_3$; pyridin; pyrimidin; oxazol; and thiazol.

In a still further embodiment B1 is selected from a heteroaryl, optionally substituted with a group selected from a halogen; $C_2$-alkynyl; CN; methyl optionally substituted with a F; a spiro heterocycle; $SC_{1-3}$ alkyl, optionally substituted with a F; a $CONR^{12}R^{13}$, wherein $R^{12}$ and $R^{13}$ are independently selected from H, $C_{1-3}$ alkyl, cyclopropyl, and iso-propyl or $R^{12}$ and $R^{13}$ together with the nitrogen form a heterocycloalkyl; and a heterocycle, such as a tetrahydropyridin.

In a further embodiment B1 is selected from a pyridinyl, optionally substituted with a group selected from a Cl; Br; F; ethynyl; N-(2-oxa)-6-azaspiro[3.3]heptanyl; CO-azetidinyl; $CONHCH_3$; $CONHCH_2CH_3$; $CON(CH_3)_2$; CN; methyl; $SCH_3$; $SCF_3$; $CF_3$; imidazole; pyridin; pyrimidin; oxazol; and thiazol.

In a further embodiment B1 is selected from a pyridinyl substituted with a group selected from one or more of Cl, Br, and CN. Typically, B1 is selected from a pyridinyl substituted with a group selected from one, two or three, such as one or two, of Cl, Br, and CN.

In a still further embodiment B1 is selected from a heterocycloalkyl, such as a tetrahydro-bipyridin.

In a further embodiment $B^1$ is selected from a heteroaryl, optionally substituted with a group selected from a spiro heterocycle; a $CONR^{12}R^{13}$, wherein $R^{12}$ and $R^{13}$ are independently selected from H, $C_{1-3}$ alkyl, cyclopropyl, and iso-propyl or $R^{12}$ and $R^{13}$ together with the nitrogen form a heterocycloalkyl. Typically, B1 is selected from a pyridinyl, optionally substituted with a group selected from a N-(2-oxa)-6-azaspiro[3.3]heptanyl; CO-azetidinyl; $CONHCH_3$; $CONHCH_2CH_3$; $CON(CH_3)_2$; and imidazole.

In a still further embodiment B1 is selected from a benzothiazolyl or a thiazolpyridyl optionally substituted with a group selected from a Cl; Br; F; ethynyl; N-(2-oxa)-6-azaspiro[3.3]heptanyl; CO-azetidinyl; $CONHCH_3$; $CONHCH_2CH_3$; $CON(CH_3)_2$; CN; methyl; $SCH_3$; $SCF_3$; $CF_3$; imidazole; pyridin; pyrimidin; oxazol; and thiazol.

In a further embodiment $B^1$ is selected from a phenyl, optionally substituted with a group selected from a halogen; and $C_{1-3}$ alkyl, optionally substituted with a F.

In a still further embodiment $B^1$ is selected from a phenyl, optionally substituted with a group selected from a CN; —$CONR^6R^7$, wherein $R^6$ and $R^7$ are independently selected from H, $C_{1-3}$ alkyl, cyclopropyl, and iso-propyl. Typically, B1 is selected from a phenyl, optionally substituted with a group selected from a CN and $CONHCH_3$.

In a further embodiment B1 is selected from a phenyl, optionally substituted with a group selected from a halogen; CN; —$CONR^6R^7$, wherein $R^6$ and $R^7$ are independently selected from H, $C_{1-3}$ alkyl, cyclopropyl, and iso-propyl; and $C_{1-3}$ alkyl, optionally substituted with a F.

In a still further embodiment B1 is selected from a phenyl, optionally substituted with a group selected from a Cl; F; Br; CN; $CONHCH_3$; and $C_{1-3}$ alkyl, optionally substituted with a F.

In a still further embodiment B1 is selected from a phenyl substituted with a group selected from Cl, F, and methyl. Typically, B1 is selected from a phenyl substituted with one, two or three, such as one or two, selected from Cl, F, and methyl.

In a still further embodiment the compound of formula (1) is selected from any one of:

3,5-dichloro-4-fluoro-phenyl 3-deoxy-2-O-methyl-3-[4-(2-thiazolyl)-1H-1,2,3-triazol-1-yl]-1-thio-α-D-galactopyranoside, 5-bromopyridin-3-yl 3-deoxy-2-O-methyl-3-[4-(2-thiazolyl)-1H-1,2,3-triazol-1-yl]-1-thio-α-D-galactopyranoside, 5-bromo-2-cyano-pyridin-3-yl 3-deoxy-2-O-methyl-3-[4-(2-thiazolyl)-1H-1,2,3-triazol-1-yl]-1-thio-α-D-galactopyranoside, 5-chloro-2-cyano-pyridin-3-yl 3-deoxy-2-O-methyl-3-[4-(2-thiazolyl)-1H-1,2,3-triazol-1-yl]-1-thio-α-D-galactopyranoside, 5-chloro-2-cyano-pyridin-3-yl 2-O-benzyl-3-deoxy-3-[4-(2-thiazolyl)-1H-1,2,3-triazol-1-yl]-1-thio-α-D-galactopyranoside, 5-chloro-2-cyano-pyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside, 3,5-dichloro-4-fluoro-phenyl 3-deoxy-2-O-methyl-3-[4-(2-hydroxythiazol-4-yl)-1H-1,2,3-triazol-1-yl]-1-thio-α-D-galactopyranoside, 3,4-dichlorophenyl 3-deoxy-3-[4-(2-hydroxythiazol-4-yl)-1H-1,2,3-triazol-1-yl]-2-O-isopropyl-1-thio-α-D-galactopyranoside, 3,4-dichlorophenyl 3-deoxy-3-[4-(2-hydroxythiazol-4-yl)-1H-1,2,3-triazol-1-yl]-2-O-methyl-1-thio-α-D-galactopyranoside, 3,4-dichlorophenyl 2,3-dideoxy-3-[4-(2-hydroxythiazol-4-yl)-1H-1,2,3-triazol-1-yl]-1-thio-α-D-galactopyranoside, 5-bromo-2-cyano-pyridine-3-yl 3-deoxy-3-[4-(4-chloro-thiazol-2-yl)-1H-1,2,3-triazol-1-yl]-2-O-methyl-1-thio-α-D-galactopyranoside, 5-bromo-6-cyano-3-pyridyl 3-deoxy-3-[4-(4-chloro-thiazol-2-yl)-1H-1,2,3-triazol-1-yl]-2-O-methyl-1-thio-α-D-galactopyranoside, 5-chloro-2-cyano-pyridine-3-yl 3-deoxy-3-[4-(4-chloro-thiazol-2-yl)-1H-1,2,3-triazol-1-yl]-2-O-methyl-1-thio-α-D-galactopyranoside, 5-chloro-6-cyano-pyridine-3-yl 3-deoxy-3-[4-(4-chloro-thiazol-2-yl)-1H-1,2,3-triazol-1-yl]-2-O-methyl-1-thio-α-D-galactopyranoside, 5-chloro-2-cyano-pyridine-3-yl 3-deoxy-3-[4-(2-chlorothiazol-4-yl)-1H-1,2,3-triazol-1-yl]-2-O-methyl-1-thio-α-D-galactopyranoside, 3,5-dichloro-4-fluoro-phenyl 3-[4-(2-aminothiazol-4-yl)-1H-1,2,3-triazol-1-yl]-3-deoxy-2-O-methyl-1-thio-α-D-galactopyranoside, 5-chloro-2-cyano-pyridine-3-yl 3-[4-(2-aminothiazol-4-yl)-1H-1,2,3-triazol-1-yl]-3-deoxy-2-O-methyl-1-thio-α-D-galactopyranoside, 5-chloro-2-methyl-pyridine-3-yl 3-[4-(2-aminothiazol-4-yl)-1H-1,2,3-triazol-1-yl]-3-deoxy-2-O-methyl-1-thio-α-D-galactopyranoside, 5-chloro-2-cyano-pyridine-3-yl 3-[4-(2-aminothiazol-4-yl)-1H-1,2,3-triazol-1-yl]-2-O-benzyl-3-deoxy-1-thio-α-D-galactopyranoside, 5-chloro-2-methyl-pyridine-3-yl 3-[4-(2-aminothiazol-4-yl)-1H-1,2,3-triazol-1-yl]-3-deoxy-2-O-ethyl-1-thio-α-D-galactopyranoside, 5-chloro-2-(pyrimidin-5-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-chloro-2-(pyridin-4-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-chloro-2-(pyridin-3-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-chloro-1',2',3',6'-tetrahydro-[2,4'-bipyridin]-3-yl 3-[4-(2-aminothiazol-4-yl)-1H-1,2,3-triazol-1-yl]-3-deoxy-2-O-methyl-1-thio-α-D-galactopyranoside, 5-chloro-2-cyano-pyridine-3-yl 3-[4-(2-aminothiazol-4-yl)-1H-1,2,3-triazol-1-yl]-3-deoxy-2-O-(3,5-difluoro-4-hydroxybenzyl)-1-thio-α-D-galactopyranoside, 5-chloro-2-(pyridin-3-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-chloro-2-(oxazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3,4-dichlorphenyl 3-[4-(2-aminothiazol-4-yl)-1H-1,2,3-triazol-1-yl]-3-deoxy-2-O-methyl-1-thio-α-D-galactopyranoside, 5-chloro-2-(thiazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3-chloro-4-(trifluoromethyl)phenyl 3-[4-(2-aminothiazol-4-yl)-1H-1,2,3-triazol-1-yl]-3-deoxy-2-O-methyl-1-thio-α-D-galactopyranoside, 3-chlorophenyl 3-[4-(2-aminothiazol-4-yl)-1H-1,2,3-triazol-1-yl]-3-deoxy-2-O-methyl-1-thio-α-D-galactopyranoside, 3,5-dichloro-4-fluoro-phenyl 3-[4-(2-aminothiazol-4-yl)-1H-1,2,3-triazol-1-yl]-3-deoxy-1-thio-α-D-galactopyranoside, 5-bromo-6-trifluoromethylpyridine-3-yl 3-[4-(2-aminothiazol-4-yl)-1H-1,2,3-triazol-1-yl]-3-deoxy-1-thio-α-D-galactopyranoside; or a pharmaceutically acceptable salt or solvate thereof.

In a further embodiment the compound of formula (1) is selected from any one of:

3,5-Dichloro-4-fluorophenyl 3-deoxy-2-O-methyl-3-[4-(2-thiazolyl)-1H-1,2,3-triazol-1-yl]-1-thio-α-D-galactopyranoside, 5-Bromopyridin-3-yl 3-deoxy-2-O-methyl-3-[4-(2-thiazolyl)-1H-1,2,3-triazol-1-yl]-1-thio-α-D-galactopyranoside, 5-Bromo-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 2-O-benzyl-3-deoxy-3-[4-(2-thiazolyl)-1H-1,2,3-triazol-1-yl]-1-thio-α-D-galactopyranoside, 5-Chloro-2-cyanopyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside, 3,5-Dichloro-4-fluorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 3-deoxy-3-[4-(2-hydroxythiazol-4-yl)-1H-1,2,3-triazol-1-yl]-2-O-isopropyl-1-thio-α-D-galactopyranoside, 3,4-Dichlorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 2,3-dideoxy-3-[4-(2-hydroxythiazol-4-yl)-1H-1,2,3-triazol-1-yl]-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Bromo-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Chloro-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(2-chlorothiazol-4-yl)-1H-1,2,3-triazol-1-yl]-3-deoxy-2-O-methyl-1-thio-α-D-galactopyranoside, 3,5-Dichloro-4-fluorophenyl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-2-O-benzyl-3-deoxy-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-(pyrimidin-5-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-4-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-3-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(1,2,3,6-tetrahydropyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-0-(3,5-difluoro-4-hydroxybenzyl)-1-thio-α-D-galactopyranoside, 5-Chloro-2-(pyridin-2-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(oxazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3,4-Dichlorphenyl 3-[4-(2-aminothiazol-4-yl)-1H-1,2,3-triazol-1-yl]-3-deoxy-2-O-methyl-1-thio-α-D-galactopyranoside, 5-Chloro-2-(thiazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-(trifluoromethyl)phenyl 3-[4-(2-aminothiazol-4-yl)-1H-1,2,3-triazol-1-yl]-3-deoxy-2-O-methyl-1-thio-α-D-galactopyranoside, 3-Chlorophenyl 3-[4-(2-aminothiazol-4-yl)-1H-1,2,3-triazol-1-yl]-3-deoxy-2-O-methyl-1-thio-α-D-galactopyranoside, 3,5-Dichloro-4-fluorophenyl 3-[4-(2-aminothiazol-4-yl)-1H-1,2,3-triazol-1-yl]-3-deoxy-1-thio-α-D-galactopyranoside, 3-Bromo-2-trifluoromethylpyridin-5-yl 3-[4-(2-aminothiazol-4-yl)-1H-1,2,3-triazol-1-yl]-3-deoxy-1-thio-α-D-galactopyranoside, 5-Bromo-2-cyanopyridin-3-yl 3-deoxy-3-[4-(4-methylthiazol-2-yl)-1H-1,2,3-triazol-1-yl]-2-O-methyl-1-thio-α-D-galactopyranoside, 2-Cyano-5-methylpyridin-3-yl 3-deoxy-3-[4-(4-methyltriazol-2-yl)-1H-1,2,3-thiazol-1-yl]-2-O-methyl-1-thio-α-D-galactopyranoside, 2-Cyano-5-methylpyridin-3-yl 3-[4-(4-chlorothiazol-2-yl)-1H-1,2,3-triazol-1-yl]-3-deoxy-2-O-methyl-1-thio-α-D-galactopyranoside, 5-Ethynylpyridin-3-yl 3-[4-(4-chlorothiazol-2-yl)-1H-1,2,3-triazol-1-yl]-3-deoxy-2-O-methyl-1-thio-α-D-galactopyranoside, 5-Chloro-2-{N-(2-oxa)-6-azaspiro[3.3]heptanyl}-pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-cyanophenyl 3-[4-(2-aminothiazol-4-yl)-1H-1,2,3-triazol-1-yl]-3-deoxy-2-O-methyl-1-thio-α-D-galactopyranoside, 5-Cyanopyridin-3yl 3-[4-(2-aminothiazol-4-yl)-1H-1,2,3-triazol-1-yl]-3-deoxy-2-O-methyl-1-thio-α-D-galactopyranoside, 3,5-Dichloro-4-fluorophenyl 2,3-dideoxy-3-[4-(2-hydroxythiazol-4-yl)-1H-1,2,3-triazol-1-yl]-1-thio-α-D-galactopyranoside, 3-Chloro-4-cyanophenyl 3-[4-(2-aminothiazol-4-yl)-1H-1,2,3-triazol-1-yl]-2,3-dideoxy-1-thio-α-D-galactopyranoside, 5-Chloro-2-cyanophenyl 3-[4-(4-chlorothiazol-2-yl)-1H-1,2,3-triazol-1-yl]-2,3-dideoxy-1-thio-α-D-galactopyranoside, 3-Cyano-2-(trifluoromethyl)pyridin-5-yl 3-[4-(2-aminothiazol-4-yl)-1H-1,2,3-triazol-1-yl]-3-deoxy-2-O-methyl-1-thio-α-D-galactopyranoside, 5-Chloro-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(pyridin-2-yl)-pyridin-3-yl 3-deoxy-3-[4-(4-methylthiazol-2-yl)-1H-1,2,3-triazol-1-yl]-2-O-methyl-1-thio-α-D-galactopyranoside, 5-Ethynylpyridin-3-yl 3-deoxy-2-O-methyl-3-[4-(2-thiazolyl)-1H-1,2,3-triazol-1-yl]-1-thio-α-D-galactopyranoside, 5-Chloropyridin-3-yl 3-[4-(4-chlorothiazol-2-yl)-1H-1,2,3-triazol-1-yl]-3-deoxy-1-thio-α-D-galactopyranoside, 5-Bromopyridin-3-yl 3-[4-(4-chlorothiazol-2-yl)-1H-1,2,3-triazol-1-yl]-3-deoxy-1-thio-α-D-galactopyranoside, 5-Chloro-2-cyanophenyl 3-[4-(4-chlorothiazol-2-yl)-1H-1,2,3-triazol-1-yl]-3-deoxy-1-thio-α-D-galactopyranoside, 3-Chloro-5-cyanophenyl 3-[4-(4-chlorothiazol-2-yl)-1H-1,2,3-triazol-1-yl]-3-deoxy-1-thio-α-D-galactopyranoside, 3-Chloro-4-cyanophenyl 3-[4-(4-chlorothiazol-2-yl)-1H-1,2,3-triazol-1-yl]-3-deoxy-1-thio-α-D-galactopyranoside, 5-Chloropyridin-3-yl 3-[4-(4-chlorothiazol-2-yl)-1H-1,2,3-triazol-1-yl]-3-deoxy-2-O-methyl-1-thio-α-D-galactopyranoside, 5-Bromopyridin-3-yl 3-[4-(4-chlorothiazol-2-yl)-1H-1,2,3-triazol-1-yl]-3-deoxy-2-O-methyl-1-thio-α-D-galactopyranoside, 5-Bromo-2-cyanopyridin-3-yl 3-[4-(4,5-dichlorothiazol-2-yl)-1H-1,2,3-triazol-1-yl]-3-deoxy-2-O-methyl-1-thio-α-D-galactopyranoside, 5-Bromo-2-cyanophenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-[4-(4-chlorothiazol-2-yl)-1H-1,2,3-triazol-1-yl]-3-deoxy-2-O-methyl-1-thio-α-D-galactopyranoside, 5-Bromo-2-cyanophenyl 3-deoxy-3-[4-(2-hydroxythiazol-4-yl)-1H-1,2,3-triazol-1-yl]-2-O-methyl-1-thio-α-D-galactopyranoside, 5-Bromo-2-cyanophenyl 3-[4-(2-aminothiazol-4-yl)-1H-1,2,3-triazol-1-yl]-3-deoxy-2-O-methyl-1-thio-α-D-galactopyranoside, 5-Bromo-2-(N-methyl-carbonyl)phenyl 3-[4-(4-chlorothiazol-2-yl)-1H-1,2,3-triazol-1-yl]-3-deoxy-2-O-methyl-1-thio-α-D-galactopyranoside, 5-Bromo-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Chloro-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-deoxy-3-[4-(4-methylthiazol-2-yl)-1H-1,2,3-triazol-1-yl]-2-O-methyl-1-thio-α-D-galactopyranoside, 5-Bromo-2-cyanopyridin-3-yl 3-[4-(5-chloro-4-methylthiazol-2-yl)-1H-1,2,3-triazol-1-yl]-3-deoxy-2-O-methyl-1-thio-α-D-galactopyranoside, 5-Bromo-2-cyanophenyl 3-[4-(5-chloro-4-methylthiazol-2-yl)-1H-1,2,3-triazol-1-yl]-3-deoxy-2-O-methyl-1-thio-α-D-galactopyranoside, 2,5-Dichlorophenyl 3-deoxy-2-O-methyl-3-[4-(2-thiazolyl)-1H-1,2,3-triazol-1-yl]-1-thio-α-D-galactopyranoside, 5-Bromo-2-chlorophenyl 3-deoxy-2-O-methyl-3-[4-(2-thiazolyl)-1H-1,2,3-triazol-1-yl]-1-thio-α-D-galactopyranoside, 5-Chloro-2-fluorophenyl 3-deoxy-2-O-methyl-3-[4-(2-thiazolyl)-1H-1,2,3-triazol-1-yl]-1-thio-α-D-galactopyranoside, 5-Bromo-2-fluorophenyl 3-deoxy-3-[4-(4-methylthiazol-2-yl)-1H-1,2,3-triazol-1-yl]-2-O-methyl-1-thio-α-D-galactopyranoside, 5-Chloro-2-cyanopyridin-3-yl 3-[4-(4-chlorothiazol-2-yl)-1H-1,2,3-triazol-1-yl]-3-deoxy-1-thio-α-D-galactopyranoside, 5-Chloro-2-cyanopyridin-3-yl 3-deoxy-2-O-ethyl-3-[4-(2-thiazolyl)-1H-1,2,3-triazol-1-yl]-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(1H-imidazol-2-yl)pyridin-3-yl 3-[4-(2-aminothiazol-4-yl)-1H-1,2,3-triazol-1-yl]-3-deoxy-1-thio-α-D-galactopyranoside, 5-Chloro-2-(1H-imidazol-2-yl)pyridin-3-yl 3-deoxy-3-[4-(2-hydroxythiazol-4-yl)-1H-1,2,3-triazol-1-yl]-1-thio-α-D-galactopyranoside, 5-Chloro-2-(pyridin-2-yl)pyridin-3-yl 3-[4-(4-chlorothiazol-2-yl)-1H-1,2,3-triazol-1-yl]-3-deoxy-2-O-methyl-1-thio-α-D-galactopyranoside, 2-Cyano-5-methylpyridin-3-yl 3-[4-(4-chlorothiazol-2-yl)-1H-1,2,3-triazol-1-yl]-3-deoxy-1-thio-α-D-galactopyranoside, 3,4-Dichlorophenyl 3-[4-(2-aminothiazol-4-yl)-1H-1,2,3-triazol-1-yl]-3-deoxy-2-O-(2,2,2-trifluoroethyl)-1-thio-α-D-galactopyranoside, 3,4-Dichlorophenyl 3-deoxy-2-O-(2,2,2-trifluoroethyl)-3-[4-(2-hydroxythiazol-4-yl)-1H-1,2,3-triazol-1-yl]-1-thio-α-D-galactopyranoside, 5-Ethynylpyridin-3-yl 3-[4-(4-chlorothiazol-2-yl)-1H-1,2,3-triazol-1-yl]-3-deoxy-1-thio-α-D-galactopyranoside, 5-Ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Cyanopyridin-3-yl 3-[4-(4-chlorothiazol-2-yl)-1H-1,2,3-triazol-1-yl]-3-deoxy-2-O-methyl-1-thio-α-D-galactopyranoside, 5-Cyanopyridin-3-yl 3-deoxy-3-[4-(2-hydroxythiazol-4-yl)-1H-1,2,3-triazol-1-yl]-2-O-methyl-1-thio-α-D-galactopyranoside, 2-Cyano-5-ethynylpyridin-3-yl 3-[4-(2-aminothiazol-4-yl)-1H-1,2,3-triazol-1-yl]-3-deoxy-1-thio-α-D-galactopyranoside, 2-Cyano-5-ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-ethyl-1-thio-α-D-galactopyranoside, 3,4-Dichlorophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 2,3-dideoxy-3-[4-(2-hydroxythiazol-4-yl)-1H-1,2,3-triazol-1-yl]-1-thio-α-D-galactopyranoside, 5-Bromo-2-(N,N-dimethylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside, 5-Ethynyl-2-(N,N-dimethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Ethynyl-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-ethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside; 5-Chloro-2-cyanophenyl 3-[4-(4-chlorothiazol-2-yl)-1H-1,2,3-triazol-1-yl]-3-deoxy-2-O-methyl-1-thio-α-D-galactopyranoside, 1,3-Benzothiazol-6-yl 3-[4-(4-chlorothiazol-2-yl)-1H-1,2,3-triazol-1-yl]-3-deoxy-2-O-methyl-1-thio-α-D-galactopyranoside, 1,3-Benzothiazol-6-yl 3-deoxy-3-[4-(2-hydroxythiazol-4-yl)-1H-1,2,3-triazol-1-yl]-2-O-methyl-1-thio-α-D-galactopyranoside, 1,3-Benzothiazol-6-yl 3-[4-(2-aminothiazol-4-yl)-1H-1,2,3-triazol-1-yl]-3-deoxy-2-O-methyl-1-thio-α-D-galactopyranoside, 5-Cyano-1,3-benzothiazol-6-yl 3-[4-(4-chlorothiazol-2-yl)-1H-1,2,3-triazol-1-yl]-3-deoxy-2-O-methyl-1-thio-α-D-galactopyranoside, Thiazolo[4,5-b]pyridin-6-yl 3-[4-(4-chlorothiazol-2-yl)-1H-1,2,3-triazol-1-yl]-3-deoxy-2-O-methyl-1-thio-α-D-galactopyranoside, 5-Methylsulfanylpyridin-3-yl 3-[4-(4-chlorothiazol-2-yl)-1H-1,2,3-triazol-1-yl]-3-deoxy-2-O-methyl-1-thio-α-D-galactopyranoside, and 5-(Trifluoromethylsulfanyl)pyridin-3-yl 3-[4-(4-chlorothiazol-2-yl)-1H-1,2,3-triazol-1-yl]-3-deoxy-2-O-methyl-1-thio-α-D-galactopyranoside; or a pharmaceutically acceptable salt or solvate thereof.

In a further aspect the present invention relates to a compound of formula (1) for use as a medicine.

In a still further aspect, the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-1 and/or a galectin 3 to a ligand in a mammal, such as a human.

In a further embodiment the disorder is selected from the group consisting of inflammation; Inflammation induced thrombosis; Atopic dermatitis; Acute coronary syndrome; fibrosis, such as pulmonary fibrosis, liver fibrosis, kidney fibrosis, ophthalmological fibrosis and fibrosis of the skin and heart; local fibrosis such as Dupuytren's disease and Peyronie's disease; fibrotic complications of other therapies such as coronary stents, bile duct stents, cerebral artery stents, ureter stents; scleroderma; scarring; keloid formation; covid-19; acute lung injury; ARDS; viral pneumonitis, aberrant scar formation; surgical adhesions; septic shock; cancer, such as colorectal cancer, other gastrointestinal carcinomas such as pancreatic cancer, gastric cancer, biliary tract cancer, lung cancers, mesothelioma, female cancers like breast cancer, ovarian cancer, uterine cancer, cancer of the cervix uteri, cancer of the salpingx, cerebral cancers such as medulloblastomao, glioma, meningioma, sarcomas of the bones and muscles and other sarcomas, leukemias and lymphomas, such as T-cell lymphomas; transplant rejection; metastasising cancers; ageing; Dementia; Alzheimers; TGF-beta driven bone disease such as osteogenesis imperfecta; Pulmonary hypertension; autoimmune diseases, such as psoriasis, rheumatoid arthritis, Rheumatoid lung; Crohn's disease, ulcerative colitis, ankylosing spondylitis, systemic lupus erythematosus; viral infections such as influenza virus, HIV, Herpes virus, Coronaviruses, Hepatitis C; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases; diabetes; type I diabetes; type 2 diabetes; insulin resistens; obesity; Marfans syndrome; Loeys-Dietz syndrome; nephropathy; Diastolic HF; fibrotic lung complications of aPD1 and other CPI therapies; asthma and other interstitial lung diseases, including Hermansky-Pudlak syndrome, liver disorders, such as non-alcoholic steatohepatitis or non-alcoholic fatty liver disease; uterine disease such as uterine fibroids and uterine or cervical fibrosis.

In a still further aspect the present invention relates to a method for treatment of a disorder relating to the binding of a galectin-1 and/or -3 to a ligand in a mammal, such as a human, wherein a therapeutically effective amount of at least one compound of formula (1) of the present invention is administered to a mammal in need of said treatment. In a further embodiment the disorder is selected from the group consisting of inflammation; Inflammation induced thrombosis; Atopic dermatitis; Acute coronary syndrome; fibrosis, such as pulmonary fibrosis, liver fibrosis, kidney fibrosis, ophthalmological fibrosis and fibrosis of the skin and heart; local fibrosis such as Dupuytren's disease and Peyronie's disease; fibrotic complications of other therapies such as coronary stents, bile duct stents, cerebral artery stents, ureter stents; scleroderma; scarring; keloid formation; covid-19; acute lung injury; ARDS; viral pneumonitis, aberrant scar formation; surgical adhesions; septic shock; cancer, such as colorectal cancer, other gastrointestinal carcinomas such as pancreatic cancer, gastric cancer, biliary tract cancer, lung cancers, mesothelioma, female cancers like breast cancer, ovarian cancer, uterine cancer, cancer of the cervix uteri, cancer of the salpingx, cerebral cancers such as medulloblastomao, glioma, meningioma, sarcomas of the bones and muscles and other sarcomas, leukemias and lymphomas, such as T-cell lymphomas; transplant rejection; metastasising cancers; ageing; Dementia; Alzheimers; TGFbeta driven bone disease such as osteogenesis imperfecta; Pulmonary hypertension; autoimmune diseases, such as psoriasis, rheumatoid arthritis, Rheumatoid lung; Crohn's disease, ulcerative colitis, ankylosing spondylitis, systemic lupus erythematosus; viral infections such as influenza virus, HIV, Herpes virus, Coronaviruses, Hepatitis C; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases; diabetes; type I diabetes; type 2 diabetes; insulin resistens; obesity; Marfans syndrome; Loeys-Dietz syndrome; nephropathy; Diastolic HF; fibrotic lung complications of aPD1 and other CPI therapies; asthma and other interstitial lung diseases, including Hermansky-Pudlak syndrome, liver disorders, such as non-alcoholic steatohepatitis or non-alcoholic fatty liver disease; uterine disease such as uterine fibroids and uterine or cervical fibrosis.

Another aspect of the present invention concerns combination therapy involving administering a compound of formula (I) of the present invention together with a therapeutically active compound different from the compound of formula (I) (interchangeable with "a different therapeutically active compound"). In one embodiment the present invention relates to a combination of a compound of formula (I) and a different therapeutically active compound for use in treatment of a disorder relating to the binding of a galectin-1 and/or -3 to a ligand in a mammal. Such disorders are disclosed below.

In an embodiment of the present invention, a therapeutically effective amount of at least one compound of formula (I) of the present invention is administered to a mammal in need thereof in combination with a different therapeutically active compound. In a further embodiment, said combination of a compound of formula (I) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistens; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

A non-limiting group of cancers given as examples of cancers that may be treated, managed and/or prevented by administration of a compound of formula (I) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, carniopharyngiomas, schwannomas, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (I) of the present invention and at least one additional therapeutic agent demonstrates therapeutic synergy. In some aspects of the methods of the present invention, a measurement of response to treatment observed after administering both at least one compound of formula (I) of the present invention and the additional therapeutic agent is improved over the same measurement of response to treatment observed after administering either the at least one compound of formula (I) of the present invention or the additional therapeutic agent alone.

A further aspect of the present invention concerns combination therapy involving administering a compound of formula (I) of the present invention together with an anti-fibrotic compound different form the compound of formula (I) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, PAT-1251 and PBI-4050.

A still further aspect of the present invention concerns combination therapy involving administering a compound of formula (I) in combination with a further conventional cancer treatment such as chemotherapy or radiotherapy, or treatment with immunostimulating substances, gene therapy, treatment with antibodies and treatment using dendritic cells, or mRNA based therapeutics including mRNA based cancer vaccines, and/or virus based cancer vaccines, to a mammal in need thereof.

In an embodiment the compound of formula (I) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (I) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO, kynurenine antagonists. These are known targets and some of these targets are described in Melero et al., Nature Reviews Cancer (2015). Examples of check point inhibitors administered together with the compound of formula (1) are Anti-PD-1: Nivolumab, Pembrolizumab, Cemiplimab. Anti-PD-L1: Atezolizumab, Avelumab, Durvalumab and one Anti-CTLA-4: Ipilimumab. Each one of these check point inhibitors can be made the subject of an embodiment in combination with any one of the compounds of formula (1).

In some embodiments of the present invention the compound of formula (I) is administered together with at least one additional therapeutic agent selected from an inhibitor of indoleamine-2,3-dioxygenase (IDO).

In some embodiments of the present invention the compound of formula (I) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (I) is administered together with at least one additional therapeutic agent selected from one or more inhibitors of the PD-1/PD-L pathway. In some embodiments, the one or more inhibitors of the PD-1/PD-L pathway are selected from one or more antibodies or antibody fragments against PD-1, PD-L1, and/or PD-L2, or other ways by which an anti-PD1 antibodies can be induced such as mRNA based introduction of genetic material which sets forth in-body production of anti-PD1 or anti-PDL1 antibodies or fragments of such antibodies.

In a still further aspect the present invention relates to a process of preparing a compound of formula II or a pharmaceutically acceptable salt or solvate thereof comprising the step a1 where $A^1$, $B^1$ and $R^1$ are defined as above under formula 1;

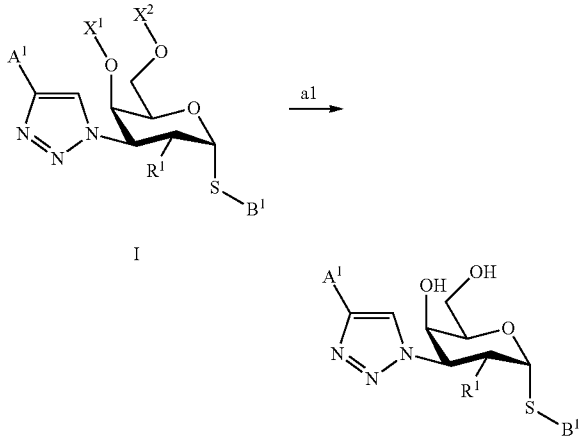

I

II a1) Reacting a compound of formula I wherein $X^1$ and $X^2$ together form a protective group such as benzylidene in the presence of an acid, such as TFA, in an inert organic solvent, such as DCM, followed by neutralisation with an base, such as triethylamine, optionally at temperatures below room temperature, to give a compound of formula II; optionally reacting a compound of formula 1 wherein $X^1$ and $X^2$ are two protective groups, such as acetates, in the presence of a base, such as triethylamine, sodium hydroxide or sodium methoxide in an organic solvent, such as methanol, optionally in the presence of water followed by neutralization using an acid, such as HCl, to give a compound to formula II.

In a still further aspect the present invention relates to a process of preparing a compound of formula II or a pharmaceutically acceptable salt or solvate thereof comprising the step a2 where $A^1$ and $B^1$ are defined as above under formula 1;

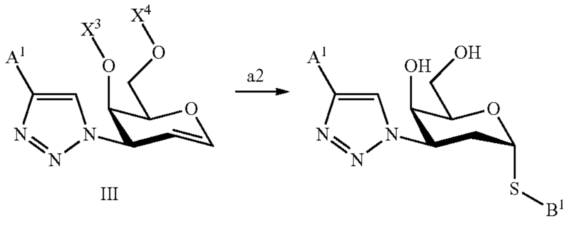

III IV a2) Reacting a compound of formula III, wherein $X^3$ and $X^4$ are hydrogen or protective groups, such as acetates, with a compound of formula $B^1$—SH in an organic solvent, such as toluene, optionally in the presence of a catalyst such as oxotrichloro[(dimethylsulfide)triphenylphosphine oxide] rhenium (V) or $BF3OEt_2$, optionally at elevated temperatures to give a compound of formula IV; when $X^3$ and X4 are protective groups, such as acetates, these could be removed in an additional step in the presence of base, such as triethylamine, LiOH or sodium methoxide in a suitable solvent, such as methanol and water, to give a compound of formula IV.

In a still further aspect the present invention relates to a process of preparing a compound of formula II or a pharmaceutically acceptable salt or solvate thereof comprising the step a3 where $A^1$, $B^1$ and $R^1$ are defined as above under formula 1;

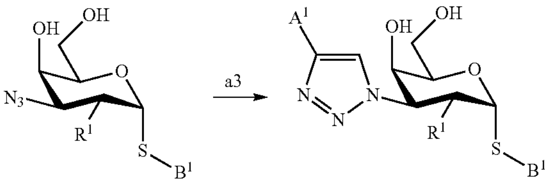

V II a3) Reacting the compound of formula V with a compound of formula $A^1$-CC—H or $A^1$-CC-TMS in an inert solvent, such as DMF or acetonitrile, using a base, such as diisopropylethylamine or L-ascorbic acid sodium salt, catalyzed by a cupper salt such as CuI or copper (II) sulfate, optionally using a reagent such as CsF to provide a compound of the formula II.

In a still further aspect, the present invention relates to a process of preparing a compound of formula VIII or a pharmaceutically acceptable salt or solvate thereof comprising the steps a4-a5 where $A^1$ and $B^1$ are defined as above under formula 1;

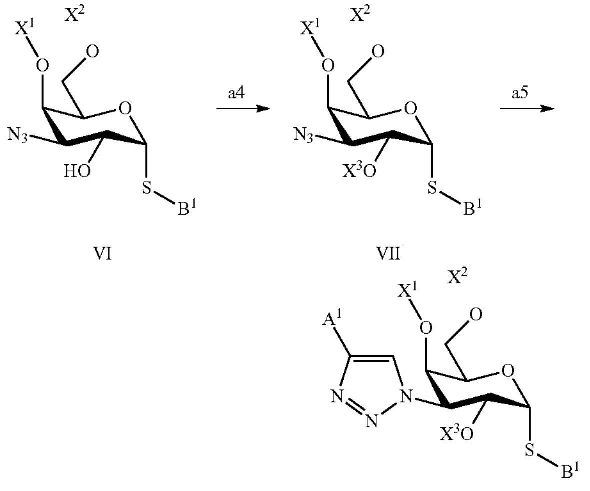

VI VII

VIII a4) Reacting a compound of formula VI with a compound of formula $X^3$-$L^1$, where $X^3$ taken together with O is $OX^3$ which is selected from c) under the definition of R1 above under formula 1, and $L^1$ is defined as a leaving groups such as a halide, such as Cl, Br, I or a sulfate ester such as a mesylate, tosylate or triflate in an organic solvent such as DMF, optionally in the presence of a reagent such as NaH, $CsCO_3$ or AgO, to give a compound of the formula VII.

a5) Reacting the compound of formula VII with a compound of formula $A^1$-CC—H or $A^1$-CC-TMS in an inert solvent, such as DMF or acetonitrile, using a base, such as diisopropylethylamine or L-ascorbic acid sodium salt, catalyzed by a cupper salt such as CuI or copper (II) sulfate, optionally using a reagent such as CsF to provide a compound of the formula VIII.

In a still further aspect, the present invention relates to a process of preparing a compound of formula VIII or a pharmaceutically acceptable salt or solvate thereof comprising the steps a6-a7 where $A^1$, $B^1$ and $R^1$ are defined as above under formula 1;

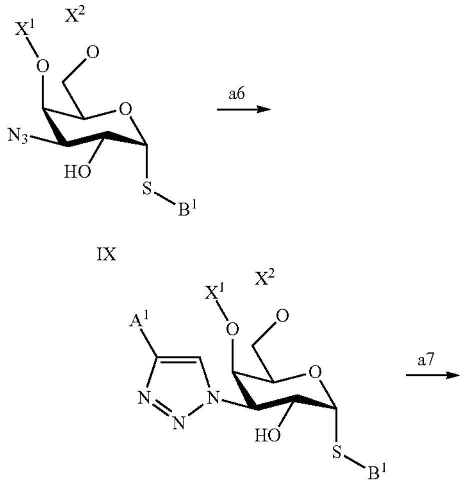

IX

X

-continued

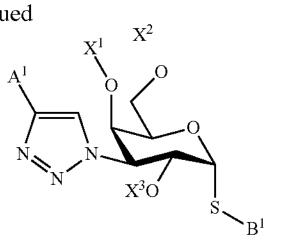

VIII a6) Reacting the compound of formula IX with a compound of formula $A^1$-CC—H or $A^1$-CC-TMS in an inert solvent, such as DMF or acetonitrile, using a base, such as diisopropylethylamine or L-ascorbic acid sodium salt, catalyzed by a cupper salt such as CuI or copper (II) sulfate, optionally using a reagent such as CsF to provide a compound of the formula X.

a7) Reacting a compound of formula X with a compound of formula $X^3$-$L^1$, where $X^3$ taken together with O is $OX^3$, which is selected from c) under the definition of R1 above under formula 1 and $L^1$ is defined as a leaving groups such as a halide such as Cl, Br, I or a sulfate ester such as a mesylate, tosylate or triflate in an organic solvent such as DMF, optionally in the presence of a reagent such as NaH, $CsCO_3$ or AgO to provide a compound of the formula VIII.

In a still further aspect, the present invention relates to a process of preparing a compound of formula XII or a pharmaceutically acceptable salt or solvate thereof comprising the step a8 where $A^1$, $B^1$ and $R^1$ are defined as above under formula 1;

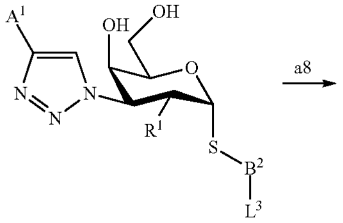

XI

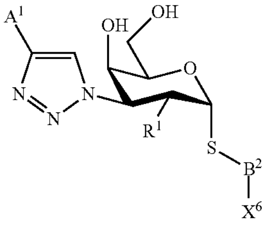

XII a8) Reacting a compound of formula XI wherein $B^2$ is selected from $B^1$ section b) and d) under formula 1 and $L^3$ is defined as a halide such as I, Br or Cl, with a metalorganic compound such $Zn(CN)_2$ in the presence of Zn and 1,1'-bis(diphenylphosphino)ferrocene and $Pd_2(dba)_3$ in a suitable organic solvent such as DMF optionally at elevated temperatures to give a compound XII wherein $X^6$ is defined as —CN; optionally a compound of formula XI defined as above is reacted with a borinane such as 2,4,6-trimethyl-1,3,5,2,4,6-trioxatriborinane in the presence of a metalorganic catalyst such as $Pd(PPh_4)_3$ and an inorganic base such as $K_2CO_3$ in a suitable solvent such as 1,4-dioxane optionally at elevated temperatures to give a compound of formula XII wherein $X^6$ is defined as methyl; optionally a compound of formula XI defined as above is reacted with a stannane such as tributyl(oxazol-2-yl)stannane or tributyl(thiazole-2-yl)stannane in the presence of an metalorganic catalyst such as $Pd(PPh_3)_4$, optionally in the presence CsF, optionally at elevated temperatures to give a compound of formula XII wherein $X^6$ is a five or six membered heteroaromatic ring optionally substituted; optionally a compound of formula XI defined as above is reacted with a heterocyclic borinate, such as tert-butyl 4-(4,4,5,5-tetramethyl-1,3,2-dioxaborolan-2-yl)-3,6-dihydro-2H-pyridine-1-carboxylate in the presence of a catalyst such as bis(triphenylphosphine)palladium(II) chloride optionally in the presence of base such as potassium carbonate, optionally in the presence of water in an organic solvent such as 1,4 dioxane, optionally at elevated temperatures. to give a compound of formula XII wherein $X^6$ is defined as a five or six membered heteroaromatic ring or a heterocyclic ring; optionally a compound of formula XI could be reacted with an alkyne or protected alkyne such as ethynyl(trimethyl)silane in the presence of one or more metalorganic reagents such as CuI, bis(triphenylphosphine) palladium (II) chloride in an inert solvent such as THF. Optionally in the presence of an organic base such as triethylamine or DIPEA. Optionally at elevated temperatures such as 30-80° C. If the alkyne reagent was protected with a silyl protective group such as trimethylsilane the protective group could be removed by addition of a reagent such as TBAF or KF in a consecutive step.

In a still further aspect, the present invention relates to a process of preparing a compound of formula III or a pharmaceutically acceptable salt or solvate thereof comprising the step a9-a10 where $A^1$ is defined as above under formula 1 and $X^7$ and $X^8$ are optionally and independently selected from hydrogen and acetate;

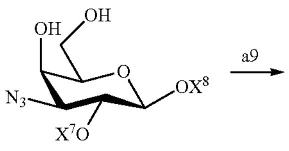

XIII

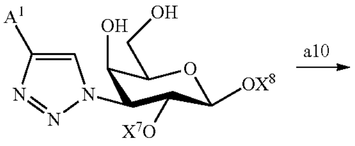

XIV

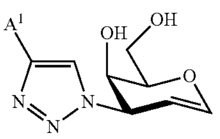

III a9) Reacting the compound of formula XIII with a compound of formula $A^1$-CC—H or $A^1$-CC-TMS in an inert solvent, such as DMF or acetonitrile, using a base, such as diisopropylethylamine or L-ascorbic acid sodium salt, catalyzed by a cupper salt such as CuI or copper (II) sulfate, optionally using a reagent such as CsF to provide a compound of the formula XIV.

a10) Reacting a compound of formula XIV with and acid such as HBr and acetic acid in an inert solvent such as DCM over 0-10 h after which the product is isolated and reacted further in the presence of ammonium chloride and Zinc in a solvent such as acetonitrile over 3-7 days to give a compound of formula III.

In a still further aspect, the present invention relates to a process of preparing a compound of formula XIX or a pharmaceutically acceptable salt or solvate thereof comprising the step a11-a14 where $A^1$ and $B^1$ is defined as above under formula 1;

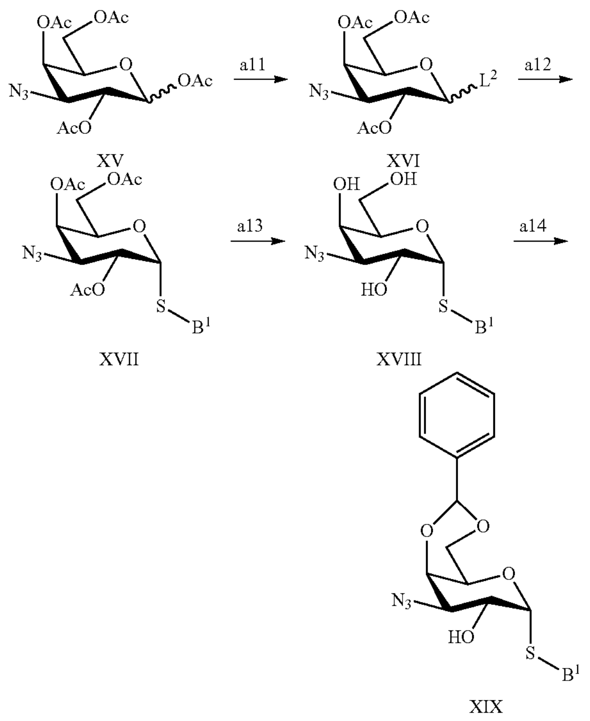

XV XVI XVII XVIII XIX a11) Reacting a compound XV with a chlorinating reagent such as dichloromethylmethylether or $PCl_5$ in the presence of a lewis acid such as $BF_3$ $Et_2O$ in an inert solvent such as dichloromethane or chloroform to give a compound of formula XVI wherein $L^2$ is defined as a chlorine.

a12) Reacting a compound of the formula VII with a nucleophile like the compound of formula HS-$B^1$ in the presence of a base like sodium hydride in an inert solvent such as DMF to give a compound of formula IX.

a13) Reacting a compound of formula XVII in the presence of a base, such as triethylamine, sodium hydroxide or sodium methoxide in an organic solvent, such as methanol, optionally in the presence of water followed by neutralization using an acid, such as HCl, to give a compound to formula XVIII.

a14) Reacting a compound of formula XVIII with a reagent such as benzaldehyde dimethyl acetal in the presence of an acid such as D(+)-10-Camphorsulfonic acid, in an inert solvent such as DMF For toluene optionally at elevated temperature and optionally at reduced pressure distilling off methanol to give a compound of formula XIX.

In a still further aspect, the present invention relates to a process of preparing a compound of formula VI or a pharmaceutically acceptable salt or solvate thereof comprising the step a15-a20 where $A^1$ and $B^1$ is defined as above under formula 1, $X^9$ and $X^{10}$ are optionally and independently selected from hydrogen and acetate or together form a protective group such as benzylidene;

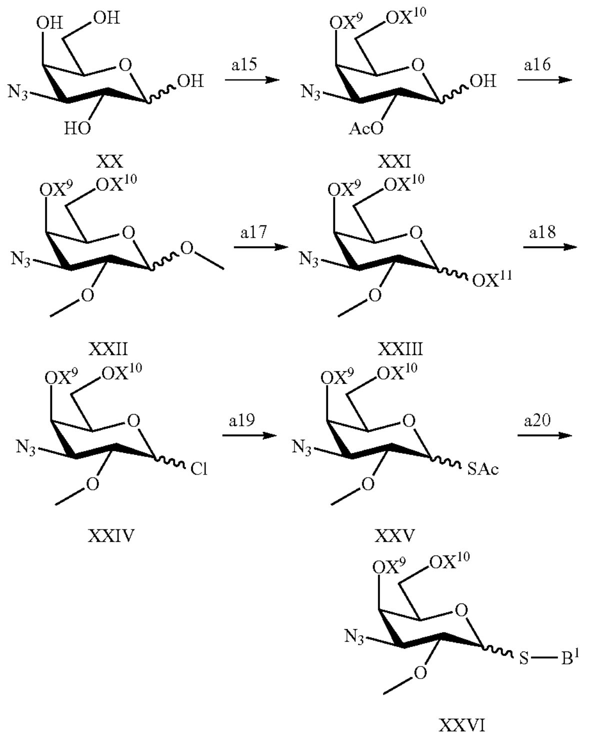

XX XXI XXII XXIII XXIV XXV XXVI a15) Reacting a compound of formula XX with a reagent such as benzaldehyde dimethyl acetal in the presence of an acid such as D(+)-10-Camphorsulfonic acid, in an inert solvent such as DMF or toluene, optionally at elevated temperatures and optionally at reduced pressure distilling off methanol to give a compound of formula XXI wherein $X^9$ and $X^{10}$ together form a benzylidene.

a16) Reacting a compound of formula XXI with a methylating reagent such as methyl iodide in the presence of a base such as sodium hydride in an inert solvent such as DMF to give a compound of formula XXII.

a17) Reacting a compound of formula XXII with acetic anhydride in the presence of an acid such as $H_2SO_4$ to give a compound of formula XXIII wherein $X^9$-$X^{11}$ are defined as acetate.

a18) Reacting a compound XXIII with a chlorinating reagent such as dichloromethylmethylether or $PCl_5$ in the presence of a lewis acid such as $BF_3$ $Et_2O$ in an inert solvent such as dichloromethane or chloroform to give a compound of formula XXIV.

a19) Reacting a compound of the formula XXIV with a thioacetate salt such as potassium thioacetate in an inert solvent such as DMF to give a compound of the formula XXV.

a20) Reacting a compound of formula XXV with a compound such as $B^1$-$L^4$, wherein $L^4$ is defined as a leaving group such as fluoride or a sulfate ester such as a triflate in the presence of a base such as diethylamine in an inert solvent such as DMF to give a compound of formula XXVI.

In a still further aspect the present invention relates to a process of preparing a compound of formula $A^1$-CC—H or $A^1$-CC-TMS comprising the step a20 wherein $A^1$ is defined as above under formula (1):

a21) Reacting a compound of formula $A^1$-$L^5$ wherein $L^5$ is defined as a leaving group such as chlorine or bromine with trimethylsilane-acetylene using a palladium catalyst such as bis(triphenylphosphine)palladium-(II)-chloride, copper iodide and a base like diisopropylethylamine in an inert solvent, such as tetrahydrofuran THF, to give a compound of the formula $A^1$-CC—H or $A^1$-CC-TMS.

In a still further aspect the present invention relates to a process of preparing a compound of formula XXVII comprising the step a22-a23:

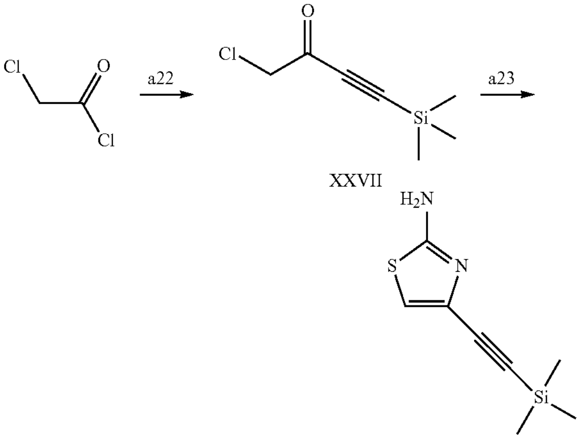

XXVII

XXVIII a22) Reacting chloro acetylchloride with trimethyl(2-trimethylsilylethynyl)silane in the presence of $AlCl_3$ in an inert solvent such as DCM to give XXVII.
a23) Reacting a compound of formula XXVII with thiourea in an inert solvent such as DMF to give a compound of formula XXVIII.

In a still further aspect the present invention relates to a process of preparing a compound of the formula XXXI comprising step a24-a25, wherein $B^1$ is defined as above under formula (1);

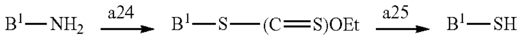

XXIX XXX XXXI a24) A compound of the formula XXIX could upon treatment with sodium nitrite form the corresponding diazocompound. This compound could be further reacted with a sulfurus source such as potassium ethyl xantogenate to form a compound of the formula XXX.
a25) Reacting a compound of formula XXX with a base such as potassium hydroxide to give a compound of formula XXXI.

In a still further aspect the present invention relates to a process of preparing a compound of the formula XXXIII comprising step a26, wherein $B^1$ is defined as above under formula (1);

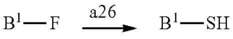

XXXII XXXIII a25) Reacting a compound of the formula XXXII with $Na_2S.10H_2O$ in the presence of a base such as NaOH in an inert solvent such as DMF to give a compound of formula XXXIII.

In a still further aspect the present invention relates to a process of preparing a compound of the formula XXXVII comprising step a27-a29, wherein $B^1$ is defined as above under formula (1);

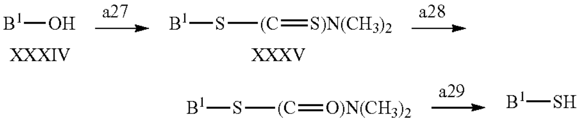

XXXIV XXXV XXXVI XXXVII a27) Reacting a compound of the formula XXXIV with an activated thioamide such as dimethylcarbamoyl chloride using a base such as sodium hydride in an inert solvent such as DMF to give a compound of formula XXXV.

a28) Heating a compound of the formula XXXV at elevated temperatures to form compound XXXVI.

a29) Reacting a compound of formula XXXVI with a base such as potassium hydroxide to give a compound of the formula XXXVII.

In a still further aspect the present invention relates to a process of preparing a compound of the formula XXXIX comprising step a30, wherein $B^1$ is defined as above under formula (1);

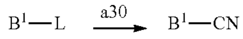

XXXVIII XXXIX a30) Reacting a compound of the formula XXXVIII, wherein L is a leaving group such as Bromine, with CuCN in an inert solvent such as dimethylformamide, optionally at elevated temperatures, to give a compound of formula XXXIX.

In a still further aspect the present invention relates to a process of preparing a compound of the formula XLI comprising step a31, wherein $B^1$ is defined as above under formula (1);

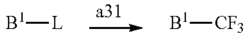

XL XLI a31) Reacting a compound of the formula XL, wherein $B^1$ is defined as above and L is a leaving group such as Iodine, with KF and CuI, optionally at elevated temperatures to give an intermediate which is further reacted with trimethyl (trifluoromethyl)silane to give an intermediate which is dissolved in an inert solvent such as 1-Methyl-2-pyrrolidinone (NMP) and added 3,5-dichloro-2-iodopyridine to give a compound of formula XLI.

In a still further aspect the present invention relates to a process of preparing a compound of formula V wherein $B^1$ and $R^1$ is defined as for formula 1 or a pharmaceutically acceptable salt or solvate thereof comprising the steps a31 and a32;

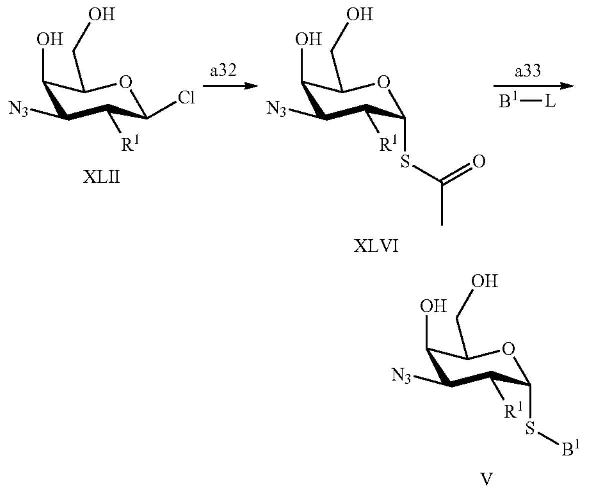

XLII XLVI V

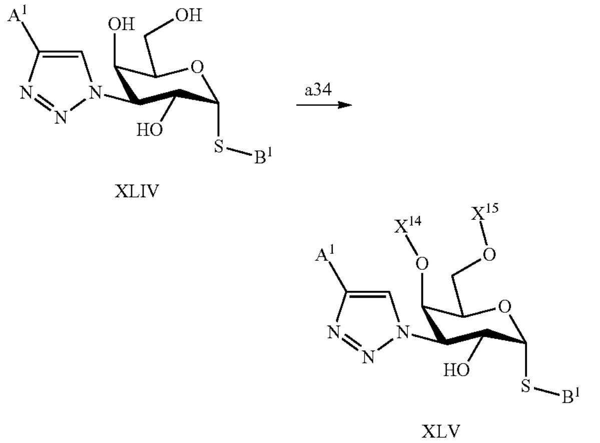

XLIV XLV a32) Reacting a compound of formula XLII with a sulfurus nucleophile such as potassium thioacetate to give compound XLVI in an inert solvent such as DMF.

a33) Reacting a compound of the formula XLVI with a compound of the formula $B^1$-L, wherein L is defined as a leaving group such as fluorine, chlorine or bromine, in an inert solvent as DMF using a base such as dimethylamine to give a compound of the formula V.

In a still further aspect the present invention relates to a process of preparing a compound of the formula XLIV comprising the step a34 wherein $A^1$ and $B^1$ is defined as for formula 1;

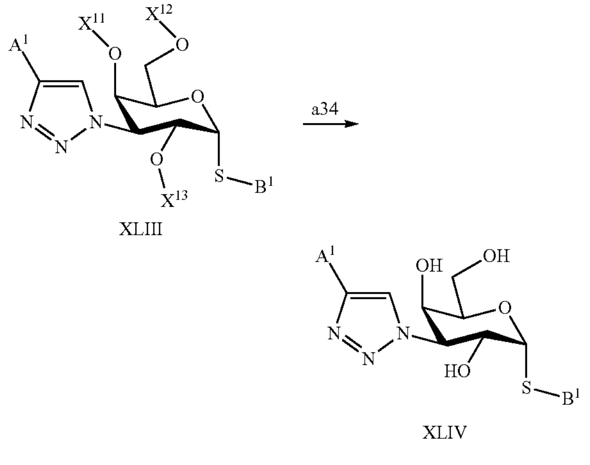

XLIII XLIV a34) reacting a compound of formula XLIII wherein $X^{11-13}$ are protective groups, such as acetates, in the presence of a base, such as triethylamine, sodium hydroxide or sodium methoxide in an organic solvent, such as methanol, optionally in the presence of water followed by neutralization using an acid, such as HCl, to give a compound to formula XLIV.

In a still further aspect the present invention relates to a process of preparing a compound of formula XLV wherein $A^1$ and $B^1$ is defined as for formula 1 or a pharmaceutically acceptable salt or solvate thereof comprising the step a35;

a35) Reacting a compound of formula XLIV with a reagent such as benzaldehyde dimethyl acetal in the presence of an acid such as D(+)-10-Camphorsulfonic acido r p-toluenesulphonic acid, in an inert solvent such as DMF or toluene, optionally at elevated temperatures and optionally at reduced pressure distilling off methanol to give a compound of formula XLV wherein $X^{14}$ and $X^{15}$ together form a benzylidene.

In a still further aspect the present invention relates to a process of preparing a compound of formula XLVII wherein $A^1$ is defined as for the compound of formula 1 and $B^3$ is selected from $B^1$ section b) and d) under the compound of formula 1 wherein $X^{17}$ is defined as —$CONR^6R^7$ or —$CONR^{12}R^{13}$ wherein $R^6$, $R^7$, $R^{12}$ and $R^{13}$ is defined as for the compound of formula 1, methyl, heterocycle, —CN, ethynyl, spiroheterocycle, $CONH_2$, COOH, —$SCH_3$, —$COOCH_3$ comprising the step a36;

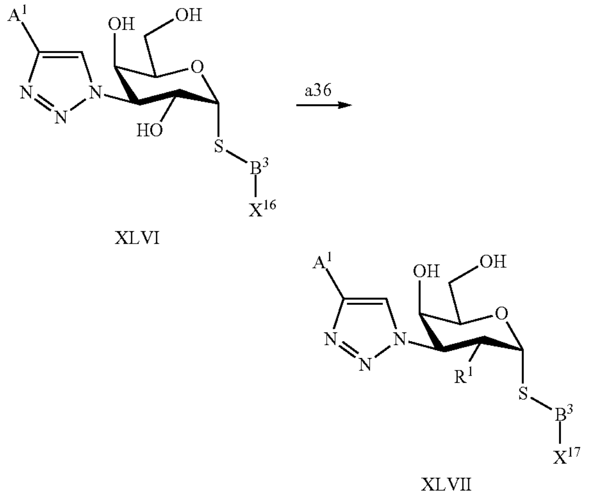

XLVI XLVII a36) Reacting a compound of formula XLVI wherein $X^{16}$ is defined as —COOH with a an amine reagent such as $HNR^6R^7$ or $HNR^{12}R^{13}$ in the presence of an amide coupling reagent such as HATU optionally in the presence of an organic base such as DIPEA in an inert solvent such as DMF to give a compound formula XLVII wherein $X^{17}$ is defined as —$CONR^6R^7$ or $CONR^{12}R^{13}$; optionally reacting a compound of formula XLVI wherein $X^{16}$ is a halide such as I, Br and Cl with an heterocyclic borinane such as 2,4,6-trimethyl-1,3,5,2,4,6-trioxatriborinane, in the presence of $Pd(PPh_4)_3$, $K_2CO_3$ in an inert solvent such as dioxane optionally at elevated temperature and optionally under an inert atmosphere to give a compound formula XLVII wherein $X^{17}$ is defined as a methyl; optionally reacting a compound of formula XLVI wherein $X^{16}$ is a halide such as I, Br and Cl with a heterocyclic dioxaborolane such as 5-(4,4,5,5-tetramethyl-1,3,2-dioxaborolan-2-yl)pyrimidine, 4-(4,4,5,5-tetramethyl-1,3,2-dioxaborolan-2-yl)pyridine, tert-butyl 4-(4,4,5,5-tetramethyl-1,3,2-dioxaborolan-2-yl)-3,6-dihydro-2H-pyridine-1-carboxylate in an inert solvent such as 1,4-dioxane/water using a metalorganic reagent such as bis(triphenylphosphine)palladium(II) chloride and a base such as $K_2CO_3$ to give a compound formula XLVII wherein $X^{17}$ is defined as an heterocycle optionally heating to 100° C. for 1 h in microwave reactor; optionally reacting a compound of formula XLVI wherein $X^{16}$ is a halide such as I, Br and Cl with an heterocyclic boronic acid such as 3-pyridylboronic acid in an inert solvent such as DMF using a metalloorganic reagent such as bis(triphenylphosphine) palladium(II) chloride and a base such as $K_2CO_3$ at room temperature to give a compound formula XLVII wherein $X^{17}$ is defined as an heterocycle; optionally reacting a compound of formula XLVI wherein $X^{16}$ is a halide such as I, Br and Cl with a heterocyclic stannane such as tributyl-(2-pyridyl)stannane, tributyl(oxazol-2-yl)stannane, tributyl (thiazole-2-yl)stannane in an inert solvent such as DMF using a metalloorganic reagent such as bis(triphenylphosphine)palladium(II) chloride or palladium tetrakis optionally with CsF at room temperature or elevated temperatures to give a compound formula XLVII wherein $X^{17}$ is defined as an heterocycle; optionally reacting a compound of formula XLVI wherein $X^{16}$ is a halide such as I, Br and Cl with a metallocyanoreagent such as $Zn(CN)_2$ in an inert solvent such as DMF using a metalloorganic reagent such as $Pd_2$ (dibenzylideneacetone) and Zn at elevated temperatures to give a compound formula XLVII wherein $X^{17}$ is defined as a —CN; optionally reacting a compound of formula XLVI wherein $X^{16}$ is a halide such as I, Br and Cl with ethynyl or TMS-ethynyl in the presence of metallorganic reagents such as bis(triphenylphosphine)palladium (II) chloride and CuI in the presence of an organic base in an inert solvent as DMF optionally at elevated temperature to give a compound formula XLVII wherein $X^{17}$ is defined as an ethynyl; optionally reacting a compound of formula XLVI wherein $X^{16}$ is a halide such as I, Br and Cl with a heterocycle or spiro heterocycle such as a spiro heterocycle, such as N-(2-oxa)-6-azaspiro[3.3]heptanyl using an organic base such as DIPEA in a n inert solvent such as DMF at elevated temperatures such as 130° C. in a microwave reactor to give a compound formula XLVII wherein $X^{17}$ is defined as an heterocycle or a spirocycle; optionally reacting a compound of formula XLVI wherein $X^{16}$ is a cyanogroup could be reacted with a base such as sodium hydroxide at elevated temperatures in a solvent such as ethanol and water to give a compound of formula XLVII wherein $X^{17}$ is —COOH; Optionally reacting a compound of formula XLVI wherein $X^{16}$ is a —$COOX^{22}$ and $X^{22}$ is defined as an aryl or a straight or branched c1-c5 alkyl optionally substituted with an aryl, with a base such as lithium hydroxide or sodium hydroxide at elevated temperatures in water optionally mixed with another organic solvent such as ethanol or acetonitrile to give a compound of formula XLVII wherein $X^{17}$ is —COOH; optionally reacting a compound of formula XLVI wherein $X^{16}$ is a halide such as I, Br and Cl with an alkyl thiol nucleophile such as sodium thiomethoxide in a solvent such as DMF to give a compound of formula XLVII wherein $X^{17}$ is —$SCH_3$; optionally reacting a compound of formula XLVI wherein $X^{16}$ is COOH with an alkyl halide such as methyliodide in a solvent such as DMF in the presence of a base such as $CsCO_3$ to give a compound of formula XLVII wherein $X^{17}$ is —$COOCH_3$ In a still further aspect the present invention relates to a process of preparing a compound of formula XLIX wherein $B^4$ is selected from $B^1$ section b) and d) under formula 1 wherein $X^{17}$ is defined as —$CONR^6R^7$ or —$CONR^{12}R^{13}$ wherein $R^6$, $R^7$, $R^{12}$ and $R^{13}$ is defined as for formula I, methyl, heterocycle, —CN, ethynyl, spiroheterocycle, $CONH_2$, COOH, —$SCH_3$, —$COOCH_3$ comprising the step a37;

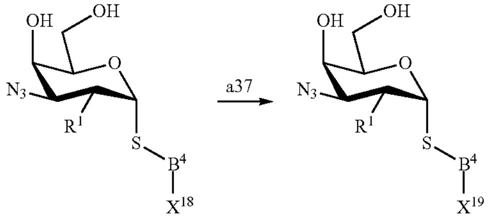

XLVIII XLIX a37) Reacting a compound of formula XLVIII wherein $X^{18}$ is defined as —COOH with a an amine reagent such as $HNR^6R^7$ or $HNR^{12}R^{13}$ in the presence of an amide coupling reagent such as HATU optionally in the presence of an organic base such as DIPEA in an inert solvent such as DMF to give a compound formula XLIX wherein $X^{19}$ is defined as —$CONR^6R^7$ or $CONR^{12}R^{13}$; optionally reacting a compound of formula XLVIII wherein $X^{18}$ is a halide such as I, Br and Cl with an heterocyclic borinane such as 2,4,6-trimethyl-1,3,5,2,4,6-trioxatriborinane, in the presence of $Pd(PPh_4)_3$, $K_2CO_3$ in an inert solvent such as dioxane optionally at elevated temperature and optionally under an inert atmosphere to give a compound formula XLIX wherein $X^{19}$ is defined as a methyl; optionally reacting a compound of formula XLVIII wherein $X^{18}$ is a halide such as I, Br and Cl with a heterocyclic dioxaborolane such as 5-(4,4,5,5-tetramethyl-1,3,2-dioxaborolan-2-yl)pyrimidine, 4-(4,4,5,5-tetramethyl-1,3,2-dioxaborolan-2-yl)pyridine, tert-butyl 4-(4,4,5,5-tetramethyl-1,3,2-dioxaborolan-2-yl)-3,6-dihydro-2H-pyridine-1-carboxylate in an inert solvent such as 1,4-dioxane/water using a metalloorganic reagent such as bis(triphenylphosphine)palladium(II) chloride and a base such as $K_2CO_3$ to give a compound formula XLIX wherein $X^{19}$ is defined as an heterocycle optionally heating to 100° C. for 1 h in microwave reactor; optionally reacting a compound of formula XLVIII wherein $X^{18}$ is a halide such as I, Br and Cl with an heterocyclic boronic acid such as 3-pyridylboronic acid in an inert solvent such as DMF using a metalloorganic reagent such as bis(triphenylphosphine) palladium(II) chloride and a base such as $K_2CO_3$ at room temperature to give a compound formula XLIX wherein $X^{19}$ is defined as an heterocycle; optionally reacting a compound of formula XLVIII wherein $X^{18}$ is a halide such as I, Br and Cl with a heterocyclic stannane such as tributyl-(2-pyridyl) stannane, tributyl(oxazol-2-yl)stannane, tributyl(thiazole-2-yl)stannane in an inert solvent such as DMF using a metalloorganic reagent such as bis(triphenylphosphine) palladium(II) chloride or palladium tetrakis optionally with CsF at room temperature or elevated temperatures to give a compound formula XLIX wherein $X^{19}$ is defined as an heterocycle; optionally reacting a compound of formula XLVIII wherein $X^{18}$ is a halide such as I, Br and Cl with a metallocyanoreagent such as $Zn(CN)_2$ in an inert solvent such as DMF using a metalloorganic reagent such as $Pd_2$ (dibenzylideneacetone) and Zn at elevated temperatures to give a compound formula XLIX wherein $X^{19}$ is defined as a —CN; optionally reacting a compound of formula XLVIII wherein $X^{18}$ is a halide such as I, Br and Cl with ethynyl or TMS-ethynyl in the presence of metallorganic reagents such as bis(triphenylphosphine)palladium (II) chloride and CuI in the presence of an organic base in an inert solvent as DMF optionally at elevated temperature to give a compound formula XLIX wherein $X^{19}$ is defined as an ethynyl; optionally reacting a compound of formula XLVIII wherein $X^{18}$ is a halide such as I, Br and Cl with a heterocycle or spiro heterocycle such as a spiro heterocycle, such as N-(2-oxa)-6-azaspiro[3.3]heptanyl using an organic base such as DIPEA in a n inert solvent such as DMF at elevated temperatures such as 130° C. in a microwave reactor to give a compound formula XLIX wherein $X^{19}$ is defined as an heterocycle or a spirocycle; optionally reacting a compound of formula XLVIII wherein $X^{18}$ is a cyanogroup could be reacted with a base such as sodium hydroxide at elevated temperatures in a solvent such as ethanol and water to give a compound of formula XLIX wherein $X^{19}$ is —COOH; Optionally reacting a compound of formula XLVIII wherein $X^{18}$ is a —$COOX^{22}$ and $X^{22}$ is defined as an aryl or a straight or branched c1-c5 alkyl optionally substituted with an aryl, with a base such as lithium hydroxide or sodium hydroxide at elevated temperatures in water optionally mixed with another organic solvent such as ethanol or acetonitrile to give a compound of formula XLIX wherein $X^{19}$ is —COOH; optionally reacting a compound of formula XLVIII wherein $X^{18}$ is a halide such as I, Br and Cl with an alkyl thiol nucleophile such as sodium thiomethoxide in a solvent such as DMF to give a compound of formula XLIX wherein $X^{19}$ is —$SCH_3$; optionally reacting a compound of formula XLVIII wherein $X^{18}$ is COOH with an alkyl halide such as methyliodide in a solvent such as DMF in the presence of a base such as $CsCO_3$ to give a compound of formula XLIX wherein $X^{19}$ is —$COOCH_3$.

In a still further aspect the present invention relates to a process of preparing a compound of formula XLXII wherein $B^1$ is defined as under formula 1 and $X^{20}$ is defined as a protective group the steps a38-a39;

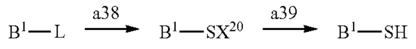

L LI LII a38) Reacting a compound of the formula L with a compound of the formula $X^{20}$—SH wherein $X^{20}$ is a protective group such as a benzyl group in the presence of a base such as DIPEA in an inert solvent such as dioxane at elevated temperatures to give a compound of formula LI; optionally reacting a compound of formula L with (2,4-dimethoxyphenyl)methanethiol in the presence of a metalloorganic ligand such as bis(dibenzylideneacetone)palladium optionally in the presence of a ligand such as 4,5-bis(diphenylphosphino)-9,9-dimethylxanthene to give a compound of the formula LI.

a39) reacting a compound of formula LI with $AlCl_3$ in a solvent such as toluene to give a compound of the formula LII; optionally reacting a compound of the formula LI in the presence of TFA and triethyl silane to give a compound of formula LII.

In a still further aspect the present invention relates to a process of preparing a compound of formula LIV wherein $B^5X^{22}$ is defined as $B^1$ under b) and d) formula 1;

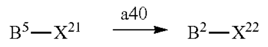

LIII LIV a40) Reacting a compound of the formula LIII wherein $X^{21}$ is defined as cyano with 2,2-dimethoxyethanamine in the presence of a strong base such as sodium methoxide followed by addition of an acid such as acetic acid to give a compound of formula LIV wherein $X^{22}$ is an imidazole.

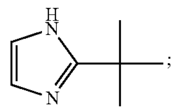;

optionally reacting a compound of the formula LIII wherein $X^{21}$ is defined as SH with a defined as 3,3-dimethyl-1-(trifluoromethyl)-1,2-benziodoxole in a solvent such as DCM to give a compound of formula LIV wherein $X^{22}$ is a $CF_3$.

In a still further aspect the present invention relates to a process of preparing a compound of formula $B^1$—$CH_3$ where $B^1$ is defined as for formula 1 under section b) and d) by reacting a compound $B^1$—Br with 2,4,6-trimethyl-1,3,5,2,4,6-trioxatriborinane in the presence of $Pd(PPh_4)_3$, $K_2CO_3$ in an inert solvent such as dioxane optionally at elevated temperature and optionally under an inert atmosphere.

In the above reaction steps a1 to a40 whenever a diastereoisomeric compound is made it can be separated by chromatography such as using HPLC. Furthermore, in above process steps a1 to a40 an anomeric Sulphur can be replaced by an O, SO, or $SO_2$ under similar reaction conditions to prepare analogs where S has been replaced.

DETAILED DESCRIPTION OF THE INVENTION

The present compounds of formula (1) differ from prior art compounds particularly in that the pyranose ring is α-D-galactopyranose. It is important to emphasize that alpha and beta anomers are very different isomers and it is by no means considered to be obvious to the skilled person to expect same or similar activity of both anomers. Consequently, alpha and beta anomers do not in general posses the same activity, and this is common knowledge to the skilled person. The compounds of the present invention are novel α-D-galactopyranose compounds that unexpectedly have shown very high affinity and specificity for galectin-1 and are considered novel potent drug candidates. Some of the novel α-D-galactopyranose compounds have both galectin-1 and galectin-3 affinity and, as such have a broader disease treatment profile compared to selective galectin-1 inhibitors.

In broad aspect the present invention concerns a D-galactopyranose compound of formula (1)

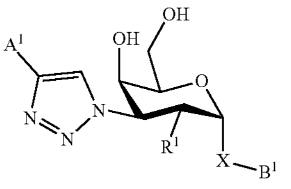

wherein the pyranose ring is α-D-galactopyranose, and A1, R1, X and B1 are as defined above.

When A1 is formula 2 it is preferably selected from

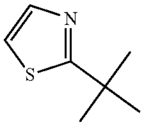,
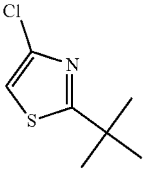
or
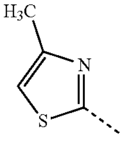

When A1 is

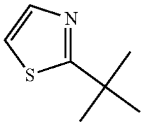

and X is S, then R1 is selected from $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen, and B1 is selected from a pyridinyl, optionally substituted with a group selected from a Cl, Br, CN; $C_2$-alkynyl; methyl; $CF_3$; pyridin; pyrimidin; oxazol; and thiazol; and a phenyl, optionally substituted with a group selected from a halogen, CN, —$CONR^6R^7$, wherein $R^6$ and $R^7$ are independently selected from H, $C_{1-3}$ alkyl, cyclopropyl, and iso-propyl, and $C_{1-3}$ alkyl, optionally substituted with a F. Preferably, $R^1$ is selected from methoxy, methoxy substituted with one phenyl and methoxy substituted with one phenyl substituted with one to three groups selected from OH and halogen, such as F and Cl. Preferably, B1 is selected from a pyridinyl substituted with a group selected from a Cl, Br, $C_2$-alkynyl, CN; and a phenyl substituted with a group selected from one to three halogen, such as selected from F, Br and/or Cl; CN, and $CONR^6R^7$, wherein $R^6$ and $R^7$ are independently selected from H and $C_{1-3}$ alkyl.

When A1 is

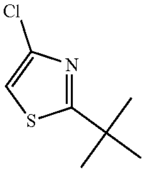

and X is S, then R1 is selected from H, OH, $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen, and B1 is selected from a pyridinyl, optionally substituted with a group selected from a Cl, Br, CN, $C_2$-alkynyl, methyl, $CF_3$, —$CONR^{12}R^{13}$, wherein $R^{12}$ and $R^{13}$ are independently selected from H, $C_{1-3}$ alkyl, cyclopropyl, and iso-propyl or $R^{12}$ and $R^{13}$ together with the nitrogen form a heterocycloalkyl; pyridin, pyrimidin, oxazol, and thiazol or a phenyl optionally substituted with a group selected from Br, Cl, CN and $CONR^6R^7$, wherein $R^6$ and $R^7$ are independently selected from H and $C_{1-3}$ alkyl. Preferably, R1 is selected from H, OH, methoxy or ethoxy, such as methoxy. Preferably B1 is selected from a pyridinyl substituted with a group selected from one to three substituents selected from Cl, $C_2$-alkynyl, methyl, Br, CO-azetidinyl, $CON(CH_3)_2$, $CONHCH_3$, $CONHCH_2CH_3$, pyridinyl, or CN. Preferably B1 is selected from a phenyl substituted with a group selected from one to three substituents selected from Br, Cl, CN and $CONHCH_3$.

When A1 is

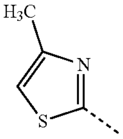

and X is S, then R1 is selected from $OC_{1-4}$ alkyl, such as O-methyl, O-ethyl, or O-isopropyl, $OC_{1-4}$ alkyl substituted with at least one from the group consisting of phenyl and phenyl substituted with one or more groups selected form OH and halogen, and B1 is selected from a pyridinyl, optionally substituted with a group selected from a Cl, Br, $C_2$-alkynyl, CN; methyl; $CF_3$; pyridin; pyrimidin; oxazol; and thiazol; and a phenyl, optionally substituted with a group selected from a halogen and $C_{1-3}$ alkyl, optionally substituted with a F. Preferably R1 is O-methyl. Preferably, B1 is pyridinyl substituted with a group selected from Cl, Br, CN; methyl; and pyridine. Preferably, B1 is phenyl substituted with a group selected from a halogen, such as F or Br.

When A1 is formula 3 it is preferably selected from

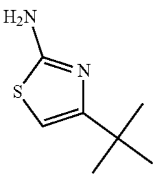,
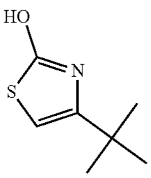
or
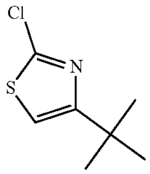.

When A1 is

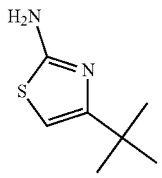

and X is S, then R1 is selected from H, OH, $OC_{1-4}$ alkyl, such as O-methyl, O-ethyl, or O-isopropyl, $OC_{1-4}$ alkyl optionally substituted with one or more halogen, or $OC_{1-4}$ alkyl substituted with at least one from the group consisting of phenyl and phenyl substituted with one or more groups selected from OH and halogen, and B1 is selected from a pyridinyl, optionally substituted with a group selected from a Cl; Br; $C_2$-alkynyl; CN; methyl; $CF_3$; pyridin; imidazol; pyrimidin; oxazol; tetrahydro bipyridin; a spiro heterocycle; and thiazol; and a phenyl, optionally substituted with a group selected from a halogen and $C_{1-3}$ alkyl, optionally substituted with a F. Preferably, R1 is selected from H, OH, methoxy, ethoxy, $OCH_2CF_3$, or methoxy substituted with one to three selected from the group consisting of phenyl and phenyl substituted with one to three groups selected from OH and halogen. Preferably B1 is selected from a pyridinyl, a pyridinyl substituted with one to three groups selected from Cl, Br, $C_2$-alkynyl; CN; methyl; $CF_3$; N-(2-oxa)-6-azaspiro[3.3]heptanyl; pyridin; imidazole; pyrimidin; oxazol; tetrahydro bipyridin; and thiazol. Preferably B1 is selected from a phenyl substituted with one to three groups selected from F, Cl, Br, CN and $C_{1-3}$ alkyl, optionally substituted with a F.

When A1 is

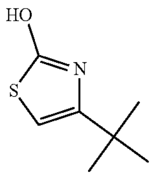

and X is S, then R1 is selected from H, OH, $OC_{1-4}$ alkyl, such as O-methyl, O-ethyl, or O-isopropyl, $OC_{1-4}$ alkyl substituted with a halogen, or $OC_{1-4}$ alkyl substituted with at least one from the group consisting of phenyl and phenyl substituted with one or more groups selected from OH and halogen, and B1 is selected from a pyridinyl, optionally substituted with a group selected from a Cl; Br; CN; $C_2$-alkynyl; methyl; $CF_3$; pyridin; imidazol; pyrimidin; oxazol; tetrahydro bipyridin; and thiazol; and a phenyl, optionally substituted with a group selected from a halogen, CN and $C_{1-3}$ alkyl, optionally substituted with a F. Preferably, R1 is selected from H, OH, methoxy, ethoxy, iso-propyloxy, or $OCH_2CF_3$. Preferably B1 is selected from a phenyl substituted with one to three groups selected from CN, Cl, Br or F. Preferably B1 is selected from a pyridin substituted with one to three groups selected from CN, Cl, and imidazol.

When A1 is

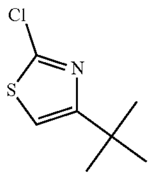

and X is S, then R1 is selected from $OC_{1-4}$ alkyl, such as O-methyl, O-ethyl, or O-isopropyl, or $OC_{1-4}$ alkyl substituted with at least one from the group consisting of phenyl and phenyl substituted with one or more groups selected from OH and halogen, and B1 is selected from a pyridinyl, optionally substituted with a group selected from a Cl, Br, CN; $C_2$-alkynyl; methyl; $CF_3$; pyridin; pyrimidin; oxazol; tetrahydro bipyridin; and thiazol. Preferably, R1 is selected from methoxy, ethoxy or isopropyloxy, such as methoxy. Preferably, B1 is selected from a pyridinyl, optionally substituted with one to three groups selected from a Cl, Br, CN.

When A1 is formula 2 and $R^2$ is a halogen, and $R^3$ is selected from the group consisting of $C_{1-6}$ alkyl and halogen, and X is S, then R1 is $OC_{1-4}$ alkyl, such as O-methyl, and B1 is pyridine substituted with a group selected from halogen and CN. In one embodiment A1 is formula 2 and $R^2$ is Cl, and $R^3$ is selected from the group consisting of methyl and halogen, In a further embodiment the compound of formula (1) is selected from any one of:

3,5-Dichloro-4-fluorophenyl 3-deoxy-2-O-methyl-3-[4-(2-thiazolyl)-1H-1,2,3-triazol-1-yl]-1-thio-α-D-galactopyranoside, 5-Bromopyridin-3-yl 3-deoxy-2-O-methyl-3-[4-(2-thiazolyl)-1H-1,2,3-triazol-1-yl]-1-thio-α-D-galactopyranoside, 5-Bromo-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 2-O-benzyl-3-deoxy-3-[4-(2-thiazolyl)-1H-1,2,3-triazol-1-yl]-1-thio-α-D-galactopyranoside, 5-Chloro-2-cyanopyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside, 3,5-Dichloro-4-fluorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 3-deoxy-3-[4-(2-hydroxythiazol-4-yl)-1H-1,2,3-triazol-1-yl]-2-O-isopropyl-1-thio-α-D-galactopyranoside, 3,4-Dichlorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 2,3-dideoxy-3-[4-(2-hydroxythiazol-4-yl)-1H-1,2,3-triazol-1-yl]-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Bromo-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Chloro-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(2-chlorothiazol-4-yl)-1H-1,2,3-triazol-1-yl]-3-deoxy-2-O-methyl-1-thio-α-D-galactopyranoside, 3,5-Dichloro-4-fluorophenyl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-2-O-benzyl-3-deoxy-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-(pyrimidin-5-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-4-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-3-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(1,2,3,6-tetrahydropyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-0-(3,5-difluoro-4-hydroxybenzyl)-1-thio-α-D-galactopyranoside, 5-Chloro-2-(pyridin-2-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(oxazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3,4-Dichlorphenyl 3-[4-(2-aminothiazol-4-yl)-1H-1,2,3-triazol-1-yl]-3-deoxy-2-O-methyl-1-thio-α-D-galactopyranoside, 5-Chloro-2-(thiazol-2-yl)pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-(trifluoromethyl)phenyl 3-[4-(2-aminothiazol-4-yl)-1H-1,2,3-triazol-1-yl]-3-deoxy-2-O-methyl-1-thio-α-D-galactopyranoside, 3-Chlorophenyl 3-[4-(2-aminothiazol-4-yl)-1H-1,2,3-triazol-1-yl]-3-deoxy-2-O-methyl-1-thio-α-D-galactopyranoside, 3,5-Dichloro-4-fluorophenyl 3-[4-(2-aminothiazol-4-yl)-1H-1,2,3-triazol-1-yl]-3-deoxy-1-thio-α-D-galactopyranoside, 3-Bromo-2-trifluoromethylpyridin-5-yl 3-[4-(2-aminothiazol-4-yl)-1H-1,2,3-triazol-1-yl]-3-deoxy-1-thio-α-D-galactopyranoside, 5-Bromo-2-cyanopyridin-3-yl 3-deoxy-3-[4-(4-methylthiazol-2-yl)-1H-1,2,3-triazol-1-yl]-2-O-methyl-1-thio-α-D-galactopyranoside, 2-Cyano-5-methylpyridin-3-yl 3-deoxy-3-[4-(4-methyltriazol-2-yl)-1H-1,2,3-thiazol-1-yl]-2-O-methyl-1-thio-α-D-galactopyranoside, 2-Cyano-5-methylpyridin-3-yl 3-[4-(4-chlorothiazol-2-yl)-1H-1,2,3-triazol-1-yl]-3-deoxy-2-O-methyl-1-thio-α-D-galactopyranoside, 5-Ethynylpyridin-3-yl 3-[4-(4-chlorothiazol-2-yl)-1H-1,2,3-triazol-1-yl]-3-deoxy-2-O-methyl-1-thio-α-D-galactopyranoside, 5-Chloro-2-{N-(2-oxa)-6-azaspiro[3.3]heptanyl}-pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-cyanophenyl 3-[4-(2-aminothiazol-4-yl)-1H-1,2,3-triazol-1-yl]-3-deoxy-2-O-methyl-1-thio-α-D-galactopyranoside, 5-Cyanopyridin-3yl 3-[4-(2-aminothiazol-4-yl)-1H-1,2,3-triazol-1-yl]-3-deoxy-2-O-methyl-1-thio-α-D-galactopyranoside, 3,5-Dichloro-4-fluorophenyl 2,3-dideoxy-3-[4-(2-hydroxythiazol-4-yl)-1H-1,2,3-triazol-1-yl]-1-thio-α-D-galactopyranoside, 3-Chloro-4-cyanophenyl 3-[4-(2-aminothiazol-4-yl)-1H-1,2,3-triazol-1-yl]-2,3-dideoxy-1-thio-α-D-galactopyranoside, 5-Chloro-2-cyanophenyl 3-[4-(4-chlorothiazol-2-yl)-1H-1,2,3-triazol-1-yl]-2,3-dideoxy-1-thio-α-D-galactopyranoside, 3-Cyano-2-(trifluoromethyl)pyridin-5-yl 3-[4-(2-aminothiazol-4-yl)-1H-1,2,3-triazol-1-yl]-3-deoxy-2-O-methyl-1-thio-α-D-galactopyranoside, 5-Chloro-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(pyridin-2-yl)-pyridin-3-yl 3-deoxy-3-[4-(4-methylthiazol-2-yl)-1H-1,2,3-triazol-1-yl]-2-O-methyl-1-thio-α-D-galactopyranoside, 5-Ethynylpyridin-3-yl 3-deoxy-2-O-methyl-3-[4-(2-thiazolyl)-1H-1,2,3-triazol-1-yl]-1-thio-α-D-galactopyranoside, 5-Chloropyridin-3-yl 3-[4-(4-chlorothiazol-2-yl)-1H-1,2,3-triazol-1-yl]-3-deoxy-1-thio-α-D-galactopyranoside, 5-Bromopyridin-3-yl 3-[4-(4-chlorothiazol-2-yl)-1H-1,2,3-triazol-1-yl]-3-deoxy-1-thio-α-D-galactopyranoside, 5-Chloro-2-cyanophenyl 3-[4-(4-chlorothiazol-2-yl)-1H-1,2,3-triazol-1-yl]-3-deoxy-1-thio-α-D-galactopyranoside, 3-Chloro-5-cyanophenyl 3-[4-(4-chlorothiazol-2-yl)-1H-1,2,3-triazol-1-yl]-3-deoxy-1-thio-α-D-galactopyranoside, 3-Chloro-4-cyanophenyl 3-[4-(4-chlorothiazol-2-yl)-1H-1,2,3-triazol-1-yl]-3-deoxy-1-thio-α-D-galactopyranoside, 5-Chloropyridin-3-yl 3-[4-(4-chlorothiazol-2-yl)-1H-1,2,3-triazol-1-yl]-3-deoxy-2-O-methyl-1-thio-α-D-galactopyranoside, 5-Bromopyridin-3-yl 3-[4-(4-chlorothiazol-2-yl)-1H-1,2,3-triazol-1-yl]-3-deoxy-2-O-methyl-1-thio-α-D-galactopyranoside, 5-Bromo-2-cyanopyridin-3-yl 3-[4-(4,5-dichlorothiazol-2-yl)-1H-1,2,3-triazol-1-yl]-3-deoxy-2-O-methyl-1-thio-α-D-galactopyranoside, 5-Bromo-2-cyanophenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-[4-(4-chlorothiazol-2-yl)-1H-1,2,3-triazol-1-yl]-3-deoxy-2-O-methyl-1-thio-α-D-galactopyranoside, 5-Bromo-2-cyanophenyl 3-deoxy-3-[4-(2-hydroxythiazol-4-yl)-1H-1,2,3-triazol-1-yl]-2-O-methyl-1-thio-α-D-galactopyranoside, 5-Bromo-2-cyanophenyl 3-[4-(2-aminothiazol-4-yl)-1H-1,2,3-triazol-1-yl]-3-deoxy-2-O-methyl-1-thio-α-D-galactopyranoside, 5-Bromo-2-(N-methyl-carbonyl)phenyl 3-[4-(4-chlorothiazol-2-yl)-1H-1,2,3-triazol-1-yl]-3-deoxy-2-O-methyl-1-thio-α-D-galactopyranoside, 5-Bromo-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Chloro-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-deoxy-3-[4-(4-methylthiazol-2-yl)-1H-1,2,3-triazol-1-yl]-2-O-methyl-1-thio-α-D-galactopyranoside, 5-Bromo-2-cyanopyridin-3-yl 3-[4-(5-chloro-4-methylthiazol-2-yl)-1H-1,2,3-triazol-1-yl]-3-deoxy-2-O-methyl-1-thio-α-D-galactopyranoside, 5-Bromo-2-cyanophenyl 3-[4-(5-chloro-4-methylthiazol-2-yl)-1H-1,2,3-triazol-1-yl]-3-deoxy-2-O-methyl-1-thio-α-D-galactopyranoside, 2,5-Dichlorophenyl 3-deoxy-2-O-methyl-3-[4-(2-thiazolyl)-1H-1,2,3-triazol-1-yl]-1-thio-α-D-galactopyranoside, 5-Bromo-2-chlorophenyl 3-deoxy-2-O-methyl-3-[4-(2-thiazolyl)-1H-1,2,3-triazol-1-yl]-1-thio-α-D-galactopyranoside, 5-Chloro-2-fluorophenyl 3-deoxy-2-O-methyl-3-[4-(2-thiazolyl)-1H-1,2,3-triazol-1-yl]-1-thio-α-D-galactopyranoside, 5-Bromo-2-fluorophenyl 3-deoxy-3-[4-(4-methylthiazol-2-yl)-1H-1,2,3-triazol-1-yl]-2-O-methyl-1-thio-α-D-galactopyranoside, 5-Chloro-2-cyanopyridin-3-yl 3-[4-(4-chlorothiazol-2-yl)-1H-1,2,3-triazol-1-yl]-3-deoxy-1-thio-α-D-galactopyranoside, 5-Chloro-2-cyanopyridin-3-yl 3-deoxy-2-O-ethyl-3-[4-(2-thiazolyl)-1H-1,2,3-triazol-1-yl]-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(1H-imidazol-2-yl)pyridin-3-yl 3-[4-(2-aminothiazol-4-yl)-1H-1,2,3-triazol-1-yl]-3-deoxy-1-thio-α-D-galactopyranoside, 5-Chloro-2-(1H-imidazol-2-yl)pyridin-3-yl 3-deoxy-3-[4-(2-hydroxythiazol-4-yl)-1H-1,2,3-triazol-1-yl]-1-thio-α-D-galactopyranoside, 5-Chloro-2-(pyridin-2-yl)pyridin-3-yl 3-[4-(4-chlorothiazol-2-yl)-1H-1,2,3-triazol-1-yl]-3-deoxy-2-O-methyl-1-thio-α-D-galactopyranoside, 2-Cyano-5-methylpyridin-3-yl 3-[4-(4-chlorothiazol-2-yl)-1H-1,2,3-triazol-1-yl]-3-deoxy-1-thio-α-D-galactopyranoside, 3,4-Dichlorophenyl 3-[4-(2-aminothiazol-4-yl)-1H-1,2,3-triazol-1-yl]-3-deoxy-2-O-(2,2,2-trifluoroethyl)-1-thio-α-D-galactopyranoside, 3,4-Dichlorophenyl 3-deoxy-2-O-(2,2,2-trifluoroethyl)-3-[4-(2-hydroxythiazol-4-yl)-1H-1,2,3-triazol-1-yl]-1-thio-α-D-galactopyranoside, 5-Ethynylpyridin-3-yl 3-[4-(4-chlorothiazol-2-yl)-1H-1,2,3-triazol-1-yl]-3-deoxy-1-thio-α-D-galactopyranoside, 5-Ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Cyanopyridin-3-yl 3-[4-(4-chlorothiazol-2-yl)-1H-1,2,3-triazol-1-yl]-3-deoxy-2-O-methyl-1-thio-α-D-galactopyranoside, 5-Cyanopyridin-3-yl 3-deoxy-3-[4-(2-hydroxythiazol-4-yl)-1H-1,2,3-triazol-1-yl]-2-O-methyl-1-thio-α-D-galactopyranoside, 2-Cyano-5-ethynylpyridin-3-yl 3-[4-(2-aminothiazol-4-yl)-1H-1,2,3-triazol-1-yl]-3-deoxy-1-thio-α-D-galactopyranoside, 2-Cyano-5-ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-ethyl-1-thio-α-D-galactopyranoside, 3,4-Dichlorophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 2,3-dideoxy-3-[4-(2-hydroxythiazol-4-yl)-1H-1,2,3-triazol-1-yl]-1-thio-α-D-galactopyranoside, 5-Bromo-2-(N,N-dimethylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside, 5-Ethynyl-2-(N,N-dimethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Ethynyl-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-ethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside, 1,3-Benzothiazol-6-yl 3-[4-(4-chlorothiazol-2-yl)-1H-1,2,3-triazol-1-yl]-3-deoxy-2-O-methyl-1-thio-α-D-galactopyranoside, 1,3-Benzothiazol-6-yl 3-deoxy-3-[4-(2-hydroxythiazol-4-yl)-1H-1,2,3-triazol-1-yl]-2-O-methyl-1-thio-α-D-galactopyranoside, 1,3-Benzothiazol-6-yl 3-[4-(2-aminothiazol-4-yl)-1H-1,2,3-triazol-1-yl]-3-deoxy-2-O-methyl-1-thio-α-D-galactopyranoside, 5-Cyano-1,3-benzothiazol-6-yl 3-[4-(4-chlorothiazol-2-yl)-1H-1,2,3-triazol-1-yl]-3-deoxy-2-O-methyl-1-thio-α-D-galactopyranoside, Thiazolo[4,5-b]pyridin-6-yl 3-[4-(4-chlorothiazol-2-yl)-1H-1,2,3-triazol-1-yl]-3-deoxy-2-O-methyl-1-thio-α-D-galactopyranoside, 5-Methylsulfanylpyridin-3-yl 3-[4-(4-chlorothiazol-2-yl)-1H-1,2,3-triazol-1-yl]-3-deoxy-2-O-methyl-1-thio-α-D-galactopyranoside, and 5-(Trifluoromethylsulfanyl)pyridin-3-yl 3-[4-(4-chlorothiazol-2-yl)-1H-1,2,3-triazol-1-yl]-3-deoxy-2-O-methyl-1-thio-α-D-galactopyranoside.

The skilled person will understand that it may be necessary to adjust or change the order of steps in the processes a1 to a40, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldiphenylsilyl or trimethylsilyl), AcO (acetoxy), TBS (t-butyldimethylsilyl), TMS (trimethylsilyl), PMB (p-methoxybenzyl), and tetrahydropyranyl. Suitable protecting groups for carboxylic acid include ($C_{1-6}$)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(═N)$NH_2$, TIPS.

The protection and deprotection of functional groups may take place before or after any reaction in the above-mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substitutents. The free form does not have any acid salt or base salt in addition. In one embodiment the free form is an anhydrate. In another embodiment the free form is a solvate, such as a hydrate.

In a further embodiment the compound of formula (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "C2-alkynyl" as used herein means —CCH. Wherein the two carbons are connected by a triple bond.

The term "Oxo" as used herein means an oxygen atom with double bonds, also indicated as ═O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isoxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoyl, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to benzothiazolyl, oxazolyl, oxadiazolyl, thiophenyl, thiadiazolyl, thiazolyl, thiazolopyridinyl, pyridyl, pyrimidinyl, pyridonyl, pyrimidinyl, quinolinyl, azaquionolyl, isoquinolinyl, azaisoquinolyl, quinazolinyl, azaquinazolinyl, benzooxazoyl, azabensoxazoyl, benzothiazoyl, or azabenzotriazol. The term "a heterocycloalkyl" as used herein means a mono or bicyclic 3-7 membered aliphatic heterocycle containing one or more heteroatoms, such as 1-7, e.g. 1-5, selected from O, S, and N, including but not limited to azetidinyl, piperidinyl, tetrahydropyranyl, tetrahydrothiopyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect, the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99% by weight of said at least one pharmaceutically acceptable adjuvant, diluent, excipient and/or carrier and from 1 to 99% by weight of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The term "and/or" as used herein is intended to mean both alternatives as well as each of the alternatives individually. For instance, the expression "xxx and/or yyy" means "xxx and yyy"; "xxx"; or "yyy", all three alternatives are subject to individual embodiments.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures (Evaluation of Kd Values)

The affinity of Example 1-103 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010).

| Example | Name | Structure | Galectin-1 Kd (μM) | Galectin-3 Kd (μM) |
|---|---|---|---|---|
| 1 | 3,5-Dichloro-4-fluorophenyl 3-deoxy-2-O-methyl-3-[4-(2-thiazolyl)-1H-1,2,3-triazol-1-yl]-1-thio-α-D-galactopyranoside | 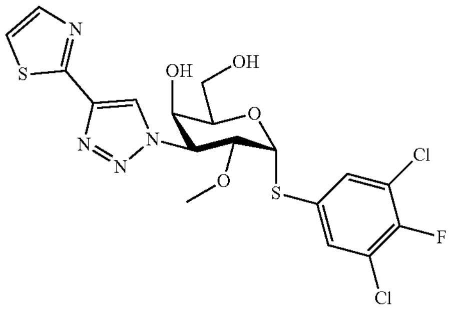 | 0.175 | 8 |
| 2 | 5-Bromopyridin-3-yl 3-deoxy-2-O-methyl-3-[4-(2-thiazolyl)-1H-1,2,3-triazol-1-yl]-1-thio-α-D-galactopyranoside | 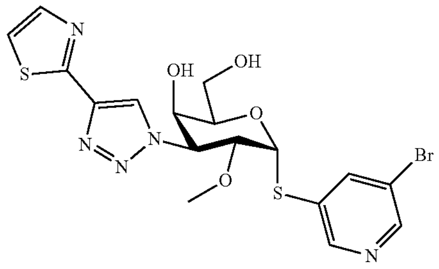 | 0.23 | 3 |
| 3 | 5-Bromo-2-cyanopyridin-3-yl 3-deoxy-2-O-methyl-3-[4-(2-thiazolyl)-1H-1,2,3-triazol-1-yl]-1-thio-α-D-galactopyranoside | 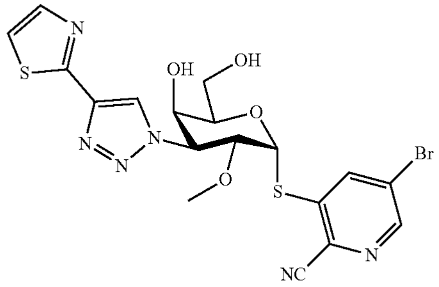 | 0.11 | 1.1 |
| 4 | 5-Chloro-2-cyanopyridin-3-yl 3-deoxy-2-O-methyl-3-[4-(2-thiazolyl)-1H-1,2,3-triazol-1-yl]-1-thio-α-D-galactopyranoside | 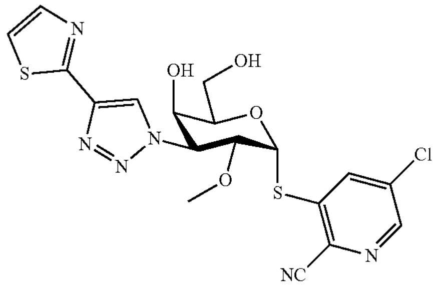 | 0.11 | 1.2 |

-continued

| Example | Name | Structure | Galectin-1 Kd (μM) | Galectin-3 Kd (μM) |
|---|---|---|---|---|
| 5 | 5-Chloro-2-cyanopyridin-3-yl 2-O-benzyl-3-deoxy-3-[4-(2-thiazolyl)-1H-1,2,3-triazol-1-yl]-1-thio-α-D-galactopyranoside | 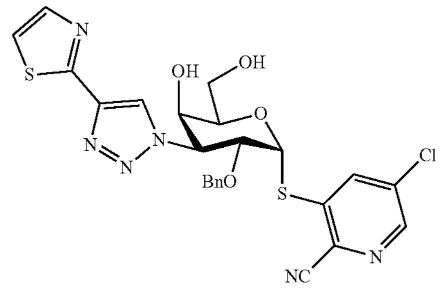 | 0.19 | 1.8 |
| 6 | 5-Chloro-2-cyanopyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside | 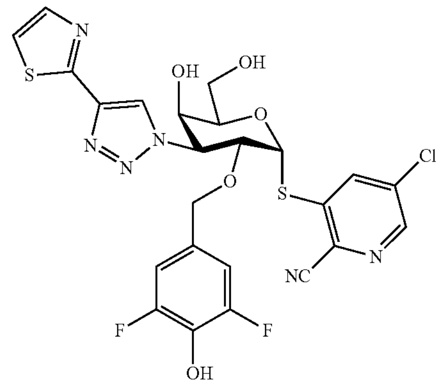 | 0.096 | 0.95 |
| 7 | 3,5-Dichloro-4-fluorophenyl 3-deoxy-3-[4-(2-hydroxythiazol-4-yl)-1H-1,2,3-triazol-1-yl]-2-O-methyl-1-thio-α-D-galactopyranoside | 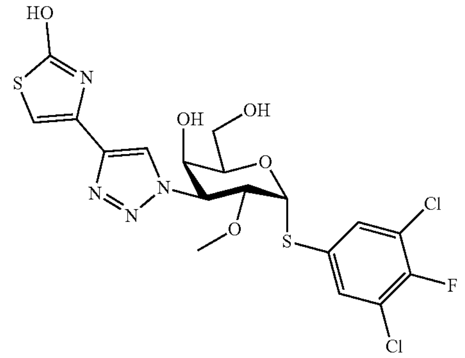 | 0.029 | 2.6 |
| 8 | 3,4-Dichlorophenyl 3-deoxy-3-[4-(2-hydroxythiazol-4-yl)-1H-1,2,3-triazol-1-yl]-2-O-isopropyl-1-thio-α-D-galactopyranoside | 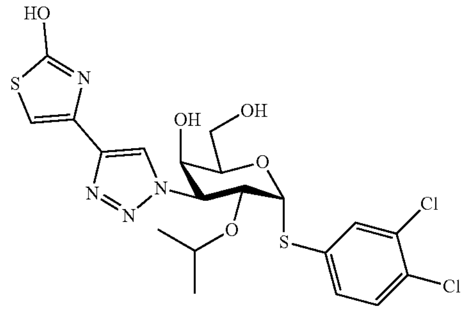 | 0.1 | >100 |

-continued

| Example | Name | Structure | Galectin-1 Kd (μM) | Galectin-3 Kd (μM) |
|---|---|---|---|---|
| 9 | 3,4-Dichlorophenyl 3-deoxy-3-[4-(2-hydroxythiazol-4-yl)-1H-1,2,3-triazol-1-yl]-2-O-methyl-1-thio-α-D-galactopyranoside | 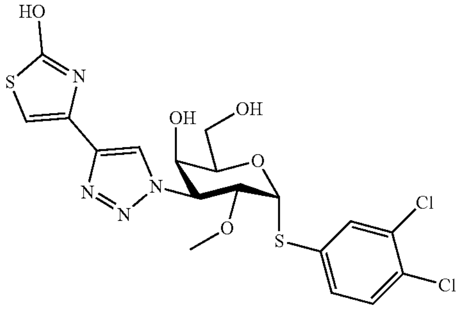 | 0.041 | 4.6 |
| 10 | 3,4-Dichlorophenyl 2,3-dideoxy-3-[4-(2-hydroxythiazol-4-yl)-1H-1,2,3-triazol-1-yl]-1-thio-α-D-galactopyranoside | 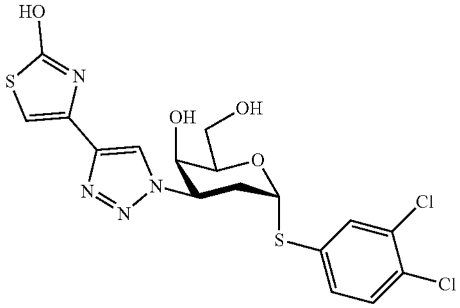 | 0.082 | 5.3 |
| 11 | 5-Bromo-2-cyanopyridin-3-yl 3-[4-(4-chlorothiazol-2-yl)-1H-1,2,3-triazol-1-yl]-3-deoxy-2-O-methyl-1-thio-α-D-galactopyranoside | 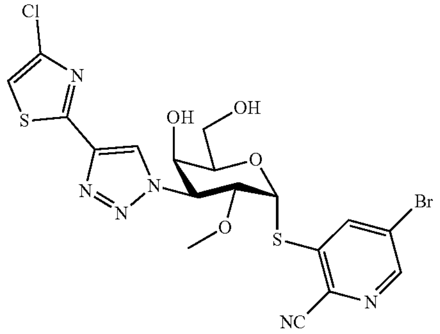 | 0.019 | 0.17 |
| 12 | 3-Bromo-2-cyanopyridin-5-yl 3-[4-(4-chlorothiazol-2-yl)-1H-1,2,3-triazol-1-yl]-3-deoxy-2-O-methyl-1-thio-α-D-galactopyranoside | 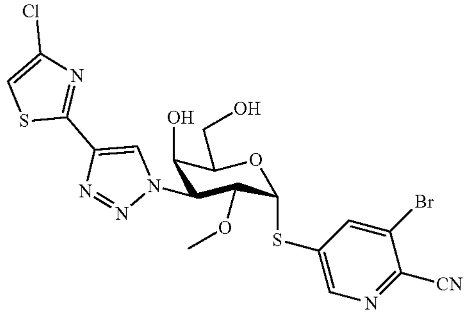 | 0.024 | 0.27 |

-continued

| Example | Name | Structure | Galectin-1 Kd (μM) | Galectin-3 Kd (μM) |
|---|---|---|---|---|
| 13 | 5-Chloro-2-cyanopyridin-3-yl 3-[4-(4-chlorothiazol-2-yl)-1H-1,2,3-triazol-1-yl]-3-deoxy-2-O-methyl-1-thio-α-D-galactopyranoside | 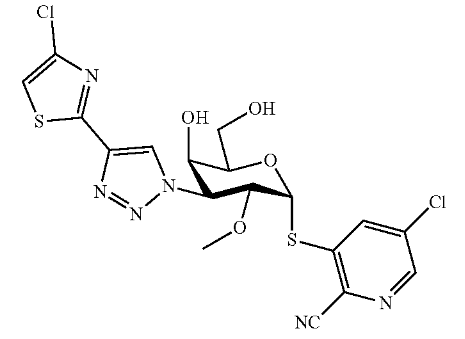 | 0.025 | 0.16 |
| 14 | 3-Chloro-2-cyanopyridin-5-yl 3-[4-(4-chlorothiazol-2-yl)-1H-1,2,3-triazol-1-yl]-3-deoxy-2-O-methyl-1-thio-α-D-galactopyranoside | 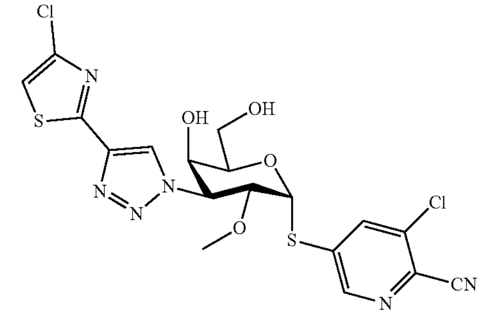 | 0.030 | 0.37 |
| 15 | 5-Chloro-2-cyanopyridin-3-yl 3-[4-(2-chlorothiazol-4-yl)-1H-1,2,3-triazol-1-yl]-3-deoxy-2-O-methyl-1-thio-α-D-galactopyranoside | 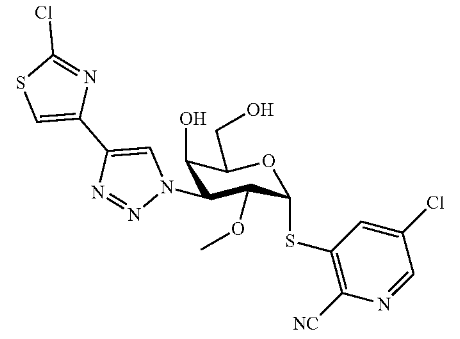 | 0.056 | 0.2 |
| 16 | 3,5-Dichloro-4-fluorophenyl 3-[4-(2-aminothiazol-4-yl)-1H-1,2,3-triazol-1-yl]-3-deoxy-2-O-methyl-1-thio-α-D-galactopyranoside | 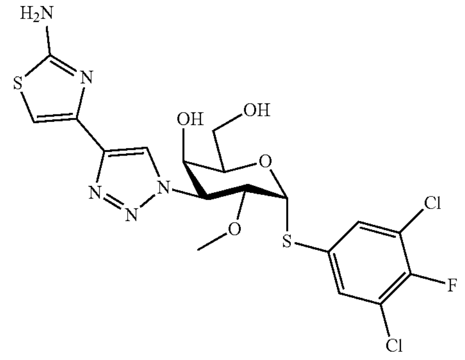 | 0.069 | 8.4 |

-continued

| Example | Name | Structure | Galectin-1 Kd (μM) | Galectin-3 Kd (μM) |
|---|---|---|---|---|
| 17 | 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside | 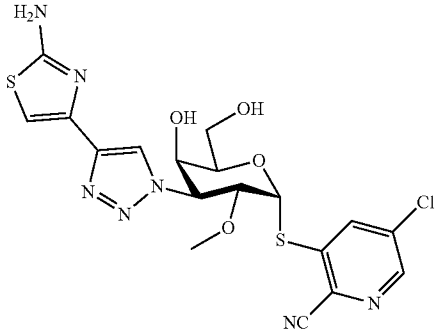 | 0.033 | 1.9 |
| 18 | 5-Chloro-2-methylpyridin-3-yl 3-[4-(2-aminothiazol-4-yl)-1H-1,2,3-triazol-1-yl]-3-deoxy-2-O-methyl-1-thio-α-D-galactopyranoside | 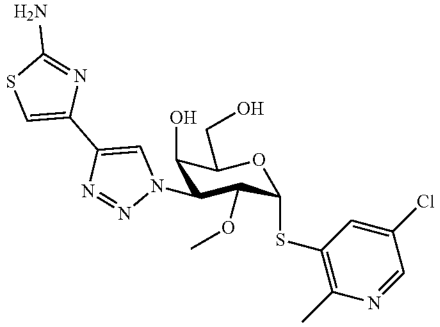 | 0.12 | 5.4 |
| 19 | 5-Chloro-2-cyanopyridin-3-yl 3-[4-(2-aminothiazol-4-yl)-1H-1,2,3-triazol-1-yl]-2-O-benzyl-3-deoxy-1-thio-α-D-galactopyranoside | 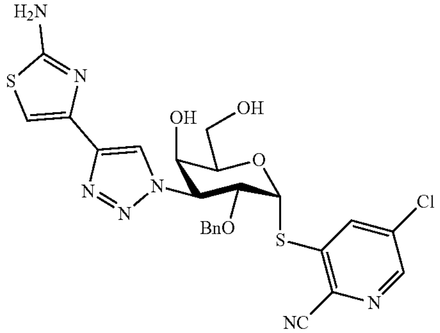 | 0.079 | 1.8 |
| 20 | 5-Chloro-2-methylpyridin-3-yl 3-[4-(2-aminothiazol-4-yl)-1H-1,2,3-triazol-1-yl]-3-deoxy-2-O-ethyl-1-thio-α-D-galactopyranoside | 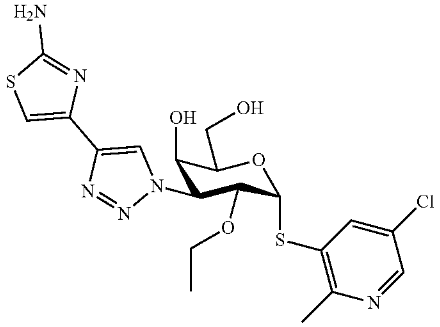 | 0.067 | 6.2 |

-continued

| Example | Name | Structure | Galectin-1 Kd (μM) | Galectin-3 Kd (μM) |
|---|---|---|---|---|
| 21 | 5-Chloro-2-(pyrimidin-5-yl)pyridin-3-yl 3-[4-(2-aminothiazol-4-yl)-1H-1,2,3-triazol-1-yl]-3-deoxy-2-O-methyl-1-thio-α-D-galactopyranoside | 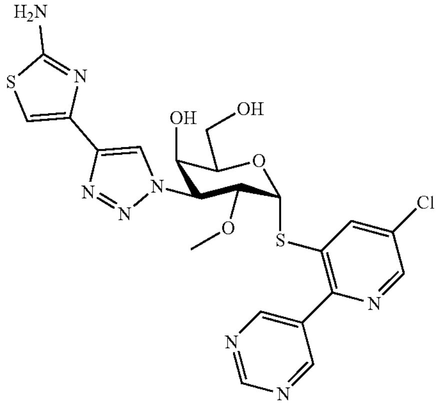 | 0.045 | 2.3 |
| 22 | 5-Chloro-2-(pyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside | 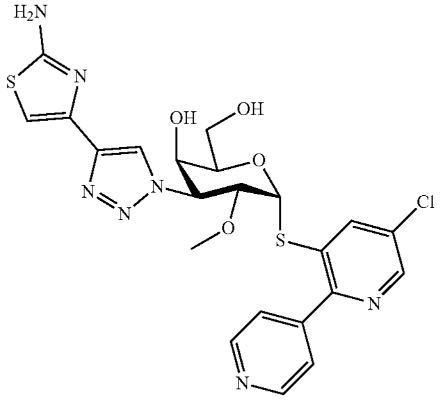 | 0.026 | 4.1 |
| 23 | 5-Chloro-2-(pyridin-3-yl)pyridin-3-yl 3-[4-(2-aminothiazol-4-yl)-1H-1,2,3-triazol-1-yl]-3-deoxy-2-O-methyl-1-thio-α-D-galactopyranoside | 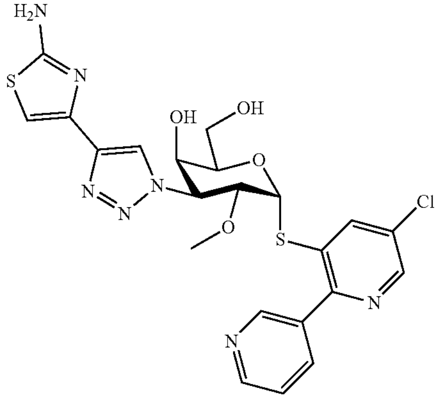 | 0.030 | 4.2 |

-continued

| Example | Name | Structure | Galectin-1 Kd (μM) | Galectin-3 Kd (μM) |
|---|---|---|---|---|
| 24 | 5-Choro-2-(1,2,3,6-tetrahydropyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside | 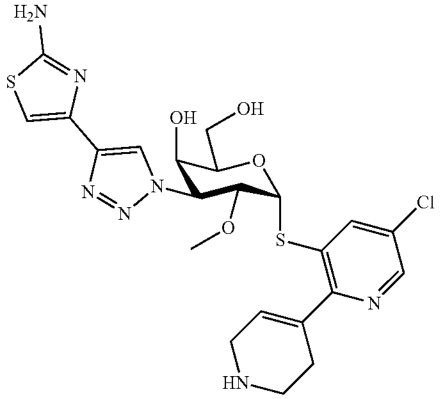 | 0.15 | 3.3 |
| 25 | 5-Chloro-2-cyanopyridin-3-yl 3-[4-(2-aminothiazol-4-yl)-1H-1,2,3-triazol-1-yl]-3-deoxy-2-O-(3,5-difluoro-4-hydroxybenzyl)-1-thio-α-D-galactopyranoside | 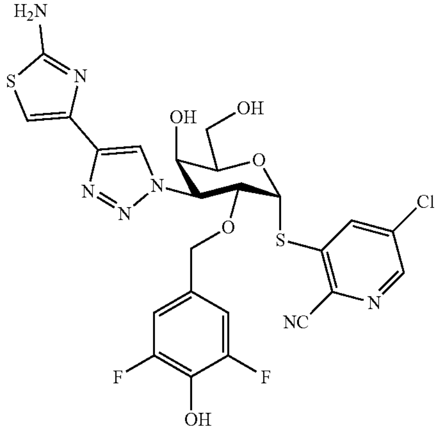 | 0.024 | 0.74 |
| 26 | 5-Chloro-2-(pyridin-2-yl)pyridin-3-yl 3-[4-(2-aminothiazol-4-yl)-1H-1,2,3-triazol-1-yl]-3-deoxy-2-O-methyl-1-thio-α-D-galactopyranoside | 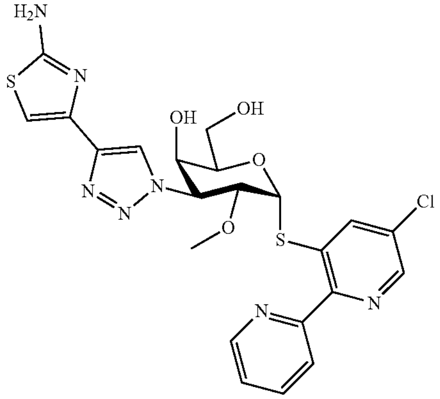 | 0.017 | 1.7 |

-continued

| Example | Name | Structure | Galectin-1 Kd (μM) | Galectin-3 Kd (μM) |
|---|---|---|---|---|
| 27 | 5-Chloro-2-(oxazol-2-yl)pyridin-3-yl 3-[4-(2-aminothiazol-4-yl)-1H-1,2,3-triazol-1-yl]-3-deoxy-2-O-methyl-1-thio-α-D-galactopyranoside | 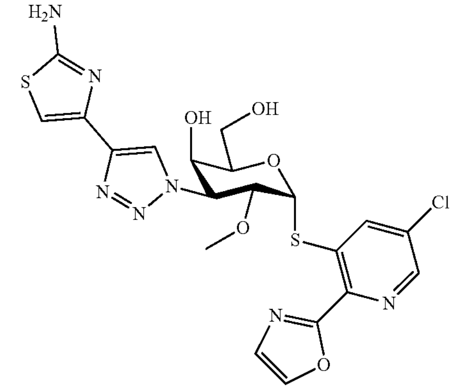 | 0.028 | 3.2 |
| 28 | 3,4-Dichlorphenyl 3-[4-(2-aminothiazol-4-yl)-1H-1,2,3-triazol-1-yl]-3-deoxy-2-O-methyl-1-thio-α-D-galactopyranoside | 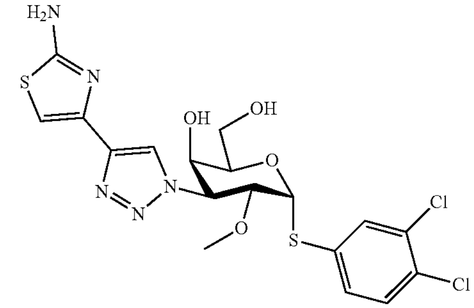 | 0.063 | 2.4 |
| 29 | 5-Chloro-2-(thiazol-2-yl)pyridin-3-yl 3-[4-(2-aminothiazol-4-yl)-1H-1,2,3-triazol-1-yl]-3-deoxy-2-O-methyl-1-thio-α-D-galactopyranoside | 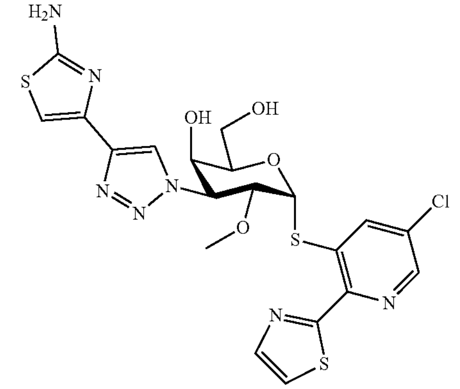 | 0.048 | 8.7 |
| 30 | 3-Chloro-4-(trifluoromethyl) phenyl 3-[4-(2-aminothiazol-4-yl)-1H-1,2,3-triazol-1-yl]-3-deoxy-2-O-methyl-1-thio-α-D-galactopyranoside | 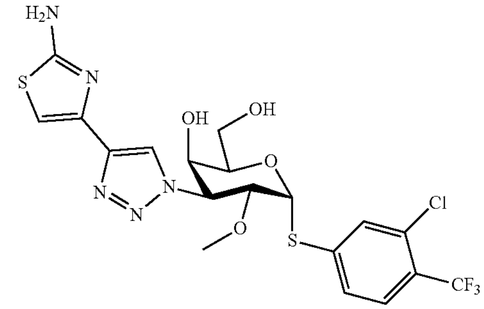 | 0.12 | 2.5 |

-continued

| Example | Name | Structure | Galectin-1 Kd (μM) | Galectin-3 Kd (μM) |
|---|---|---|---|---|
| 31 | 3-Chlorophenyl 3-[4-(2-aminothiazol-4-yl)-1H-1,2,3-triazol-1-yl]-3-deoxy-2-O-methyl-1-thio-α-D-galactopyranoside | 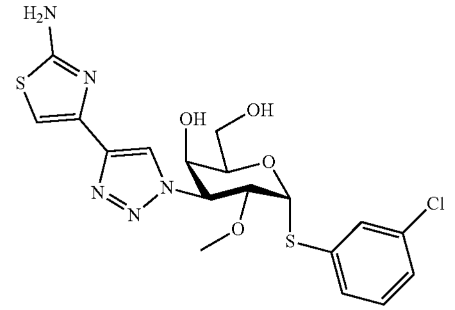 | 0.2 | 5.6 |
| 32 | 3,5-Dichloro-4-fluorophenyl 3-[4-(2-aminothiazol-4-yl)-1H-1,2,3-triazol-1-yl]-3-deoxy-1-thio-α-D-galactopyranoside | 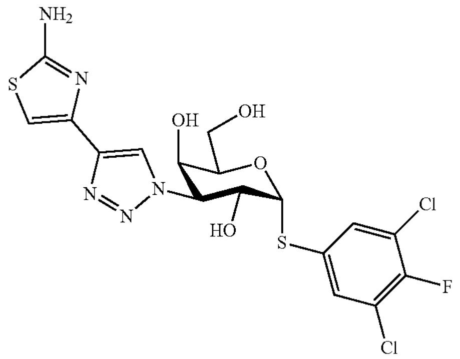 | 0.15 | 5.0 |
| 33 | 3-Bromo-2-(trifluoromethyl) pyridin-5-yl 3-[4-(2-aminothiazol-4-yl)-1H-1,2,3-triazol-1-yl]-3-deoxy-1-thio-α-D-galactopyranoside | 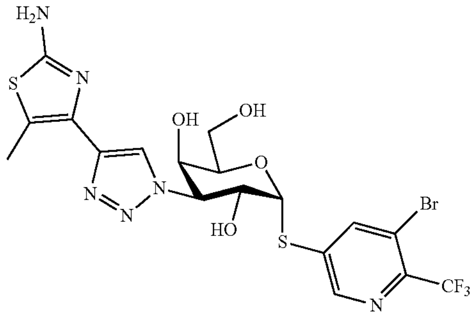 | 0.5 | 3.0 |
| 34 | 5-Bromo-2-cyanopyridin-3-yl 3-deoxy-3-[4-(4-methylthiazol-2-yl)-1H-1,2,3-triazol-1-yl]-2-O-methyl-1-thio-α-D-galactopyranoside | 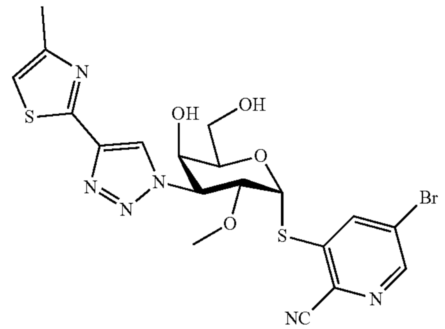 | 0.053 | 1.4 |

-continued

| Example | Name | Structure | Galectin-1 Kd (μM) | Galectin-3 Kd (μM) |
|---|---|---|---|---|
| 35 | 2-Cyano-5-methylpyridin-3-yl 3-deoxy-3-[4-(4-methyltriazol-2-yl)-1H-1,2,3-thiazol-1-yl]-2-O-methyl-1-thio-α-D-galactopyranoside | 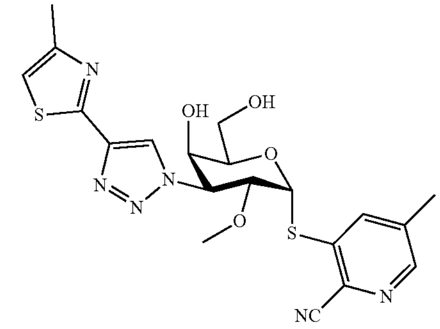 | 0.49 | 9 |
| 36 | 2-Cyano-5-methylpyridin-3-yl 3-[4-(4-chlorothiazol-2-yl)-1H-1,2,3-triazol-1-yl]-3-deoxy-2-O-methyl-1-thio-α-D-galactopyranoside | 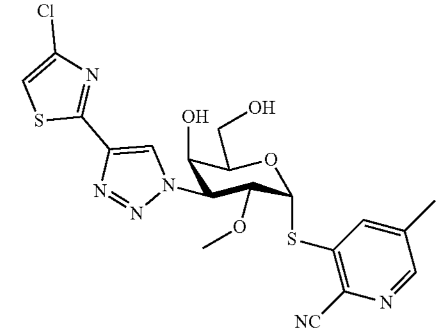 | 0.19 | 0.7 |
| 37 | 5-Ethynylpyridin-3-yl 3-[4-(4-chlorothiazol-2-yl)-1H-1,2,3-triazol-1-yl]-3-deoxy-2-O-methyl-1-thio-α-D-galactopyranoside | 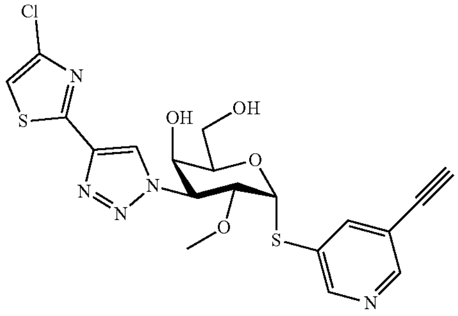 | 0.2 | 0.39 |
| 38 | 5-Chloro-2-{N-(2-oxa)-6-azaspiro[3.3]heptanyl}-pyridin-3-yl 3-[4-(2-aminothiazol-4-yl)-1H-1,2,3-triazol-1-yl]-3-deoxy-2-O-methyl-1-thio-α-D-galactopyranoside | 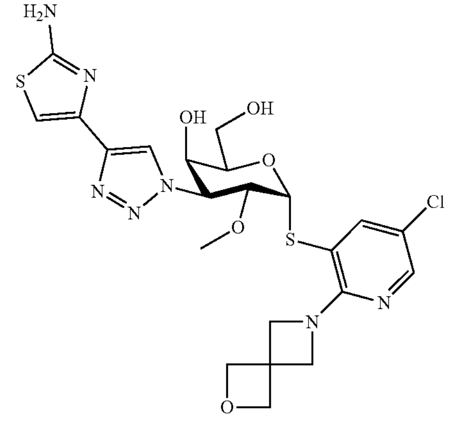 | 0.1 | 6.1 |

-continued

| Example | Name | Structure | Galectin-1 Kd (μM) | Galectin-3 Kd (μM) |
|---|---|---|---|---|
| 39 | 3-Chloro-4-cyanophenyl 3-[4-(2-aminothiazol-4-yl)-1H-1,2,3-triazol-1-yl]-3-deoxy-2-O-methyl-1-thio-α-D-galactopyranoside | 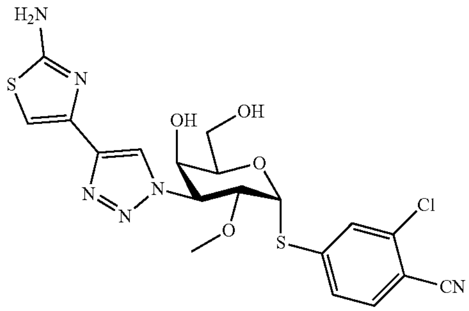 | 0.071 | 3.6 |
| 40 | 5-Cyanopyridin-3yl 3-[4-(2-aminothiazol-4-yl)-1H-1,2,3-triazol-1-yl]-3-deoxy-2-O-methyl-1-thio-α-D-galactopyranoside | 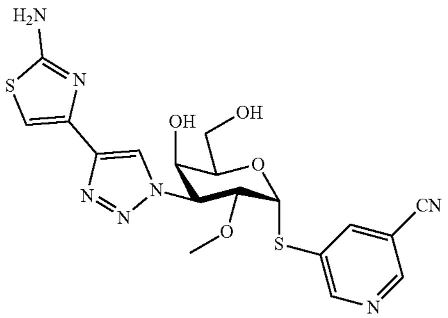 | 0.24 | 10.7 |
| 41 | 3,5-Dichloro-4-fluorophenyl 2,3-dideoxy-3-[4-(2-hydroxythiazol-4-yl)-1H-1,2,3-triazol-1-yl]-1-thio-α-D-galactopyranoside | 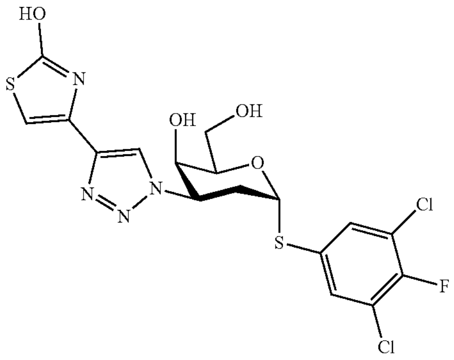 | 0.13 | 9.3 |
| 42 | 3-Chloro-4-cyanophenyl 3-[4-(2-aminothiazol-4-yl)-1H-1,2,3-triazol-1-yl]-2,3-dideoxy-1-thio-α-D-galactopyranoside | 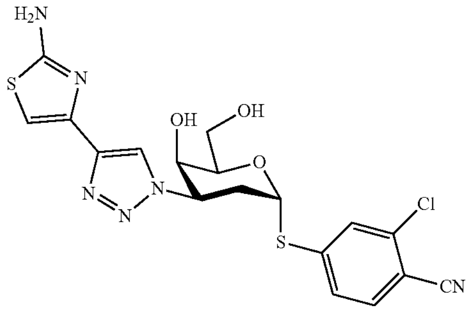 | 0.73 | 10.3 |

-continued

| Example | Name | Structure | Galectin-1 Kd (μM) | Galectin-3 Kd (μM) |
|---|---|---|---|---|
| 43 | 5-Chloro-2-cyanophenyl 3-[4-(4-chlorothiazol-2-yl)-1H-1,2,3-triazol-1-yl]-2,3-dideoxy-1-thio-α-D-galactopyranoside | 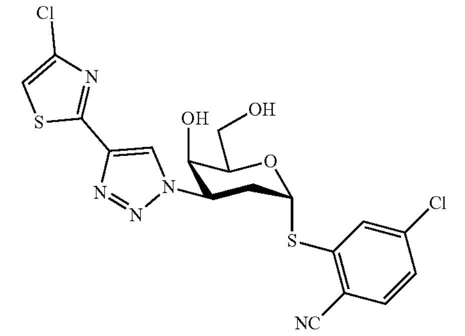 | 0.13 | 1.2 |
| 44 | 3-Cyano-2-(trifluoromethyl) pyridin-5-yl 3-[4-(2-aminothiazol-4-yl)-1H-1,2,3-triazol-1-yl]-3-deoxy-2-O-methyl-1-thio-α-D-galactopyranoside | 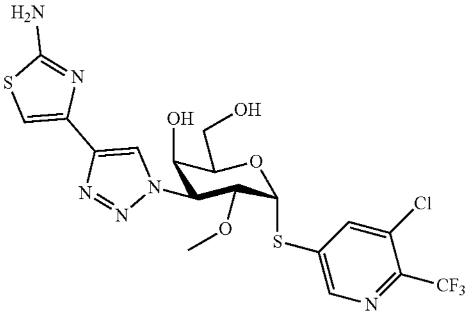 | 0.36 | 16.7 |
| 45 | 2-(N-Azetidinylcarbamoyl)-5-chloro-pyridin-3-yl 3-[4-(4-chlorothiazol-2-yl)-1H-1,2,3-triazol-1-yl]-3-deoxy-2-O-methyl-1-thio-α-D-galactopyranoside | 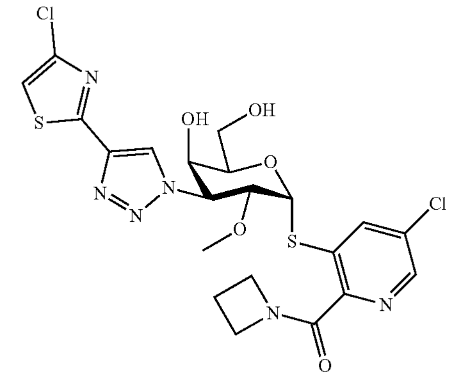 | 0.022 | 0.074 |
| 46 | 5-Chloro-2-(pyridin-2-yl)pyridin-3-yl 3-deoxy-3-[4-(4-methylthiazol-2-yl)-1H-1,2,3-triazol-1-yl]-2-O-methyl-1-thio-α-D-galactopyranoside | 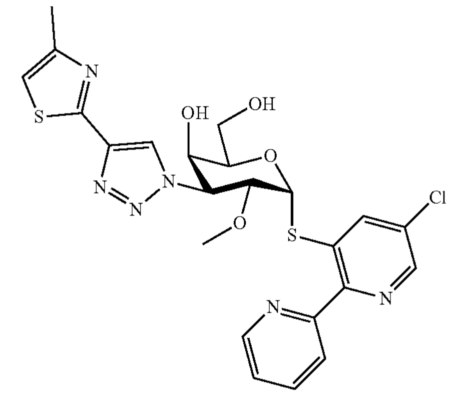 | 0.035 | 2.53 |

-continued

| Example | Name | Structure | Galectin-1 Kd (μM) | Galectin-3 Kd (μM) |
|---|---|---|---|---|
| 47 | 5-Ethynylpyridin-3-yl 3-deoxy-2-O-methyl-3-[4-(2-thiazolyl)-1H-1,2,3-triazolyl)-yl]-1-thio-α-D-galactopyranoside | 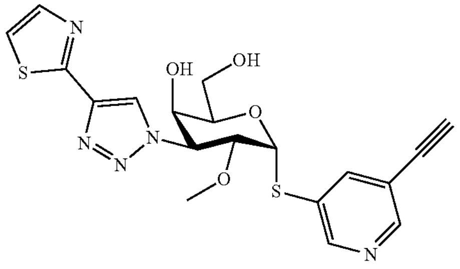 | 0.57 | 3.2 |
| 48 | 5-Chloropyridin-3-yl 3-[4-(4-chlorothiazol-2-yl)-1H-1,2,3-triazol-1-yl]-3-deoxy-1-thio-α-D-galactopyranoside | 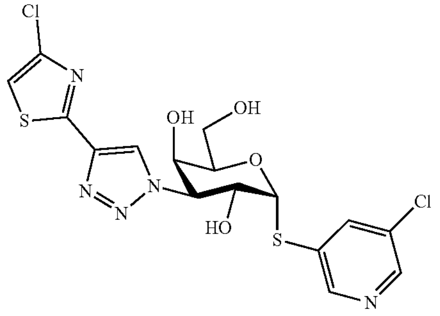 | 0.15 | 0.42 |
| 49 | 5-Bromopyridin-3-yl 3-[4-(4-chlorothiazol-2-yl)-1H-1,2,3-triazol-1-yl]-3-deoxy-1-thio-α-D-galactopyranoside | 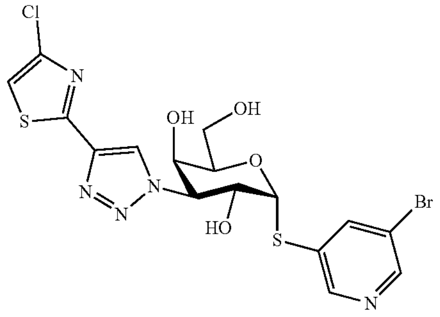 | 0.15 | 0.19 |
| 50 | 5-Chloro-2-cyanophenyl 3-[4-(4-chlorothiazol-2-yl)-1H-1,2,3-triazol-1-yl]-3-deoxy-1-thio-α-D-galactopyranoside | 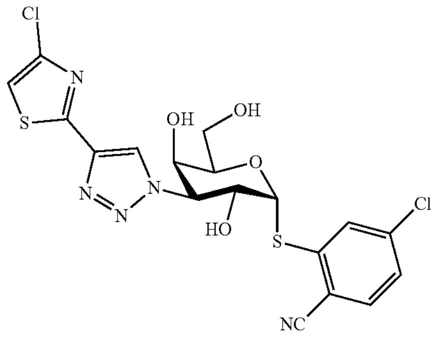 | 0.11 | 0.23 |

-continued

| Example | Name | Structure | Galectin-1 Kd (μM) | Galectin-3 Kd (μM) |
|---|---|---|---|---|
| 51 | 3-Chloro-5-cyanophenyl 3-[4-(4-chlorothiazol-2-yl)-1H-1,2,3-triazol-1-yl]-3-deoxy-1-thio-α-D-galactopyranoside | 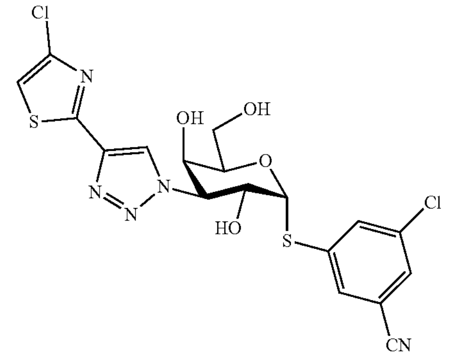 | 0.25 | 0.37 |
| 52 | 3-Chloro-4-cyanophenyl 3-[4-(4-chlorothiazol-2-yl)-1H-1,2,3-triazol-1-yl]-3-deoxy-1-thio-α-D-galactopyranoside | 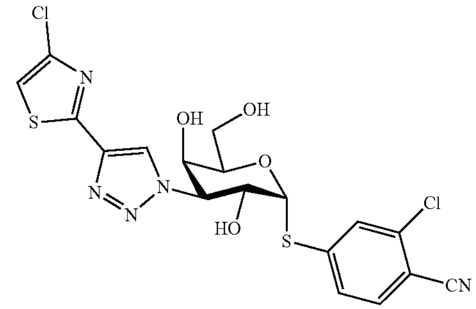 | 0.17 | 0.41 |
| 53 | 5-Chloropyridin-3-yl 3-[4-(4-chlorothiazol-2-yl)-1H-1,2,3-triazol-1-yl]-3-deoxy-2-O-methyl-1-thio-α-D-galactopyranoside | 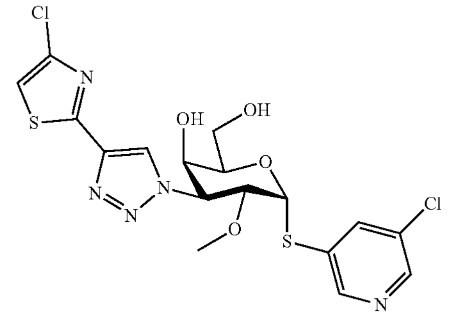 | 0.054 | 0.34 |
| 54 | 5-Bromopyridin-3-yl 3-[4-(4-chlorothiazol-2-yl)-1H-1,2,3-triazol-1-yl]-3-deoxy-2-O-methyl-1-thio-α-D-galactopyranoside | 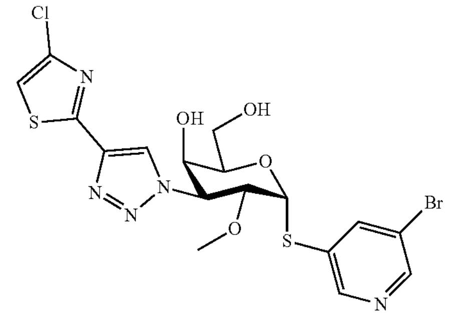 | 0.090 | 0.19 |

-continued

| Example | Name | Structure | Galectin-1 Kd (μM) | Galectin-3 Kd (μM) |
|---|---|---|---|---|
| 55 | 5-Bromo-2-cyanopyridin-3-yl 3-[4-(4,5-dichlorothiazol-2-yl)-1H-1,2,3-triazol-1-yl]-3-deoxy-2-O-methyl-1-thio-α-D-galactopyranoside | 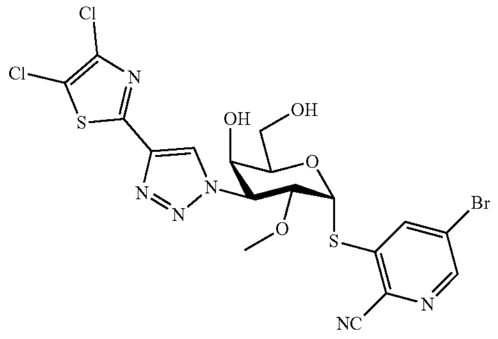 | 0.15 | 0.028 |
| 56 | 5-Bromo-2-cyanophenyl 3-deoxy-2-O-methyl-3-[4-(2-thiazolyl)-1H-1,2,3-triazol-1-yl]-1-thio-α-D-galactopyranoside | 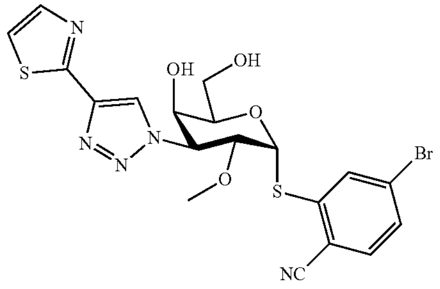 | 0.096 | 2.1 |
| 57 | 5-Bromo-2-cyanophenyl 3-[4-(4-chlorothiazol-2-yl)-1H-1,2,3-triazol-1-yl]-3-deoxy-2-O-methyl-1-thio-α-D-galactopyranoside | 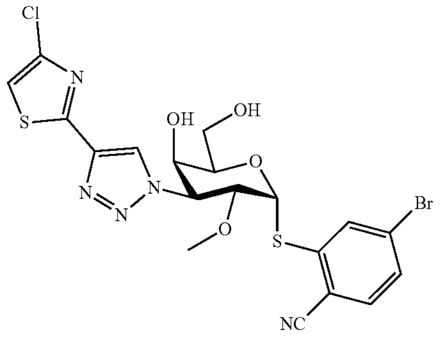 | 0.021 | 0.14 |
| 58 | 5-Bromo-2-cyanophenyl 3-deoxy-3-[4-(2-hydroxythiazol-4-yl)-1H-1,2,3-triazol-1-yl]-2-O-methyl-1-thio-α-D-galactopyranoside | 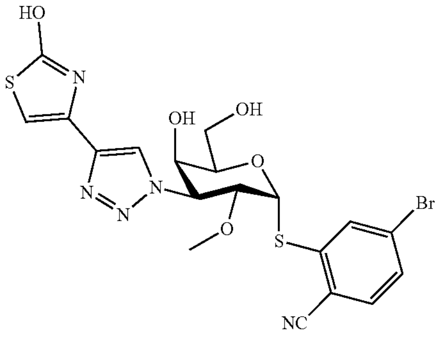 | 0.022 | 2 |

-continued

| Example | Name | Structure | Galectin-1 Kd (μM) | Galectin-3 Kd (μM) |
|---|---|---|---|---|
| 59 | 5-Bromo-2-cyanophenyl 3-[4-(2-aminothiazol-4-yl)-1H-1,2,3-triazol-1-yl]-3-deoxy-2-O-methyl-1-thio-α-D-galactopyranoside | 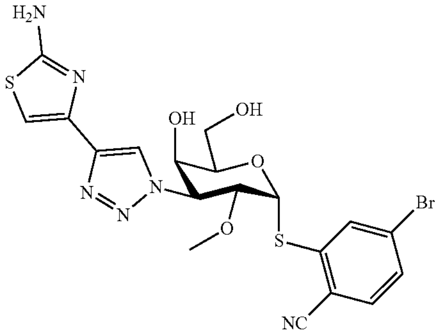 | 0.054 | 2.2 |
| 60 | 5-Bromo-2-(N-methyl-carbonyl)phenyl 3-[4-(4-chlorothiazol-2-yl)-1H-1,2,3-triazol-1-yl]-3-deoxy-2-O-methyl-1-thio-α-D-galactopyranoside | 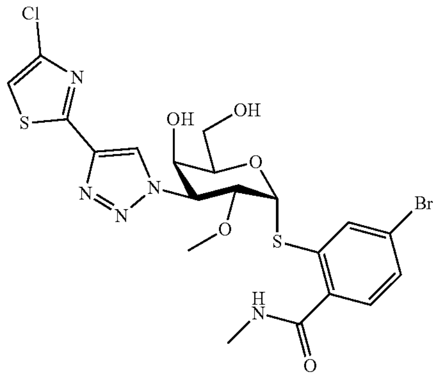 | 0.039 | 0.18 |
| 61 | 5-Bromo-2-(N-methyl-carbonyl)phenyl 3-deoxy-2-O-methyl-3-[4-(2-thiazolyl)-1H-1,2,3-triazol-1-yl]-1-thio-α-D-galactopyranoside | 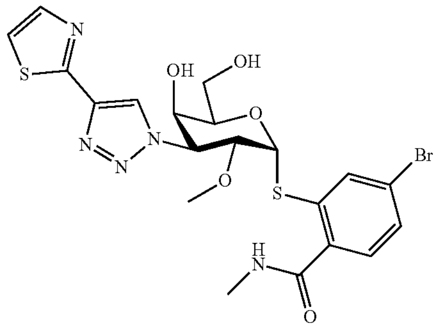 | 0.080 | 3 |
| 62 | 5-Chloro-2-(N-methyl-carbonyl)phenyl 3-deoxy-2-O-methyl-3-[4-(2-thiazolyl)-1H-1,2,3-triazol-1-yl]-1-thio-α-D-galactopyranoside | 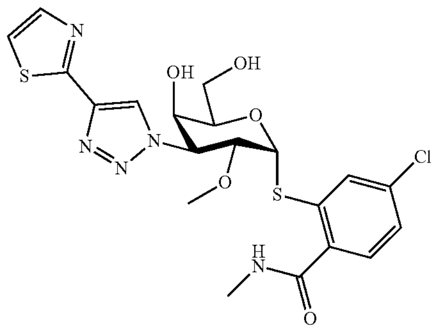 | 0.078 | 3.1 |

-continued

| Example | Name | Structure | Galectin-1 Kd (μM) | Galectin-3 Kd (μM) |
|---|---|---|---|---|
| 63 | 5-Bromo-2-cyanophenyl 3-deoxy-3-[4-(4-methylthiazol-2-yl)-1H-1,2,3-triazol-1-yl]-2-O-methyl-1-thio-α-D-galactopyranoside | 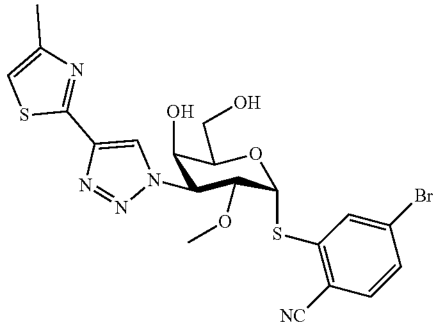 | 0.054 | 2.9 |
| 64 | 5-Bromo-2-cyanopyridin-3-yl 3-[4-(5-chloro-4-methylthiazol-2-yl)-1H-1,2,3-triazol-1-yl]-3-deoxy-2-O-methyl-1-thio-α-D-galactopyranoside | 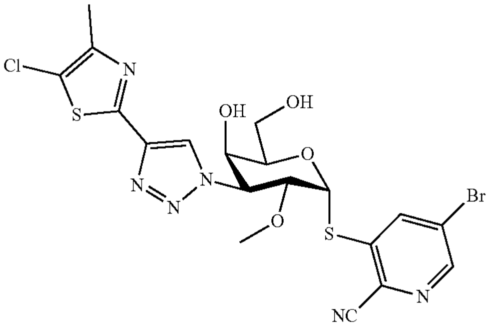 | 0.28 | 0.22 |
| 65 | 5-Bromo-2-cyanophenyl 3-[4-(5-chloro-4-methylthiazol-2-yl)-1H-1,2,3-triazol-1-yl]-3-deoxy-2-O-methyl-1-thio-α-D-galactopyranoside | 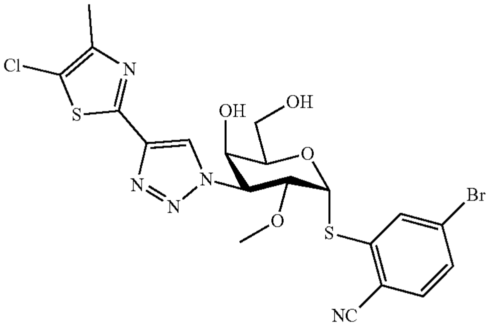 | 0.46 | 0.24 |
| 66 | 2,5-Dichlorophenyl 3-deoxy-2-O-methyl-3-[4-(2-thiazolyl)-1H-1,2,3-triazol-1-yl]-1-thio-α-D-galactopyranoside | 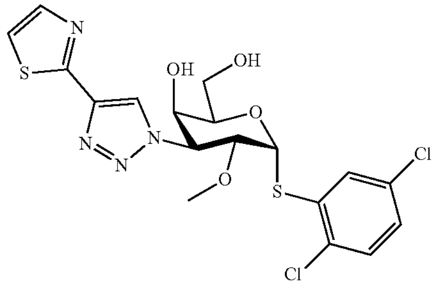 | 0.22 | 4.1 |

-continued

| Example | Name | Structure | Galectin-1 Kd (μM) | Galectin-3 Kd (μM) |
|---|---|---|---|---|
| 67 | 5-Bromo-2-chlorophenyl 3-deoxy-2-O-methyl-3-[4-(2-thiazolyl)-1H-1,2,3-triazol-1-yl]-1-thio-α-D-galactopyranoside | 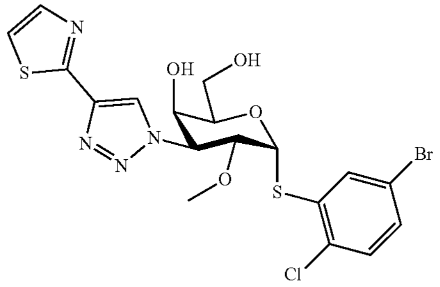 | 0.26 | 3.5 |
| 68 | 5-Chloro-2-fluorophenyl 3-deoxy-2-O-methyl-3-[4-(2-thiazolyl)-1H-1,2,3-triazol-1-yl]-1-thio-α-D-galactopyranoside | 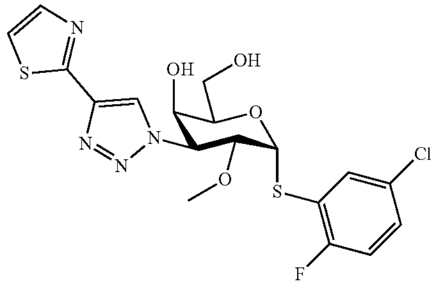 | 0.25 | 4.4 |
| 69 | 5-Bromo-2-fluorophenyl 3-deoxy-3-[4-(4-methylthiazol-2-yl)-1H-1,2,3-triazol-1-yl]-2-O-methyl-1-thio-α-D-galactopyranoside | 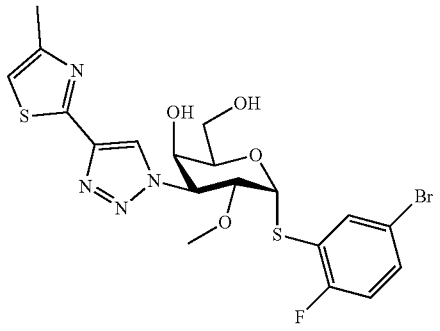 | 0.65 | 12 |
| 70 | 5-Chloro-2-cyanopyridin-3-yl 3-[4-(2-chlorothiazol-4-yl)-1H-1,2,3-triazol-1-yl]-3-deoxy-1-thio-α-D-galactopyranoside | 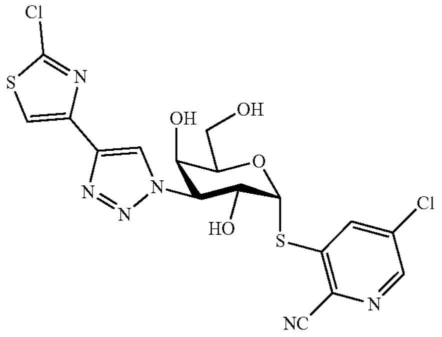 | 0.33 | 0.42 |
| 71 | 5-Chloro-2-cyanopyridin-3-yl 3-deoxy-2-O-ethyl-3-[4-(2-thiazolyl)-1H-1,2,3-triazol-1-yl]-1-thio-α-D-galactopyranoside | 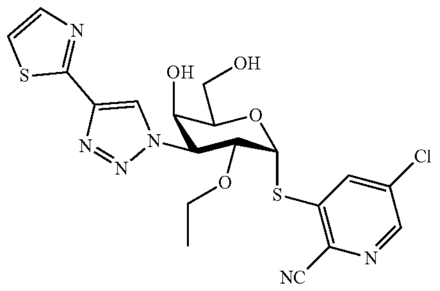 | 0.12 | 3.6 |

-continued

| Example | Name | Structure | Galectin-1 Kd (μM) | Galectin-3 Kd (μM) |
|---|---|---|---|---|
| 72 | 5-Chloro-2-cyanopyridin-3-yl 3-[4-(2-aminothiazol-4-yl)-1H-1,2,3-triazol-1-yl]-3-deoxy-2-O-ethyl-1-thio-α-D-galactopyranoside | 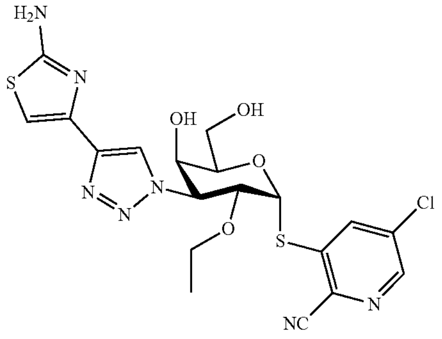 | 0.44 | 3 |
| 73 | 5-Chloro-2-cyanophenyl 3-[4-(2-aminothiazol-4-yl)-1H-1,2,3-triazol-1-yl]-3-deoxy-2-O-methyl-1-thio-α-D-galactopyranoside | 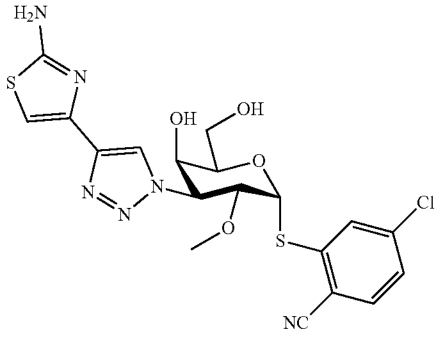 | 0.056 | 3.2 |
| 74 | 5-Chloro-2-(1H-imidazol-2-yl)pyridin-3-yl 3-[4-(2-aminothiazol-4-yl)-1H-1,2,3-triazol-1-yl]-3-deoxy-1-thio-α-D-galactopyranoside | 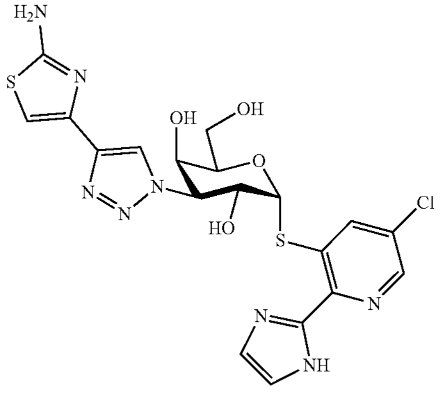 | 0.36 | 11.3 |
| 75 | 5-Chloro-2-(1H-imidazol-2-yl)pyridin-3-yl 3-deoxy-3-[4-(2-hydroxythiazol-4-yl)-1H-1,2,3-triazol-1-yl]-1-thio-α-D-galactopyranoside | 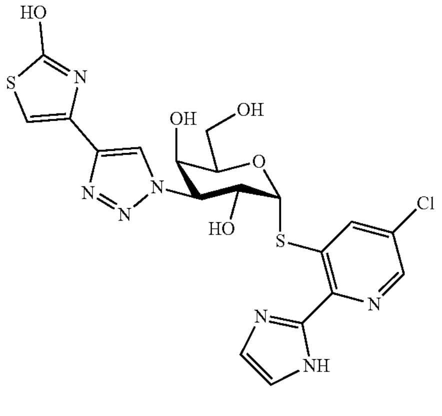 | 0.13 | 7.7 |

-continued

| Example | Name | Structure | Galectin-1 Kd (μM) | Galectin-3 Kd (μM) |
|---|---|---|---|---|
| 76 | 5-Chloro-2-(pyridin-2-yl)pyridin-3-yl 3-[4-(4-chlorothiazol-2-yl)-1H-1,2,3-triazol-1-yl]-3-deoxy-2-O-methyl-1-thio-α-D-galactopyranoside | 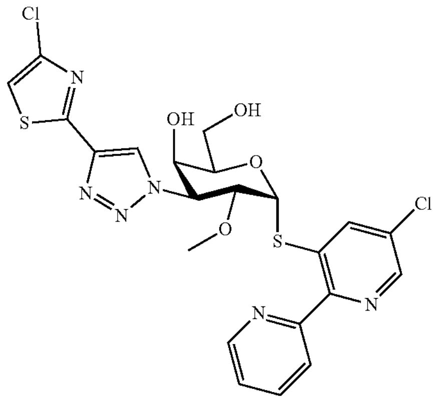 | 0.010 | 0.15 |
| 77 | 2-Cyano-5-methylpyridin-3-yl 3-[4-(4-chlorothiazol-2-yl)-1H-1,2,3-triazol-1-yl]-3-deoxy-1-thio-α-D-galactopyranoside | 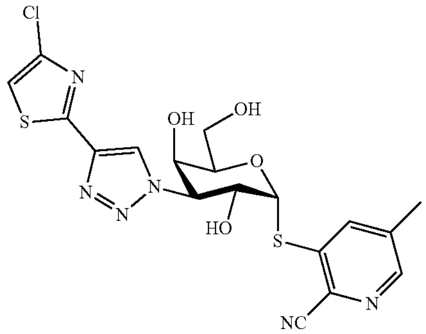 | 0.83 | 0.86 |
| 78 | 3,4-Dichlorophenyl 3-[4-(2-aminothiazol-4-yl)-1H-1,2,3-triazol-1-yl]-3-deoxy-2-O-(2,2,2-trifluoroethyl)-1-thio-α-D-galactopyranoside | 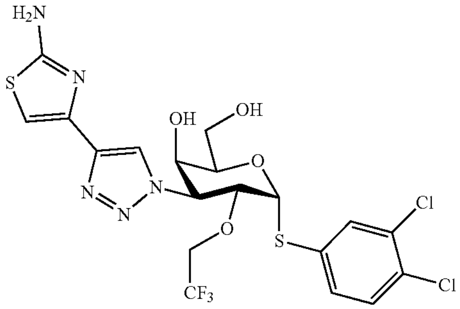 | 0.52 | 7.2 |
| 79 | 3,4-Dichlorophenyl 3-deoxy-2-O-(2,2,2-trifluoroethyl)-3-[4-(2-hydroxythiazol-4-yl)-1H-1,2,3-triazol-1-yl]-1-thio-α-D-galactopyranoside | 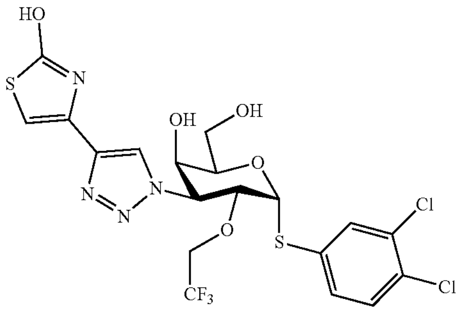 | 0.46 | 6.8 |

-continued

| Example | Name | Structure | Galectin-1 Kd (μM) | Galectin-3 Kd (μM) |
|---|---|---|---|---|
| 80 | 5-Ethynylpyridin-3-yl 3-[4-(4-chlorothiazol-2-yl)-1H-1,2,3-triazol-1-yl]-3-deoxy-1-thio-α-D-galactopyranoside | 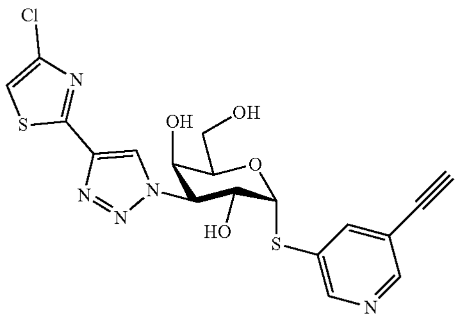 | 0.31 | 0.36 |
| 81 | 5-Ethynylpyridin-3-yl 3-[4-(2-aminothiazol-4-yl)-1H-1,2,3-triazol-1-yl]-3-deoxy-2-O-methyl-1-thio-α-D-galactopyranoside | 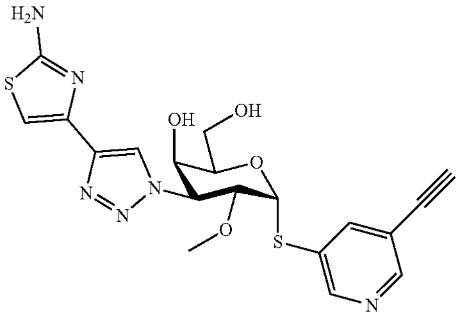 | 0.19 | 6.6 |
| 82 | 5-Cyanopyridin-3-yl 3-[4-(4-chlorothiazol-2-yl)-1H-1,2,3-triazol-1-yl]-3-deoxy-2-O-methyl-1-thio-α-D-galactopyranoside | 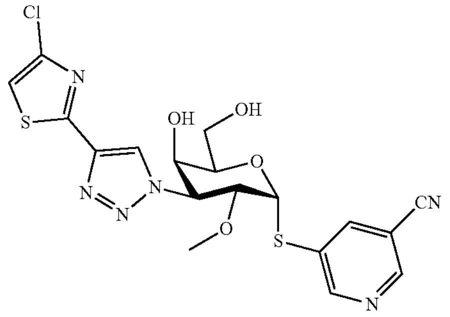 | 0.17 | 0.52 |
| 83 | 5-Cyanopyridin-3-yl 3-deoxy-3-[4-(2-hydroxythiazol-4-yl)-1H-1,2,3-triazol-1-yl]-2-O-methyl-1-thio-α-D-galactopyranoside | 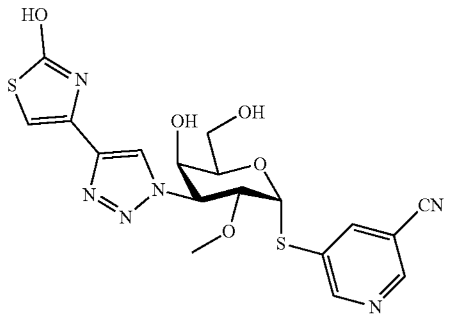 | 0.15 | 5.7 |

-continued

| Example | Name | Structure | Galectin-1 Kd (μM) | Galectin-3 Kd (μM) |
|---|---|---|---|---|
| 84 | 2-Cyano-5-ethynylpyridin-3-yl 3-[4-(2-aminothiazol-4-yl)-1H-1,2,3-triazol-1-yl]-3-deoxy-1-thio-α-D-galactopyranoside | 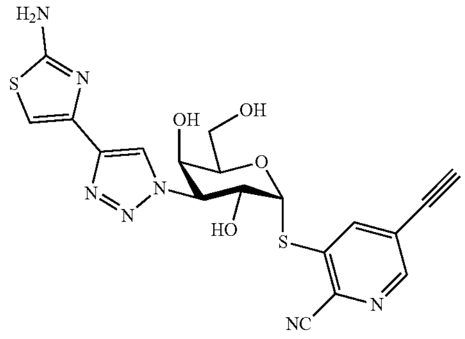 | 0.54 | 4.1 |
| 85 | 2-Cyano-5-ethynylpyridin-3-yl 3-[4-(2-aminothiazol-4-yl)-1H-1,2,3-triazol-1-yl]-3-deoxy-2-O-methyl-1-thio-α-D-galactopyranoside | 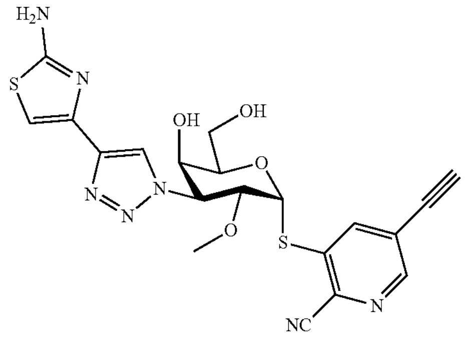 | 0.11 | 7.7 |
| 86 | 5-Bromo-2-cyanopyridin-3-yl 3-[4-(4-chlorothiazol-2-yl)-1H-1,2,3-triazol-1-yl]-3-deoxy-2-O-ethyl-1-thio-α-D-galactopyranoside | 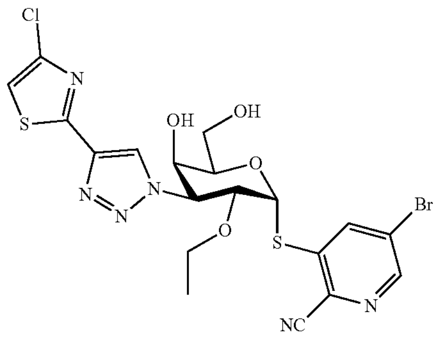 | 0.022 | 0.17 |
| 87 | 3,4-Dichlorophenyl 3-[4-(2-aminothiazol-4-yl)-1H-1,2,3-triazol-1-yl]-3-deoxy-2-O-ethyl-1-thio-α-D-galactopyranoside | 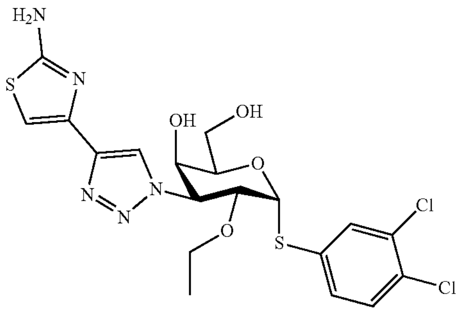 | 0.11 | 5.5 |

-continued

| Example | Name | Structure | Galectin-1 Kd (μM) | Galectin-3 Kd (μM) |
|---|---|---|---|---|
| 88 | 3-Chloro-4-cyanophenyl 3-[4-(2-aminothiazol-4-yl)-1H-1,2,3-triazol-1-yl]-3-deoxy-2-O-ethyl-1-thio-α-D-galactopyranoside | 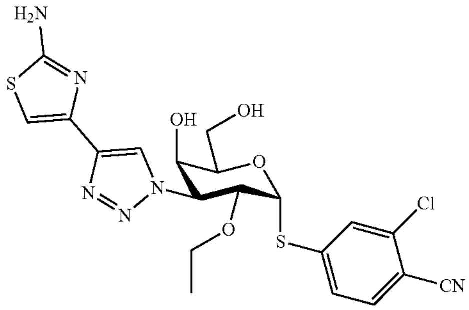 | 0.13 | 7.7 |
| 89 | 3-Chloro-4-cyanophenyl 2,3-dideoxy-3-[4-(2-hydroxythiazol-4-yl)-1H-1,2,3-triazol-1-yl]-1-thio-α-D-galactopyranoside | 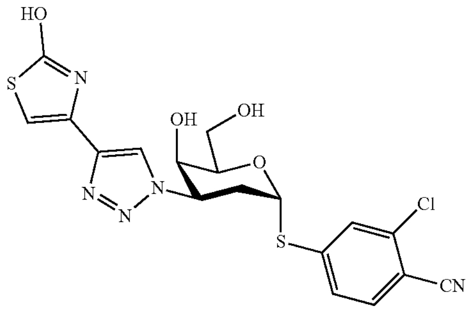 | 0.21 | 10.5 |
| 90 | 5-Bromo-2-(N,N-dimethylcarbamoyl) pyridin-3-yl 3-[4-(4-chlorothiazol-2-yl)-1H-1,2,3-triazol-1-yl]-3-deoxy-2-O-ethyl-1-thio-α-D-galactopyranoside | 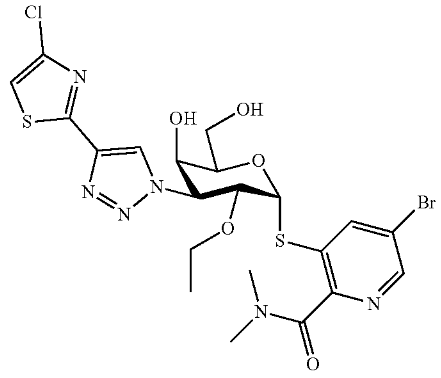 | 0.0085 | 0.044 |
| 91 | 5-Ethynyl-2-(N,N-dimethylcarbamoyl) pyridin-3-yl 3-[4-(4-chlorothiazol-2-yl)-1H-1,2,3-triazol-1-yl]-3-deoxy-2-O-methyl-1-thio-α-D-galactopyranoside | 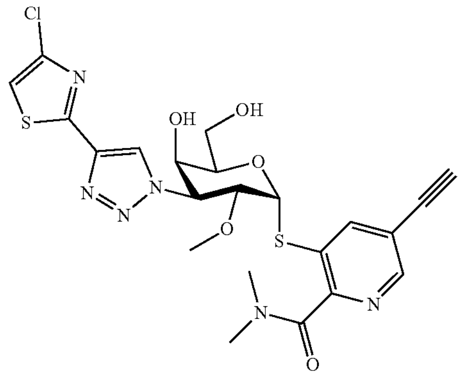 | 0.024 | 0.051 |

-continued

| Example | Name | Structure | Galectin-1 Kd (μM) | Galectin-3 Kd (μM) |
|---|---|---|---|---|
| 92 | 2-(N-Azetidinylcarbamoyl)-5-ethynylpyridin-3-yl 3-[4-(4-chlorothiazol-2-yl)-1H-1,2,3-triazol-1-yl]-3-deoxy-2-O-methyl-1-thio-α-D-galactopyranoside | 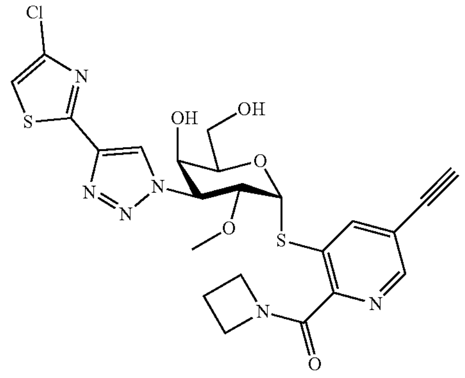 | 0.032 | 0.099 |
| 93 | 5-Chloro-2-(N-methylcarbamoyl) pyridin-3-yl 3-[4-(4-chlorothiazol-2-yl)-1H-1,2,3-triazol-1-yl]-3-deoxy-2-O-methyl-1-thio-α-D-galactopyranoside | 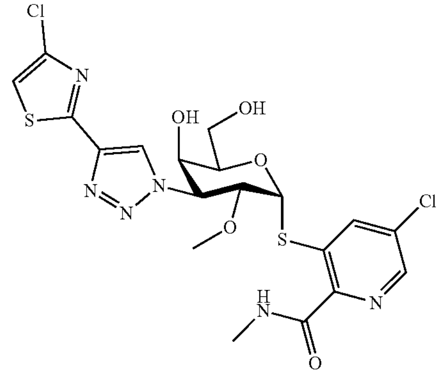 | 0.015 | 0.048 |
| 94 | 5-Chloro-2-(N-ethylcarbamoyl) pyridin-3-yl 3-[4-(4-chlorothiazol-2-yl)-1H-1,2,3-triazol-1-yl]-3-deoxy-2-O-methyl-1-thio-α-D-galactopyranoside | 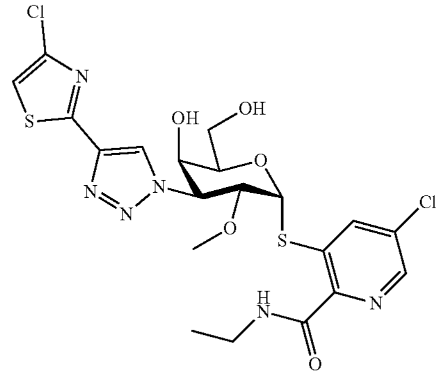 | 0.012 | 0.074 |
| 95 | 5-Chloro-2-(N-methylcarbamoyl) pyridin-3-yl 3-[4-(4-chlorothiazol-2-yl)-1H-1,2,3-triazol-1-yl]-3-deoxy-2-O-ethyl-1-thio-α-D-galactopyranoside | 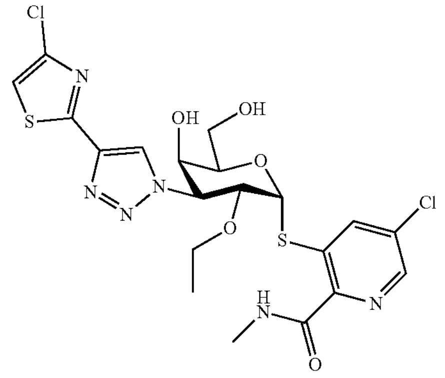 | 0.0080 | 0.093 |

-continued

| Example | Name | Structure | Galectin-1 Kd (μM) | Galectin-3 Kd (μM) |
|---|---|---|---|---|
| 96 | 5-Chloro-2-cyanophenyl 3-[4-(4-chlorothiazol-2-yl)-1H-1,2,3-triazol-1-yl]-3-deoxy-2-O-methyl-1-thio-α-D-galactopyranoside | 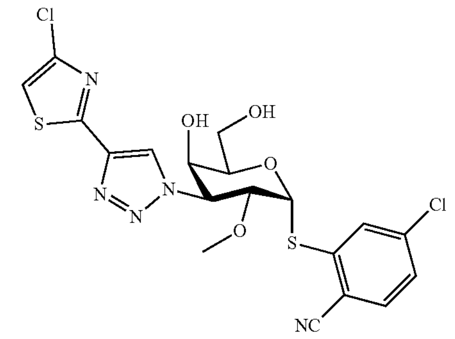 | 0.022 | 0.21 |
| 97 | 1,3-Benzothiazol-6-yl 3-[4-(4-chlorothiazol-2-yl)-1H-1,2,3-triazol-1-yl]-3-deoxy-2-O-methyl-1-thio-α-D-galactopyranoside | 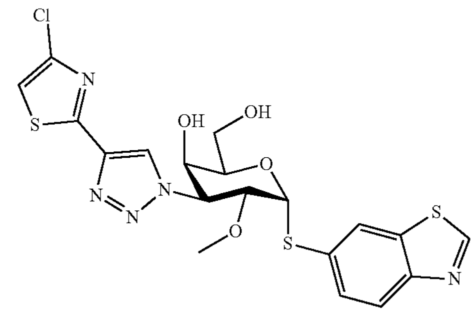 | 0.083 | 0.32 |
| 98 | 1,3-Benzothiazol-6-yl 3-deoxy-3-[4-(2-hydroxythiazol-4-yl)-1H-1,2,3-triazol-1-yl]-2-O-methyl-1-thio-α-D-galactopyranoside | 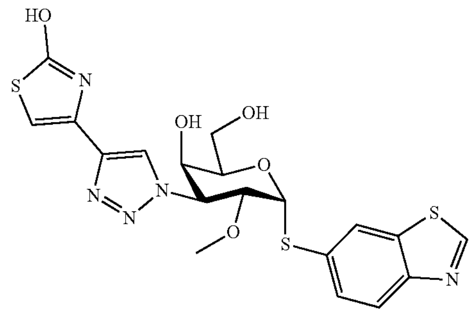 | 0.064 | 6.5 |
| 99 | 1,3-Benzothiazol-6-yl 3-[4-(2-aminothiazol-4-yl)-1H-1,2,3-triazol-1-yl]-3-deoxy-2-O-methyl-1-thio-α-D-galactopyranoside | 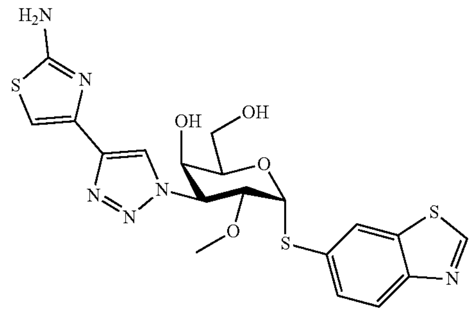 | 0.18 | 7.5 |

-continued

| Example | Name | Structure | Galectin-1 Kd (μM) | Galectin-3 Kd (μM) |
|---|---|---|---|---|
| 100 | 5-Cyano-1,3-benzothiazol-6-yl 3-[4-(4-chlorothiazol-2-yl)-1H-1,2,3-triazol-1-yl]-3-deoxy-2-O-methyl-1-thio-α-D-galactopyranoside | 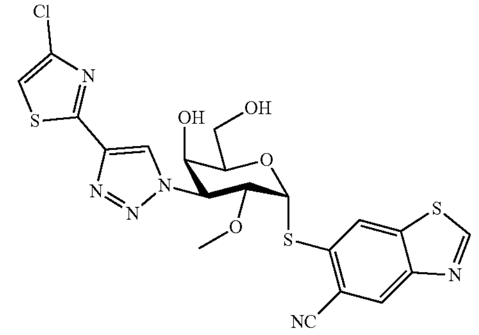 | 0.032 | 0.18 |
| 101 | Thiazolo[4,5-b]pyridin-6-yl 3-[4-(4-chlorothiazol-2-yl)-1H-1,2,3-triazol-1-yl]-3-deoxy-2-O-methyl-1-thio-α-D-galactopyranoside | 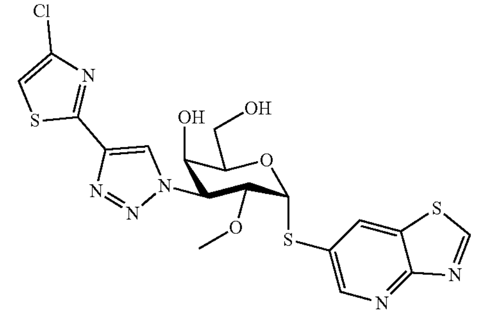 | 0.11 | 0.4 |
| 102 | 5-Methylsulfanylpyridin-3-yl 3-[4-(4-chlorothiazol-2-yl)-1H-1,2,3-triazol-1-yl]-3-deoxy-2-O-methyl-1-thio-α-D-galactopyranoside | 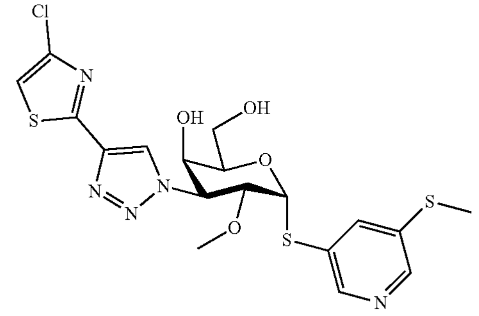 | 0.19 | 0.42 |
| 103 | 5-(Trifluoromethylsulfanyl)pyridin-3-yl 3-[4-(4-chlorothiazol-2-yl)-1H-1,2,3-triazol-1-yl]-3-deoxy-2-O-methyl-1-thio-α-D-galactopyranoside | 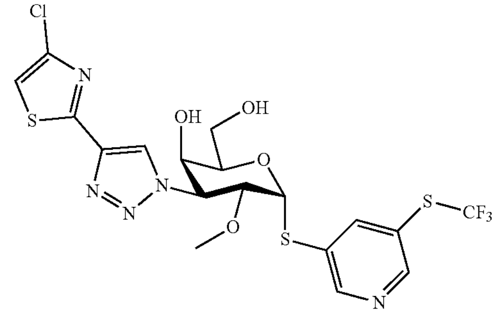 | 0.33 | 1 |

For some compounds of this invention wherein $R^1$ of formula 1 is an alkylated hydroxy, for example —$OCH_3$ high uptake and no efflux is observed in a CACO-2 model of uptake ver the human intestine. That predicts high likeliness of high human oral bioavailability. In that model (see Artursson, P.; Ungell, A. L.; Löfroth, J. E. Selective Paracellular Permeability in Two Models of Intestinal Absorption: Cultured Monolayers of Human Intestinal Epithelial Cells and Rat Intestinal Segments. *Pharm. Res.* 1993, 10 (8), 1123-1129.) Example 1 has a Papp from the apical to the basolateral side (A>B) of 20*10^-6 cm/s and a Papp of 28*10^-6 cm/s from the basolateral to the apical side B>A. Meaning the uptake is very high and virtually no efflux is observed.

SYNTHESIS OF EXAMPLES AND INTERMEDIATES

General Experimental

Nuclear Magnetic Resonance (NMR) spectra were recorded on a 400 MHz Bruker AVANCE III 500 instrument or a Varian instrument at 400 MHz, at 25° C. Chemical shifts are reported in ppm (d) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet. In the case of anomeric mixtures, the shifts of the individual anomers are reported separately and the α/β ratio was calculated based on the integration of the anomeric peaks. LC-MS were acquired on an Agilent 1200 HPLC coupled with an Agilent MSD mass spectrometer operating in ES (+) ionization mode. Column: XBridge C18 (4.6×50 mm, 3.5 μm) or SunFire C18 (4.6×50 mm, 3.5 μm). Solvent A water+0.1% TFA and solvent B Acetonitrile+0.1% TFA or solvent A water (10 mM Ammonium hydrogen carbonate) and solvent B Acetonitrile. Wavelength: 254 nM. Alternatively, LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength 254 nm.

Preparative HPLC was performed on a Gilson 281. Flow: 20 mL/min Column: X-Select 10 μm 19×250 mm column. Wavelength: 254 nm or 214 nm. Solvent A water (10 mM Ammonium hydrogen carbonate) and solvent B Acetonitrile. Alternatively, preparative HPLC was performed on a Gilson 215. Flow: 25 mL/min Column: XBrige prep C18 10 μm OBD (19×250 mm) column. Wavelength: 254 nM. Solvent A water (10 mM Ammonium hydrogen carbonate) and solvent B Acetonitrile. Alternatively, preparative HPLC were acquired on a Gilson system. Flow: 15 ml/min Column: kromasil 100-5-C18 column. Wavelength: 220 nm. Solvent A water+0.1% TFA and solvent B Acetonitrile+0.1% TFA.

The following abbreviations are used aq: aqueous
Calcd: Calculated
MeCN: Acetonitrile
CuI: Copper Iodide
DCM: Dichloromethane
DIPEA: Diisopropylethylamine
DMF: N,N-dimethylformamide
ESI-MS: Electrospray ionization mass spectrometry
EtOAc or EA: Ethylacetate
$Et_3N$: Triethylamine
GC: Gas chromatography
h: hour(s)
HATU: 1-[Bis(dimethylamino)methylene]-1H-1,2,3-triazolo[4,5-b]pyridinium 3-oxid hexafluorophosphate
HPLC: High performance liquid chromatography
LC: Liquid Chromatography
MeCN: Acetonitrile
mL: milliliter
MeOH: Methanol
MeOD: Deuterated methanol
mm: millimeter
mM: millimolar
MS: Mass spectroscopy
nm: nanometer NaI: Sodium Iodide
NaOMe: Sodium methoxide
$N_2$: Nitrogen gas
NMR: Nuclear magnetic resonance
$Pd(PPh_3)_4$: Tetrakis(triphenylphosphine)palladium(0)
PE: petroleum ether
pH: acidity
Prep: Preparative
rt: Room temperature
TBAF: Tetrabutylammonium fluoride
TFA: trifluoroacetic acid
THF: Tetrahydrofuran
TMS: Trimethylsilyl
UV: Ultraviolet
Å: Ångstrom

SYNTHESIS OF EXAMPLE 1-103 FROM THEIR RESPECTIVE INTERMEDIATES 1-103

Example 1

3,5-Dichloro-4-fluorophenyl 3-deoxy-2-O-methyl-3-[4-(2-thiazolyl)-1H-1,2,3-triazol-1-yl]-1-thio-α-D-galactopyranoside

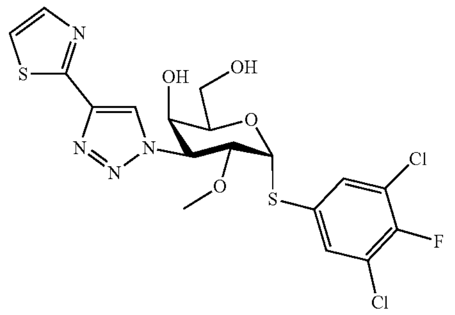

To a solution of 3,5-dichloro-4-fluorophenyl 4,6-O-benzylidene-3-deoxy-2-O-methyl-3-[4-(2-thiazolyl)-1H-1,2,3-triazol-1-yl]-1-thio-α-D-galactopyranoside (76 mg, 0.13 mmol) in DCM (10 mL) TFA (0.5 mL, 6.73 mmol) and $H_2O$ (0.5 mL) were added. The mixture was stirred 12 h at rt. $Et_3N$ (2.0 mL) was added dropwise at 0° C. The mixture was concentrated and purified by prep HPLC [MeCN/$H_2O$ (10 mmol/L $NH_4HCO_3$), X-Select 10 μm 19*250 mm, 20 mL/min, UV 254] to give the title compound (54 mg, 84%). ESI-MS m/z calcd for $[C_{18}H_{17}Cl_2FN_4O_4S_2]$ $[M+H]^+$: 507.0; found: 507.0. $^1H$ NMR (400 MHz, Methanol-$d_4$) δ 8.50 (s, 1H), 7.79 (d, J=3.2 Hz, 1H), 7.66 (d, J=6.0 Hz, 2H), 7.54 (d, J=3.2, 1H), 6.08 (d, J=5.2 Hz, 1H), 4.95 (dd, J=11.2, 2.8 Hz, 1H), 4.52 (dd, J=11.2, 5.2 Hz, 1H), 4.39-4.36 (m, 1H), 4.10 (d, J=2.4 Hz, 1H), 3.62-3.60 (m, 2H), 3.31 (s, 3H).

Example 2

5-Bromopyridin-3-yl 3-deoxy-2-O-methyl-3-[4-(2-thiazolyl)-1H-1,2,3-triazol-1-yl]-1-thio-α-D-galactopyranoside

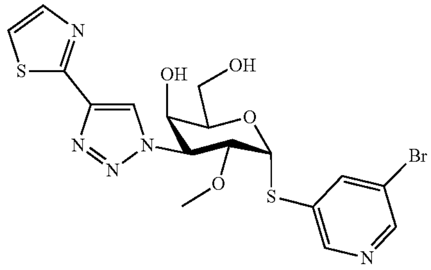

A solution of 5-bromopyridin-3-yl 4,6-O-benzylidene-3-deoxy-2-O-methyl-3-[4-(2-thiazolyl)-1H-1,2,3-triazol-1-yl]-1-thio-α-D-galactopyranoside (200 mg, 0.34 mmol) in TFA (0.5 mL) and DCM (5 mL) was stirred 2 h at rt. Saturated aq $NaHCO_3$ was added dropwise to adjust pH to 7-8. Water (10 mL) and DCM (15 mL) were added and the phases were separated. The isolated aqueous phase was further extracted with DCM (2×10 mL). The combined organic layers were concentrated and purified by prep HPLC (X-Select 10 μm 19*250 mm, 20 mL/min, $MeCN/H_2O$ (10 mmol/L $NH_4HCO_3$)=40-90%) to afford the title compound (90 mg, 63%). ESI-MS m/z calcd for $[C_{17}H_{18}BrN_5O_4S_2]$ $[M+H]^+$: 500.0, found: 500.0 $^1H$ NMR (400 MHz, Methanol-$d_4$) δ 8.60 (d, J=1.8 Hz, 1H), 8.51 (s, 1H), 8.48 (d, J=2.1 Hz, 1H), 8.26 (t, J=2.0 Hz, 1H), 7.80 (d, J=3.3 Hz, 1H), 7.55 (d, J=3.3 Hz, 1H), 6.18 (d, J=5.3 Hz, 1H), 4.99 (dd, J=11.4, 2.9 Hz, 1H), 4.55 (dd, J=11.4, 5.3 Hz, 1H), 4.37 (t, J=5.9 Hz, 1H), 4.11 (d, J=1.9 Hz, 1H), 3.63-3.52 (m, 2H), 3.32 (s, 3H).

Example 3

5-Bromo-2-cyanopyridin-3-yl 3-deoxy-2-O-methyl-3-[4-(2-thiazolyl)-1H-1,2,3-triazol-1-yl]-1-thio-α-D-galactopyranoside

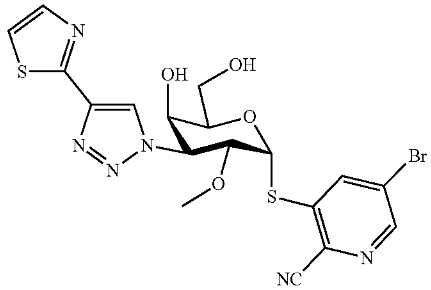

A solution of 5-bromo-2-cyanopyridin-3-yl 4,6-di-O-acetyl-3-deoxy-2-O-methyl-3-[4-(thiazol-2-yl)-1H-1,2,3-triazol-1-yl]-1-thio-α-D-galactopyranoside (57.0 mg, 0.094 mmol) in the MeOH (3.0 mL), $Et_3N$ (2.0 mL) and water (1.0 mL) was stirred 4 h at rt. The mixture was concentrated and purified by prep HPLC (X-Select 10 μm 19*250 mm, 20 mL/min, $MeCN/H_2O$ (10 mmol/L $NH_4HCO_3$)=40-90%) to afford the title compound (22.0 mg, 45%). ESI-MS m/z calcd for $[C_{18}H_{17}BrN_6O_4S_2]$ $[M+H]^+$: 525.0, found: 525.0. $^1H$ NMR (400 MHz, Methanol-$d_4$) δ 8.73 (d, J=2.0 Hz, 1H), 8.65 (d, J=2.0 Hz, 1H), 8.64 (s, 1H), 7.91 (d, J=3.6 Hz, 1H), 7.66 (d, J=3.2 Hz, 1H), 6.53 (d, J=5.2 Hz, 1H), 5.16 (dd, J=11.2, 2.8 Hz, 1H), 4.74 (dd, J=11.2, 5.2 Hz, 1H), 4.43 (t, J=6.0 Hz, 1H), 4.24 (d, J=2.4 Hz, 1H), 3.70 (d, J=6.0 Hz, 2H), 3.40 (s, 3H).

Example 4

5-Chloro-2-cyanopyridin-3-yl 3-deoxy-2-O-methyl-3-[4-(2-thiazolyl)-1H-1,2,3-triazol-1-yl]-1-thio-α-D-galactopyranoside

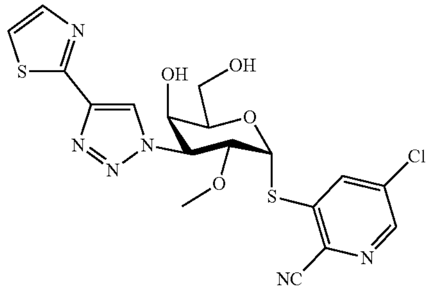

A solution of 5-chloro-2-cyanopyridin-3-yl 4,6-O-benzylidene-3-deoxy-2-O-methyl-3-[4-(2-thiazolyl)-1H-1,2,3-triazol-1-yl]-1-thio-α-D-galactopyranoside (90.0 mg, 0.16 mmol) in DCM/TFA (10.0 mL, 19:1) was stirred 1 h at rt. The pH value of the mixture was adjusted to ~8 with $Et_3N$ followed by evaporation of the solvent. The residue was purified by prep HPLC ($MeCN/H_2O$ (10 mmol/L $NH_4HCO_3$)=0~20%, X-Select 10 μm 19*250 mm, 20 mL/min, UV 254) to give the title compound (40.5 mg, 53%). ESI-MS m/z calcd for $[C18H_{17}ClN_6O_4S_2]$ $[M+H]^+$: 481.0, found: 481.0. $^1H$ NMR (400 MHz, Methanol-$d_4$) δ 8.56-8.47 (m, 2H), 8.38 (d, J=2.1 Hz, 1H), 7.80 (d, J=3.3 Hz, 1H), 7.55 (d, J=3.3 Hz, 1H), 6.42 (d, J=5.3 Hz, 1H), 5.04 (dd, J=11.3, 2.8 Hz, 1H), 4.62 (dd, J=11.3, 5.3 Hz, 1H), 4.31 (t, J=6.0 Hz, 1H), 4.13 (d, J=2.4 Hz, 1H), 3.66-3.52 (m, 2H), 3.37 (s, 3H).

Example 5

5-Chloro-2-cyanopyridin-3-yl 2-O-benzyl-3-deoxy-3-[4-(2-thiazolyl)-1H-1,2,3-triazol-1-yl]-1-thio-α-D-galactopyranoside

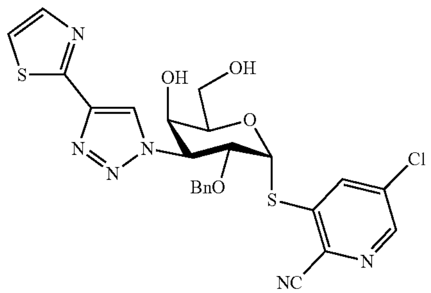

A solution of 5-chloro-2-cyanopyridin-3-yl 2-O-benzyl-4,6-O-benzylidene-3-deoxy-3-[4-(2-thiazolyl)-1H-1,2,3-triazol-1-yl]-1-thio-α-D-galactopyranoside (68 mg, 0.11 mmol) in DCM/TFA (5 mL, 4:1) was stirred 3 h at rt. The mixture was neutralized with $Et_3N$ and evaporated. The residue was purified by prep HPLC [MeCN/$H_2O$ (10 mmol/L $NH_4HCO_3$), X-Select 10 μm 19*250 mm, 20 mL/min, UV 254] to give the title compound (23.3 mg, 40%). ESI-MS m/z calcd for [$C_{24}H_{21}ClN_6O_4S_2$] [M+H]$^+$: 557.1; found: 557.0. $^1$H NMR (400 MHz, DMSO-$d_6$) δ 8.75 (d, J=2.0 Hz, 1H), 8.69 (s, 1H), 8.56 (d, J=2.0 Hz, 1H), 7.95 (d, J=3.2 Hz, 1H), 7.80 (d, J=3.2 Hz, 1H), 7.26-7.16 (m, 3H), 7.16-7.07 (m, 2H), 6.69 (d, J=5.2 Hz, 1H), 5.67 (d, J=6.0 Hz, 1H), 5.01 (ddd, J=16.8, 11.2, 4.0 Hz, 2H), 4.86-4.72 (m, 2H), 4.54 (d, J=11.2 Hz, 1H), 4.31-4.20 (m, 1H), 4.15-4.06 (m, 1H), 3.59-3.39 (m, 2H).

Example 6

5-Chloro-2-cyanopyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside

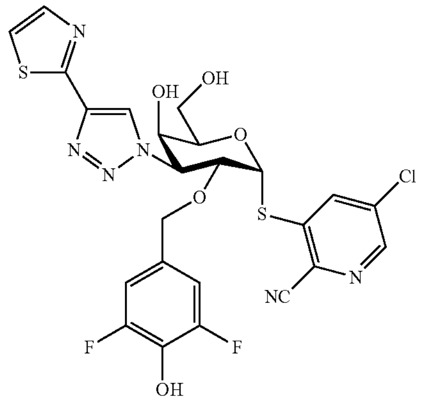

To a solution of 5-chloro-2-cyanopyridin-3-yl 4,6-O-benzylidene-3-deoxy-2-O-(3,5-difluoro-4-(4-methoxybenzyloxy)benzyl)-3-[4-(2-thiazolyl)-1H-1,2,3-triazol-1-yl]-1-thio-α-D-galactopyranoside (120 mg, 0.14 mmol) in DCM (5 mL) TFA (502 mg, 4.4 mmol) and $H_2O$ (0.5 mL) were added and the mixture was stirred 12 h at rt. $Et_3N$ (1.0 mL) was added dropwise at 0° C. The mixture was concentrated and purified by prep HPLC [MeCN/$H_2O$ (10 mmol/L $NH_4HCO_3$), X-Select 10 μm 19*250 mm, 20 mL/min, UV 254] to give the title compound (30 mg, 34%). ESI-MS m/z calcd for [$C_{24}H_{19}ClF_2N_6O_5S_2$] [M+H]$^+$: 609.1; found: 609.1. $^1$H NMR (400 MHz, Methanol-$d_4$) δ 8.51 (d, J=2.0 Hz, 1H), 8.39-8.37 (m, 1H), 8.34 (d, J=2.0 Hz, 1H), 7.80 (d, J=3.2 Hz, 1H), 7.54 (d, J=3.6 Hz, 1H), 6.59-6.50 (m, 2H), 6.30 (d, J=5.6 Hz, 1H), 5.08 (dd, J=11.2, 2.8 Hz, 1H), 4.73 (dd, J=11.2, 5.6 Hz, 1H), 4.56 (d, J=11.6 Hz, 1H), 4.35-4.29 (m, 2H), 4.12 (d, J=2.8 Hz, 1H), 3.60-3.58 (m, 2H).

Example 7

3,5-Dichloro-4-fluorophenyl 3-deoxy-3-[4-(2-hydroxythiazol-4-yl)-1H-1,2,3-triazol-1-yl]-2-O-methyl-1-thio-α-D-galactopyranoside

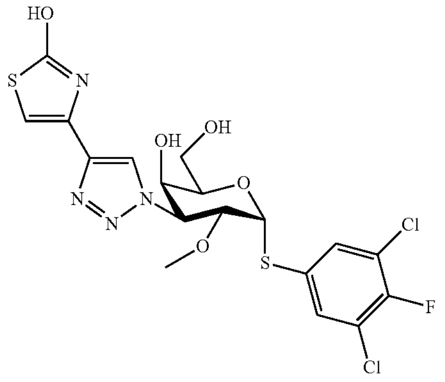

A solution of 3,5-dichloro-4-fluorophenyl 4,6-O-benzylidene-3-deoxy-3-[4-(2-hydroxythiazol-4-yl)-1H-1,2,3-triazol-1-yl]-2-O-methyl-1-thio-α-D-galactopyranoside (35.0 mg, 0.057 mmol) in DCM/TFA (3 mL, 19:1) was stirred 3 h at rt. $Et_3N$ was added to neutralize the TFA. The mixture was concentrated and purified by prep HPLC (MeCN/$H_2O$ (10 mmol/L $NH_4HCO_3$)=40~80%, X-Select 10 μm 19*250 mm, 20 mL/min, UV 254) to give the title compound (20.9 mg, 70%). ESI-MS m/z calcd for [$C_{18}H_{17}Cl_2FN_4O_5S_2$] [M+H]$^+$: 523.0; found: 523.0. $^1$H NMR (400 MHz, Methanol-$d_4$) δ 8.35 (s, 1H), 7.74 (d, J=6.3 Hz, 2H), 6.70 (s, 1H), 6.16 (d, J=5.3 Hz, 1H), 4.99 (dd, J=11.4, 2.8 Hz, 1H), 4.53 (dd, J=11.4, 5.3 Hz, 1H), 4.45 (t, J=6.0 Hz, 1H), 4.16 (d, J=2.4 Hz, 1H), 3.75-3.61 (m, 2H), 3.38 (s, 3H).

Example 8

3,4-Dichlorophenyl 3-deoxy-3-[4-(2-hydroxythiazol-4-yl)-1H-1,2,3-triazol-1-yl]-2-O-isopropyl-1-thio-α-D-galactopyranoside

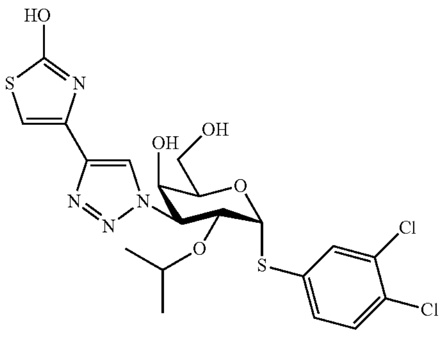

To a solution of 3,4-dichlorophenyl 3-azido-4,6-O-benzylidene-3-deoxy-2-O-isopropyl-1-thio-α-D-galactopyranoside (80 mg, 0.16 mmol) and 4-(2-trimethylsilylethynyl)thiazol-2-ol (63.6 mg, 0.32 mmol) in DMF (2 mL) DIPEA (0.138 mL, 0.81 mmol) was added followed by CsF (49 mg, 0.32 mmol) and CuI (9.21 mg, 0.048 mmol) and the mixture was stirred 4 h at rt. The mixture was diluted with water (5 mL) and extracted with DCM. The organic phase was washed with water (6×5 mL) and concentrated. The residue was stirred 2 h at rt in DCMTFA (5.25 mL, 20:1). The pH of the mixture was adjusted to pH=8 using $Et_3N$. The mixture was concentrated and purified by prep HPLC ($MeCN/H_2O$ (10 mmol/L $NH_4HCO_3$)=0~50%, X-Select 10 μm 19*250 mm, 20 mL/min, UV 254) to give the title compound (10.1 mg, 12%). ESI-MS m/z calcd for [$C_{20}H_{22}Cl_2N_4O_5S_2$] $[M+H]^+$: 533.0, found: 533.0. $^1H$ NMR (400 MHz, Methanol-$d_4$) δ 8.30 (s, 1H), 7.68 (d, J=1.9 Hz, 1H), 7.41 (dt, J=16.1, 5.2 Hz, 2H), 6.61 (s, 1H), 6.00 (d, J=5.3 Hz, 1H), 4.91 (dd, J=11.3, 2.8 Hz, 1H), 4.60 (dd, J=11.3, 5.3 Hz, 1H), 4.51 (s, 1H), 4.33 (t, J=6.2 Hz, 1H), 4.08 (d, J=2.4 Hz, 1H), 3.71-3.51 (m, 3H), 1.02 (d, J=6.1 Hz, 3H), 0.77 (d, J=6.0 Hz, 3H).

Example 9

3,4-Dichlorophenyl 3-deoxy-3-[4-(2-hydroxythiazol-4-yl)-1H-1,2,3-triazol-1-yl]-2-O-methyl-1-thio-α-D-galactopyranoside

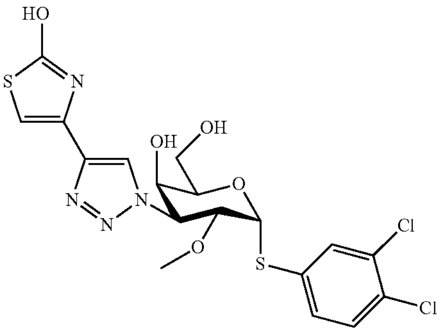

To a solution of 3,4-dichlorophenyl 4,6-O-benzylidene-3-deoxy-3-[4-(2-hydroxythiazol-4-yl)-1H-1,2,3-triazol-1-yl]-2-O-methyl-1-thio-α-D-galactopyranoside (160 mg, 0.26 mmol) in DCM (10 mL) TFA (1.46 g, 12.8 mmol) and $H_2O$ (0.5 mL) were added and the mixture was stirred 12 h at rt. $Et_3N$ (3.0 mL) was added dropwise at 0° C. The mixture was concentrated and purified by prep HPLC [$MeCN/H_2O$ (10 mmol/L $NH_4HCO_3$), X-Select 10 μm 19*250 mm, 20 mL/min, UV 254] to give the title compound (90 mg, 70%). ESI-MS m/z calcd for [$C_{18}H_{18}Cl_2N_4O_5S_2$] $[M+H]^+$: 505.0; found: 504.8. $^1H$ NMR (400 MHz, Methanol-$d_4$) δ 8.38 (s, 1H), 7.84 (d, J=2.0 Hz, 1H), 7.56-7.50 (m, 2H), 6.73 (s, 1H), 6.19 (d, J=5.6 Hz, 1H), 5.03 (dd, J=11.2, 2.8 Hz, 1H), 4.56 (dd, J=11.2, 5.2 Hz, 1H), 4.49-4.46 (m, 1H), 4.19 (d, J=2.0 Hz, 1H), 3.74-3.67 (m, 2H), 3.40 (s, 3H).

Example 10

3,4-Dichlorophenyl 2,3-dideoxy-3-[4-(2-hydroxythiazol-4-yl)-1H-1,2,3-triazol-1-yl]-1-thio-α-D-galactopyranoside

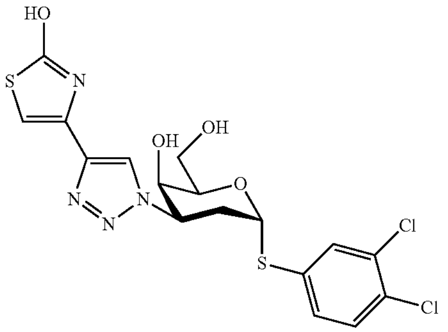

To a solution of 4,6-di-O-acetyl 3-deoxy-3-[4-(2-hydroxythiazol-4-yl)-1H-1,2,3-triazol-1-yl]-D-galactal (25 mg, 0.066 mmol) and oxotrichloro[(dimethylsulfide)triphenylphosphine oxide]rhenium (V) (4.3 mg, 0.0066 mmol) in toluene (1 mL) 3,4-dichlorobenzenethiol (13 μL, 0.099 mmol) was added and the mixture was stirred 20 h at 70° C. The mixture was evaporated, and the residue was stirred 30 min at rt in NaOMe (0.1 mL, 1 M) and MeOH (0.5 mL). The solution was concentrated and purified by prep HPLC ($C_{18}$, $H_2O$/MeCN/0.1% TFA) to afford the title compound (1.02 mg, 3%). ESI-MS m/z calcd for [$C_{17}H_{16}Cl_2N_4O_4S_2$] $[M+H]^+$: 475.0; found: 475.0, $^1H$ NMR (400 MHz, Methanol-$d_4$) δ 8.29 (s, 1H), 7.78 (d, J=1.9 Hz, 1H), 7.51 (dd, J=8.4, 2.0 Hz, 1H), 7.48 (d, J=8.4 Hz, 1H), 6.68 (s, 1H), 5.93 (d, J=5.5 Hz, 1H), 5.19-5.12 (m, 1H), 4.47 (t, J=6.1 Hz, 1H), 4.16 (s, 1H), 3.78-3.68 (m, 2H), 3.09 (td, J=13.6, 5.9 Hz, 1H), 2.32 (dd, J=13.3, 4.1 Hz, 1H).

Example 11

5-Bromo-2-cyanopyridin-3-yl 3-[4-(4-chlorothiazol-2-yl)-1H-1,2,3-triazol-1-yl]-3-deoxy-2-O-methyl-1-thio-α-D-galactopyranoside

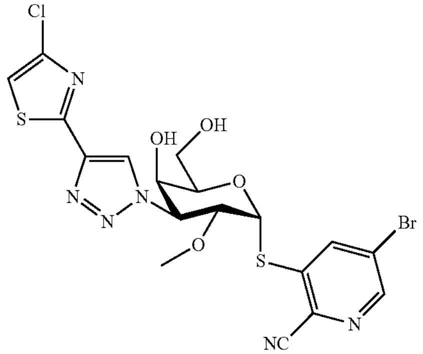

A solution of 5-bromo-2-cyanopyridin-3-yl 4,6-di-O-acetyl-3-[4-(4-chlorothiazol-2-yl)-1H-1,2,3-triazol-1-yl]-3-deoxy-2-O-methyl-1-thio-α-D-galactopyranoside (28.0 mg, 0.044 mmol) in MeOH (6.0 mL), Et3N (3.0 mL) and water (1.0 mL) was stirred 3 h at rt. The mixture was concentrated and purified by prep HPLC ($MeCN/H_2O$ (10 mmol/L $NH_4HCO_3$), X-Select 10 μm 19*250 mm, 20 mL/min, UV 254) to give the title compound (10.3 mg, 42%). ESI-MS m/z calcd for $[C_{18}H_{16}BrClN_6O_4S_2]$ $[M+H]^+$: 559.0; found: 558.9. $^1H$ NMR (400 MHz, Methanol-$d_4$) δ 8.73 (d, J=2.0 Hz, 1H), 8.67 (s, 1H), 8.65 (d, J=2.0 Hz, 1H), 7.50 (s, 1H), 6.53 (d, J=5.2 Hz, 1H), 5.16 (dd, J=11.2, 3.2 Hz, 1H), 4.73 (dd, J=11.2, 5.6 Hz, 1H), 4.43 (t, J=6.0 Hz, 1H), 4.24 (d, J=2.4 Hz, 1H), 3.70 (d, J=6.0 Hz, 2H), 3.49 (s, 3H).

Example 12

3-Bromo-2-cyanopyridin-5-yl 3-[4-(4-chlorothiazol-2-yl)-1H-1,2,3-triazol-1-yl]-3-deoxy-2-O-methyl-1-thio-α-D-galactopyranoside

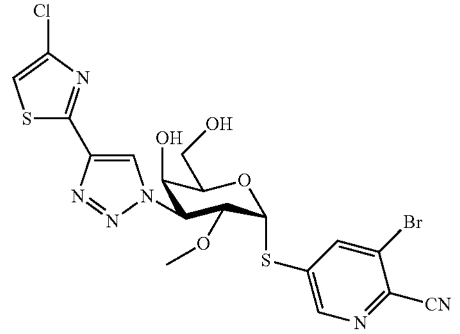

A solution of 3-bromo-2-cyanopyridin-5-yl 4,6-di-O-acetyl-3-[4-(4-chlorothiazol-2-yl)-1H-1,2,3-triazol-1-yl]-3-deoxy-2-O-methyl-1-thio-α-D-galactopyranoside (35.0 mg, 0.054 mmol) in MeOH (3.0 mL), $Et_3N$ (2.0 mL) and water (1.0 mL) was stirred 3 h at rt. The mixture was concentrated and purified by prep HPLC ($MeCN/H_2O$ (10 mmol/L $NH_4HCO_3$), X-Select 10 μm 19*250 mm, 20 mL/min, UV 254) to give the title compound (13.3 mg, 44%). ESI-MS m/z calcd for $[C_{18}H_{16}BrClN_6O_4S_2]$ $[M+H]^+$: 559.0; found: 559.0. $^1H$ NMR (400 MHz, Methanol-$d_4$) δ 8.80 (d, J=2.0 Hz, 1H), 8.67 (s, 1H), 8.53 (d, J=2.0 Hz, 1H), 7.49 (s, 1H), 6.58 (d, J=5.6 Hz, 1H), 5.14 (dd, J=11.6, 2.8 Hz, 1H), 4.74 (dd, J=11.6, 5.2 Hz, 1H), 4.35 (t, J=6.0 Hz, 1H), 4.20 (d, J=2.4 Hz, 1H), 3.70 (d, J=6.0 Hz, 2H), 3.42 (s, 3H).

Example 13

5-Chloro-2-cyanopyridin-3-yl 3-[4-(4-chlorothiazol-2-yl)-1H-1,2,3-triazol-1-yl]-3-deoxy-2-O-methyl-1-thio-α-D-galactopyranoside

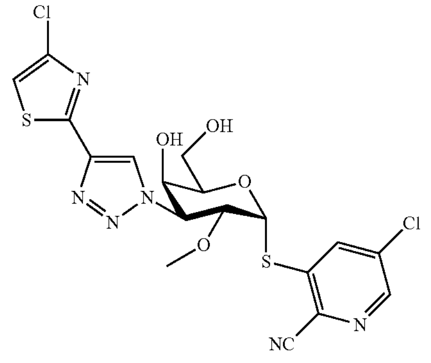

A solution of 5-chloro-2-cyanopyridin-3-yl 4,6-O-benzylidene-3-[4-(4-chloro-thiazol-2-yl)-1H-1,2,3-triazol-1-yl]-3-deoxy-2-O-methyl-1-thio-α-D-galactopyranoside (70 mg, 0.12 mmol) in DCM/TFA (10 mL, 19:1) was stirred 1 h at rt before the pH was adjusted to pH=8 with $Et_3N$. The mixture was concentrated and purified by prep HPLC ($MeCN/H_2O$ (10 mmol/L $NH_4HCO_3$)=20~70%, X-Select 10 μm 19*250 mm, 20 mL/min, UV 254) to give the title compound (25.0 mg, 42%). ESI-MS m/z calcd for $[C_{18}H_{16}Cl_2N_6O_4S_2]$ $[M+H]^+$: 515.0, found: 515.0. $^1H$ NMR (400 MHz, Methanol-$d_4$) δ 8.55 (s, 1H), 8.50 (d, J=2.1 Hz, 1H), 8.38 (d, J=2.1 Hz, 1H), 7.37 (s, 1H), 6.41 (d, J=5.3 Hz, 1H), 5.04 (dd, J=11.3, 2.8 Hz, 1H), 4.63 (dd, J=11.3, 5.3 Hz, 1H), 4.31 (t, J=6.0 Hz, 1H), 4.12 (d, J=2.3 Hz, 1H), 3.58 (t, J=10.3 Hz, 2H), 3.37 (s, 3H).

Example 14

3-Chloro-2-cyanopyridin-5-yl 3-[4-(4-chlorothiazol-2-yl)-1H-1,2,3-triazol-1-yl]-3-deoxy-2-O-methyl-1-thio-α-D-galactopyranoside

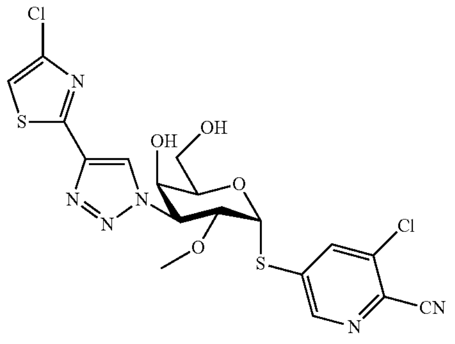

A solution of 3-chloro-2-cyanopyridin-3-yl 4,6-di-O-acetyl-3-[4-(4-chlorothiazol-2-yl)-1H-1,2,3-triazol-1-yl]-3-deoxy-2-O-methyl-1-thio-α-D-galactopyranoside (48 mg, 0.080 mmol) in MeOH (3.0 mL), $Et_3N$ (2.0 mL) and water (1.0 mL) was stirred 3 h at rt. The mixture was concentrated and purified by prep HPLC (MeCN/$H_2O$ (10 mmol/L $NH_4HCO_3$), X-Select 10 μm 19*250 mm, 20 mL/min, UV 254) to give the title compound (24.5 mg, 59%). ESI-MS m/z calcd for $[C_{18}H_{16}Cl_2N_6O_4S_2]$ $[M+H]^+$: 515.0; found: 515.1. $^1H$ NMR (400 MHz, Methanol-$d_4$) δ 8.76 (d, J=2.0 Hz, 1H), 8.67 (s, 1H), 8.40 (d, J=1.6 Hz, 1H), 7.49 (s, 1H), 6.59 (d, J=5.6 Hz, 1H), 5.14 (dd, J=11.2, 2.8 Hz, 1H), 4.74 (dd, J=11.2, 5.2 Hz, 1H), 4.35 (t, J=6.0 Hz, 1H), 4.20 (d, J=2.0 Hz, 1H), 3.70-3.72 (m, 2H), 3.42 (s, 3H).

Example 15

5-Chloro-2-cyanopyridin-3-yl 3-[4-(2-chlorothiazol-4-yl)-1H-1,2,3-triazol-1-yl]-3-deoxy-2-O-methyl-1-thio-α-D-galactopyranoside

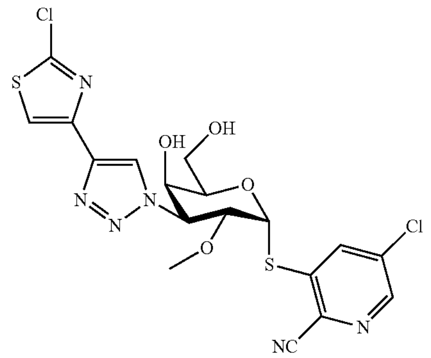

A solution of 5-chloro-2-cyanopyridin-3-yl 4,6-O-benzylidene-3-[4-(2-chlorothiazol-4-yl)-1H-1,2,3-triazol-1-yl]-3-deoxy-2-O-methyl-1-thio-α-D-galactopyranoside (55.0 mg, 0.091 mmol) in DCM/TFA (10 mL, 19:1) was stirred 1 h at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (28.5 mg, 61%). ESI-MS m/z calcd for $[C_{18}H_{16}Cl_2N_6O_4S_2]$ $[M+H]^+$: 515.0; found: 515.0. $^1H$ NMR (400 MHz, Methanol-$d_4$) δ 8.51 (d, J=2.0 Hz, 1H), 8.38 (d, J=2.0 Hz, 1H), 8.36 (s, 1H), 7.77 (s, 1H), 6.42 (d, J=5.2 Hz, 1H), 5.00 (dd, J=11.2, 2.8 Hz, 1H), 4.61 (dd, J=11.2, 5.2 Hz, 1H), 4.31 (t, J=6.0 Hz, 1H), 4.11 (d, J=2.4 Hz, 1H), 3.64-3.48 (m, 2H), 3.36 (s, 3H).

Example 16

3,5-Dichloro-4-fluorophenyl 3-[4-(2-aminothiazol-4-yl)-1H-1,2,3-triazol-1-yl]-3-deoxy-2-O-methyl-1-thio-α-D-galactopyranoside

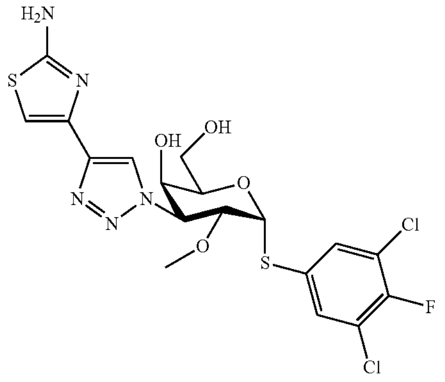

To a solution of 3,5-dichloro-4-fluorophenyl 3-[4-(2-aminothiazol-4-yl)-1H-1,2,3-triazol-1-yl]-4,6-O-benzylidene-3-deoxy-2-O-methyl-1-thio-α-D-galactopyranoside (54.0 mg, 0.089 mmol) in DCM (5 mL) TFA (0.263 mL, 3.54 mmol) was added and the mixture was stirred overnight at rt. The mixture was evaporated and purified by column chromatography (MeCN/$H_2O$=0/100~1/5, C-18 column, 20 mL/min, UV 254) to afford the title compound (17.9 mg, 39%). ESI-MS m/z calcd for $[C_{18}H_{18}Cl_2FN_5O_4S_2]$ $[M+H]^+$: 522.0; found: 522.0. $^1H$ NMR (400 MHz, Methanol-$d_4$) δ 8.23 (s, 1H), 7.75 (d, J=6.3 Hz, 2H), 6.95 (s, 1H), 6.16 (d, J=5.3 Hz, 1H), 4.97 (dd, J=11.3, 2.6 Hz, 1H), 4.55 (dd, J=11.4, 5.3 Hz, 1H), 4.45 (t, J=6.2 Hz, 1H), 4.17 (s, 1H), 3.77-3.63 (m, 2H), 3.38 (s, 3H).

Example 17

5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside

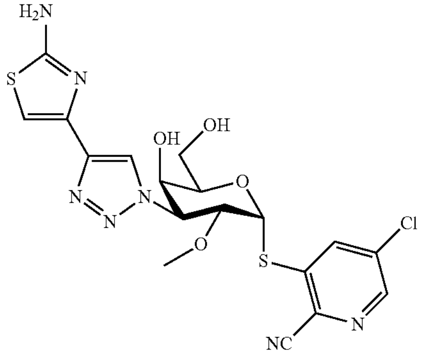

A solution of 5-chloro-2-cyanopyridin-3-yl 3-[4-(2-aminothiazol-4-yl)-1H-1,2,3-triazol-1-yl]-4,6-O-benzylidene 3-deoxy-2-O-methyl-1-thio-α-D-galactopyranoside (75 mg, 0.13 mmol) in DCM/TFA (10 mL, 19:1) was stirred 3 h at rt before the pH was adjusted to 8 using $Et_3N$. The mixture was concentrated and purified by prep HPLC ($MeCN/H_2O$ (10 mmol/L $NH_4HCO_3$)=0~60%, X-Select 10 μm 19*250 mm, 20 mL/min, UV 254) to give the title compound (26.4 mg, 42%). ESI-MS m/z calcd for [$C_{18}H_{18}ClN_7O_4S_2$] $[M+H]^+$: 496.1, found: 496.0. $^1H$ NMR (400 MHz, Methanol-$d_4$) δ 8.50 (d, J=2.2 Hz, 1H), 8.38 (d, J=2.2 Hz, 1H), 8.16 (s, 1H), 6.87 (s, 1H), 6.41 (d, J=5.3 Hz, 1H), 4.96 (dd, J=11.3, 2.9 Hz, 1H), 4.56 (dd, J=11.3, 5.3 Hz, 1H), 4.29 (t, J=6.0 Hz, 1H), 4.09 (d, J=2.5 Hz, 1H), 3.58 (d, J=6.1 Hz, 2H), 3.37 (d, J=12.0 Hz, 3H).

Example 18

5-Chloro-2-methylpyridin-3-yl 3-[4-(2-aminothiazol-4-yl)-1H-1,2,3-triazol-1-yl]-3-deoxy-2-O-methyl-1-thio-α-D-galactopyranoside

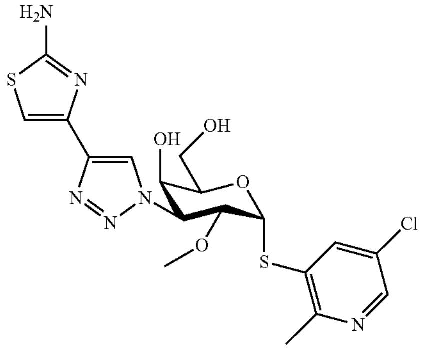

To a solution of 5-chloro-2-methylpyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (85 mg, 0.14 mmol) in DCM (10 mL) TFA (820 mg, 7.19 mmol) and $H_2O$ (0.5 mL) were added and the mixture was stirred 12 h at rt. $Et_3N$ (3.0 mL) was added dropwise at 0° C., and the mixture was concentrated and purified prep HPLC [$MeCN/H_2O$ (10 mmol/L $NH_4HCO_3$), X-Select 10 μm 19*250 mm, 20 mL/min, UV 254] to give the title compound (25 mg, 36%). ESI-MS m/z calcd for [C18$H_{21}ClN_6O_4S_2$] $[M+H]^+$: 485.1; found: 485.0. $^1H$ NMR (400 MHz, Methanol-$d_4$) δ 8.30 (d, J=2.4 Hz, 1H), 8.26 (s, 1H), 8.20 (d, J=2.4 Hz, 1H), 6.97 (s, 1H), 6.30 (d, J=5.2 Hz, 1H), 5.06 (dd, J=11.6, 2.8 Hz, 1H), 4.73-4.56 (m, 1H), 4.39 (t, J=6.4 Hz, 1H), 4.19 (d, J=2.4 Hz, 1H), 3.82-3.58 (m, 2H), 3.40 (s, 3H), 2.66 (s, 3H).

Example 19

5-Chloro-2-cyanopyridin-3-yl 3-[4-(2-aminothiazol-4-yl)-1H-1,2,3-triazol-1-yl]-2-O-benzyl-3-deoxy-1-thio-α-D-galactopyranoside

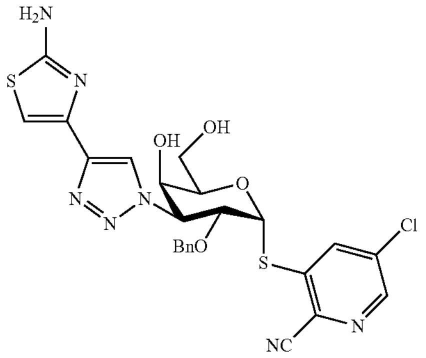

A solution of 5-chloro-2-cyanopyridin-3-yl 3-[4-(2-aminothiazol-4-yl)-1H-1,2,3-triazol-1-yl]-2-O-benzyl-4,6-O-benzylidene-3-deoxy-1-thio-α-D-galactopyranoside (98.0 mg, 0.15 mmol) in DCM/TFA (6 mL, 5:1) was stirred 3 h at rt. The mixture was neutralized with $Et_3N$, concentrated and purified by prep HPLC [$MeCN/H_2O$ (10 mmol/L $NH_4HCO_3$), X-Select 10 μm 19*250 mm, 20 mL/min, UV 254] to give the title compound (17.8 mg, 21%). ESI-MS m/z calcd for [$C_{24}H_{22}ClN_7O_4S_2$] $[M+H]^+$: 572.1; found: 572.2. $^1H$ NMR (400 MHz, Methanol-$d_4$) δ 8.61 (d, J=2.4 Hz, 1H), 8.42 (d, J=2.4 Hz, 1H), 8.12 (s, 1H), 7.24-7.09 (m, 5H), 6.97 (s, 1H), 6.36 (d, J=5.2 Hz, 1H), 5.12 (dd, J=11.2, 2.8 Hz, 1H), 4.82-4.71 (m, 2H), 4.63 (s, 1H), 4.51 (d, J=11.2 Hz, 1H), 4.41 (t, J=6.0 Hz, 1H), 4.20 (d, J=2.4 Hz, 1H), 3.72-3.63 (m, 2H).

Example 20

5-Chloro-2-methylpyridin-3-yl 3-[4-(2-aminothiazol-4-yl)-1H-1,2,3-triazol-1-yl]-3-deoxy-2-O-ethyl-1-thio-α-D-galactopyranoside

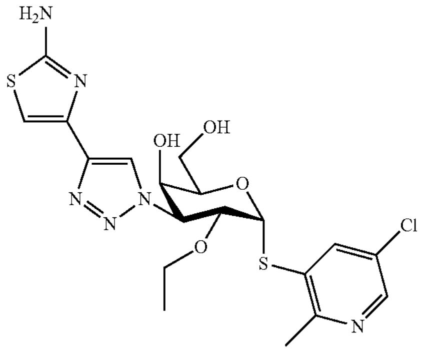

To a solution of 5-chloro-2-methylpyridin-3-yl 3-[4-(2-aminothiazol-4-yl)-1H-1,2,3-triazol-1-yl]-4,6-O-benzylidene-3-deoxy-2-O-ethyl-1-thio-α-D-galactopyranoside (115 mg, 0.15 mmol) in DCM (10 mL) TFA (860 mg, 7.54 mmol) and $H_2O$ (0.5 mL) were added and the mixture was stirred 12 h at rt. $Et_3N$ (3.0 mL) was added dropwise at 0° C., and the mixture was concentrated and purified by prep HPLC [MeCN/$H_2O$ (10 mmol/L $NH_4HCO_3$), X-Select 10 μm 19*250 mm, 20 mL/min, UV 254] to give the title compound (42 mg, 56%). ESI-MS m/z calcd for [$C_{19}H_{23}ClN_6O_4S_2$] [M+H]$^+$: 499.1; found: 499.0. $^1$H NMR (400 MHz, Methanol-$d_4$) δ 8.30 (d, J=2.4 Hz, 1H), 8.26 (s, 1H), 8.18 (d, J=2.4 Hz, 1H), 6.97 (s, 1H), 6.26 (d, J=5.2 Hz, 1H), 5.07 (dd, J=11.6, 2.8 Hz, 1H), 4.70 (dd, J=11.6, 5.3 Hz, 1H), 4.48-4.33 (m, 1H), 4.20 (d, J=2.4 Hz, 1H), 3.84-3.61 (m, 3H), 3.51-3.35 (m, 1H), 2.65 (s, 3H), 1.03 (t, J=7.0 Hz, 3H).

Example 21

5-Chloro-2-(pyrimidin-5-yl)pyridin-3-yl 3-[4-(2-aminothiazol-4-yl)-1H-1,2,3-triazol-1-yl]-3-deoxy-2-O-methyl-1-thio-α-D-galactopyranoside

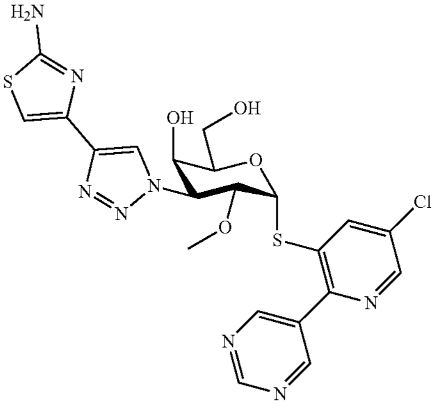

A solution of 5-chloro-2-(pyrimidin-5-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (70 mg, 0.11 mmol) in DCM/TFA (10.0 mL, 19:1) was stirred 1 h at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (27 mg, 45%). ESI-MS m/z calcd for [$C_{21}H_{21}ClN_8O_4S_2$][M+H]$^+$: 549.1; found: 549.1. $^1$H NMR (400 MHz, Methanol-$d_4$) δ 9.13 (s, 1H), 9.06 (s, 2H), 8.54 (d, J=2.0 Hz, 1H), 8.36 (d, J=2.0 Hz, 1H), 8.11 (s, 1H), 6.85 (s, 1H), 6.00 (d, J=4.8 Hz, 1H), 4.80-4.70 (s, 1H), 4.41 (d, J=5.6 Hz, 1H), 4.13 (t, J=5.6 Hz, 1H), 4.01 (s, 1H), 3.56 (d, J=6.0 Hz, 2H), 3.07 (s, 3H).

Example 22

5-Chloro-2-(pyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside

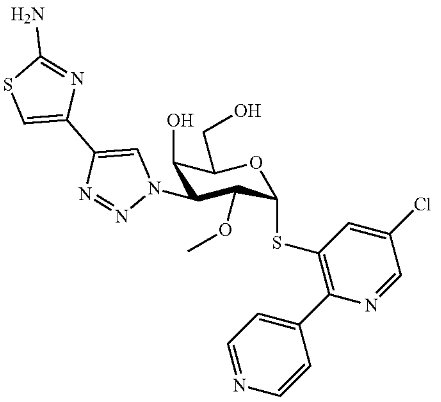

To a solution of 5-chloro-2-(pyridin-4-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (70.0 mg, 0.11 mmol) in DCM (10 mL) TFA (0.409 mL, 5.50 mmol) was added and the mixture was stirred 2 h at rt. $Et_3N$ (1 mL) was added at 0° C., and the mixture was concentrated and purified by prep HPLC [MeCN/$H_2O$ (10 mmol/L $NH_4HCO_3$), X-Select 10 μm 19*250 mm, 20 mL/min, UV 254] to afford the title compound (33.0 mg, 55%). ESI-MS m/z calcd for [$C_{22}H_{22}ClN_7O_4S_2$] [M+H]$^+$: 548.1; found: 547.9. $^1$H NMR (400 MHz, Methanol-$d_4$) δ 8.89-8.54 (m, 3H), 8.45 (d, J=2.0 Hz, 1H), 8.21 (s, 1H), 7.89-7.68 (m, 2H), 7.10-6.85 (m, 1H), 6.11 (d, J=5.2 Hz, 1H), 4.90-4.87 (m, 1H), 4.58-4.46 (m, 1H), 4.25 (t, J=6.0 Hz, 1H), 4.13 (s, 1H), 3.73-3.58 (m, 2H), 3.16 (s, 3H).

Example 23

5-Chloro-2-(pyridin-3-yl)pyridin-3-yl 3-[4-(2-aminothiazol-4-yl)-1H-1,2,3-triazol-1-yl]-3-deoxy-2-O-methyl-1-thio-α-D-galactopyranoside

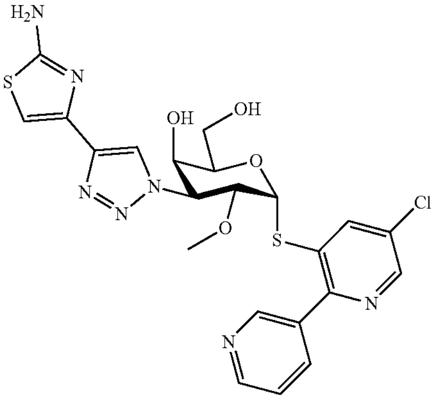

A solution of 5-chloro-2-(pyridin-3-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (68 mg, 0.12 mmol) in DCM/TFA (6 mL, 5:1) was stirred 3 h at rt, and was then neutralized with $Et_3N$. The mixture was concentrated and purified by prep HPLC [MeCN/$H_2O$ (10 mmol/L $NH_4HCO_3$), X-Select 10 μm 19*250 mm, 20 mL/min, UV 254] to give the title compound (32.8 mg, 56%). ESI-MS m/z calcd for [$C_{22}H_{22}ClN_7O_4S_2$] [M+H]$^+$: 548.1; found: 548.2. $^1$H NMR (400 MHz, DMSO-$d_6$) δ 8.83 (s, 1H), 8.65 (d, J=2.4 Hz, 2H), 8.41 (d, J=1.6 Hz, 1H), 8.11-8.05 (m, 2H), 7.56 (q, J=7.6, 4.8 Hz, 1H), 7.07 (s, 2H), 6.89 (s, 1H), 6.27 (d, J=5.2 Hz, 1H), 5.52 (d, J=6.4 Hz, 1H), 4.76-4.71 (m, 2H), 4.52 (dd, J=11.6, 5.2 Hz, 1H), 4.07 (t, J=6.4 Hz, 1H), 3.96 (q, J=6.4, 2.4 Hz, 1H), 3.53-3.47 (m, 1H), 3.41-3.36 (m, 1H), 3.08 (s, 3H).

Example 24

5-Chloro-2-(1,2,3,6-tetrahydropyridin-4-yl)pyridin-3-yl 3-[4-(2-aminothiazol-4-yl)-1H-1,2,3-triazol-1-yl]-3-deoxy-2-O-methyl-1-thio-α-D-galactopyranoside

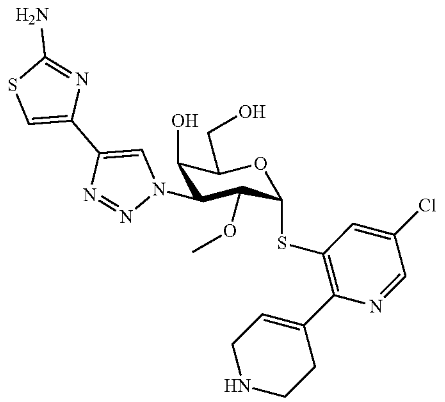

To a solution of 5-chloro-2-(1,2,3,6-tetrahydropyridin-4-yl)pyridin-3-yl 3-azido-3-deoxy-2-O-methyl-1-thio-α-D-galactopyranoside (40 mg, 0.094 mmol) in DMF (2 mL) 4-(2-trimethylsilylethynyl)thiazol-2-amine (20.2 mg, 0.10 mmol), (+)-sodium L-ascorbate (18.5 mg, 0.094 mmol), copper (II) sulfate pentahydrate (23.3 mg, 0.094 mmol) and CsF (21.3 mg, 0.14 mmol) were added and the mixture was stirred overnight at rt. The mixture was filtered, and the filtrate was purified by prep HPLC [MeCN/$H_2O$ (10 mmol/L $NH_4HCO_3$), X-Select 10 μm 19*250 mm, 20 mL/min, UV 254] to give the title compound (8.0 mg, 16%). ESI-MS m/z calcd for [$C_{22}H_{26}ClN_7O_4S_2$] [M+H]$^+$: 552.1; found: 551.8. $^1$H NMR (400 MHz, Methanol-$d_4$) δ 8.55-8.04 (m, 3H), 7.10-6.81 (m, 1H), 6.37-6.22 (m, 1H), 6.14-5.99 (m, 1H), 5.12-5.01 (m, 1H), 4.68-4.53 (m, 1H), 4.43-4.28 (m, 1H), 4.25-4.14 (m, 1H), 3.85-3.57 (m, 4H), 3.37 (s, 3H), 3.23-3.14 (m, 2H), 2.76-2.49 (m, 2H).

Example 25

5-Chloro-2-cyanopyridin-3-yl 3-[4-(2-aminothiazol-4-yl)-1H-1,2,3-triazol-1-yl]-3-deoxy-2-O-(3,5-difluoro-4-hydroxybenzyl)-1-thio-α-D-galactopyranoside

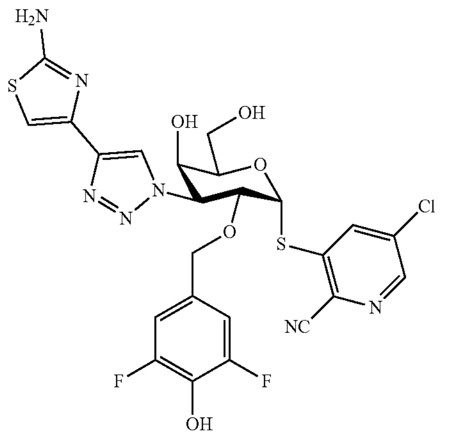

To a solution of 5-chloro-2-cyanopyridin-3-yl 3-[4-(2-aminothiazol-4-yl)-1H-1,2,3-triazol-1-yl]-4,6-O-benzylidene-3-deoxy-2-O-(3,5-difluoro-4-(4-methoxybenzyloxy)benzyl)-1-thio-α-D-galactopyranoside (60 mg, 0.071 mmol) in DCM (3 mL) TFA (248 mg, 2.16 mmol) and $H_2O$ (0.5 mL) were added and the mixture was stirred 12 h at rt. $Et_3N$ (1.0 mL) was added dropwise at 0° C., and the mixture was concentrated and purified by prep HPLC [MeCN/$H_2O$ (10 mmol/L $NH_4HCO_3$), X-Select 10 μm 19*250 mm, 20 mL/min, UV 254] to give the title compound (33 mg, 73%). ESI-MS m/z calcd for [$C_{24}H_{20}ClF_2N_7O_5S_2$] [M+H]$^+$: 624.1; found: 624.1. $^1$H NMR (400 MHz, Methanol-$d_4$) δ 8.51 (d, J=2.0 Hz, 1H), 8.34 (d, J=2.0 Hz, 1H), 8.04 (s, 1H), 6.87 (s, 1H), 6.62-6.54 (m, 2H), 6.29 (d, J=5.2 Hz, 1H), 5.01 (dd, J=11.2, 2.8 Hz, 1H), 4.70 (dd, J=11.2, 5.2 Hz, 1H), 4.56 (d, J=11.6 Hz, 1H), 4.33-4.26 (m, 2H), 4.10 (d, J=2.4 Hz, 1H), 3.63-3.5 (m, 2H).

Example 26

5-Chloro-2-(pyridin-2-yl)pyridin-3-yl 3-[4-(2-aminothiazol-4-yl)-1H-1,2,3-triazol-1-yl]-3-deoxy-2-O-methyl-1-thio-α-D-galactopyranoside

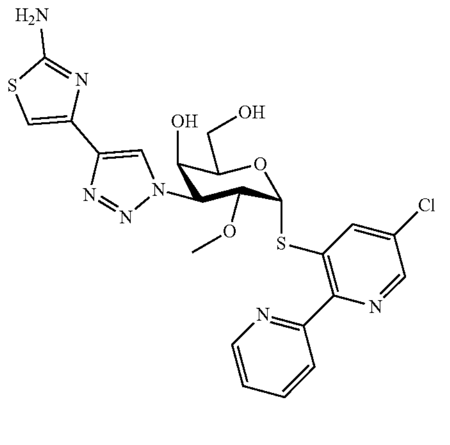

A solution of 5-chloro-2-(pyridin-2-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (35.0 mg, 0.055 mmol) in DCM/TFA (10 mL, 19:1) was stirred 1 h at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (14.5 mg, 48%). ESI-MS m/z calcd for [$C_{22}H_{22}ClN_7O_4S_2$] $[M+H]^+$: 548.1; found: 548.0. $^1H$ NMR (400 MHz, Methanol-$d_4$) δ 8.58 (d, J=4.4 Hz, 1H), 8.42 (d, J=2.4 Hz, 1H), 8.36 (d, J=2.4 Hz, 1H), 8.09 (s, 1H), 7.89 (td, J=7.6, 1.6 Hz, 1H), 7.75 (d, J=7.6 Hz, 1H), 7.41 (ddd, J=7.6, 5.2, 0.8 Hz, 1H), 6.83 (s, 1H), 6.09 (d, J=5.2 Hz, 1H), 4.78 (m, 1H), 4.41 (dd, J=11.2, 5.2 Hz, 1H), 4.18 (t, J=6.0 Hz, 1H), 4.01 (d, J=2.4 Hz, 1H), 3.65-3.50 (m, 2H), 3.08 (s, 3H).

Example 27

5-Chloro-2-(oxazol-2-yl)pyridin-3-yl 3-[4-(2-aminothiazol-4-yl)-1H-1,2,3-triazol-1-yl]-3-deoxy-2-O-methyl-1-thio-α-D-galactopyranoside

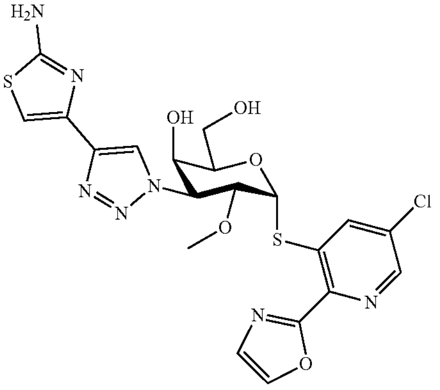

To a solution of 5-chloro-2-(oxazol-2-yl)pyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside (120 mg, 0.22 mmol) in DCM (5 mL) TFA (528 mg, 4.63 mmol) and $H_2O$ (0.5 mL) were added and the mixture was stirred 12 h at rt. $Et_3N$ (1.5 mL) was added dropwise at 0° C., and the mixture was concentrated and purified by prep HPLC [MeCN/$H_2O$ (10 mmol/L $NH_4HCO_3$), X-Select 10 μm 19*250 mm, 20 mL/min, UV 254] to give the title compound (16 mg, 26%). ESI-MS m/z calcd for [$C_{20}H_{20}ClN_7O_5S_2$] $[M+H]^+$: 538.1; found: 538.0. $^1H$ NMR (400 MHz, Methanol-$d_4$) δ 8.43 (d, J=2.0 Hz, 1H), 8.38 (d, J=2.0 Hz, 1H), 8.15 (s, 1H), 8.03 (s, 1H), 7.36 (s, 1H), 6.86 (s, 1H), 6.39 (d, J=5.6 Hz, 1H), 4.98 (dd, J=11.2, 2.8 Hz, 1H), 4.53 (dd, J=11.2, 5.2 Hz, 1H), 4.25-4.22 (m, 1H), 4.07 (d, J=2.4 Hz, 1H), 3.60-3.53 (m, 2H), 3.26 (s, 3H).

Example 28

3,4-Dichlorphenyl 3-[4-(2-aminothiazol-4-yl)-1H-1,2,3-triazol-1-yl]-3-deoxy-2-O-methyl-1-thio-α-D-galactopyranoside

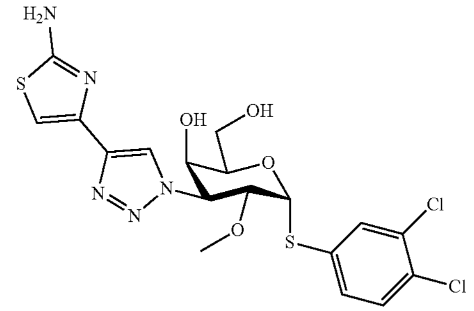

A solution of 3,4-dichlorphenyl 3-[4-(2-aminothiazol-4-yl)-1H-1,2,3-triazol-1-yl]-4,6-O-benzylidene-3-deoxy-2-O-methyl-1-thio-α-D-galactopyranoside (90.0 mg, 0.15 mmol) in DCM/TFA (10.0 mL, 19:1) was stirred 1 h at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (37.5 mg, 49%). ESI-MS m/z calcd for [$C18H_{19}Cl_2N_5O_4S_2$] $[M+H]^+$: 504.0; found: 504.0. $^1H$ NMR (400 MHz, Methanol-$d_4$) δ 8.25 (s, 1H), 7.81 (d, J=2.0 Hz, 1H), 7.54 (dd, J=8.4, 2.0 Hz, 1H), 7.47 (d, J=8.4 Hz, 1H), 6.96 (s, 1H), 6.16 (d, J=5.2 Hz, 1H), 4.98 (dd, J=11.2, 1.6 Hz, 1H), 4.55 (dd, J=11.2, 5.2 Hz, 1H), 4.45 (t, J=6.4 Hz, 1H), 4.18 (s, 1H), 3.69 (qd, J=11.6, 6.4 Hz, 2H), 3.37 (s, 3H).

Example 29

5-Chloro-2-(thiazol-2-yl)pyridin-3-yl 3-[4-(2-aminothiazol-4-yl)-1H-1,2,3-triazol-1-yl]-3-deoxy-2-O-methyl-1-thio-α-D-galactopyranoside

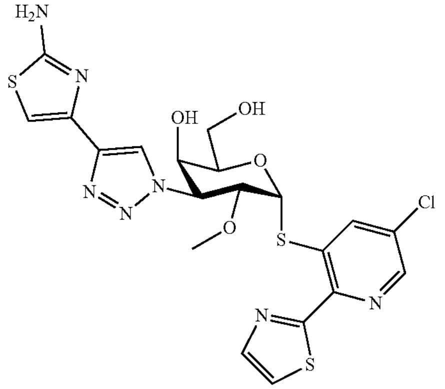

To a solution of 5-chloro-2-(thiazol-2-yl)pyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside (50 mg, 0.033 mmol) in DCM (5 mL) TFA (192 mg, 1.68 mmol) and $H_2O$ (0.5 mL) were added and the mixture was stirred 12 h at rt. $Et_3N$ (1.5 mL) was added dropwise at 0° C., and the mixture was concentrated and purified by prep HPLC [MeCN/$H_2O$ (10 mmol/L $NH_4HCO_3$), X-Select 10 μm 19*250 mm, 20 mL/min, UV 254] to give the title compound (2.7 mg, 14%). ESI-MS m/z calcd for [$C_{20}H_{20}ClN_7O_4S_3$] $[M+H]^+$: 554.0; found: 554.0. $^1H$ NMR (400 MHz, Methanol-$d_4$) δ 8.44 (dd, J=6.8, 2.0 Hz, 2H), 8.27 (s, 1H), 8.02 (d, J=3.2 Hz, 1H), 7.71 (d, J=3.2 Hz, 1H), 6.98 (s, 1H), 6.52 (d, J=5.6 Hz, 1H), 5.15 (dd, J=11.2, 2.8 Hz, 1H), 4.66 (dd, J=11.2, 5.2 Hz, 1H), 4.38-4.35 (m, 1H), 4.19 (d, J=2.8 Hz, 1H), 3.74-3.64 (m, 2H), 3.38 (s, 3H).

Example 30

3-Chloro-4-(trifluoromethyl)phenyl 3-[4-(2-aminothiazol-4-yl)-1H-1,2,3-triazol-1-yl]-3-deoxy-2-O-methyl-1-thio-α-D-galactopyranoside

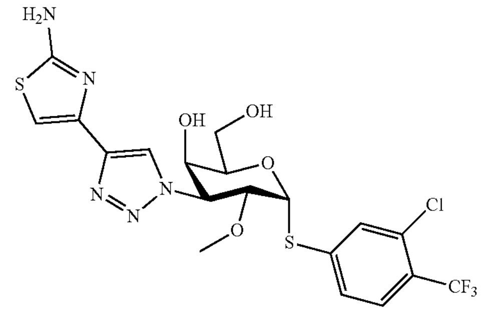

A solution of 3-chloro-4-(trifluoromethyl)phenyl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside (260 mg, 0.35 mmol) in DCM/TFA (20 mL, 19:1) was stirred 6 h at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (102 mg, 54%). ESI-MS m/z calcd for [$C_{19}H_{19}ClF_3N_5O_4S_2$] $[M+H]^+$: 538.1; found: 538.0. $^1H$ NMR (400 MHz, Methanol-$d_4$) δ 8.27 (s, 1H), 7.88 (s, 1H), 7.72 (d, J=7.6 Hz, 2H), 6.98 (s, 1H), 6.41 (d, J=5.6 Hz, 1H), 5.02 (dd, J=11.6, 2.8 Hz, 1H), 4.62 (dd, J=11.2, 5.2 Hz, 1H), 4.43-4.40 (m, 1H), 4.20 (d, J=2.0 Hz, 1H), 3.76-3.66 (m, 2H), 3.40 (s, 3H).

Example 31

3-Chlorophenyl 3-[4-(2-aminothiazol-4-yl)-1H-1,2,3-triazol-1-yl]-3-deoxy-2-O-methyl-1-thio-α-D-galactopyranoside

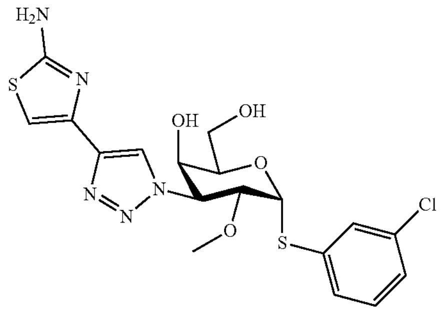

To a solution of 3-chlorophenyl 3-[4-(2-aminothiazol-4-yl)-1H-1,2,3-triazol-1-yl]-4,6-O-benzylidene-3-deoxy-2-O-methyl-1-thio-α-D-galactopyranoside (70 mg, 0.13 mmol) in DCM (10 mL) TFA (0.409 mL, 5.50 mmol) was added and the mixture was stirred 2 h at rt. $Et_3N$ (1 mL) was added at 0° C., and the mixture was concentrated. The residue was purified by prep HPLC [MeCN/$H_2O$ (10 mmol/L $NH_4HCO_3$), X-Select 10 μm 19*250 mm, 20 mL/min, UV 254] to afford the title compound (16.0 mg, 27%). ESI-MS m/z calcd for [$C_{18}H_{20}ClN_5O_4S_2$] $[M+H]^+$: 470.1; found: 470.0. $^1H$ NMR (400 MHz, Methanol-$d_4$) δ 8.24 (s, 1H), 7.70-7.65 (m, 1H), 7.60-7.51 (m, 1H), 7.36-7.28 (m, 2H), 6.96 (s, 1H), 6.15 (d, J=5.2 Hz, 1H), 4.99 (dd, J=11.2, 2.8 Hz, 1H), 4.56 (dd, J=11.2, 5.2 Hz, 1H), 4.48 (t, J=6.0 Hz, 1H), 4.19 (d, J=2.4 Hz, 1H), 3.69 (ddd, J=26.4, 11.2, 6.0 Hz, 2H), 3.38 (s, 3H).

Example 32

3,5-Dichloro-4-fluorophenyl 3-[4-(2-aminothiazol-4-yl)-1H-1,2,3-triazol-1-yl]-3-deoxy-1-thio-α-D-galactopyranoside

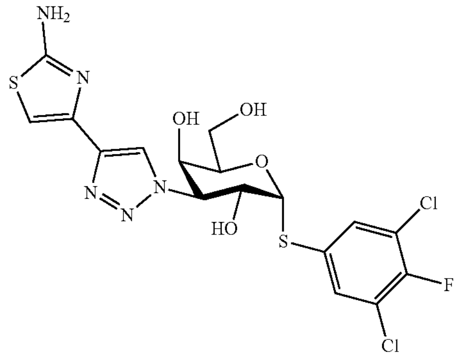

A solution of 3,5-dichloro-4-fluorophenyl 2,4,6-tri-O-acetyl-3-[4-(2-aminothiazol-4-yl)-1H-1,2,3-triazol-1-yl]-3-deoxy-1-thio-α-D-galactopyranoside (75 mg, 0.12 mmol) in MeOH (5.0 mL), $Et_3N$ (2.49 mL, 17.9 mmol) and water (829 mg, 46 mmol) was stirred overnight at rt. The mixture was concentrated and purified by column chromatography (MeCN/$H_2O$=1/20~1/7, C-18 column, 20 mL/min, UV 254) to afford the title compound (36.0 mg, 60%). ESI-MS m/z calcd for [$C_{17}H_{16}Cl_2FN_5O_4S_2$]$[M+H]^+$: 508.0; found: 508.0. $^1H$ NMR (400 MHz, Methanol-$d_4$) δ 8.13 (s, 1H), 7.63 (d, J=6.3 Hz, 2H), 6.86 (s, 1H), 5.72 (d, J=5.2 Hz, 1H), 4.85 (dd, J=11.4, 2.7 Hz, 1H), 4.78 (m, 1H), 4.38 (t, J=6.0 Hz, 1H), 4.08 (s, 1H), 3.68-3.55 (m, 2H).

Example 33

3-Bromo-2-(trifluoromethyl)pyridin-5-yl 3-[4-(2-aminothiazol-4-yl)-1H-1,2,3-triazol-1-yl]-3-deoxy-1-thio-α-D-galactopyranoside

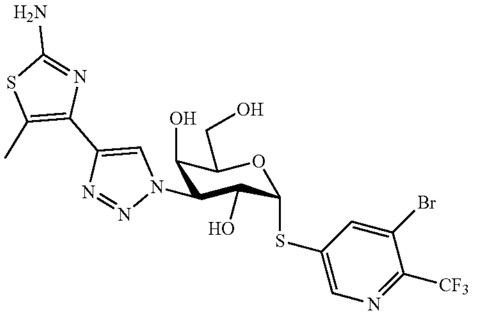

A solution of 3-bromo-2-(trifluoromethyl)pyridin-5-yl 2,4,6-tri-O-acetyl-3-[4-(2-aminothiazol-4-yl)-1H-1,2,3-triazol-1-yl]-3-deoxy-1-thio-α-D-galactopyranoside (13.0 mg, 0.018 mmol) in MeOH/$Et_3N/H_2O$ (9 mL, 5:3:1) was stirred overnight at rt. The mixture was concentrated and purified by prep HPLC [MeCN/$H_2O$ (10 mmol/L $NH_4HCO_3$), X-Select 10 μm 19*250 mm, 20 mL/min, UV 254) to give the title compound (8.70 mg, 71%). ESI-MS m/z calcd for [$C_{18}H_{18}BrF_3N_6O_4S_2$] $[M+H]^+$: 583.0; found: 583.0. $^1H$ NMR (400 MHz, Methanol-$d_4$) δ 8.74 (d, J=1.6 Hz, 1H), 8.50 (d, J=1.6 Hz, 1H), 8.19 (s, 1H), 6.11 (d, J=5.6 Hz, 1H), 5.02 (dd, J=11.2, 2.8 Hz, 1H), 4.95-4.91 (m, 1H), 4.39 (t, J=6.0 Hz, 1H), 4.18 (d, J=2.0 Hz, 1H), 3.75-3.57 (m, 2H), 2.52 (s, 3H).

Example 34

5-Bromo-2-cyanopyridin-3-yl 3-deoxy-3-[4-(4-methylthiazol-2-yl)-1H-1,2,3-triazol-1-yl]-2-O-methyl-1-thio-α-D-galactopyranoside

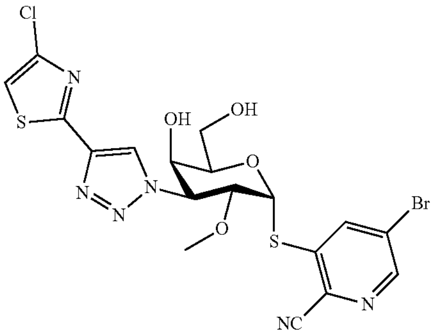

A solution of 5-bromo-2-cyanopyridin-3-yl 4,6-di-O-acetyl-3-deoxy-3-[4-(4-methylthiazol-2-yl)-1H-1,2,3-triazol-1-yl]-2-O-methyl-1-thio-α-D-galactopyranoside (52.0 mg, 0.084 mmol) in MeOH (3.0 mL), Et3N (2.0 mL) and water (1.0 mL) was stirred 4 h at rt. The mixture was concentrated and purified by prep HPLC (MeCN/$H_2O$ (10 mmol/L $NH_4HCO_3$), X-Select 10 μm 19*250 mm, 20 mL/min, UV 254) to give the title compound (34.0 mg, 76%). ESI-MS m/z calcd for [$C_{19}H_{19}BrN_6O_4S_2$] $[M+H]^+$:

539.0; found: 539.1. $^1H$ NMR (400 MHz, Methanol-$d_4$) δ 8.73 (d, J=2.0 Hz, 1H), 8.65 (d, J=2.0 Hz, 1H), 8.61 (s, 1H), 7.20 (d, J=0.8 Hz, 1H), 6.53 (d, J=5.2 Hz, 1H), 5.15 (dd, J=11.2, 2.8 Hz, 1H), 4.74-4.70 (m, 1H), 4.43 (t, J=6.0 Hz, 1H), 4.23 (d, J=2.4 Hz, 1H), 3.70 (d, J=6.0 Hz, 2H), 3.49 (s, 3H), 2.49 (s, 3H).

Example 35

2-Cyano-5-methylpyridin-3-yl 3-deoxy-3-[4-(4-methylthiazol-2-yl)-1H-1,2,3-triazol-1-yl]-2-O-methyl-1-thio-α-D-galactopyranoside

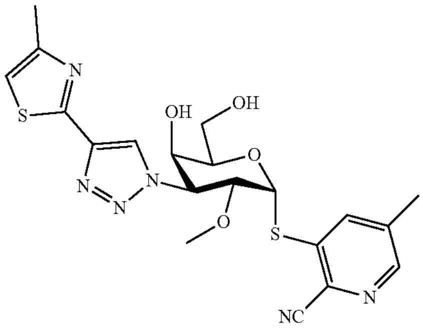

A solution of 2-cyano-5-methylpyridin-3-yl 4,6-O-benzylidene-3-deoxy-3-[4-(4-methylthiazol-2-yl)-1H-1,2,3-triazol-1-yl]-2-O-methyl-1-thio-α-D-galactopyranoside (95.0 mg, 0.16 mmol) in DCM/TFA (10 mL, 19:1) was stirred 6 h at rt. $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (58.0 mg, 75%). ESI-MS m/z calcd for [$C_{20}H_{22}N_6O_4S_2$] $[M+H]^+$: 475.1; found: 475.2. $^1H$ NMR (400 MHz, Methanol-$d_4$) δ 8.58 (s, 1H), 8.46 (dd, J=2.0, 0.8 Hz, 1H), 8.20 (dd, J=2.0, 0.8 Hz, 1H), 7.17 (d, J=0.8 Hz, 1H), 6.37 (d, J=5.2 Hz, 1H), 5.12 (dd, J=11.2, 2.8 Hz, 1H), 4.67 (dd, J=11.2, 5.2 Hz, 1H), 4.47 (t, J=6.0 Hz, 1H), 4.21 (d, J=2.4 Hz, 1H), 3.67 (d, J=6.0 Hz, 2H), 3.47 (s, 3H), 2.47 (s, 3H), 2.44 (s, 3H).

Example 36

2-Cyano-5-methylpyridin-3-yl 3-[4-(4-chlorothiazol-2-yl)-1H-1,2,3-triazol-1-yl]-3-deoxy-2-O-methyl-1-thio-α-D-galactopyranoside

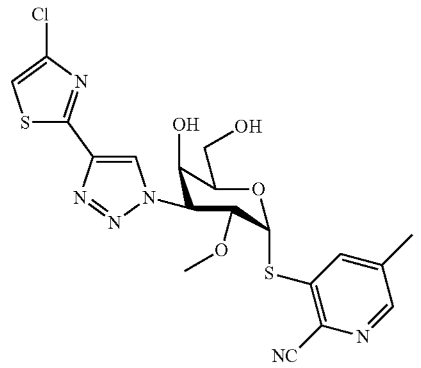

A solution of 2-cyano-5-methylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (220 mg, 0.37 mmol) in DCM/TFA (20 mL, 19:1) was stirred 6 h at rt. $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (95.0 mg, 51%). ESI-MS m/z calcd for [$C_{19}H_{19}ClN_6O_4S_2$] $[M+H]^+$: 495.1; found: 495.2. $^1H$ NMR (400 MHz, Methanol-$d_4$) δ 8.64 (s, 1H), 8.45 (d, J=1.6 Hz, 1H), 8.20 (dd, J=1.6, 0.8 Hz, 1H), 7.46 (s, 1H), 6.36 (d, J=5.2 Hz, 1H), 5.12 (dd, J=11.2, 3.2 Hz, 1H), 4.69 (dd, J=11.2, 2.8 Hz, 1H), 4.46 (t, J=6.0 Hz, 1H), 4.21 (d, J=2.4 Hz, 1H), 3.67 (d, J=6.0 Hz, 2H), 3.47 (s, 3H), 2.44 (s, 3H).

Example 37

5-Ethynylpyridin-3-yl 3-[4-(4-chlorothiazol-2-yl)-1H-1,2,3-triazol-1-yl]-3-deoxy-2-O-methyl-1-thio-α-D-galactopyranoside

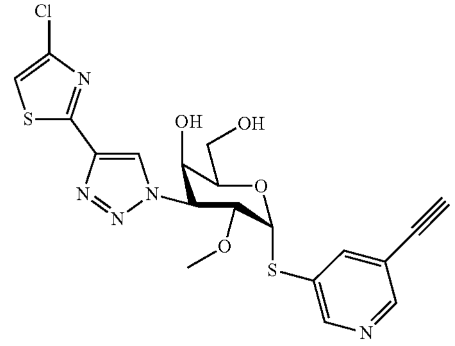

To a solution of 5-(2-trimethylsilyl-1-ethynyl)-pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (35 mg, 0.055 mmol) in DCM (6 mL) TFA (0.406 mL, 5.47 mmol) was added and the mixture was stirred overnight at rt. $Et_3N$ (1 mL) was added at 0° C. to neutralize the TFA and the mixture was concentrated. The residue was dissolved in DMF (3 mL) and KF (6.35 mg, 0.11 mmol) was added and the mixture was stirred 1 h at rt. The mixture was filtered and purified by prep HPLC [MeCN/$H_2O$ (10 mmol/L $NH_4HCO_3$), X-Select 10 μm 19*250 mm, 20 mL/min, UV 254] to afford the title compound (13.5 mg, 52%). ESI-MS m/z calcd for [$C_{19}H_{18}ClN_5O_4S_2$] $[M+H]^+$: 480.0; found: 480.2. $^1H$ NMR (400 MHz, Methanol-$d_4$) δ 8.70 (d, J=2.0 Hz, 1H), 8.63 (s, 1H), 8.54 (d, J=1.6 Hz, 1H), 8.20 (t, J=2.0 Hz, 1H), 7.46 (s, 1H), 6.24 (d, J=5.2 Hz, 1H), 5.08 (dd, J=11.2, 2.8 Hz, 1H), 4.63 (dd, J=11.2, 5.2 Hz, 1H), 4.47 (t, J=6.0 Hz, 1H), 4.20 (d, J=2.4 Hz, 1H), 3.76-3.57 (m, 2H), 3.41 (s, 3H).

Example 38

5-Chloro-2-{N-(2-oxa)-6-azaspiro[3.3]heptanyl}-pyridin-3-yl 3-[4-(2-aminothiazol-4-yl)-1H-1,2,3-triazol-1-yl]-3-deoxy-2-O-methyl-1-thio-α-D-galactopyranoside

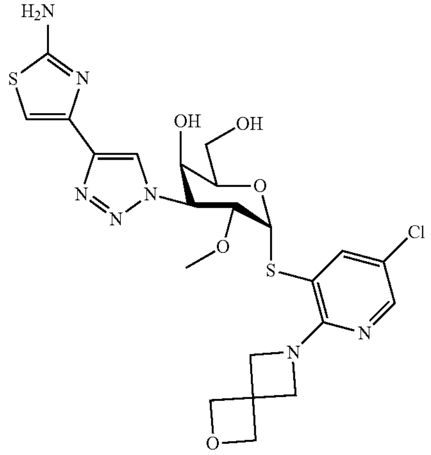

A solution of 5-chloro-2-{N-(2-oxa)-6-azaspiro[3.3]heptanyl}-pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (120 mg, 0.18 mmol) in DCM/TFA (10 mL, 19:1) was stirred 1 h at rt. $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (39.6 mg, 38%). ESI-MS m/z calcd for [$C_{22}H_{26}ClN_7O_5S_2$] $[M+H]^+$: 568.1; found: 568.0. $^1H$ NMR (400 MHz, DMSO-$d_6$) δ 8.18 (s, 1H), 8.08 (d, J=2.4 Hz, 1H), 7.85 (d, J=2.4 Hz, 1H), 7.10 (s, 2H), 6.92 (s, 1H), 6.04 (d, J=5.2 Hz, 1H), 5.52 (d, J=6.8 Hz, 1H), 4.87 (dd, J=11.6, 2.0 Hz, 1H), 4.77 (t, J=5.2 Hz, 1H), 4.74-4.62 (m, 4H), 4.53 (dd, J=11.2, 5.2 Hz, 1H), 4.36 (d, J=9.2 Hz, 2H), 4.29 (d, J=9.2 Hz, 2H), 4.25 (t, J=6.0 Hz, 1H), 4.03 (d, J=3.6 Hz, 1H), 3.57-3.49 (m, 1H), 3.40 (dd, J=11.6, 6.0 Hz, 1H), 3.29 (s, 3H).

Example 39

3-Chloro-4-cyanophenyl 3-[4-(2-aminothiazol-4-yl)-1H-1,2,3-triazol-1-yl]-3-deoxy-2-O-methyl-1-thio-α-D-galactopyranoside

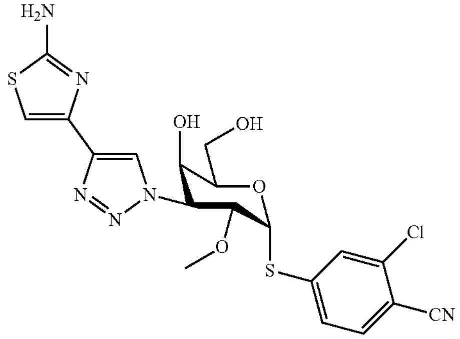

A solution of 3-chloro-4-cyanophenyl 4,6-di-O-acetyl-3-[4-(2-aminotriazol-4-yl)-1H-1,2,3-triazol-1-yl]-3-deoxy-2-O-methyl-1-thio-α-D-galactopyranoside (25 mg, 0.043 mmol) in MeOH (5.0 mL), Et3N (3.0 mL) and water (1.0 mL) was stirred overnight at rt. The mixture was concentrated and purified by prep HPLC (MeCN/$H_2O$ (10 mmol/L $NH_4HCO_3$), X-Select 10 μm 19*250 mm, 20 mL/min, UV 254) to give the title compound (8.8 mg, 41%). ESI-MS m/z calcd for [$C_{19}H_{19}ClN_6O_4S_2$] $[M+H]^+$: 495.1; found: 495.0. $^1H$ NMR (400 MHz, Methanol-$d_4$) δ 8.24 (s, 1H), 7.88 (d, J=1.2 Hz, 1H), 7.74-7.63 (m, 2H), 6.95 (s, 1H), 6.45 (d, J=5.2 Hz, 1H), 5.00 (dd, J=11.6, 2.8 Hz, 1H), 4.61 (dd, J=11.6, 5.2 Hz, 1H), 4.34 (t, J=6.0 Hz, 1H), 4.17 (d, J=2.4 Hz, 1H), 3.77-3.62 (m, 2H), 3.36 (s, 3H).

Example 40

5-Cyanopyridin-3yl 3-[4-(2-aminothiazol-4-yl)-1H-1,2,3-triazol-1-yl]-3-deoxy-2-O-methyl-1-thio-α-D-galactopyranoside

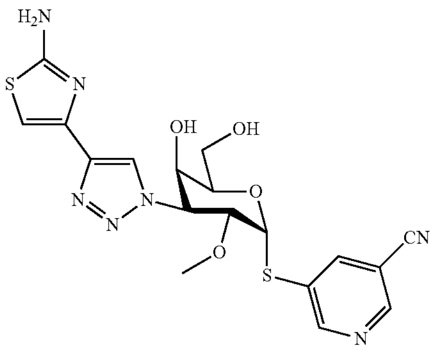

A solution of 5-cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside (110 mg, 0.15 mmol) in DCM/TFA (10 mL, 19:1) was stirred overnight at rt. The mixture was neutralized with $Et_3N$, concentrated and purified by prep HPLC [MeCN/$H_2O$ (10 mmol/L $NH_4HCO_3$), X-Select 10 μm 19*250 mm, 20 mL/min, UV 254] to give the title compound (40.2 mg, 59%). ESI-MS m/z calcd for [$C_{18}H_{19}N_7O_4S_2$] $[M+H]^+$: 462.1; found: 462.1. $^1H$ NMR (400 MHz, Methanol-$d_4$) δ 8.95 (d, J=2.4 Hz, 1H), 8.79 (d, J=2.0 Hz, 1H), 8.49 (t, J=2.0 Hz, 1H), 8.24 (s, 1H), 6.95 (s, 1H), 6.33 (d, J=5.6 Hz, 1H), 5.03 (dd, J=11.2, 2.8 Hz, 1H), 4.59 (dd, J=11.2, 5.6 Hz, 1H), 4.42 (t, J=6.0 Hz, 1H), 4.17 (d, J=2.4 Hz, 1H), 3.68 (d, J=6.0 Hz, 2H), 3.39 (s, 3H).

Example 41

3,5-Dichloro-4-fluorophenyl 2,3-dideoxy-3-[4-(2-hydroxythiazol-4-yl)-1H-1,2,3-triazol-1-yl]-1-thio-α-D-galactopyranoside

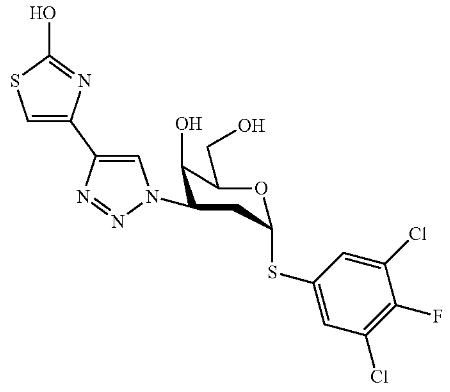

HBr (1 mL) was added to a suspension of 4,6-di-O-acetyl 3-deoxy-3-[4-(2-hydroxythiazol-4-yl)-1H-1,2,3-triazol-1-yl]-D-galactal (400 mg, 1.05 mmol) in THF (20 mL) and the mixture was stirred 22 h at rt. Water (10 mL) was added followed by $Na_2CO_3$ (446 mg, 4.21 mmol) and the mixture was stirred 30 min at rt. The mixture was concentrated and stirred 24 h at rt in pyridine (10 mL) and acetic anhydride (10 mL). The mixture was concentrated and partitioned between EtOAc and water. The organic phase was dried, evaporated and purified by chromatography ($SiO_2$, PE/EtOAc) to give crude acetyl 3-[4-(2-acetoxythiazol-4-yl)-1H-1,2,3-triazol-1-yl]-4,6-di-O-acetyl-2,3-dideoxy-D-galactopyranoside. A solution of 5-benzylsulfanyl-1,3-di-chloro-2-fluorobenzene (327 mg, 1.14 mmol) in toluene (2.5 mL) was added to a cooled (0° C.) suspension of $AlCl_3$ (258 g, 1.94 mmol) in toluene (7.5 mL) and the resulting mixture reached rt in 15 min, and was then stirred 2 h at rt. The mixture was cooled to 0° C. and quenched by addition of water. The phases were separated, and the organic phase was washed with water, dried and concentrated. The residue and the crude acetyl 3-[4-(2-acetoxythiazol-4-yl)-1H-1,2,3-triazol-1-yl]-4,6-di-O-acetyl-2,3-dideoxy-D-galactopyranoside were dissolved in DCM (6 mL). Boron trifluoride diethyl etherate (0.11 mL, 0.91 mmol) was added and the mixture was stirred 16 h at rt. The mixture was diluted with DCM and washed with saturated aq $NaHCO_3$. The aqueous phase was extracted with EtOAc and the combined organic phases were dried and evaporated. The residue was stirred 28 h at rt with MeOH (3 mL), $Et_3N$ (1 mL) and $H_2O$ (0.5 mL). The mixture was evaporated and purified by prep HPLC ($C_{18}$, $H_2O$/MeCN/0.1% TFA) to afford the title compound (6.6 mg, 1.3%). ESI-MS m/z calcd for [$C_{17}H_{15}Cl_2FN_4O_4S_2$] $[M+H]^+$: 493.0; found: 492.7, $^1H$ NMR (500 MHz, Methanol-$d_4$) δ 8.31 (s, 1H), 7.73 (d, J=6.2 Hz, 2H), 6.70 (s, 1H), 5.93 (d, J=5.5 Hz, 1H), 5.17 (ddd, J=13.6, 3.9, 2.5 Hz, 1H), 4.50 (t, J=6.1 Hz, 1H), 4.17 (d, J=2.2 Hz, 1H), 3.76 (d, J=6.0 Hz, 2H), 3.10 (td, J=13.5, 5.8 Hz, 1H), 2.33 (dd, J=13.4, 4.3 Hz, 1H).

Example 42

3-Chloro-4-cyanophenyl 3-[4-(2-aminothiazol-4-yl)-1H-1,2,3-triazol-1-yl]-2,3-dideoxy-1-thio-α-D-galactopyranoside

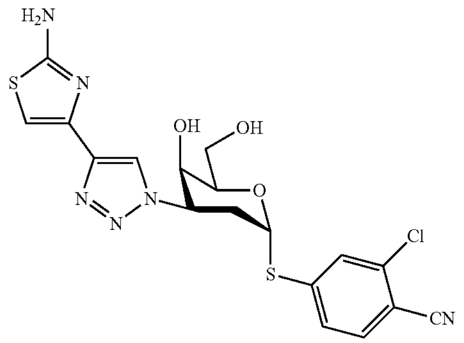

HBr (0.12 mL) was added to a solution of 4,6-di-O-acetyl 3-[4-(2-aminothiazol-4-yl)-1H-1,2,3-triazol-1-yl]-3-deoxy-D-galactal (100 mg, 0.26 mmol) in THF (7.5 mL) and the mixture was stirred 3 h at rt. Water (2.5 mL) was added followed by $Na_2CO_3$ (56 mg, 0.53 mmol) and the mixture was stirred 40 min at rt. The mixture was concentrated and stirred 2 h at rt in pyridine (3 mL) and acetic anhydride (3 mL). The mixture was concentrated and partitioned between EtOAc and water. The organic phase was dried, evaporated and purified by chromatography ($SiO_2$, PE/EtOAc). The obtained material was dissolved together with 2-chloro-4-sulfanylbenzonitrile (53 mg, 0.31 mmol) in DCM (3 mL). Boron trifluoride diethyl etherate (0.10 mL, 0.83 mmol) was added and the mixture was stirred 18 h at rt. The mixture was diluted with DCM and washed with saturated aq $NaHCO_3$. The organic phase was dried, evaporated and the residue was stirred 50 h at 50° C. in methylamine (40% in MeOH, 2 mL). The mixture was evaporated and purified by prep HPLC ($C_{18}$, $H_2O$/MeCN/0.1% TFA) to afford the title compound (21 mg, 17%). ESI-MS m/z calcd for $[C_{18}H_{17}ClN_6O_3S_2]$ $[M+H]^+$: 465.0; found: 464.8, $^1H$ NMR (400 MHz, Methanol-$d_4$) δ 8.42 (s, 1H), 7.85 (d, J=1.5 Hz, 1H), 7.71 (d, J=8.2 Hz, 1H), 7.64 (dd, J=8.2, 1.6 Hz, 1H), 7.09 (s, 1H), 6.19 (d, J=5.6 Hz, 1H), 5.20 (dt, J=13.6, 3.4 Hz, 1H), 4.39 (t, J=6.1 Hz, 1H), 4.18 (s, 1H), 3.78-3.70 (m, 2H), 3.16 (td, J=13.5, 5.6 Hz, 1H), 2.35 (dd, J=13.6, 4.1 Hz, 1H).

Example 43

5-Chloro-2-cyanophenyl 3-[4-(4-chlorothiazol-2-yl)-1H-1,2,3-triazol-1-yl]-2,3-dideoxy-1-thio-α-D-galactopyranoside

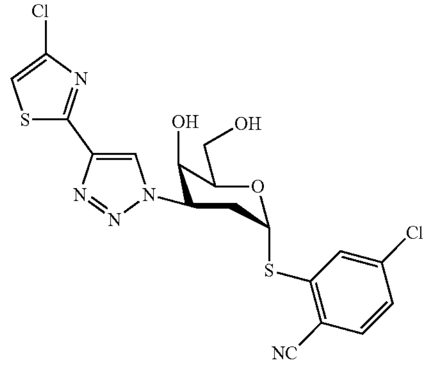

HBr (0.075 mL) was added to a solution of 4,6-di-O-acetyl 3-[4-(4-chlorothiazol-2-yl)-1H-1,2,3-triazol-1-yl]-3-deoxy-D-galactal (100 mg, 0.25 mmol) in THF (5 mL) and the mixture was stirred 3 h at rt. Water (2.5 mL) was added followed by $Na_2CO_3$ (53 mg, 0.50 mmol) and the mixture was stirred 20 min at rt. The mixture was extracted with EtOAc and washed with water. The organic phase was dried, evaporated and purified by chromatography ($SiO_2$, PE/EtOAc). The obtained material was dissolved together with 4-chloro-2-sulfanylbenzonitrile (39 mg, 0.23 mmol) in DCM (5 mL). Trifluoromethanesulfonic acid (41 μL, 0.46 mmol) was added and the mixture was stirred 1 h at rt. The mixture was diluted with DCM and washed with saturated aq $NaHCO_3$. The organic phase was dried, evaporated and purified by chromatography ($SiO_2$, PE/EtOAc). The obtained material was stirred 20 min at rt in MeOH (4 mL) and NaOMe (0.5 mL, 1 M). The mixture was concentrated and purified by prep HPLC ($C_{18}$, $H_2O$/MeCN/0.1% TFA) to afford the title compound (11 mg, 9%). ESI-MS m/z calcd for $[C_{18}H_{15}Cl_2N_5O_3S_2]$ $[M+H]^+$: 484.0; found: 484.0, $^1H$ NMR (400 MHz, Methanol-$d_4$) δ 8.58 (s, 1H), 8.02 (d, J=2.0 Hz, 1H), 7.74 (d, J=8.4 Hz, 1H), 7.50-7.44 (m, 2H), 6.16 (d, J=5.5 Hz, 1H), 5.26 (d, J=13.0 Hz, 1H), 4.46 (t, J=6.0 Hz, 1H), 4.23 (s, 1H), 3.79-3.68 (m, 2H), 3.22 (td, J=13.5, 5.8 Hz, 1H), 2.45 (dd, J=13.7, 4.5 Hz, 1H).

Example 44

3-Cyano-2-(trifluoromethyl)pyridin-5-yl 3-[4-(2-aminothiazol-4-yl)-1H-1,2,3-triazol-1-yl]-3-deoxy-2-O-methyl-1-thio-α-D-galactopyranoside

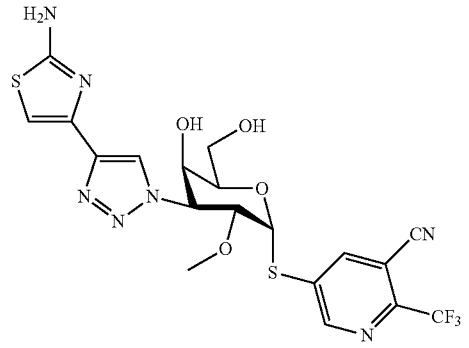

To a solution of 3-cyano-2-(trifluoromethyl)pyridin-5-yl 4,6-di-O-acetyl-3-azido-3-deoxy-2-O-methyl-1-thio-α-D-galactopyranoside (52 mg, 0.11 mmol), CuI (2.0 mg, 0.11 mmol) and tert-butyl N-[4-(2-trimethylsilylethynyl)thiazol-2-yl]carbamate (38 mg, 0.13 mmol) in MeCN (1.0 mL) TBAF (106 μL, 1 M in THF, 0.11 mmol) was added and the mixture was stirred 5 h at rt. The mixture was diluted with EtOAc (20 mL) and washed with water (3×10 mL) and brine (10 mL). The organic phase was dried and evaporated. The residue was dissolved in DCM (2 mL) and TFA (0.2 mL) and stirred 16 h at rt. The mixture was evaporated, and the residue was stirred 20 min at rt in MeOH (2 mL) and NaOMe (0.11 mL, 1 M). Acetic acid (20 μL) was added and the mixture was concentrated and purified by prep HPLC ($C_{18}$, $H_2O$/MeCN/0.1% TFA) to afford the title compound as a TFA salt (23 mg, 34%). ESI-MS m/z calcd for $[C_{19}H_{18}F_3N_7O_4S_2]$ $[M+H]^+$: 530.1; found: 529.9, $^1H$ NMR (400 MHz, Methanol-$d_4$) δ 9.03 (d, J=2.0 Hz, 1H), 8.68 (d, J=2.0 Hz, 1H), 8.26 (s, 1H), 6.97 (s, 1H), 6.57 (d, J=5.3 Hz, 1H), 5.06 (dd, J=11.2, 2.7 Hz, 1H), 4.64 (dd, J=11.3, 5.3 Hz, 1H), 4.35 (dd, J=7.1, 4.7 Hz, 1H), 4.17 (d, J=2.4 Hz, 1H), 3.78-3.63 (m, 2H), 3.40 (s, 3H).

Example 45

5-Chloro-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside

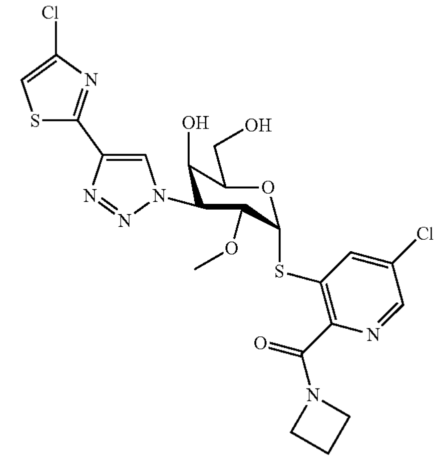

To a solution of 5-chloro-2-(N-azetidinylcarbamoyl)-3-pyridyl 3-azido-3-deoxy-2-O-methyl-1-thio-α-D-galactopyranoside (51 mg, 0.12 mmol), CuI (28 mg, 0.15 mmol) and 2-(4-chlorothiazol-2-yl)ethynyltrimethylsilane (38 mg, 0.18 mmol) in MeCN (1.5 mL) DIPEA (61 μL, 0.36 mmol) was added and the mixture was stirred 2 h at 50° C. The mixture was purified by prep HPLC ($C_{18}$, $H_2O$/MeCN/0.1% TFA) to afford the title compound (48 mg, 71%). ESI-MS m/z calcd for $[C_{21}H_{22}Cl_2N_6O_5S_2]$ $[M+H]^+$: 573.0; found: 572.8. $^1H$ NMR (400 MHz, Methanol-$d_4$) δ 8.63 (s, 1H), 8.48 (d, J=2.1 Hz, 1H), 8.38 (d, J=2.1 Hz, 1H), 7.47 (d, J=2.7 Hz, 1H), 6.36 (d, J=5.4 Hz, 1H), 5.11 (dd, J=11.3, 2.9 Hz, 1H), 4.66 (dd, J=11.4, 5.4 Hz, 1H), 4.44 (t, J=6.0 Hz, 1H), 4.27-4.16 (m, 5H), 3.74-3.64 (m, 2H), 3.41 (s, 3H), 2.39 (p, J=7.8 Hz, 2H).

Example 46

5-Chloro-2-(pyridin-2-yl)pyridin-3-yl 3-deoxy-3-[4-(4-methylthiazol-2-yl)-1H-1,2,3-triazol-1-yl]-2-O-methyl-1-thio-α-D-galactopyranoside

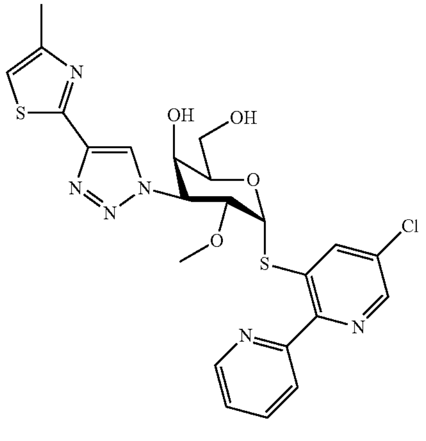

To a solution of 5-chloro-2-(pyridin-2-yl)pyridin-3-yl 3-azido-3-deoxy-2-O-methyl-1-thio-α-D-galactopyranoside (76 mg, 0.18 mmol), CuI (43 mg, 0.22 mmol) and trimethyl-[2-(4-methylthiazol-2-yl)ethynyl]silane (44 mg, 0.22 mmol) in MeCN (2.0 mL) DIPEA (92 μL, 0.54 mmol) was added and the mixture was stirred 2 h at 50° C. The mixture was concentrated and partitioned between EtOAc and saturated aq $NaHCO_3$. The organic phase was dried, evaporated and purified by prep HPLC ($C_{18}$, $H_2O$/MeCN/0.1% TFA) to afford the title compound (41 mg, 42%). ESI-MS m/z calcd for $[C_{23}H_{23}ClN_6O_4S_2]$ $[M+H]^+$: 547.1; found: 547.1. $^1H$ NMR (500 MHz, Methanol-$d_4$) δ 8.80 (d, J=5.0 Hz, 1H), 8.62 (d, J=2.1 Hz, 1H), 8.55-8.52 (m, 2H), 8.29 (td, J=7.8, 1.6 Hz, 1H), 8.22 (d, J=7.9 Hz, 1H), 7.79-7.74 (m, 1H), 7.18 (d, J=1.0 Hz, 1H), 6.25 (d, J=5.3 Hz, 1H), 4.98 (dd, J=11.4, 2.9 Hz, 1H), 4.58 (dd, J=11.4, 5.3 Hz, 1H), 4.24 (t, J=6.1 Hz, 1H), 4.13 (d, J=2.3 Hz, 1H), 3.70-3.64 (m, 2H), 3.23 (s, 3H), 2.47 (d, J=0.9 Hz, 3H).

Example 47

5-Ethynylpyridin-3-yl 3-deoxy-2-O-methyl-3-[4-(2-thiazolyl)-1H-1,2,3-triazol-1-yl]-1-thio-α-D-galactopyranoside

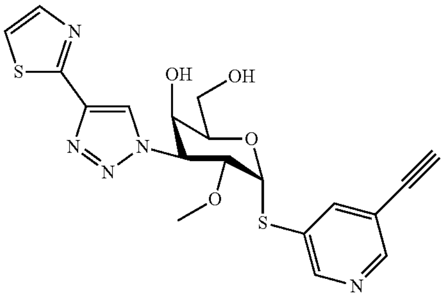

To a nitrogen purged solution of 5-bromopyridin-3-yl 3-deoxy-2-O-methyl-3-[4-(2-thiazolyl)-1H-1,2,3-triazol-1-yl]-1-thio-α-D-galactopyranoside (30 mg, 0.60 mmol), CuI (0.6 mg, 0.003 mmol) and bis(triphenylphosphine)palladium (II) chloride (2.1 mg, 0.003 mmol) in THF (0.75 mL) ethynyl(trimethyl)silane (11.6 μL, 0.084 mmol) was added followed by and DIPEA (14.6 μL, 0.084 mmol) and the mixture was stirred 20 h at 50° C. The mixture was cooled to rt and TBAF (0.15 mL, 1 M in THF, 0.15 mmol) was added. After stirring 30 min at rt, the mixture was partitioned between EtOAc and water. The organic phase was dried, evaporated and purified by prep HPLC ($C_{18}$, $H_2O$/MeCN/0.1% TFA) to afford the title compound (14 mg, 52%). ESI-MS m/z calcd for $[C_{19}H_{19}N_5O_4S_2]$ $[M+H]^+$: 446.1; found: 446.1. $^1H$ NMR (400 MHz, Methanol-$d_4$) δ 8.65 (d, J=1.9 Hz, 1H), 8.51 (s, 1H), 8.48 (s, 1H), 8.18 (t, J=2.0 Hz, 1H), 7.79 (d, J=3.0 Hz, 1H), 7.54 (d, J=3.1 Hz, 1H), 6.19 (d, J=5.3 Hz, 1H), 4.99 (dd, J=11.3, 2.8 Hz, 1H), 4.54 (dd, J=11.3, 5.3 Hz, 1H), 4.36 (t, J=6.0 Hz, 1H), 4.11 (d, J=2.2 Hz, 1H), 3.80 (s, 1H), 3.64-3.54 (m, 2H), 3.31 (d, J=2.0 Hz, 3H).

Example 48

5-Chloropyridin-3-yl 3-[4-(4-chlorothiazol-2-yl)-1H-1,2,3-triazol-1-yl]-3-deoxy-1-thio-α-D-galacto-pyranoside

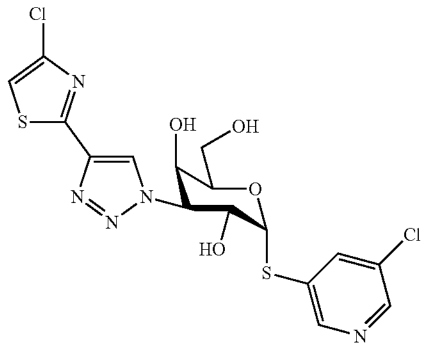

To a solution of 5-chloropyridin-3-yl 2,4,6-tri-O-acetyl-3-azido-3-deoxy-1-thio-α-D-galactopyranoside (92 mg, 0.20 mmol), CuI (7.6 mg, 0.04 mmol) and 2-(4-chlorothiazol-2-yl)ethynyltrimethylsilane (52 mg, 0.24 mmol) in MeCN (2.0 mL) $Et_3N$ (0.11 mL, 0.80 mmol) and TBAF (0.02 mL, 1 M in THF, 0.020 mmol) were added and the mixture was stirred 90 min at 50° C. The mixture was filtered through a plug of celite and concentrated. The residue was stirred 16 h at rt in MeOH (1 mL), $Et_3N$ (0.45 mL) and water (0.15 mL). The mixture was filtered, concentrated and purified by prep HPLC ($C_{18}$, $H_2O$/MeCN/0.1% TFA) to afford the title compound (61 mg, 64%). ESI-MS m/z calcd for $[C_{16}H_{15}Cl_2N_5O_4S_2]$ $[M+H]^+$: 476.0; found: 476.0. $^1H$ NMR (500 MHz, Methanol-$d_4$) δ 8.68 (s, 1H), 8.62 (s, 1H), 8.51 (s, 1H), 8.24 (t, J=2.0 Hz, 1H), 7.48 (s, 1H), 5.96 (d, J=5.4 Hz, 1H), 5.09 (dd, J=11.4, 2.9 Hz, 1H), 4.96 (dd, J=11.4, 5.4 Hz, 1H), 4.50 (t, J=6.1 Hz, 1H), 4.24 (d, J=2.0 Hz, 1H), 3.77-3.68 (m, 2H).

Example 49

5-Bromopyridin-3-yl 3-[4-(4-chlorothiazol-2-yl)-1H-1,2,3-triazol-1-yl]-3-deoxy-1-thio-α-D-galacto-pyranoside

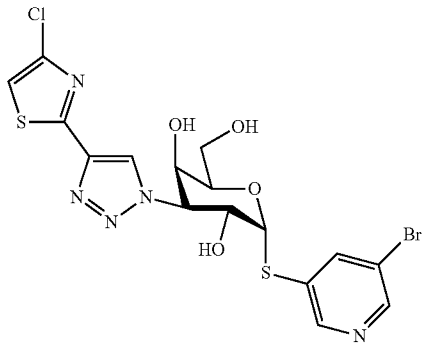

A solution of (+)-sodium L-ascorbate (59 mg, 0.30 mmol) and copper (II) sulfate pentahydrate (37 mg, 0.15 mmol) in water (2.5 mL) was added to a solution of 5-bromopyridin-3-yl 2,4,6-tri-O-acetyl-3-azido-3-deoxy-1-thio-α-D-galacto-pyranoside (745 mg, 1.48 mmol), 2-(4-chlorothiazol-2-yl) ethynyltrimethylsilane (479 mg, 2.22 mmol) and $K_2CO_3$ (2.05 g, 14.8 mmol) in MeOH/THF (35 mL, 1:1) and the mixture was stirred 16 h at rt, then 24 h at 50° C. The mixture was concentrated and partitioned between EtOAc and water. The aqueous phase was extracted with EtOAc and the combined organic phases were dried and evaporated. The residue was suspended in DCM and the solids were filtered off to yield the title compound (589 mg, 76%). ESI-MS m/z calcd for $[C_{16}H_{15}BrClN_5O_4S_2]$ $[M+H]^+$: 519.9; found: 519.9. $^1H$ NMR (400 MHz, Methanol-$d_4$) δ 8.69 (d, J=1.8 Hz, 1H), 8.60 (s, 1H), 8.58 (d, J=2.1 Hz, 1H), 8.36 (t, J=2.0 Hz, 1H), 7.47 (s, 1H), 5.93 (d, J=5.4 Hz, 1H), 5.07 (dd, J=11.4, 2.9 Hz, 1H), 4.93 (dd, J=11.4, 5.4 Hz, 1H), 4.48 (t, J=6.1 Hz, 1H), 4.21 (d, J=2.0 Hz, 1H), 3.76-3.66 (m, 2H).

Example 50

5-Chloro-2-cyanophenyl 3-[4-(4-chlorothiazol-2-yl)-1H-1,2,3-triazol-1-yl]-3-deoxy-1-thio-α-D-galacto-pyranoside

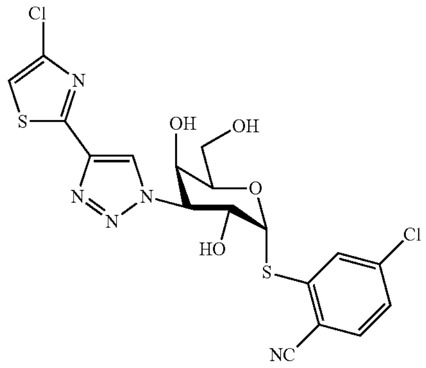

To a solution of 4-chloro-2-cyanophenyl 2,4,6-tri-O-acetyl-3-azido-3-deoxy-1-thio-α-D-galactopyranoside (125 mg, 0.26 mmol), CuI (9.9 mg, 0.052 mmol) and 2-(4-chlorothiazol-2-yl)ethynyltrimethylsilane (67 mg, 0.31 mmol) in MeCN (2.0 mL) $Et_3N$ (0.14 mL, 1.04 mmol) and TBAF (26 μL, 1 M in THF, 0.026 mmol) were added and the mixture was stirred 90 min at 50° C. The mixture was filtered, concentrated and the residue was stirred 16 h at 50° C. in MeOH (2 mL), $Et_3N$ (0.3 mL) and water (0.1 mL). The mixture was filtered, concentrated and purified by prep HPLC ($C_{18}$, $H_2O$/MeCN/0.1% TFA). The obtained material was filtered through a SCX-column to afford the title compound (93 mg, 72%). ESI-MS m/z calcd for $[C_{16}H_{15}Cl_2N_5O_4S_2][M+H]^+$: 500.0; found: 500.0. $^1H$ NMR (400 MHz, Methanol-$d_4$) δ 8.61 (s, 1H), 7.98 (d, J=1.9 Hz, 1H), 7.74 (d, J=8.3 Hz, 1H), 7.51-7.43 (m, 2H), 6.13 (d, J=5.3 Hz, 1H), 5.11 (dd, J=11.3, 2.8 Hz, 1H), 4.98 (dd, J=11.4, 5.4 Hz, 1H), 4.42 (t, J=6.2 Hz, 1H), 4.28-4.21 (m, 1H), 3.70 (dd, J=11.4, 5.6 Hz, 1H), 3.64 (dd, J=11.4, 6.6 Hz, 1H).

Example 51

3-Chloro-5-cyanophenyl 3-[4-(4-chlorothiazol-2-yl)-1H-1,2,3-triazol-1-yl]-3-deoxy-1-thio-α-D-galactopyranoside

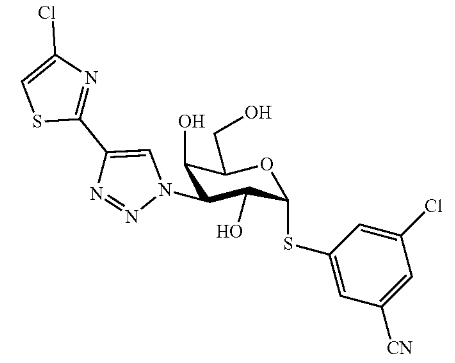

To a solution of 3-chloro-5-cyanophenyl 2,4,6-tri-O-acetyl-3-azido-3-deoxy-1-thio-α-D-galactopyranoside (80 mg, 0.17 mmol), CuI (6.3 mg, 0.033 mmol) and 2-(4-chlorothiazol-2-yl)ethynyltrimethylsilane (43 mg, 0.20 mmol) in MeCN (1.3 mL) $Et_3N$ (92 μL, 0.66 mmol) and TBAF (17 μL, 1 M in THF, 0.017 mmol) were added and the mixture was stirred 1 h at 50° C. The mixture was filtered, concentrated and the residue was stirred 16 h at 50° C. in MeOH (2 mL), $Et_3N$ (0.3 mL) and water (0.1 mL). The mixture was filtered, concentrated and purified by prep HPLC ($C_{18}$, $H_2O$/MeCN/0.1% TFA). The obtained material was filtered through a SCX-column to afford the title compound (35 mg, 42%). ESI-MS m/z calcd for $[C_{16}H_{15}Cl_2N_5O_4S_2]$ $[M+H]^+$: 500.0; found: 500.0. $^1H$ NMR (400 MHz, Methanol-$d_4$) δ 8.60 (s, 1H), 7.95 (s, 1H), 7.93 (s, 1H), 7.71 (s, 1H), 7.46 (s, 1H), 5.98 (d, J=5.2 Hz, 1H), 5.05 (dd, J=11.5, 2.7 Hz, 1H), 4.93 (dd, J=11.5, 5.4 Hz, 1H), 4.44 (t, J=6.2 Hz, 1H), 4.23-4.17 (m, 1H), 3.77-3.65 (m, 2H).

Example 52

3-Chloro-4-cyanophenyl 3-[4-(4-chlorothiazol-2-yl)-1H-1,2,3-triazol-1-yl]-3-deoxy-1-thio-α-D-galactopyranoside

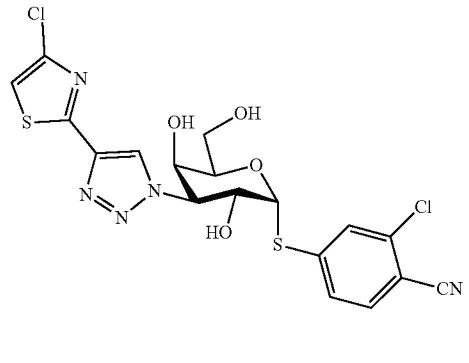

To a solution of 3-chloro-4-cyanophenyl 2,4,6-tri-O-acetyl-3-azido-3-deoxy-1-thio-α-D-galactopyranoside (111 mg, 0.23 mmol), CuI (8.8 mg, 0.046 mmol) and 2-(4-chlorothiazol-2-yl)ethynyltrimethylsilane (60 mg, 0.28 mmol) in MeCN (2.0 mL) $Et_3N$ (128 μL, 0.92 mmol) and TBAF (23 μL, 1 M in THF, 0.023 mmol) were added and the mixture was stirred 90 min at 50° C. The mixture was filtered, concentrated and the residue was stirred 20 h at 50° C. in MeOH (2 mL), $Et_3N$ (0.3 mL) and water (0.1 mL). The mixture was filtered, concentrated and purified by prep HPLC ($C_{18}$, $H_2O$/MeCN/0.1% TFA). The obtained material was filtered through a SCX-column to afford the title compound (81 mg, 70%). ESI-MS m/z calcd for $[C_{16}H_{15}Cl_2N_5O_4S_2][M+H]^+$: 500.0; found: 500.0. $^1H$ NMR (400 MHz, Methanol-$d_4$) δ 8.60 (s, 1H), 7.86 (d, J=1.4 Hz, 1H), 7.71 (d, J=8.3 Hz, 1H), 7.66 (dd, J=8.2, 1.5 Hz, 1H), 7.46 (s, 1H), 6.11 (d, J=5.3 Hz, 1H), 5.06 (dd, J=11.4, 2.8 Hz, 1H), 4.96 (dd, J=11.3, 5.5 Hz, 1H), 4.38 (t, J=6.1 Hz, 1H), 4.23-4.17 (m, 1H), 3.77-3.63 (m, 2H).

Example 53

5-Chloropyridin-3-yl 3-[4-(4-chlorothiazol-2-yl)-1H-1,2,3-triazol-1-yl]-3-deoxy-2-O-methyl-1-thio-α-D-galactopyranoside

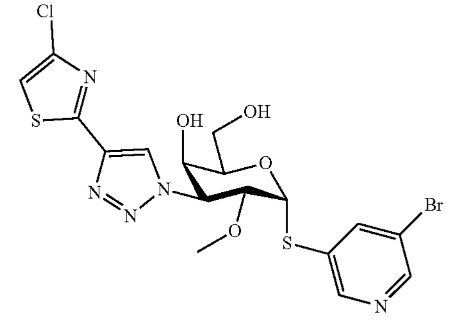

To a solution of 5-chloropyridin-3-yl 3-azido-3-deoxy-2-O-methyl-1-thio-α-D-galactopyranoside (69.4 mg, 0.20 mmol), CuI (7.6 mg, 0.040 mmol) and 2-(4-chlorothiazol-2-yl)ethynyltrimethylsilane (51.8 mg, 0.24 mmol) in MeCN (2.0 mL) $Et_3N$ (112 μL, 0.80 mmol) and TBAF (20 μL, 1 M in THF, 0.020 mmol) were added and the mixture was stirred 90 min at 50° C. The mixture was filtered, concentrated and purified by prep HPLC ($C_{18}$, $H_2O$/MeCN/0.1% TFA) to afford the title compound (13 mg, 13%). ESI-MS m/z calcd for $[C_{17}H_{17}Cl_2N_5O_4S_2]$ $[M+H]^+$: 490.0; found: 490.0. $^1H$ NMR (500 MHz, Methanol-$d_4$) δ 8.68 (s, 1H), 8.66 (s, 1H), 8.50 (s, 1H), 8.24 (t, J=2.0 Hz, 1H), 7.49 (s, 1H), 6.30 (d, J=5.3 Hz, 1H), 5.11 (dd, J=11.4, 2.9 Hz, 1H), 4.67 (dd, J=11.3, 5.3 Hz, 1H), 4.49 (t, J=6.1 Hz, 1H), 4.22 (d, J=2.2 Hz, 1H), 3.78-3.66 (m, 2H), 3.44 (s, 3H).

Example 54

5-Bromopyridin-3-yl 3-[4-(4-chlorothiazol-2-yl)-1H-1,2,3-triazol-1-yl]-3-deoxy-2-O-methyl-1-thio-α-D-galactopyranoside

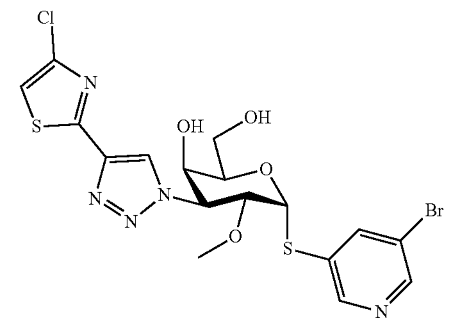

To a solution of 5-bromopyridin-3-yl 3-[4-(4-chlorothiazol-2-yl)-1H-1,2,3-triazol-1-yl]-3-deoxy-1-thio-α-D-galactopyranoside (516 mg, 0.99 mmol) in MeCN (40 mL) benzaldehyde dimethylacetal (0.30 mL, 1.98 mmol) followed by p-toluenesulfonic acid monohydrate (94 mg, 0.50 mmol) were added and the mixture was stirred 20 h at rt. $Et_3N$ (0.14 mL, 0.99 mmol) was added and the mixture was concentrated. The residue was partitioned between EtOAc and saturated aq $NaHCO_3$. The organic phase was dried, evaporated and the residue was dissolved together with NaH (60% in oil, 60 mg, 1.56 mmol) in DMF (5 mL). Iodomethane (78 μL, 1.17 mmol) was added and the mixture was stirred 1 h at rt. The mixture was diluted with EtOAc, washed twice with water and the organic phase was dried and evaporated. The residue was stirred 30 min at rt in TFA/water (5 mL, 4:1). The mixture was concentrated to half its volume and partitioned between EtOAc and aqueous NaOH (1 M). The organic phase was dried, evaporated and purified by chromatography ($SiO_2$, PE/EtOAc). Further purification by prep HPLC ($C_{18}$, $H_2O$/MeCN/0.1% TFA) yielded the title compound (191 mg, 46%). ESI-MS m/z calcd for $[C_{17}H_{17}BrClN_5O_4S_2]$ $[M+H]^+$: 534.0; found: 534.0. $^1H$ NMR (500 MHz, Methanol-$d_4$) δ 8.74 (s, 1H), 8.65 (s, 1H), 8.62 (s, 1H), 8.41 (t, J=1.9 Hz, 1H), 7.49 (s, 1H), 6.31 (d, J=5.3 Hz, 1H), 5.11 (dd, J=11.3, 2.9 Hz, 1H), 4.67 (dd, J=11.3, 5.3 Hz, 1H), 4.48 (t, J=6.1 Hz, 1H), 4.23 (d, J=2.3 Hz, 1H), 3.76-3.68 (m, 2H), 3.44 (s, 3H).

Example 55

5-Bromo-2-cyanopyridin-3-yl 3-[4-(4,5-dichlorothiazol-2-yl)-1H-1,2,3-triazol-1-yl]-3-deoxy-2-O-methyl-1-thio-α-D-galactopyranoside

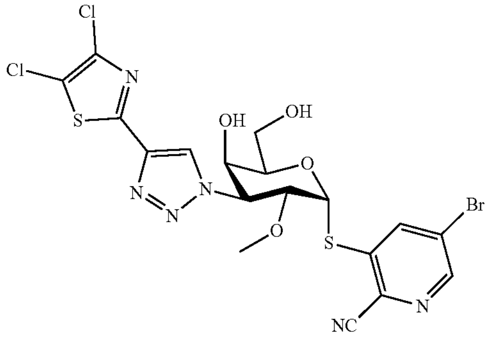

To a solution of 5-bromo-2-cyanopyridin-3-yl 4,6-di-O-acetyl-3-azido-3-deoxy-2-O-methyl-1-thio-α-D-galactopyranoside (75 mg, 0.15 mmol), CuI (7.1 mg, 0.038 mmol) and 4,5-dichloro-2-ethynylthiazole (57 mg, 0.32 mmol) in MeCN (4 mL) DIPEA (77 μL, 0.45 mmol) was added and the mixture was stirred 16 h at 50° C. The mixture was concentrated and partitioned between EtOAc and water. The organic phase was dried, evaporated and purified by chromatography ($SiO_2$, PE/EtOAc). The obtained material was stirred 3 h at rt in MeOH (2.25 mL), $Et_3N$ (0.75 mL) and water (0.25 mL). The mixture was concentrated and purified by prep HPLC ($C_{18}$, $H_2O$/MeCN/0.1% TFA) to afford the title compound (60 mg, 67%). ESI-MS m/z calcd for $[C_{18}H_{15}BrCl_2N_6O_4S_2][M+H]^+$: 592.9; found: 592.9. $^1H$ NMR (400 MHz, Methanol-$d_4$) δ 8.71 (d, J=2.0 Hz, 1H), 8.67 (s, 1H), 8.62 (d, J=2.0 Hz, 1H), 6.50 (d, J=5.3 Hz, 1H), 5.13 (dd, J=11.3, 2.9 Hz, 1H), 4.72 (dd, J=11.3, 5.3 Hz, 1H), 4.41 (t, J=6.0 Hz, 1H), 4.20 (d, J=2.6 Hz, 1H), 3.68 (d, J=6.0 Hz, 2H), 3.46 (s, 3H).

Example 56

5-Bromo-2-cyanophenyl 3-deoxy-2-O-methyl-3-[4-(2-thiazolyl)-1H-1,2,3-triazol-1-yl]-1-thio-α-D-galactopyranoside

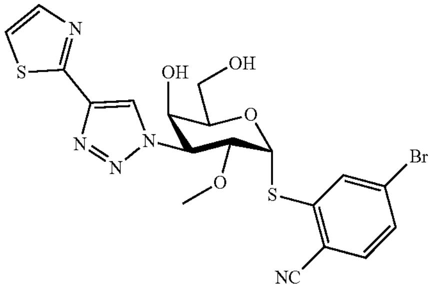

To a solution of 5-bromo-2-cyanophenyl 3-azido-3-deoxy-2-O-methyl-1-thio-α-D-galactopyranoside (75 mg, 0.18 mmol), CuI (6.9 mg, 0.036 mmol) and trimethyl(2-thiazol-2-ylethynyl)silane (98 mg, 0.27 mmol) in MeCN (2.0 mL)

$Et_3N$ (101 μL, 0.72 mmol) and TBAF (18 μL, 1 M in THF, 0.018 mmol) were added and the mixture was stirred 5 h at 50° C. The mixture was filtered, concentrated and purified by prep HPLC ($C_{18}$, $H_2O$/MeCN/0.1% TFA). The obtained material was further purified by chromatography ($SiO_2$, PE/EtOAc) to afford the title compound (30 mg, 32%). ESI-MS m/z calcd for $[C_{19}H_{18}BrN_5O_4S_2]$ $[M+H]^+$: 524.0; found: 524.0. $^1H$ NMR (500 MHz, Methanol-$d_4$) δ 8.64 (s, 1H), 8.18 (d, J=1.5 Hz, 1H), 7.92 (d, J=3.3 Hz, 1H), 7.73-7.68 (m, 2H), 7.67 (d, J=3.3 Hz, 1H), 6.42 (d, J=5.4 Hz, 1H), 5.14 (dd, J=11.3, 2.9 Hz, 1H), 4.71 (dd, J=11.3, 5.3 Hz, 1H), 4.47 (t, J=6.1 Hz, 1H), 4.26 (d, J=2.8 Hz, 1H), 3.73 (dd, J=11.5, 5.5 Hz, 1H), 3.67 (dd, J=11.5, 6.7 Hz, 1H), 3.49 (s, 3H).

Example 57

5-Bromo-2-cyanophenyl 3-[4-(4-chlorothiazol-2-yl)-1H-1,2,3-triazol-1-yl]-3-deoxy-2-O-methyl-1-thio-α-D-galactopyranoside

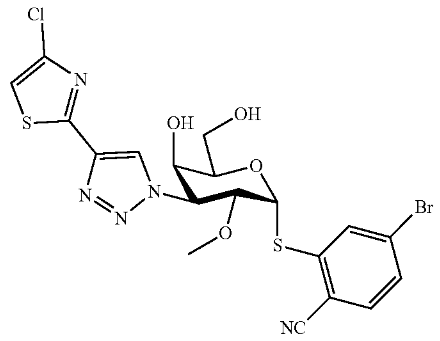

To a solution of 5-bromo-2-cyanophenyl 3-azido-3-deoxy-2-O-methyl-1-thio-α-D-galactopyranoside (75 mg, 0.18 mmol), CuI (6.9 mg, 0.036 mmol) and 2-(4-chlorothiazol-2-yl)ethynyltrimethylsilane (59 mg, 0.27 mmol) in MeCN (2.0 mL) $Et_3N$ (101 μL, 0.72 mmol) and TBAF (18 μL, 1 M in THF, 0.018 mmol) were added and the mixture was stirred 4 h at 50° C. The mixture was filtered, concentrated and purified by prep HPLC ($C_{18}$, $H_2O$/MeCN/0.1% TFA) to afford the title compound (71 mg, 70%). ESI-MS m/z calcd for $[C_{19}H_{17}BrClN_5O_4S_2]$ $[M+H]^+$: 558.0; found: 558.0. $^1H$ NMR (500 MHz, Methanol-$d_4$) δ 8.66 (s, 1H), 8.17 (s, 1H), 7.73-7.66 (m, 2H), 7.49 (s, 1H), 6.42 (d, J=5.3 Hz, 1H), 5.13 (dd, J=11.3, 2.9 Hz, 1H), 4.72 (dd, J=11.3, 5.3 Hz, 1H), 4.47 (t, J=6.1 Hz, 1H), 4.25 (d, J=2.7 Hz, 1H), 3.73 (dd, J=11.5, 5.5 Hz, 1H), 3.67 (dd, J=11.4, 6.7 Hz, 1H), 3.49 (s, 3H).

Example 58

5-Bromo-2-cyanophenyl 3-deoxy-3-[4-(2-hydroxythiazol-4-yl)-1H-1,2,3-triazol-1-yl]-2-O-methyl-1-thio-α-D-galactopyranoside

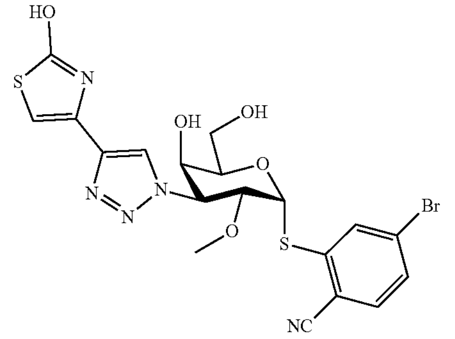

To a solution of 5-bromo-2-cyanophenyl 3-azido-3-deoxy-2-O-methyl-1-thio-α-D-galactopyranoside (75 mg, 0.18 mmol), CuI (6.9 mg, 0.036 mmol) and 4-(2-trimethylsilylethynyl)thiazol-2-ol (54 mg, 0.27 mmol) in MeCN (2.0 mL) $Et_3N$ (101 μL, 0.72 mmol) and TBAF (18 μL, 1 M in THF, 0.018 mmol) were added and the mixture was stirred 4 h at 50° C. More 4-(2-trimethylsilylethynyl)thiazol-2-ol (54 mg, 0.27 mmol) was added and the mixture was stirred an additional 2 h at 50° C. The mixture was filtered, concentrated and purified by prep HPLC ($C_{18}$, $H_2O$/MeCN/0.1% TFA) to afford the title compound (45 mg, 46%). ESI-MS m/z calcd for $[C_{19}H_{18}BrN_5O_5S_2]$ $[M+H]^+$: 540.0; found: 540.0. $^1H$ NMR (500 MHz, Methanol-$d_4$) δ 8.39 (s, 1H), 8.17 (d, J=1.0 Hz, 1H), 7.73-7.66 (m, 2H), 6.73 (s, 1H), 6.41 (d, J=5.3 Hz, 1H), 5.08 (dd, J=11.3, 2.9 Hz, 1H), 4.63 (dd, J=11.3, 5.3 Hz, 1H), 4.45 (t, J=6.0 Hz, 1H), 4.23 (d, J=2.3 Hz, 1H), 3.72 (dd, J=11.4, 5.5 Hz, 1H), 3.66 (dd, J=11.4, 6.7 Hz, 1H), 3.47 (s, 3H).

Example 59

5-Bromo-2-cyanophenyl 3-[4-(2-aminothiazol-4-yl)-1H-1,2,3-triazol-1-yl]-3-deoxy-2-O-methyl-1-thio-α-D-galactopyranoside

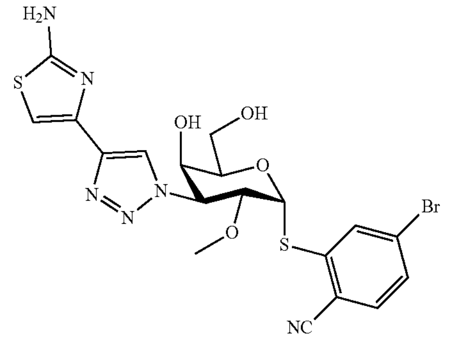

To a solution of 5-bromo-2-cyanophenyl 3-azido-3-deoxy-2-O-methyl-1-thio-α-D-galactopyranoside (75 mg, 0.18 mmol), CuI (6.9 mg, 0.036 mmol) and 4-(2-trimethylsilylethynyl)thiazol-2-amine (53 mg, 0.27 mmol) in MeCN (2.0 mL) $Et_3N$ (101 μL, 0.72 mmol) and TBAF (18 μL, 1 M in THF, 0.018 mmol) were added and the mixture was stirred 5 h at 50° C. The mixture was filtered, concentrated and purified by prep HPLC ($C_{18}$, $H_2O$/MeCN/0.1% TFA) to afford the title compound (63 mg, 65%). ESI-MS m/z calcd for [$C_{19}H_{19}BrN_6O_4S_2$] $[M+H]^+$: 539.0; found: 539.0. $^1H$ NMR (500 MHz, Methanol-$d_4$) δ 8.79-8.37 (m, 1H), 8.20-8.11 (m, 1H), 7.75-7.66 (m, 2H), 7.37-6.93 (m, 1H), 6.49-6.40 (m, 1H), 5.26-5.06 (m, 1H), 4.75-4.62 (m, 1H), 4.47 (t, J=5.9 Hz, 1H), 4.37-4.19 (m, 1H), 3.73 (dd, J=11.4, 5.4 Hz, 1H), 3.68 (dd, J=11.4, 6.6 Hz, 1H), 3.48 (s, 3H).

Example 60

5-Bromo-2-(N-methyl-carbonyl)phenyl 3-[4-(4-chlorothiazol-2-yl)-1H-1,2,3-triazol-1-yl]-3-deoxy-2-O-methyl-1-thio-α-D-galactopyranoside

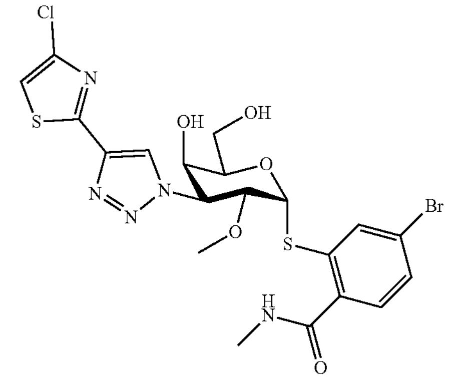

To a solution of 5-bromo-2-(N-methyl-carbonyl)phenyl 3-azido-3-deoxy-2-O-methyl-1-thio-α-D-galactopyranoside (100 mg, 0.20 mmol), CuI (8.5 mg, 0.045 mmol) and 2-(4-chlorothiazol-2-yl)ethynyltrimethylsilane (60 mg, 0.28 mmol) in MeCN (2.5 mL) DIPEA (0.12 mL, 0.67 mmol) was added and the mixture was stirred 3 h at 50° C. The mixture was purified by prep HPLC ($C_{18}$, $H_2O$/MeCN/0.1% TFA) to afford the title compound (89 mg, 67%). ESI-MS m/z calcd for [$C_{20}H_{21}BrClN_5O_5S_2$] $[M+H]^+$: 590.0; found: 590.0. $^1H$ NMR (500 MHz, Methanol-$d_4$) δ 8.61 (s, 1H), 8.00 (d, J=1.9 Hz, 1H), 7.56 (dd, J=8.2, 1.9 Hz, 1H), 7.46 (s, 1H), 7.32 (d, J=8.2 Hz, 1H), 6.18 (d, J=5.3 Hz, 1H), 5.05 (dd, J=11.4, 2.9 Hz, 1H), 4.60 (dd, J=11.4, 5.4 Hz, 1H), 4.49 (t, J=6.4 Hz, 1H), 4.20 (d, J=2.1 Hz, 1H), 3.73 (dd, J=11.4, 5.6 Hz, 1H), 3.69 (dd, J=11.4, 6.7 Hz, 1H), 3.40 (s, 3H), 2.91 (s, 3H).

Example 61

5-Bromo-2-(N-methyl-carbonyl)phenyl 3-deoxy-2-O-methyl-3-[4-(2-thiazolyl)-1H-1,2,3-triazol-1-yl]-1-thio-α-D-galactopyranoside

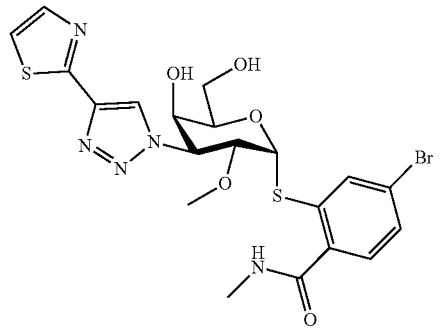

To a solution of 5-bromo-2-(N-methyl-carbonyl)phenyl 4,6-O-benzylidene-3-deoxy-2-O-methyl-3-[4-(2-thiazolyl)-1H-1,2,3-triazol-1-yl]-1-thio-α-D-galactopyranoside (85.0 mg, 0.13 mmol) in DCM (5 mL) TFA (0.3 mL) was added at 0° C. and the mixture was stirred overnight at rt. Et3N (0.5 mL) was added at 0° C., and the mixture was concentrated. The residue was purified by prep HPLC [MeCN/$H_2O$ (10 mmol/L $NH_4HCO_3$), X-Select 10 μm 19*250 mm, 20 mL/min, UV 254] to afford the title compound (60.7 mg, 83%). ESI-MS m/z calcd for [$C_{20}H_{22}BrN_5O_5S_2$] $[M+H]^+$: 556.0; found: 556.0. $^1H$ NMR (400 MHz, Methanol-$d_4$) δ 8.61 (s, 1H), 8.03 (d, J=2.0 Hz, 1H), 7.91 (d, J=3.2 Hz, 1H), 7.66 (d, J=3.2 Hz, 1H), 7.58 (dd, J=8.0, 2.0 Hz, 1H), 7.34 (d, J=8.0 Hz, 1H), 6.20 (d, J=5.2 Hz, 1H), 5.08 (dd, J=11.2, 2.8 Hz, 1H), 4.62 (dd, J=11.2, 5.2 Hz, 1H), 4.51 (t, J=6.0 Hz, 1H), 4.25-4.20 (m, 1H), 3.79-3.66 (m, 2H), 3.41 (s, 3H), 2.93 (s, 3H).

Example 62

5-Chloro-2-(N-methyl-carbonyl)phenyl 3-deoxy-2-O-methyl-3-[4-(2-thiazolyl)-1H-1,2,3-triazol-1-yl]-1-thio-α-D-galactopyranoside

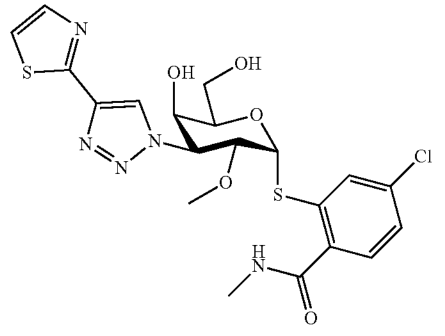

To a solution of 5-chloro-2-(N-methyl-carbonyl)phenyl 4,6-O-benzylidene-3-deoxy-2-O-methyl-3-[4-(2-thiazolyl)-1H-1,2,3-triazol-1-yl]-1-thio-α-D-galactopyranoside (120 mg, 0.20 mmol) in DCM (5 mL) TFA (0.3 mL) was added at 0° C. and the mixture was stirred overnight at rt. $Et_3N$ (0.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (60 mg, 59%). ESI-MS m/z calcd for [$C_{20}H_{22}ClN_5O_5S_2$] $[M+H]^+$: 512.1; found: 512.0. $^1H$ NMR (400 MHz, Methanol-$d_4$) δ 8.59 (m, 1H), 7.95-7.84 (m, 2H), 7.64 (d, J=3.2 Hz, 1H), 7.39 (d, J=2.8 Hz, 2H), 6.20 (t, J=4.0 Hz, 1H), 5.06 (d, J=11.2 Hz, 1H), 4.66-4.57 (m, 1H), 4.54-4.45 (m, 1H), 4.20 (s, 1H), 3.78-3.66 (m, 2H), 3.40 (s, 3H), 2.92 (m, 3H).

Example 63

5-Bromo-2-cyanophenyl 3-deoxy-3-[4-(4-methylthiazol-2-yl)-1H-1,2,3-triazol-1-yl]-2-O-methyl-1-thio-α-D-galactopyranoside

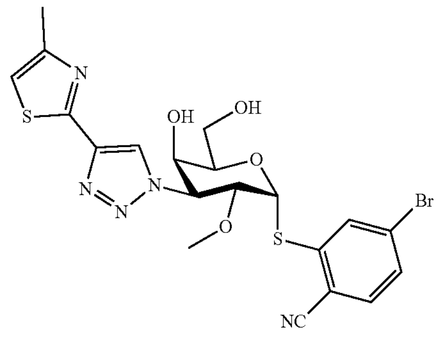

To a solution of 5-bromo-2-cyanophenyl 4,6-O-benzylidene-3-deoxy-3-[4-(4-methylthiazol-2-yl)-1H-1,2,3-triazol-1-yl]-2-O-methyl-1-thio-α-D-galactopyranoside (90 mg, 0.14 mmol) in DCM (5 mL) TFA (0.32 mL) was added at 0° C. and the mixture was stirred overnight at rt. $Et_3N$ (0.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (40.1 mg, 52%). ESI-MS m/z calcd for [$C_{20}H_{20}BrN_5O_4S_2$] $[M+H]^+$: 538.0; found: 538.0. $^1H$ NMR (400 MHz, Methanol-$d_4$) δ 8.61 (s, 1H), 8.20-8.15 (m, 1H), 7.74-7.65 (m, 2H), 7.23-7.18 (m, 1H), 6.42 (d, J=5.2 Hz, 1H), 5.17-5.09 (m, 1H), 4.74-4.65 (m, 1H), 4.49-4.45 (m, 1H), 4.28-4.23 (m, 1H), 3.77-3.62 (m, 2H), 3.49 (s, 3H), 2.52-2.48 (m, 3H).

Example 64

5-Bromo-2-cyanopyridin-3-yl 3-[4-(5-chloro-4-methylthiazol-2-yl)-1H-1,2,3-triazol-1-yl]-3-deoxy-2-O-methyl-1-thio-α-D-galactopyranoside

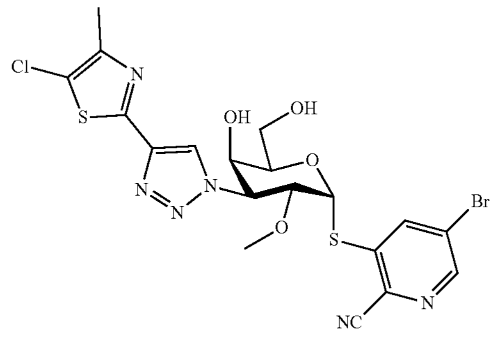

A solution of 5-bromo-2-cyanopyridin-3-yl 4,6-O-benzylidene-3-[4-(5-chloro-4-methylthiazol-2-yl)-1H-1,2,3-triazol-1-yl]-3-deoxy-2-O-methyl-1-thio-α-D-galactopyranoside (100 mg, 0.17 mmol) in DCM/TFA (10 mL, 19:1) was stirred overnight at rt. $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (52.5 mg, 55%). ESI-MS m/z calcd for [$C_{19}H_{18}BrClN_6O_4S_2$] $[M+H]^+$: 573.0; found: 573.0. $^1H$ NMR (400 MHz, Methanol-$d_4$) δ 8.71 (d, J=2.0 Hz, 1H), 8.62 (d, J=2.0 Hz, 1H), 8.59 (s, 1H), 6.50 (d, J=5.2 Hz, 1H), 5.12 (dd, J=11.2, 2.8 Hz, 1H), 4.70 (dd, J=11.2, 5.2 Hz, 1H), 4.40 (t, J=6.0 Hz, 1H), 4.20 (d, J=2.4 Hz, 1H), 3.68 (d, J=6.0 Hz, 2H), 3.46 (s, 3H), 2.41 (s, 3H).

Example 65

5-Bromo-2-cyanophenyl 3-[4-(5-chloro-4-methylthiazol-2-yl)-1H-1,2,3-triazol-1-yl]-3-deoxy-2-O-methyl-1-thio-α-D-galactopyranoside

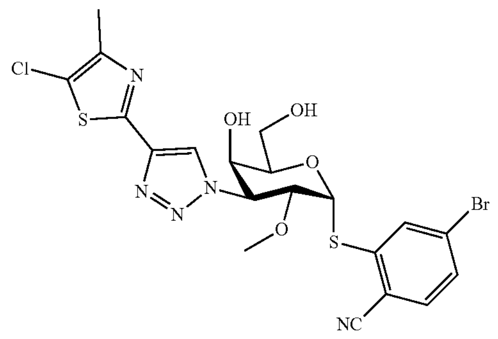

To a solution of 5-bromo-2-cyanophenyl 4,6-O-benzylidene-3-[4-(5-chloro-4-methylthiazol-2-yl)-1H-1,2,3-triazol-1-yl]-3-deoxy-2-O-methyl-1-thio-α-D-galactopyranoside (95 mg, 0.14 mmol) in DCM (5 mL) TFA (0.32 mL) was added at 0° C. and the mixture was stirred overnight at rt. $Et_3N$ (0.5 mL) was added at 0° C. to neutralize the TFA. The mixture was concentrated and purified by prep HPLC

[MeCN/$H_2O$ (10 mmol/L $NH_4HCO_3$), X-Select 10 μm 19*250 mm, 20 mL/min, UV 254] to afford the title compound (32 mg, 39%). ESI-MS m/z calcd for [$C_{20}H_{19}BrClN_5O_4S_2$] [M+H]$^+$: 572.0; found: 572.0. $^1$H NMR (400 MHz, Methanol-$d_4$) δ 8.61 (s, 1H), 8.20-8.15 (m, 1H), 7.74-7.65 (m, 2H), 6.42 (d, J=5.2 Hz, 1H), 5.12 (dd, J=11.2, 2.8 Hz, 1H), 4.69 (dd, J=11.2, 5.2 Hz, 1H), 4.46 (t, J=6.0 Hz, 1H), 4.26-4.21 (m, 1H), 3.76-3.62 (m, 2H), 3.48 (s, 3H), 2.43 (s, 3H).

Example 66

2,5-Dichlorophenyl 3-deoxy-2-O-methyl-3-[4-(2-thiazolyl)-1H-1,2,3-triazol-1-yl]-1-thio-α-D-galactopyranoside

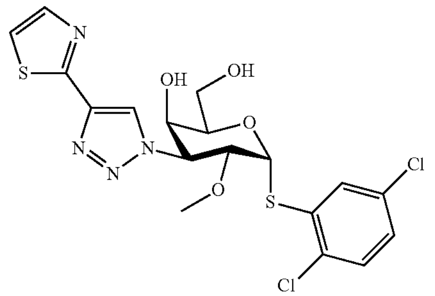

To a solution of 2,5-dichlorophenyl 4,6-O-benzylidene-3-deoxy-2-O-methyl-3-[4-(2-thiazolyl)-1H-1,2,3-triazol-1-yl]-1-thio-α-D-galactopyranoside (120 mg, 0.21 mmol) in DCM (5 mL) TFA (0.4 mL) was added at 0° C. and the mixture was stirred overnight at rt. $Et_3N$ (0.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (72 mg, 71%). ESI-MS m/z calcd for [$C_{18}H_{18}Cl_2N_4O_4S_2$] [M+H]$^+$: 489.0; found: 489.0. $^1$H NMR (400 MHz, Methanol-$d_4$) δ 8.86 (s, 1H), 8.14 (d, J=3.2 Hz, 1H), 8.09 (d, J=2.4 Hz, 1H), 7.89 (d, J=3.2 Hz, 1H), 7.70 (d, J=8.4 Hz, 1H), 7.54 (dd, J=8.4, 2.4 Hz, 1H), 6.57 (d, J=5.2 Hz, 1H), 5.36 (dd, J=11.2, 2.8 Hz, 1H), 4.92 (dd, J=11.2, 5.2 Hz, 1H), 4.67 (t, J=6.0 Hz, 1H), 4.50-4.45 (m, 1H), 4.00-3.91 (m, 1H), 3.91-3.83 (m, 1H), 3.68 (s, 3H).

Example 67

5-Bromo-2-chlorophenyl 3-deoxy-2-O-methyl-3-[4-(2-thiazolyl)-1H-1,2,3-triazol-1-yl]-1-thio-α-D-galactopyranoside

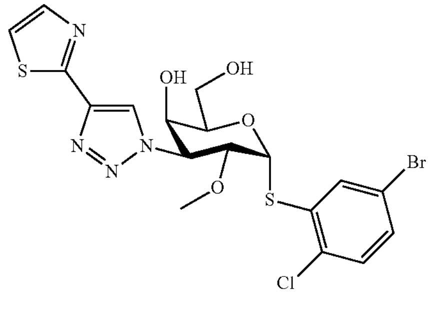

To a solution of 5-bromo-2-chlorophenyl 4,6-O-benzylidene-3-deoxy-2-O-methyl-3-[4-(2-thiazolyl)-1H-1,2,3-triazol-1-yl]-1-thio-α-D-galactopyranoside (180 mg, 0.29 mmol) in DCM (15 mL) TFA (0.75 mL) was added and the mixture was stirred overnight at rt. $Et_3N$ (1.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (75 mg, 49%). ESI-MS m/z calcd for [$C_{18}H_{18}BrClN_4O_4S_2$] [M+H]$^+$: 535.0; found: 535.0. $^1$H NMR (400 MHz, Methanol-$d_4$) δ 8.61 (s, 1H), 7.98 (d, J=2.0 Hz, 1H), 7.89 (d, J=3.2 Hz, 1H), 7.64 (d, J=3.2 Hz, 1H), 7.45-7.37 (m, 2H), 6.31 (d, J=5.2 Hz, 1H), 5.11 (dd, J=11.2, 3.2 Hz, 1H), 4.67 (dd, J=11.2, 5.2 Hz, 1H), 4.43 (t, J=6.4 Hz, 1H), 4.23 (d, J=2.4 Hz, 1H), 3.73-3.60 (m, 2H), 3.31 (s, 3H).

Example 68

5-Chloro-2-fluorophenyl 3-deoxy-2-O-methyl-3-[4-(2-thiazolyl)-1H-1,2,3-triazol-1-yl]-1-thio-α-D-galactopyranoside

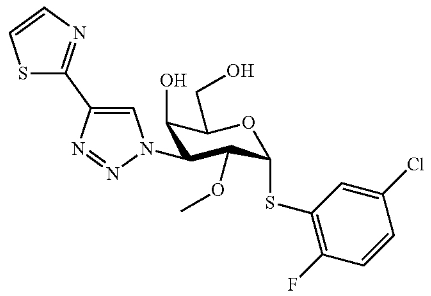

A solution of 5-chloro-2-fluorophenyl 4,6-O-benzylidene-3-deoxy-2-O-methyl-3-[4-(2-thiazolyl)-1H-1,2,3-triazol-1-yl]-1-thio-α-D-galactopyranoside (180 mg, 0.32 mmol) in DCM/TFA (10 mL, 19:1) was stirred overnight at rt. $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (76.7 mg, 51%). ESI-MS m/z calcd for [$C_{18}H_{18}ClFN_4O_4S_2$] [M+H]$^+$: 473.0; found: 473.2. $^1$H NMR (400 MHz, Methanol-$d_4$) δ 8.61 (s, 1H), 7.89 (d, J=3.2 Hz, 1H), 7.76 (dd, J=6.4, 2.8 Hz, 1H), 7.64 (d, J=3.2 Hz, 1H), 7.41-7.32 (m, 1H), 7.18 (t, J=8.8 Hz, 1H), 6.23 (d, J=5.8 Hz, 1H), 5.11 (dd, J=11.2, 2.8 Hz, 1H), 4.64 (dd, J=11.2, 5.2 Hz, 1H), 4.48-4.40 (m, 1H), 4.25-4.20 (m, 1H), 3.68 (dd, J=11.2, 6.0 Hz, 1H), 3.58 (dd, J=11.2, 6.0 Hz, 1H), 3.43 (s, 3H).

Example 69

5-Bromo-2-fluorophenyl 3-deoxy-3-[4-(4-methylthiazol-2-yl)-1H-1,2,3-triazol-1-yl]-2-O-methyl-1-thio-α-D-galactopyranoside

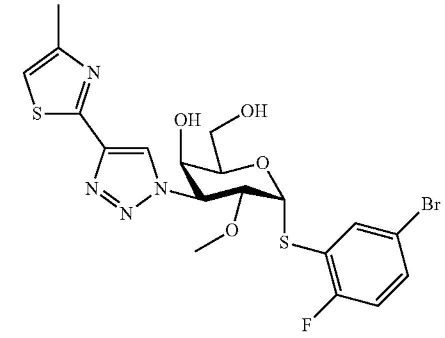

To a solution of 5-bromo-2-fluorophenyl 4,6-O-benzylidene-3-deoxy-3-[4-(4-methylthiazol-2-yl)-1H-1,2,3-triazol-1-yl]-2-O-methyl-1-thio-α-D-galactopyranoside (110 mg, 0.18 mmol) in DCM (5 mL) TFA (0.40 mL) was added and the mixture was stirred overnight at rt. $Et_3N$ (0.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (63.4 mg, 67%). ESI-MS m/z calcd for [$C_{19}H_{20}BrFN_4O_4S_2$] [M+H]$^+$: 531.0; found: 531.0. $^1$H NMR (400 MHz, Methanol-$d_4$) δ 8.60 (s, 1H), 7.91 (dd, J=6.4, 2.4 Hz, 1H), 7.57-7.49 (m, 1H), 7.23-7.18 (m, 1H), 7.14 (t, J=8.8 Hz, 1H), 6.23 (d, J=5.2 Hz, 1H), 5.12 (dd, J=11.2, 2.8 Hz, 1H), 4.64 (dd, J=11.2, 5.2 Hz, 1H), 4.50-4.42 (m, 1H), 4.27-4.22 (m, 1H), 3.75-3.66 (m, 1H), 3.64-3.56 (m, 1H), 3.45 (s, 3H), 2.52-2.47 (m, 3H).

Example 70

5-Chloro-2-cyanopyridin-3-yl 3-[4-(2-chlorothiazol-4-yl)-1H-1,2,3-triazol-1-yl]-3-deoxy-1-thio-α-D-galactopyranoside

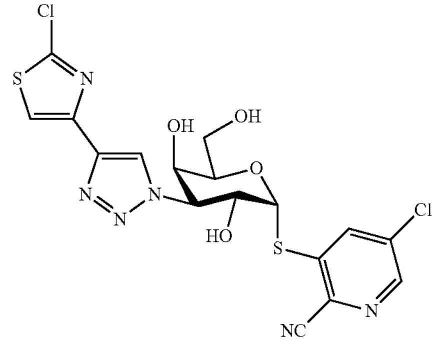

A solution of 5-cloro-2-cyanopyridin-3-yl 2,4,6-tri-O-acetyl-3-[4-(2-chlorothiazol-4-yl)-1H-1,2,3-triazol-1-yl]-3-deoxy-1-thio-α-D-galactopyranoside (90 mg, 0.14 mmol) in MeOH (5 mL), $Et_3N$ (3 mL) and water (1 mL) was stirred overnight at rt. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (47.9 mg, 67%). ESI-MS m/z calcd for [$C_{17}H_{14}Cl_2N_6O_4S_2$] [M+H]$^+$: 501.0; found: 501.0. $^1$H NMR (400 MHz, Methanol-$d_4$) δ 8.46 (d, J=2.0 Hz, 1H), 8.35 (d, J=2.0 Hz, 1H), 8.33 (s, 1H), 7.77 (s, 1H), 6.13 (d, J=5.0 Hz, 1H), 5.00 (dd, J=11.2, 2.8 Hz, 1H), 4.90 (dd, J=11.2, 5.2 Hz, 1H), 4.27 (t, J=6.0 Hz, 1H), 4.12 (d, J=2.0 Hz, 1H), 3.57 (d, J=6.0 Hz, 2H).

Example 71

5-Chloro-2-cyanopyridin-3-yl 3-deoxy-2-O-ethyl-3-[4-(2-thiazolyl)-1H-1,2,3-triazol-1-yl]-1-thio-α-D-galactopyranoside

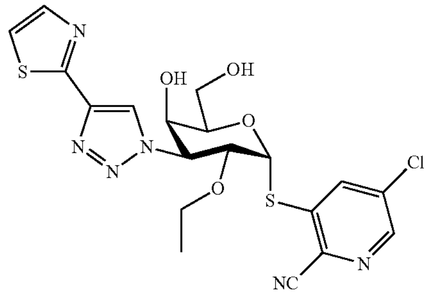

To a solution of 5-chloro-2-cyanopyridin-3-yl 4,6-O-benzylidene-3-deoxy-2-O-ethyl-3-[4-(2-thiazolyl)-1H-1,2,3-triazol-1-yl]-1-thio-α-D-galactopyranoside (85 mg, 0.15 mmol) in DCM (10 mL) TFA (0.54 mL) was added and the mixture was stirred 6 h at rt. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (45 mg, 62%). ESI-MS m/z calcd for [$C_{19}H_{19}ClN_6O_4S_2$] [M+H]$^+$: 495.1; found: 495.2. $^1$H NMR (400 MHz, Methanol-$d_4$) δ 8.60 (d, J=2.4 Hz, 1H), 8.59 (s, 1H), 8.46 (d, J=2.4 Hz, 1H), 7.89 (d, J=3.2 Hz, 1H), 7.64 (d, J=3.6 Hz, 1H), 6.48 (d, J=5.2 Hz, 1H), 5.13 (dd, J=11.2, 2.8 Hz, 1H), 4.79 (dd, J=11.2, 5.2 Hz, 1H), 4.39 (t, J=6.0 Hz, 1H), 4.21 (d, J=2.4 Hz, 1H), 3.91-3.84 (m, 1H), 3.67 (t, J=6.0 Hz, 2H), 3.51-3.44 (m, 1H), 1.07-1.03 (m, 3H).

Example 72

5-Chloro-2-cyanopyridin-3-yl 3-[4-(2-aminothiazol-4-yl)-1H-1,2,3-triazol-1-yl]-3-deoxy-2-O-ethyl-1-thio-α-D-galactopyranoside

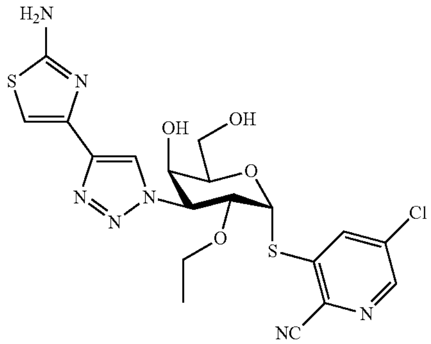

To a solution of 5-chloro-2-cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside (180 mg, 0.21 mmol) in DCM (16 mL) TFA (0.79 mL) was added and the mixture was stirred 6 h at rt. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (26.5 mg, 56%). ESI-MS m/z calcd for [$C_{19}H_{20}ClN_7O_4S_2$] $[M+H]^+$: 510.1; found: 510.2. $^1H$ NMR (400 MHz, Methanol-$d_4$) δ 8.59 (d, J=2.0 Hz, 1H), 8.46 (d, J=2.0 Hz, 1H), 8.25 (s, 1H), 6.96 (s, 1H), 6.46 (d, J=5.2 Hz, 1H), 5.05 (dd, J=11.2, 2.8 Hz, 1H), 4.73 (dd, J=11.6, 5.6 Hz, 1H), 4.37 (t, J=6.0 Hz, 1H), 4.19 (d, J=2.4 Hz, 1H), 3.89-3.82 (m, 1H), 3.66 (d, J=6.0 Hz, 2H), 3.48-3.42 (m, 1H), 1.06-1.03 (m, 3H).

Example 73

5-Chloro-2-cyanophenyl 3-[4-(2-aminothiazol-4-yl)-1H-1,2,3-triazol-1-yl]-3-deoxy-2-O-methyl-1-thio-α-D-galactopyranoside

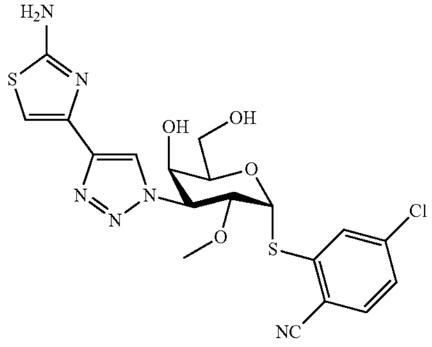

To a solution of 5-chloro-2-cyanophenyl 3-[4-(2-aminothiazol-4-yl)-1H-1,2,3-triazol-1-yl]-4,6-O-benzylidene-3-deoxy-2-O-methyl-1-thio-α-D-galactopyranoside (62 mg, 0.11 mmol) in DCM (4 mL) TFA (0.40 mL) was added and the mixture was stirred 2 h at rt. $Et_3N$ (1 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (17 mg, 32%). ESI-MS m/z calcd for [$C_{19}H_{19}ClN_6O_4S_2$] $[M+H]^+$: 495.1; found: 495.2. $^1H$ NMR (400 MHz, Methanol-$d_4$) δ 8.25 (s, 1H), 7.99 (d, J=2.0 Hz, 1H), 7.75 (d, J=4.4 Hz, 1H), 7.49 (dd, J=8.4, 2.0 Hz, 1H), 6.96 (s, 1H), 6.39 (d, J=5.2 Hz, 1H), 5.03 (dd, J=11.2, 2.8 Hz, 1H), 4.62 (dd, J=11.2, 5.2 Hz, 1H), 4.42 (t, J=6.0 Hz, 1H), 4.20 (d, J=2.4 Hz, 1H), 3.71-3.61 (m, 2H), 3.44 (s, 3H).

Example 74

5-Chloro-2-(1H-imidazol-2-yl)pyridin-3-yl 3-[4-(2-aminothiazol-4-yl)-1H-1,2,3-triazol-1-yl]-3-deoxy-1-thio-α-D-galactopyranoside

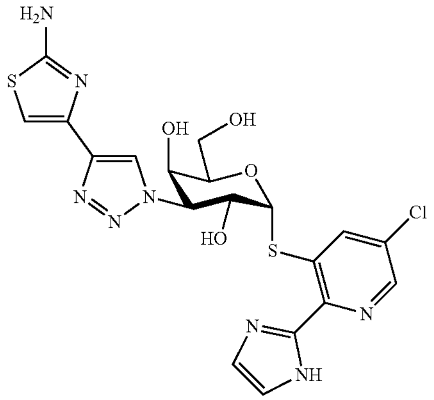

A solution of 5-chloro-2-(1H-imidazol-2-yl)pyridin-3-yl 2,4,6-tri-O-acetyl-3-[4-(2-aminothiazol-4-yl)-1H-1,2,3-triazol-1-yl]-3-deoxy-1-thio-α-D-galactopyranoside (15 mg, 0.023 mmol) in MeOH (5 mL), $Et_3N$ (1 mL) and water (0.5 mL) was stirred overnight at rt. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (5.4 mg, 45%). ESI-MS m/z calcd for [$C_{19}H_{19}ClN_8O_4S_2$] $[M+H]^+$: 523.1; found: 523.2. $^1H$ NMR (400 MHz, DMSO-$d_6$) δ 12.85-12.73 (m, 1H), 8.45 (d, J=2.0 Hz, 1H), 8.28 (d, J=2.0 Hz, 1H), 8.07 (s, 1H), 7.28 (s, 1H), 7.20 (s, 1H), 7.07 (s, 2H), 6.91 (s, 1H), 6.02 (d, J=5.2 Hz, 1H), 5.93 (d, J=5.2 Hz, 1H), 5.47 (d, J=6.8 Hz, 1H), 4.93-4.85 (m, 1H), 4.83-4.73 (m, 1H), 4.64 (t, J=5.6 Hz, 1H), 4.15 (t, J=6.4 Hz, 1H), 4.03-3.97 (m, 1H), 3.60-3.50 (m, 1H), 3.45-3.35 (m, 1H).

Example 75

5-Chloro-2-(1H-imidazol-2-yl)pyridin-3-yl 3-deoxy-3-[4-(2-hydroxythiazol-4-yl)-1H-1,2,3-triazol-1-yl]-1-thio-α-D-galactopyranoside

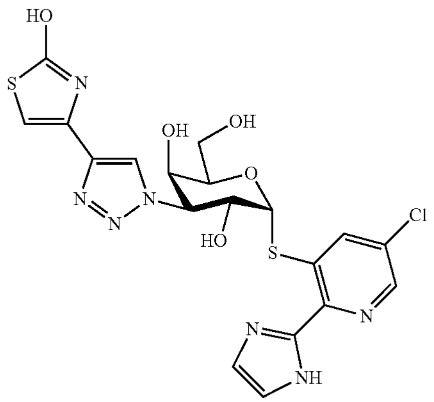

To a solution of 5-chloro-2-(1H-imidazol-2-yl)pyridin-3-yl 3-azido-3-deoxy-1-thio-α-D-galactopyranoside (80 mg, 0.20 mmol) in DMF (4 mL) 4-(2-trimethylsilylethynyl) thiazol-2-ol (39.6 mg, 0.20 mmol), copper (II) sulfate pentahydrate (50.1 mg, 0.20 mmol), (+)-sodium L-ascorbate (39.7 mg, 0.20 mmol), CsF (30.5 mg, 0.20 mmol) and N,N,N',N'-tetramethyl ethylenediamine (60 μL, 0.40 mmol) were added and the mixture was stirred 72 h at rt. The mixture was filtered and the filtrate was purified by prep HPLC ($MeCN/H_2O$ (10 mmol/L $NH_4HCO_3$), X-Select 10 μm 19*250 mm, 20 mL/min, UV 254) to afford the title compound (1.65 mg, 2%). ESI-MS m/z calcd for $[C_{19}H_{18}ClN_7O_5S_2]$ $[M+H]^+$: 524.0; found: 524.0. $^1H$ NMR (400 MHz, Methanol-$d_4$) δ 8.47-8.42 (m, 1H), 8.35 (s, 1H), 8.31 (d, J=2.0 Hz, 1H), 7.25-7.21 (m, 2H), 6.69 (s, 1H), 6.00 (d, J=5.6 Hz, 1H), 5.15-5.07 (m, 1H), 4.93-4.88 (m, 1H), 4.41-4.34 (m, 1H), 4.19-4.15 (m, 1H), 3.77-3.62 (m, 2H).

Example 76

5-Chloro-2-(pyridin-2-yl)-pyridin-3-yl 3-[4-(4-chlorothiazol-2-yl)-1H-1,2,3-triazol-1-yl]-3-deoxy-2-O-methyl-1-thio-α-D-galactopyranoside

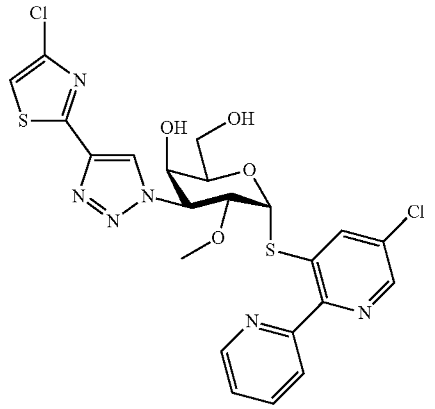

A solution of 5-chloro-2-(pyridin-2-yl)-pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (36 mg, 0.055 mmol) in DCM/TFA (4 mL, 19:1) was stirred 6 h at rt. Et3N was added to neutralize the TFA. The mixture was concentrated and purified by prep HPLC [$MeCN/H_2O$ (10 mmol/L $NH_4HCO_3$), X-Select 10 μm 19*250 mm, 20 mL/min, UV 254] to afford the title compound (9.1 mg, 29%). ESI-MS m/z calcd for $[C_{22}H_{20}Cl_2N_6O_4S_2]$ $[M+H]^+$: 567.0; found: 567.0. $^1H$ NMR (400 MHz, Methanol-$d_4$) δ 8.68-8.66 (m, 1H), 8.56 (s, 1H), 8.51 (d, J=2.0 Hz, 1H), 8.44 (d, J=2.4 Hz, 1H), 8.00-7.96 (m, 1H), 7.85-7.83 (m, 1H), 7.51-7.48 (m, 1H), 7.44 (s, 1H), 6.19 (d, J=5.2 Hz, 1H), 4.98-4.92 (m, 1H), 4.59 (dd, J=11.6, 5.2 Hz, 1H), 4.28 (t, J=6.0 Hz, 1H), 4.11 (d, J=2.0 Hz, 1H), 3.70-3.62 (m, 2H), 3.18 (s, 3H).

Example 77

2-Cyano-5-methylpyridin-3-yl 3-[4-(4-chlorothiazol-2-yl)-1H-1,2,3-triazol-1-yl]-3-deoxy-1-thio-α-D-galactopyranoside

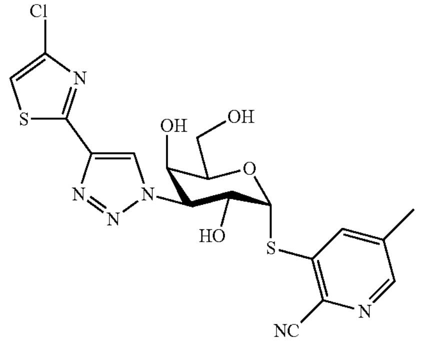

A solution of 2-cyano-5-methylpyridin-3-yl 2,4,6-tri-O-acetyl-3-[4-(4-chlorothiazol-2-yl)-1H-1,2,3-triazol-1-yl]-3-deoxy-1-thio-α-D-galactopyranoside (55 mg, 0.091 mmol) in MeOH (10 mL), $Et_3N$ (0.8 mL) and water (0.5 mL) was stirred overnight at rt. The mixture was concentrated and purified by prep HPLC [$MeCN/H_2O$ (10 mmol/L $NH_4HCO_3$), X-Select 10 μm 19*250 mm, 20 mL/min, UV 254] to afford the title compound (36 mg, 83%). ESI-MS m/z calcd for $[C18H_{17}ClN_6O_4S_2]$ $[M+H]^+$: 481.0; found: 481.0. $^1H$ NMR (400 MHz, DMSO-$d_6$) δ 8.72 (s, 1H), 8.49-8.44 (m, 1H), 8.23-8.18 (m, 1H), 7.79 (s, 1H), 6.13 (dd, J=17.2, 4.4 Hz, 2H), 5.50 (d, J=6.8 Hz, 1H), 5.00-4.87 (m, 2H), 4.70 (t, J=5.6 Hz, 1H), 4.21-4.16 (m, 1H), 4.11-4.04 (m, 1H), 3.55-3.45 (m, 1H), 3.42-3.33 (m, 1H), 2.39 (s, 3H).

Example 78

3,4-Dichlorophenyl 3-[4-(2-aminothiazol-4-yl)-1H-1,2,3-triazol-1-yl]-3-deoxy-2-O-(2,2,2-trifluoroethyl)-1-thio-α-D-galactopyranoside

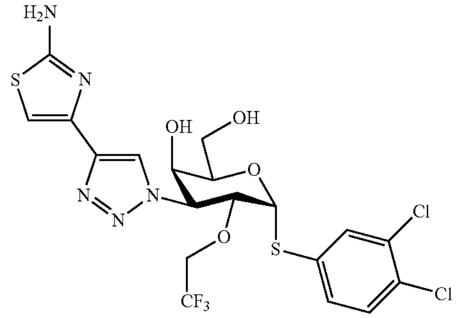

To a solution of 3,4-dichlorophenyl 3-azido-3-deoxy-2-O-(2,2,2-trifluoroethyl)-1-thio-α-D-galactopyranoside (38 mg, 0.085 mmol) in DMF (2 mL) 4-(2-trimethylsilylethynyl)thiazol-2-amine (25 mg, 0.13 mmol), copper (II) sulfate pentahydrate (10.6 mg, 0.042 mmol) and (+)-sodium L-ascorbate (8 mg, 0.042 mmol) were added and the mixture was stirred 4 h at rt. The mixture was concentrated and purified by prep HPLC ($MeCN/H_2O$ (10 mmol/L $NH_4HCO_3$), X-Select 10 µm 19*250 mm, 20 mL/min, UV 254) to afford the title compound (11.4 mg, 24%). ESI-MS m/z calcd for $[C_{19}H_{18}Cl_2F_3N_5O_4S_2]$ $[M+H]^+$: 572.0; found: 572.1. $^1H$ NMR (400 MHz, Methanol-$d_4$) δ 8.28 (s, 1H), 7.82 (d, J=2.0 Hz, 1H), 7.55-7.48 (m, 2H), 8.95 (s, 1H), 6.13 (d, J=4.8 Hz, 1H), 5.08-5.03 (m, 2H), 4.49 (t, J=6.0 Hz, 1H), 4.19-4.12 (m, 2H), 3.97-3.92 (m, 1H), 3.73-3.64 (m, 2H).

Example 79

3,4-Dichlorophenyl 3-deoxy-2-O-(2,2,2-trifluoroethyl)-3-[4-(2-hydroxythiazol-4-yl)-1H-1,2,3-triazol-1-yl]-1-thio-α-D-galactopyranoside

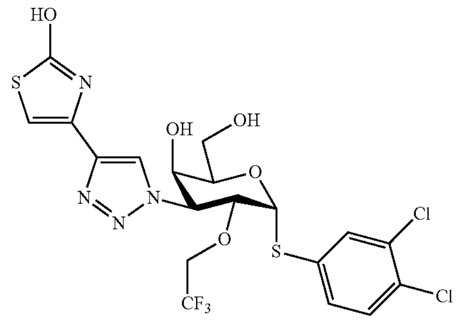

To a solution of 3,4-dichlorophenyl 3-azido-3-deoxy-2-O-(2,2,2-trifluoroethyl)-1-thio-α-D-galactopyranoside (38 mg, 0.085 mmol) in DMF (2 mL) 4-(2-trimethylsilylethynyl)thiazol-2-amine (25 mg, 0.13 mmol), copper (II) sulfate pentahydrate (10.6 mg, 0.042 mmol) and (+)-sodium L-ascorbate (8 mg, 0.042 mmol) were added and the mixture was stirred 4 h at rt. The mixture was concentrated and purified by prep HPLC ($MeCN/H_2O$ (10 mmol/L $NH_4HCO_3$), X-Select 10 µm 19*250 mm, 20 mL/min, UV 254) to afford the title compound (8.9 mg, 18%). ESI-MS m/z calcd for $[C_{19}H_{17}Cl_2F_3N_4O_5S_2]$ $[M+H]^+$: 573.0; found: 573.0. $^1H$ NMR (400 MHz, Methanol-$d_4$) δ 8.28 (s, 1H), 7.82 (s, 1H), 7.55-7.48 (m, 2H), 6.67 (s, 1H), 6.13 (d, J=4.4 Hz, 1H), 5.10-4.98 (m, 2H), 4.46 (t, J=4.0 Hz, 1H), 4.20-4.12 (m, 2H), 3.97-3.93 (m, 1H), 3.73-3.65 (m, 2H).

Example 80

5-Ethynylpyridin-3-yl 3-[4-(4-chlorothiazol-2-yl)-1H-1,2,3-triazol-1-yl]-3-deoxy-1-thio-α-D-galactopyranoside

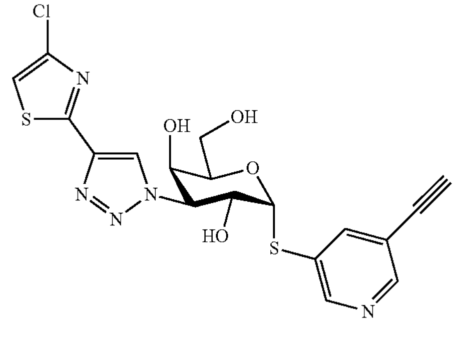

To a solution of 5-(2-trimethylsilyl-1-ethynyl)pyridin-3-yl 2,4,6-tri-O-acetyl-3-[4-(4-chlorothiazol-2-yl)-1H-1,2,3-triazol-1-yl]-3-deoxy-1-thio-α-D-galactopyranoside (100 mg, 0.15 mmol) in MeOH (5 mL) KF (13.1 mg, 0.23 mmol) was added and the mixture was stirred 30 min at rt. $Et_3N$ (1.05 mL, 7.53 mmol) and water (0.5 mL) were added and the mixture was stirred overnight at rt. The mixture was concentrated and purified by prep HPLC ($MeCN/H_2O$ (10 mmol/L $NH_4HCO_3$), X-Select 10 µm 19*250 mm, 20 mL/min, UV 254) to afford the title compound (42 mg, 60%). ESI-MS m/z calcd for $[C18H_{16}ClN_5O_4S_2]$ $[M+H]^+$: 466.0; found: 466.2. $^1H$ NMR (400 MHz, Methanol-$d_4$) δ 8.68 (d, J=2.0 Hz, 1H), 8.59 (s, 1H), 8.52 (d, J=2.0 Hz, 1H), 8.16 (t, J=2.0 Hz, 1H), 7.46 (s, 1H), 5.88 (d, J=5.2 Hz, 1H), 5.10-5.02 (m, 1H), 4.96-4.87 (m, 1H), 4.48 (t, J=6.4 Hz, 1H), 4.24-4.18 (m, 1H), 3.84 (s, 1H), 3.76-3.62 (m, 2H).

Example 81

5-Ethynylpyridin-3-yl 3-[4-(2-aminothiazol-4-yl)-1H-1,2,3-triazol-1-yl]-3-deoxy-2-O-methyl-1-thio-α-D-galactopyranoside

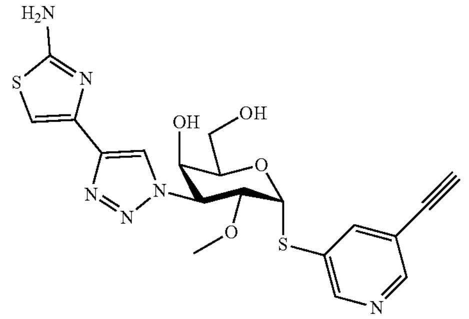

To a solution of 5-(2-trimethylsilyl-1-ethynyl)pyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside (110 mg, 0.13 mmol) in DCM (6 mL) TFA (1.0 mL) was added and the mixture was stirred overnight at rt. $Et_3N$ (2 mL) was added at 0° C. to neutralize the TFA. The mixture was evaporated, and the residue was dissolved in DMF (3 mL). KF (15.6 mg, 0.27 mmol) was added and the mixture was stirred 1 h at rt. The mixture was filtered and the filtrate was purified by prep HPLC ($MeCN/H_2O$ (10 mmol/L $NH_4HCO_3$), X-Select 10 µm 19*250 mm, 20 mL/min, UV 254) to afford the title compound (45 mg, 73%). ESI-MS m/z calcd for $[C_{19}H_{20}N_6O_4S_2]$ $[M+H]^+$: 461.1; found: 461.2. $^1H$ NMR (400 MHz, Methanol-$d_4$) δ 8.70 (d, J=2.0 Hz, 1H), 8.53 (d, J=2.0 Hz, 1H), 8.24 (s, 1H), 8.19 (t, J=2.0 Hz, 1H), 6.95 (s, 1H), 6.23 (d, J=5.2 Hz, 1H), 5.01 (dd, J=11.2, 2.8 Hz, 1H), 4.57 (dd, J=11.2, 5.2 Hz, 1H), 4.45 (dd, J=7.2, 5.6 Hz, 1H), 4.18 (dd, J=2.8, 1.2 Hz, 1H), 3.74-3.60 (m, 2H), 3.39 (s, 3H).

Example 82

5-Cyanopyridin-3-yl 3-[4-(4-chlorothiazol-2-yl)-1H-1,2,3-triazol-1-yl]-3-deoxy-2-O-methyl-1-thio-α-D-galactopyranoside

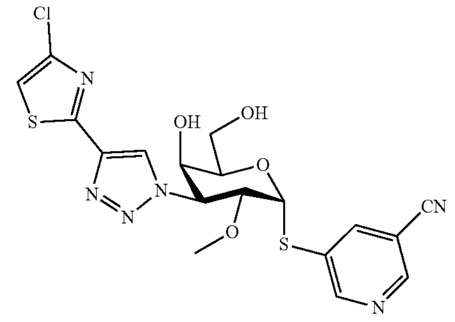

To a solution of 5-cyanopyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (90 mg, 0.16 mmol) in DCM (4 mL) TFA (0.25 mL) was added and the mixture was stirred overnight at rt. $Et_3N$ (0.5 mL) was added at 0° C. to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (48 mg, 63%). ESI-MS m/z calcd for [C18$H_{17}ClN_6O_4S_2$] $[M+H]^+$: 481.0; found: 481.0. $^1H$ NMR (400 MHz, Methanol-$d_4$) δ 8.95 (d, J=2.0 Hz, 1H), 8.80 (d, J=2.0 Hz, 1H), 8.63 (s, 1H), 8.50 (t, J=2.0 Hz, 1H), 7.46 (s, 1H), 6.35 (d, J=5.2 Hz, 1H), 5.10 (dd, J=11.2, 2.8 Hz, 1H), 4.70-4.61 (m, 1H), 4.43 (t, J=6.0 Hz, 1H), 4.21-4.16 (m, 1H), 3.68 (d, J=6.0 Hz, 2H), 3.41 (s, 3H).

Example 83

5-Cyanopyridin-3-yl 3-deoxy-3-[4-(2-hydroxythiazol-4-yl)-1H-1,2,3-triazol-1-yl]-2-O-methyl-1-thio-α-D-galactopyranoside

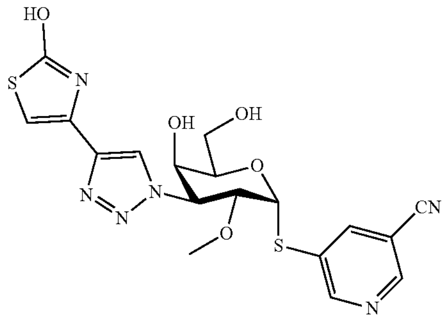

A solution of 5-cyanopyridin-3-yl 4,6-O-benzylidene-3-deoxy-3-[4-(2-hydroxythiazol-4-yl)-1H-1,2,3-triazol-1-yl]-2-O-methyl-1-thio-α-D-galactopyranoside (50 mg, 0.091 mmol) in DCM/TFA (10 mL, 19:1) was stirred 3 h at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (15.8 mg, 38%). ESI-MS m/z calcd for [$C_{18}H_{18}N_6O_5S_2$] $[M+H]^+$: 463.1; found: 463.0. $^1H$ NMR (400 MHz, Methanol-$d_4$) δ 8.95 (d, J=2.0 Hz, 1H), 8.79 (d, J=2.0 Hz, 1H), 8.49 (t, J=2.0 Hz, 1H), 8.31 (s, 1H), 6.68 (s, 1H), 6.33 (d, J=5.2 Hz, 1H), 5.03 (dd, J=11.2, 2.8 Hz, 1H), 4.58 (dd, J=11.2, 5.2 Hz, 1H), 4.42 (t, J=6.0 Hz, 1H), 4.16 (d, J=3.6 Hz, 1H), 3.68 (d, J=6.0 Hz, 2H), 3.39 (s, 3H).

Example 84

2-Cyano-5-ethynylpyridin-3-yl 3-[4-(2-aminothiazol-4-yl)-1H-1,2,3-triazol-1-yl]-3-deoxy-1-thio-α-D-galactopyranoside

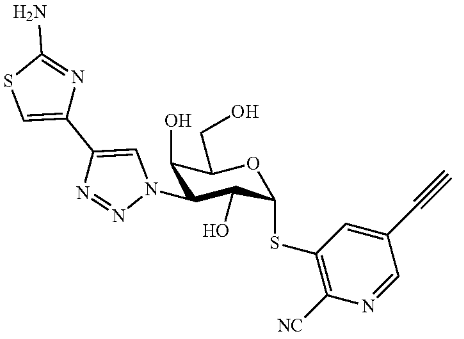

A solution of 2-cyano-5-(2-trimethylsilyl-1-ethynyl)pyridin-3-yl 2,4,6-tri-O-acetyl-3-{4-[2-(di-tert-butoxycarbonylamino)thiazol-4-yl]-1H-1,2,3-triazol-1-yl}-3-deoxy-1-thio-α-D-galactopyranoside (100 mg, 0.12 mmol) in DCM/TFA (10 mL, 19:1) was stirred 1 h at rt. The reaction was neutralized with $Et_3N$, concentrated, and purified by prep HPLC [MeCN/$H_2O$ (10 mmol/L $NH_4HCO_3$), X-Select 10 μm 19*250 mm, 20 mL/min, UV 254]. The obtained material was stirred 15 min at rt in MeOH (5 mL) and a catalytic amount of NaOMe. The mixture was neutralized with acidic resin, filtered, concentrated and purified by prep HPLC [MeCN/$H_2O$ (10 mmol/L $NH_4HCO_3$), X-Select 10 μm 19*250 mm, 20 mL/min, UV 254] to afford the title compound (19.6 mg, 51%). ESI-MS m/z calcd for [$C_{19}H_{17}N_7O_4S_2$] $[M+H]^+$: 472.1; found: 472.2. $^1H$ NMR (400 MHz, Methanol-$d_4$) δ 8.60 (d, J=2.0 Hz, 1H), 8.40 (d, J=2.0 Hz, 1H), 8.24 (s, 1H), 6.95 (s, 1H), 6.18 (d, J=5.2 Hz, 1H), 5.05 (dd, J=11.2, 2.8 Hz, 1H), 4.94 (dd, J=11.2, 5.2 Hz, 1H), 4.35 (dd, J=6.8, 5.2 Hz, 1H), 4.20 (dd, J=2.8, 1.2 Hz, 1H), 3.71-3.58 (m, 2H).

Example 85

2-Cyano-5-ethynylpyridin-3-yl 3-[4-(2-aminothiazol-4-yl)-1H-1,2,3-triazol-1-yl]-3-deoxy-2-O-methyl-1-thio-α-D-galactopyranoside

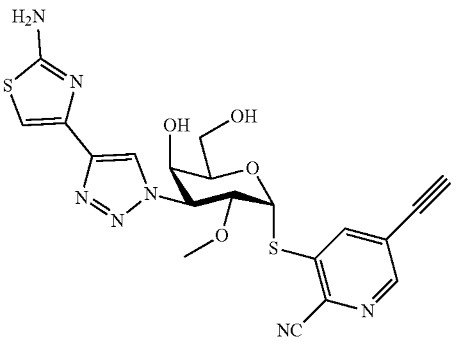

A solution of 2-cyano-5-(2-trimethylsilyl-1-ethynyl)pyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside (110 mg, 0.13 mmol) in DCM (6 mL) TFA (0.97 mL) was added and the mixture was stirred overnight at rt. $Et_3N$ (2 mL) was added at 0° C. to neutralize the TFA. The mixture was concentrated, and the residue was dissolved together with KF (15.6 mg, 0.27 mmol) in DMF (3 mL). The mixture was stirred 1 h at rt before it was filtered and purified by prep HPLC [MeCN/$H_2O$ (10 mmol/L $NH_4HCO_3$), X-Select 10 μm 19*250 mm, 20 mL/min, UV 254] to afford the title compound (27 mg, 43%). ESI-MS m/z calcd for [$C_{20}H_{19}N_7O_4S_2$] $[M+H]^+$: 486.1; found: 486.2. $^1H$ NMR (400 MHz, Methanol-$d_4$) δ 8.64 (d, J=2.0 Hz, 1H), 8.43 (d, J=2.0 Hz, 1H), 8.25 (s, 1H), 6.96 (s, 1H), 6.47 (d, J=5.2 Hz, 1H), 5.06 (dd, J=11.2, 2.8 Hz, 1H), 4.64 (dd, J=11.2, 5.2 Hz, 1H), 4.39 (t, J=6.0 Hz, 1H), 4.22-4.16 (m, 1H), 3.72-3.59 (m, 2H), 3.44 (s, 3H).

Example 86

5-Bromo-2-cyanopyridin-3-yl 3-[4-(4-chlorothiazol-2-yl)-1H-1,2,3-triazol-1-yl]-3-deoxy-2-O-ethyl-1-thio-α-D-galactopyranoside

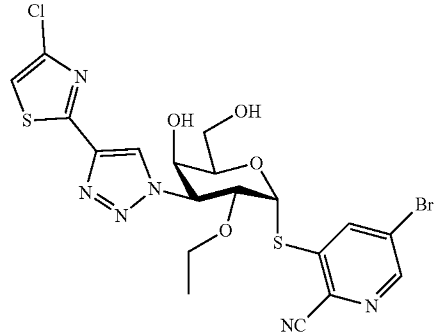

A solution of 5-bromo-2-cyanopyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside (85 mg, 0.13 mmol) in DCM/TFA (10 mL, 19:1) was stirred 1 h at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (45.4 mg, 62%). ESI-MS m/z calcd for [$C_{19}H_{18}BrClN_6O_4S_2$] $[M+H]^+$: 573.0; found: 573.0. $^1H$ NMR (400 MHz, Methanol-$d_4$) δ 8.70 (d, J=2.0 Hz, 1H), 8.64 (s, 1H), 8.61 (d, J=2.0 Hz, 1H), 7.46 (s, 1H), 6.46 (d, J=5.2 Hz, 1H), 5.12 (dd, J=11.2, 2.8 Hz, 1H), 4.80 (dd, J=11.2, 5.2 Hz, 1H), 4.40 (t, J=6.0 Hz, 1H), 4.21 (dd, J=2.8, 1.2 Hz, 1H), 3.92-3.80 (m, 1H), 3.68 (d, J=6.0 Hz, 2H), 3.52-3.39 (m, 1H), 1.05 (t, J=6.8 Hz, 3H).

Example 87

3,4-Dichlorophenyl 3-[4-(2-aminothiazol-4-yl)-1H-1,2,3-triazol-1-yl]-3-deoxy-2-O-ethyl-1-thio-α-D-galactopyranoside

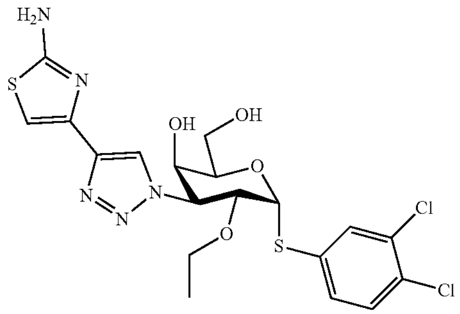

A solution of 3,4-dichlorophenyl 3-[4-(2-aminothiazol-4-yl)-1H-1,2,3-triazol-1-yl]-4,6-O-benzylidene-3-deoxy-2-O-ethyl-1-thio-α-D-galactopyranoside (130 mg, 0.16 mmol) in DCM/TFA (10 mL, 19:1) was stirred overnight at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (49 mg, 59%). ESI-MS m/z calcd for [$C_{19}H_{21}Cl_2N_5O_4S_2$] $[M+H]^+$: 518.0; found: 518.2. $^1H$ NMR (400 MHz, Methanol-$d_4$) δ 8.23 (s, 1H), 7.79 (d, J=2.0 Hz, 1H), 7.52 (dd, J=8.4, 2.0 Hz, 1H), 7.47 (d, J=8.4 Hz, 1H), 6.95 (s, 1H), 6.13 (d, J=5.2 Hz, 1H), 4.98 (dd, J=11.2, 2.8 Hz, 1H), 4.64 (dd, J=11.2, 5.2 Hz, 1H), 4.43 (t, J=6.4 Hz, 1H), 4.18 (dd, J=2.8, 1.2 Hz, 1H), 3.84-3.55 (m, 3H), 3.46-3.35 (m, 1H), 1.01 (t, J=6.8 Hz, 3H).

Example 88

3-Chloro-4-cyanophenyl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside

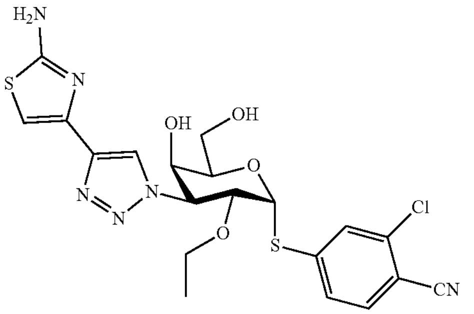

A solution of 3-chloro-4-cyanophenyl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside (90 mg, 0.11 mmol) in DCM/TFA (10 mL, 19:1) was stirred overnight at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (30 mg, 47%). ESI-MS m/z calcd for [$C_{20}H_{21}ClN_6O_4S_2$] $[M+H]^+$: 509.1; found: 509.0. $^1H$ NMR (400 MHz, Methanol-$d_4$) δ 8.24 (s, 1H), 7.86 (d, J=1.6 Hz, 1H), 7.70 (d, J=8.4 Hz, 1H), 7.65 (dd, J=8.4, 1.6 Hz, 1H), 6.95 (s, 1H), 6.43 (d, J=5.2 Hz, 1H), 5.01 (dd, J=11.2, 2.8 Hz, 1H), 4.69 (dd, J=11.2, 5.2 Hz, 1H), 4.32 (t, J=6.0 Hz, 1H), 4.17 (dd, J=2.8, 1.2 Hz, 1H), 3.83-3.59 (m, 3H), 3.46-3.35 (m, 1H), 0.99 (t, J=6.8 Hz, 3H).

Example 89

3-Chloro-4-cyanophenyl 2,3-dideoxy-3-[4-(2-hydroxythiazol-4-yl)-1H-1,2,3-triazol-1-yl]-1-thio-α-D-galactopyranoside

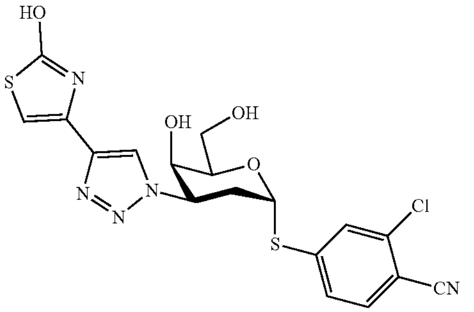

To a solution of 4,6-di-O-acetyl 3-deoxy-3-[4-(2-hydroxythiazol-4-yl)-1H-1,2,3-triazol-1-yl]-D-galactal (880 mg, 2.31 mmol) and oxotrichloro[(dimethylsulfide)triphenylphosphine oxide]rhenium (V) (150 mg, 0.23 mmol) in toluene (20 mL) 2-chloro-4-sulfanylbenzonitrile (589 mg, 3.47 mmol) was added and the mixture was stirred 20 h at 70° C. The mixture was evaporated and purified by prep HPLC [MeCN/$H_2O$ (10 mmol/L $NH_4HCO_3$), X-Select 10 μm 19*250 mm, 20 mL/min, UV254]. The obtained material was stirred 1 h at rt in MeOH (5 mL) and catalytic amount of NaOMe. The mixture was neutralized with acidic resin, filtered, concentrated and purified by preparative-SFC to afford the title compound (13.5 mg, 1%). ESI-MS m/z calcd for [$C18H_{16}ClN_5O_4S_2$] $[M+H]^+$: 466.0; found: 466.0, $^1H$ NMR (400 MHz, Methanol-$d_4$) δ 8.28 (s, 1H), 7.84 (d, J=1.6 Hz, 1H), 7.71-7.62 (m, 2H), 6.67 (s, 1H), 6.18 (d, J=5.2 Hz, 1H), 5.19-5.14 (m, 1H), 4.37 (t, J=6.0 Hz, 1H), 4.21 (dd, J=5.2, 2.0 Hz, 1H), 4.15 (s, 1H), 3.73-3.71 (m, 1H), 3.17-3.09 (m, 1H), 2.33 (dd, J=13.6, 4.4 Hz, 1H).

Example 90

5-Bromo-2-(N,N-dimethylcarbamoyl)pyridin-3-yl 3-[4-(4-chlorothiazol-2-yl)-1H-1,2,3-triazol-1-yl]-3-deoxy-2-O-ethyl-1-thio-α-D-galactopyranoside

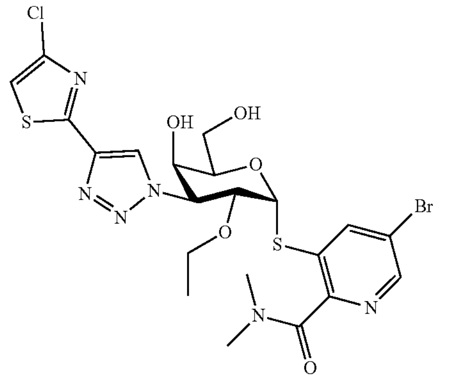

To a solution of 5-bromo-2-carboxypyridin-3-yl 3-[4-(4-chlorothiazol-2-yl)-1H-1,2,3-triazol-1-yl]-3-deoxy-2-O-ethyl-1-thio-α-D-galactopyranoside (30 mg, 0.051 mmol) in DMF (2 mL) dimethylamine hydrochloride (16.5 mg, 0.20 mmol), HATU (96.2 mg, 0.25 mmol) and DIPEA (87 μL, 0.51 mmol) were added and the mixture was stirred overnight at rt. The mixture was filtered and purified by prep HPLC (MeCN/$H_2O$ (10 mmol/L $NH_4HCO_3$), X-Select 10 μm 19*250 mm, 20 mL/min, UV 254) to afford the title compound (10 mg, 32%). ESI-MS m/z calcd for [$C_{21}H_{24}BrClN_6O_5S_2$] $[M+H]^+$: 619.0; found: 619.0. $^1H$ NMR (400 MHz, Methanol-$d_4$) δ 8.63 (d, J=2.0 Hz, 1H), 8.61 (s, 1H), 8.50 (d, J=2.0 Hz, 1H), 7.46 (s, 1H), 6.25 (d, J=5.2 Hz, 1H), 5.04 (dd, J=11.2, 2.8 Hz, 1H), 4.70 (dd, J=11.2, 5.2 Hz, 1H), 4.49 (t, J=6.0 Hz, 1H), 4.18 (d, J=2.8 Hz, 1H), 3.85-3.68 (m, 3H), 3.47-3.35 (m, 1H), 3.13 (s, 3H), 2.88 (s, 3H), 1.02 (t, J=7.2 Hz, 3H).

Example 91

5-Ethynyl-2-(N,N-dimethylcarbamoyl)pyridin-3-yl 3-[4-(4-chlorothiazol-2-yl)-1H-1,2,3-triazol-1-yl]-3-deoxy-2-O-methyl-1-thio-α-D-galactopyranoside

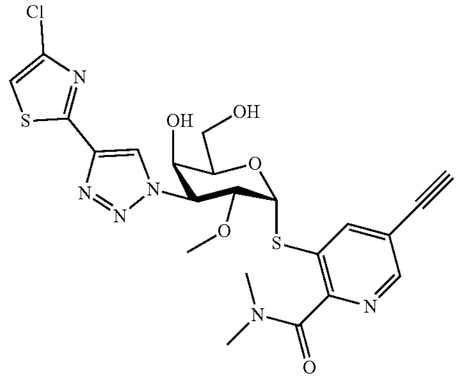

To a solution of 5-ethynyl-2-(N,N-dimethylcarbamoyl) pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (30 mg, 0.047 mmol) in DCM (5 mL) TFA (0.3 mL) was added and the mixture was stirred overnight at rt. $Et_3N$ was added at 0° C. to neutralize the TFA. The mixture was concentrated and purified by prep HPLC [$MeCN/H_2O$ (10 mmol/L $NH_4HCO_3$), X-Select 10 μm 19*250 mm, 20 mL/min, UV 254] to afford the title compound (15 mg, 58%). ESI-MS m/z calcd for [$C_{22}H_{23}ClN_6O_5S_2$] $[M+H]^+$: 551.1; found: 551.2. $^1H$ NMR (400 MHz, Methanol-$d_4$) δ 8.65-8.59 (m, 2H), 8.38-8.33 (m, 1H), 7.47 (s, 1H), 6.28 (d, J=5.2 Hz, 1H), 5.08-5.01 (m, 1H), 4.66-4.57 (m, 1H), 4.54-4.46 (m, 1H), 4.19 (s, 1H), 3.92 (s, 1H), 3.70 (d, J=6.0 Hz, 2H), 3.39 (s, 3H), 3.15 (s, 3H), 2.88 (s, 3H).

Example 92

2-(N-Azetidinylcarbamoyl)-5-ethynylpyridin-3-yl 3-[4-(4-chlorothiazol-2-yl)-1H-1,2,3-triazol-1-yl]-3-deoxy-2-O-methyl-1-thio-α-D-galactopyranoside

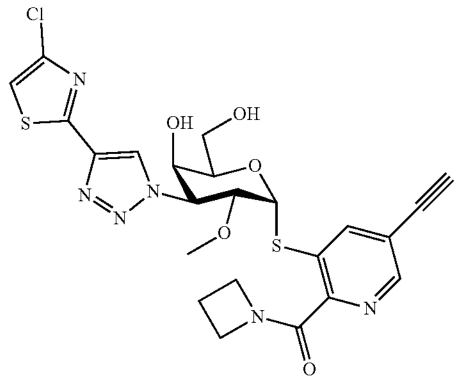

To a solution of 2-(N-azetidinylcarbamoyl)-5-ethynylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (30 mg, 0.046 mmol) in DCM (5 mL) TFA (0.3 mL) was added and the mixture was stirred overnight at rt. $Et_3N$ was added at 0° C. to neutralize the TFA. The mixture was concentrated and purified by prep HPLC [$MeCN/H_2O$ (10 mmol/L $NH_4HCO_3$), X-Select 10 μm 19*250 mm, 20 mL/min, UV 254] to afford the title compound (5 mg, 19%). ESI-MS m/z calcd for [$C_{23}H_{23}ClN_6O_5S_2$] $[M+H]^+$: 563.1; found: 563.2. $^1H$ NMR (400 MHz, Methanol-$d_4$) δ 8.63 (s, 1H), 8.55 (d, J=1.6 Hz, 1H), 8.36 (d, J=1.6 Hz, 1H), 7.47 (s, 1H), 6.34 (d, J=5.2 Hz, 1H), 5.11 (dd, J=11.2, 3.2 Hz, 1H), 4.64 (dd, J=11.2, 5.2 Hz, 1H), 4.45 (t, J=6.0 Hz, 1H), 4.28-4.13 (m, 5H), 3.93 (s, 1H), 3.75-3.61 (m, 2H), 3.41 (s, 3H), 2.45-2.33 (m, 2H).

Example 93

5-Chloro-2-(N-methylcarbamoyl)pyridin-3-yl 3-[4-(4-chlorothiazol-2-yl)-1H-1,2,3-triazol-1-yl]-3-deoxy-2-O-methyl-1-thio-α-D-galactopyranoside

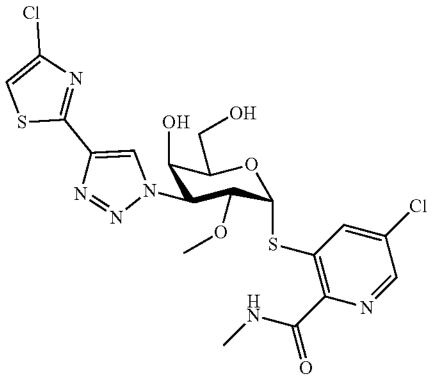

A solution of 5-chloro-2-(N-methylcarbamoyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (40 mg, 0.063 mmol) in DCM/TFA (10 mL, 19:1) was stirred overnight at rt before $Et_3N$ was added to neutralize the TFA. The mixture was concentrated and purified by prep HPLC [$MeCN/H_2O$ (10 mmol/L $NH_4HCO_3$), X-Select 10 μm 19*250 mm, 20 mL/min, UV 254] to afford the title compound (13.5 mg, 39%). ESI-MS m/z calcd for [$C_{19}H_{20}Cl_2N_6O_5S_2$] $[M+H]^+$: 547.0; found: 547.1. $^1H$ NMR (400 MHz, Methanol-$d_4$) δ 8.53 (s, 1H), 8.30 (s, 2H), 7.37 (s, 1H), 6.31 (d, J=5.6 Hz, 1H), 5.08 (dd, J=11.6, 3.2 Hz, 1H), 4.59 (dd, J=11.6, 5.6 Hz, 1H), 4.27 (dd, J=6.8, 5.6 Hz, 1H), 4.09 (dd, J=3.2, 1.2 Hz, 1H), 3.67-3.46 (m, 2H), 3.29 (s, 3H), 2.83 (s, 3H).

Example 94

5-Chloro-2-(N-ethylcarbamoyl)pyridin-3-yl 3-[4-(4-chlorothiazol-2-yl)-1H-1,2,3-triazol-1-yl]-3-deoxy-2-O-methyl-1-thio-α-D-galactopyranoside

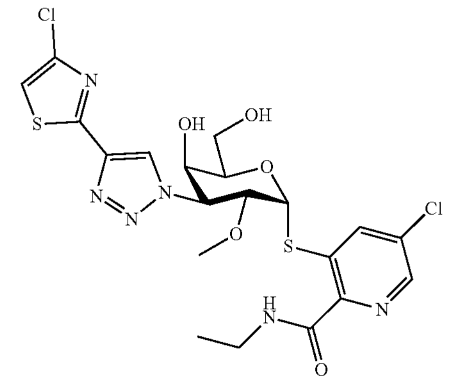

A solution of 5-chloro-2-(N-ethylcarbamoyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (95 mg, 0.15 mmol) in DCM/TFA (6.33 mL, 18:1) was stirred overnight at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (40 mg, 49%). ESI-MS m/z calcd for [$C_{20}H_{22}Cl_2N_6O_5S_2$] [M+H]$^+$: 561.0; found: 561.1. $^1$H NMR (400 MHz, Methanol-$d_4$) δ 8.63 (s, 1H), 8.40 (dd, J=4.4, 2.0 Hz, 2H), 7.47 (s, 1H), 6.39 (d, J=5.2 Hz, 1H), 5.17 (dd, J=11.2, 3.2 Hz, 1H), 4.68 (dd, J=11.2, 5.6 Hz, 1H), 4.38 (t, J=6.0 Hz, 1H), 4.19 (d, J=2.4 Hz, 1H), 3.73-3.64 (m, 2H), 3.44-3.20 (m, 2H), 3.38 (s, 3H), 1.25-1.21 (m, 3H).

Example 95

5-Chloro-2-(N-methylcarbamoyl)pyridin-3-yl 3-[4-(4-chlorothiazol-2-yl)-1H-1,2,3-triazol-1-yl]-3-deoxy-2-O-ethyl-1-thio-α-D-galactopyranoside

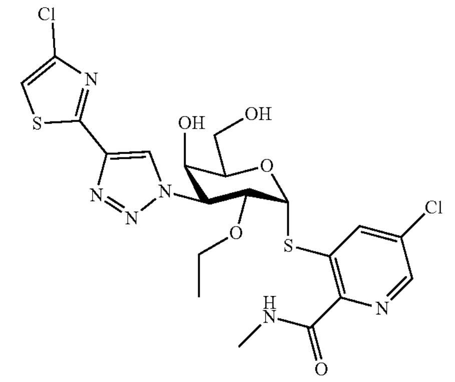

A solution of 5-chloro-2-(N-methylcarbamoyl)pyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside (80 mg, 0.12 mmol) in DCM/TFA (10 mL, 19:1) was stirred overnight at rt before $Et_3N$ was added to neutralize the TFA. The mixture was concentrated and purified by prep HPLC [MeCN/$H_2O$ (10 mmol/L $NH_4HCO_3$), X-Select 10 μm 19*250 mm, 20 mL/min, UV 254] to afford the title compound (47.1 mg, 68%). ESI-MS m/z calcd for [$C_{20}H_{22}Cl_2N_6O_5S_2$] [M+H]$^+$: 561.0; found: 561.2. $^1$H NMR (400 MHz, Methanol-$d_4$) δ 8.88 (s, 1H), 8.70-8.58 (m, 2H), 7.71 (s, 1H), 6.61 (d, J=5.6 Hz, 1H), 5.43 (dd, J=11.2, 2.8 Hz, 1H), 5.03 (dd, J=11.2, 5.6 Hz, 1H), 4.62 (t, J=6.0 Hz, 1H), 4.45 (d, J=2.0 Hz, 1H), 4.10-3.84 (m, 3H), 3.75-3.63 (m, 1H), 3.17 (s, 3H), 1.26 (t, J=6.8 Hz, 3H).

Example 96

5-Chloro-2-cyanophenyl 3-[4-(4-chlorothiazol-2-yl)-1H-1,2,3-triazol-1-yl]-3-deoxy-2-O-methyl-1-thio-α-D-galactopyranoside

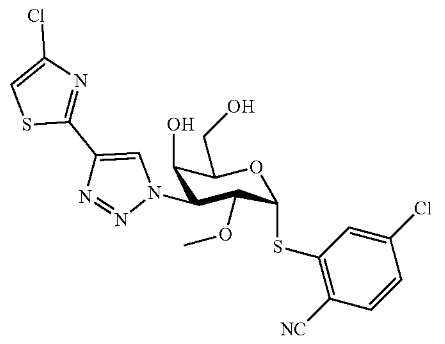

A solution of copper (II) sulfate pentahydrate (4.4 mg, 0.018 mmol) and (+)-sodium L-ascorbate (7.0 mg, 0.035 mmol) in water (0.6 mL) was added to a solution of 5-chloro-2-cyanophenyl 4,6-di-O-acetyl-3-azido-3-deoxy-2-O-methyl-1-thio-α-D-galactopyranoside (80 mg, 0.18 mmol), 2-(4-chlorothiazol-2-yl)ethynyl-trimethyl-silane (57 mg, 0.26 mmol) and $K_2CO_3$ (243 mg, 1.76 mmol) in MeOH/THF (8 mL). The mixture was stirred 18 h at 50° C. before being concentrated and partitioned between EtOAc and water. The organic phase was dried, evaporated and purified by prep HPLC ($C_{18}$, $H_2O$/MeCN/0.1% TFA) to afford the title compound (32 mg, 35%). ESI-MS m/z calcd for [$C_{19}H_{17}Cl_2N_5O_4S_2$] [M+H]$^+$: 514.0; found: 514.0. $^1$H NMR (500 MHz, Methanol-$d_4$) δ 8.65 (s, 1H), 8.01 (d, J=2.0 Hz, 1H), 7.77 (d, J=8.4 Hz, 1H), 7.51 (dd, J=8.4, 2.0 Hz, 1H), 7.47 (s, 1H), 6.41 (d, J=5.3 Hz, 1H), 5.12 (dd, J=11.3, 2.9 Hz, 1H), 4.70 (dd, J=11.3, 5.3 Hz, 1H), 4.45 (t, J=6.2 Hz, 1H), 4.23 (d, J=2.8 Hz, 1H), 3.70 (dd, J=11.5, 5.5 Hz, 1H), 3.65 (dd, J=11.5, 6.7 Hz, 1H), 3.47 (s, 3H).

Example 97

1,3-Benzothiazol-6-yl 3-[4-(4-chlorothiazol-2-yl)-1H-1,2,3-triazol-1-yl]-3-deoxy-2-O-methyl-1-thio-α-D-galactopyranoside

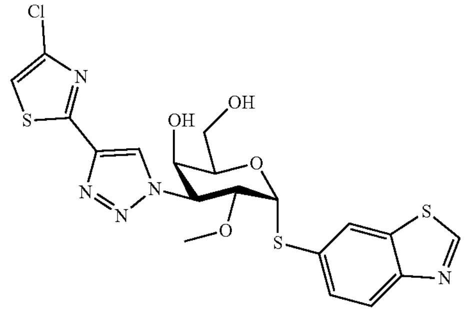

To a solution of 1,3-benzothiazol-6-yl 3-azido-3-deoxy-2-O-methyl-1-thio-α-D-galactopyranoside (100 mg, 0.27 mmol), CuI (10 mg, 0.54 mmol) and 2-(4-chlorothiazol-2-yl)ethynyltrimethylsilane (73 mg, 0.34 mmol) in MeCN (2.0 mL) DIPEA (0.14 mL, 0.81 mmol) was added and the mixture was stirred 2 h at 50° C. The mixture was purified by prep HPLC ($C_{18}$, $H_2O$/MeCN/0.1% TFA) to afford the title compound (63 mg, 45%). ESI-MS m/z calcd for [$C_{19}H_{18}ClN_5O_4S_3$] $[M+H]^+$: 512.0; found: 512.0. $^1$H NMR (500 MHz, Methanol-$d_4$) δ 9.26 (s, 1H), 8.64 (s, 1H), 8.40 (d, J=1.5 Hz, 1H), 8.03 (d, J=8.5 Hz, 1H), 7.80 (dd, J=8.5, 1.8 Hz, 1H), 7.47 (s, 1H), 6.18 (d, J=5.3 Hz, 1H), 5.10 (dd, J=11.4, 2.9 Hz, 1H), 4.64 (dd, J=11.4, 5.3 Hz, 1H), 4.59 (t, J=6.3 Hz, 1H), 4.22 (d, J=2.1 Hz, 1H), 3.73 (dd, J=11.5, 5.5 Hz, 1H), 3.69 (dd, J=11.5, 6.7 Hz, 1H), 3.43 (s, 3H).

Example 98

1,3-Benzothiazol-6-yl 3-deoxy-3-[4-(2-hydroxythiazol-4-yl)-1H-1,2,3-triazol-1-yl]-2-O-methyl-1-thio-α-D-galactopyranoside

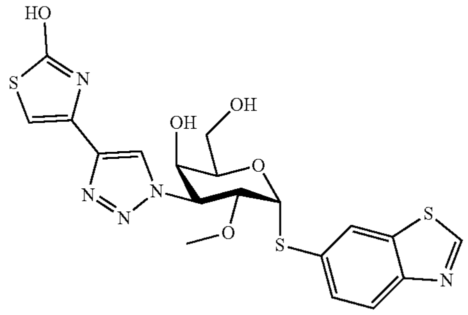

To a solution of 1,3-benzothiazol-6-yl 3-azido-3-deoxy-2-O-methyl-1-thio-α-D-galactopyranoside (100 mg, 0.27 mmol), CuI (10 mg, 0.54 mmol) and 4-(2-trimethylsilylethynyl)thiazol-2-ol (67 mg, 0.34 mmol) in MeCN (2.0 mL) DIPEA (0.14 mL, 0.81 mmol) was added and the mixture was stirred 3 h at 50° C. The mixture was purified by prep HPLC ($C_{18}$, $H_2O$/MeCN/0.1% TFA) to afford the title compound (35 mg, 26%). ESI-MS m/z calcd for [$C_{19}H_{19}N_5O_5S_3$] $[M+H]^+$: 494.1; found: 494.1. $^1$H NMR (500 MHz, Methanol-$d_4$) δ 9.26 (s, 1H), 8.40 (d, J=1.6 Hz, 1H), 8.37 (s, 1H), 8.04 (d, J=8.5 Hz, 1H), 7.79 (dd, J=8.5, 1.8 Hz, 1H), 6.71 (s, 1H), 6.16 (d, J=5.3 Hz, 1H), 5.06 (dd, J=11.4, 2.9 Hz, 1H), 4.59-4.54 (m, 2H), 4.20 (d, J=2.1 Hz, 1H), 3.72 (dd, J=11.5, 5.5 Hz, 1H), 3.68 (dd, J=11.5, 6.7 Hz, 1H), 3.42 (s, 3H).

Example 99

1,3-Benzothiazol-6-yl 3-[4-(2-aminothiazol-4-yl)-1H-1,2,3-triazol-1-yl]-3-deoxy-2-O-methyl-1-thio-α-D-galactopyranoside

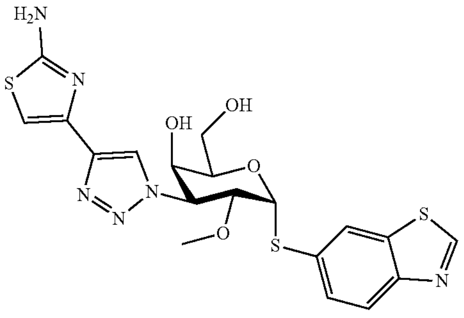

To a solution of 1,3-benzothiazol-6-yl 3-azido-3-deoxy-2-O-methyl-1-thio-α-D-galactopyranoside (100 mg, 0.27 mmol), CuI (10 mg, 0.54 mmol) and 4-(2-trimethylsilylethynyl)thiazol-2-amine (67 mg, 0.34 mmol) in MeCN (2.0 mL) DIPEA (0.14 mL, 0.81 mmol) was added and the mixture was stirred 2 h at 50° C. The mixture was purified by prep HPLC ($C_{18}$, $H_2O$/MeCN/0.1% TFA) to afford the title compound (96 mg, 72%). ESI-MS m/z calcd for [$C_{19}H_{20}N_6O_4S_3$] $[M+H]^+$: 493.1; found: 493.1. $^1$H NMR (500 MHz, Methanol-$d_4$) δ 9.28 (s, 1H), 8.59 (s, 1H), 8.42 (d, J=1.5 Hz, 1H), 8.06 (d, J=8.5 Hz, 1H), 7.81 (dd, J=8.5, 1.7 Hz, 1H), 7.16 (s, 1H), 6.21 (s, 1H), 5.14 (s, 1H), 4.68-4.56 (m, 2H), 4.26 (s, 1H), 3.77-3.69 (m, 2H), 3.45 (s, 3H).

Example 100

5-Cyano-1,3-benzothiazol-6-yl 3-[4-(4-chlorothiazol-2-yl)-1H-1,2,3-triazol-1-yl]-3-deoxy-2-O-methyl-1-thio-α-D-galactopyranoside

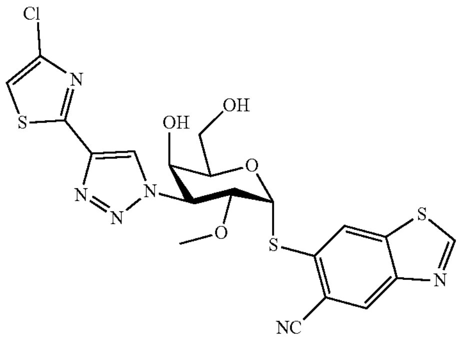

To a solution of 5-cyano-1,3-benzothiazol-6-yl 3-azido-3-deoxy-2-O-methyl-1-thio-α-D-galactopyranoside (37 mg, 0.094 mmol), CuI (3.6 mg, 0.019 mmol) and 2-(4-chlorothiazol-2-yl)ethynyltrimethylsilane (30 mg, 0.14 mmol) in MeCN (1.5 mL) $Et_3N$ (52 μL, 0.38 mmol) and TBAF (9.4 μL, 1 M in THF, 0.0094 mmol) were added and the mixture was stirred 1 h at 50° C. The mixture was filtered and purified by prep HPLC ($C_{18}$, $H_2O$/MeCN/0.1% TFA) to afford the title compound (43 mg, 48%). ESI-MS m/z calcd for $[C_{20}H_{17}ClN_6O_4S_3]$ $[M+H]^+$: 537.0; found: 537.0. $^1H$ NMR (500 MHz, Methanol-$d_4$) δ 9.41 (s, 1H), 8.67 (s, 1H), 8.65 (s, 1H), 8.53 (s, 1H), 7.47 (s, 1H), 6.35 (d, J=5.3 Hz, 1H), 5.16 (dd, J=11.3, 2.9 Hz, 1H), 4.70 (dd, J=11.3, 5.3 Hz, 1H), 4.57 (t, J=6.1 Hz, 1H), 4.23 (d, J=2.5 Hz, 1H), 3.71-3.63 (m, 2H), 3.52 (s, 3H).

Example 101

Thiazolo[4,5-b]pyridin-6-yl 3-[4-(4-chlorothiazol-2-yl)-1H-1,2,3-triazol-1-yl]-3-deoxy-2-O-methyl-1-thio-α-D-galactopyranoside

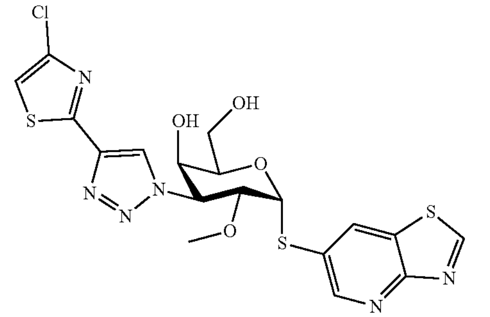

To a solution of thiazolo[4,5-b]pyridin-6-yl 3-azido-3-deoxy-2-O-methyl-1-thio-α-D-galactopyranoside (112 mg, 0.30 mmol), CuI (11.5 mg, 0.061 mmol) and 2-(4-chlorothiazol-2-yl)ethynyltrimethylsilane (98 mg, 0.46 mmol) in MeCN (3.0 mL) $Et_3N$ (0.17 mL, 1.21 mmol) and TBAF (30 μL, 1 M in THF, 0.030 mmol) were added and the mixture was stirred 2.5 h at 50° C. The mixture was filtered and purified by prep HPLC ($C_{18}$, $H_2O$/MeCN/0.1% TFA). The obtained product was further purified by chromatography ($SiO_2$, EtOAc/MeOH) to afford the title compound (2.1 mg, 1%). ESI-MS m/z calcd for $[C18H_{17}ClN_6O_4S_3]$ $[M+H]^+$: 513.0; found: 513.0. $^1H$ NMR (500 MHz, Methanol-$d_4$) δ 9.59 (s, 1H), 8.95 (d, J=2.1 Hz, 1H), 8.91 (d, J=2.0 Hz, 1H), 8.66 (s, 1H), 7.49 (s, 1H), 6.25 (d, J=5.3 Hz, 1H), 5.15 (dd, J=11.4, 2.8 Hz, 1H), 4.68 (dd, J=11.3, 5.2 Hz, 1H), 4.60 (t, J=6.0 Hz, 1H), 4.26-4.22 (m, 1H), 3.73 (d, J=6.1 Hz, 2H), 3.47 (s, 3H).

Example 102

5-Methylsulfanylpyridin-3-yl 3-[4-(4-chlorothiazol-2-yl)-1H-1,2,3-triazol-1-yl]-3-deoxy-2-O-methyl-1-thio-α-D-galactopyranoside

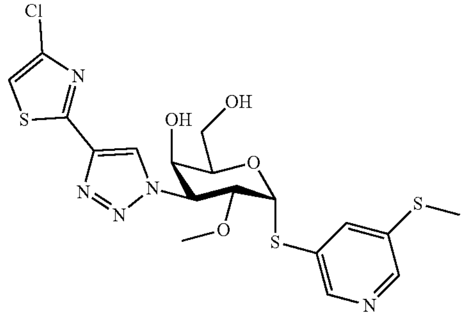

To a solution of 5-bromopyridin-3-yl 3-[4-(4-chlorothiazol-2-yl)-1H-1,2,3-triazol-1-yl]-3-deoxy-2-O-methyl-1-thio-α-D-galactopyranoside (50 mg, 0.094 mmol) in DMF (1.0 mL) sodium thiomethoxide (33 mg, 0.47 mmol) was added and the mixture was stirred 22 h at rt. The mixture was partitioned between EtOAc and water. The organic phase was dried, evaporated and purified by prep HPLC ($C_{18}$, $H_2O$/MeCN/0.1% TFA) to afford the title compound (7 mg, 15%). ESI-MS m/z calcd for $[C_{18}H_{20}ClN_5O_4S_3][M+H]^+$: 502.0; found: 502.0. $^1H$ NMR (500 MHz, Methanol-$d_4$) δ 8.66 (s, 1H), 8.60 (s, 1H), 8.47-8.43 (m, 1H), 8.25 (t, J=2.0 Hz, 1H), 7.49 (s, 1H), 6.36 (d, J=5.3 Hz, 1H), 5.12 (dd, J=11.3, 2.9 Hz, 1H), 4.68 (dd, J=11.3, 5.3 Hz, 1H), 4.48 (t, J=6.1 Hz, 1H), 4.22 (d, J=2.3 Hz, 1H), 3.76-3.69 (m, 2H), 3.44 (s, 3H), 2.64 (s, 3H).

Example 103

5-(Trifluoromethylsulfanyl)pyridin-3-yl 3-[4-(4-chlorothiazol-2-yl)-1H-1,2,3-triazol-1-yl]-3-deoxy-2-O-methyl-1-thio-α-D-galactopyranoside

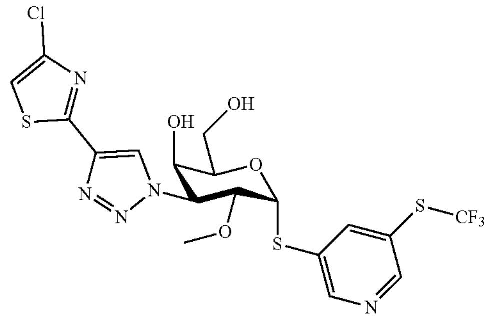

To a solution of 5-(trifluoromethylsulfanyl)pyridin-3-yl 3-azido-3-deoxy-2-O-methyl-1-thio-α-D-galactopyranoside (39 mg, 0.095 mmol), CuI (3.6 mg, 0.019 mmol) and 2-(4-chlorothiazol-2-yl)ethynyltrimethylsilane (31 mg, 0.14 mmol) in MeCN (1.5 mL) $Et_3N$ (53 μL, 0.38 mmol) and TBAF (9.5 μL, 1 M in THF, 0.0095 mmol) were added and the mixture was stirred 2 h at 50° C. The mixture was filtered and purified by prep HPLC ($C_{18}$, $H_2O$/MeCN/0.1% TFA) to afford the title compound (38 mg, 72%). ESI-MS m/z calcd for [C18$H_{17}ClF_3N_5O_4S_3$] $[M+H]^+$: 556.0; found: 556.0. $^1H$ NMR (500 MHz, Methanol-$d_4$) δ 8.93 (d, J=2.0 Hz, 1H), 8.74 (d, J=1.8 Hz, 1H), 8.66 (s, 1H), 8.48 (t, J=1.9 Hz, 1H), 7.49 (s, 1H), 6.35 (d, J=5.3 Hz, 1H), 5.13 (dd, J=11.3, 2.9 Hz, 1H), 4.69 (dd, J=11.3, 5.3 Hz, 1H), 4.48 (t, J=6.2 Hz, 1H), 4.24 (d, J=2.4 Hz, 1H), 3.73 (dd, J=11.4, 5.4 Hz, 1H), 3.67 (dd, J=11.4, 6.8 Hz, 1H), 3.44 (s, 3H).

Intermediate 1

O-Ethyl (3,5-dichloro-4-fluorophenyl)sulfanylmethanethioate

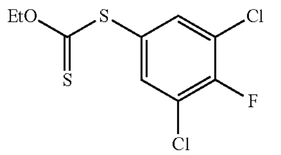 [SMILES: CCOC(=S)Sc1cc(Cl)c(F)c(Cl)c1]

3,5-Dichloro-4-fluoroaniline (6.70 g, 37.2 mmol) was suspended in a HCl/$H_2O$ (V/V=1:4, 100 mL) and the suspension was cooled to −5° C. A solution of $NaNO_2$ (5.14 g, 74.4 mmol) in $H_2O$ (20 mL) was added dropwise to the suspension. The mixture was stirred at −5° C. until the solution was clear (2~3 h). The mixture was then added to a solution of potassium ethyl xanthate (17.90 g, 112 mmol) in $H_2O$ (50 mL). The mixture was stirred 3 h at 50° C. and was then extracted with EtOAc (3×100 mL). The combined organic phases were dried over $Na_2SO_4$, concentrated, and purified by column chromatography (PE, Silica-CS 80 g, 40 mL/min, silica gel, UV 254) to give the product (7.30 g, 60%). $^1H$ NMR (400 MHz, Methanol-$d_4$) δ 7.67 (d, J=6.3 Hz, 2H), 4.66 (q, J=7.1 Hz, 2H), 1.36 (t, J=7.1 Hz, 3H).

3,5-Dichloro-4-fluorobenzenethiol

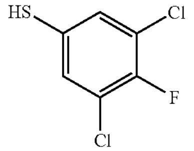

To a solution of O-ethyl (3,5-dichloro-4-fluorophenyl) sulfanylmethanethioate (7.30 g, 22.3 mmol) in MeOH (50 mL) NaOH (22 mL, 2 M) was added and the mixture was stirred 2 h at 70° C. Most of the MeOH was removed through evaporation and the remaining solution was extracted with EtOAc (100 mL). The aqueous layer was acidified with aqueous $NaHSO_4$ and extracted with EtOAc (100 mL) and diethyl ether (2×100 mL). The combined organic phases were dried and evaporated to afford the product (4.60 g, 88%). $^1H$ NMR (400 MHz, DMSO) δ 7.58 (d, J=5.0 Hz, 2H), 6.03 (s, 1H).

2,4,6-Tri-O-acetyl-3-azido-3-deoxy-β-D-galactopyranosyl Chloride

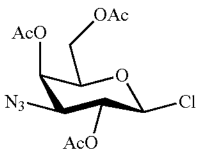

A solution of 1,2,4,6-tetra-O-acetyl-3-azido-3-deoxy-β-D-galactopyranoside (12.0 g, 32.1 mmol), $PCl_5$ (7.5 g, 36.0 mmol) and boron trifluoride diethyl etherate (50 μL, 0.41 mmol) in DCM (150 mL) was stirred 1 h at rt. The mixture was partitioned between saturated aq $NaHCO_3$ and DCM. The organic phase was dried, concentrated, and the residue was triturated in diethyl ether/PE to afford the product as a crystalline solid (10.2 g, 91%). $^1H$ NMR (400 MHz, Chloroform-d) δ 5.48 (d, J=3.2 Hz, 1H), 5.34 (t, J=9.2 Hz, 1H), 5.24 (d, J=8.7 Hz, 1H), 4.18 (dd, J=11.5, 6.1 Hz, 1H), 4.10 (dd, J=11.6, 6.7 Hz, 1H), 3.98 (t, J=6.4 Hz, 1H), 3.60 (dd, J=10.3, 3.3 Hz, 1H), 2.20 (s, 3H), 2.17 (s, 3H), 2.07 (s, 3H).

3,5-Dichloro-4-fluorophenyl 2,4,6-tri-O-acetyl-3-azido-3-deoxy-1-thio-α-D-galactopyranoside

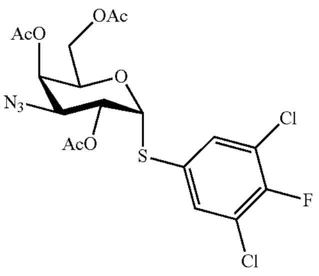

To a solution of 2,4,6-tri-O-acetyl-3-azido-3-deoxy-β-D-galactopyranosyl chloride (6.20 g, 17.7 mmol) and 3,5-dichloro-4-fluorobenzenethiol (3.77 g, 19.1 mmol) in DMF (20 mL) $Cs_2CO_3$ (17.3 g, 53.2 mmol) was added and the mixture was stirred 2 h at rt. Water (60 mL) was added and the mixture was extracted with EtOAc (50 mL). The organic phase was evaporated and purified by column chromatography (PE/EtOAc=10/1~5/1, Silica-CS 120 g, 40 mL/min, silica gel, UV 254). Further purification by reversed-phase chromatography (MeCN/$H_2O$=1/20~3/1, C-18 column, 20 mL/min, UV 254) afforded the product (2.2 g, 24%). ESI-MS m/z calcd for [$C_{18}H_{18}Cl_2FN_3O_7S$] $[M+NH_4]^+$: 527.0; found: 527.0. $^1H$ NMR (400 MHz, $CDCl_3$) δ 7.40 (t, J=18.0 Hz, 2H), 5.86 (d, J=5.5 Hz, 1H), 5.41 (d, J=2.7 Hz, 1H), 5.26-5.07 (m, 1H), 4.54 (dd, J=7.7, 4.6 Hz, 1H), 4.13-4.03 (m, 1H), 4.03-3.90 (m, 1H), 3.84 (dd, J=11.0, 3.3 Hz, 1H), 2.11 (d, J=11.0 Hz, 6H), 2.04-1.90 (m, 3H).

3,5-Dichloro-4-fluorophenyl 3-azido-3-deoxy-1-thio-α-D-galactopyranoside

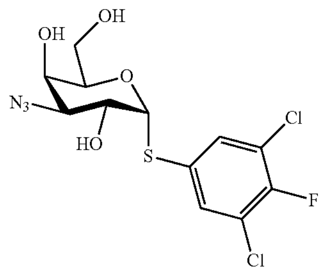

A solution of 3,5-dichloro-4-fluorophenyl 2,4,6-tri-O-acetyl-3-azido-3-deoxy-1-thio-α-D-galactopyranoside (2.20 g, 4.31 mmol) in $MeOH/Et_3N/H_2O$ (18 mL, 5:3:1) was stirred overnight at rt. The mixture was evaporated and purified by prep HPLC ($MeCN/H_2O$ (10 mmol/L $NH_4HCO_3$=30~90%, X-Select 10 μm 19*250 mm, 20 mL/min, UV 254) to give the product (860 mg, 52%). ESI-MS m/z calcd for $[C_{12}H_{12}Cl_2FN_3O_4S]$ $[M+NH_4]^+$: 401.0; found: 401.0. $^1H$ NMR (400 MHz, Methanol-$d_4$) δ 7.66 (d, J=6.3 Hz, 2H), 5.64 (d, J=5.5 Hz, 1H), 4.36 (dd, J=10.8, 5.5 Hz, 1H), 4.24 (t, J=5.9 Hz, 1H), 4.02 (d, J=2.1 Hz, 1H), 3.74-3.60 (m, 2H), 3.47 (dd, J=10.8, 2.9 Hz, 1H).

3,5-Dichloro-4-fluorophenyl 3-azido-4,6-O-benzylidene-3-deoxy-1-thio-α-D-galactopyranoside

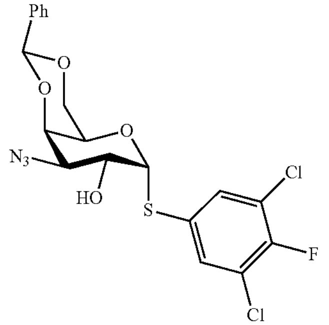

To a stirred solution of 3,5-dichloro-4-fluorophenyl 3-azido-3-deoxy-1-thio-α-D-galactopyranoside (510 mg, 1.33 mmol) in DMF (10 mL) benzaldehyde dimethylacetal (444 mg, 2.92 mmol) followed by D(+)-10-camphorsulfonic acid (67.8 mg, 0.29 mmol) were added. The mixture was stirred 3 h at 50° C. under vacuum using a water pump. The mixture was added dropwise to an aq $NaHCO_3$ (100 mL) solution and the solution was filtered. The obtained white solid was dried in vacuum to afford the product (600 mg, 96%). ESI-MS m/z calcd for $[C_{19}H_{16}Cl_2FN_3O_4S]$ $[M+H]^+$: 472.0; found: 472.0. $^1H$ NMR (400 MHz, Methanol-$d_4$) δ 7.52 (d, J=6.2 Hz, 2H), 7.39 (d, J=3.7 Hz, 2H), 7.25 (dd, J=5.1, 1.9 Hz, 3H), 5.71 (d, J=5.2 Hz, 1H), 5.57 (s, 1H), 4.80 (m, 1H), 4.40 (dd, J=10.9, 5.1 Hz, 1H), 4.34 (d, J=3.0 Hz, 1H), 4.06 (d, J=7.6 Hz, 1H), 3.96 (d, J=12.6 Hz, 1H), 3.50 (dd, J=10.9, 3.2 Hz, 1H).

3,5-Dichloro-4-fluorophenyl 3-azido-4,6-O-benzylidene-3-deoxy-2-O-methyl-1-thio-α-D-galactopyranoside

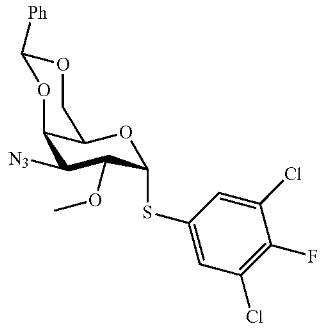

To a solution of 3,5-dichloro-4-fluorophenyl 3-azido-4,6-O-benzylidene-3-deoxy-1-thio-α-D-galactopyranoside (300 mg, 0.64 mmol) in DMF (5 mL) NaH (60% in oil, 73.0 mg, 1.91 mmol) was added. The mixture was stirred 30 min before iodomethane (79.1 μL, 1.27 mmol) was added dropwise. The mixture was stirred 1 h at rt and was then poured into of water (15 mL). The solution was extracted with EtOAc and the organic phase was evaporated to afford the product (300 mg, 97%). ESI-MS m/z calcd for $[C_{20}H_{18}Cl_2FN_3O_4S]$ $[M+H]^+$: 486.0; found: 486.0. $^1H$ NMR (400 MHz, $CDCl_3$) δ 7.45 (dd, J=7.5, 2.0 Hz, 2H), 7.37 (t, J=4.6 Hz, 2H), 7.34-7.25 (m, 3H), 5.91 (d, J=5.2 Hz, 1H), 5.56 (s, 1H), 4.26 (d, J=2.7 Hz, 1H), 4.18 (ddd, J=8.0, 5.6, 3.4 Hz, 2H), 4.12-3.97 (m, 2H), 3.60 (dd, J=10.7, 3.3 Hz, 1H), 3.50-3.45 (m, 3H).

3,5-Dichloro-4-fluorophenyl 4,6-O-benzylidene-3-deoxy-2-O-methyl-3-[4-(2-thiazolyl)-1H-1,2,3-triazol-1-yl]-1-thio-α-D-galactopyranoside

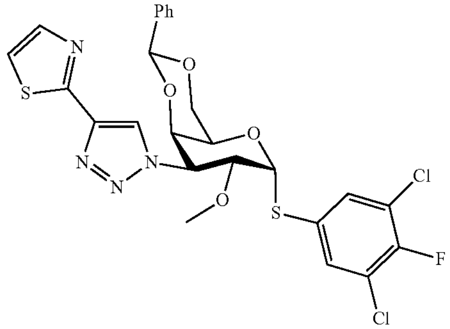

To a solution of 3,5-dichloro-4-fluorophenyl 3-azido-4,6-O-benzylidene-3-deoxy-2-O-methyl-1-thio-α-D-galactopyranoside (135 mg, 0.28 mmol) in DMF (5 mL) trimethyl(2-thiazol-2-ylethynyl)silane (75.5 mg, 0.42 mmol), (+)-sodium L-ascorbate (55.0 mg, 0.28 mmol) and copper (II) sulfate pentahydrate (70.0 mg, 0.28 mmol) were added and the mixture was stirred 6 h at rt. The mixture was concentrated and purified by column chromatography (PE/EtOAc=10/0~1/1, Silica-CS 12 g, 20 mL/min, silica gel, UV 254) to give the product (76 mg, 46%). ESI-MS m/z calcd for $[C_{25}H_{21}Cl_2FN_4O_4S_2]$ $[M+H]^+$: 595.0; found: 595.0. $^1H$ NMR (400 MHz, DMSO-$d_6$) δ 8.82 (s, 1H), 7.89-7.75 (m, 4H), 7.39-7.34 (m, 5H), 6.63 (d, J=5.2 Hz, 1H), 5.58 (s, 1H), 5.16 (dd, J=11.2, 2.8 Hz, 1H), 4.84 (dd, J=11.6, 5.2 Hz, 1H), 4.58 (d, J=2.8 Hz, 1H), 4.11 (s, 1H), 4.09 (d, J=12.4 Hz, 1H), 3.92 (d, J=11.6 Hz, 1H), 3.34 (s, 3H).

Intermediate 2

5-Bromopyridin-3-yl 2,4,6-tri-O-acetyl-3-azido-3-deoxy-1-thio-α-D-galactopyranoside

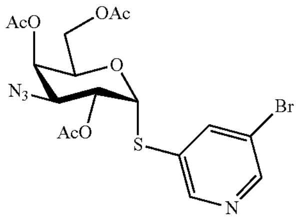

To a solution of 2,4,6-tri-O-acetyl-3-azido-3-deoxy-β-D-galactopyranosyl chloride (1.20 g, 3.43 mmol) and 5-bromopyridine-3-thiol (1.30 g, 6.86 mol) in DMF (10 mL) $Cs_2CO_3$ (4.47 g, 13.7 mol) was added and the mixture was stirred overnight at rt. The mixture was concentrated and purified by column chromatography (EtOAc/PE=10~60%, Silica-CS 20 g, 30 mL/min, silica gel, UV 254) to give the product (1.25 g, 72%). ESI-MS m/z calcd for $[C_{17}H_{19}BrN_4O_7S]$ $[M+H]^+$: 503.0; found: 503.0. $^1H$ NMR (400 MHz, $CDCl_3$) δ 8.50 (dd, J=10.7, 2.0 Hz, 2H), 7.90 (t, J=2.0 Hz, 1H), 5.91 (d, J=5.5 Hz, 1H), 5.42 (d, J=2.7 Hz, 1H), 5.22 (dd, J=10.9, 5.5 Hz, 1H), 4.56 (dd, J=7.6, 4.6 Hz, 1H), 4.15-4.00 (m, 1H), 3.92 (ddd, J=14.3, 11.3, 5.6 Hz, 2H), 2.12 (d, J=13.2 Hz, 6H), 1.97 (s, 3H).

5-Bromopyridin-3-yl 3-azido-3-deoxy-1-thio-α-D-galactopyranoside

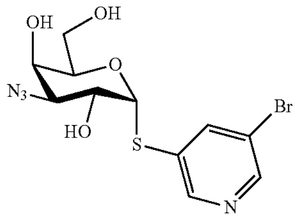

A solution of 5-bromopyridin-3-yl 2,4,6-tri-O-acetyl-3-azido-3-deoxy-1-thio-α-D-galactopyranoside (300 mg, 0.60 mmol) in $MeOH/Et_3N/H_2O$ (0.9 mL, 5:3:1) was stirred 4 h at rt. The mixture was evaporated and purified by prep HPLC (X-Select 10 μm 19*250 mm, 20 mL/min, MeOH/$H_2O$ (10 mmol/L $NH_4HCO_3$)=40~95%) to afford the product (208 mg, 93%). ESI-MS m/z calcd for $[C_{11}H_{13}BrN_4O_4S]$ $[M+H]^+$: 377.0, found: 377.0. $^1H$ NMR (400 MHz, Methanol-$d_4$) δ 8.52 (d, J=1.8 Hz, 1H), 8.43 (d, J=2.0 Hz, 1H), 8.16 (t, J=2.0 Hz, 1H), 5.63 (d, J=5.4 Hz, 1H), 4.29 (dd, J=10.8, 5.4 Hz, 1H), 4.15 (t, J=6.0 Hz, 1H), 3.95 (d, J=2.1 Hz, 1H), 3.61-3.52 (m, 2H), 3.42 (dt, J=14.5, 7.3 Hz, 1H).

5-Bromopyridin-3-yl 3-azido-4,6-O-benzylidene-3-deoxy-2-O-methyl-1-thio-α-D-galactopyranoside

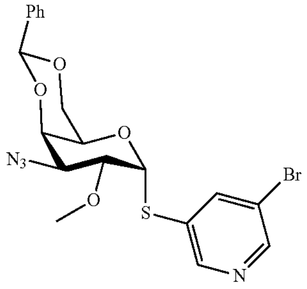

To a solution of 5-bromopyridin-3-yl 3-azido-3-deoxy-1-thio-α-D-galactopyranoside (208 mg, 0.55 mmol) in DMF (3 mL) D(+)-10-camphorsulfonic acid (25.6 mg, 0.11 mmol) and benzaldehyde dimethylacetal (168 mg, 1.10 mmol) were added and the mixture was stirred 5 h at 50° C. under reduce pressure. The mixture was partitioned between water (10 mL) and DCM (15 mL). The aqueous phase was extracted with DCM (3×5 mL) and the combined organic phases were dried and evaporated. The obtained material was dissolved in DMF (3 mL) and cooled to 0° C. NaH (60% in oil, 21.2 mg, 0.92 mol) was added and the mixture was stirred 30 min. Iodomethane (197 mg, 1.39 mol) was added slowly and the mixture was stirred 2 h at rt. Water (10 mL) and DCM (15 mL) were added and the aqueous layer was extracted with DCM (3×5 mL). The combined organic layers were dried over $Na_2SO_4$, concentrated and purified by column chromatography (EA/PE=0~40%, Silica-CS 12 g, 20 mL/min, silica gel, UV 254) to give the product (200 mg, 76%). ESI-MS m/z calcd for $[C_{19}H_{19}BrN_4O_4S][M+H]^+$: 479.0, found: 479.0. $^1H$ NMR (400 MHz, $CDCl_3$) δ 8.01-7.90 (m, 1H), 7.51-7.38 (m, 3H), 7.38-7.25 (m, 4H), 5.97 (d, J=5.1 Hz, 1H), 5.55 (s, 1H), 4.26 (d, J=3.1 Hz, 1H), 4.19 (dd, J=10.7, 5.1 Hz, 2H), 4.08-4.06 (m, 1H), 4.04 (s, 1H), 3.67-3.63 (m, 1H), 3.50 (d, J=5.7 Hz, 3H).

5-Bromopyridin-3-yl 4,6-O-benzylidene-3-deoxy-2-O-methyl-3-[4-(2-thiazolyl)-1H-1,2,3-triazol-1-yl]-1-thio-α-D-galactopyranoside

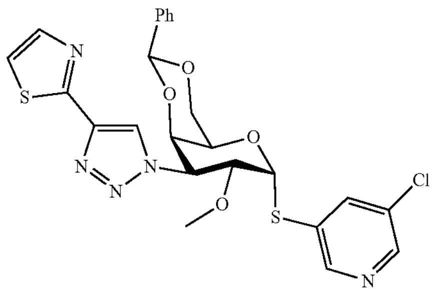

To a solution of 5-bromopyridin-3-yl 3-azido-4,6-O-benzylidene-3-deoxy-2-O-methyl-1-thio-α-D-galactopyranoside (200 mg, 0.42 mmol) in DMF (5 mL) trimethyl(2-thiazol-2-ylethynyl)silane (113 mg, 0.63 mmol), copper (II) sulfate pentahydrate (51.9 mg, 0.21 mmol), (+)-sodium L-ascorbate (82.6 mg, 0.42 mmol) were added and the mixture was stirred 3 h at rt. The mixture was partitioned between water (10 mL) and DCM (10 mL) and the aqueous phase was extracted with DCM (2×5 mL). The combined organic phases were washed with water (20 mL) and brine (20 mL), dried over $Na_2SO_4$, evaporated and purified by column chromatography (EA/PE=10~70%, Silica-CS 4 g, 12 mL/min, silica gel, UV 254) to afford the product (200 mg, 82%). ESI-MS m/z calcd for $[C_{24}H_{22}BrN_5O_4S_2]$ $[M+H]^+$: 588.0, found: 588.0. $^1H$ NMR (400 MHz, $CDCl_3$) δ 8.39 (s, 1H), 7.96 (d, J=8.7 Hz, 2H), 7.64 (dt, J=7.2, 3.6 Hz, 1H), 7.46 (dd, J=5.8, 3.3 Hz, 1H), 7.37-7.26 (m, 6H), 6.12 (d, J=4.5 Hz, 1H), 5.46 (s, 1H), 5.31-5.21 (m, 1H), 4.61-4.45 (m, 2H), 4.24 (t, J=6.7 Hz, 2H), 4.11 (s, 1H), 3.36 (s, 3H).

Intermediate 3

3-Azido-4,6-O-benzylidene-3-deoxy-D-galactopyranose

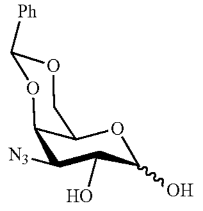

To a solution of 3-azido-3-deoxy-D-galactopyranose (Lowary, T. L.; Hindsgaul, O. Recognition of Synthetic O-Methyl, Epimeric, and Amino Analogues of the Acceptor A-L-Fucp-(1→2)-B-D-Galp-or Glycosyltransferases. *Carbohydrate Research* 1994, 251, 33-67) (16.4 g, 79.9 mmol) in DMF (120 mL) benzaldehyde dimethylacetal (18.2 g, 120 mmol) was added followed by D(+)-10-Camphorsulfonic acid (3.71 g, 16.0 mmol). The mixture was stirred 4 h at 50° C. The mixture was added dropwise to saturated aq $NaHCO_3$ (200 mL). The mixture was filtered, and the white solid was washed with water and dried in vacuum to afford the product (15.0 g, 64%, α/β=1:1).

3-Azido-4,6-O-benzylidene-3-deoxy-α-D-galactopyranose $^1H$ NMR (400 MHz, $CD_3OD$) δ 7.51-7.53 (m, 2H), 7.35-7.39 (m, 3H), 5.65 (s, 1H), 5.25 (d, J=3.2 Hz, 1H, H-1α), 3.35-3.45 (m, 6H).

3-Azido-4,6-O-benzylidene-3-deoxy-beta-D-galactopyranose $^1H$ NMR (400 MHz, $CD_3OD$) δ 7.51-7.53 (m, 2H), 7.35-7.39 (m, 3H), 5.65 (s, 1H), 4.58 (d, J=7.6 Hz, 1H, H-10), 3.35-3.45 (m, 6H).

Methyl 3-azido-4,6-O-benzylidene-3-deoxy-2-O-methyl-D-galactopyranoside

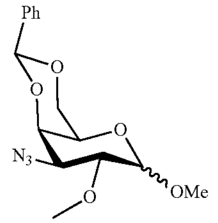

To a solution of 3-azido-4,6-O-benzylidene-3-deoxy-D-galactopyranose (5.00 g, 17.0 mmol) in DMF (40 mL) NaH (60% in oil, 1.96 g, 51.1 mmol) was added at 0° C. under a nitrogen atmosphere and the mixture was stirred 20 min. Iodomethane (3.18 mL, 51.1 mmol) was added and the mixture was stirred 1 h at rt. After diluting with water (50 mL), the mixture was extracted with EtOAc (3×50 mL). The combined organic layers were washed with brine, dried over $Na_2SO_4$ and concentrated in vacuo. The residue was purified by column chromatography (PE/EtOAc=10/1~1/1, Silica-CS 20 g, 25 mL/min, silica gel, UV 254) to give the product (5.10 g, 93%, α/β=0.5:1).

Methyl 3-azido-4,6-O-benzylidene-3-deoxy-2-O-methyl-α-D-galactopyranoside $^1H$ NMR (400 MHz, $CD_3OD$) δ 7.42-7.44 (m, 2H), 7.27-7.29 (m, 3H), 5.56 (s, 1H), 4.99 (d, J=3.2 Hz, 1H, H-1α), 3.62-4.27 (m, 4H), 3.44 (s, 3H), 3.39 (s, 3H), 3.32-3.40 (m, 1H), 3.23-3.25 (m, 1H).

Methyl 3-azido-4,6-O-benzylidene-3-deoxy-2-O-methyl-β-D-galactopyranoside $^1H$ NMR (400 MHz, $CD_3OD$) δ 7.42-7.44 (m, 2H), 7.27-7.29 (m, 3H), 5.55 (s, 1H), 4.31 (d, J=7.6 Hz, 1H, H-10), 3.62-4.27 (m, 4H), 3.51 (s, 3H), 3.49 (s, 3H), 3.32-3.40 (m, 1H), 3.23-3.25 (m, 1H).

Acetyl 4,6-di-O-acetyl-3-azido-3-deoxy-2-O-methyl-D-galactopyranoside

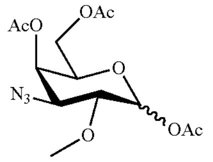

To a solution of methyl 3-azido-4,6-O-benzylidene-3-deoxy-2-O-methyl-D-galactopyranoside (5.10 g, 15.9 mmol) in acetic anhydride (40.0 mL) and acetic acid (20 mL), drops of concentrated $H_2SO_4$ was added at 0° C. The mixture was stirred 4 h at 0° C., followed by dropwise addition to a saturated aq $NaHCO_3$ solution. The mixture was extracted with DCM (3×100 mL). The combined organic layers were washed with brine, dried over $Na_2SO_4$ and concentrated in vacuo. The residue was purified by column chromatography (PE/EtOAc=10/1~1/1, Silica-CS 4 g, 12 mL/min, silica gel, UV 254). The obtained material was suspended in EtOAc (4.00 mL). The mixture was heated to 60° C., then cooled to 25° C. and n-heptane (20.0 mL) was added while stirring. The mixture was cooled to 0° C. and stirred for 1 h, filtered, washed with n-heptane/EtOAc (4:1, 10 mL), to give the product (1.2 g) as a white solid used as is in the next step. $^1$H NMR (400 MHz, $CDCl_3$) δ 6.38 (d, J=3.6 Hz, 1H), 5.33 (dd, J=3.2, 1.2 Hz, 1H), 4.14-4.17 (m, 1H), 3.91-4.03 (m, 2H), 3.80 (dd, J=6.4, 3.2 Hz, 1H), 3.62 (dd, J=10.4, 3.6 Hz, 1H), 3.43 (s, 3H), 2.11 (s, 3H), 2.10 (s, 3H), 1.98 (s, 3H).

Acetyl 4,6-di-O-acetyl-3-azido-3-deoxy-2-O-methyl-1-thio-D-galactopyranoside

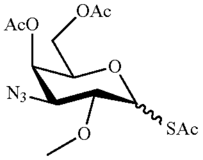

To a solution of acetyl 4,6-di-O-acetyl-3-azido-3-deoxy-2-O-methyl-D-galactopyranoside (1.17 g, 3.39 mmol) in DCM (15 mL) $PCl_5$ (1.06 g, 5.08 mmol) was added followed by boron trifluoride diethyl etherate (0.209 mL, 1.69 mmol) at 30° C. under a nitrogen atmosphere. The mixture was stirred 30 min at 30° C. followed by dropwise addition to a saturated aq $NaHCO_3$ solution. The mixture was extracted with DCM (3×100 mL). The combined organic layers were washed with brine, dried over $Na_2SO_4$ and concentrated in vacuum. The residue was dissolved in DMF (4.0 mL) and potassium thioacetate (731 mg, 6.4 mmol) was added. The mixture was stirred overnight at rt under a nitrogen atmosphere. After diluting with water (50 mL), the mixture was extracted with EtOAc (3×30 mL). The combined organic layers were washed with brine, dried over $Na_2SO_4$ and concentrated in vacuum. The residue was purified by column chromatography (PE/EtOAc=10/1~3/1, Silica-CS 20 g, 18 mL/min, silica gel, UV 254) to give the product (1.15 g, 75%, α/β=0.23:1).

Acetyl 4,6-di-O-acetyl-3-azido-2-O-methyl-3-deoxy-1-thio-α-D-galactopyranoside $^1$H NMR (400 MHz, $CDCl_3$) δ 6.25 (d, J=5.2 Hz, 1H, H-1α), 5.27-5.29 (m, 1H), 3.85-4.08 (m, 4H), 3.42-3.45 (m, 1H), 3.39 (s, 3H), 2.39 (s, 3H), 2.09 (s, 3H), 1.97 (s, 3H).

Acetyl 4,6-di-O-acetyl-3-azido-2-O-methyl-3-deoxy-1-thio-β-D-galactopyranoside $^1$H NMR (400 MHz, $CDCl_3$) δ 5.32-5.33 (m, 1H), 5.04 (d, J=10.0 Hz, 1H, H-10), 3.85-4.08 (m, 3H), 3.57 (dd, J=9.2, 3.2 Hz, 1H), 3.52 (s, 3H), 3.33 (t, J=9.6 Hz, 1H), 2.36 (s, 3H), 2.08 (s, 3H), 1.97 (s, 3H).

5-Bromo-2-cyanopyridin-3-yl 4,6-di-O-acetyl-3-azido-3-deoxy-2-O-methyl-1-thio-D-galactopyranoside

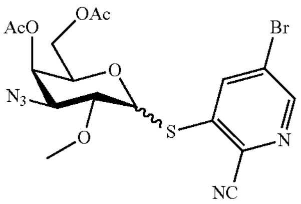

To a solution of acetyl 4,6-di-O-acetyl-3-azido-3-deoxy-2-O-methyl-1-thio-D-galactopyranoside (210 mg, 0.58 mmol) and 5-bromo-3-fluoro-pyridine-2-carbonitrile (175 mg, 0.87 mmol) in DMF (4.0 mL) diethylamine (85.0 mg, 1.16 mmol) was added and the mixture was stirred 1 h at rt. The mixture was diluted with water (20 mL) and extracted with EtOAc (3×10 mL). The combined organic layers were washed with brine, dried over $Na_2SO_4$ and concentrated. The residue was purified by column chromatography (PE/EA=10/1~3/1, Silica-CS 4 g, 12 mL/min, silica gel, UV 254) to give the product (180 mg, 62%, a/0=0.3:1). ESI-MS m/z calcd for $[C_{17}H_{18}BrN_5O_6S][M+H]^+$: 500.0, found: 500.0.

5-Bromo-2-cyanopyridin-3-yl 4,6-di-O-acetyl-3-azido-3-deoxy-2-O-methyl-1-thio-α-D-galactopyranoside $^1$H NMR (400 MHz, $CDCl_3$) δ 8.57-8.58 (m, 1H), 8.13 (d, J=2.0 Hz, 1H), 6.05 (d, J=5.2 Hz, 1H), 5.35 (d, J=3.2 Hz, 1H), 4.41-4.44 (m, 1H), 3.78-4.08 (m, 3H), 3.54 (s, 3H), 3.34-3.44 (m, 1H), 2.09 (s, 3H), 1.98 (s, 3H).

5-Bromo-2-cyanopyridin-3-yl 4,6-di-O-acetyl-3-azido-3-deoxy-2-O-methyl-1-thio-β-D-galactopyranoside $^1$H NMR (400 MHz, $CDCl_3$) δ 8.57-8.58 (m, 1H), 8.18 (d, J=2.0 Hz, 1H), 5.33 (dd, J=3.2, 1.2 Hz, 1H), 4.68 (d, J=9.2 Hz, 1H), 3.78-4.08 (m, 3H), 3.63 (s, 3H), 3.55-3.57 (m, 1H), 3.34-3.44 (m, 1H), 2.12 (s, 3H), 2.01 (s, 3H).

5-Bromo-2-cyanopyridin-3-yl 4,6-di-O-acetyl-3-deoxy-2-O-methyl-3-[4-(thiazol-2-yl)-1H-1,2,3-triazol-1-yl]-1-thio-α-D-galactopyranoside

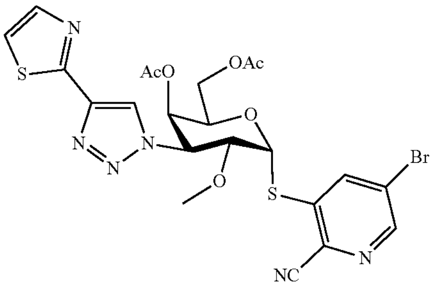

To a solution of 5-bromo-2-cyanopyridin-3-yl 4,6-di-O-acetyl-3-azido-3-deoxy-2-O-methyl-1-thio-D-galactopyranoside (240 mg, 0.48 mmol) and trimethyl(2-thiazol-2-ylethynyl)silane (217 mg, 1.20 mmol) in the DMF (6.0 mL) copper (II) sulfate pentahydrate (59.9 mg, 0.24 mmol) and (+)-sodium L-ascorbate (95.0 mg, 0.48 mmol) were added and the mixture was stirred 3 h at rt. The mixture was diluted with water (20 mL) and extracted with EtOAc (3×10 mL). The combined organic layers were washed with brine, dried over $Na_2SO_4$, concentrated and purified by column chromatography (PE/EA=10/1~1/1, Silica-CS 4 g, 12 mL/min, silica gel, UV 254). The obtained product was further purified by preparative-SFC to give the product (57.0 mg, 20%). ESI-MS m/z calcd for $[C_{22}H_{21}BrN_6O_6S_2]$ $[M+H]^+$: 609.0; found: 609.0. $^1H$ NMR (400 MHz, $CDCl_3$) δ 8.60 (d, J=2.0 Hz, 1H), 8.20 (d, J=2.0 Hz, 1H), 8.16 (s, 1H), 7.78 (d, J=3.2 Hz, 1H), 7.30 (d, J=3.6 Hz, 1H), 6.26 (d, J=5.6 Hz, 1H), 5.58 (d, J=2.0 Hz, 1H), 4.99 (dd, J=11.2, 3.2 Hz, 1H), 4.76 (dd, J=11.2, 5.2 Hz, 1H), 4.64-4.67 (m, 1H), 3.96-4.04 (m, 2H), 3.39 (s, 3H), 2.01 (s, 3H), 1.90 (s, 3H).

Intermediate 4

Acetyl 2,4,6-tri-O-acetyl-3-azido-3-deoxy-1-thio-α-D-galactopyranoside

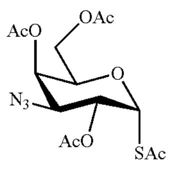

A solution of 2,4,6-tri-O-acetyl-3-azido-3-deoxy-β-D-galactopyranosyl chloride (4.0 g, 11.4 mmol) and potassium thioacetate (2.02 g, 17.1 mmol) in DMF (25 mL) was stirred 1 h at 40° C. The mixture was partitioned between EtOAc and saturated aq $NaHCO_3$, the organic phase was separated, dried and evaporated. The residue was purified by chromatography ($SiO_2$, PE/EtOAc) to afford the product (2.90 g, 52%). ESI-MS m/z calcd for $[C_{14}H_{19}N_3O_8S]$ $[M+Na]^+$: 412.1; found: 411.9. $^1H$ NMR (400 MHz, Chloroform-d) δ 6.25 (d, J=5.3 Hz, 1H), 5.43 (d, J=2.9 Hz, 1H), 5.40 (dd, J=11.0, 5.3 Hz, 1H), 4.16-3.97 (m, 3H), 3.71 (dd, J=10.9, 3.3 Hz, 1H), 2.43 (s, 3H), 2.16 (s, 3H), 2.08 (s, 3H), 2.04 (s, 3H).

2-Bromo-5-chloropyridin-3-yl 2,4,6-tri-O-acetyl-3-azido-3-deoxy-1-thio-α-D-galactopyranoside

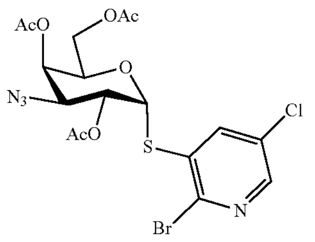

To a solution of acetyl 2,4,6-tri-O-acetyl-3-azido-3-deoxy-1-thio-α-D-galactopyranoside (1.30 g, 3.34 mmol) and 2-bromo-5-chloro-3-fluoro-pyridine (843 mg, 4.01 mmol) in DMF (6 mL) diethylamine (488 mg, 6.68 mmol) was added and the mixture was stirred overnight at rt. After diluting with water (15 mL), the mixture was extracted with EtOAc (3×20 mL). The combined organic layers were washed with brine (20 mL), dried over $Na_2SO_4$, concentrated and purified by column chromatography (PE/EA=10/1~5/1, Silica-CS 20 g, 20 mL/min, silica gel, UV 254) to afford the product as a white solid (770 mg, 43%). ESI-MS m/z calcd for $[C_{17}H_{18}BrClN_4O_7S]$ $[M+H]^+$: 537.0; found: 537.0. $^1H$ NMR (400 MHz, $CDCl_3$) δ 8.13 (d, J=2.4 Hz, 1H), 7.76 (d, J=2.4 Hz, 1H), 6.05 (d, J=5.6 Hz, 1H), 5.43 (t, J=6.2 Hz, 1H), 5.27 (dd, J=11.0, 5.6 Hz, 1H), 4.47 (dd, J=7.4, 5.1 Hz, 1H), 4.08-4.01 (m, 1H), 3.96 (dq, J=7.9, 5.6 Hz, 2H).

2-Bromo-5-chloropyridin-3-yl 3-azido-4,6-O-benzylidene-3-deoxy-1-thio-α-D-galactopyranoside

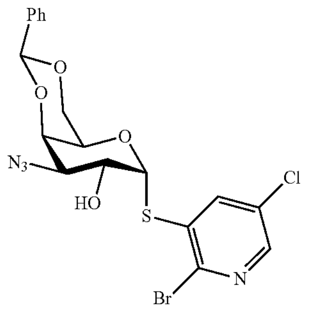

A solution of 2-bromo-5-chloropyridin-3-yl 2,4,6-tri-O-acetyl-3-azido-3-deoxy-1-thio-α-D-galactopyranoside (770 mg, 1.43 mmol) in MeOH (5.0 mL) and a catalytical amount of NaOMe was stirred 20 min at rt. The mixture was neutralized with acidic ion resin and filtered. The filtrate was concentrated, and the obtained material was dissolved in DMF (5 mL). Benzaldehyde dimethylacetal (404 mg, 2.65 mmol) followed by D(+)-10-camphorsulfonic acid (30.8 mg, 0.13 mmol) were added and the mixture was stirred 4 h at 50° C. under vacuum using a water-pump. After cooling to rt, the mixture was diluted with water (15 mL) and extracted with EtOAc (2×10 mL). The combined organic layers were concentrated and purified by column chromatography (PE/EA=10/1~5/1, Silica-CS 12 g, 20 mL/min, silica gel, UV 254) to give the product. (300 mg, 42%). ESI-MS m/z calcd for $[C_{18}H_{16}BrClN_4O_4S]$ $[M+H]^+$: 499.0, found: 499.0. $^1H$ NMR (400 MHz, $CDCl_3$) δ 8.09 (d, J=2.3 Hz, 1H), 7.82 (d, J=2.3 Hz, 1H), 7.45 (dd, J=7.5, 1.9 Hz, 2H), 7.38-7.27 (m, 3H), 5.91 (d, J=5.3 Hz, 1H), 5.58 (s, 1H), 4.64 (dt, J=10.8, 5.4 Hz, 1H), 4.36 (d, J=3.0 Hz, 1H), 4.18 (dd, J=12.8, 1.4 Hz, 1H), 4.07-3.97 (m, 2H), 3.65 (dd, J=10.8, 3.3 Hz, 1H), 2.59 (d, J=5.7 Hz, 1H).

2-Bromo-5-chloropyridin-3-yl 3-azido-4,6-O-benzylidene-3-deoxy-2-O-methyl-1-thio-α-D-galactopyranoside

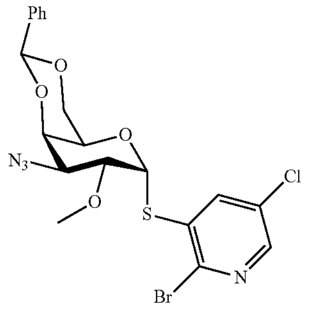

To a solution of 2-bromo-5-chloropyridin-3-yl 3-azido-4,6-O-benzylidene-3-deoxy-1-thio-α-D-galactopyranoside (300 mg, 0.60 mmol) in DMF (8.0 mL) silver (I) oxide (696 mg, 3.00 mmol) was added followed by iodomethane (426 mg, 3.00 mmol). The mixture was stirred 48 h at rt and filtered. The filtrate was evaporated and purified by column chromatography (PE/EA=10/1~5/1, Silica-CS 12 g, 20 mL/min, silica gel, UV 254) to give the product (240 mg, 78%). ESI-MS m/z calcd for $[C_{19}H_{18}BrClN_4O_4S][M+H]^+$: 513.0, found: 513.0. $^1H$ NMR (400 MHz, $CDCl_3$) δ 8.08 (d, J=2.4 Hz, 1H), 7.81 (t, J=3.6 Hz, 1H), 7.46 (dd, J=7.5, 1.9 Hz, 2H), 7.31 (ddd, J=6.7, 5.1, 1.5 Hz, 3H), 6.09 (d, J=5.2 Hz, 1H), 5.56 (s, 1H), 4.28-4.21 (m, 2H), 4.13 (dd, J=12.7, 1.5 Hz, 1H), 4.07-4.04 (m, 1H), 3.96 (s, 1H), 3.76 (dd, J=10.6, 3.3 Hz, 1H), 3.50 (s, 3H).

5-Chloro-2-cyanopyridin-3-yl 3-azido-4,6-O-benzylidene-3-deoxy-2-O-methyl-1-thio-α-D-galactopyranoside

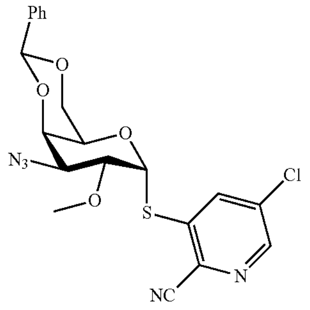

To a solution of 2-bromo-5-chloropyridin-3-yl 3-azido-4,6-O-benzylidene-3-deoxy-2-O-methyl-1-thio-α-D-galactopyranoside (230 mg, 0.45 mmol) in DMF (4.0 mL) Zn (14.6 mg, 0.22 mmol), $Zn(CN)_2$ (52.6 mg, 0.45 mmol), 1,1'-bis(diphenylphosphino)ferrocene (20.2 mg, 0.036 mmol) and tris(dibenzylideneacetone)dipalladium(0) (32.8 mg, 0.036 mmol) were added and the mixture was stirred 3 h at 100° C. under a nitrogen atmosphere. The mixture was concentrated and purified by column chromatography (PE/EA=10/1~5/1, Silica-CS 12 g, 20 mL/min, silica gel, UV 254) to give the product (105 mg, 51%). ESI-MS m/z calcd for $[C_{20}H_{18}ClN_5O_4S]$ [M+H]$^+$: 460.1, found: 460.0. $^1H$ NMR (400 MHz, $CDCl_3$) δ 8.44 (d, J=2.1 Hz, 1H), 7.98 (d, J=2.1 Hz, 1H), 7.46-7.39 (m, 2H), 7.32-7.25 (m, 3H), 6.06 (t, J=7.6 Hz, 1H), 5.56 (d, J=7.2 Hz, 1H), 4.27 (t, J=5.2 Hz, 1H), 4.21 (dd, J=10.6, 5.2 Hz, 1H), 4.12 (dd, J=13.0, 1.8 Hz, 1H), 4.06 (d, J=4.4 Hz, 2H), 3.71 (dd, J=10.6, 3.3 Hz, 1H), 3.52 (s, 3H).

5-Chloro-2-cyanopyridin-3-yl 4,6-O-benzylidene-3-deoxy-2-O-methyl-3-[4-(2-thiazolyl)-1H-1,2,3-triazol-1-yl]-1-thio-α-D-galactopyranoside

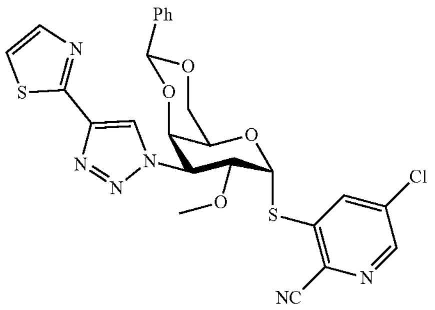

To a solution of 5-chloro-2-cyanopyridin-3-yl 3-azido-4,6-O-benzylidene-3-deoxy-2-O-methyl-1-thio-α-D-galactopyranoside (130 mg, 0.28 mmol) and trimethyl(2-thiazol-2-ylethynyl)silane (103 mg, 0.57 mmol) in DMF (3 mL) (+)-sodium L-ascorbate (112 mg, 0.57 mmol) and copper (II) sulfate pentahydrate (35.3 mg, 0.14 mmol) were added and the mixture was stirred overnight at rt. The mixture was evaporated and purified by column chromatography (PE/EA=10/1~5/1, Silica-CS 4 g, 12 mL/min, silica gel, UV 254) to give the product (90 mg, 56%). ESI-MS m/z calcd for $[C_{25}H_{21}ClN_6O_4S_2][M+H]^+$: 569.1, found: 569.0. $^1H$ NMR (400 MHz, $CDCl_3$) δ 8.50 (d, J=2.1 Hz, 1H), 8.24 (s, 1H), 8.02 (d, J=2.1 Hz, 1H), 7.78 (s, 1H), 7.32 (ddd, J=9.1, 7.6, 4.0 Hz, 6H), 6.21 (d, J=5.1 Hz, 1H), 5.46 (s, 1H), 5.27 (dd, J=11.3, 2.7 Hz, 1H), 4.57 (dd, J=11.2, 5.2 Hz, 1H), 4.52 (d, J=2.2 Hz, 1H), 4.32 (s, 1H), 4.19 (d, J=11.8 Hz, 1H), 4.09 (d, J=12.0 Hz, 1H), 3.34 (s, 3H).

Intermediate 5

2-Bromo-5-chloropyridin-3-yl 3-azido-2-O-benzyl-4,6-O-benzylidene-3-deoxy-1-thio-α-D-galactopyranoside

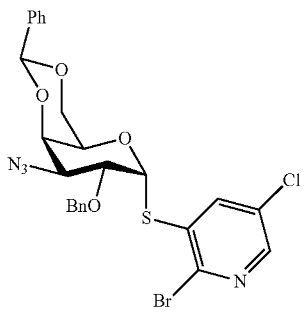

To a cooled solution (0° C.) of 2-bromo-5-chloropyridin-3-yl 3-azido-4,6-O-benzylidene-3-deoxy-1-thio-α-D-galactopyranoside (630 mg, 1.27 mmol) in DMF (10 mL), $Cs_2CO_3$ (1.7 g, 5.0 mmol) was added and the mixture was stirred 10 min. Benzylbromide (0.31 mL, 2.54 mmol) was added and the mixture was stirred 2 h at rt. Water (50 mL) was added and the mixture was extracted with EtOAc (3×20 mL). The combined organic layers were washed with brine, dried over $Na_2SO_4$, concentrated and purified by column chromatography (PE/EtOAc=10/1~5/1, Silica-CS 12 g, 12 mL/min, silica gel, UV 254) to give the product (460 mg, 62%). ESI-MS m/z calcd for $[C_{25}H_{22}BrClN_4O_4S]$ $[M+H]^+$: 589.0; found: 589.0. $^1H$ NMR (400 MHz, $CDCl_3$) δ 8.07 (d, J=2.4 Hz, 1H), 7.61 (d, J=2.4 Hz, 1H) 7.45-7.42 (m, 2H), 7.36-7.29 (m, 5H), 7.26-7.21 (m, 3H), 5.77 (d, J=5.2 Hz, 1H), 5.55 (s, 1H), 4.75 (d, J=11.6 Hz, 1H), 4.66 (d, J=11.6 Hz, 1H), 4.44 (dd, J=5.6, 10.8 Hz, 1H), 4.28 (d, J=2.8 Hz, 1H), 4.12-4.01 (m, 2H), 3.96 (s, 1H), 4.82 (dd, J=3.2, 10.4 Hz, 1H).

5-Chloro-2-cyanopyridin-3-yl 3-azido-2-O-benzyl-4,6-O-benzylidene-3-deoxy-1-thio-α-D-galactopyranoside

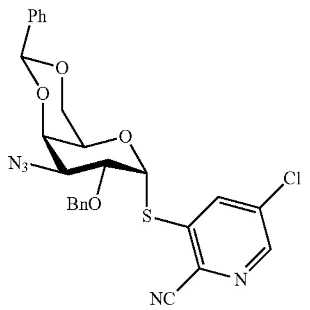

To a solution of 2-bromo-5-chloropyridin-3-yl 3-azido-2-O-benzyl-4,6-O-benzylidene-3-deoxy-1-thio-α-D-galactopyranoside (460 mg, 0.78 mmol) in DMF (4.0 mL) Zn (25.4 mg, 0.39 mmol), $Zn(CN)_2$ (182.5 mg, 1.56 mmol), 1,1'-bis (diphenylphosphino)ferrocene (34.6 mg, 0.062 mmol) and tris(dibenzylideneacetone)dipalladium(0) (28.5 mg, 0.031 mmol) were added and the mixture was stirred 3 h at 100° C. under a nitrogen atmosphere. The mixture was concentrated and purified by column chromatography (PE/EA=10/1~5/1, Silica-CS 12 g, 20 mL/min, silica gel, UV 254) to give the product (187 mg, 45%). ESI-MS m/z calcd for $[C_{26}H_{22}ClN_5O_4S]$ $[M+H]^+$: 536.1; found: 536.0. $^1H$ NMR (400 MHz, Chloroform-d) δ 8.41 (d, J=2.4 Hz, 1H), 7.65 (d, J=2.0 Hz, 1H), 7.43-7.41 (m, 2H), 7.39-7.36 (m, 2H), 7.34-7.26 (m, 6H), 5.67 (d, J=5.6 Hz, 1H), 5.54 (s, 1H), 4.81 (d, J=11.6 Hz, 1H) 4.64 (d, J=11.6 Hz, 1H), 4.40 (dd, J=10.8, 5.2, 1H), 4.29 (d, J=3.2 Hz, 1H), 4.07 (t, J=4.0 Hz, 3H), 3.78 (dd, J=10.8, 3.2 Hz, 1H).

5-Chloro-2-cyanopyridin-3-yl 2-O-benzyl-4,6-O-benzylidene-3-deoxy-3-[4-(2-thiazolyl)-1H-1,2,3-triazol-1-yl]-1-thio-α-D-galactopyranoside

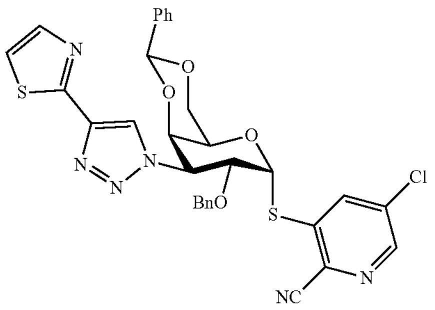

To a solution of 5-chloro-2-cyanopyridin-3-yl 3-azido-2-O-benzyl-4,6-O-benzylidene-3-deoxy-1-thio-D-galactopyranoside (75 mg, 0.14 mmol) and trimethyl(2-thiazol-2-yl-ethynyl)silane (38 mg, 0.21 mmol) in DMF (2 mL) (+)-sodium L-ascorbate (14 mg, 0.07 mmol) and copper (II) sulfate pentahydrate (17.6 mg, 0.07 mmol) were added and the mixture was stirred overnight at rt. The mixture was concentrated and purified by column chromatography (PE/EtOAc=5/1~3/2, Silica-CS 12 g, 20 mL/min, silica gel, UV 254) to give the product (74.0 mg, 82%). ESI-MS m/z calcd for $[C_{31}H_{25}ClN_6O_4S_2][M+H]^+$: 645.1, found: 645.1. $^1H$ NMR (400 MHz, DMSO-$d_6$) δ 8.45 (d, J=2.0 Hz, 1H), 8.23 (s, 1H), 7.95 (s, 1H), 7.67 (d, J=2.0 Hz, 1H), 7.33-7.29 (m, 6H), 7.19-7.14 (m, 5H), 5.79 (d, J=5.2 Hz, 1H), 5.45 (s, 1H), 5.32 (d, J=10.8 Hz, 1H), 4.76 (q, J=11.6, 5.2 Hz, 1H), 4.56-4.44 (m, 3H), 4.31 (s, 1H), 4.17 (d, J=12.4 Hz, 1H), 4.09-4.04 (m, 1H).

Intermediate 6

2-Bromo-5-chloropyridin-3-yl 3-azido-4,6-O-benzylidene-3-deoxy-2-O-(3,5-difluoro-4-(4-methoxybenzyloxy)benzyl)-1-thio-α-D-galactopyranoside

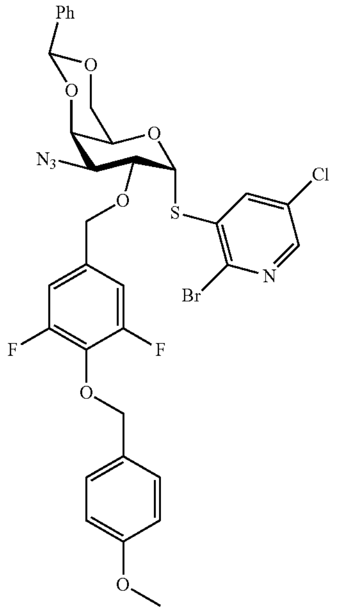

To a solution of 2-bromo-5-chloropyridin-3-yl 3-azido-4,6-O-benzylidene-3-deoxy-1-thio-α-D-galactopyranoside (620 mg, 1.15 mmol) in DMF (10 mL) cesium carbonate (748 mg, 2.30 mmol) was added followed by 5-(bromomethyl)-1,3-difluoro-2-(4-methoxybenzyloxy)benzene (420 mg, 1.20 mmol) and the mixture was stirred 3 h at 25° C. Water (100 mL) was added and the mixture was extracted with EtOAc (3×50 mL). The organic layers were washed with brine (3×50 mL), dried over $Na_2SO_4$, evaporated and purified by column chromatography (PE/EA=10/1~1/1, Silica-CS 40 g, 30 mL/min, silica gel, UV 254) to afford the product (700 mg, 79%). ESI-MS m/z calcd for $[C_{33}H_{28}BrClF_2N_4O_6S]$ $[M+H]^+$: 761.1; found: 761.0. $^1H$ NMR (400 MHz, Methanol-$d_4$) δ 8.09 (d, J=2.0 Hz, 1H), 7.75 (d, J=2.4 Hz, 1H), 7.49-7.41 (m, 2H), 7.34-7.26 (m, 5H), 6.90-6.84 (m, 2H), 6.82-6.79 (m, 2H), 5.96 (d, J=5.2 Hz, 1H), 5.56 (s, 1H), 4.99 (s, 2H), 4.60-4.50 (m, 2H), 4.40 (dd, J=10.4, 5.2 Hz, 1H), 4.29 (d, J=3.2 Hz, 1H), 4.14-4.02 (m, 2H), 3.97 (s, 1H), 3.81 (dd, J=10.4, 3.2 Hz, 1H), 3.72 (s, 3H).

5-Chloro-2-cyanopyridin-3-yl 3-azido-4,6-O-benzylidene-3-deoxy-2-O-(3,5-difluoro-4-(4-methoxybenzyloxy)benzyl)-1-thio-α-D-galactopyranoside

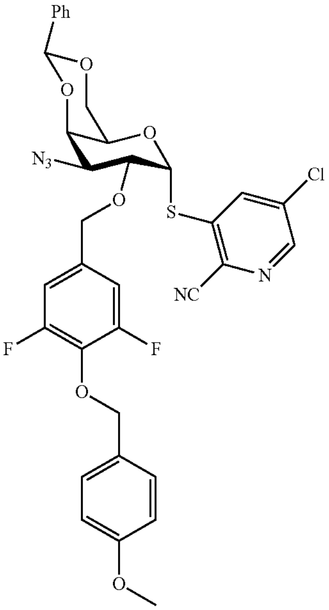

To a solution of 2-bromo-5-chloropyridin-3-yl 3-azido-4,6-O-benzylidene-3-deoxy-2-O-(3,5-difluoro-4-(4-methoxybenzyloxy)benzyl)-1-thio-α-D-galactopyranoside (700 mg, 0.91 mmol) in DMF (10 mL) 1,1'-bis(diphenylphosphino)ferrocene (103 mg, 0.18 mmol), Zn (89 mg, 0.14 mol), $Zn(CN)_2$ (214 mg, 1.82 mmol) and tris(dibenzylideneacetone)dipalladium(0) (105 mg, 0.18 mmol) were added and the mixture was stirred 3 h at 100° C. under a nitrogen atmosphere. The mixture was evaporated and purified by column chromatography (DCM/MeOH=10/0~10/1, Silica-CS 20 g, 20 mL/min, silica gel, UV 254) to give the product (320 mg, 37%). ESI-MS m/z calcd for $[C_{34}H_{28}ClF_2N_5O_6S]$ $[M+NH_4]^+$: 725.1, found: 725.0. $^1H$ NMR (400 MHz, Chloroform-d) δ 8.52 (d, J=2.4 Hz, 1H), 7.96 (d, J=2.0 Hz, 1H), 7.52-7.48 (m, 2H), 7.41-7.32 (m, 5H), 7.00-6.95 (m, 2H), 6.89-6.85 (m, 2H), 6.00 (d, J=4.8 Hz, 1H), 5.63 (s, 1H), 5.08 (s, 2H), 4.72-4.62 (m, 2H), 4.44 (dd, J=10.4, 4.8 Hz, 1H), 4.39 (d, J=3.2 Hz, 1H), 4.20-4.10 (m, 2H), 3.86 (dd, J=10.4, 2.8 Hz, 1H), 3.80 (s, 3H), 3.79-3.77 (m, 1H).

5-Chloro-2-cyanopyridin-3-yl 4,6-O-benzylidene-3-deoxy-2-O-(3,5-difluoro-4-(4-methoxybenzyloxy)benzyl)-3-[4-(2-thiazolyl)-1H-1,2,3-triazol-1-yl]-1-thio-α-D-galactopyranoside

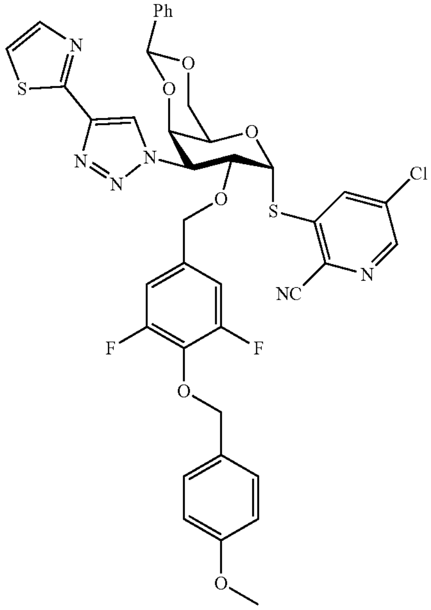

To a solution of 5-chloro-2-cyanopyridin-3-yl 3-azido-4,6-O-benzylidene-3-deoxy-2-O-(3,5-difluoro-4-(4-methoxybenzyloxy)benzyl)-1-thio-α-D-galactopyranoside (150 mg, 0.16 mmol) in DMF (5 mL) trimethyl(2-thiazol-2-ylethynyl)silane (75 mg, 0.36 mmol), copper (II) sulfate pentahydrate (40.0 mg, 0.16 mmol) and (+)-sodium L-ascorbate (32 mg, 0.16 mmol) were added and the mixture was stirred 6 h at rt. The mixture was partitioned between water (50 mL) and DCM (50 mL). The aqueous phase was extracted with DCM (2×50 mL). The combined organic layers were washed with water (50 mL) and brine (50 mL), dried over $Na_2SO_4$ and evaporated. The residue was purified by column chromatography ($DCM/CH_3OH$=10/0~10/1, Silica-CS 12 g, 20 mL/min, silica gel, UV 254) to afford the product (120 mg, 85%). ESI-MS m/z calcd for $[C_{39}H_{31}ClF_2N_6O_6S_2]$ $[M+H]^+$: 817.1; found: 817.1. $^1H$ NMR (400 MHz, Chloroform-d) δ 8.57 (d, J=2.0 Hz, 1H), 7.98 (d, J=2.4 Hz, 1H), 7.88 (s, 1H), 7.52-7.40 (m, 7H), 7.31 (d, J=8.8 Hz, 2H), 6.87-6.82 (m, 2H), 6.74-6.67 (m, 2H), 6.11 (d, J=5.2 Hz, 1H), 5.54 (s, 1H), 5.43-5.34 (m, 1H), 5.00 (s, 2H), 4.95-4.88 (m, 1H), 4.60-4.57 (m, 2H), 4.49-4.40 (m, 2H), 4.27-4.17 (m, 2H), 3.79 (s, 3H).

Intermediate 7

3,5-Dichloro-4-fluorophenyl 4,6-O-benzylidene-3-deoxy-3-[4-(2-hydroxythiazol-4-yl)-1H-1,2,3-triazol-1-yl]-2-O-methyl-1-thio-α-D-galactopyranoside

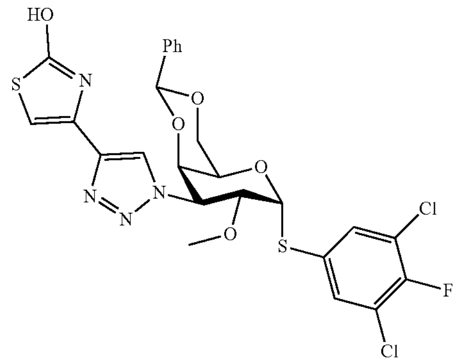

To a solution of 3,5-dichloro-4-fluorophenyl 3-azido-4,6-O-benzylidene-3-deoxy-2-O-methyl-1-thio-α-D-galactopyranoside (300 mg, 0.62 mmol) in DMF (10 mL) 4-(2-trimethylsilylethynyl)thiazol-2-ol (243 mg, 1.23 mmol), copper (II) sulfate pentahydrate (77.0 mg, 0.31 mmol) and (+)-sodium L-ascorbate (122 mg, 0.62 mmol) were added and the mixture was stirred 2 h at rt. The mixture was partitioned between water (10 mL) and DCM (10 mL) and the aqueous phase was extracted with DCM (2×5 mL). The combined organic phases were washed with water (20 mL), brine (20 mL), dried over $Na_2SO_4$, evaporated and purified by column chromatography (PE/EA=1/5~1/1, Silica-CS 12 g, 12 mL/min, silica gel, UV 254) to afford the product (310 mg, 82%). ESI-MS m/z calcd for $[C_{25}H_{21}Cl_2FN_4O_5S_2]$ $[M+H]^+$: 611.0; found: 611.0. $^1H$ NMR (400 MHz, Chloroform-d) δ 10.02 (s, 1H), 8.12 (s, 1H), 7.44 (d, J=6.0 Hz, 2H), 7.33 (s, 5H), 6.40 (s, 1H), 6.15 (d, J=5.1 Hz, 1H), 5.43 (s, 1H), 5.23 (dd, J=11.3, 3.1 Hz, 1H), 4.53 (dd, J=11.3, 5.1 Hz, 1H), 4.42 (d, J=3.0 Hz, 1H), 4.29 (t, J=6.0 Hz, 2H), 4.15 (d, J=12.4 Hz, 1H), 3.34 (s, 3H).

Intermediate 8

3,4-Dichlorophenyl 2,4,6-tri-O-acetyl-3-azido-3-deoxy-1-thio-α-D-galactopyranoside

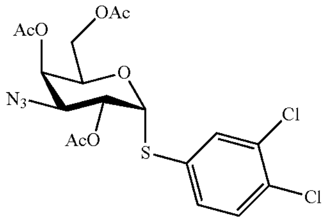

To a solution of 2,4,6-tri-O-acetyl-3-azido-3-deoxy-β-D-galactopyranosyl chloride (600 mg, 1.72 mmol) and 3,4-dichlorobenzenethiol (369 mg, 2.06 mmol) in DMF (10.0 mL) $Cs_2CO_3$ (1.1 g, 3.43 mmol) was added and the mixture was stirred 3 h at rt. Water (30 mL) was added and the mixture was extracted with EtOAc (2×20 mL). The combined organic phases were dried, concentrated and purified by column chromatography (PE/EA=10/1~5/1, Silica-CS 12 g, 20 mL/min, silica gel, UV 254) to give the product (550 mg, 65%). ESI-MS m/z calcd for $[C_{18}H_{19}C_2N_3O_7S]$ $[M+NH_4]^+$: 509.0, found: 509.0. $^1H$ NMR (400 MHz, Chloroform-d) δ 7.50 (d, J=2.1 Hz, 1H), 7.31 (d, J=8.4 Hz, 1H), 7.21 (dd, J=8.5, 2.2 Hz, 1H), 5.90 (d, J=5.5 Hz, 1H), 5.40 (d, J=2.7 Hz, 1H), 5.20 (dd, J=10.9, 5.5 Hz, 1H), 4.53 (dd, J=7.0, 5.4 Hz, 1H), 3.99 (ddd, J=19.3, 11.6, 6.3 Hz, 2H), 3.87 (dd, J=11.0, 3.3 Hz, 1H), 2.12 (s, 3H), 2.10 (s, 3H), 1.93 (s, 3H)

3,4-Dichlorophenyl 3-azido-3-deoxy-1-thio-α-D-galactopyranoside

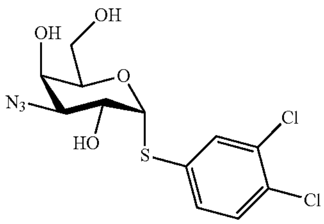

A solution of 3,4-dichlorophenyl 2,4,6-tri-O-acetyl-3-azido-3-deoxy-1-thio-α-D-galactopyranoside (550 mg, 1.12 mmol) in MeOH (10.0 mL) and a catalytic amount of NaOMe was stirred 30 min at rt. Acidic resin was added to adjust the pH value to 6-7. The solid was removed by filtration and the filtrate was concentrated to give the product (400 mg, 98%). ESI-MS m/z calcd for $[C_{12}H_{13}Cl_2N_3O_4S]$ $[M+NH_4]^+$: 383.0, found: 383.0. $^1H$ NMR (400 MHz, Chloroform-d) δ 7.55 (d, J=2.1 Hz, 1H), 7.33 (d, J=8.4 Hz, 1H), 7.27 (dd, J=8.4, 2.1 Hz, 1H), 5.63 (d, J=5.4 Hz, 1H), 4.49-4.33 (m, 1H), 4.20 (t, J=4.4 Hz, 1H), 4.12 (s, 1H), 3.87 (ddd, J=33.9, 12.0, 4.5 Hz, 2H), 3.49 (dd, J=10.5, 2.9 Hz, 1H), 2.87 (s, 1H), 2.28 (d, J=7.3 Hz, 1H), 2.09 (d, J=12.5 Hz, 1H).

3,4-Dichlorophenyl 3-azido-4,6-O-benzylidene-3-deoxy-1-thio-α-D-galactopyranoside

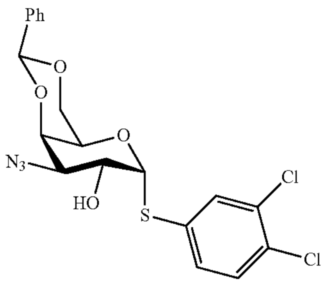

To a solution of 3,4-dichlorophenyl 3-azido-3-deoxy-1-thio-α-D-galactopyranoside (400 mg, 1.09 mmol) in DMF (10 mL) benzaldehyde dimethylacetal (416 mg, 2.73 mmol) followed by D(+)-10-camphorsulfonic acid (76.1 mg, 0.33 mmol) were added. The mixture was stirred 4 h at 50° C. with a water pump connected. The mixture was added dropwise to an aq $NaHCO_3$ solution (50 mL) and filtered. The white solid was collected and dried in vacuum to give the product (450 mg, 91%). ESI-MS m/z calcd for $[C_{19}H_{17}Cl_2N_3O_4S]$ $[M+H]^+$: 454.0, found: 454.0. $^1H$ NMR (400 MHz, DMSO-$d_6$) δ 7.74 (d, J=2.1 Hz, 1H), 7.60 (d, J=8.5 Hz, 1H), 7.51-7.33 (m, 6H), 6.18 (s, 1H), 5.97 (d, J=5.2 Hz, 1H), 5.67 (s, 1H), 4.42 (d, J=2.9 Hz, 1H), 4.31 (dd, J=10.9, 5.2 Hz, 1H), 4.16-4.04 (m, 1H), 4.01 (s, 1H), 3.92 (d, J=12.5 Hz, 1H), 3.65 (dd, J=10.9, 3.3 Hz, 1H).

3,4-Dichlorophenyl 3-azido-4,6-O-benzylidene-3-deoxy-2-O-isopropyl-1-thio-α-D-galactopyranoside

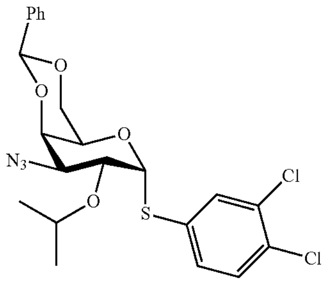

To a solution of 3,4-dichlorophenyl 3-azido-4,6-O-benzylidene-3-deoxy-1-thio-α-D-galactopyranoside (20.0 mg, 0.044 mmol) in DMF (2.0 mL) NaH (60% in oil, 4.1 mg, 0.18 mmol) was added and the mixture was stirred 30 min at 0° C. 2-Iodopropane (29.9 mg, 0.18 mmol) was added and the mixture was stirred overnight at rt. The mixture was diluted with water (5 mL) and extracted with EtOAc (2×5 mL). The combined organic layers were concentrated and purified by prep TLC (PE/EA=4/1, silica gel, UV 254) to give the product (15 mg, 69%). ESI-MS m/z calcd for $[C_{22}H_{23}Cl_2N_3O_4S]$ $[M+H]^+$: 496.1, found: 496.0. $^1H$ NMR (400 MHz, Chloroform-d) δ 7.50 (d, J=2.1 Hz, 1H), 7.45 (dd, J=7.5, 1.9 Hz, 2H), 7.29 (dd, J=10.1, 4.9 Hz, 4H), 7.21 (dd, J=8.5, 2.1 Hz, 1H), 5.90 (d, J=5.2 Hz, 1H), 5.54 (s, 1H), 4.31 (dd, J=10.6, 5.2 Hz, 1H), 4.25 (d, J=3.0 Hz, 1H), 4.13 (dd, J=12.6, 1.4 Hz, 1H), 4.03 (dd, J=15.8, 3.1 Hz, 2H), 3.80 (dt, J=12.2, 6.1 Hz, 1H), 3.64 (dd, J=10.6, 3.3 Hz, 1H), 1.19 (dd, J=14.2, 6.1 Hz, 6H).

Intermediate 9

3,4-Dichlorophenyl 3-azido-4,6-O-benzylidene-3-deoxy-2-O-methyl-1-thio-α-D-galactopyranoside

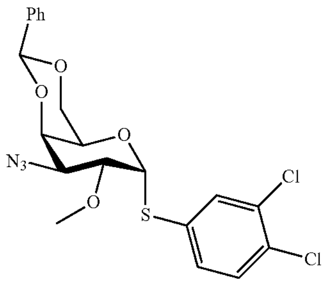

To a solution of 3,4-dichlorophenyl 3-azido-4,6-O-benzylidene-3-deoxy-1-thio-α-D-galactopyranoside (150 mg, 0.33 mmol) in DMF (5 mL) NaH (60% in oil, 26 mg, 0.65 mmol) was added followed by iodomethane (92 mg, 0.65 mmol) and the mixture was stirred 6 h at rt. The mixture was diluted with water (100 mL) and extracted with EtOAc (3×50 mL). The combined organic layers were washed with brine (3×50 mL), dried over $Na_2SO_4$, concentrated and purified by column chromatography (PE/EtOAc=10/1~1/1, Silica-CS 12 g, 20 mL/min, silica gel, UV 254) to afford the product (150 mg, 94%). ESI-MS m/z calcd for $[C_{20}H_{19}Cl_2N_3O_4S]$ $[M+H]^+$: 468.1; found: 468.0. $^1H$ NMR (400 MHz, Chloroform-d) δ 7.52 (d, J=2.0 Hz, 1H), 7.47-7.45 (m, 2H), 7.33-7.29 (m, 5H), 5.95 (d, J=5.2 Hz, 1H), 5.55 (s, 1H), 4.26 (d, J=3.2 Hz, 1H), 4.19-4.15 (m, 2H), 4.08-4.04 (m, 2H), 3.63 (dd, J=10.8, 3.6 Hz, 1H), 3.48 (s, 3H).

3,4-Dichlorophenyl 4,6-O-benzylidene-3-deoxy-3-[4-(2-hydroxythiazol-4-yl)-1H-1,2,3-triazol-1-yl]-2-O-methyl-1-thio-α-D-galactopyranoside

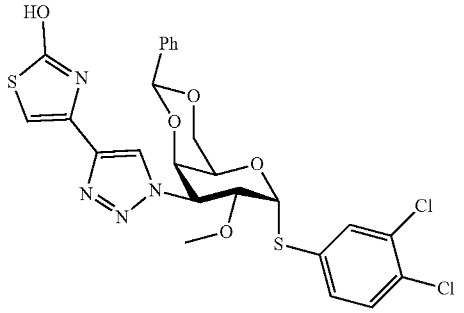

To a solution of 3,4-dichlorophenyl 3-azido-4,6-O-benzylidene-3-deoxy-2-O-methyl-1-thio-α-D-galactopyranoside (150 mg, 0.30 mmol) in DMF (5 mL) 4-(trimethylsilyl)ethynyl)thiazol-2-ol (95 mg, 0.46 mmol), copper (II) sulfate pentahydrate (38 mg, 0.11 mmol) and (+)-sodium L-ascorbate (30 mg, 0.11 mmol) were added and the mixture was stirred 6 h at rt. The mixture was partitioned between water (50 mL) and DCM (50 mL). The aqueous phase was extracted with DCM (2×50 mL). The combined organic layers were washed with water (50 mL) and brine (50 mL), dried over $Na_2SO_4$ and concentrated. The residue was purified by column chromatography (PE/EtOAc=10/1~1/2, Silica-CS 12 g, 20 mL/min, silica gel, UV 254) to afford the product (160 mg, 84%). ESI-MS m/z calcd for $[C_{25}H_{22}Cl_2N_4O_5S_2]$ $[M+H]^+$: 593.1; found: 593.0. $^1H$ NMR (400 MHz, DMSO-$d_6$) δ 11.90 (s, 1H), 8.51 (s, 1H), 7.86 (d, J=2.0 Hz, 1H), 7.65 (d, J=8.8 Hz, 1H), 7.54 (dd, J=8.4, 2.4 Hz, 1H), 7.40-7.33 (m, 5H), 6.73 (s, 1H), 6.60 (d, J=4.8 Hz, 1H), 5.60 (s, 1H), 5.17 (dd, J=11.6, 3.6 Hz, 1H), 4.59-4.54 (m, 2H), 4.29 (s, 1H), 4.15-3.96 (m, 2H), 3.34 (s, 3H).

Intermediate 10

1,2,4,6-Tetra-O-acetyl 3-deoxy-3-[4-(2-hydroxythiazol-4-yl)-1H-1,2,3-triazol-1-yl]-β-D-galactopyranose

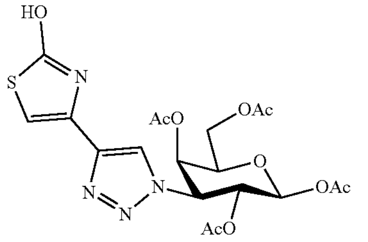

To a solution of 1,2,4,6-tetra-O-acetyl-3-azido-3-deoxy-β-D-galactopyranoside (600 mg, 1.61 mmol), 4-(2-trimethylsilylethynyl)thiazol-2-ol (396 mg, 2.01 mmol) and CuI (31 mg, 0.16 mmol) in MeCN (20 mL) DIPEA (0.55 mL, 3.21 mmol) was added and the mixture was stirred 18 h at rt. The mixture was concentrated, diluted with EtOAc and washed with brine. The organic phase was dried, evaporated and purified by chromatography ($SiO_2$, EtOAc/PE) to yield the product (521 mg, 65%). ESI-MS m/z calcd for $[C_{19}H_{22}N_4O_{10}S]$ $[M+H]^+$: 499.1; found: 498.9, $^1H$ NMR (400 MHz, Chloroform-d) δ 10.20 (s, 1H), 7.94 (s, 1H), 6.54 (s, 1H), 5.90-5.80 (m, 2H), 5.58 (s, 1H), 5.22 (d, J=12.1 Hz, 1H), 4.30-4.10 (m, 3H), 2.18 (s, 3H), 2.13 (s, 3H), 2.06 (s, 3H), 1.92 (s, 3H).

4,6-Di-O-acetyl 3-deoxy-3-[4-(2-hydroxythiazol-4-yl)-1H-1,2,3-triazol-1-yl]-D-galactal

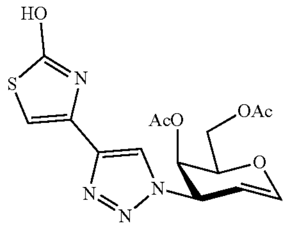

To a cooled (0° C.) solution of 1,2,4,6-tetra-O-acetyl 3-deoxy-3-[4-(2-hydroxythiazol-4-yl)-1H-1,2,3-triazol-1-yl]-β-D-galactopyranose (500 mg, 1.00 mmol) in DCM (15 mL) HBr/AcOH (1.04 mL, 6.02 mmol) was added. The mixture reached rt in 25 min and after stirring 6 h at rt the mixture was diluted with DCM and washed with saturated aq $NaHCO_3$ and water. The organic phase was dried, evaporated and the obtained residue was dissolved together with $NH_4Cl$ (401 mg, 7.50 mmol) in MeCN (20 mL). Zinc (491 mg, 7.50 mmol) was added to the mixture and after stirring 4 days at rt the mixture was filtered through silica using EtOAc. The filtrate was concentrated and purified by chromatography ($SiO_2$, EtOAc/petroleum ether) to yield the product (25 mg, 7%). ESI-MS m/z calcd for $[C_{15}H_{16}N_4O_6S]$ $[M+H]^+$: 381.1; found: 381.1, $^1H$ NMR (400 MHz, Chloroform-d) δ 10.73 (s, 1H), 7.95 (s, 1H), 6.76 (dd, J=6.2, 2.2 Hz, 1H), 6.59 (s, 1H), 5.85 (m, 1H), 5.65 (d, J=3.6 Hz, 1H), 4.91 (d, J=6.3 Hz, 1H), 4.51 (t, J=6.5 Hz, 1H), 4.22 (dd, J=6.5, 2.9 Hz, 2H), 2.11 (s, 3H), 1.98 (s, 3H).

Intermediate 11

5-Bromo-2-cyanopyridin-3-yl 4,6-di-O-acetyl-3-[4-(4-chlorothiazol-2-yl)-1H-1,2,3-triazol-1-yl]-3-deoxy-2-O-methyl-1-thio-α-D-galactopyranoside

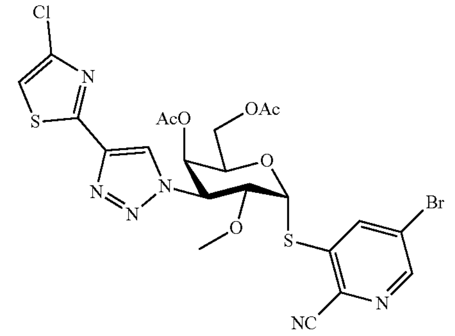

To a solution of 5-bromo-2-cyanopyridin-3-yl 4,6-di-O-acetyl-3-azido-3-deoxy-2-O-methyl-1-thio-D-galactopyranoside (180 mg, 0.36 mmol) and 2-(4-chlorothiazol-2-yl)ethynyl-trimethyl-silane (155 mg, 0.72 mmol) in the DMF (4.0 mL) copper (II) sulfate pentahydrate (44.9 mg, 0.18 mmol) and (+)-sodium L-ascorbate (71.3 mg, 0.36 mmol) were added and the mixture was stirred 3 h at rt. The mixture was diluted with water (20 mL) and extracted with EtOAc (3×10 mL). The combined organic layers were washed with brine, dried over $Na_2SO_4$, concentrated and purified by column chromatography (PE/EA=10/1~1/1, Silica-CS 4 g, 12 mL/min, silica gel, UV 254). The obtained material was further purified by preparative-SFC to give the product (28 mg, 12%). ESI-MS m/z calcd for $[C_{22}H_{20}BrClN_6O_6S_2]$ $[M+H]^+$: 643.0; found: 642.9. $^1H$ NMR (400 MHz, Chloroform-d) δ 8.62 (d, J=2.0 Hz, 1H), 8.20 (d, J=2.0 Hz, 1H), 8.14 (s, 1H), 7.06 (s, 1H), 6.27 (d, J=5.2 Hz, 1H), 5.55 (d, J=2.0 Hz, 1H), 5.00 (dd, J=11.2, 2.8 Hz, 1H), 4.72 (dd, J=10.8, 5.2 Hz, 1H), 4.64 (t, J=6.0 Hz, 1H), 3.96-4.07 (m, 2H), 3.39 (s, 3H), 2.00 (s, 3H), 1.91 (s, 3H).

Intermediate 12

3-Bromo-2-cyanopyridin-5-yl 3-azido-4,6-di-O-acetyl-3-deoxy-2-O-methyl-1-thio-D-galactopyranoside

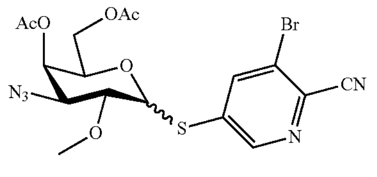

To a cooled (0° C.) solution of acetyl 4,6-di-O-acetyl-3-azido-3-deoxy-2-O-methyl-1-thio-D-galactopyranoside (230 mg, 0.64 mmol) and 3-bromo-5-fluoropyridine-2-carbonitrile (154 mg, 0.76 mmol) in DMF (5.0 mL) diethylamine (93.1 mg, 1.27 mmol) was added and the mixture was stirred 8 h at 0° C. The mixture was diluted with water (20 mL) and extracted with EtOAc (3×10 mL). The combined organic layers were washed with brine, dried over $Na_2SO_4$, concentrated and purified by column chromatography (PE/EA=10/

1~3/1, Silica-CS 4 g, 12 mL/min, silica gel, UV 254) to give the product (203 mg, 64%, α/β=0.25:1). ESI-MS m/z calcd for $[C_{17}H_{18}BrN_5O_6S][M+H]^+$: 500.0; found: 500.0.

3-Bromo-2-cyanopyridin-5-yl 3-azido-4,6-di-O-acetyl-3-deoxy-2-O-methyl-1-thio-α-D-galactopyranoside $^1$H NMR (400 MHz, Chloroform-d) δ 8.58 (d, J=2.0 Hz, 1H), 8.08 (d, J=2.0 Hz, 1H), 6.07 (d, J=5.6 Hz, 1H), 5.35 (d, J=2.8 Hz, 1H), 4.37-4.41 (m, 1H), 4.06-4.10 (m, 1H), 3.90-3.95 (m, 1H), 3.75 (dd, J=10.8, 3.2 Hz, 1H), 3.49 (s, 3H), 3.32-3.38 (m, 1H), 2.10 (s, 3H), 1.90 (s, 3H).

3-Bromo-2-cyanopyridin-5-yl 3-azido-4,6-di-O-acetyl-3-deoxy-2-O-methyl-1-thio-β-D-galactopyranoside $^1$H NMR (400 MHz, Chloroform-d) δ 8.62 (d, J=2.0 Hz, 1H), 8.08 (d, J=2.0 Hz, 1H), 5.35 (d, J=2.8 Hz, 1H), 4.74 (d, J=9.2 Hz, 1H), 4.06-4.10 (m, 1H), 3.90-3.95 (m, 2H), 3.64 (dd, J=10.8, 3.2 Hz, 1H), 3.56 (s, 3H), 3.32-3.38 (m, 1H), 2.11 (s, 3H), 2.02 (s, 3H).

3-Bromo-2-cyanopyridin-5-yl 4,6-di-O-acetyl-3-deoxy-3-[4-(4-chloro-thiazol-2-yl)-1H-1,2,3-triazol-1-yl]-2-O-methyl-1-thio-α-D-galactopyranoside

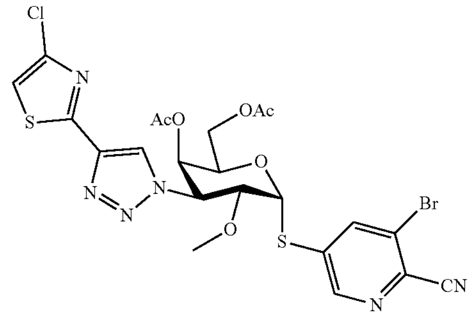

To a solution of 3-bromo-2-cyanopyridin-5-yl 3-azido-4,6-diacetyl-3-deoxy-2-O-methyl-1-thio-D-galactopyranoside (203 mg, 0.41 mmol) and 2-(4-chlorothiazol-2-yl)ethynyl-trimethyl-silane (175 mg, 0.81 mmol) in DMF (6.0 mL) copper (II) sulfate pentahydrate (50.7 mg, 0.20 mmol) and (+)-sodium L-ascorbate (80.4 mg, 0.41 mmol) were added and the mixture was stirred 3 h at rt. The mixture was diluted with water (20 mL) and extracted with EtOAc (3×10 mL). The combined organic layers were washed with brine, dried over $Na_2SO_4$, concentrated, and purified by column chromatography (PE/EA=10/1~1/1, Silica-CS 4 g, 12 mL/min, silica gel, UV 254). The obtained material was further purified by preparative-SFC to give the product (35 mg, 13%). ESI-MS m/z calcd for $[C_{22}H_{20}BrClN_6O_6S_2]$ $[M+H]^+$: 643.0; found: 643.0. $^1$H NMR (400 MHz, Chloroform-d) δ 8.64 (d, J=2.0 Hz, 1H), 8.13 (s, 1H), 8.11 (d, J=2.0 Hz, 1H), 7.07 (s, 1H), 6.22 (d, J=5.2 Hz, 1H), 5.54 (d, J=2.4 Hz, 1H), 4.96 (dd, J=11.2, 3.2 Hz, 1H), 4.71 (dd, J=11.2, 5.2 Hz, 1H), 4.59-4.62 (m, 1H), 4.01-4.06 (m, 2H), 3.34 (s, 3H), 2.01 (s, 3H), 1.91 (s, 3H).

Intermediate 13

5-Chloro-2-cyanopyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

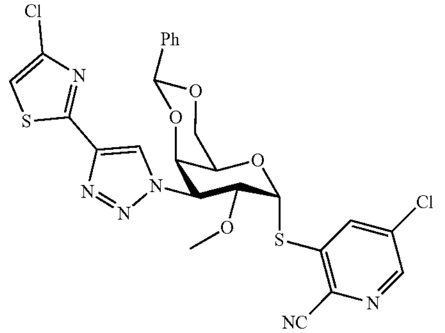

To a solution of 5-chloro-2-cyanopyridin-3-yl 3-azido-4,6-O-benzylidene-3-deoxy-2-O-methyl-1-thio-α-D-galactopyranoside (130 mg, 0.28 mmol) and 2-(4-chlorothiazol-2-yl)ethynyl-trimethyl-silane (103 mg, 0.57 mmol) in DMF (5 mL) (+)-sodium L-ascorbate (112 mg, 0.57 mmol) and copper (II) sulfate pentahydrate (35.3 mg, 0.14 mmol) were added and the mixture was stirred overnight at rt. The mixture was concentrated and purified by column chromatography (PE/EA=10/1~5/1, Silica-CS 12 g, 20 mL/min, silica gel, UV 254) to give the product (70 mg, 41%). ESI-MS m/z calcd for $[C_{25}H_{20}Cl_2N_6O_4S_2]$ $[M+H]^+$: 603.0, found: 603.0. $^1$H NMR (400 MHz, Chloroform-d) δ 8.50 (d, J=2.1 Hz, 1H), 8.24 (s, 1H), 8.02 (d, J=2.1 Hz, 1H), 7.36-7.28 (m, 5H), 7.05 (s, 1H), 6.21 (d, J=5.2 Hz, 1H), 5.45 (s, 1H), 5.26 (dt, J=11.2, 5.6 Hz, 1H), 4.58-4.46 (m, 2H), 4.32 (s, 1H), 4.19 (dd, J=12.9, 1.4 Hz, 1H), 4.09-4.00 (m, 1H), 3.34 (s, 3H).

Intermediate 14

3-Chloro-2-cyanopyridin-3-yl 4,6-di-O-acetyl-3-azido-3-deoxy-2-O-methyl-1-thio-D-galactopyranoside

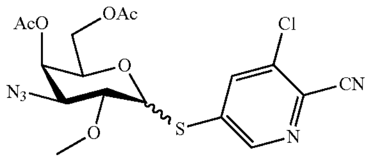

To a cooled (0° C.) solution of acetyl 4,6-di-O-acetyl-3-azido-3-deoxy-2-O-methyl-1-thio-D-galactopyranoside (280 mg, 0.78 mmol) and 3-chloro-5-fluoropyridine-2-carbonitrile (146 mg, 0.93 mmol) in DMF (5.0 mL) diethylamine (113 mg, 1.55 mmol) was added and the mixture was stirred 8 h at 0° C. The mixture was diluted with water (20 mL) and extracted with EtOAc (3×10 mL). The combined organic layers were washed with brine, dried over $Na_2SO_4$, concentrated and purified by column chromatography (PE/EA=10/1~3/1, Silica-CS 4 g, 12 mL/min, silica gel, UV 254) to give the product (260 mg, 74%, α/β=0.25:1). ESI-MS m/z calcd for $[C_{17}H_{18}ClN_5O_6S][M+H]^+$: 456.1; found: 456.1.

3-Chloro-2-cyanopyridin-3-yl 4,6-di-O-acetyl-3-azido-3-deoxy-2-O-methyl-1-thio-α-D-galactopyranoside $^1$H NMR (400 MHz, Chloroform-d) δ 8.55 (d, J=2.0 Hz, 1H), 8.08 (d, J=1.6 Hz, 1H), 6.02 (d, J=5.6 Hz, 1H), 5.34 (d, J=2.8 Hz, 1H), 4.37-4.39 (m, 1H), 3.91-4.01 (m, 2H), 3.74 (dd, J=10.4, 3.2 Hz, 1H), 3.49 (s, 3H), 3.32-3.38 (m, 1H), 2.11 (s, 3H), 1.91 (s, 3H).

3-Chloro-2-cyanopyridin-3-yl 4,6-di-O-acetyl-3-azido-3-deoxy-2-O-methyl-1-thio-β-D-galactopyranoside $^1$H NMR (400 MHz, Chloroform-d) δ 8.57 (d, J=2.0 Hz, 1H), 7.30 (d, J=1.6 Hz, 1H), 5.34 (d, J=2.8 Hz, 1H), 4.68 (d, J=9.6 Hz, 1H), 3.91-4.01 (m, 2H), 3.86-3.88 (m, 1H), 3.57 (s, 3H), 3.55-3.36 (m, 1H), 3.32-3.38 (m, 1H), 2.12 (s, 3H), 2.03 (s, 3H).

3-Chloro-2-cyanopyridin-3-yl 4,6-di-O-acetyl-3-[4-(4-chlorothiazol-2-yl)-1H-1,2,3-triazol-1-yl]-3-deoxy-2-O-methyl-1-thio-α-D-galactopyranoside

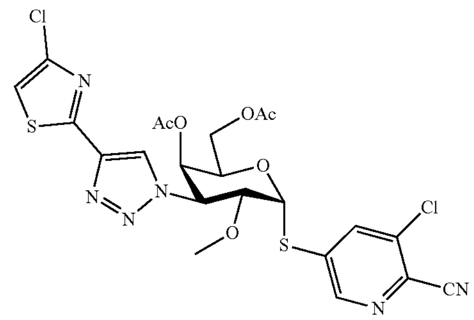

To a solution of 3-chloro-2-cyanopyridin-3-yl 4,6-di-O-acetyl-3-azido-3-deoxy-2-O-methyl-1-thio-D-galactopyranoside (260 mg, 0.57 mmol) and 2-(4-chlorothiazol-2-yl) ethynyl-trimethyl-silane (246 mg, 1.14 mmol) in the DMF (6.0 mL) copper (II) sulfate pentahydrate (71.2 mg, 0.29 mmol) and (+)-sodium L-ascorbate (113 mg, 0.57 mmol) were added and the mixture was stirred 3 h at rt. The mixture was diluted with water (20 mL) and extracted with EtOAc (3×10 mL). The combined organic layers were washed with brine, dried over $Na_2SO_4$, concentrated, and purified by column chromatography (PE/EA=10/1~1/1, Silica-CS 4 g, 12 mL/min, silica gel, UV 254). The obtained material was further purified by preparative-SFC to give the product (48 mg, 14%). ESI-MS m/z calcd for $[C_{22}H_{20}Cl_2N_6O_6S_2]$ $[M+H]^+$: 599.0; found: 599.0 $^1$H NMR (400 MHz, Chloroform-d) δ 8.60 (d, J=2.0 Hz, 1H), 8.15 (s, 1H), 7.98 (d, J=2.0 Hz, 1H), 7.07 (s, 1H), 6.25 (d, J=5.2 Hz, 1H), 5.54 (d, J=2.0 Hz, 1H), 5.00 (dd, J=11.2, 2.8 Hz, 1H), 4.71 (dd, J=11.2, 5.2 Hz, 1H), 4.60-4.63 (m, 1H), 4.01-4.07 (m, 2H), 3.34 (s, 3H), 2.01 (s, 3H), 1.90 (s, 3H).

Intermediate 15

5-Chloro-2-cyanopyridin-3-yl 4,6-O-benzylidene-3-[4-(2-chlorothiazol-4-yl)-1H-1,2,3-triazol-1-yl]-3-deoxy-2-O-methyl-1-thio-α-D-galactopyranoside

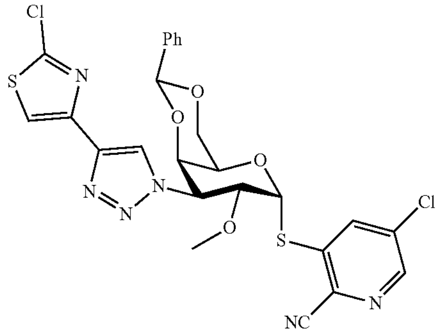

To a solution of 5-chloro-2-cyanopyridin-3-yl 3-azido-4,6-O-benzylidene-3-deoxy-2-O-methyl-1-thio-α-D-galactopyranoside (70 mg, 0.15 mmol) and 2-(2-chlorothiazol-4-yl)ethynyl-trimethylsilane (65.7 mg, 0.30 mmol) in DMF (3 mL) (+)-sodium L-ascorbate (60.3 mg, 0.30 mmol) and copper (II) sulfate pentahydrate (19.0 mg, 0.076 mmol) were added and the mixture was stirred overnight at rt. The mixture was concentrated and purified by prep HPLC $[MeCN/H_2O$ (10 mmol/L $NH_4HCO_3)$, X-Select 10 μm 19*250 mm, 20 mL/min, UV 254] to give the product (55 mg, 60%). ESI-MS m/z calcd for $[C_{25}H_{20}Cl_2N_6O_4S_2]$ $[M+H]^+$: 603.0; found: 603.0. $^1$H NMR (400 MHz, Chloroform-d) δ 8.49 (s, 1H), 8.13 (s, 1H), 8.02 (d, J=2.4 Hz, 1H), 7.74 (s, 1H), 7.33 (m, 5H), 6.20 (d, J=5.2 Hz, 1H), 5.46 (s, 1H), 5.26 (dd, J=11.2, 2.8 Hz, 1H), 4.55 (dd, J=11.2, 5.2 Hz, 1H), 4.49 (d, J=2.4 Hz, 1H), 4.31 (s, 1H), 4.20 (d, J=12.4 Hz, 1H), 4.09 (d, J=12.4 Hz, 1H), 3.32 (s, 3H).

Intermediate 16

3,5-Dichloro-4-fluorophenyl 3-[4-(2-aminothiazol-4-yl)-1H-1,2,3-triazol-1-yl]-4,6-O-benzylidene-3-deoxy-2-O-methyl-1-thio-α-D-galactopyranoside

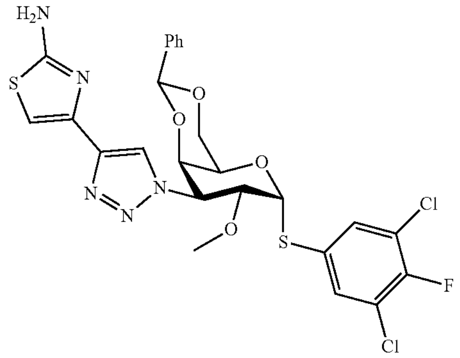

To a solution of 3,5-dichloro-4-fluorophenyl 3-azido-4,6-O-benzylidene-3-deoxy-2-O-methyl-1-thio-α-D-galactopyranoside (90 mg, 0.19 mmol) in DMF (2 mL) 4-(2-trimethylsilyl-ethynyl)thiazol-2-amine (54.5 mg, 0.28 mmol), CuI (10.6 mg, 0.056 mmol), CsF (42.2 mg, 0.28 mmol) and DIPEA (0.127 mL, 0.74 mmol) were added and the mixture was stirred overnight at rt. The mixture was concentrated and purified by column chromatography (EA/PE=5~40%, Silica-CS 4 g, 12 mL/min, silica gel, UV 254) to afford the product (54 mg, 48%). ESI-MS m/z calcd for $[C_{25}H_{22}Cl_2FN_5O_4S_2][M+H]^+$: 610.0; found: 610.0. $^1H$ NMR (400 MHz, DMSO-$d_6$) δ 8.15 (s, 1H), 7.83 (d, J=6.3 Hz, 2H), 7.39 (d, J=2.0 Hz, 5H), 6.89 (s, 1H), 6.60 (d, J=4.9 Hz, 1H), 5.60 (s, 1H), 5.32 (s, 1H), 5.11 (d, J=10.9 Hz, 1H), 4.73 (d, J=11.7 Hz, 1H), 4.26 (s, 1H), 4.09 (s, 1H), 3.93 (d, J=12.6 Hz, 1H), 3.32-3.29 (s, 3H).

Intermediate 17

5-Chloro-2-cyanopyridin-3-yl 3-[4-(2-aminothiazol-4-yl)-1H-1,2,3-triazol-1-yl]-4,6-O-benzylidene 3-deoxy-2-O-methyl-1-thio-α-D-galactopyranoside

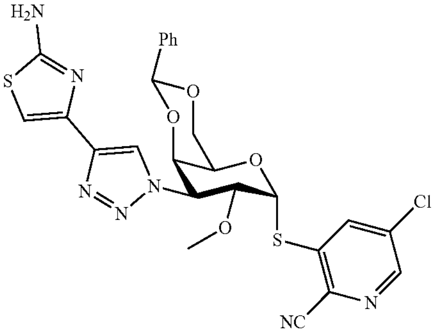

To a solution of 5-chloro-2-cyanopyridin-3-yl 3-azido-4,6-O-benzylidene-3-deoxy-2-O-methyl-1-thio-α-D-galactopyranoside (105 mg, 0.23 mmol) and 4-(2-trimethylsilylethynyl)thiazol-2-amine (67.2 mg, 0.34 mmol) in DMF (5.0 mL) (+)-sodium L-ascorbate (67.8 mg, 0.34 mmol) and copper (II) sulfate pentahydrate (28.5 mg, 0.11 mmol) were added and the mixture was stirred 3 h at rt. The mixture was concentrated and purified by column chromatography (PE/EA=10/1~5/1, Silica-CS 4 g, 10 mL/min, silica gel, UV 254) to give the product (75 mg, 56%). ESI-MS m/z calcd for $[C_{25}H_{22}ClN_7O_4S_2]$ $[M+H]^+$: 584.1, found: 584.0. $^1H$ NMR (400 MHz, Chloroform-d) δ 8.48 (d, J=2.1 Hz, 1H), 8.01 (d, J=2.1 Hz, 1H), 7.95 (d, J=3.5 Hz, 1H), 7.38-7.28 (m, 5H), 7.04 (s, 1H), 6.19 (d, J=5.1 Hz, 1H), 5.45 (s, 1H), 5.22 (dd, J=11.3, 3.0 Hz, 1H), 5.06 (s, 2H), 4.55 (dd, J=11.3, 5.2 Hz, 1H), 4.47 (d, J=2.7 Hz, 1H), 4.29 (s, 1H), 4.23 (dd, J=14.7, 8.0 Hz, 1H), 4.08 (dd, J=17.1, 5.6 Hz, 1H), 3.31 (d, J=6.5 Hz, 3H).

Intermediate 18

5-Chloro-2-methylpyridin-3-yl 3-azido-4,6-O-benzylidene-3-deoxy-2-O-methyl-1-thio-α-D-galactopyranoside

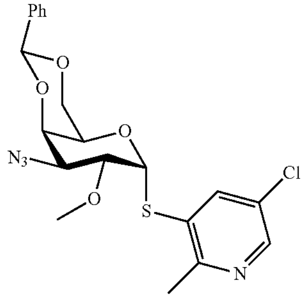

To a solution of 2-bromo-5-chloropyridin-3-yl 3-azido-4,6-O-benzylidene-3-deoxy-2-O-methyl-1-thio-α-D-galactopyranoside (220 mg, 0.43 mmol) in 1,4-dioxane (10 mL) 2,4,6-trimethyl-1,3,5,2,4,6-trioxatriborinane (108 mg, 0.86 mmol), $K_2CO_3$ (178 mg, 1.28 mmol) and $Pd(PPh_4)_3$ (160 mg, 0.13 mmol) were added and the mixture was stirred 6 h at 100° C. under a nitrogen atmosphere. The mixture was cooled to rt, concentrated and purified by column chromatography (PE/EtOAc=1/0~1/1, Silica-CS 12 g, 20 mL/min, silica gel, UV 254) to give the product (100 mg, 51%). ESI-MS m/z calcd for $[C_{20}H_{21}ClN_4O_4S]$ $[M+H]^+$: 449.1; found: 449.0. $^1H$ NMR (400 MHz, Chloroform-d) δ 8.29 (d, J=2.4 Hz, 1H), 7.87 (d, J=2.4 Hz, 1H), 7.59-7.48 (m, 2H), 7.45-7.33 (m, 3H), 6.09 (d, J=5.2 Hz, 1H), 5.63 (s, 1H), 4.38-4.02 (m, 5H), 3.79 (dd, J=10.8, 3.2 Hz, 1H), 3.55 (s, 3H), 2.58 (s, 3H).

5-Chloro-2-methylpyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

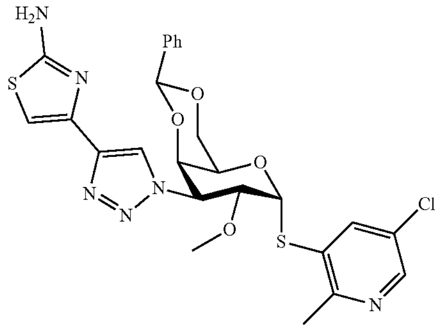

To a solution of 5-chloro-2-methylpyridin-3-yl 3-azido-4,6-O-benzylidene-3-deoxy-2-O-methyl-1-thio-α-D-galactopyranoside (100 mg, 0.22 mmol) in DMF (3 mL) 2-amine-4-[(trimethylsilyl)ethynyl]thiazol (86 mg, 0.44 mmol), copper (II) sulfate pentahydrate (27.0 mg, 0.11 mmol) and (+)-sodium L-ascorbate (22 mg, 0.11 mmol) were added and the mixture was stirred 6 h at rt. The mixture was partitioned between water (50 mL) and DCM (50 mL) and the aqueous phase was extracted with DCM (2×50 mL). The combined organic layers were washed with water (50 mL) and brine (50 mL), dried over $Na_2SO_4$, concentrated and purified by column chromatography (DCM/MeOH=10/0~10/1, Silica-CS 12 g, 20 mL/min, silica gel, UV 254) to give the product (85 mg, 66%). ESI-MS m/z calcd for $[C_{25}H_{25}ClN_6O_4S_2]$ $[M+H]^+$: 573.1; found: 573.1. $^1H$ NMR (400 MHz, DMSO-$d_6$) δ 8.38 (d, J=2.0 Hz, 1H), 8.24-8.05 (m, 2H), 7.47-7.32 (m, 5H), 7.05 (s, 2H), 6.90 (s, 1H), 6.71 (d, J=5.2 Hz, 1H), 5.60 (s, 1H), 5.28-5.14 (m, 1H), 4.81-4.68 (m, 1H), 4.64-4.52 (m, 1H), 4.21 (s, 1H), 4.16-4.04 (m, 1H), 4.00-3.85 (m, 1H), 3.32 (s, 3H), 2.57 (s, 3H).

Intermediate 19

5-Chloro-2-cyanopyridin-3-yl 3-[4-(2-aminothiazol-4-yl)-1H-1,2,3-triazol-1-yl]-2-O-benzyl-4,6-O-benzylidene-3-deoxy-1-thio-α-D-galactopyranoside

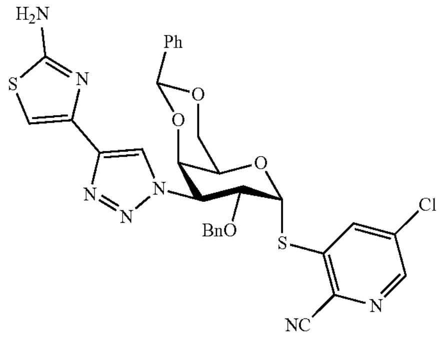

To a solution of 5-chloro-2-cyanopyridin-3-yl 3-azido-2-O-benzyl-4,6-O-benzylidene-3-deoxy-1-thio-α-D-galactopyranoside (136 mg, 0.25 mmol) and 4-(2-trimethylsilylethynyl)thiazol-2-amine (75.0 mg, 0.38 mmol) in DMF (3.0 mL) (+)-sodium L-ascorbate (25.2 mg, 0.13 mmol) and copper (II) sulfate pentahydrate (31.7 mg, 0.13 mmol) were added and the mixture was stirred 3 h at rt. The mixture was concentrated and purified by column chromatography (PE/EtOAc=3/1~1/1, Silica-CS 12 g, 20 mL/min, silica gel, UV 254) to give the product (99 mg, 59%). ESI-MS m/z calcd for $[C_{31}H_{26}ClN_7O_4S_2]$ $[M+H]^+$: 660.1; found: 660.0. $^1H$ NMR (400 MHz, Chloroform-d) 8.43 (d, J=2.0 Hz, 1H), 7.74 (s, 1H), 7.66 (d, J=2.0 Hz, 1H), 7.31-7.16 (m, 11H), 5.79 (d, J=4.0 Hz, 1H), 5.42 (s, 1H), 5.23 (s, 1H), 4.78 (s, 1H), 4.56-4.44 (m, 3H), 4.30 (s, 1H), 4.20-4.01 (m, 2H).

Intermediate 20

2-Bromo-5-chloropyridin-3-yl 3-azido-4,6-O-benzylidene-3-deoxy-2-O-ethyl-1-thio-α-D-galactopyranoside

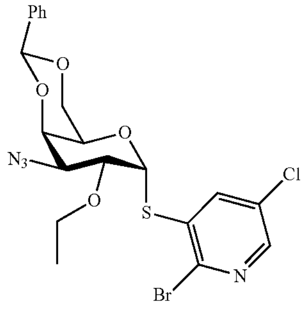

To a solution of 2-bromo-5-chloropyridin-3-yl 3-azido-4,6-O-benzylidene-3-deoxy-1-thio-α-D-galactopyranoside (320 mg, 0.63 mmol) in DMF (5 mL) cesium carbonate (618 mg, 1.90 mmol) was added followed by iodoethane (296 mg, 1.90 mmol) and the mixture was stirred 5 h at 25° C. Water (100 mL) was added, and the mixture was extracted with EtOAc (3×50 mL). The organic layers were washed with brine (3×50 mL), dried over $Na_2SO_4$, concentrated and purified by column chromatography (PE/EtOAc=10/1~1/1, Silica-CS 20 g, 30 mL/min, silica gel, UV 254) to afford the product (300 mg, 85%). ESI-MS m/z calcd for $[C_{20}H_{20}BrClN_4O_4S]$ $[M+H]^+$: 527.0; found: 527.0. $^1H$ NMR (400 MHz, DMSO-$d_6$) δ 8.32 (d, J=2.4 Hz, 1H), 8.11 (d, J=2.4 Hz, 1H), 7.51-7.31 (m, 5H), 6.66 (d, J=5.2 Hz, 1H), 5.68 (s, 1H), 4.41 (d, J=3.2 Hz, 1H), 4.23-4.13 (m, 1H), 4.11-4.03 (m, 1H), 4.00-3.87 (m, 3H), 3.83-3.73 (m, 1H), 3.63-3.53 (m, 1H), 1.15 (t, J=7.0 Hz, 3H).

5-Chloro-2-methylpyridin-3-yl 3-azido-4,6-O-benzylidene-3-deoxy-2-O-ethyl-1-thio-α-D-galactopyranoside

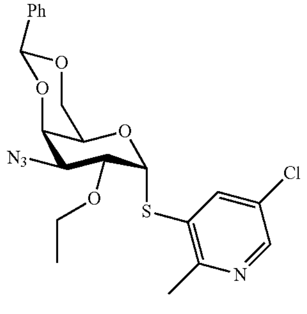

To a solution of 2-bromo-5-chloropyridin-3-yl 3-azido-4,6-O-benzylidene-3-deoxy-2-O-ethyl-1-thio-α-D-galactopyranoside (300 mg, 0.54 mmol) in 1,4-dioxane (10 mL) 2,4,6-trimethyl-1,3,5,2,4,6-trioxatriborinane (203 mg, 1.62 mmol), $K_2CO_3$ (224 mg, 1.62 mmol) and $Pd(PPh_4)_3$ (202 mg, 0.16 mmol) were added and the mixture was stirred 6 h at 100° C. under a nitrogen atmosphere. After cooling to rt, the mixture was concentrated and purified by column chromatography (PE/EtOAc=10/1~1/1, Silica-CS 20 g, 20 mL/min, silica gel, UV 254) to give the product (130 mg, 49%). ESI-MS m/z calcd for $[C_{21}H_{23}ClN_4O_4S]$ $[M+H]^+$: 463.1; found: 462.9. $^1H$ NMR (400 MHz, DMSO-$d_6$) δ 8.36 (d, J=2.2 Hz, 1H), 8.02 (d, J=2.4 Hz, 1H), 7.47-7.31 (m, 5H), 6.49 (d, J=5.2 Hz, 1H), 5.68 (s, 1H), 4.40 (d, J=3.2 Hz, 1H), 4.20-3.70 (m, 6H), 3.61-3.50 (m, 1H), 2.52 (s, 3H), 1.15 (t, J=7.0 Hz, 3H).

5-Chloro-2-methylpyridin-3-yl 3-[4-(2-aminothiazol-4-yl)-1H-1,2,3-triazol-1-yl]-4,6-O-benzylidene-3-deoxy-2-O-ethyl-1-thio-α-D-galactopyranoside

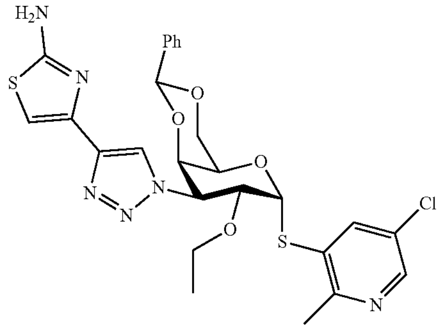

To a solution of 5-chloro-2-methylpyridin-3-yl 3-azido-4,6-O-benzylidene-3-deoxy-2-O-ethyl-1-thio-α-D-galactopyranoside (130 mg, 0.27 mmol) in DMF (3 mL) 4-(2-trimethylsilylethynyl)thiazol-2-amine (100 mg, 0.53 mmol), copper (II) sulfate pentahydrate (66.0 mg, 0.27 mmol) and (+)-sodium L-ascorbate (53 mg, 0.27 mmol) were added and the mixture was stirred 6 h at rt. The mixture was partitioned between water (50 mL) and DCM (50 mL) and the aqueous phase was extracted with DCM (2×50 mL). The organic layers were washed with water (50 mL) and brine (50 mL), dried over $Na_2SO_4$, concentrated and purified by column chromatography (DCM/MeOH=10/0~10/1, Silica-CS 20 g, 20 mL/min, silica gel, UV 254) to afford the product (115 mg, 57%). ESI-MS m/z calcd for $[C_{26}H_{27}ClN_6O_4S_2]$ $[M+H]^+$: 587.1; found: 587.0. $^1H$ NMR (400 MHz, Methanol-$d_4$) δ 8.31 (d, J=2.2 Hz, 1H), 8.16 (s, 1H), 8.11 (d, J=2.4 Hz, 1H), 7.43 (dd, J=6.7, 3.2 Hz, 2H), 7.38-7.30 (m, 3H), 6.95 (s, 1H), 6.43 (d, J=5.2 Hz, 1H), 5.58 (s, 1H), 5.32 (dd, J=11.6, 3.2 Hz, 1H), 4.84-4.76 (m, 1H), 4.62 (d, J=3.2 Hz, 1H), 4.29 (s, 1H), 4.23-4.02 (m, 2H), 3.85-3.67 (m, 1H), 3.52-3.39 (m, 1H), 2.64 (s, 3H), 1.01 (t, J=7.0 Hz, 3H).

Intermediate 21

5-Chloro-2-(pyrimidin-5-yl)pyridin-3-yl 3-azido-4,6-O-benzylidene-3-deoxy-2-O-methyl-1-thio-α-D-galactopyranoside

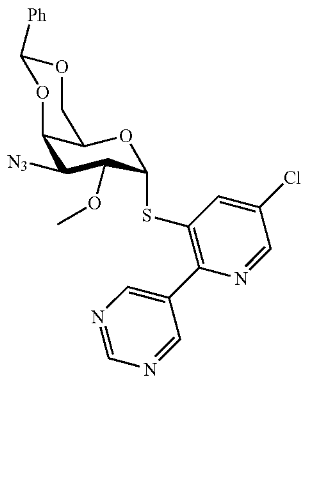

To a solution of 2-bromo-5-chloropyridin-3-yl 3-azido-4,6-O-benzylidene-3-deoxy-2-O-methyl-1-thio-α-D-galactopyranoside (350 mg, 0.68 mmol) and 5-(4,4,5,5-tetramethyl-1,3,2-dioxaborolan-2-yl)pyrimidine (281 mg, 1.36 mmol) in 1,4-dioxane/water (3.3 mL, 10:1) in a microwave tube, bis(triphenylphosphine)palladium(II) chloride (47.8 mg, 0.068 mmol) and $K_2CO_3$ (282 mg, 2.04 mmol) were added. The mixture was degassed by bubbling argon through the solution and it was then stirred 1 h at 100° C. in a microwave reactor. The mixture was concentrated and purified by column chromatography (PE/EtOAc=5/1~1/1, Silica-CS 20 g, 30 mL/min, silica gel, UV 254) to give the product (260 mg, 74%). ESI-MS m/z calcd for $[C_{23}H_{21}ClN_6O_4S]$ $[M+H]^+$: 513.1; found: 513.1. $^1H$ NMR (400 MHz, $CDCl_3$) δ 9.22 (s, 1H), 9.01 (s, 2H), 8.49 (d, J=2.4 Hz, 1H), 8.03 (d, J=2.4 Hz, 1H), 7.42 (m, 2H), 7.35-7.26 (m, 3H), 5.86 (d, J=5.2 Hz, 1H), 5.52 (s, 1H), 4.19 (d, J=2.4 Hz, 1H), 4.12 (dd, J=10.4, 5.2 Hz, 1H), 4.07-3.93 (m, 2H), 3.72 (s, 1H), 3.54 (dd, J=10.4, 2.8 Hz, 1H), 3.37 (s, 3H).

5-Chloro-2-(pyrimidin-5-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

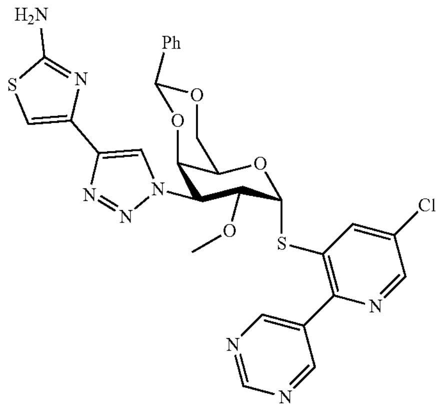

To a solution of 5-chloro-2-(pyrimidin-5-yl)pyridin-3-yl 3-azido-4,6-O-benzylidene-3-deoxy-2-O-methyl-1-thio-α-D-galactopyranoside (130 mg, 0.25 mmol) and 4-(2-trimethylsilylethynyl)thiazol-2-amine (59.7 mg, 0.30 mmol) in DMF (3 mL) (+)-sodium L-ascorbate (100 mg, 0.51 mmol) and copper (II) sulfate pentahydrate (31.6 mg, 0.13 mmol) were added and the mixture was stirred overnight at rt. The mixture was purified by prep HPLC [MeCN/$H_2O$ (10 mmol/L $NH_4HCO_3$), X-Select 10 μm 19*250 mm, 20 mL/min, UV 254] to give the product (70 mg, 43%). ESI-MS m/z calcd for $[C_{28}H_{25}ClN_8O_4S_2]$ $[M+H]^+$: 637.1; found: 637.2. $^1H$ NMR (400 MHz, DMSO-$d_6$) δ 9.32 (s, 1H), 9.15 (s, 2H), 8.74 (s, 1H), 8.41 (s, 1H), 8.12 (s, 1H), 7.37 (s, 5H), 7.04 (s, 2H), 6.88 (s, 1H), 6.54 (d, J=2.8 Hz, 1H), 5.57 (s, 1H), 5.01 (d, J=10.8 Hz, 1H), 4.69 (d, J=7.6 Hz, 1H), 4.49 (s, 1H), 4.15-3.74 (m, 3H), 3.17 (s, 3H).

Intermediate 22

5-Chloro-2-(pyridin-4-yl)pyridin-3-yl 3-azido-4,6-O-benzylidene-3-deoxy-2-O-methyl-1-thio-α-D-galactopyranoside

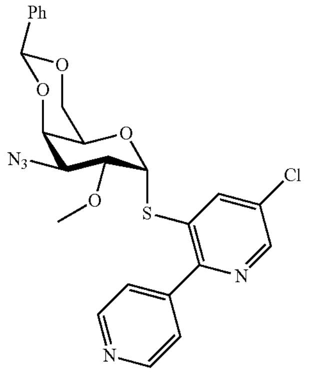

To a solution of 2-bromo-5-chloropyridin-3-yl 3-azido-4,6-O-benzylidene-3-deoxy-2-O-methyl-1-thio-α-D-galactopyranoside (180 mg, 0.35 mmol) in 1,4-dioxane (4.0 mL), 4-(4,4,5,5-tetramethyl-1,3,2-dioxaborolan-2-yl)pyridine (144 mg, 0.70 mmol), $K_2CO_3$ (145 mg, 1.05 mmol), bis(triphenylphosphine)palladium(II) chloride (12.3 mg, 0.018 mmol) and $H_2O$ (0.5 mL) were added and the mixture was stirred 1 h at 100° C. in a microwave reactor. The mixture was concentrated, dissolved in EtOAc (100 mL) and washed with water (80 mL) and brine (80 mL). The organic phase was dried over $Na_2SO_4$, concentrated and purified by column chromatography (PE/EtOAc=10/1~2/1, Silica-CS 12 g, 20 mL/min, silica gel, UV 254) to afford the product (130 mg, 73%). ESI-MS m/z calcd for [$C_{24}H_{22}ClN_5O_4S$] [M+H]$^+$: 512.1; found: 511.9. $^1$H NMR (400 MHz, Chloroform-d) δ 8.55 (d, J=2.0 Hz, 1H), 8.10 (d, J=2.0 Hz, 1H), 7.72-7.62 (m, 1H), 7.58-7.31 (m, 8H), 5.93 (d, J=5.2 Hz, 1H), 5.59 (s, 1H), 4.26 (d, J=2.4 Hz, 1H), 4.19 (dd, J=10.4, 5.2 Hz, 1H), 4.16-4.09 (m, 1H), 4.07-4.01 (m, 1H), 3.81-3.75 (m, 1H), 3.63 (dd, J=10.8, 2.4 Hz, 1H), 3.43 (s, 3H).

5-Chloro-2-(pyridin-4-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

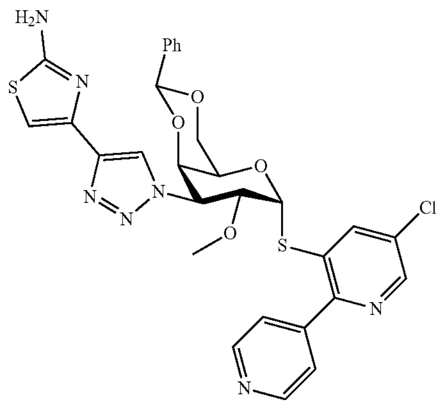

To a solution of 5-chloro-2-(pyridin-4-yl)pyridin-3-yl 3-azido-4,6-O-benzylidene-3-deoxy-2-O-methyl-1-thio-α-D-galactopyranoside (80 mg, 0.16 mmol) in DMF (4 mL) 4-(2-trimethylsilylethynyl)thiazol-2-amine (36.8 mg, 0.19 mmol), (+)-sodium L-ascorbate (31.0 mg, 0.16 mmol), copper (II) sulfate pentahydrate (39.0 mg, 0.16 mmol) and CsF (23.7 mg, 0.16 mmol) were added and the mixture was stirred overnight at rt. The mixture was filtered, and the filtrate was purified by prep HPLC [MeCN/$H_2O$ (0.01% TFA), X-Select 10 μm 19*250 mm, 20 mL/min, UV 254] to give the product (60 mg, 60%). ESI-MS m/z calcd for [$C_{29}H_{26}ClN_7O_4S_2$] [M+H]$^+$: 636.1; found: 636.1. $^1$H NMR (400 MHz, Methanol-$d_4$) δ 8.68 (d, J=2.0 Hz, 1H), 8.43 (d, J=2.0 Hz, 1H), 8.37-8.28 (m, 1H), 8.38-7.99 (m, 3H), 7.49-7.30 (m, 6H), 7.11-6.93 (m, 1H), 6.42-6.25 (m, 1H), 5.55 (s, 1H), 5.30-5.08 (m, 1H), 4.79-4.49 (m, 2H), 4.31-3.90 (m, 3H), 3.25 (s, 3H).

Intermediate 23

5-Chloro-2-(pyridin-3-yl)pyridin-3-yl 3-azido-4,6-O-benzylidene-3-deoxy-2-O-methyl-1-thio-α-D-galactopyranoside

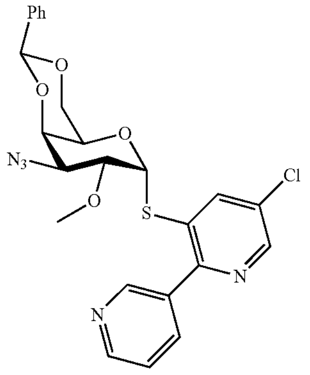

To a solution of 2-bromo-5-chloropyridin-3-yl 3-azido-4,6-O-benzylidene-3-deoxy-2-O-methyl-1-thio-α-D-galactopyranoside (320 mg, 0.62 mmol) in DMF (5 mL) 3-pyridylboronic acid (153 mg, 1.25 mmol), bis(triphenylphosphine)palladium(II) chloride (91 mg, 0.013 mmol) and $K_2CO_3$ (172 mg, 1.25 mmol) were added and the mixture was stirred 6 h at rt. The mixture was concentrated and purified by column chromatography (DCM/MeOH=10/1, Silica-CS 12 g, 20 mL/min, silica gel, UV 254) to give the product (150 mg, 47%). ESI-MS m/z calcd for [$C_{24}H_{22}ClN_5O_4S$] [M+H]$^+$: 512.1, found: 512.0. $^1$H NMR (400 MHz, DMSO-$d_6$) δ 8.90 (s, 1H), 8.65 (d, J=3.6 Hz, 1H), 8.47 (d, J=2.0 Hz, 1H), 8.12 (d, J=8.0 Hz, 1H), 8.02 (d, J=2.4 Hz, 1H), 7.52-7.49 (m, 1H), 7.43-7.39 (m, 2H), 7.33-7.28 (m, 3H), 5.87 (d, J=4.8 Hz, 1H), 5.52 (s, 1H), 4.19 (d, J=2.8 Hz, 1H), 4.13-4.04 (m, 2H), 3.99 (d, J=12.8 Hz, 1H), 3.72 (d, J=4.4 Hz, 1H), 3.57 (dd, J=10.8, 3.2 Hz, 1H), 3.36 (s, 3H).

5-Chloro-2-(pyridin-3-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

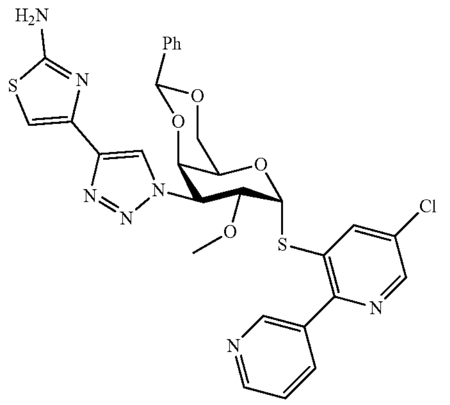

To a solution of 5-chloro-2-(pyridin-3-yl)pyridin-3-yl 3-azido-4,6-O-benzylidene-3-deoxy-2-O-methyl-1-thio-α-D-galactopyranoside (72 mg, 0.14 mmol) in DMF (2 mL) 4-(2-trimethylsilylethynyl)thiazol-2-amine (30.4 mg, 0.16 mmol), (+)-sodium L-ascorbate (14.0 mg, 0.07 mmol) and copper (II) sulfate pentahydrate (17.6 mg, 0.07 mmol) were added and the mixture was stirred overnight at rt. The mixture was filtered and purified by column chromatography (DCM/MeOH=60/1~20/1, Silica-CS 12 g, 20 mL/min, silica gel, UV 254) to give the product (73 mg, 82%). ESI-MS m/z calcd for [$C_{29}H_{26}ClN_7O_4S_2$] [M+H]$^+$: 636.1, found: 636.0. $^1$H NMR (400 MHz, Methanol-$d_4$) δ 8.50 (s, 1H), 8.24 (s, 1H), 8.09-8.04 (m, 2H), 7.81 (s, 1H), 7.60-7.40 (bs, 1H), 7.27-7.21 (m, 6H), 6.97-6.69 (m, 1H), 6.09 (d, J=2.8 Hz, 1H), 5.39 (s, 1H), 4.99 (s, 1H), 4.62-4.39 (m, 2H), 3.99-3.88 (m, 3H), 3.08 (s, 3H).

Intermediate 24

5-Chloro-2-[1-(N-tert-butoxycarbonyl)-1,2,3,6-tetrahydropyridin-4-yl]pyridin-3-yl 3-azido-4,6-O-benzylidene-3-deoxy-2-O-methyl-1-thio-α-D-galactopyranoside

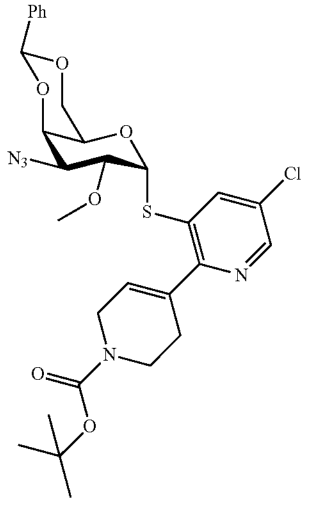

To a solution of 2-bromo-5-chloro-3-pyridin-3-yl 3-azido-4,6-O-benzylidene-3-deoxy-2-O-methyl-1-thio-α-D-galactopyranoside (400 mg, 0.78 mmol) in 1,4-dioxane (10 mL), tert-butyl 4-(4,4,5,5-tetramethyl-1,3,2-dioxaborolan-2-yl)-3,6-dihydro-2H-pyridine-1-carboxylate (361 mg, 1.17 mmol), $K_2CO_3$ (215 mg, 1.56 mmol), bis(triphenylphosphine)palladium(II) chloride (546 mg, 0.78 mmol) and $H_2O$ (1 mL) were added and the mixture was stirred 1 h at 100° C. in a microwave reactor. The mixture was concentrated, dissolved in EtOAc (100 mL) and washed with water (80 mL) and brine (80 mL). the organic phase was dried over $Na_2SO_4$, concentrated and purified by column chromatography (PE/EtOAc=10/1~3/1, Silica-CS 12 g, 20 mL/min, silica gel, UV 254) to give the product (220 mg, 46%). ESI-MS m/z calcd for [$C_{29}H_{34}ClN_5O_6S$] [M+Na]$^+$: 638.2; found: 637.9. $^1$H NMR (400 MHz, $CDCl_3$) δ 8.29 (d, J=2.0 Hz, 1H), 7.89 (d, J=2.0 Hz, 1H), 7.48-7.45 (m, 1H), 7.35-7.27 (m, 4H), 5.99-5.82 (m, 2H), 5.56 (s, 1H), 4.26 (d, J=3.2 Hz, 1H), 4.20 (dd, J=10.4, 5.2 Hz, 1H), 4.16-4.11 (m, 1H), 4.09-4.03 (m, 2H), 3.92 (d, J=11.6 Hz, 1H), 3.71-3.57 (m, 4H), 3.45 (s, 3H), 2.57-2.41 (m, 2H), 1.44 (s, 9H).

5-Chloro-2-(1,2,3,6-tetrahydropyridin-4-yl)pyridin-3-yl 3-azido-3-deoxy-2-O-methyl-1-thio-α-D-galactopyranoside

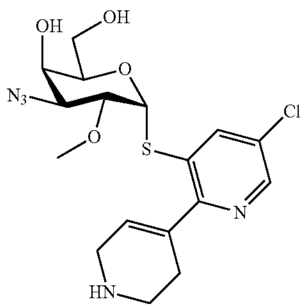

To a solution of 5-chloro-2-[1-(N-tert-butoxycarbonyl)-1,2,3,6-tetrahydropyridin-4-yl]pyridin-3-yl 3-azido-4,6-O-benzylidene-3-deoxy-2-O-methyl-1-thio-α-D-galactopyranoside (400 mg, 0.65 mmol) in DCM (15 mL) TFA (2.41 mL, 32.5 mmol) was added. The mixture was stirred 2 h at rt and $Et_3N$ (4 mL) was added at 0° C. The mixture was concentrated and purified by prep HPLC [MeCN/$H_2O$ (0.01% TFA), X-Select 10 μm 19*250 mm, 20 mL/min, UV 254] to give the product (97 mg, 35%). ESI-MS m/z calcd for [$C_{17}H_{22}ClN_5O_4S$] [M+H]$^+$: 428.1; found: 428.0. $^1$H NMR (400 MHz, $CD_3OD$) δ 8.35 (d, J=2.0 Hz, 1H), 8.25 (d, J=2.0 Hz, 1H), 6.09 (d, J=5.2 Hz, 1H), 6.05-5.95 (m, 1H), 4.16-4.04 (m, 2H), 4.00 (d, J=2.4 Hz, 1H), 3.73-3.55 (m, 5H), 3.51 (s, 3H), 3.18-3.13 (m, 2H), 2.61-2.48 (m, 2H).

Intermediate 25

5-Chloro-2-cyanopyridin-3-yl 3-[4-(2-aminothiazol-4-yl)-1H-1,2,3-triazol-1-yl]-4,6-O-benzylidene-3-deoxy-2-O-(3,5-difluoro-4-(4-methoxybenzyloxy)benzyl)-1-thio-α-D-galactopyranoside

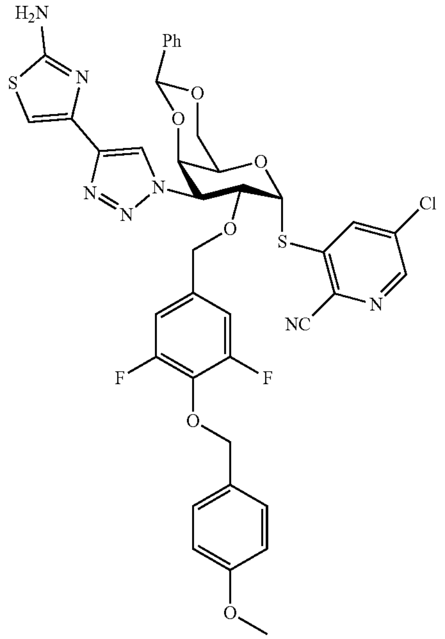

To a solution of 5-chloro-2-cyanopyridin-3-yl 3-azido-4,6-O-benzylidene-3-deoxy-2-O-(3,5-difluoro-4-(4-methoxybenzyloxy)benzyl)-1-thio-α-D-galactopyranoside (150 mg, 0.16 mmol) in DMF (5 mL) 4-(2-trimethylsilylethynyl)thiazol-2-amine (94 mg, 0.48 mmol), copper (II) sulfate pentahydrate (40.0 mg, 0.16 mmol) and (+)-sodium L-ascorbate (32 mg, 0.16 mmol) were added and the mixture was stirred 6 h at rt. The mixture was partitioned between water (50 mL) and DCM (50 mL) and the aqueous phase was extracted with DCM (2×50 mL). The combined organic layers were washed with water (50 mL) and brine (50 mL), dried over $Na_2SO_4$, concentrated and purified by column chromatography (PE/EtOAc=10/1~1/1, Silica-CS 12 g, 20 mL/min, silica gel, UV 254) to afford the product (60 mg, 45%). ESI-MS m/z calcd for $[C_{39}H_{32}ClF_2N_7O_6S_2]$ $[M+H]^+$: 832.2; found: 832.0. $^1H$ NMR (400 MHz, Chloroform-d) δ 8.51 (d, J=2.0 Hz, 1H), 8.36 (s, 1H), 7.96 (d, J=2.0 Hz, 1H), 7.34-7.22 (m, 6H), 6.83-6.76 (m, 6H), 6.18 (d, J=4.8 Hz, 1H), 5.41-5.35 (m, 2H), 5.01-4.96 (m, 3H), 4.66-4.55 (m, 2H), 4.42-4.36 (m, 2H), 4.25 (d, J=12.8 Hz, 1H), 4.10 (d, J=13.2 Hz, 1H), 3.75 (s, 3H).

Intermediate 26

2-Bromo-5-chloropyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

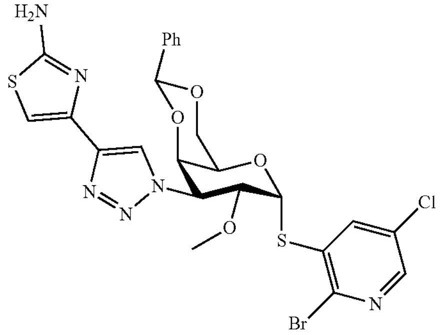

To a solution of 2-bromo-5-chloropyridin-3-yl 3-azido-4,6-O-benzylidene-3-deoxy-2-O-methyl-1-thio-α-D-galactopyranoside (300 mg, 0.58 mmol) in DMF (3 mL) 4-(2-trimethylsilylethynyl)thiazol-2-amine (230 mg, 1.13 mmol), copper (II) sulfate pentahydrate (73.0 mg, 0.29 mmol) and (+)-sodium L-ascorbate (58 mg, 0.29 mmol) were added and the mixture was stirred 3 h at rt. The mixture was partitioned between water (50 mL) and DCM (50 mL) and the aqueous phase was extracted with DCM (2×50 mL). The combined organic layers were washed with water (50 mL) and brine (50 mL), dried over $Na_2SO_4$, concentrated and purified by column chromatography (PE/EA=10/1~1/1, Silica-CS 20 g, 20 mL/min, silica gel, UV 254) to give the product (260 mg, 65%). ESI-MS m/z calcd for $[C_{24}H_{22}BrClN_6O_4S_2]$ $[M+H]^+$: 637.0; found: 637.1. $^1H$ NMR (400 MHz, DMSO-$d_6$) δ 8.14 (d, J=2.4 Hz, 1H), 7.99 (s, 2H), 7.19-7.16 (m, 5H), 6.84 (s, 2H), 6.70 (s, 1H), 6.66 (d, J=5.2 Hz, 1H), 5.39 (s, 1H), 5.00 (dd, J=11.6, 3.2 Hz, 1H), 4.61 (dd, J=11.6, 5.2 Hz, 1H), 4.37 (d, J=2.4, 1H), 3.97 (s, 1H), 3.90-3.73 (m, 2H), 3.11 (s, 3H).

5-Chloro-2-(pyridin-2-yl)pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

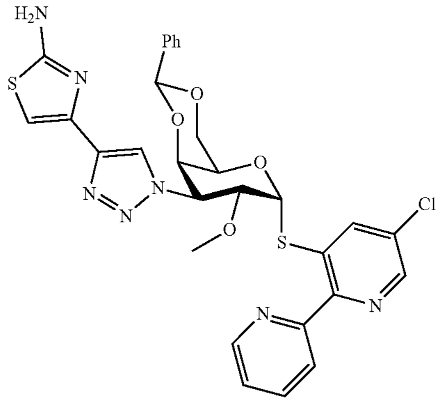

To a solution of 2-bromo-5-chloropyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (130 mg, 0.20 mmol) and tributyl-(2-pyridyl)stannane (75.0 mg, 0.20 mmol) in DMF (4.0 mL) bis(triphenylphosphine)palladium(II) chloride (14.3 mg, 0.020 mmol) was added and the mixture was stirred 3 h at 110° C. under a nitrogen atmosphere. The mixture was concentrated and purified by prep HPLC [MeCN/$H_2O$ (10 mmol/L $NH_4HCO_3$), X-Select 10 μm 19*250 mm, 20 mL/min, UV 254] to give the product (35.0 mg, 27%). ESI-MS m/z calcd for [$C_{29}H_{26}ClN_7O_4S_2$] [M+H]$^+$: 636.1; found: 635.5. $^1$H NMR (400 MHz, Chloroform-d) δ 8.65 (s, 1H), 8.34 (s, 1H), 8.18 (s, 1H), 8.14 (s, 1H), 7.86 (d, J=8.0 Hz, 1H), 7.75 (t, J=7.6 Hz, 1H), 7.26 (m, 7H), 6.15 (s, 1H), 5.37 (s, 1H), 5.31 (dd, J=11.2, 2.8 Hz, 1H), 4.54 (dd, J=11.2, 5.2 Hz, 1H), 4.43 (s, 1H), 4.31 (s, 1H), 4.24 (d, J=12.8 Hz, 1H), 4.08 (d, J=12.8 Hz, 1H), 3.18 (s, 3H).

Intermediate 27

2-Bromo-5-chloropyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside

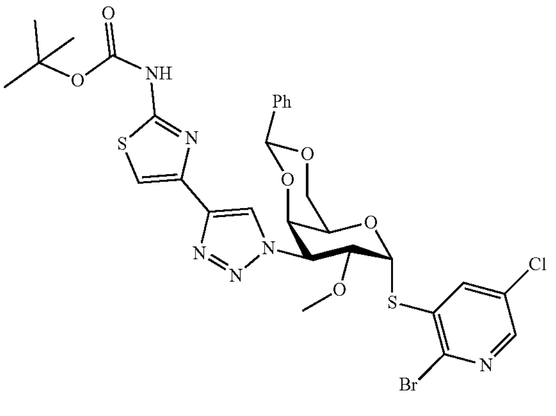

To a solution of 2-bromo-5-chloropyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside (260 mg, 0.38 mmol) in DCM (20 mL) 4-dimethylaminopyridine (5.0 mg, 0.038 mmol), di-tert-butyl dicarbonate (166 mg, 0.76 mmol) and $Et_3N$ (154 mg, 1.52 mmol) were added and the mixture was stirred 3 h at rt. The mixture was evaporated and purified by column chromatography (PE/EtOAc=10/1~1/1, Silica-CS 20 g, 20 mL/min, silica gel, UV 254) to give the product (180 mg, 58%). ESI-MS m/z calcd for [$C_{29}H_{30}BrClN_6O_6S_2$] [M+H]$^+$: 737.1; found: 736.9. $^1$H NMR (400 MHz, DMSO-$d_6$) δ 11.62 (s, 1H), 8.36 (d, J=2.4 Hz, 1H), 8.29 (s, 1H), 8.19 (d, J=2.4 Hz, 1H), 7.46 (s, 1H), 7.41-7.36 (m, 5H), 6.87 (d, J=5.2 Hz, 1H), 5.61 (s, 1H), 5.24 (dd, J=11.6, 3.2 Hz, 1H), 4.84 (dd, J=11.6, 5.2 Hz, 1H), 4.60 (d, J=3.6, 1H), 4.19 (s, 1H), 4.12-3.96 (m, 2H), 3.34 (s, 3H), 1.47 (s, 9H).

5-Chloro-2-(oxazol-2-yl)pyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside

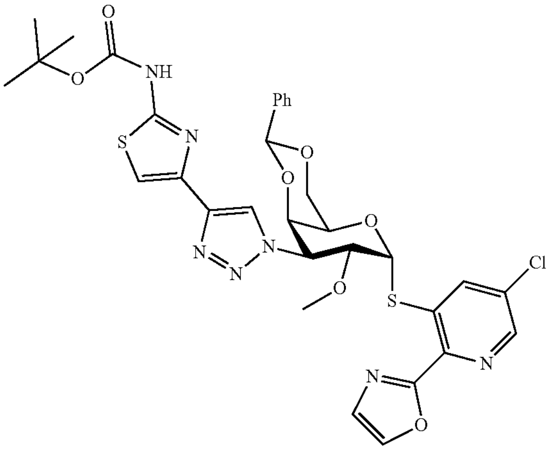

To a solution of 2-bromo-5-chloropyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside (180 mg, 0.22 mmol) in DMF (3 mL) tributyl(oxazol-2-yl)stannane (236 mg, 0.66 mmol), $Pd(PPh_3)_4$ (46 mg, 0.066 mmol) and CsF (67 mg, 0.44 mmol) were added and the mixture was stirred 3 h at 60° C. under a nitrogen atmosphere. The mixture was evaporated and purified by column chromatography (PE/EtOAc=10/1~1/2, Silica-CS 20 g, 20 mL/min, silica gel, UV 254) to give the product (120 mg, 53%). ESI-MS m/z calcd for [$C_{32}H_{32}ClN_7O_7S_2$] [M+H]$^+$: 726.1; found: 726.1. $^1$H NMR (400 MHz, DMSO-$d_6$) δ 11.62 (s, 1H), 8.62 (d, J=2.0 Hz, 1H), 8.39 (d, J=2.0 Hz, 1H), 8.38 (s, 1H), 8.27 (s, 1H), 7.54-7.53 (m, 1H), 7.46 (s, 1H), 7.41-7.36 (m, 5H), 6.84 (d, J=5.2 Hz, 1H), 5.60 (s, 1H), 5.24 (dd, J=11.6, 3.2 Hz, 1H), 4.81 (dd, J=11.6, 5.2 Hz, 1H), 4.57 (d, J=3.2, 1H), 4.15 (s, 1H), 4.06-3.94 (m, 2H), 3.30 (s, 3H), 1.49 (s, 9H).

Intermediate 28

3,4-Dichlorophenyl 3-[4-(2-aminothiazol-4-yl)-1H-1,2,3-triazol-1-yl]-4,6-O-benzylidene-3-deoxy-2-O-methyl-1-thio-α-D-galactopyranoside

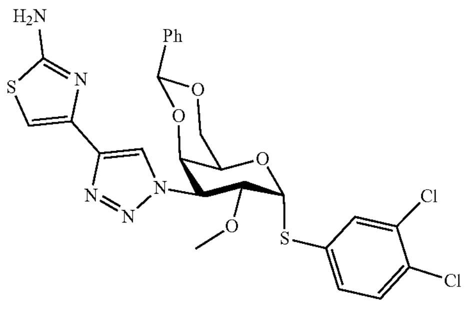

To a solution of 3,4-dichlorophenyl 3-azido-4,6-O-benzylidene-3-deoxy-2-O-methyl-1-thio-α-D-galactopyranoside (100 mg, 0.21 mmol) and 4-(2-trimethylsilylethynyl)thiazol-2-amine (54.5 mg, 0.28 mmol) in DMF (3 mL) (+)-sodium L-ascorbate (55.0 mg, 0.28 mmol) and copper (II) sulfate pentahydrate (26.7 mg, 0.11 mmol) were added and the mixture was stirred overnight at rt. The mixture was purified by prep HPLC [MeCN/$H_2O$ (10 mmol/L $NH_4HCO_3$), X-Select 10 μm 19*250 mm, 20 mL/min, UV 254] to give the product (90 mg, 71%). ESI-MS m/z calcd for [$C_{25}H_{23}Cl_2N_5O_4S_2$] $[M+H]^+$: 592.1; found: 592.0. $^1H$ NMR (400 MHz, DMSO-$d_6$) δ 8.14 (s, 1H), 7.87 (d, J=2.0 Hz, 1H), 7.64 (d, J=8.4 Hz, 1H), 7.55 (dd, J=8.4, 2.0 Hz, 1H), 7.38 (m, 5H), 7.05 (s, 2H), 6.90 (s, 1H), 6.57 (d, J=5.2 Hz, 1H), 5.60 (s, 1H), 5.12 (dd, J=11.2, 2.8 Hz, 1H), 4.72 (dd, J=11.2, 5.2 Hz, 1H), 4.57 (d, J=2.8 Hz, 1H), 4.26 (s, 1H), 4.12 (d, J=12.4 Hz, 1H), 3.95 (d, J=12.4 Hz, 1H), 3.32 (s, 3H).

Intermediate 29

5-Chloro-2-(thiazol-2-yl)pyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside

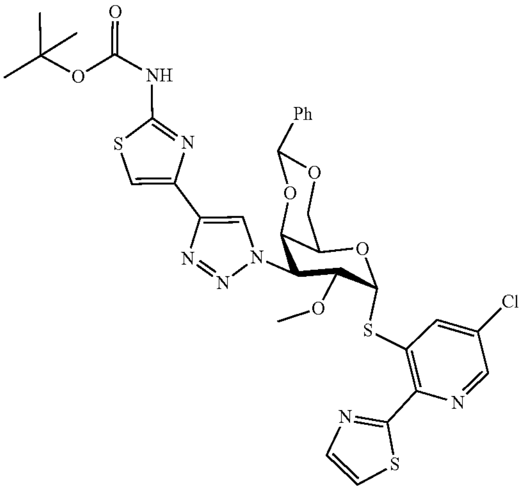

To a solution of 2-bromo-5-chloropyridin-3-yl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside (120 mg, 0.16 mmol) in DMF (5 mL) tributyl(thiazole-2-yl)stannane (122 mg, 0.33 mmol), $Pd(PPh_3)_4$ (34 mg, 0.049 mmol) and CsF (50 mg, 0.33 mmol) were added and the mixture was stirred 3 h at 100° C. under a nitrogen atmosphere. The mixture was evaporated and purified by column chromatography (PE/EtOAc=10/1~1/1, Silica-CS 12 g, 20 mL/min, silica gel, UV 254) to afford the product (50 mg, 21%). ESI-MS m/z calcd for [$C_{32}H_{32}ClN_7O_7S_2$] $[M+H]^+$: 742.1; found: 742.1. $^1H$ NMR (400 MHz, DMSO-$d_6$) δ 11.61 (s, 1H), 8.53 (d, J=2.0 Hz, 1H), 8.29 (s, 1H), 8.23-8.21 (m, 2H), 7.47 (d, J=2.8 Hz, 1H), 7.39-7.38 (m, 5H), 7.14 (d, J=5.2 Hz, 1H), 6.76 (d, J=5.2 Hz, 1H), 5.59 (s, 1H), 5.21 (dd, J=11.6, 2.8 Hz, 1H), 4.86 (m, 1H), 4.59 (d, J=2.8, 1H), 4.20 (s, 1H), 4.10-4.08 (m, 1H), 3.95-3.92 (m, 1H), 3.37 (s, 3H), 1.49 (s, 9H).

Intermediate 30

Tert-Butyl N-[4-(2-trimethylsilylethynyl)thiazol-2-yl]carbamate

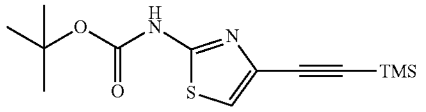 [SMILES: CC(C)(C)OC(=O)Nc1nc(C#C[Si](C)(C)C)cs1]

To a solution of 4-(2-trimethylsilylethynyl)thiazol-2-amine (200 mg, 1.02 mmol) in DCM (30 mL) di-tert-butyl dicarbonate (445 mg, 2.04 mmol), $Et_3N$ (0.568 mL, 4.07 mmol) and 4-dimethylaminopyridine (12.4 mg, 0.10 mmol) were added and the mixture was stirred 5 h at rt. Water (100 mL) was added and the mixture was extracted with diethyl ether (3×100 mL). The combined organic layers were washed with brine (3×100 mL), dried over $Na_2SO_4$, concentrated and purified by column chromatography (PE/EA=1/0~10/1, Silica-CS 40 g, 40 mL/min, silica gel, UV 254) to give the product (230 mg, 74%). ESI-MS m/z calcd for [$C_{13}H_{20}N_2O_2SSi$] $[M+H]^+$: 297.1; found: 297.1. $^1H$ NMR (400 MHz, Chloroform-d) δ 7.99 (s, 1H), 7.07 (s, 1H), 1.53 (s, 9H), 0.23 (s, 9H).

3-Chloro-4-(trifluoromethyl)phenyl 2,4,6-tri-O-acetyl-3-azido-3-deoxy-1-thio-α-D-galactopyranoside

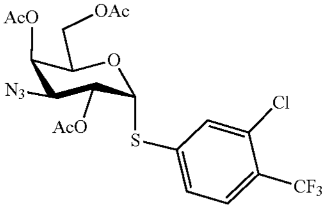

To a solution of 2,4,6-tri-O-acetyl-3-azido-β-deoxy-β-D-galactopyranosyl chloride (1.10 g, 2.20 mmol) and 3-chloro-4-trifluoromethylbenzenethiol (562 mg, 2.64 mmol) in DMF (15 mL) cesium carbonate (1.43 g, 4.4 mmol) was added and the mixture was stirred 6 h at rt. Water (200 mL) was added and the mixture was extracted with EtOAc (3×50 mL). The organic layers were washed with brine (3×100 mL), dried over $Na_2SO_4$, concentrated and purified by column chromatography (PE/EtOAc=10/1~1/1, Silica-CS 20 g, 30 mL/min, silica gel, UV 254) to give the product (0.6 g, 51%). ESI-MS m/z calcd for [$C_{19}H_{19}ClF_3N_3O_7S$] $[M+NH_4]^+$: 543.1; found: 543.0. $^1H$ NMR (400 MHz, Methanol-$d_4$) δ 7.73 (d, J=0.8 Hz, 1H), 7.71 (d, J=8.4 Hz, 1H), 7.56 (dd, J=8.4, 1.2 Hz, 1H), 6.20 (d, J=5.6 Hz, 1H), 5.51 (d, J=2.8 Hz, 1H), 5.27 (dd, J=11.2, 5.6 Hz, 1H), 4.63 (dd, J=8.0, 4.4 Hz, 1H), 4.23 (dd, J=11.2, 3.6 Hz, 1H), 4.12-3.97 (m, 2H), 2.14 (s, 3H), 2.13 (s, 3H), 1.86 (s, 3H).

3-Chloro-4-(trifluoromethyl)phenyl 3-azido-3-deoxy-1-thio-α-D-galactopyranoside

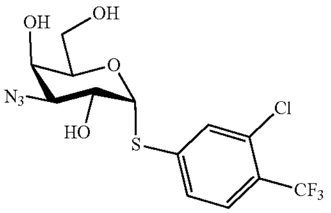

To a solution of 3-chloro-4-(trifluoromethyl)phenyl 2,4,6-tri-O-acetyl-3-azido-3-deoxy-1-thio-α-D-galactopyranoside (0.60 g, 1.12 mmol) in MeOH (20 mL) solid sodium methoxide (0.03 g, 0.56 mmol) was added and the mixture was stirred 2 h at rt. The mixture was evaporated and purified by prep HPLC [MeCN/$H_2O$ (10 mmol/L $NH_4HCO_3$), X-Select 10 μm 19*250 mm, 20 mL/min, UV 254] to give the product (430 mg, 95%). ESI-MS m/z calcd for [$C_{13}H_{13}ClF_3N_3O_4S$] [M+$NH_4$]$^+$: 417.0; found: 417.0. $^1$H NMR (400 MHz, Methanol-$d_4$) δ 7.77 (s, 1H), 7.66-7.60 (m, 2H), 5.86 (d, J=5.2 Hz, 1H), 4.42-4.38 (m, 1H), 4.20-4.17 (m, 1H), 4.03 (d, J=2.0 Hz, 1H), 3.70-3.61 (m, 2H), 3.51 (dd, J=10.8, 2.8 Hz, 1H).

3-Chloro-4-(trifluoromethyl)phenyl 3-azido-4,6-O-benzylidene-3-deoxy-1-thio-α-D-galactopyranoside

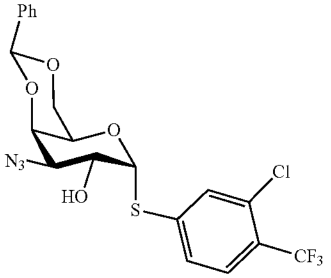

To a solution of 3-chloro-4-(trifluoromethyl)phenyl 3-azido-3-deoxy-1-thio-α-D-galactopyranoside (430 mg, 1.06 mmol) in DMF (10 mL) benzaldehyde dimethylacetal (484 mg, 3.18 mmol) was added followed by D(+)-10-camphorsulfonic acid (73.8 mg, 0.32 mmol) and the mixture was stirred 2 h at 50° C. Aqueous $NaHCO_3$ (100 mL) was added to the mixture. The precipitate was collected and dried in vacuo to afford the product (350 mg, 66%). ESI-MS m/z calcd for [$C_{20}H_{17}ClF_3N_3O_4S$] [M+H]$^+$: 488.1; found: 488.0. $^1$H NMR (400 MHz, Methanol-$d_4$) δ 7.72 (s, 1H), 7.68 (d, J=8.4 Hz, 1H), 7.57 (dd, J=8.4, 0.8 Hz, 1H), 7.50-7.48 (m, 2H), 7.37-7.34 (m, 3H), 6.01 (d, J=5.2 Hz, 1H), 5.66 (s, 1H), 4.53 (dd, J=10.8, 5.2 Hz, 1H), 4.43 (d, J=2.8 Hz, 1H), 4.17-4.03 (m, 3H), 3.62 (dd, J=10.8, 3.2 Hz, 1H).

3-Chloro-4-(trifluoromethyl)phenyl 3-azido-4,6-O-benzylidene-3-deoxy-2-O-methyl-1-thio-α-D-galactopyranoside)

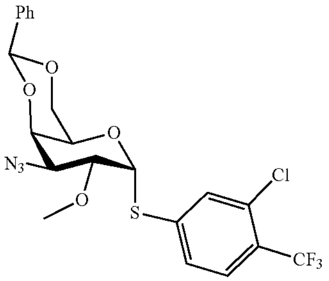

To a solution of 3-chloro-4-(trifluoromethyl)phenyl 3-azido-4,6-O-benzylidene-3-deoxy-1-thio-α-D-galactopyranoside (350 mg, 0.70 mmol) in DMF (15 mL) cesium carbonate (455 mg, 1.40 mmol) was added followed by iodomethane (198 mg, 1.40 mmol) and the mixture was stirred 6 h at rt. Water (100 mL) was added, and the mixture was extracted with EtOAc (3×50 mL). The combined organic layers were washed with brine (3×50 mL), dried over $Na_2SO_4$, concentrated and purified by column chromatography (PE/EtOAc=10/1~1/1, Silica-CS 20 g, 20 mL/min, silica gel, UV 254) to give the product (310 mg, 86%). ESI-MS m/z calcd for [$C_{21}H_{19}ClF_3N_3O_4S$] [M+H]$^+$: 502.1; found: 502.0. $^1$H NMR (400 MHz, Methanol-$d_4$) δ 7.75 (s, 1H), 7.69 (d, J=8.4 Hz, 1H), 7.59 (d, J=8.0 Hz, 1H), 7.50-7.49 (m, 2H), 7.36-7.35 (m, 3H), 6.37 (d, J=5.2 Hz, 1H), 5.65 (s, 1H), 4.39 (s, 1H), 4.23-4.19 (m, 1H), 4.16-4.03 (m, 3H), 3.73 (dd, J=10.8, 2.8 Hz, 1H), 3.52 (s, 3H).

3-Chloro-4-(trifluoromethyl)phenyl 4,6-O-benzylidene-3-[4-(N-tert-butoxycarbonyl-2-aminothiazol-4-yl)-1H-1,2,3-triazol-1-yl]-3-deoxy-2-O-methyl-1-thio-α-D-galactopyranoside

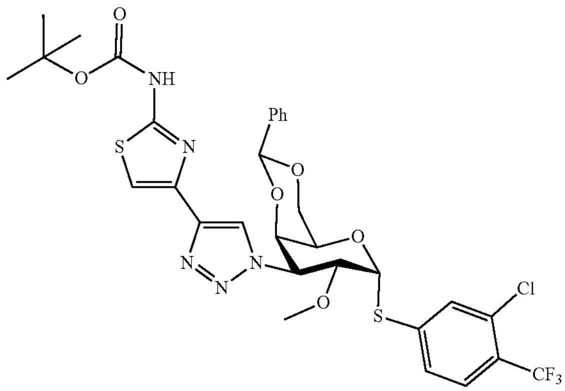

To a solution of 3-chloro-4-(trifluoromethyl)phenyl 3-azido-4,6-O-benzylidene-3-deoxy-2-O-methyl-1-thio-α-D-galactopyranoside (310 mg, 0.60 mmol) in DMF (10 mL) tert-butyl N-[4-(2-trimethylsilylethynyl)thiazol-2-yl]carbamate (214 mg, 0.72 mol), (+)-sodium L-ascorbate (60 mg, 0.3 mmol) and copper (II) sulfate pentahydrate (75.0 mg, 0.30 mmol) were added and the mixture was stirred 3 h at rt. The mixture was partitioned between water (50 mL) and DCM (50 mL) and the aqueous phase was extracted with DCM (2×50 mL). The organic layers were washed with water (50 mL) and brine (50 mL), dried over $Na_2SO_4$, concentrated and purified by column chromatography (PE/EtOAc=10/1~1/1, Silica-CS 20 g, 20 mL/min, silica gel, UV 254) to give the product (260 mg, 58%). ESI-MS m/z calcd for $[C_{31}H_{31}ClF_3N_5O_6S_2][M+H]^+$: 726.1; found: 726.1. $^1H$ NMR (400 MHz, DMSO-$d_6$) δ 11.58 (s, 1H), 8.23 (s, 1H), 7.90 (s, 1H), 7.81 (d, J=8.4 Hz, 1H), 7.67 (d, J=9.2 Hz, 1H), 7.43 (s, 1H), 7.38-7.37 (m, 5H), 6.76 (d, J=5.2 Hz, 1H), 5.59 (s, 1H), 5.16 (dd, J=11.6, 3.2 Hz, 1H), 4.76 (dd, J=11.6, 5.2 Hz 1H), 4.57 (d, J=3.2 Hz, 1H), 4.22 (s, 1H), 4.11-3.95 (m, 2H), 3.30 (s, 3H), 1.47 (s, 9H).

Intermediate 31

3-Chlorophenyl 2,4,6-tri-O-acetyl-3-azido-3-deoxy-1-thio-α-D-galactopyranoside

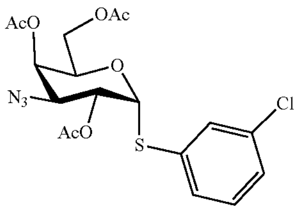

To a solution of 2,4,6-tri-O-acetyl-3-azido-3-deoxy-β-D-galactopyranosyl chloride (0.9 g, 2.57 mmol), and 3-chlorobenzenethiol (507 mg, 3.51 mmol) in DMF (20 mL) cesium carbonate (1.26 g, 3.86 mmol) was added and the mixture was stirred 16 h at rt. Water was added (50 mL) and the mixture was extracted with EtOAc (200 mL). The organic layer was washed with brine (80 mL), dried over $Na_2SO_4$, concentrated and purified by column chromatography (PE/EtOAc=10/1~2/1, Silica-CS 12 g, 20 mL/min, silica gel, UV 254) to afford the product (850 mg, 65%). ESI-MS m/z calcd for $[C_{18}H_{20}ClN_3O_7S][M+Na]^+$: 480.1; found: 480.1. $^1H$ NMR (400 MHz, Chloroform-d) δ 7.49-7.45 (m, 1H), 7.35-7.30 (m, 1H), 7.26-7.20 (m, 2H), 5.99 (d, J=5.6 Hz, 1H), 5.47 (d, J=2.4 Hz, 1H), 5.28 (dd, J=11.2, 5.6 Hz, 1H), 4.69-4.58 (m, 1H), 4.17-4.05 (m, 1H), 4.05-4.00 (m, 1H), 3.99-3.92 (m, 1H), 2.18 (s, 3H), 2.16 (s, 3H), 1.99 (s, 3H).

3-Chlorophenyl 3-azido-3-deoxy-1-thio-α-D-galactopyranoside

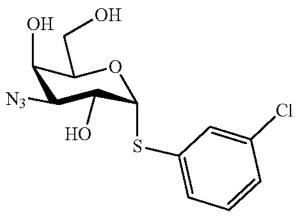

To a solution of 3-chlorophenyl 2,4,6-tri-O-acetyl-3-azido-3-deoxy-1-thio-α-D-galactopyranoside (850 mg, 1.86 mmol) in MeOH (10 mL) NaOMe (100 mg) was added and the mixture was stirred 2 h at rt. The mixture was neutralized with acidic resin, filtered and concentrated. The residue was purified by column chromatography (PE/EtOAc=1/1~1/2, Silica-CS 4 g, 12 mL/min, silica gel, UV 254) to give the product (600 mg, 97%). ESI-MS m/z calcd for $[C_{12}H_{14}ClN_3O_4S]$ $[M+Na]^+$: 354.0; found: 354.1. $^1H$ NMR (400 MHz, Methanol-$d_4$) δ 7.61-7.57 (m, 1H), 7.51-7.46 (m, 1H), 7.31-7.24 (m, 2H), 5.66 (d, J=5.6 Hz, 1H), 4.38 (dd, J=10.8, 5.6 Hz, 1H), 4.28 (t, J=6.0 Hz, 1H), 4.05 (d, J=2.0 Hz, 1H), 3.67 (ddd, J=18.0, 11.2, 6.0 Hz, 2H), 3.49 (dd, J=10.8, 2.8 Hz, 1H).

3-Chlorophenyl 3-azido-4,6-O-benzylidene-3-deoxy-1-thio-α-D-galactopyranoside

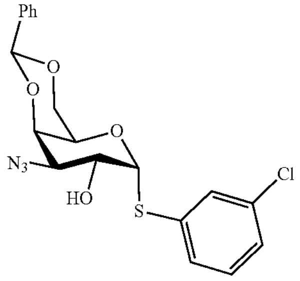

To a solution of 3-chlorophenyl 3-azido-3-deoxy-1-thio-α-D-galactopyranoside (600 mg, 1.81 mmol) in DMF (5 mL) D(+)-10-camphorsulfonic acid (126 mg, 0.54 mmol) and benzaldehyde dimethylacetal (826 mg, 5.43 mmol) were added and the mixture was stirred 2 h at 60° C. The mixture was concentrated and purified by column chromatography (PE/EtOAc=2/1~1/1, Silica-CS 4 g, 12 mL/min, silica gel, UV 254) to give the product (470 mg, 62%). ESI-MS m/z calcd for $[C_{19}H_{18}ClN_3O_4S]$ $[M+H]^+$: 420.1; found: 420.1. $^1H$ NMR (400 MHz, Methanol-$d_4$) δ 7.55 (t, J=1.6 Hz, 1H), 7.53-7.47 (m, 2H), 7.47-7.42 (m, 1H), 7.40-7.25 (m, 5H), 5.81 (d, J=5.2 Hz, 1H), 5.67 (s, 1H), 4.50 (dd, J=10.8, 5.2 Hz, 1H), 4.45 (d, J=2.8 Hz, 1H), 4.21-4.16 (m, 2H), 4.10-4.02 (m, 1H), 3.61 (dd, J=10.8, 3.2 Hz, 1H).

3-Chlorophenyl 3-azido-4,6-O-benzylidene-3-deoxy-2-O-methyl-1-thio-α-D-galactopyranoside

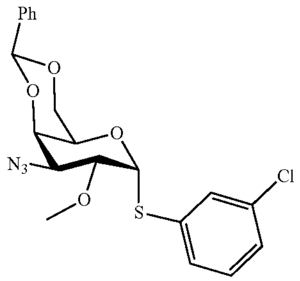

To a solution of 3-chlorophenyl 3-azido-4,6-O-benzylidene-3-deoxy-1-thio-α-D-galactopyranoside (200 mg, 0.42 mmol) in DMF (5 mL) cesium carbonate (207 mg, 0.64 mmol) was added followed by iodomethane (79.1 μL, 1.27 mmol) and the mixture was stirred 16 h at rt. Ice-water was added to the mixture and the precipitate was collected and dried in vacuo to afford the product (160 mg, 87%). ESI-MS m/z calcd for $[C_{20}H_{20}ClN_3O_4S]$ $[M+Na]^+$: 456.1; found: 456.1. $^1H$ NMR (400 MHz, Methanol-$d_4$) δ 7.56 (t, J=1.6 Hz, 1H), 7.53-7.43 (m, 3H), 7.38-7.27 (m, 5H), 6.13 (d, J=5.2 Hz, 1H), 5.65 (s, 1H), 4.40 (d, J=3.2 Hz, 1H), 4.22-4.13 (m, 3H), 4.11-3.98 (m, 1H), 3.71 (dd, J=10.8, 3.2 Hz, 1H), 3.53 (s, 3H).

3-Chlorophenyl 3-[4-(2-aminothiazol-4-yl)-1H-1,2,3-triazol-1-yl]-4,6-O-benzylidene-3-deoxy-2-O-methyl-1-thio-α-D-galactopyranoside

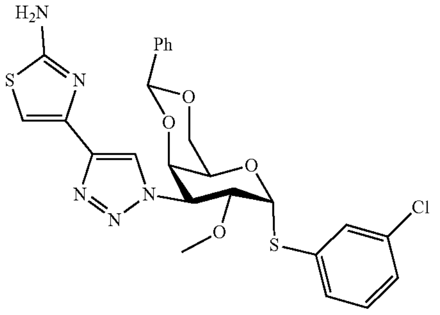

To a solution of 3-chlorophenyl 3-azido-4,6-O-benzylidene-3-deoxy-2-O-methyl-1-thio-α-D-galactopyranoside (100 mg, 0.23 mmol) in DMF (2 mL) 4-(2-trimethylsilylethynyl)thiazol-2-amine (49.8 mg, 0.25 mmol), (+)-sodium L-ascorbate (45.7 mg, 0.23 mmol) and copper (II) sulfate pentahydrate (57.5 mg, 0.23 mmol) were added and the mixture was stirred overnight at rt. Water was added (50 mL) and the mixture was extracted with EtOAc (80 mL). The organic layer was washed with brine (80 mL), dried over $Na_2SO_4$, concentrated and purified by column chromatography (PE/EtOAc=2/1~1/1, Silica-CS 4 g, 12 mL/min, silica gel, UV 254) to give the product (70 mg, 54%). ESI-MS m/z calcd for $[C_{25}H_{24}ClN_5O_4S_2]$ $[M+H]^+$: 558.1; found: 558.1. $^1H$ NMR (400 MHz, Methanol-$d_4$) δ 8.15 (s, 1H), 7.63 (t, J=1.6 Hz, 1H), 7.52 (dt, J=7.2, 1.6 Hz, 1H), 7.46-7.39 (m, 2H), 7.37-7.30 (m, 5H), 6.94 (s, 1H), 6.32 (d, J=5.2 Hz, 1H), 5.57 (s, 1H), 5.24 (dd, J=11.4, 3.2 Hz, 1H), 4.68 (dd, J=11.4, 5.2 Hz, 1H), 4.60 (d, J=2.8 Hz, 1H), 4.39 (s, 1H), 4.28-4.16 (m, 1H), 4.12-4.06 (m, 1H), 3.39 (s, 3H).

Intermediate 32

3,5-Dichloro-4-fluorophenyl 2,4,6-tri-O-acetyl-3-[4-(2-aminothiazol-4-yl)-1H-1,2,3-triazol-1-yl]-3-deoxy-1-thio-α-D-galactopyranoside

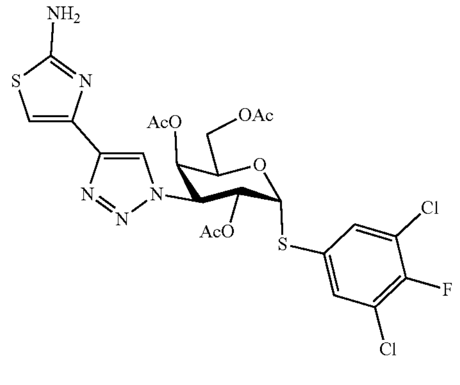

To a solution of 3,5-dichloro-4-fluorophenyl 2,4,6-tri-O-acetyl-3-azido-3-deoxy-1-thio-α-D-galactopyranoside (40 mg, 0.078 mmol) in DMF (3.0 mL) 4-(2-trimethylsilylethynyl)thiazol-2-amine (38.4 mg, 0.20 mmol), CuI (4.48 mg, 0.024 mmol), CsF (23.8 mg, 0.16 mmol) and DIPEA (67.1 μL, 0.39 mmol) were added and the mixture was stirred overnight at rt. Water (10 mL) was added, and the mixture was extracted with EtOAc (2×5 mL). The organic layers were concentrated and purified by column chromatography (EA/PE=1/20~1/1, Silica-CS 12 g, 15 mL/min, silica gel, UV 254) to afford the product (25 mg, 33%). ESI-MS m/z calcd for $[C_{23}H_{22}Cl_2FN_5O_7S_2]$ $[M+H]^+$: 634.0; found: 634.0. $^1H$ NMR (400 MHz, Chloroform-d) δ 7.83 (s, 1H), 7.50 (d, J=6.1 Hz, 2H), 7.10 (s, 1H), 6.11 (d, J=5.5 Hz, 1H), 6.07-5.93 (m, 1H), 5.62 (d, J=2.1 Hz, 1H), 5.36-5.05 (m, 3H), 4.83 (d, J=5.1 Hz, 1H), 4.17-4.07 (m, 2H), 2.07 (d, J=12.4 Hz, 6H), 1.99 (s, 3H).

Intermediate 33

3-Bromo-5-fluoro-2-trifluoromethylpyridine

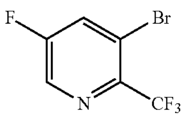

To a solution of 3-bromo-5-fluoro-2-iodopyridine (800 mg, 2.65 mmol) in DMF (15 mL) CuI (3.53 g, 18.6 mmol) and methyl fluorosulfonyldifluoroacetate (3.56 g, 18.6 mmol) were added and the mixture was stirred 3 h under a nitrogen atmosphere at 80° C. The mixture was cooled to rt, water (50 mL) was added and the mixture was extracted with EtOAc (3×15 mL). The organic layers were washed with brine, dried over $Na_2SO_4$, concentrated and purified by column chromatography (PE/EA=20/1~2.5/1, Silica-CS 40 g, 30 mL/min, silica gel, UV 254) to afford the product (400 mg, 62%). GCMS m/z calcd for $[C_6H_2BrF_4N]$ [M]: 242.9; found: 243.0.

3-Bromo-2-(trifluoromethyl)pyridine-5-thiol

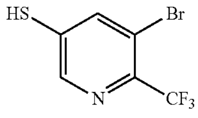

To a solution of 3-bromo-5-fluoro-2-trifluoromethylpyridine (410 mg, 1.68 mmol) in DMF (10 mL) $Na_2S$ (393 mg, 5.04 mmol) was added and the mixture was stirred 3 h under a nitrogen atmosphere at rt. NaOH (10% aq) was added to adjust pH to approximately 9 and the mixture was washed with diethyl ether (3×30 mL). The aqueous layer was acidified to pH 3 using $NaHSO_4$ (2 M) and the aqueous phase was extracted with EtOAc (2×20 mL). The combined organic layers were washed with brine and evaporated to afford the product (280 mg, 65%). ESI-MS m/z calcd for $[C_6H_3BrF_3NS]$ $[M-H]^-$: 255.9; found: 255.9. $^1H$ NMR (400 MHz, Chloroform-d) δ 8.43 (m, 1H), 8.19 (m, 1H), 3.66 (m, 1H).

5-Methyl-4-(2-trimethylsilylethynyl)thiazol-2-amine

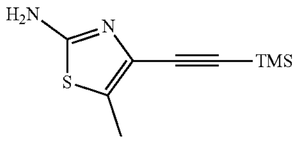

To a solution of 4-bromo-1-trimethylsilyl-pent-1-yn-3-one (2.20 g, 9.43 mmol) in DMF (10 mL) thiourea (1.08 g, 14.2 mmol) was added and the mixture was stirred overnight at rt. Water (50 mL) was added and the mixture was extracted with EA (5×20 mL). The combined organic phases were dried, concentrated and purified by silica gel chromatography to afford the product (1.2 g, 61%). ESI-MS m/z calcd for $[C_9H_{14}N_2SSi]$ $[M+H]^+$: 211.1; found: 211.2. $^1H$ NMR (400 MHz, Chloroform-d) δ 4.79 (s, 2H), 2.35 (s, 3H).

3-Bromo-2-(trifluoromethyl)pyridin-5-yl 2,4,6-tri-O-acetyl-3-azido-3-deoxy-1-thio-α-D-galactopyranoside

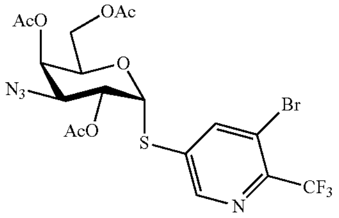

To a solution of 2,4,6-tri-O-acetyl-3-azido-3-deoxy-β-D-galactopyranosyl chloride (759 mg, 2.17 mmol) and 3-bromo-2-trifluoromethylpyridine-5-thiol (280 mg, 1.09 mmol) in DMF (20 mL) cesium carbonate (707 mg, 2.17 mmol) was added and the mixture was stirred 8 h under a nitrogen atmosphere at rt. The mixture was concentrated and purified by column chromatography (PE/EA=20/1~2.5/1, Silica-CS 20 g, 30 mL/min, silica gel, UV 254) to afford the product (300 mg, 48%). ESI-MS m/z calcd for $[C_{18}H_{18}BrF_3N_4O_7S]$ $[M+H]^+$: 571.0; found: 571.0. $^1H$ NMR (400 MHz, Chloroform-d) δ 8.53 (d, J=1.6 Hz, 1H), 8.07 (d, J=1.6 Hz, 1H), 6.06 (d, J=5.2 Hz, 1H), 5.42 (d, J=2.8 Hz, 1H), 5.25 (dd, J=11.2, 5.6 Hz, 1H), 4.48 (dd, J=7.6, 4.8 Hz, 1H), 4.12-4.02 (m, 1H), 3.92 (m, 1H), 3.65 (dd, J=7.2, 5.2 Hz, 1H), 2.13 (s, 3H), 2.11 (s, 3H), 1.91 (s, 3H).

3-Bromo-2-(trifluoromethyl)pyridin-5-yl 2,4,6-tri-O-acetyl-3-[4-(2-amino-5-methylthiazol-4-yl)-1H-1,2,3-triazol-1-yl]-3-deoxy-1-thio-α-D-galactopyranoside

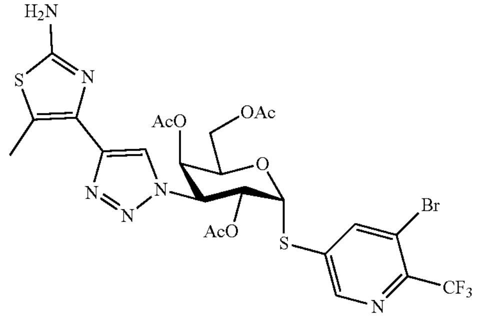

To a solution of 3-bromo-2-(trifluoromethyl)pyridin-5-yl 2,4,6-tri-O-acetyl-3-azido-3-deoxy-1-thio-α-D-galactopyranoside (40 mg, 0.07 mmol) in DMF (5 mL) CuI (4.0 mg, 0.021 mmol), CsF (21.3 mg, 0.14 mmol), 5-methyl-4-(2-trimethylsilylethynyl)thiazol-2-amine (29.5 mg, 0.14 mmol) and DIPEA (59.9 μL, 0.35 mmol) were added and the mixture was stirred 20 h at rt. Water (10 mL) was added and the mixture was extracted with DCM (2×5 mL). The combined organic layers were washed with water (20 mL) and brine (20 mL), dried over $Na_2SO_4$, concentrated and purified by column chromatography (PE/EA=5/1~1/1, Silica-CS 20 g, 200 mL/min, silica gel, UV 254) to afford the product (13 mg, 26%). ESI-MS m/z calcd for $[C_{24}H_{24}BrF_3N_6O_7S_2]$ $[M+H]^+$: 709.0; found:709.0.

Intermediate 34

4-Methyl-2-((trimethylsilyl)ethynyl)thiazole

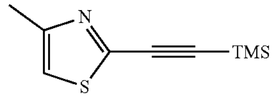

To a nitrogen purged solution of bis(triphenylphosphine) palladium(II) chloride (91 mg, 0.13 mmol) and CuI (48 mg, 0.25 mmol) in THF (3.4 mL) and $Et_3N$ (1.7 mL) 2-bromo-4-methylthiazole (445 mg, 2.50 mmol) and trimethylsilylacetylene (0.416 mL, 3.00 mmol) were added and the mixture was stirred 2.5 h at 50° C. The mixture was filtered through a plug of celite, concentrated and purified by chromatography ($SiO_2$, PE/EtOAc) to afford the product (200 mg, 41%). ESI-MS m/z calcd for $[C_9H_{13}NSSi][M+H]^+$: 196.1; found: 196.0. $^1H$ NMR (400 MHz, $CDCl_3$) δ 6.90 (s, 1H), 2.48 (s, 3H), 0.28 (s, 9H).

5-Bromo-2-cyanopyridin-3-yl 4,6-di-O-acetyl-3-deoxy-3-[4-(4-methylthiazol-2-yl)-1H-1,2,3-triazol-1-yl]-2-O-methyl-1-thio-α-D-galactopyranoside

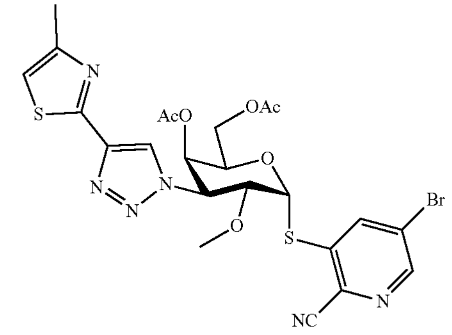

To a solution of 5-bromo-2-cyanopyridin-3-yl 4,6-di-O-acetyl-3-azido-3-deoxy-2-O-methyl-1-thio-D-galactopyranoside (210 mg, 0.42 mmol) and 4-methyl-2-((trimethylsilyl)ethynyl)thiazole (164 mg, 0.84 mmol) in the DMF (5.0 mL) copper (II) sulfate pentahydrate (52.4 mg, 0.21 mmol) and (+)-sodium L-ascorbate (83.2 mg, 0.42 mmol) were added and the mixture was stirred 3 h at rt. The mixture was diluted with water (20 mL) and extracted with EtOAc (3×10 mL). The combined organic layers were washed with brine, dried over $Na_2SO_4$, evaporated and purified by column chromatography (PE/EA=10/1~1/1, Silica-CS 4 g, 12 mL/min, silica gel, UV 254). The obtained material was further purified by preparative-SFC to give the product (52 mg, 20%). ESI-MS m/z calcd for $[C_{23}H_{23}BrN_6O_6S_2]$ $[M+H]^+$: 623.0; found: 623.2. $^1H$ NMR (400 MHz, Chloroform-d) δ 8.65 (d, J=2.0 Hz, 1H), 8.24 (d, J=2.0 Hz, 1H), 8.17 (s, 1H), 6.88 (s, 1H), 6.30 (d, J=5.2 Hz, 1H), 5.59 (d, J=2.0 Hz, 1H), 5.05 (dd, J=11.2, 2.8 Hz, 1H), 4.80-4.76 (m, 1H), 4.70-4.67 (m, 1H), 4.11-3.98 (m, 2H), 3.44 (s, 3H), 2.46 (s, 3H), 2.04 (s, 3H), 1.94 (s, 3H).

Intermediate 35

2-Bromo-5-methylpyridin-3-yl 2,4,6-tri-O-acetyl-3-azido-3-deoxy-1-thio-α-D-galactopyranoside

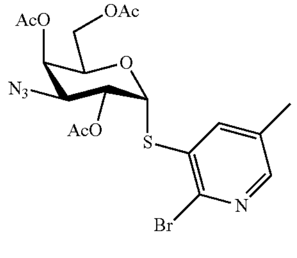

To a solution of 2-bromo-3-fluoro-5-methylpyridine (300 mg, 1.58 mmol) in DMF (10 mL) $Na_2S$ (246 mg, 3.16 mmol) was added and the mixture was stirred 1 h at 100° C. in a microwave reactor. The mixture was cooled to rt, and 2,4,6-tri-O-acetyl-3-azido-3-deoxy-β-D-galactopyranosyl chloride (300 mg, 0.86 mmol) and $Cs_2CO_3$ (559 mg, 1.72 mmol) were added and the mixture was stirred overnight at rt. The mixture was extracted with EtOAc (30 mL) and washed with brine. The organic phase was concentrated and purified by column chromatography (PE/EA=10/1~5/1, Silica-CS 20 g, 20 mL/min, silica gel, UV 254) to afford the crude product. ESI-MS m/z calcd for $[C_{18}H_{21}BrN_4O_7S]$ $[M+H]^+$: 517.0; found: 517.0.

2-Bromo-5-methylpyridin-3-yl 3-azido-3-deoxy-1-thio-α-D-galactopyranoside

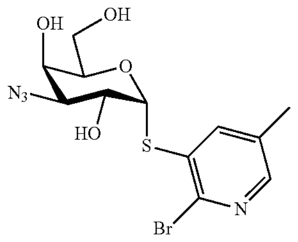

A solution of 2-bromo-5-methylpyridin-3-yl 2,4,6-tri-O-acetyl-3-azido-3-deoxy-1-thio-α-D-galactopyranoside (300 mg, 0.33 mmol) in $MeOH/Et_3N/H_2O$ (9 mL, 5:3:1) was stirred overnight at rt. The mixture was concentrated and purified by prep HPLC [$MeCN/H_2O$ (10 mmol/L $NH_4HCO_3$), X-Select 10 μm 19*250 mm, 20 mL/min, UV 254] to afford the product (65 mg). ESI-MS m/z calcd for $[Cl_2H_{15}BrN_4O_4S]$ $[M+H]^+$: 391.0; found: 391.0. $^1H$ NMR (400 MHz, DMSO-$d_6$) δ 8.00 (d, J=1.2 Hz, 1H), 7.86 (d, J=2.0 Hz, 1H), 6.03 (d, J=4.8 Hz, 1H), 5.85 (d, J=5.2 Hz, 1H), 5.30 (d, J=6.0 Hz, 1H), 4.60 (t, J=6.0 Hz, 1H), 4.28 (dt, J=10.8, 5.2 Hz, 1H), 3.89 (m, 2H), 3.47 (m 2H), 3.34 (m, 1H), 2.22 (s, 3H).

2-Bromo-5-methylpyridin-3-yl 3-azido-4,6-O-benzylidene-3-deoxy-1-thio-α-D-galactopyranoside

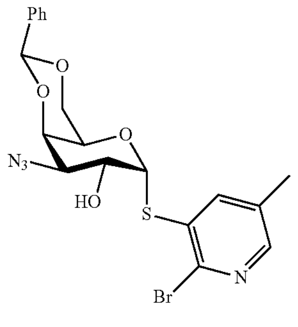

To a solution of 2-bromo-5-methylpyridin-3-yl 3-azido-3-deoxy-1-thio-α-D-galactopyranoside (300 mg, 0.77 mmol) in DMF (6 mL) benzaldehyde dimethylacetal (350 mg, 2.30 mmol) was added followed by D(+)-10-camphorsulfonic acid (35.6 mg, 0.15 mmol). The mixture was stirred 3 h at 50° C. The mixture was neutralized with $Et_3N$, concentrated and purified by column chromatography (PE/EtOAc=5/1~3/1, Silica-CS 12 g, 20 mL/min, silica gel, UV 254) to give the product (250 mg, 68%). ESI-MS m/z calcd for $[C_{19}H_{19}BrN_4O_4S]$ $[M+H]^+$: 479.0; found: 479.0. $^1H$ NMR (400 MHz, $CDCl_3$) δ 8.04 (d, J=2.0 Hz, 1H), 7.71 (d, J=2.0 Hz, 1H), 7.51-7.49 (m, 2H), 7.42-7.34 (m, 3H), 5.94 (d, J=5.2 Hz, 1H), 5.64 (s, 1H), 4.72-4.62 (m, 1H), 4.41 (d, J=3.2 Hz, 1H), 4.24 (dd, J=13.2, 2.0 Hz, 1H), 4.12-4.10 (m, 2H), 3.68 (dd, J=10.8, 3.2 Hz, 1H), 2.46 (d, J=7.2 Hz, 1H), 2.28 (s, 3H).

2-Bromo-5-methylpyridin-3-yl 3-azido-4,6-O-benzylidene-3-deoxy-2-O-methyl-1-thio-α-D-galactopyranoside

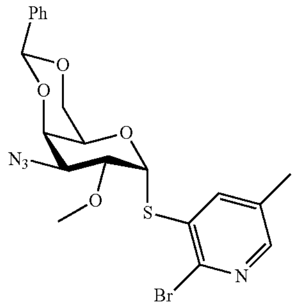

To a solution of 2-bromo-5-methylpyridin-3-yl 3-azido-4,6-O-benzylidene-3-deoxy-1-thio-α-D-galactopyranoside (250 mg, 0.52 mmol) and iodomethane (370 mg, 2.61 mmol) in DMF (5 mL) $Cs_2CO_3$ (510 mg, 1.56 mmol) was added and the mixture was stirred 4 h at rt. The mixture was diluted with water and extracted with EtOAc (30 mL). The mixture was concentrated and purified by column chromatography (PE/EtOAc=5/1~2/1, Silica-CS 20 g, 20 mL/min, silica gel, UV 254) to give the product (180 mg, 70%). ESI-MS m/z calcd for $[C_{20}H_{21}BrN_4O_4S]$ $[M+H]^+$: 493.0; found: 493.0. $^1H$ NMR (400 MHz, $CDCl_3$) δ 8.02 (d, J=1.6 Hz, 1H), 7.68 (d, J=1.6 Hz, 1H), 7.55-7.48 (m, 2H), 7.41-7.33 (m, 3H), 6.14 (d, J=5.2 Hz, 1H), 5.62 (s, 1H), 4.33 (d, J=3.2 Hz, 1H), 4.28 (dd, J=10.4, 5.2 Hz, 1H), 4.18-4.05 (m, 3H), 3.83 (dd, J=10.4, 3.2 Hz, 1H), 3.57 (s, 3H), 2.27 (s, 3H).

2-Cyano-5-methylpyridin-3-yl 3-azido-4,6-O-benzylidene-3-deoxy-2-O-methyl-1-thio-α-D-galactopyranoside

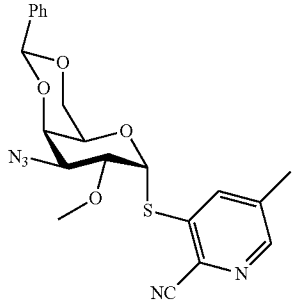

To a solution of 2-bromo-5-methylpyridin-3-yl 3-azido-4,6-O-benzylidene-3-deoxy-2-O-methyl-1-thio-α-D-galactopyranoside (180 mg, 0.37 mmol) in DMF (10.0 mL) Zn (23.9 mg, 0.37 mmol), tris(dibenzylideneacetone)dipalladium(0) (26.7 mg, 0.029 mmol) $Zn(CN)_2$ (129 mg, 1.09 mmol) and 1,1'-bis(diphenylphosphino)ferrocene (16.5 mg, 0.029 mmol) were added and the mixture was stirred 2.5 h at 100° C. under nitrogen atmosphere. The mixture was concentrated and purified by column chromatography (PE/EtOAc=10/1~3/1, Silica-CS 12 g, 20 mL/min, silica gel, UV 254) to give the product (100 mg, 62%). ESI-MS m/z calcd for $[C_{21}H_{21}N_5O_4S]$ $[M+H]^+$: 440.1; found: 440.1. $^1H$ NMR (400 MHz, $CDCl_3$) δ 8.42 (d, J=1.2 Hz, 1H), 7.83 (d, J=0.8 Hz, 1H), 7.49 (m, 2H), 7.40-7.31 (m, 3H), 6.04 (d, J=5.2 Hz, 1H), 5.60 (s, 1H), 4.34 (d, J=2.8 Hz, 1H), 4.25 (dd, J=10.6, 5.2 Hz, 1H), 4.21 (s, 1H), 4.16 (dd, J=12.8, 1.6 Hz, 1H), 4.11 (dd, J=12.8, 1.6 Hz, 1H), 3.78 (dd, J=10.6, 3.2 Hz, 1H), 3.60 (s, 3H), 2.41 (s, 3H).

2-Cyano-5-methylpyridin-3-yl 4,6-O-benzylidene-3-deoxy-3-[4-(4-methylthiazol-2-yl)-1H-1,2,3-triazol-1-yl]-2-O-methyl-1-thio-α-D-galactopyranoside

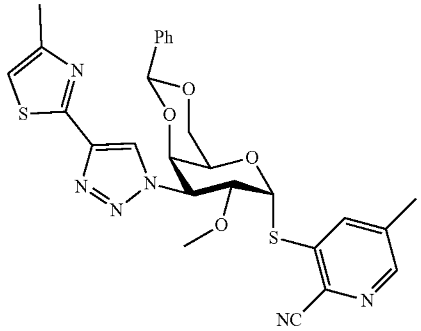

To a solution of 2-cyano-5-methylpyridin-3-yl 3-azido-4,6-O-benzylidene-3-deoxy-2-O-methyl-1-thio-α-D-galactopyranoside (95 mg, 0.20 mmol) in DMF (4 mL) 4-methyl-2-((trimethylsilyl)ethynyl)thiazole (64.3 mg, 0.30 mmol), (+)-sodium L-ascorbate (19.6 mg, 0.098 mmol) and copper (II) sulfate pentahydrate (24.7 mg, 0.098 mmol) were added and the mixture was stirred overnight at rt. After diluting with water (50 mL), the mixture was extracted with EtOAc (2×50 mL). The combined organic layers were washed with water (50 mL) and brine (50 mL), dried over $Na_2SO_4$, evaporated and purified by column chromatography (PE/EA=10/1~1/1, Silica-CS 12 g, 20 mL/min, silica gel, UV 254) to give the product (95.0 mg, 83%). ESI-MS m/z calcd for $[C_{27}H_{26}N_6O_4S_2]$ $[M+H]^+$: 563.1; found: 563.2. $^1H$ NMR (400 MHz, $CDCl_3$) δ 8.46 (d, J=1.6 Hz, 1H), 8.27 (s, 1H), 7.86 (dd, J=2.0, 0.8 Hz, 1H), 7.40-7.34 (m, 5H), 6.90 (d, J=1.2 Hz, 1H), 6.17 (d, J=5.2 Hz, 1H), 5.50 (s, 1H), 5.33 (dd, J=11.2, 3.2 Hz, 1H), 4.58 (dd, J=11.2, 5.2 Hz, 2H), 4.47 (s, 1H), 4.25-4.13 (m, 2H), 3.41 (s, 3H), 2.48 (s, 3H), 2.44 (s, 3H).

Intermediate 36

2-Cyano-5-methylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

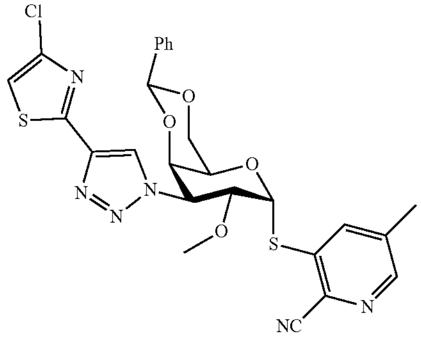

To a solution of 2-cyano-5-methylpyridin-3-yl 3-azido-4,6-O-benzylidene-3-deoxy-2-O-methyl-1-thio-α-D-galactopyranoside (190 mg, 0.40 mmol) in DMF (8 mL) 2-(4-chlorothiazol-2-yl)ethynyltrimethylsilane (244 mg, 0.79 mmol), (+)-sodium L-ascorbate (39.2 mg, 0.20 mmol) and copper (II) sulfate pentahydrate (49.4 mg, 0.20 mmol) were added and the mixture was stirred overnight at rt. After diluting with water (50 mL), the mixture was extracted with EtOAc (2×50 mL). The combined organic layers were washed with water (50 mL) and brine (50 mL), dried over $Na_2SO_4$, evaporated and purified by column chromatography (PE/EA=10/1~1/1, Silica-CS 12 g, 20 mL/min, silica gel, UV 254) to give the product (220 mg, 94%). ESI-MS m/z calcd for $[C_{26}H_{23}ClN_6O_4S_2]$ $[M+H]^+$: 583.1; found: 583.2. $^1H$ NMR (400 MHz, $CDCl_3$) δ 8.47 (d, J=1.2 Hz, 1H), 8.30 (s, 1H), 7.87 (dd, J=6.0, 0.8 Hz, 1H), 7.39-7.35 (m, 5H), 7.12 (s, 1H), 6.17 (d, J=5.2 Hz, 1H), 5.51 (s, 1H), 5.34 (dd, J=11.2, 2.8 Hz, 1H), 4.60-4.56 (m, 2H), 4.48 (s, 1H), 4.26-4.11 (m, 2H), 3.42 (s, 3H), 2.45 (s, 3H).

Intermediate 37

5-Bromopyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

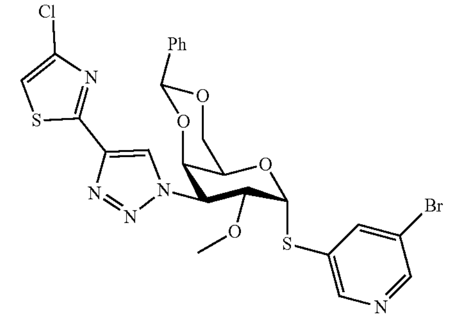

To a solution of 5-bromopyridin-3-yl 3-azido-4,6-O-benzylidene-3-deoxy-2-O-methyl-1-thio-α-D-galactopyranoside (130 mg, 0.27 mmol) in DMF (5 mL) 2-(4-chlorothiazol-2-yl)ethynyltrimethylsilane (117 mg, 0.54 mmol), (+)-sodium L-ascorbate (39.2 mg, 0.20 mmol) and copper (II) sulfate pentahydrate (49.4 mg, 0.20 mmol) were added and the mixture was stirred overnight at rt. After diluting with water (50 mL), the mixture was extracted with EtOAc (2×50 mL). The combined organic layers were washed with water (50 mL) and brine (50 mL), dried over $Na_2SO_4$, evaporated and purified by column chromatography (PE/EA=10/1~1/1, Silica-CS 4 g, 10 mL/min, silica gel, UV 254) to give the product (100 mg, 59%). ESI-MS m/z calcd for $[C_{24}H_{21}BrClN_5O_4S_2][M+H]^+$: 622.0; found: 622.0. $^1H$ NMR (400 MHz, $CDCl_3$) δ 8.59 (dd, J=12.8, 2.0 Hz, 2H), 8.29 (s, 1H), 8.02 (t, J=2.0 Hz, 1H), 7.43-7.32 (m, 5H), 7.11 (s, 1H), 6.17 (d, J=5.2 Hz, 1H), 5.51 (s, 1H), 5.32 (dd, J=11.2, 3.2 Hz, 1H), 4.68-4.46 (m, 2H), 4.29 (dd, J=16.4, 3.6 Hz, 2H), 4.21-4.05 (m, 1H), 3.36 (s, 3H).

5-(2-Trimethylsilyl-1-ethynyl)-pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

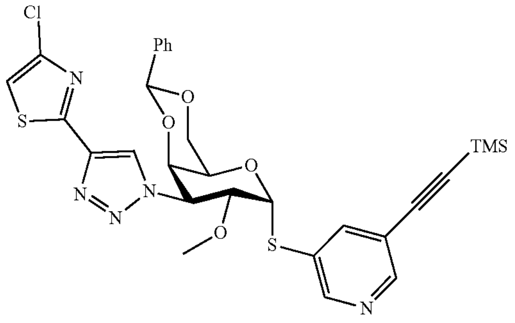

To a solution of 5-bromopyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (100 mg, 0.16 mmol) in DMF (4 mL) ethynyl(trimethyl)silane (78.8 mg, 0.80 mmol), CuI (3.06 mg, 0.016 mmol), bis(triphenylphosphine)palladium (II) chloride (7.03 mg, 0.0096 mmol) and DIPEA (0.275 mL, 1.61 mmol) were added and the mixture was stirred 2 h at 100° C. in a microwave reactor. After diluting with water (20 mL), the mixture was extracted with EtOAc (2×20 mL). The combined organic layers were washed with water (30 mL) and brine (30 mL), dried over $Na_2SO_4$, evaporated and purified by column chromatography (PE/EA=10/1~1/1, Silica-CS 20 g, 25 mL/min, silica gel, UV 254) to afford the product (40 mg, 39%). ESI-MS m/z calcd for $[C_{29}H_{30}ClN_5O_4S_2Si][M+H]^+$: 640.1; found: 640.1. $^1H$ NMR (400 MHz, $CDCl_3$) δ 8.31 (s, 1H), 7.96 (s, 1H), 7.56-7.45 (m, 1H), 7.43-7.31 (m, 6H), 7.11 (s, 1H), 6.18 (dd, J=16.0, 5.2 Hz, 1H), 5.50 (s, 1H), 5.36-5.30 (m, 1H), 4.64-4.50 (m, 2H), 4.38-4.24 (m, 2H), 4.18-4.13 (m, 1H), 3.36 (s, 3H), 0.27 (s, 9H).

Intermediate 38

5-Chloro-2-{N-(2-oxa)-6-azaspiro[3.3]heptanyl}-pyridin-3-yl 3-azido-4,6-O-benzylidene-3-deoxy-2-O-methyl-1-thio-α-D-galactopyranoside

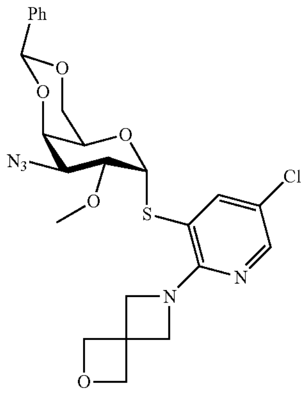

A solution of 2-bromo-5-chloropyridin-3-yl 3-azido-4,6-O-benzylidene-3-deoxy-2-O-methyl-1-thio-α-D-galactopyranoside (400 mg, 0.78 mmol), 2-oxa-6-azaspiro[3.3]heptane; oxalic acid (736 mg, 3.89 mmol) and DIPEA (1.33 mL, 7.79 mmol) in DMF (5.0 mL) was stirred 4 h at 130° C. in a microwave reactor. The mixture was evaporated and purified by column chromatography (PE/EA=5/1~2/1, Silica-CS 20 g, 20 mL/min, silica gel, UV 254) to afford the product (190 mg, 46%). ESI-MS m/z calcd for $[C_{24}H_{26}ClN_5O_5S]$ $[M+H]^+$: 532.1; found: 532.2 $^1H$ NMR (400 MHz, $CDCl_3$) δ 8.01 (d, J=2.4 Hz, 1H), 7.59 (d, J=2.4 Hz, 1H), 7.53-7.47 (m, 2H), 7.39-7.32 (m, 3H), 5.84 (d, J=5.1 Hz, 1H), 5.60 (s, 1H), 4.82 (s, 4H), 4.40 (d, J=9.2 Hz, 2H), 4.32 (d, J=3.2 Hz, 1H), 4.27 (d, J=9.2 Hz, 2H), 4.16 (m, 4H), 3.72 (dd, J=10.4, 3.2 Hz, 1H), 3.54 (s, 3H).

5-Chloro-2-{N-(2-oxa)-6-azaspiro[3.3]heptanyl}-pyridin-3-yl 3-[4-(2-aminothiazol-4-yl)-1H-1,2,3-triazol-1-yl]-4,6-O-benzylidene-3-deoxy-2-O-methyl-1-thio-α-D-galactopyranoside

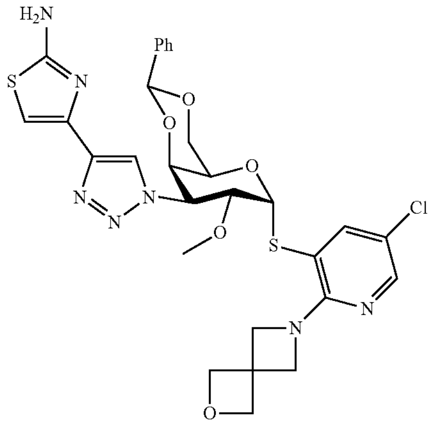

To a solution of 5-chloro-2-{N-(2-oxa)-6-azaspiro[3.3]heptanyl}-pyridin-3-yl 3-azido-4,6-O-benzylidene-3-deoxy-2-O-methyl-1-thio-α-D-galactopyranoside (160 mg, 0.30 mmol) and 4-(2-trimethylsilylethynyl)thiazol-2-amine (70.9 mg, 0.36 mmol) in DMF (4 mL) (+)-sodium L-ascorbate (72.6 mg, 0.37 mmol) and copper (II) sulfate pentahydrate (30.5 mg, 0.12 mmol) were added and the mixture was stirred 4 h at rt. The mixture was purified by prep HPLC ($MeCN/H_2O$ (10 mmol/L $NH_4HCO_3$), X-Select 10 μm 19*250 mm, 20 mL/min, UV 254) to afford the product (120 mg, 57%). ESI-MS m/z calcd for $[C_{29}H_{30}ClN_7O_5S_2]$ $[M+H]^+$: 656.1; found: 656.2. $^1H$ NMR (400 MHz, DMSO-$d_6$) δ 8.16 (s, 1H), 8.08 (d, J=2.4 Hz, 1H), 7.82 (d, J=2.4 Hz, 1H), 7.35 (m, 5H), 7.06 (s, 2H), 6.89 (s, 1H), 6.29 (d, J=4.8 Hz, 1H), 5.57 (s, 1H), 5.15 (dd, J=11.6, 3.2 Hz, 1H), 4.74-4.63 (m, 5H), 4.56 (d, J=2.4 Hz, 1H), 4.31 (m, 4H), 4.22 (s, 1H), 4.10 (d, J=12.0 Hz, 1H), 3.85 (d, J=12.0 Hz, 1H), 3.30 (s, 3H).

Intermediate 39

2-Chloro-4-sulfanylbenzonitrile

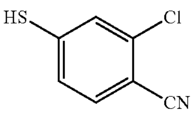

To a solution of 2-chloro-4-fluorobenzonitrile (1.56 g, 10.0 mmol) in DMF (10.0 mL) $Na_2S$ (1.56 g, 20.1 mmol) was added and the mixture was stirred 3 h at rt. Water (30 mL) was added and the pH was adjusted to 6-7 using HCl (1 M). The precipitate was collected and dried under vacuum to give the product (1.6 g, 94%). ESI-MS m/z calcd for $[C_7H_4ClNS]$ $[M-H]^-$: 168.0; found: 167.9. $^1H$ NMR (400 MHz, $CDCl_3$) δ 7.49 (d, J=8.0 Hz, 1H), 7.37 (d, J=1.6 Hz, 1H), 7.19 (dd, J=8.0, 1.6 Hz, 1H), 3.73 (s, 1H).

3-Chloro-4-cyanophenyl 4,6-di-O-acetyl-3-azido-3-deoxy-2-O-methyl-1-thio-α-D-galactopyranoside

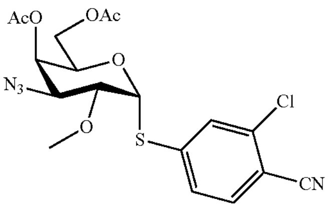

To a solution of acetyl 4,6-di-O-acetyl-3-azido-3-deoxy-2-O-methyl-D-galactopyranoside (600 mg, 1.74 mmol) in DCM (6.0 mL) $PCl_5$ (543 mg, 2.61 mmol) was added followed by boron trifluoride diethyl etherate (0.107 mL, 0.87 mmol) at 30° C. under a nitrogen atmosphere. The mixture was stirred 30 min at rt followed by dropwise addition to a saturated aq $NaHCO_3$ solution under vigorous stirring. The mixture was extracted with DCM and the organic phase was dried and concentrated. A part of the obtained material (320 mg) and 2-chloro-4-sulfanyl-benzonitrile (219 mg, 1.29 mmol) were dissolved in DMF (4.0 mL). Cesium carbonate (648 mg, 1.99 mmol) was added and the mixture was stirred overnight at rt. The mixture was concentrated and purified by column chromatography (PE/EA=10/1~5/1, Silica-CS 120 g, 40 mL/min, silica gel, UV 254) to give the product (290 mg, 64%). ESI-MS m/z calcd for $[C_{18}H_{19}ClN_4O_6S]$ $[M+NH_4]^+$: 472.1; found: 472.1.

3-Chloro-4-cyanophenyl 4,6-di-O-acetyl-3-[4-(2-aminothiazol-4-yl)-1H-1,2,3-triazol-1-yl]-3-deoxy-2-O-methyl-1-thio-α-D-galactopyranoside

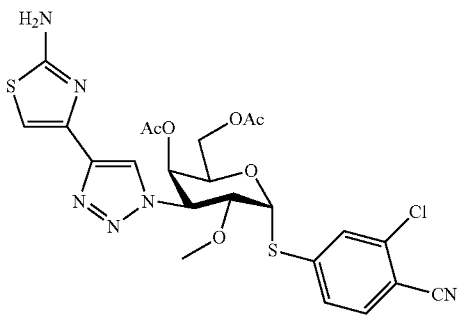

To a solution of 3-chloro-4-cyanophenyl 4,6-di-O-acetyl-3-azido-3-deoxy-2-O-methyl-1-thio-α-D-galactopyranoside (290 mg, 0.64 mmol) and 4-(2-trimethylsilylethynyl)thiazol-2-amine (150 mg, 0.77 mmol) in DMF (3 mL) (+)-sodium L-ascorbate (189 mg, 0.96 mmol) and copper (II) sulfate pentahydrate (79.6 mg, 0.32 mmol) were added and the mixture was stirred overnight at rt. The mixture was purified by preparative-SFC to afford the product (25 mg, 7%). ESI-MS m/z calcd for $[C_{23}H_{23}ClN_6O_6S_2]$ $[M+H]^+$: 579.1; found: 579.0. $^1H$ NMR (400 MHz, $CDCl_3$) δ 7.86 (s, 1H), 7.68 (d, J=1.6 Hz, 1H), 7.61-7.55 (m, 1H), 7.50-7.43 (m, 1H), 7.06 (s, 1H), 6.25 (d, J=5.6 Hz, 1H), 5.54 (d, J=2.4 Hz, 1H), 5.39-5.19 (m, 2H), 4.93 (dd, J=11.2, 2.8 Hz, 1H), 4.77 (dd, J=11.2, 5.6 Hz, 1H), 4.70-4.62 (m, 1H), 4.16-4.00 (m, 2H), 3.35 (s, 3H), 2.06 (s, 3H), 1.92 (s, 3H).

Intermediate 40 tert-Butyl N-tert-butoxycarbonyl-N-[4-(2-trimethylsilylethynyl)thiazol-2-yl]carbamate

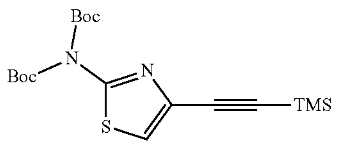 [SMILES: CC(C)(C)OC(=O)N(C(=O)OC(C)(C)C)c1nc(C#C[Si](C)(C)C)cs1]

To a solution of 4-(2-trimethylsilylethynyl)thiazol-2-amine (2.00 g, 10.2 mmol) in DCM (50 mL) di-tert-butyl dicarbonate (4.45 g, 20.4 mmol), $Et_3N$ (5.68 mL, 40.8 mmol) and 4-(dimethylamino)pyridine (12.4 mg, 1.02 mmol) were added and the mixture was stirred 5 h at rt. Water (100 mL) was added, and the mixture was extracted with diethyl ether (3×100 mL). The combined organic layers were washed with brine (100 mL), dried over $Na_2SO_4$, evaporated and purified by column chromatography (PE/EA=1/0~10/1, Silica-CS 40 g, 40 mL/min, silica gel, UV 254) to give the product (3.60 g, 89%). ESI-MS m/z calcd for $[C_{18}H_{28}N_2O_4SSi]$ $[M+H]^+$: 397.2; found: 397.3. $^1H$ NMR (400 MHz, $CDCl_3$) δ 7.25-7.18 (m, 1H), 1.45 (d, J=2.8 Hz, 18H), 0.18 (d, J=2.8 Hz, 9H).

5-Cyanopyridin-3-yl 3-azido-4,6-O-benzylidene-3-deoxy-2-O-methyl-1-thio-α-D-galactopyranoside

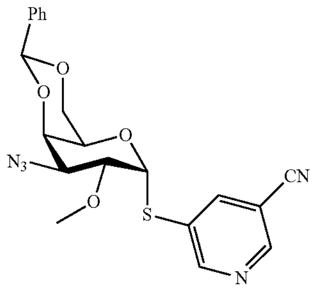

To a solution of 5-bromopyridin-3-yl 3-azido-4,6-O-benzylidene-3-deoxy-2-O-methyl-1-thio-α-D-galactopyranoside (500 mg, 1.04 mmol) in DMF (10.0 mL) Zn (68.2 mg, 1.04 mmol), $Zn(CN)_2$ (368 mg, 3.13 mmol), 1,1'-bis(diphenylphosphino)ferrocene (58.9 mg, 0.10 mmol) and tris(dibenzylideneacetone)dipalladium(0) (95.4 mg, 0.10 mmol) were added and the mixture was stirred 2.5 h at 100° C. under a nitrogen atmosphere. After diluting with water (20 mL), the mixture was extracted with EtOAc (3×10 mL). The combined organic layers were washed with brine, dried over $Na_2SO_4$, evaporated and purified by column chromatography (PE/EA=10/1~2/1, Silica-CS 12 g, 20 mL/min, silica gel, UV 254) to give the product (200 mg, 45%). ESI-MS m/z calcd for $[C_{20}H_{19}N_5O_4S]$ $[M+H]^+$: 426.1; found: 426.1. $^1H$ NMR (400 MHz, $CDCl_3$) δ 8.83 (d, J=2.4 Hz, 1H), 8.72 (d, J=2.0 Hz, 1H), 8.07 (t, J=2.0 Hz, 1H), 7.57-7.46 (m, 2H), 7.42-7.32 (m, 3H), 6.08 (d, J=5.2 Hz, 1H), 5.62 (s, 1H), 4.34 (d, J=2.8 Hz, 1H), 4.26 (dd, J=10.8, 5.2 Hz, 1H), 4.21 (dd, J=12.8, 1.6 Hz, 1H), 4.12 (dd, J=12.8, 1.6 Hz, 1H), 4.05 (s, 1H), 3.71 (dd, J=10.4, 3.6 Hz, 1H), 3.56 (s, 3H).

5-Cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside

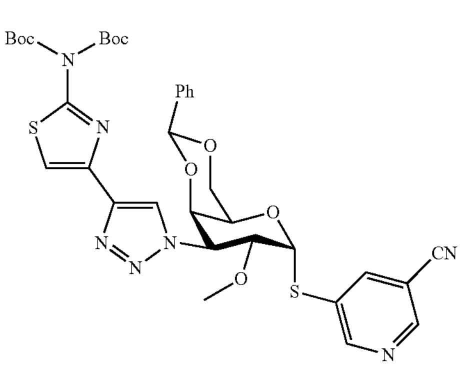

To a solution of 5-cyanopyridin-3-yl 3-azido-4,6-O-benzylidene-3-deoxy-2-O-methyl-1-thio-α-D-galactopyranoside (80 mg, 0.19 mmol) and tert-butyl N-tert-butoxycarbonyl-N-[4-(2-trimethylsilylethynyl)thiazol-2-yl]carbamate (89.5 mg, 0.23 mmol) in DMF (5 mL) copper (II) sulfate pentahydrate (23.5 mg, 0.094 mmol) and (+)-sodium L-ascorbate (55.9 mg, 0.28 mmol) were added and the mixture was stirred 4 h at rt. The mixture was diluted with water (20 mL) and extracted with EtOAc (3×10 mL). The combined organic layers were washed with brine, dried over $Na_2SO_4$, evaporated and purified by prep HPLC (MeCN/$H_2O$ (10 mmol/L $NH_4HCO_3$), X-Select 10 μm 19*250 mm, 20 mL/min, UV 254) to afford the product (110 mg, 78%). ESI-MS m/z calcd for $[C_{35}H_{39}N_7O_8S_2]$ $[M+H]^+$: 750.2, found: 750.2. $^1H$ NMR (400 MHz, $CDCl_3$) δ 8.88 (d, J=2.4 Hz, 1H), 8.75 (d, J=1.6 Hz, 1H), 8.11 (t, J=2.0 Hz, 1H), 8.01 (s, 1H), 7.72 (s, 1H), 7.42-7.31 (m, 5H), 6.22 (d, J=5.2 Hz, 1H), 5.52 (s, 1H), 5.28 (dd, J=10.4, 3.2 Hz, 1H), 4.58 (dd, J=11.2, 5.2 Hz, 1H), 4.54 (d, J=2.8 Hz, 1H), 4.32-4.23 (m, 2H), 4.18-4.11 (m, 1H), 3.33 (s, 3H), 1.47 (s, 18H).

Intermediate 41

5-Benzylsulfanyl-1,3-dichloro-2-fluorobenzene

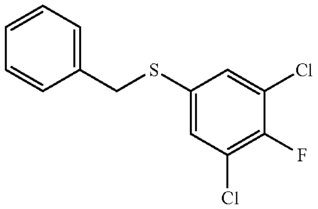 [SMILES: Fc1c(Cl)cc(SCc2ccccc2)cc1Cl]

To a nitrogen purged solution of 5-bromo-1,3-difluoro-2-fluorobenzene (2.00 g, 7.95 mmol), bis(dibenzylideneacetone)palladium(0) (274 mg, 0.48 mmol) and 4,5-bis(diphenylphosphino)-9,9-dimethylxanthene (230 mg, 0.40 mmol) in 1,4-dioxane (20 mL) benzyl mercaptan (1.04 mL, 8.75 mmol) and DIPEA (2.78 ml, 15.9 mmol) were added and the mixture was stirred 17 h at 80° C. The mixture was filtered through silica (eluting with EtOAc), concentrated and purified by chromatography ($SiO_2$, PE/EtOAc) to afford the product (2.36 g, quantitative yield). $^1H$ NMR (400 MHz, $CDCl_3$) δ 7.36-7.23 (m, 5H), 7.21 (d, J=6.1 Hz, 2H), 4.08 (s, 2H).

Intermediate 42

1,2,4,6-Tetra-O-acetyl 3-[4-(2-aminothiazol-4-yl)-1H-1,2,3-triazol-1-yl]-3-deoxy-β-D-galactopyranose

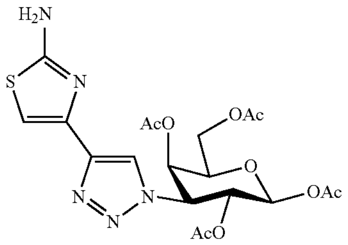

To a solution of 1,2,4,6-tetra-O-acetyl-3-azido-3-deoxy-β-D-galactopyranose (4.00 g, 10.7 mmol) in DMF (50 mL) 4-(2-trimethylsilylethynyl)thiazol-2-amine (2.31 g, 11.8 mmol), copper (II) sulfate pentahydrate (1.34 g, 5.36 mmol) and (+)-sodium L-ascorbate (1.06 g, 5.36 mmol) were added and the mixture was stirred 3 h at rt. The mixture was partitioned between water (50 mL) and DCM (50 mL) and the aqueous phase was extracted with DCM (2×50 mL). The combined organic layers were washed with water (50 mL) and brine (3×50 mL), dried over $Na_2SO_4$, concentrated and purified by column chromatography (PE/EA=10/1~0/1, Silica-CS 80 g, 50 mL/min, silica gel, UV 254) to yield the product (4.20 g, 78%). ESI-MS m/z calcd for $[C_{19}H_{23}N_5O_9S][M+H]^+$: 498.1; found: 498.1, $^1H$ NMR (400 MHz, DMSO-$d_6$) δ 7.98 (s, 1H), 7.09 (s, 2H), 6.90 (s, 1H), 5.98 (d, J=7.6 Hz, 1H), 5.73-5.67 (m, 2H), 5.40 (d, J=1.2 Hz, 1H), 4.48 (t, J=12.4 Hz, 1H), 4.08-3.98 (m, 2H), 2.07 (s, 3H), 1.98 (s, 6H), 1.84 (s, 3H).

4,6-Di-O-acetyl 3-[4-(2-aminothiazol-4-yl)-1H-1,2,3-triazol-1-yl]-3-deoxy-D-galactal

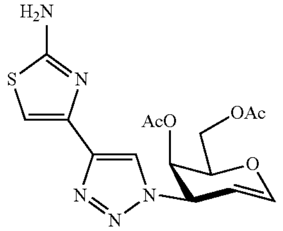

To a solution of 1,2,4,6-tetra-O-acetyl 3-[4-(2-aminothiazol-4-yl)-1H-1,2,3-triazol-1-yl]-3-deoxy-β-D-galactopyranose (4.20 g, 8.36 mmol) in DCM (300 mL) HBr/AcOH (4.06 g, 50.1 mmol) was added and the mixture was stirred 24 h at rt. The mixture was evaporated, and the residue was dissolved in MeCN (200 mL). Zinc (1.98 mg, 30.3 mmol) and $NH_4Cl$ (1.62 g, 30.3 mmol) were added and the mixture was stirred 24 h at rt. The mixture was filtered, concentrated and purified by prep HPLC (MeCN/$H_2O$ (10 mmol/L $NH_4HCO_3$), X-Select 10 μm 19*250 mm, 20 mL/min, UV 254) to yield the product (120 mg, 4%). ESI-MS m/z calcd for $[C_{15}H_{17}N_5O_5S]$ $[M+H]^+$: 380.1; found: 380.2, $^1H$ NMR (400 MHz, Methanol-$d_4$) δ 8.05 (s, 1H), 6.94 (s, 1H), 6.75 (dd, J=6.4, 2.4 Hz, 1H), 5.90 (d, J=2.0 Hz, 1H), 5.59 (d, J=4.4 Hz, 1H), 4.98 (t, J=6.0 Hz, 1H), 4.60 (t, J=12.8 Hz, 1H), 4.23-4.15 (m, 2H), 2.04 (s, 3H), 1.88 (s, 3H).

Intermediate 43

4-Chloro-2-sulfanylbenzonitrile

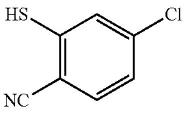

A solution of 4-chloro-2-fluorobenzonitrile (2.0 g, 12.6 mmol) and sodium hydrosulfide monohydrate (1.00 g, 12.6 mmol) in DMF (10.0 mL) was stirred 1 h at rt. The mixture was partitioned between diethyl ether and HCl (0.5 M) and the organic phase was extracted with aq NaOH (1 M). The aqueous phase was acidified with HCl (5 M) and the precipitate was collected by filtration and dried under vacuum to give the product (1.02 g, 48%). $^1H$ NMR (400 MHz, $CDCl_3$) δ 7.53 (d, J=8.4 Hz, 1H), 7.43 (d, J=1.8 Hz, 1H), 7.22 (dd, J=8.4, 1.5 Hz, 1H), 4.15 (s, 1H).

1,2,4,6-Tetra-O-acetyl 3-[4-(4-chlorothiazol-2-yl)-1H-1,2,3-triazol-1-yl]-3-deoxy-β-D-galactopyranose

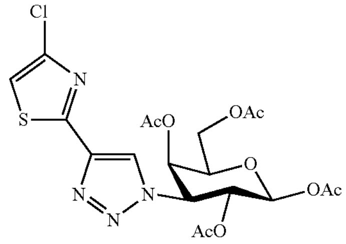

To a solution of 1,2,4,6-tetra-O-acetyl-3-azido-3-deoxy-β-D-galactopyranose (1.40 g, 3.75 mmol) and 2-(4-chlorothiazol-2-yl)ethynyltrimethylsilane (800 mg, 3.71 mmol) in DMF (20 mL) copper (II) sulfate pentahydrate (468 mg, 1.88 mmol) and (+)-sodium L-ascorbate (743 mg, 3.75 mmol) were added and the mixture was stirred overnight at rt. The mixture was purified by column chromatography (EtOAc, Silica-CS 40 g, 40 mL/min, silica gel, UV 254) to yield the product (1.64 g, 85%). ESI-MS m/z calcd for $[C_{19}H_{21}ClN_4O_9S]$ $[M+H]^+$: 517.1; found: 517.0, $^1H$ NMR (400 MHz, Chloroform-d) δ 8.17 (s, 1H), 7.11 (s, 1H), 5.94-5.75 (m, 2H), 5.56 (dd, J=3.2, 1.2 Hz, 1H), 5.20 (dd, J=10.4, 3.2 Hz, 1H), 4.32-3.99 (m, 3H), 2.15 (s, 3H), 2.11 (s, 3H), 2.04 (s, 3H), 1.89 (s, 3H).

4,6-Di-O-acetyl 3-[4-(4-chlorothiazol-2-yl)-1H-1,2,3-triazol-1-yl]-3-deoxy-D-galactal

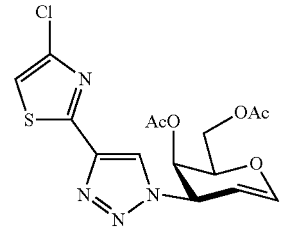

To a cooled (0° C.) solution of 1,2,4,6-tetra-O-acetyl 3-[4-(4-chlorothiazol-2-yl)-1H-1,2,3-triazol-1-yl]-3-deoxy-β-D-galactopyranose (1.60 g, 3.10 mmol) in DCM (20 mL) HBr/AcOH (1.50 mg, 18.6 mmol) was added. The mixture reach rt in 25 min and was then stirred 6 h at rt. The mixture was diluted with DCM and washed with saturated aq $NaHCO_3$ and water. The organic phase was dried, evaporated and the obtained residue was dissolved together with $NH_4Cl$ (739 mg, 13.8 mmol) in MeCN (100 mL). Zinc (903 mg, 13.8 mmol) was added and after stirring 5 days at rt the mixture was filtered through silica using EtOAc. The filtrate was concentrated and purified by prep HPLC (MeCN/$H_2O$ (10 mmol/L $NH_4HCO_3$), X-Select 10 μm 19*250 mm, 20 mL/min, UV 254) to yield the product (219 mg, 18%). ESI-MS m/z calcd for $[C_{15}H_{15}ClN_4O_5S][M+H]^+$: 399.0; found: 399.0, $^1H$ NMR (400 MHz, DMSO-$d_6$) δ 8.62 (s, 1H), 7.78 (s, 1H), 6.78 (dd, J=6.4, 2.4 Hz, 1H), 6.05-5.90 (m, 1H), 5.51 (dd, J=4.8, 2.0 Hz, 1H), 5.06 (dt, J=6.4, 2.0 Hz, 1H), 4.59 (t, J=6.0 Hz, 1H), 4.25-4.00 (m, 2H), 2.02 (s, 3H), 1.81 (s, 3H).

Intermediate 44

5-Fluoro-2-(trifluoromethyl)pyridine-3-carbonitrile

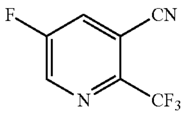

A solution of 3-bromo-5-fluoro-2-(trifluoromethyl)pyridine (200 mg, 0.82 mmol) and copper cyanide (92 mg, 1.02 mmol) in DMSO (0.8 mL) was stirred 2 h at 150° C. The mixture was cooled to rt, diluted with water (20 mL) and EtOAc (20 mL) and filtered. The phases were separated, and the organic phase was dried and evaporated to afford the product (159 mg, quantitative yield). $^1H$ NMR (400 MHz, Chloroform-d) δ 8.78 (d, J=2.5 Hz, 1H), 7.92 (dd, J=7.0, 2.4 Hz, 1H).

4,6-Di-O-acetyl-3-azido-3-deoxy-2-O-methyl-1-thio-α-D-galactopyranose

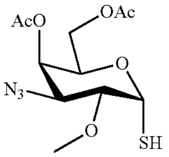

To a solution of acetyl 4,6-di-O-acetyl-3-azido-3-deoxy-2-O-methyl-D-galactopyranoside (100 mg, 0.29 mmol) in DCM (1 mL) triisopropylsilanethiol (93 μL, 0.43 mmol) and boron trifluoride diethyl etherate (107 μL, 0.87 mmol) were added and the mixture was stirred 24 h at rt. Water (10 mL) was added and the mixture was extracted with DCM (3×100 mL). The combined organic phases were washed with brine, dried over $Na_2SO_4$ and concentrated. The residue was dissolved in DMF (4.0 mL) and potassium thioacetate (731 mg, 6.4 mmol) was added. The mixture was stirred overnight at rt under a nitrogen atmosphere. After diluting with water (50 mL), the mixture was extracted with EtOAc (3×30 mL). The combined organic phases were dried, concentrated and purified by chromatography ($SiO_2$, PE/$Et_2O$) to give the product (36 g, 39%). ESI-MS m/z calcd for $[C_{11}H_{17}N_3O_6S]$ $[M+Na]^+$: 342.1; found: 341.8, $^1H$ NMR (400 MHz, Chloroform-d) δ 5.96 (t, J=4.3 Hz, 1H), 5.38 (d, J=1.7 Hz, 1H), 4.55 (t, J=6.8 Hz, 1H), 4.13 (dd, J=11.4, 6.1 Hz, 1H), 4.01 (dd, J=11.4, 6.8 Hz, 1H), 3.84 (dd, J=10.4, 4.8 Hz, 1H), 3.79 (dd, J=10.3, 3.1 Hz, 1H), 3.51 (s, 3H), 2.16 (s, 3H), 2.07 (s, 3H), 1.85 (d, J=3.8 Hz, 1H).

3-Cyano-2-(trifluoromethyl)pyridin-5-yl 4,6-di-O-acetyl-3-azido-3-deoxy-2-O-methyl-1-thio-α-D-galactopyranoside

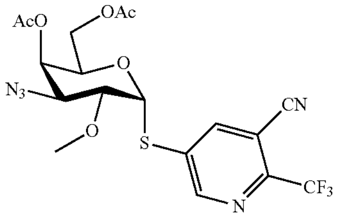

To a solution of 4,6-di-O-acetyl-3-azido-3-deoxy-2-O-methyl-1-thio-α-D-galactopyranose (36 mg, 0.11 mmol) and 5-fluoro-2-(trifluoromethyl)pyridine-3-carbonitrile (32 mg, 0.17 mmol) in DMF (0.5 mL) DIPEA (28.9 μL, 0.17 mmol) was added and the mixture was stirred 30 min at rt. The mixture was diluted with EtOAc (10 mL) and washed with HCl (1 M, 10 mL), water (3×10 mL) and brine (10 mL). The organic phase was dried, evaporated and purified by chromatography ($SiO_2$, PE/EtOAc) to give the product (52 g, 94%). ESI-MS m/z calcd for $[C18H_{18}F_3N_5O_6S][M+H]^+$: 490.1; found: 489.9, $^1H$ NMR (400 MHz, Chloroform-d) δ 8.91 (s, 1H), 8.28 (s, 1H), 6.10 (d, J=5.2 Hz, 1H), 5.42 (s, 1H), 4.54-4.40 (m, 1H), 4.11 (dd, J=10.9, 3.3 Hz, 1H), 4.06-3.95 (m, 2H), 3.82 (d, J=10.4 Hz, 1H), 3.58 (s, 3H), 2.18 (s, 3H), 1.97 (s, 3H).

Intermediate 45

2-(Azetidin-1-ylcarbonyl)-3-bromo-5-chloropyridine

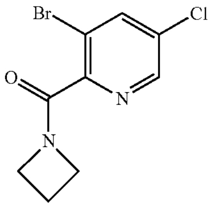 [SMILES: O=C(c1ncc(Cl)cc1Br)N1CCC1]

Azetidine (171 μL, 2.54 mmol) was added to a solution of 3-bromo-5-chloropyridine-2-carboxylic acid (500 mg, 2.11 mmol), 1-hydroxybenzotriazole hydrate (389 mg, 2.54 mmol) and N-(3-dimethylaminopropyl)-N'-ethylcarbodiimide hydrochloride (486 mg, 2.54 mmol) in DMF (8 mL) and $Et_3N$ (0.35 mL, 2.54 mmol). After stirring 26 h at rt the mixture was diluted with EtOAc and washed with water. The aqueous phase was extracted with EtOAc. The combined organic phases were dried, evaporated and purified by chromatography ($SiO_2$, PE/EtOAc) to yield the product (264 mg, 45% yield). ESI-MS m/z calcd for $[C_9H_8BrClN_2O]$ $[M+H]^+$: 275.0; found: 274.6. $^1H$ NMR (400 MHz, Chloroform-d) δ 8.49-8.46 (m, 1H), 7.97-7.94 (m, 1H), 4.29-4.21 (m, 2H), 4.14-4.07 (m, 2H), 2.40-2.29 (m, 2H).

2-(Azetidin-1-ylcarbonyl)-3-[(2,4-dimethoxyphenyl)methylsulfanyl]-5-chloropyridine

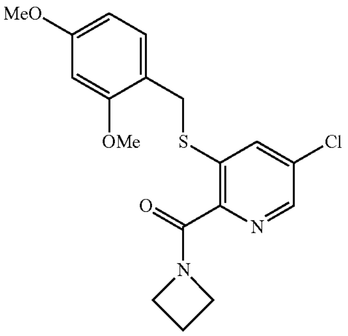 [SMILES: COc1ccc(CSc2cc(Cl)cnc2C(=O)N2CCC2)c(OC)c1]

To a nitrogen purged solution of 2-(azetidin-1-ylcarbonyl)-3-bromo-5-chloropyridine (277 mg, 1.01 mmol), bis(dibenzylideneacetone)palladium(0) (35 mg, 0.060 mmol) and 4,5-bis(diphenylphosphino)-9,9-dimethylxanthene (29 mg, 0.050 mmol) in 1,4-dioxane (1 mL) a solution of 2,4-dimethoxybenzyl thiol (278 mg, 1.51 mmol) and DIPEA (0.34 mL, 2.00 mmol) in 1,4-dioxane (2 mL) was added and the mixture was stirred 4 h at 100° C. The mixture was purified by chromatography ($SiO_2$, PE/EtOAc) to yield the product (359 mg, 94%). ESI-MS m/z calcd for $[C_{18}H_{19}ClN_2O_3S]$ $[M+H]^+$: 379.1; found: 379.1. $^1H$ NMR (400 MHz, Chloroform-d) δ 8.49 (d, J=2.0 Hz, 1H), 7.71 (d, J=2.0 Hz, 1H), 7.27 (s, 1H), 6.47-6.42 (m, 2H), 4.28 (s, 4H), 4.09 (s, 2H), 3.86 (s, 2H), 3.80 (s, 3H), 2.30 (p, J=7.8 Hz, 2H).

2-(Azetidin-1-ylcarbonyl)-5-chloropyridine-3-thiol

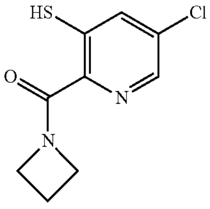 [SMILES: O=C(c1ncc(Cl)cc1S)N1CCC1]

TFA (1.5 mL) was added to a solution of 2-(azetidin-1-ylcarbonyl)-3-[(2,4-dimethoxyphenyl)methylsulfanyl]-5-chloropyridine (359 mg, 0.95 mmol) in DCM (2 mL) and triethylsilane (1.5 mL) and the mixture was stirred 20 h at rt. The mixture was concentrated and purified by chromatography ($SiO_2$, PE/EtOAc) to afford the product (199 mg, 92%). ESI-MS m/z calcd for $[C_9H_9ClN_2OS]$ $[M+H]^+$: 229.0; found: 228.7. $^1H$ NMR (400 MHz, Chloroform-d) δ 8.23 (d, J=2.2 Hz, 1H), 7.63 (d, J=2.2 Hz, 1H), 4.41 (br s, 5H), 2.34 (p, J=7.8 Hz, 2H).

2-(N-Azetidinylcarbamoyl)-5-chloropyrid-3-yl 2,4,6-tri-O-acetyl-3-azido-3-deoxy-1-thio-α-D-galactopyranoside

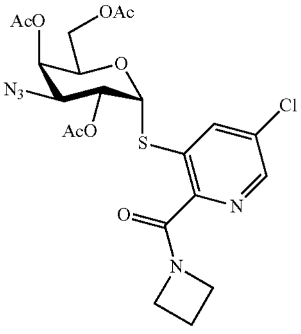

NaH (60% in oil, 70 mg, 1.81 mmol) was added to a solution of 2-(azetidin-1-ylcarbonyl)-5-chloropyridine-3-thiol (199 mg, 0.87 mmol) and 2,4,6-tri-O-acetyl-3-azido-3-deoxy-β-D-galactopyranosyl chloride (456 mg, 1.31 mmol) in DMF (6 mL) and the mixture was stirred 6 h at rt. The mixture was diluted with EtOAc and washed twice with water and once with brine. The organic phase was dried, concentrated and purified by chromatography ($SiO_2$, PE/EtOAc) to afford the product (315 mg, 67%). ESI-MS m/z calcd for $[C_{21}H_{24}ClN_5O_8S]$ $[M+H]^+$: 542.1; found: 541.9. $^1H$ NMR (400 MHz, Chloroform-d) δ 8.31 (d, J=2.0 Hz, 1H), 8.01 (d, J=2.1 Hz, 1H), 6.06 (d, J=5.6 Hz, 1H), 5.45 (d, J=2.8 Hz, 1H), 5.33 (dd, J=11.0, 5.6 Hz, 1H), 4.62-4.49 (m, 2H), 4.45-4.36 (m, 1H), 4.24 (t, J=7.7 Hz, 2H), 4.15-4.00 (m, 4H), 2.35 (p, J=7.7 Hz, 2H), 2.16 (s, 6H), 1.91 (s, 3H).

2-(N-Azetidinylcarbamoyl)-5-chloropyrid-3-yl 3-azido-3-deoxy-1-thio-α-D-galactopyranoside

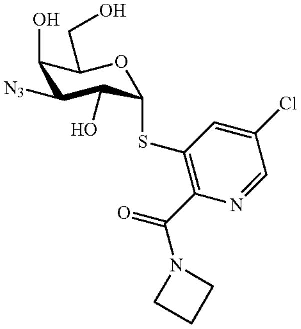

A solution of 2-(N-azetidinylcarbamoyl)-5-chloropyrid-3-yl 2,4,6-tri-O-acetyl-3-azido-3-deoxy-1-thio-α-D-galactopyranoside (275 mg, 0.51 mmol) in MeOH (10 mL), $Et_3N$ (1.5 mL) and water (0.5 mL) was stirred 24 h at rt. The mixture was concentrated and purified by prep HPLC ($C_{18}$, $H_2O$/MeCN/0.1% TFA) to afford the product (206 mg, 98%). ESI-MS m/z calcd for $[C_{15}H_{18}ClN_5O_5S]$ $[M+H]^+$: 416.1; found: 415.8. $^1H$ NMR (400 MHz, Methanol-$d_4$) δ 8.41 (d, J=2.1 Hz, 1H), 8.30 (d, J=2.1 Hz, 1H), 5.83 (d, J=5.5 Hz, 1H), 4.41 (dd, J=10.8, 5.4 Hz, 1H), 4.26-4.14 (m, 5H), 4.04 (d, J=2.2 Hz, 1H), 3.72-3.61 (m, 2H), 3.56 (dd, J=10.8, 3.0 Hz, 1H), 2.38 (p, J=7.8 Hz, 2H).

2-(N-Azetidinylcarbamoyl)-5-chloropyrid-3-yl 3-azido-3-deoxy-2-O-methyl-1-thio-α-D-galactopyranoside

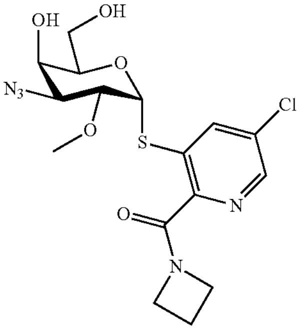

To a solution of 2-(N-azetidinylcarbamoyl)-5-chloropyrid-3-yl 3-azido-3-deoxy-1-thio-α-D-galactopyranoside (200 mg, 0.48 mmol) in MeCN (20 mL) p-toluenesulfonic acid monohydrate (92 mg, 0.48 mmol) followed by benzaldehyde dimethyl acetal (0.15 mL, 0.96 mmol) were added and the mixture was stirred 2 h at rt. $Et_3N$ (0.1 mL, 0.72 mmol) was added and the mixture was concentrated. The residue was partitioned between EtOAc and saturated aq $NaHCO_3$. The organic phase was washed with brine, dried and evaporated. The residue and NaH (60% in oil, 37 mg, 0.96 mmol) were dissolved in DMF (3 mL) and stirred 5 min before the addition of iodomethane (45 μL, 0.72 mmol). After stirring 2 h at rt the mixture was diluted with EtOAc, washed twice with water and the organic phase was dried and evaporated. The residue was stirred 1 h at rt in TFA/water (2.5 mL, 4:1). The mixture was purified by prep HPLC ($C_{18}$, $H_2O$/MeCN/0.1% TFA) to afford the product (45 mg, 22%). ESI-MS m/z calcd for $[C_{16}H_{20}ClN_5O_5S]$ $[M+H]^+$: 430.1; found: 429.9. $^1H$ NMR (400 MHz, Methanol-$d_4$) δ 8.44 (d, J=2.1 Hz, 1H), 8.31 (d, J=2.1 Hz, 1H), 6.15 (d, J=5.4 Hz, 1H), 4.26-4.14 (m, 5H), 4.06 (dd, J=10.6, 5.4 Hz, 1H), 3.99 (d, J=2.6 Hz, 1H), 3.69-3.59 (m, 3H), 3.52 (s, 3H), 2.39 (p, J=7.8 Hz, 2H).

Intermediate 46

5-Chloro-3-fluoro-2-(2-pyridyl)pyridine

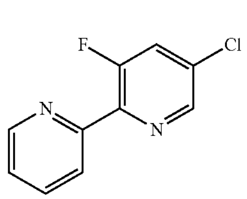 [SMILES: Fc1cc(Cl)cnc1-c1ccccn1]

To a solution of 2-bromo-5-chloro-3-fluoropyridine (600 mg, 2.85 mmol) and tributyl(2-pyridyl)stannane (0.99 mL, 2.85 mmol) in toluene (10.0 mL) $Pd(PPh_3)_4$ (165 mg, 0.143 mmol) was added and the mixture was refluxed 24 h. The mixture was cooled to rt, filtered through celite, concentrated and purified by chromatography ($SiO_2$, PE/EtOAc) to afford the product (515 mg, 87%). ESI-MS m/z calcd for $[C_{10}H_6ClFN_2]$$[M+H]^+$: 209.0; found: 209.0. $^1H$ NMR (500 MHz, Chloroform-d) δ 8.81 (d, J=4.2 Hz, 1H), 8.56 (dd, J=1.9, 0.9 Hz, 1H), 8.00-7.97 (m, 1H), 7.85 (td, J=7.8, 1.8 Hz, 1H), 7.61 (dd, J=10.2, 2.0 Hz, 1H), 7.38 (ddd, J=7.5, 4.8, 1.0 Hz, 1H).

4-Methylphenyl 3-azido-4,6-O-benzylidene-3-deoxy-1-thio-β-D-galactopyranoside

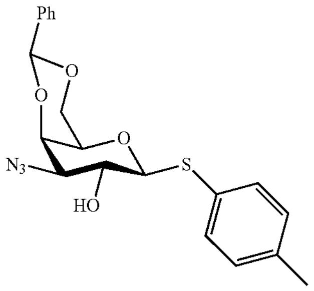

To a solution of 1,2,4,6-tetra-O-acetyl-3-azido-3-deoxy-β-D-galactopyranose (30.0 g, 78.7 mmol) and 4-methylbenzenethiol (11.0 g, 86.6 mmol) in DCM (200 mL) boron trifluoride diethyl etherate (30.2 mL, 236 mmol) was added and the mixture was stirred 1 h at rt. The mixture was partitioned between cold water and DCM. Aqueous NaOH (5 M, 140 mL) was added to maintain pH at approximately at 7. The organic phase was dried, concentrated and the residue was triturated from PE. The obtained material was stirred 19 h at rt in MeOH (300 mL) and NaOMe (1 M, 13 mL). The mixture was neutralized with silica (30 g) and filtered. The filtrate was evaporated, and the residue was dissolved in MeCN (300 mL). To the solution benzaldehyde dimethylacetal (17.9 mL, 118 mmol) followed by p-toluenesulfonic acid monohydrate (1.0 g, 5.26 mmol) were added and the mixture was stirred 1 h at rt. The mixture was neutralized with ammonia (16 M, 1.0 mL) and water (200 mL) was added. The precipitate was isolated as the product (26.61 g, 85%). ESI-MS m/z calcd for $[C_{20}H_{21}N_3O_4S]$ $[M+Na]^+$: 422.1; found: 422.1. $^1H$ NMR (400 MHz, Methanol-$d_4$) δ 7.56-7.51 (m, 2H), 7.42 (m, 2H), 7.35 (m, 3H), 7.05 (d, J=7.9 Hz, 2H), 5.59 (s, 1H), 4.57 (d, J=9.4 Hz, 1H), 4.32-4.27 (m, 1H), 4.21 (dd, J=12.4, 1.6 Hz, 1H), 4.09 (dd, J=12.4, 1.6 Hz, 1H), 3.81 (t, J=9.7 Hz, 1H), 3.63-3.58 (m, 1H), 3.44 (dd, J=10.0, 3.3 Hz, 1H), 2.31 (s, 3H).

4-Methylphenyl 4,6-di-O-acetyl-3-azido-3-deoxy-2-O-methyl-1-thio-β-D-galactopyranoside

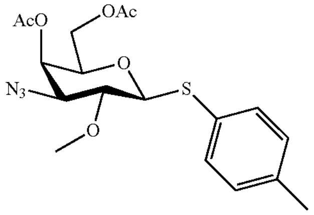

To a cooled (0° C.) solution of 4-methylphenyl 3-azido-4,6-O-benzylidene-3-deoxy-1-thio-β-D-galactopyranoside (26.61 g, 66.6 mmol) and 4-methylbenzenethiol (11.0 g, 86.6 mmol) in DMF (220 mL) NaH (60% in oil, 5.32 g, 133 mmol) was added and the mixture was stirred 5 min. A solution of iodomethane (6.33 mL, 100 mmol) in DMF (50 mL) was added over 15 min and the resulting mixture was stirred 30 min at rt. The reaction was quenched by addition of MeOH (5.0 mL) and ice/water (200 mL) was added. The precipitate was collected, washed with water, dried and stirred 2 h at rt in TFA/water (170 mL, 4:1). The mixture was cooled in an ice-bath and ammonia (16 M, 120 mL) was added cautiously. The precipitate was isolated, dissolved in pyridine (50 mL) and evaporated. The residue was stirred 4 h at 40° C. in pyridine (120 mL) and acetic anhydride (75 mL). The mixture was concentrated and partitioned between EtOAc and HCl (1 M). The organic phase was dried, evaporated and purified by chromatography ($SiO_2$, PE/EtOAc) to afford the product (26.72 g, 94%). ESI-MS m/z calcd for $[C_{18}H_{23}N_3O_6S]$ $[M+NH_4]^+$: 427.1; found: 427.2. $^1H$ NMR (400 MHz, Chloroform-d) δ 7.48 (d, J=8.1 Hz, 2H) 7.13 (d, J=8.0 Hz, 2H), 5.35 (d, J=3.0 Hz, 1H), 4.53 (d, J=9.6 Hz, 1H), 4.10 (d, J=6.5 Hz, 2H), 3.80 (t, J=6.5 Hz, 1H), 3.68 (s, 3H), 3.57 (dd, J=9.6, 3.3 Hz, 1H), 3.38 (t, J=9.6 Hz, 1H), 2.35 (s, 3H), 2.15 (s, 3H), 2.05 (s, 3H).

4,6-Di-O-acetyl-3-azido-3-deoxy-2-O-methyl-α-D-galactopyranosyl Trichloroacetimidate

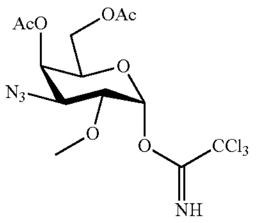

To a cooled (0° C.) solution of 4-methylphenyl 4,6-di-O-acetyl-3-azido-3-deoxy-2-O-methyl-1-thio-β-D-galactopyranoside (6.41 g, 15.6 mmol) in 1,4-dioxane (60 mL) and water (9.3 mL) N-bromosuccinimide (9.7 g, 55 mmol) was added in portions and the mixture was stirred 1 h at rt. The mixture was diluted with EtOAc and washed with aq $NaHSO_3$ (1 M), saturated aq $NaHCO_3$ and brine. The organic phase was evaporated and purified by chromatography ($SiO_2$, PE/EtOAc). The obtained material was dissolved in DCM (30 mL) and trichloroacetonitrile (1.40 mL, 13.4 mmol) was added followed by 1,8-diazabicyclo[5.4.0]undec-7-ene (0.15 mL, 0.96 mmol). After stirring 50 min at rt the mixture was concentrated and purified by chromatography ($SiO_2$, PE/EtOAc) to afford the product (3.65 g, 52%). $^1H$ NMR (400 MHz, Chloroform-d) δ 8.70 (s, 1H), 6.64 (d, J=3.3 Hz, 1H), 5.47 (d, J=2.7 Hz, 1H), 4.36 (t, J=6.5 Hz, 1H), 4.15 (dd, J=11.4, 6.2 Hz, 1H), 4.01 (dd, J=11.5, 4.6 Hz, 1H), 3.98 (dd, J=10.5, 3.3 Hz, 1H), 3.79 (dd, J=10.5, 3.3 Hz, 1H), 3.54 (s, 3H), 2.18 (s, 3H), 2.03 (s, 3H).

Triisopropylsilyl 4,6-di-O-acetyl-3-azido-3-deoxy-2-O-methyl-1-thio-α-D-galactopyranoside

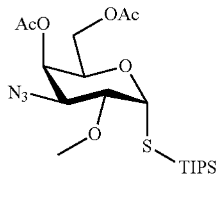

To a solution of 4,6-di-O-acetyl-3-azido-3-deoxy-2-O-methyl-α-D-galactopyranosyl trichloroacetimidate (2.00 g, 4.46 mmol) in DCM (20 mL) triisopropylsilylthiol (1.29 mL, 5.8 mmol) was added followed by boron trifluoride diethyl etherate (0.11 mL, 0.89 mmol) was added and the mixture was stirred 1 h at rt. The mixture was washed with saturated aq $NaHCO_3$ and the organic phase was evaporated and purified by chromatography ($SiO_2$, PE/EtOAc) to afford the product (1.70 g, 80%). ESI-MS m/z calcd for $[C_{20}H_{37}N_3O_6SSi]$ $[M+Na]^+$: 498.2; found: 498.2. $^1H$ NMR (400 MHz, Chloroform-d) δ 5.75 (d, J=5.0 Hz, 1H), 5.39 (d, J=2.5 Hz, 1H), 4.65 (t, J=6.5 Hz, 1H), 4.09 (dd, J=11.4, 6.6 Hz, 1H), 4.03-3.98 (m, 1H), 3.96 (dd, J=10.0, 2.5 Hz, 1H), 3.79 (dd, J=10.5, 5.0 Hz, 1H), 3.52 (s, 3H), 2.15 (s, 3H), 2.04 (s, 3H), 1.31 (m, 3H), 1.15 (d, J=7.3 Hz, 18H).

5-Chloro-2-(pyridin-2-yl)pyridin-3-yl 3-azido-3-deoxy-2-O-methyl-1-thio-α-D-galactopyranoside

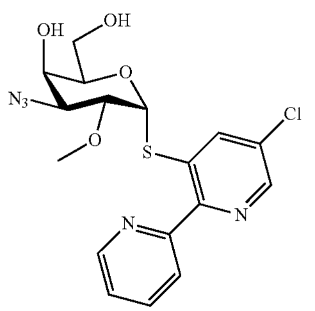

To a solution of triisopropylsilyl 4,6-di-O-acetyl-3-azido-3-deoxy-2-O-methyl-1-thio-α-D-galactopyranoside (679 mg, 1.14 mmol) and 5-chloro-3-fluoro-2-(2-pyridyl)pyridine (286 mg, 1.37 mmol) in MeCN (10 mL) TBAF (1.43 mL, 1 M in THF, 1.43 mmol) was added and the mixture was stirred 6 h at rt. $K_2CO_3$ (158 mg, 1.14 mmol) was added and the mixture was stirred 72 h at 50° C. The mixture was concentrated, dissolved in EtOAc and filtered through a plug of silica. The filtrate was concentrated and purified by chromatography ($SiO_2$, PE/EtOAc). The obtained material was stirred 20 h at rt in MeOH (7.5 mL), $Et_3N$ (2.5 mL) and water (0.75 mL). The mixture was concentrated and purified by prep HPLC ($C_{18}$, $H_2O$/MeCN/0.1% TFA) to afford the product (76 mg, 16%). ESI-MS m/z calcd for $[C_{17}H_{18}ClN_5O_4S]$ $[M+H]^+$: 424.1; found: 424.0. $^1H$ NMR (500 MHz, Methanol-$d_4$) δ 8.78 (d, J=5.0 Hz, 1H), 8.58 (d, J=1.9 Hz, 1H), 8.46 (d, J=2.2 Hz, 1H), 8.27 (td, J=7.8, 1.6 Hz, 1H), 8.18 (d, J=7.9 Hz, 1H), 7.77-7.72 (m, 1H), 6.04 (d, J=5.4 Hz, 1H), 4.03-3.98 (m, 2H), 3.92 (d, J=2.0 Hz, 1H), 3.66-3.60 (m, 2H), 3.53 (dd, J=10.6, 3.0 Hz, 1H), 3.35 (s, 3H).

Intermediate 48

5-Chloropyridin-3-yl 2,4,6-tri-O-acetyl-3-azido-3-deoxy-1-thio-α-D-galactopyranoside

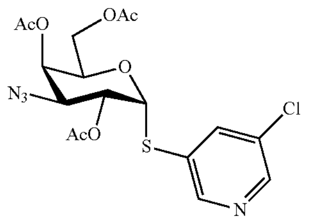

To a solution of 2,4,6-tri-O-acetyl-3-azido-3-deoxy-β-D-galactopyranosyl chloride (1.72 g, 4.91 mmol) and 5-chloropyridine-3-thiol (650 mg, 4.46 mmol) in DMF (20 mL) NaH (60% in oil, 428 mg, 11.2 mmol) was added and the mixture was stirred 3 h at rt. The mixture was diluted with EtOAc and washed twice with water and once with brine. The organic phase was dried, concentrated and purified by chromatography ($SiO_2$, PE/EtOAc) to afford the product (1.17 g, 57%). ESI-MS m/z calcd for $[C_{17}H_{19}ClN_4O_7S]$ $[M+H]^+$: 459.1; found: 459.1. $^1H$ NMR (400 MHz, Chloroform-d) δ 8.53 (d, J=1.8 Hz, 1H), 8.50 (d, J=2.2 Hz, 1H), 7.84 (t, J=2.1 Hz, 1H), 5.99 (d, J=5.5 Hz, 1H), 5.50 (d, J=3.3 Hz, 1H), 5.30 (dd, J=10.9, 5.5 Hz, 1H), 4.68-4.60 (m, 1H), 4.14 (dd, J=11.7, 4.6 Hz, 2H), 4.03 (dd, J=11.6, 7.9 Hz, 1H), 3.96 (dd, J=10.9, 3.4 Hz, 1H), 2.21 (s, 3H), 2.18 (d, J=2.1 Hz, 3H), 2.04 (s, 3H).

Intermediate 50

4-Chloro-2-cyanophenyl 2,4,6-tri-O-acetyl-3-azido-3-deoxy-1-thio-α-D-galactopyranoside

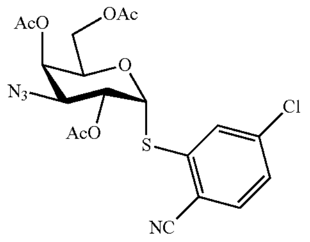

To a cooled (0° C.) solution of acetyl 2,4,6-tri-O-acetyl-3-azido-3-deoxy-1-thio-α-D-galactopyranoside (200 mg, 0.41 mmol) and 4-chloro-2-fluorobenzonitrile (77 mg, 0.49 mmol) in DMF (2 mL) diethylamine (0.11 mL, 1.03 mmol) was added and the mixture was stirred 18 h at rt. The mixture was diluted with EtOAc (40 mL), washed with water (5×20 mL) and brine (20 mL). The organic phase was dried, evaporated and purified by chromatography ($SiO_2$, PE/EtOAc) to afford the product (129 mg, 65%). ESI-MS m/z calcd for $[C_{19}H_{19}ClN_4O_7S]$ $[M+NH_4]^+$: 500.1; found: 500.0. $^1H$ NMR (500 MHz, Chloroform-d) δ 7.70 (d, J=2.0 Hz, 1H), 7.63 (d, J=8.3 Hz, 1H), 7.41 (dd, J=8.3, 2.0 Hz, 1H), 6.09 (d, J=5.5 Hz, 1H), 5.53 (dd, J=3.2, 1.1 Hz, 1H), 5.33 (dd, J=11.0, 5.5 Hz, 1H), 4.69-4.63 (m, 1H), 4.19-4.14 (m, 1H), 4.07 (dd, J=11.6, 7.6 Hz, 1H), 4.00 (dd, J=11.0, 3.3 Hz, 1H), 2.25 (s, 3H), 2.19 (s, 3H), 2.04 (s, 3H).

Intermediate 51

3-Chloro-5-cyanophenyl 2,4,6-tri-O-acetyl-3-azido-3-deoxy-1-thio-α-D-galactopyranoside

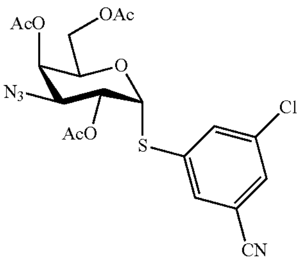

To a cooled (0° C.) solution of acetyl 2,4,6-tri-O-acetyl-3-azido-3-deoxy-1-thio-α-D-galactopyranoside (200 mg, 0.41 mmol), 3-chloro-5-fluorobenzonitrile (96 mg, 0.62 mmol) and diethylamine (0.064 mL, 0.62 mmol) in DMF (2 mL) NaH (60% in oil, 24 mg, 0.62 mmol) was added and the mixture was stirred 2 h at rt. The mixture was diluted with EtOAc (40 mL), washed with water (5×20 mL) and brine (20 mL). The organic phase was dried, evaporated and purified by chromatography ($SiO_2$, PE/EtOAc) to afford the product (84 mg, 42%). ESI-MS m/z calcd for $[C_{19}H_{19}ClN_4O_7S]$ $[M+NH_4]^+$: 500.1; found: 500.1. $^1H$ NMR (500 MHz, Chloroform-d) δ 7.71 (t, J=1.8 Hz, 1H), 7.66 (t, J=1.5 Hz, 1H), 7.58-7.54 (m, 1H), 6.08 (d, J=5.5 Hz, 1H), 5.51 (d, J=2.4 Hz, 1H), 5.31 (dd, J=11.0, 5.5 Hz, 1H), 4.60 (dd, J=7.7, 4.6 Hz, 1H), 4.18 (dd, J=11.7, 4.6 Hz, 1H), 4.04 (dd, J=11.7, 7.9 Hz, 1H), 3.94 (dd, J=11.0, 3.3 Hz, 1H), 2.21 (s, 3H), 2.20 (s, 3H), 2.04 (s, 3H).

Intermediate 52

3-Chloro-4-cyanophenyl 2,4,6-tri-O-acetyl-3-azido-3-deoxy-1-thio-α-D-galactopyranoside

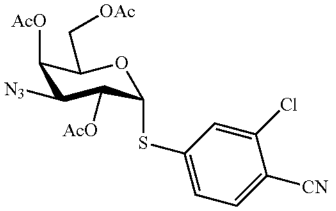

To a cooled (0° C.) solution of acetyl 2,4,6-tri-O-acetyl-3-azido-3-deoxy-1-thio-α-D-galactopyranoside (200 mg, 0.41 mmol) and 2-chloro-4-fluorobenzonitrile (77 mg, 0.49 mmol) in DMF (2 mL) diethylamine (0.11 mL, 1.03 mmol) was added and the mixture was stirred 20 h at rt. The mixture was diluted with EtOAc (40 mL), washed with water (5×20 mL) and brine (20 mL). the organic phase was dried, evaporated and purified by chromatography ($SiO_2$, PE/EtOAc) to afford the product (117 mg, 59%). ESI-MS m/z calcd for $[C_{19}H_{19}ClN_4O_7S]$ $[M+NH_4]^+$: 500.1; found: 500.1. $^1H$ NMR (500 MHz, Chloroform-d) δ 7.62 (d, J=1.7 Hz, 1H), 7.59 (d, J=8.3 Hz, 1H), 7.42 (dd, J=8.3, 1.8 Hz, 1H), 6.19 (d, J=5.6 Hz, 1H), 5.50 (d, J=2.2 Hz, 1H), 5.34 (dd, J=11.0, 5.5 Hz, 1H), 4.55 (dd, J=7.0, 5.6 Hz, 1H), 4.19-4.13 (m, 1H), 4.04 (dd, J=11.6, 7.7 Hz, 1H), 3.96 (dd, J=11.0, 3.3 Hz, 1H), 2.20 (s, 3H), 2.20 (s, 3H), 1.97 (s, 3H).

Intermediate 53

5-Chloropyridin-3-yl 3-azido-3-deoxy-2-O-methyl-1-thio-α-D-galactopyranoside

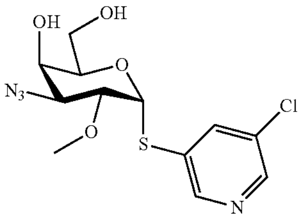

A solution of 5-chloropyridin-3-yl 2,4,6-tri-O-acetyl-3-azido-3-deoxy-1-thio-α-D-galactopyranoside (2.00 g, 4.36 mmol) in MeOH (40 mL) and NaOMe (2.18 mL, 1 M) was stirred 20 min at rt before acetic acid (0.2 mL) was added and the mixture was evaporated. NaOH (100 mL, 1 M) was added and the mixture was extracted with EtOAc (2×100 mL). The combined organic phases were dried, evaporated and the residue was dissolved in MeCN (200 mL). To the solution benzaldehyde dimethylacetal (2.62 mL, 17.4 mmol) followed by p-toluenesulfonic acid monohydrate (249 mg, 1.31 mmol) were added and the mixture was stirred 3 h at rt. The mixture was concentrated and suspended in MeCN (200 mL). More benzaldehyde dimethylacetal (1.31 mL, 8.72 mmol) was added and the mixture was stirred 20 h at rt. The mixture was concentrated and EtOAc (200 mL) was added. The mixture was washed with saturated aq $NaHCO_3$ (100 mL) and water (100 mL), concentrated and co-evaporated with toluene. The residue was dissolved together with NaH (60% in oil, 334 mg, 8.72 mmol) in DMF (20 mL). Iodomethane (0.407 mL, 6.54 mmol) was added and the mixture was stirred 45 min at rt. The mixture was diluted with EtOAc (200 mL), washed with water (5×200 mL) and the organic phase was dried and evaporated. The residue was stirred 30 min at rt in TFA/water (15 mL, 4:1). The mixture was diluted with water (25 mL) and the TFA was removed under reduced pressure. NaOH (50 mL, 1 M) was added and the mixture was extracted with EtOAc (2×50 mL). The combined organic phases were dried, evaporated and recrystallized from EtOAc/PE to afford the product (1.041 g, 69%). The filtrate from the crystallization was concentrated and purified by chromatography ($SiO_2$, PE/EtOAc) to afford more product (476 mg, 31%). ESI-MS m/z calcd for $[C_{12}H_{15}ClN_4O_4S]$ $[M+H]^+$: 347.1; found: 347.1. $^1H$ NMR (400 MHz, Chloroform-d) δ 8.59 (d, J=1.8 Hz, 1H), 8.44 (d, J=2.2 Hz, 1H), 8.15 (t, J=2.0 Hz, 1H), 6.07 (d, J=5.3 Hz, 1H), 4.23 (t, J=6.0 Hz, 1H), 4.06 (dd, J=10.5, 5.3 Hz, 1H), 4.00 (d, J=2.4 Hz, 1H), 3.71-3.59 (m, 3H), 3.53 (s, 3H).

Intermediate 55

4,5-Dichloro-2-ethynylthiazole

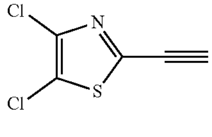

A nitrogen purged solution of 2,4,5-trichlorothiazole (150 mg, 0.80 mmol), CuI (15 mg, 0.080 mmol), bis(triphenylphosphine)palladium(II) chloride (28 mg, 0.040 mmol) and trimethylsilylacetylene (0.17 mL, 1.19 mmol) in THF (1.5 mL) and $Et_3N$ (0.56 mL) was stirred 20 min at 100° C. in a microwave reactor. The mixture was cooled to rt, TBAF (75 μL, 1 M in THF, 0.075 mmol) was added and the mixture was stirred 1 h at rt. The mixture was filtered through a plug of celite, concentrated and purified by chromatography ($SiO_2$, PE/EtOAc) to afford crude product (57 mg) that was used without further purification in subsequent steps.

5-Bromo-2-cyanopyridin-3-yl 4,6-di-O-acetyl-3-azido-3-deoxy-2-O-methyl-1-thio-α-D-galactopyranoside

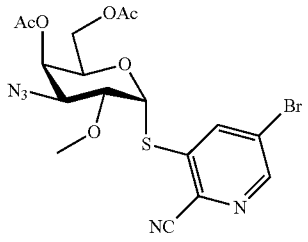

To a solution of triisopropylsilyl 4,6-di-O-acetyl-3-azido-3-deoxy-2-O-methyl-1-thio-α-D-galactopyranoside (6.09 g, 12.8 mmol) and 5-bromo-3-fluoropyridine-2-carbonitrile (3.15 g, 15.4 mmol) in MeCN (61 mL) TBAF (1.28 mL, 1 M in THF, 1.28 mmol) was added and the mixture was stirred 20 min at rt. The mixture was partitioned between brine (60 mL), HCl (2.0 mL, 1 M) and EtOAc (60 mL). The organic phase was dried, concentrated and purified by chromatography ($SiO_2$, PE/EtOAc) to afford the product (6.08 g, 95%). ESI-MS m/z calcd for $[C_{17}H_{18}BrN_5O_6S]$ $[M+Na]^+$: 522.0; found: 521.8. $^1H$ NMR (400 MHz, Chloroform-d) δ 8.65 (d, J=2.0 Hz, 1H), 8.21 (d, J=2.0 Hz, 1H), 6.12 (d, J=5.3 Hz, 1H), 5.43 (d, J=2.7 Hz, 1H), 4.53-4.46 (m, 1H), 4.06 (dd, J=11.7, 4.7 Hz, 1H), 4.01 (dd, J=10.3, 5.3 Hz, 1H), 3.98 (dd, J=11.7, 7.6 Hz, 1H), 3.87 (dd, J=10.3, 3.3 Hz, 1H), 3.62 (s, 3H), 2.16 (s, 3H), 1.98 (s, 3H).

Intermediate 56

5-Bromo-2-cyanophenyl 4,6-di-O-acetyl-3-azido-3-deoxy-2-O-methyl-1-thio-α-D-galactopyranoside

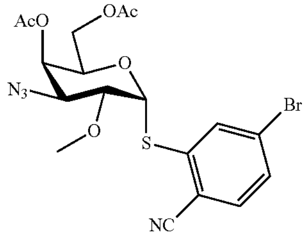

To a solution of triisopropylsilyl 4,6-di-O-acetyl-3-azido-3-deoxy-2-O-methyl-1-thio-α-D-galactopyranoside (820 mg, 1.38 mmol) and 4-bromo-2-fluorobenzonitrile (331 mg, 1.65 mmol) in MeCN (6 mL) TBAF (138 μL, 1 M in THF, 0.14 mmol) was added and the mixture was stirred 1 h at rt. The mixture was concentrated and purified by chromatography ($SiO_2$, PE/EtOAc) to afford the product (796 mg, quantitative yield). ESI-MS m/z calcd for $[C_{18}H_{19}BrN_4O_6S]$ $[M+Na]^+$: 521.0; found: 521.0. $^1H$ NMR (500 MHz, Chloroform-d) δ 7.89 (t, J=1.0 Hz, 1H), 7.57 (d, J=1.1 Hz, 2H), 6.14 (d, J=5.3 Hz, 1H), 5.44 (d, J=2.3 Hz, 1H), 4.60-4.51 (m, 1H), 4.07 (dd, J=11.6, 5.1 Hz, 1H), 4.04-3.98 (m, 2H), 3.88 (dd, J=10.4, 3.3 Hz, 1H), 3.63 (s, 3H), 2.18 (s, 3H), 1.99 (s, 3H).

5-Bromo-2-cyanophenyl 3-azido-3-deoxy-2-O-methyl-1-thio-α-D-galactopyranoside

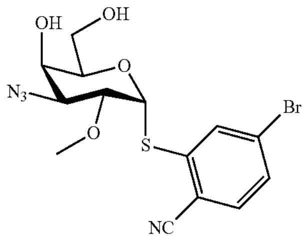

A solution of 5-bromo-2-cyanophenyl 4,6-di-O-acetyl-3-azido-3-deoxy-2-O-methyl-1-thio-α-D-galactopyranoside (796 mg, 1.59 mmol) in MeOH (5 mL) and NaOMe (80 μL, 1 M) was stirred 90 min at rt. The mixture was filtered through a SCX-column and evaporated to afford the product (620 mg, 94%). ESI-MS m/z calcd for $[C_{14}H_{15}BrN_4O_4S]$ $[M+NH_4]^+$: 432.0; found: 432.0. $^1H$ NMR (500 MHz, Methanol-$d_4$) δ 8.12-8.08 (m, 1H), 7.66 (d, J=0.5 Hz, 1H), 7.65 (d, J=1.7 Hz, 1H), 6.22 (d, J=5.4 Hz, 1H), 4.22 (t, J=6.2 Hz, 1H), 4.11 (dd, J=10.6, 5.3 Hz, 1H), 4.04 (d, J=2.0 Hz, 1H), 3.72-3.63 (m, 2H), 3.62 (dd, J=11.5, 6.8 Hz, 1H), 3.59 (s, 3H).

Intermediate 60

5-Bromo-2-(N-methyl-carbonyl)phenyl 3-azido-3-deoxy-2-O-methyl-1-thio-α-D-galactopyranoside

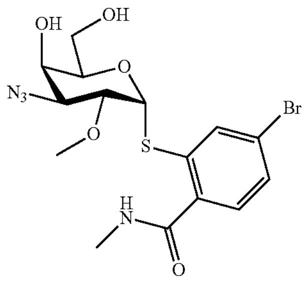

A solution of 5-bromo-2-cyanophenyl 4,6-di-O-acetyl-3-azido-3-deoxy-2-O-methyl-1-thio-α-D-galactopyranoside (793 mg, 1.59 mmol) in EtOH (16 mL) and NaOH (8 mL, 3 M) was stirred 24 h at 80° C. The mixture was concentrated to approximately half its volume. The mixture was acidified to pH 1 by addition of HCl (5 M). The precipitate was filtered off to afford the intermediate carboxylic acid (468 mg). The filtrate was extracted with EtOAc, dried and concentrated to afford more intermediate carboxylic acid (259 mg). The intermediate carboxylic acid (729 mg) was dissolved together with 1-hydroxybenzotriazole hydrate (292 mg, 1.91 mmol) and N-(3-dimethylaminopropyl)-N'-ethylcarbodiimide hydrochloride (366 mg, 1.91 mmol) in DMF (8 mL). To the solution methylamine (0.70 mL, 8 M in EtOH, 5.57 mmol) was added and the mixture was stirred 7 h at 50° C. followed by 15 h at rt. The mixture was diluted with EtOAc, washed with water and the aqueous phase was extracted with EtOAc. The combined organic phases were dried, evaporated and purified by chromatography ($SiO_2$, PE/EtOAc) to afford the product (455 mg, 64%). ESI-MS m/z calcd for $[C_{15}H_{19}BrN_4O_5S]$ $[M+Na]^+$: 469.0; found: 469.0. $^1H$ NMR (500 MHz, Methanol-$d_4$) δ 7.94 (d, J=1.9 Hz, 1H), 7.52 (dd, J=8.2, 1.9 Hz, 1H), 7.29 (d, J=8.2 Hz, 1H), 5.97 (d, J=5.4 Hz, 1H), 4.25 (t, J=6.4 Hz, 1H), 4.02 (dd, J=10.7, 5.4 Hz, 1H), 3.99 (d, J=2.0 Hz, 1H), 3.68 (dd, J=11.4, 5.5 Hz, 1H), 3.63 (dd, J=11.4, 6.8 Hz, 1H), 3.58 (dd, J=10.7, 3.0 Hz, 1H), 3.50 (s, 3H), 2.90 (s, 3H).

Intermediate 61

5-Bromo-2-cyanophenyl 2,4,6-tri-O-acetyl-3-azido-3-deoxy-1-thio-α-D-galactopyranoside

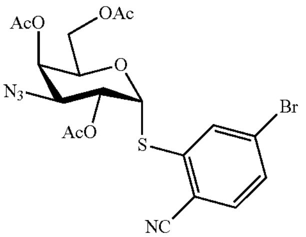

To a solution of 2,4,6-tri-O-acetyl-3-azido-3-deoxy-β-D-galactopyranosyl chloride (3.70 g, 10.6 mmol) and 4-bromo-2-sulfanyl-benzonitrile (2.94 g, 13.8 mmol) in DMF (25 mL) $Cs_2CO_3$ (6.89 g, 21.2 mmol) was added and the mixture was stirred overnight at rt. The mixture was diluted with water (100 mL) and extracted with EtOAc (150 mL). The organic phase was washed with brine, dried over $Na_2SO_4$, concentrated and purified by column chromatography (PE/EA=10/1~3/1, Silica-CS 40 g, 20 mL/min, silica gel, UV 254) to give the product (2.50 g, 45%). ESI-MS m/z calcd for $[C_{19}H_{19}BrN_4O_7S]$ $[M+NH_4]^+$: 544.0; found: 544.0. $^1H$ NMR (400 MHz, Chloroform-d) δ 7.82 (d, J=1.2 Hz, 1H), 7.59-7.46 (m, 2H), 6.06 (d, J=5.6 Hz, 1H), 5.49 (d, J=2.4 Hz, 1H), 5.29 (dd, J=11.2, 5.6 Hz, 1H), 4.75-4.48 (m, 1H), 4.12 (dd, J=11.6, 5.2 Hz, 1H), 4.00-4.05 (m, 1H), 3.97 (dd, J=10.8, 3.2 Hz, 1H), 2.21 (s, 3H), 2.16 (s, 3H), 2.01 (s, 3H).

5-Bromo-2-cyanophenyl 3-azido-3-deoxy-1-thio-α-D-galactopyranoside

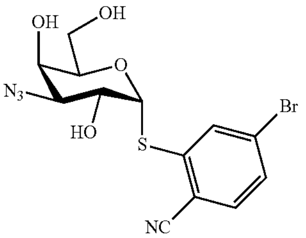

A solution of 5-bromo-2-cyanophenyl 2,4,6-tri-O-acetyl-3-azido-3-deoxy-1-thio-α-D-galactopyranoside (1.30 g, 2.47 mmol) in MeOH (10 mL), $Et_3N$ (6 mL) and $H_2O$ (2 mL) was stirred overnight at rt. The mixture was concentrated, and the residue was suspended in DCM (30 mL). The solid was collected and washed by DCM and diethyl ether to afford the product (850 mg, 86%). ESI-MS m/z calcd for $[C_{13}H_{13}BrN_4O_4S][M+NH_4]^+$: 418.0; found: 418.0. $^1H$ NMR (400 MHz, DMSO-$d_6$) δ 8.01 (d, J=2.0 Hz, 1H), 7.74 (d, J=8.4 Hz, 1H), 7.60 (dd, J=8.4, 2.0 Hz, 1H), 6.10 (d, J=5.2 Hz, 1H), 6.00 (d, J=5.2 Hz, 1H), 5.32 (d, J=6.0 Hz, 1H), 4.62 (t, J=5.6 Hz, 1H), 4.27 (dt, J=10.4, 5.2 Hz, 1H), 3.97-3.85 (m, 2H), 3.54-3.44 (m, 2H), 3.36-3.25 (m, 1H).

5-Bromo-2-cyanophenyl 3-azido-4,6-O-benzylidene-3-deoxy-1-thio-α-D-galactopyranoside

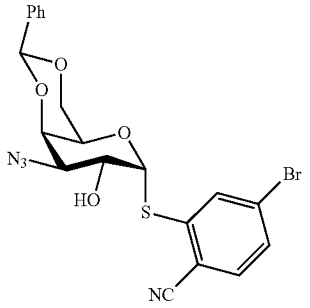

To a solution of 5-bromo-2-cyanophenyl 3-azido-3-deoxy-1-thio-α-D-galactopyranoside (850 mg, 2.12 mmol) in DMF (10 mL) benzaldehyde dimethylacetal (967 mg, 6.36 mmol) and D(+)-10-camphorsulfonic acid (98.4 mg, 0.42 mmol) were added and the mixture was stirred 3 h at 50° C. under reduced pressure. The mixture was neutralized with $Et_3N$, concentrated, and purified by column chromatography (PE/EA=5/1~3/1, Silica-CS 20 g, 20 mL/min, silica gel, UV 254) to afford the product (900 mg, 87%). ESI-MS m/z calcd for $[C_{20}H_{17}BrN_4O_4S]$ $[M+H]^+$: 489.0; found: 489.0. $^1H$ NMR (400 MHz, Chloroform-d) δ 7.92 (d, J=1.2 Hz, 1H), 7.54-7.47 (m, 4H), 7.39-7.32 (m, 3H), 5.89 (d, J=5.2 Hz, 1H), 5.63 (s, 1H), 4.64 (dd, J=10.8, 5.2 Hz, 1H), 4.42 (d, J=2.8 Hz, 1H), 4.25-4.28 (m, 2H), 4.15 (dd, J=12.4, 1.2 Hz, 1H), 3.62 (dd, J=10.8, 3.2 Hz, 1H).

5-Bromo-2-cyanophenyl 3-azido-4,6-O-benzylidene-3-deoxy-2-O-methyl-1-thio-α-D-galactopyranoside

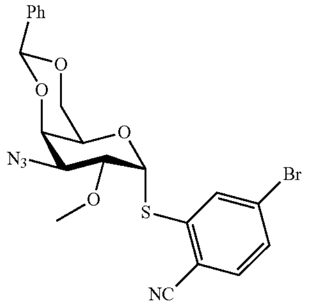

To a stirred solution of 5-bromo-2-cyanophenyl 3-azido-4,6-O-benzylidene-3-deoxy-1-thio-α-D-galactopyranoside (1.10 g, 2.25 mmol) in dry DMF (10 mL) NaH (60% in oil, 98.9 mg, 2.47 mmol) was added at 0° C. followed by iodomethane (0.327 mL, 4.50 mmol) and the mixture was stirred 5 min at 0° C. The mixture was poured into water (50 mL) and extracted with EA (2×40 mL). The combined organic layers were washed with water (50 mL), brine (50 mL), dried over $Na_2SO_4$, concentrated and purified by column chromatography (PE/EA=10/1~2/1, Silica-CS 12 g, 20 mL/min, silica gel, UV 254) to afford the product (660 mg, 67%). ESI-MS m/z calcd for $[C_{21}H_{19}BrN_4O_4S][M+H]^+$: 503.0; found: 503.0. $^1H$ NMR (400 MHz, Chloroform-d) δ 7.89-7.87 (m, 1H), 7.53-7.49 (m, 4H), 7.39-7.35 (m, 3H), 6.11 (d, J=5.2 Hz, 1H), 5.62 (s, 1H), 4.34 (d, J=3.2 Hz, 1H), 4.31-4.23 (m, 1H), 4.22-4.13 (m, 3H), 3.80-3.74 (m, 1H), 3.60 (s, 3H).

5-Bromo-2-carboxyphenyl 3-azido-4,6-O-benzylidene-3-deoxy-2-O-methyl-1-thio-α-D-galactopyranoside

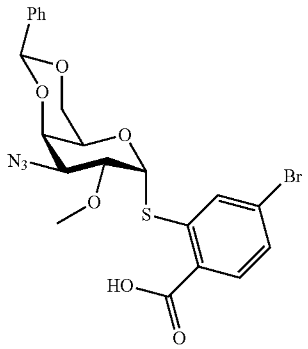

To a solution of 5-bromo-2-cyanophenyl 3-azido-4,6-O-benzylidene-3-deoxy-2-O-methyl-1-thio-α-D-galactopyranoside (450 mg, 0.89 mmol) in EtOH (20 mL) and water (10 mL) NaOH (894 mg, 22.3 mmol) was added and the mixture was stirred overnight at 90° C. The EtOH was removed under reduced pressure. The mixture was acidified to pH 6 by addition of HCl (1 M) and the mixture was extracted with EtOAc (2×60 mL). The organic layers were washed with brine, dried over $Na_2SO_4$ and concentrated to afford the product (400 mg, 86%). ESI-MS m/z calcd for $[C_{21}H_{20}BrN_3O_6S]$ $[M-H]^-$: 520.0; found: 520.0. $^1H$ NMR (400 MHz, Chloroform-d) δ 8.01-7.92 (m, 2H), 7.59-7.51 (m, 2H), 7.44-7.32 (m, 4H), 6.15 (d, J=5.2 Hz, 1H), 5.64 (s, 1H), 4.36-4.31 (m, 2H), 4.29-4.24 (m, 1H), 4.20-4.07 (m, 2H), 3.91 (dd, J=10.8, 3.2 Hz, 1H), 3.55 (s, 3H).

5-Bromo-2-(N-methyl-carbonyl)phenyl 3-azido-4,6-O-benzylidene-3-deoxy-2-O-methyl-1-thio-α-D-galactopyranoside

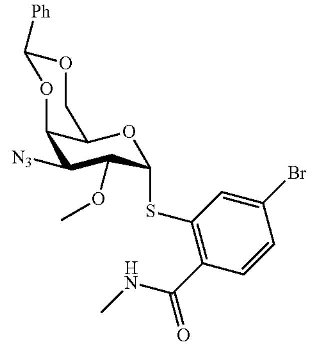

To a solution of 5-bromo-2-carboxyphenyl 3-azido-4,6-O-benzylidene-3-deoxy-2-O-methyl-1-thio-α-D-galactopyranoside (200 mg, 0.38 mmol) in DMF (4 mL) methylamine hydrochloride (77.6 mg, 1.15 mmol), DIPEA (0.328 mL, 1.91 mmol) and HATU (291 mg, 0.77 mmol) were added and the mixture was stirred overnight at rt. The mixture was poured into water (60 mL) and extracted with EA (2×50 mL). The organic layers were washed with water (50 mL) and brine (50 mL), dried over $Na_2SO_4$, concentrated and purified by column chromatography (PE/EA=1/1~0/1, Silica-CS 20 g, 25 mL/min, silica gel, UV254) to give the product (105 mg, 51%). ESI-MS m/z calcd for $[C_{22}H_{23}BrN_4O_5S]$ $[M+H]^+$: 535.1; found: 535.0. $^1H$ NMR (400 MHz, Chloroform-d) δ 7.82-7.77 (m, 1H), 7.55-7.49 (m, 2H), 7.44-7.33 (m, 5H), 6.34-6.28 (m, 1H), 6.02 (d, J=5.2 Hz, 1H), 5.61 (s, 1H), 4.37-4.29 (m, 1H), 4.27-4.18 (m, 2H), 4.17-4.07 (m, 2H), 3.77 (dd, J=10.8, 3.2 Hz, 1H), 3.53 (s, 3H), 3.01 (d, J=4.8 Hz, 3H).

5-Bromo-2-(N-methyl-carbonyl)phenyl 4,6-O-benzylidene-3-deoxy-2-O-methyl-3-[4-(2-thiazolyl)-1H-1,2,3-triazol-1-yl]-1-thio-α-D-galactopyranoside

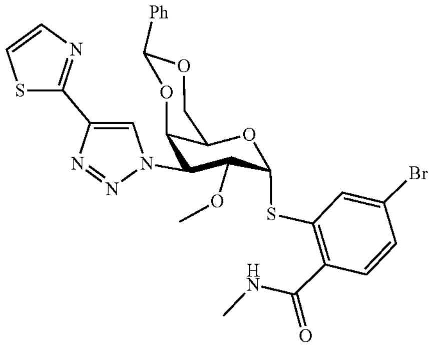

To a solution of 5-bromo-2-(N-methyl-carbonyl)phenyl 3-azido-4,6-O-benzylidene-3-deoxy-2-O-methyl-1-thio-α-D-galactopyranoside (105 mg, 0.20 mmol) in DMF (4 mL)

trimethyl(2-thiazol-2-ylethynyl)silane (142 mg, 0.78 mmol), copper (II) sulfate pentahydrate (49.0 mg, 0.20 mmol) and (+)-sodium L-ascorbate (38.9 mg, 0.20 mmol) were added and the mixture was stirred overnight at rt. The mixture was poured into water (50 mL) and extracted with EA (60 mL). The organic layer was washed with brine (50 mL), dried over $Na_2SO_4$, concentrated and purified by column chromatography (DCM/MeOH=1/0~5/1, Silica-CS 4 g, 10 mL/min, silica gel, UV 254) to give the product (85.0 mg, 67%). ESI-MS m/z calcd for $[C_{27}H_{26}BrN_5O_5S_2]$ $[M+H]^+$: 644.1; found: 644.1. $^1H$ NMR (400 MHz, Chloroform-d) δ 8.37 (s, 1H), 7.82 (d, J=2.0 Hz, 1H), 7.59-7.31 (m, 8H), 6.36 (s, 1H), 6.19 (d, J=4.8 Hz, 1H), 5.51 (s, 1H), 5.38 (d, J=11.2 Hz, 1H), 4.57 (d, J=14.8 Hz, 2H), 4.44-4.11 (m, 3H), 3.32 (s, 3H), 3.02 (d, J=4.8 Hz, 3H).

Intermediate 62

5-Chloro-2-cyanophenyl 3-azido-4,6-O-benzylidene-3-deoxy-1-thio-α-D-galactopyranoside

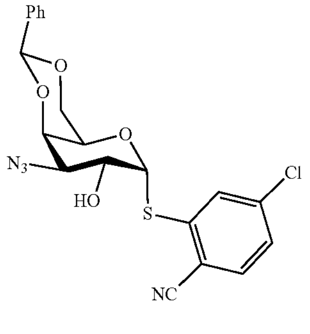

A solution of 5-chloro-2-cyanophenyl 2,4,6-tri-O-acetyl-3-azido-3-deoxy-1-thio-α-D-galactopyranoside (1.33 g, 2.75 mmol) in MeOH (5.0 mL) and catalytic amount of NaOMe was stirred 20 min at rt. The mixture was neutralized with acidic resin, filtered, and concentrated. The residue was dissolved in DMF (5 mL) and benzaldehyde dimethylacetal (1.28 g, 8.41 mmol) and D(+)-10-camphorsulfonic acid (195 mg, 0.84 mmol) were added. The mixture was stirred 2 h at 60° C. before being neutralized with $Et_3N$. The mixture was concentrated and purified by column chromatography (PE/EA=2/1~1/1, Silica-CS 12 g, 20 mL/min, silica gel, UV 254) to afford the product (768 mg, 63%). ESI-MS m/z calcd for $[C_{20}H_{17}ClN_4O_4S]$ $[M+H]^+$: 445.1; found: 445.0. $^1H$ NMR (400 MHz, Chloroform-d) δ 7.76 (d, J=2.0 Hz, 1H), 7.60 (d, J=8.4 Hz, 1H), 7.51-7.49 (m, 2H), 7.37-7.34 (m, 4H), 5.88 (d, J=5.2 Hz, 1H), 5.63 (s, 1H), 4.67-4.62 (m, 1H), 4.41 (d, J=2.8 Hz, 1H), 4.28-4.14 (m, 3H), 3.63 (dd, J=10.8, 3.2 Hz, 1H), 2.47 (d, J=6.4 Hz, 1H).

5-Chloro-2-cyanophenyl 3-azido-4,6-O-benzylidene-3-deoxy-2-O-methyl-1-thio-α-D-galactopyranoside

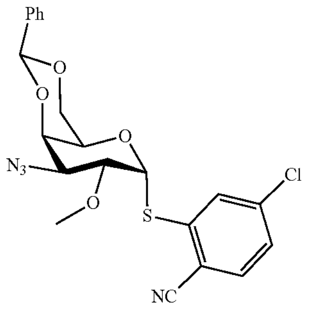

To a solution of 5-chloro-2-cyanophenyl 3-azido-4,6-O-benzylidene-3-deoxy-1-thio-α-D-galactopyranoside (300 mg, 0.67 mmol) in dry DMF (3 mL) $Cs_2CO_3$ (659 mg, 2.02 mmol) was added followed by iodomethane (0.084 mL, 1.35 mmol) and the mixture was stirred 16 h at rt. The mixture was poured into ice-water and the solids were collected by filtration to afford the product (165 mg, 53%). ESI-MS m/z calcd for $[C_{21}H_{19}ClN_4O_4S]$ $[M+H]^+$: 459.1; found: 459.2. $^1H$ NMR (400 MHz, Chloroform-d) δ 7.71 (d, J=2.0 Hz, 1H), 7.60 (d, J=8.4 Hz, 1H), 7.53-7.47 (m, 2H), 7.40-7.32 (m, 4H), 6.10 (d, J=5.2 Hz, 1H), 5.61 (s, 1H), 4.33 (d, J=3.2 Hz, 1H), 4.26 (dd, J=10.8, 5.2 Hz, 1H), 4.21-4.16 (m, 2H), 4.14-4.06 (m, 1H), 3.76 (dd, J=10.8, 3.2 Hz, 1H), 3.59 (s, 3H).

2-Carboxy-5-chlorophenyl 3-azido-4,6-O-benzylidene-3-deoxy-2-O-methyl-1-thio-α-D-galactopyranoside

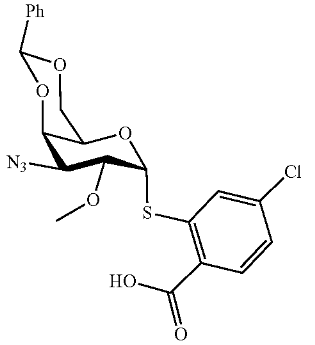

To a solution of 5-chloro-2-cyanophenyl 3-azido-4,6-O-benzylidene-3-deoxy-2-O-methyl-1-thio-α-D-galactopyranoside (165 mg, 0.36 mmol) in EtOH (10 mL) and water (3 mL) NaOH (360 mg, 8.99 mmol) was added and the mixture was stirred overnight at 90° C. The EtOH was removed under reduced pressure. The mixture was acidified to pH 6 by addition of HCl (1 M) and the mixture was extracted with EtOAc (2×60 mL). The organic layers were washed with brine, dried over $Na_2SO_4$ and concentrated to afford the product (152 mg, 89%). ESI-MS m/z calcd for $[C_{21}H_{20}ClN_3O_6S]$ $[M-H]^+$: 478.1; found: 478.2. $^1H$ NMR (400 MHz, Chloroform-d) δ 7.97 (d, J=8.4 Hz, 1H), 7.78 (d, J=2.0 Hz, 1H), 7.51-7.44 (m, 2H), 7.36-7.26 (m, 3H), 7.19-7.14 (m, 1H), 6.08 (d, J=5.2 Hz, 1H), 5.57 (s, 1H), 4.30-4.15 (m, 3H), 4.10-3.99 (m, 2H), 3.84 (dd, J=10.8, 3.2 Hz, 1H), 3.48 (s, 3H).

5-Chloro-2-(N-methyl-carbonyl)phenyl 3-azido-4,6-O-benzylidene-3-deoxy-2-O-methyl-1-thio-α-D-galactopyranoside

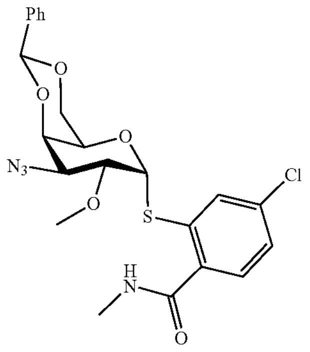

To a solution of 2-carboxy-5-chlorophenyl 3-azido-4,6-O-benzylidene-3-deoxy-2-O-methyl-1-thio-α-D-galactopyranoside (152 mg, 0.32 mmol) in DMF (3 mL) methylamine hydrochloride (64.4 mg, 0.95 mmol), DIPEA (0.272 mL, 1.59 mmol) and HATU (242 mg, 0.64 mmol) were added and the mixture was stirred overnight at rt. The mixture was poured into water (60 mL) and extracted with EA (2×50 mL). The organic layers were washed with water (50 mL) and brine (50 mL), dried over $Na_2SO_4$, concentrated and purified by column chromatography (PE/EA=1/1~0/1, Silica-CS 20 g, 25 mL/min, silica gel, UV254) to give the product (133 mg, 85%). ESI-MS m/z calcd for $[C_{22}H_{23}ClN_4O_5S]$ $[M+H]^+$: 491.1; found: 491.2. $^1$H NMR (400 MHz, Chloroform-d) δ 7.58 (d, J=2.0 Hz, 1H), 7.48-7.40 (m, 3H), 7.35-7.25 (m, 4H), 6.29-6.17 (m, 1H), 5.95 (d, J=5.2 Hz, 1H), 5.54 (s, 1H), 4.25 (d, J=3.2 Hz, 1H), 4.20-4.12 (m, 2H), 4.08-3.99 (m, 2H), 3.70 (dd, J=10.8, 3.2 Hz, 1H), 3.46 (s, 3H), 2.94 (d, J=4.8 Hz, 3H).

5-Chloro-2-(N-methyl-carbonyl)phenyl 4,6-O-benzylidene-3-deoxy-2-O-methyl-3-[4-(2-thiazolyl)-1H-1,2,3-triazol-1-yl]-1-thio-α-D-galactopyranoside

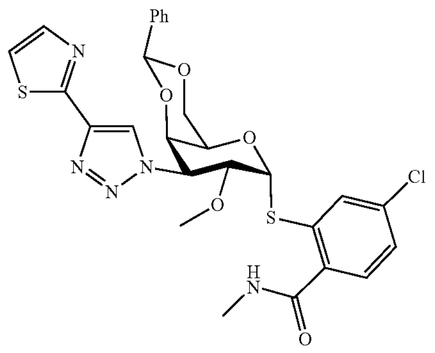

To a solution of 5-chloro-2-(N-methyl-carbonyl)phenyl 3-azido-4,6-O-benzylidene-3-deoxy-2-O-methyl-1-thio-α-D-galactopyranoside (133 mg, 0.27 mmol) in DMF (5 mL) trimethyl(2-thiazol-2-ylethynyl)silane (98.2 mg, 0.54 mmol), copper (II) sulfate pentahydrate (67.6 mg, 0.27 mmol) and (+)-sodium L-ascorbate (53.7 mg, 0.27 mmol) were added and the mixture was stirred overnight at rt. The mixture was poured into water (50 mL) and extracted with EA (60 mL). The organic layer was washed with brine (50 mL), dried over $Na_2SO_4$, concentrated and purified by column chromatography (DCM/MeOH=1/0~5/1, Silica-CS 4 g, 10 mL/min, silica gel, UV 254) to give the product (120 mg, 74%). ESI-MS m/z calcd for $[C_{27}H_{26}ClN_5O_5S_2]$ $[M+H]^+$: 600.1; found: 600.2. $^1$H NMR (400 MHz, Chloroform-d) δ 8.25 (s, 1H), 7.74 (s, 1H), 7.55 (d, J=2.0 Hz, 1H), 7.35-7.20 (m, 6H), 7.14 (dd, J=8.4, 2.0 Hz, 1H), 6.77-6.68 (m, 1H), 6.08 (d, J=5.2 Hz, 1H), 5.39 (s, 1H), 5.25 (dd, J=11.2, 3.2 Hz, 1H), 4.50 (dd, J=11.2, 5.2 Hz, 1H), 4.43 (d, J=3.2 Hz, 1H), 4.27 (s, 1H), 4.17 (dd, J=12.8, 1.6 Hz, 1H), 4.12-3.97 (m, 1H), 3.22 (s, 3H), 2.87 (d, J=4.8 Hz, 3H).

Intermediate 63

5-Bromo-2-cyanophenyl 4,6-O-benzylidene-3-deoxy-3-[4-(4-methylthiazol-2-yl)-1H-1,2,3-triazol-1-yl]-2-O-methyl-1-thio-α-D-galactopyranoside

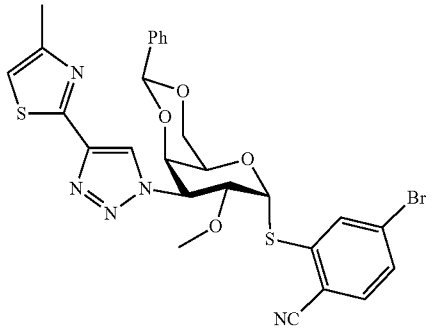

To a solution of 5-bromo-2-cyanophenyl 3-azido-4,6-O-benzylidene-3-deoxy-2-O-methyl-1-thio-α-D-galactopyranoside (130 mg, 0.26 mmol) in DMF (4 mL) trimethyl-[2-(4-methylthiazol-2-yl)ethynyl]silane (101 mg, 0.52 mmol), copper (II) sulfate pentahydrate (64.5 mg, 0.26 mmol) and (+)-sodium L-ascorbate (51.2 mg, 0.26 mmol) were added and the mixture was stirred overnight at rt. The mixture was poured into water (50 mL) and extracted with EA (60 mL). The organic layer was washed with brine (50 mL), dried over $Na_2SO_4$, concentrated and purified by column chromatography (PE/EA=10/1~1/1, Silica-CS 4 g, 10 mL/min, silica gel, UV 254) to give the product (90 mg, 56%). ESI-MS m/z calcd for $[C_{27}H_{24}BrN_5O_4S_2]$ $[M+H]^+$: 626.0; found: 626.0. $^1$H NMR (400 MHz, Chloroform-d) δ 8.29 (s, 1H), 7.91 (s, 1H), 7.60-7.54 (m, 2H), 7.44-7.31 (m, 5H), 6.93-6.89 (m, 1H), 6.24 (d, J=5.2 Hz, 1H), 5.51 (s, 1H), 5.33 (dd, J=11.2, 3.2 Hz, 1H), 4.64-4.54 (m, 2H), 4.45-4.41 (m, 1H), 4.32-4.13 (m, 2H), 3.42 (s, 3H), 2.49 (s, 3H).

Intermediate 64

2-Bromo-5-chloro-4-methylthiazole

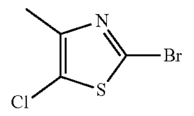

To a solution of 2-bromo-4-methylthiazole (2.60 g, 15 mmol) in MeCN (30 mL) N-chlorosuccinimide (2.34 g, 18 mmol) was added and the mixture was stirred overnight under a nitrogen atmosphere at 70° C. The mixture was concentrated, diluted with water (50 mL) and extracted with DCM (2×100 mL). The combined organic phases were washed with brine, dried over $Na_2SO_4$, evaporated and purified by column chromatography (PE/EA=1/0~5/1, Silica-CS 40 g, 40 mL/min, silica gel, UV 254) to afford the product (1.60 g, 52%). $^1H$ NMR (400 MHz, $CDCl_3$) δ 2.30 (s, 3H). 2-(5-Chloro-4-methylthiazol-2-yl)ethynyltrimethylsilane

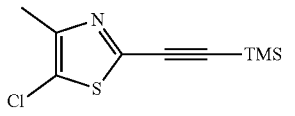

To a solution of 2-bromo-5-chloro-4-methylthiazole (1.60 g, 7.5 mmol) in THF (30 mL), bis(triphenylphosphine) palladium(II) chloride (264 mg, 0.38 mmol), CuI (72 mg, 0.38 mmol), trimethylsilylacetylene (3.2 mL, 23 mmol) and $Et_3N$ (3.1 mL, 23 mmol) were added and the mixture was stirred 4 h under a nitrogen atmosphere at 50° C. The mixture was concentrated, water (50 mL) was added and the mixture was extracted with DCM (2×100 mL). The organic phases were washed with brine, dried over $Na_2SO_4$, evaporated and purified by column chromatography (PE/EA=10/0~10/1, Silica-CS 40 g, 40 mL/min, silica gel, UV 254) to afford (600 mg, 35%). $^1H$ NMR (400 MHz, $CDCl_3$) δ 2.31 (s, 3H), 0.19 (s, 9H).

2,5-Dibromopyridin-3-yl 2,4,6-tri-O-acetyl-3-azido-3-deoxy-1-thio-α-D-galactopyranoside

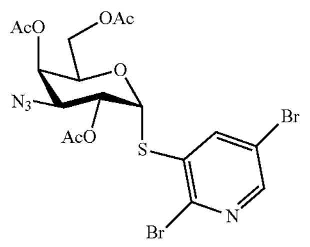

To a solution of acetyl 2,4,6-tri-O-acetyl-3-azido-3-deoxy-1-thio-α-D-galactopyranoside (3 g, 7.70 mmol) in DMF (30 mL) 2,5-dibromo-3-fluoropyridine (2.16 g, 8.47 mmol) and diethylamine (1.13 g, 15.4 mmol) were added at 0° C. and the mixture was stirred overnight at rt. The mixture was poured into water (100 mL) and extracted with EtOAc (2×100 mL). The organic layers were washed with brine (100 mL), dried over $Na_2SO_4$, concentrated and purified by column chromatography (PE/EtOAc=10/1~1/1, Silica-CS 40 g, 50 mL/min, silica gel, UV 254) to afford the product (2.6 g, 58%). ESI-MS m/z calcd for $[C_{17}H_{18}Br_2N_4O_7S]$ $[M+H]^+$: 580.9; found: 581.0. $^1H$ NMR (400 MHz, $CDCl_3$) δ 8.28 (d, J=2.4 Hz, 1H), 7.94 (d, J=2.4 Hz, 1H), 6.12 (d, J=5.6 Hz, 1H), 5.49 (d, J=2.8 Hz, 1H), 5.34 (dd, J=11.2, 5.6 Hz, 1H), 4.53 (dd, J=7.6, 4.8 Hz, 1H), 4.15-4.11 (m, 1H), 4.04-3.98 (m, 2H), 2.20 (s, 3H), 2.17 (s, 3H), 1.97 (s, 3H).

2,5-Dibromopyridin-3-yl 3-azido-3-deoxy-1-thio-α-D-galactopyranoside

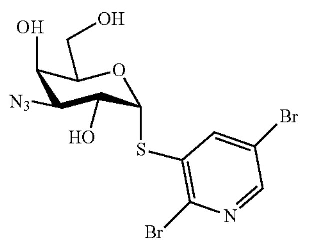

A solution of 2,5-dibromopyridin-3-yl 2,4,6-tri-O-acetyl-3-azido-3-deoxy-1-thio-α-D-galactopyranoside (2.60 g, 4.47 mmol) in MeOH (30 mL), $Et_3N$ (2 mL) and $H_2O$ (1 mL) was stirred overnight at rt. The mixture was concentrated and the residue was suspended in DCM (50 mL). The solid was collected and washed by DCM and diethyl ether to afford the product (1.10 g, 54%). ESI-MS m/z calcd for $[C_{11}H_{12}Br_2N_4O_4S][M+H]^+$: 454.9; found: 455.0. $^1H$ NMR (400 MHz, DMSO-$d_6$) δ 8.31 (d, J=2.4 Hz, 1H), 8.20 (d, J=2.4 Hz, 1H), 6.13 (d, J=5.2 Hz, 1H), 6.02 (d, J=5.2 Hz, 1H), 5.33 (d, J=6.0 Hz, 1H), 4.60 (t, J=5.6 Hz, 1H), 4.28 (dt, J=10.4, 5.2 Hz, 1H), 3.90 (dd, J=6.0, 2.4 Hz, 1H), 3.83 (t, J=6.4 Hz, 1H), 3.55-3.44 (m, 2H), 3.35-3.32 (m, 1H).

2,5-Dibromopyridin-3-yl 3-azido-4,6-O-benzylidene-3-deoxy-1-thio-α-D-galactopyranoside

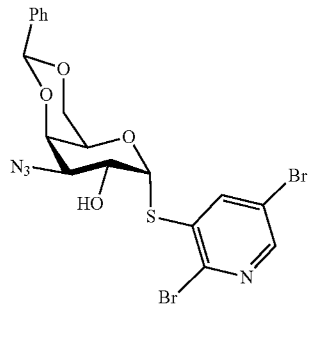

To a solution of 2,5-dibromopyridin-3-yl 3-azido-3-deoxy-1-thio-α-D-galactopyranoside (1.10 g, 2.41 mmol) in DMF (10 mL) benzaldehyde dimethyl acetal (1.1 g, 7.24 mmol) and D(+)-10-camphorsulfonic acid (112 mg, 0.48 mmol) were added and the mixture was stirred 2 h at 50° C. The mixture was cooled to rt and $Et_3N$ (1 mL) was added. The mixture was concentrated and purified by column chromatography (PE/EtOAc=1/1~1/3, Silica-CS 20 g, 25 mL/min, silica gel, UV 254) to afford the product (1.05 g, 80%). ESI-MS m/z calcd for $[C_{18}H_{16}Br_2N_4O_4S]$ $[M+H]^+$:

542.9; found: 543.0. $^1H$ NMR (400 MHz, $CDCl_3$) δ 8.19 (d, J=2.4 Hz, 1H), 7.94 (d, J=2.4 Hz, 1H), 7.48-7.42 (m, 2H), 7.36-7.28 (m, 3H), 5.92 (d, J=5.2 Hz, 1H), 5.59 (s, 1H), 4.64 (dt, J=10.4, 5.2 Hz, 1H), 4.37 (d, J=2.8 Hz, 1H), 4.19 (dd, J=12.8, 1.6 Hz, 1H), 4.08 (dd, J=12.8, 1.6 Hz, 1H), 4.05-4.02 (m, 1H), 3.65 (dd, J=10.8, 3.2 Hz, 1H), 2.42 (d, J=5.6 Hz, 1H).

2,5-Dibromopyridin-3-yl 3-azido-4,6-O-benzylidene-3-deoxy-2-O-methyl-1-thio-α-D-galactopyranoside

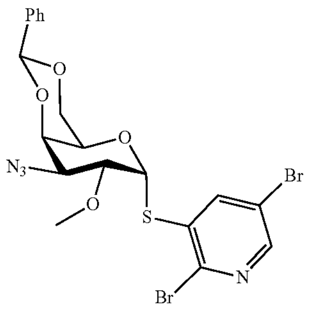

To a solution of 2,5-dibromopyridin-3-yl 3-azido-4,6-O-benzylidene-3-deoxy-1-thio-α-D-galactopyranoside (1.05 g, 1.93 mmol) in DMF (10 mL) $Cs_2CO_3$ (1.86 g, 5.79 mmol) and iodomethane (0.601 mL, 9.65 mmol) were added and the mixture was stirred overnight at rt. The mixture was poured into water (100 mL), the precipitate was collected, and dried in vacuo to afford the product (900 mg, 84%). ESI-MS m/z calcd for $[C_{19}H_{18}Br_2N_4O_4S]$ $[M+H]^+$: 556.9; found: 556.8. $^1H$ NMR (400 MHz, $CDCl_3$) δ 8.24 (d, J=2.4 Hz, 1H), 7.99 (d, J=2.4 Hz, 1H), 7.55-7.47 (m, 2H), 7.40-7.35 (m, 3H), 6.15 (d, J=5.2 Hz, 1H), 5.63 (s, 1H), 4.36-4.27 (m, 2H), 4.19 (dd, J=12.8, 1.6 Hz, 1H), 4.11-4.05 (m, 1H), 4.05-4.00 (m, 1H), 3.82 (dd, J=10.8, 3.2 Hz, 1H), 3.57 (s, 3H).

5-Bromo-2-cyanopyridin-3-yl 3-azido-4,6-O-benzylidene-3-deoxy-2-O-methyl-1-thio-α-D-galactopyranoside

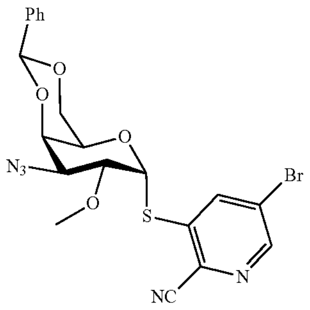

To a solution of 2,5-dibromopyridin-3-yl 3-azido-4,6-O-benzylidene-3-deoxy-2-O-methyl-1-thio-α-D-galactopyranoside (400 mg, 0.72 mmol) in DMSO (15 mL) copper(I) cyanide (77.0 mg, 0.86 mmol) was added and the mixture was stirred 2 h at 120° C. in a microwave reactor. The mixture was poured into water (50 mL) and extracted with EtOAc (2×50 mL). The organic layers were washed with brine, dried over $Na_2SO_4$, concentrated and purified by column chromatography (PE/EtOAc=10/1~1/1, Silica-CS 4 g, 10 mL/min, silica gel, UV 254) to afford the product (140 mg, 39%). ESI-MS m/z calcd for $[C_{20}H_{18}BrN_5O_4S]$ $[M+H]^+$: 504.0; found: 504.0. $^1H$ NMR (400 MHz, $CDCl_3$) δ 8.61 (d, J=2.0 Hz, 1H), 8.20 (d, J=2.0 Hz, 1H), 7.53-7.49 (m, 2H), 7.39-7.34 (m, 3H), 6.13 (d, J=5.2 Hz, 1H), 5.62 (s, 1H), 4.35 (d, J=3.2 Hz, 1H), 4.29-4.25 (m, 1H), 4.18-4.08 (m, 3H), 3.77 (dd, J=10.4, 3.2 Hz, 1H), 3.59 (s, 3H).

5-Bromo-2-cyanopyridin-3-yl 4,6-O-benzylidene-3-[4-(5-chloro-4-methylthiazol-2-yl)-1H-1,2,3-triazol-1-yl]-3-deoxy-2-O-methyl-1-thio-α-D-galactopyranoside

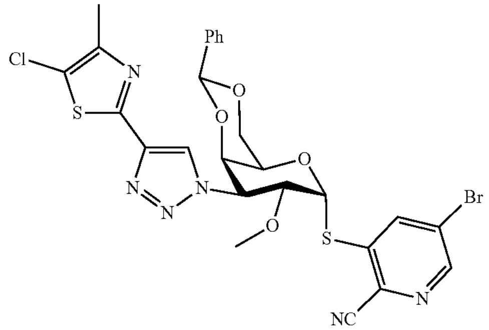

To a solution of 5-bromo-2-cyanopyridin-3-yl 3-azido-4,6-O-benzylidene-3-deoxy-2-O-methyl-1-thio-α-D-galactopyranoside (110 mg, 0.22 mmol) and 2-(5-chloro-4-methylthiazol-2-yl)ethynyltrimethylsilane (60.1 mg, 0.33 mmol) in DMF (4 mL) (+)-sodium L-ascorbate (64.8 mg, 0.33 mmol) and copper (II) sulfate pentahydrate (27.2 mg, 0.11 mmol) were added and the mixture was stirred 4 h at rt. The mixture was concentrated and purified by column chromatography (PE/EA=2/1~1/2, Silica-CS 20 g, 30 mL/min, silica gel, UV 254) to afford the product (110 mg, 76%). ESI-MS m/z calcd for $[C_{26}H_{22}BrClN_6O_4S_2]$ $[M+H]^+$: 661.0; found: 661.0. $^1H$ NMR (400 MHz, Chloroform-d) δ 8.60 (d, J=2.0 Hz, 1H), 8.17 (d, J=2.0 Hz, 2H), 7.36-7.27 (m, 5H), 6.19 (d, J=5.2 Hz, 1H), 5.46 (s, 1H), 5.25 (dd, J=11.6, 3.2 Hz, 1H), 4.54 (dd, J=11.6, 5.2 Hz, 1H), 4.51-4.48 (m, 1H), 4.31 (s, 1H), 4.19 (dd, J=12.8, 1.6 Hz, 1H), 4.13-4.05 (m, 1H), 3.33 (s, 3H), 2.34 (s, 3H).

Intermediate 65

5-Bromo-2-cyanophenyl 4,6-O-benzylidene-3-[4-(5-chloro-4-methylthiazol-2-yl)-1H-1,2,3-triazol-1-yl]-3-deoxy-2-O-methyl-1-thio-α-D-galactopyranoside

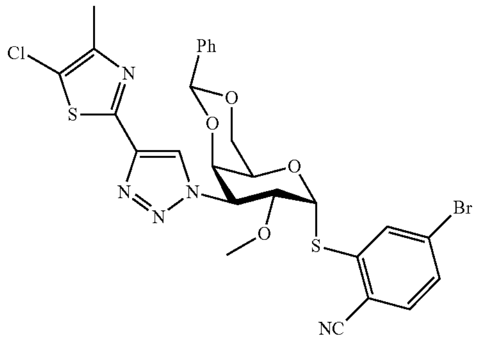

To a solution of 5-bromo-2-cyanophenyl 3-azido-4,6-O-benzylidene-3-deoxy-2-O-methyl-1-thio-α-D-galactopyranoside (130 mg, 0.26 mmol) in DMF (4 mL) 2-(5-chloro-4-methylthiazol-2-yl)ethynyltrimethylsilane (178 mg, 0.78 mmol), (+)-sodium L-ascorbate (51.2 mg, 0.26 mmol) and copper (II) sulfate pentahydrate (64.5 mg, 0.26 mmol) were added and the mixture was stirred overnight at rt. The mixture was poured into water (50 mL) and extracted with EtOAc (60 mL). The organic layer was washed with brine (50 mL), dried over $Na_2SO_4$, concentrated and purified by column chromatography (PE/EtOAc=10/1~1/1, Silica-CS 4 g, 10 mL/min, silica gel, UV 254) to afford the product (95 mg, 56%). ESI-MS m/z calcd for $[C_{27}H_{23}BrClN_5O_4S_2][M+H]^+$: 666.0; found: 660.0. $^1H$ NMR (400 MHz, $CDCl_3$) δ 8.23 (s, 1H), 7.94-7.89 (m, 1H), 7.62-7.53 (m, 2H), 7.43-7.34 (m, 5H), 6.23 (d, J=5.2 Hz, 1H), 5.52 (s, 1H), 5.38-5.28 (m, 1H), 4.62-4.53 (m, 2H), 4.45-4.41 (m, 1H), 4.30-4.14 (m, 2H), 3.42 (s, 3H), 2.41 (s, 3H).

Intermediate 66

2,5-Dichlorophenyl 2,4,6-tri-O-acetyl-3-azido-3-deoxy-1-thio-α-D-galactopyranoside

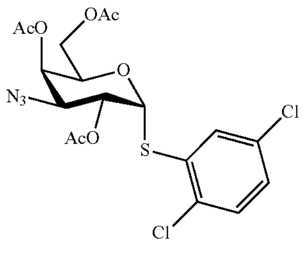

To a solution of 2,5-dichlorobenzenethiol (430 mg, 2.40 mmol) in dry DMF (4 mL) NaH (60% in oil, 96.1 mg, 2.40 mmol) was added at 0° C. and the mixture was stirred 3 min at rt. 2,4,6-Tri-O-acetyl-3-azido-3-deoxy-β-D-galactopyranosyl chloride (700 mg, 2.00 mmol) was added and the mixture was stirred 2 h at rt. The mixture was poured into water (50 mL) and extracted with EA (2×40 mL). The organic layers were washed with water (50 mL), brine (50 mL), dried over $Na_2SO_4$, concentrated and purified by column chromatography (PE/EA=10/1~2/1, Silica-CS 12 g, 20 mL/min, silica gel, UV 254) to afford the product (660 mg, 67%). ESI-MS m/z calcd for $[C18H_{19}Cl_2N_3O_7S][M+NH_4]^+$: 509.0; found: 509.0. $^1H$ NMR (400 MHz, Chloroform-d) δ 7.56 (d, J=2.4 Hz, 1H), 7.34 (d, J=8.4 Hz, 1H), 7.19 (dd, J=8.4, 2.4 Hz, 1H), 6.08 (d, J=5.6 Hz, 1H), 5.51-5.46 (m, 1H), 5.37-5.28 (m, 1H), 4.64-4.57 (m, 1H), 4.11-3.99 (m, 3H), 2.20 (s, 3H), 2.17 (s, 3H), 1.98 (s, 3H).

2,5-Dichlorophenyl 3-azido-3-deoxy-1-thio-α-D-galactopyranoside

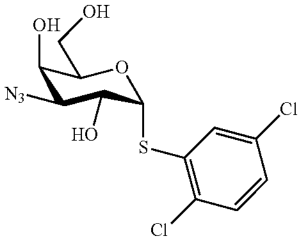

A solution of 2,5-dichlorophenyl 2,4,6-tri-O-acetyl-3-azido-3-deoxy-1-thio-α-D-galactopyranoside (660 mg, 1.34 mmol) in MeOH (20 mL), $Et_3N$ (0.93 mL) and water (2 mL) was stirred 16 h at rt. The mixture was concentrated and purified by column chromatography (PE/EA=1/1~1/4, Silica-CS 4 g, 12 mL/min, silica gel, UV 254) to give the product (360 mg, 73%). ESI-MS m/z calcd for $[C_{12}H_{13}Cl_2N_3O_4S]$ $[M+NH_4]^+$: 383.0; found: 383.1. $^1H$ NMR (400 MHz, Chloroform-d) δ 7.62 (d, J=2.4 Hz, 1H), 7.35 (d, J=8.4 Hz, 1H), 7.20 (dd, J=8.4, 2.4 Hz, 1H), 5.82 (d, J=5.2 Hz, 1H), 4.57-4.49 (m, 1H), 4.29-4.19 (m, 2H), 4.03-3.84 (m, 2H), 3.70-3.62 (m, 1H).

2,5-Dichlorophenyl 3-azido-4,6-O-benzylidene-3-deoxy-1-thio-α-D-galactopyranoside

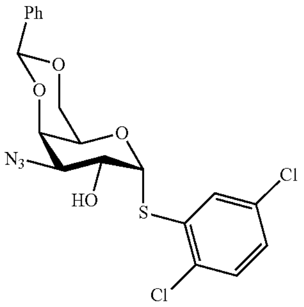

To a solution of 2,5-dichlorophenyl 3-azido-3-deoxy-1-thio-α-D-galactopyranoside (360 mg, 0.98 mmol) in DMF (4 mL) benzaldehyde dimethyl acetal (194 mg, 1.28 mmol) and D(+)-10-camphorsulfonic acid (68.5 mg, 0.30 mmol) were added and the mixture was stirred 1 h at 50° C. The mixture was cooled to rt and poured into water. The solids were collected and dried in vacuum to afford the product (380 mg, 85%). ESI-MS m/z calcd for $[C_{19}H_{17}Cl_2N_3O_4S]$ $[M+H]^+$: 454.0; found: 454.0. $^1H$ NMR (400 MHz, Chloroform-d) δ 7.65 (d, J=2.4 Hz, 1H), 7.55-7.49 (m, 2H), 7.42-7.30 (m, 4H), 7.17 (dd, J=8.4, 2.4 Hz, 1H), 5.94 (d, J=5.2 Hz, 1H), 5.64 (s, 1H), 4.72-4.62 (m, 1H), 4.43-4.38 (m, 1H), 4.32-4.24 (m, 1H), 4.19-4.11 (m, 2H), 3.66 (dd, J=10.8, 3.2 Hz, 1H).

2,5-Dichlorophenyl 3-azido-4,6-O-benzylidene-3-deoxy-2-O-methyl-1-thio-α-D-galactopyranoside

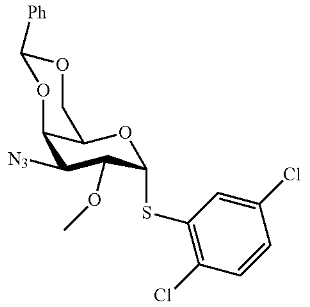

To a solution of 2,5-dichlorophenyl 3-azido-4,6-O-benzylidene-3-deoxy-1-thio-α-D-galactopyranoside (150 mg, 0.33 mmol) in DMF (3 mL) $Cs_2CO_3$ (215 mg, 0.66 mmol) and iodomethane (0.12 mL, 1.65 mmol) were added and the mixture was stirred overnight at rt. The mixture was poured into water (50 mL) and extracted with EA (50 mL). The organic layer was washed with brine (50 mL), dried over $Na_2SO_4$, concentrated and purified by column chromatography (PE/EA=10/1~1/1, Silica-CS 12 g, 20 mL/min, silica gel, UV 254) to give the product (130 mg, 84%). $^1$H NMR (400 MHz, Chloroform-d) δ 7.62 (d, J=2.4 Hz, 1H), 7.56-7.49 (m, 2H), 7.42-7.29 (m, 4H), 7.15 (dd, J=8.4, 2.4 Hz, 1H), 6.15 (d, J=5.2 Hz, 1H), 5.62 (s, 1H), 4.35-4.25 (m, 2H), 4.23-4.17 (m, 1H), 4.14-4.08 (m, 2H), 3.85-3.75 (m, 1H), 3.57 (s, 3H).

2,5-Dichlorophenyl 4,6-O-benzylidene-3-deoxy-2-O-methyl-3-[4-(2-thiazolyl)-1H-1,2,3-triazol-1-yl]-1-thio-α-D-galactopyranoside

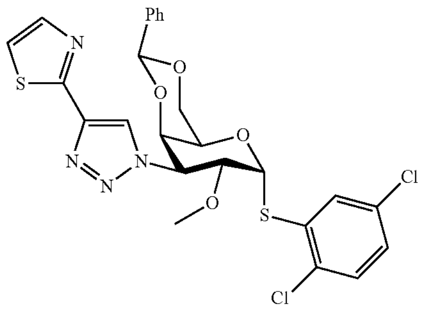

To a solution of 2,5-dichlorophenyl 3-azido-4,6-O-benzylidene-3-deoxy-2-O-methyl-1-thio-α-D-galactopyranoside (160 mg, 0.34 mmol) in DMF (4 mL) trimethyl(2-thiazol-2-ylethynyl)silane (186 mg, 1.02 mmol), (+)-sodium L-ascorbate (67.7 mg, 0.34 mmol) and copper (II) sulfate pentahydrate (85.3 mg, 0.34 mmol) were added and the mixture was stirred overnight at rt. The mixture was poured into water (50 mL) and extracted with EtOAc (60 mL). The organic layer was washed with brine (50 mL), dried over $Na_2SO_4$, concentrated and purified by column chromatography (PE/EtOAc=10/1~1/1, Silica-CS 4 g, 10 mL/min, silica gel, UV 254) to afford the product (120 mg, 61%). ESI-MS m/z calcd for [$C_{25}H_{22}Cl_2N_4O_4S_2$] $[M+H]^+$: 577.0; found: 577.1. $^1$H NMR (400 MHz, $CDCl_3$) δ 8.24 (s, 1H), 7.78 (d, J=3.2 Hz, 1H), 7.58 (d, J=2.4 Hz, 1H), 7.39-7.27 (m, 7H), 7.16-7.08 (m, 1H), 6.22 (d, J=5.2 Hz, 1H), 5.45 (s, 1H), 5.34 (dd, J=11.2, 3.2 Hz, 1H), 4.60-4.51 (m, 1H), 4.51-4.46 (m, 1H), 4.28-4.24 (m, 1H), 4.23-4.15 (m, 1H), 4.10-4.06 (m, 1H), 3.32 (s, 3H).

Intermediate 67

O-5-Bromo-2-chlorophenyl N,N-dimethylcarbamothioate

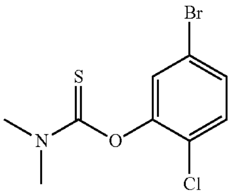

To a solution of 5-bromo-2-chlorophenol (2.0 g, 9.6 mmol) in THF (50 mL) NaH (60% in oil, 463 mg, 12.0 mmol) was added at 0° C. and the mixture was stirred 10 min under a nitrogen atmosphere. N,N-Diethylcarbamothioyl chloride (1.43 g, 12.0 mmol) was added and the mixture was stirred overnight at rt. The mixture was concentrated, dissolved in EtOAc and washed with water and brine. The organic phase was dried over $Na_2SO_4$, concentrated and purified by column chromatography (PE/EA=1/0~3/1, Silica-CS 40 g, 40 mL/min, silica gel, UV 254) to give the product (2.0 g, 70%). ESI-MS m/z calcd for [$C_9H_9BrClNOS$] $[M+H]^+$: 293.9; found: 294.1. $^1$H NMR (400 MHz, Chloroform-d) δ 7.28-7.21 (m, 3H), 3.40 (s, 3H), 3.31 (s, 3H).

S-(5-Bromo-2-chlorophenyl) N,N-dimethylcarbamothioate

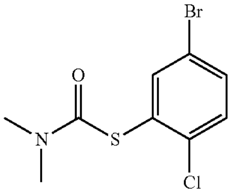

A solution of O-5-bromo-2-chlorophenyl N,N-dimethylcarbamothioate (2.0 g, 4.31 mmol) in diphenyl ether (10 mL) was stirred 3 h at 240° C. The mixture was cooled to rt and purified by column chromatography (PE/EA=10/1~3/1, Silica-CS 40 g, 40 mL/min, silica gel, UV 254) to give the product (1.9 g, 95%). ESI-MS m/z calcd for [$C_9H_9BrClNOS$] $[M+H]^+$: 293.9; found: 294.1. $^1$H NMR (400 MHz, DMSO-$d_6$) δ 7.83 (d, J=2.4 Hz, 1H), 7.70-7.67 (m, 1H), 7.58 (d, J=8.8 Hz, 1H), 3.07-2.93 (m, 6H).

5-Bromo-2-chlorobenzenethiol

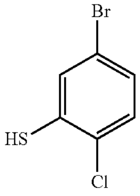

To a solution of S-(5-bromo-2-chlorophenyl) N,N-dimethylcarbamothioate (1.9 g, 6.4 mmol) in MeOH (50 mL) and $H_2O$ (10 mL) NaOH (1.29 g, 32.0 mmol) was added and the mixture was stirred 1 h under a nitrogen atmosphere at 50° C. The mixture was concentrated, water (60 mL) was added and the pH was adjusted to ~3 using aq $KHSO_4$. The mixture was extracted with DCM (2×100 mL) and the combined organic layers were washed with brine, dried over $Na_2SO_4$ and concentrated. The residue was purified by column chromatography (PE/EA=1/0~3/1, Silica-CS 40 g, 40 mL/min, silica gel, UV 254) to afford the product (1.2 g, 83%). ESI-MS m/z calcd for $[C_6H_4BrClS]$. $^1H$ NMR (400 MHz, DMSO-$d_6$) δ 7.82 (d, J=2.0 Hz, 1H), 7.40-7.32 (m, 2H), 6.11 (s, 1H).

5-Bromo-2-chlorophenyl 2,4,6-tri-O-acetyl-3-azido-3-deoxy-1-thio-α-D-galactopyranoside

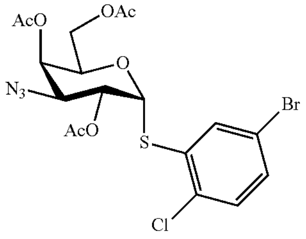

To a solution of 2,4,6-tri-O-acetyl-3-azido-3-deoxy-β-D-galactopyranosyl chloride (2.0 g, 5.7 mmol) in DMF (20 mL) 5-bromo-2-chlorobenzenethiol (1.15 g, 5.1 mmol) and $Cs_2CO_3$ (1.86 g, 5.7 mmol) were added at 0° C. and the mixture was stirred overnight at rt. The mixture was poured into water (100 mL) and extracted with DCM (2×100 mL). The organic layers were washed with brine (100 mL), dried over $Na_2SO_4$, concentrated and purified by column chromatography (PE/EA=10/1~4/1, Silica-CS 80 g, 50 mL/min, silica gel, UV 254) to afford the product (2.0 g, 65%). ESI-MS m/z calcd for $[C_{18}H_{19}BrClN_3O_7S]$ $[M+NH_4]^+$: 553.0; found: 553.0. $^1H$ NMR (400 MHz, Chloroform-d) δ 7.62 (d, J=2.4 Hz, 1H), 7.27 (dd, J=8.4, 2.4 Hz, 1H), 7.20 (d, J=5.6 Hz, 1H), 6.01 (d, J=5.6 Hz, 1H), 5.41 (d, J=2.0 Hz, 1H), 5.25 (dd, J=2.8, 1.6 Hz, 1H), 4.55-4.51 (m, 1H), 4.06-3.93 (m, 3H), 2.12 (s, 3H), 2.09 (s, 3H), 1.92 (s, 3H).

5-Bromo-2-chlorophenyl 3-azido-3-deoxy-1-thio-α-D-galactopyranoside

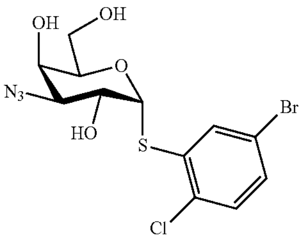

A solution of 5-bromo-2-chlorophenyl 2,4,6-tri-O-acetyl-3-azido-3-deoxy-1-thio-α-D-galactopyranoside (2.0 g, 3.7 mmol) in MeOH (50 mL), $Et_3N$ (20 mL) and water (10 mL) was stirred overnight at rt. The mixture was evaporated to give the product (1.5 g, 98%). ESI-MS m/z calcd for $[Cl_2H_{13}BrClN_3O_4S]$ $[M+NH_4]^+$: 426.9; found: 427.0. $^1H$ NMR (400 MHz, DMSO-$d_6$) δ 7.85-7.84 (m, 1H), 7.44-7.40 (m, 2H), 6.03 (d, J=5.2 Hz, 1H), 5.89 (d, J=1.6 Hz, 1H), 5.33 (d, J=6.0 Hz, 1H), 4.65-4.64 (m, 1H), 4.33-4.27 (m, 1H), 3.93-3.90 (m, 2H), 3.54-3.46 (m, 2H), 3.30 (s, 1H).

5-Bromo-2-chlorophenyl 3-azido-4,6-O-benzylidene-3-deoxy-1-thio-α-D-galactopyranoside

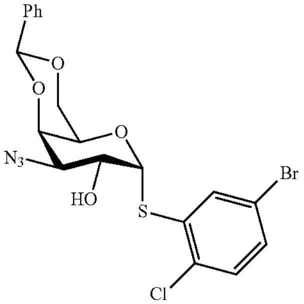

To a solution of 5-bromo-2-chlorophenyl 3-azido-3-deoxy-1-thio-α-D-galactopyranoside (1.0 g, 2.4 mmol) in DMF (10 mL) benzaldehyde dimethyl acetal (741 mg, 4.9 mmol) and D(+)-10-camphorsulfonic acid (170 mg, 0.73 mmol) were added and the mixture was stirred 90 min at 50° C. The mixture was poured into water and extracted with DCM (2×100 mL). The combined organic phases were washed with brine, dried over $Na_2SO_4$, evaporated and purified by column chromatography (PE/EA=1/0~3/1, Silica-CS 40 g, 50 mL/min, silica gel, UV 254) to afford the product (1.0 g, 82%). ESI-MS m/z calcd for $[C_{19}H_{17}BrClN_3O_4S]$ $[M+H]^+$: 454.0; found: 454.0. $^1H$ NMR (400 MHz, Chloroform-d) δ 7.71 (d, J=2.0 Hz, 1H), 7.47-7.44 (m, 2H), 7.34-7.20 (m, 5H), 5.87 (d, J=5.2 Hz, 1H), 5.58 (s, 1H), 4.63-4.57 (m, 1H), 4.34 (d, J=2.4 Hz, 1H), 4.23-4.07 (m, 3H), 3.58 (dd, J=10.8, 3.2 Hz, 1H), 2.26 (d, J=7.2 Hz, 1H).

5-Bromo-2-chlorophenyl 3-azido-4,6-O-benzylidene-3-deoxy-2-O-methyl-1-thio-α-D-galactopyranoside

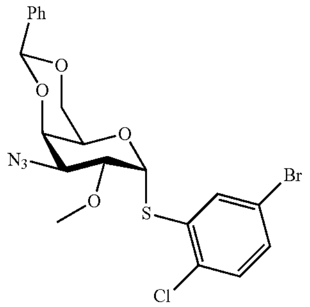

To a solution of 5-bromo-2-chlorophenyl 3-azido-4,6-O-benzylidene-3-deoxy-1-thio-α-D-galactopyranoside (540 mg, 1.1 mmol) in DMF (10 mL) $Cs_2CO_3$ (705 mg, 2.2 mmol) and iodomethane (0.34 mL, 5.4 mmol) were added and the mixture was stirred overnight at rt. The mixture was poured into water (50 mL) and extracted with DCM (50 mL). The organic layer was washed with brine (50 mL), dried over $Na_2SO_4$, concentrated and purified by column chromatography (PE/EA=10/1~1/1, Silica-CS 12 g, 20 mL/min, silica gel, UV 254) to give the product (410 mg, 74%). ESI-MS m/z calcd for $[C_{20}H_{19}BrClN_3O_4S]$ $[M+H]^+$: 512.0; found: 512.0. $^1H$ NMR (400 MHz, Chloroform-d) δ 7.68 (d, J=2.4 Hz, 1H), 7.47-7.44 (m, 2H), 7.34-7.21 (m, 5H), 6.07 (d, J=5.2 Hz, 1H), 5.55 (s, 1H), 4.26 (d, J=3.2 Hz, 1H), 4.22 (dd, J=10.8, 5.2 Hz, 1H), 4.15-4.02 (m, 3H), 3.74 (dd, J=10.8, 3.6 Hz, 1H), 3.50 (s, 3H).

5-Bromo-2-chlorophenyl 4,6-O-benzylidene-3-deoxy-2-O-methyl-3-[4-(2-thiazolyl)-1H-1,2,3-triazol-1-yl]-1-thio-α-D-galactopyranoside

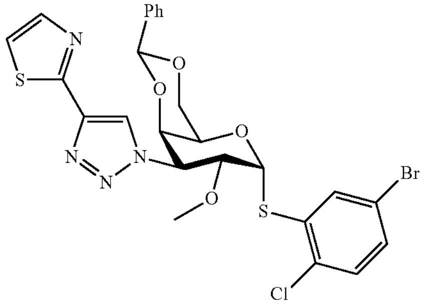

To a solution of 5-bromo-2-chlorophenyl 3-azido-4,6-O-benzylidene-3-deoxy-2-O-methyl-1-thio-α-D-galactopyranoside (195 mg, 0.38 mmol) in DMF (5 mL) trimethyl(2-thiazol-2-ylethynyl)silane (138 mg, 0.38 mmol), (+)-sodium L-ascorbate (38 mg, 0.19 mmol) and copper (II) sulfate pentahydrate (47 mg, 0.19 mmol) were added and the mixture was stirred overnight at rt. The mixture was poured into water (50 mL) and extracted with DCM (2×100 mL). The organic layers were washed with brine (50 mL), dried over $Na_2SO_4$, concentrated and purified by column chromatography (DCM/EtOAc=10/1-4/1, Silica-CS 40 g, 50 mL/min, silica gel, UV 254) to afford the product (180 mg, 76%). ESI-MS m/z calcd for $[C_{25}H_{22}BrClN_4O_4S_2][M+H]^+$: 623.0; found: 623.0. $^1H$ NMR (400 MHz, $CDCl_3$) δ 8.24 (s, 1H), 7.78 (d, J=2.8 Hz, 1H), 7.72 (d, J=2.0 Hz, 1H), 7.35-7.28 (m, 6H), 7.26-7.20 (m, 2H), 6.22 (d, J=5.2 Hz, 1H), 5.45 (s, 1H), 5.34 (dd, J=7.6, 3.2 Hz, 1H), 4.49 (d, J=2.8 Hz, 2H), 4.26 (s, 1H), 4.21-4.06 (m, 2H), 3.32 (s, 3H).

Intermediate 68

5-Chloro-2-fluoro-benzenethiol

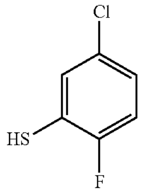

To a solution of 5-chloro-2-fluorobenzenesulfonyl chloride (1.00 g, 4.37 mmol) in DCM (30 mL) triphenylphosphine (3.66 g, 14.0 mmol) was added and the mixture was stirred overnight at rt. The mixture was extracted with NaOH (2×30 mL, 2 M) and the combined aqueous phases were acidified to pH=1 using HCl (1 M). The mixture was extracted with DCM (2×30 mL) and the combined organic phases were dried and concentrated to give the product (650 mg, 92%). $^1H$ NMR (400 MHz, Chloroform-d) δ 7.24-7.14 (m, 1H), 7.04-6.97 (m, 1H), 6.92 (t, J=8.4 Hz, 1H), 3.58 (d, J=1.6 Hz, 1H).

5-Chloro-2-fluorophenyl 2,4,6-tri-O-acetyl-3-azido-3-deoxy-1-thio-α-D-galactopyranoside

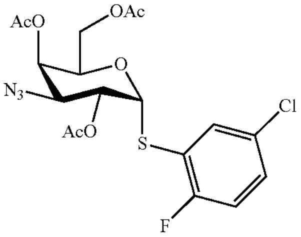

To a solution of 2,4,6-tri-O-acetyl-3-azido-3-deoxy-β-D-galactopyranosyl chloride (1.40 g, 4.00 mmol) and 5-chloro-2-fluorobenzenethiol (650 mg, 4.00 mmol) in DMF (20 mL) $Cs_2CO_3$ (2.61 g, 8.01 mmol) was added and the mixture was stirred overnight at rt. The mixture was poured into water (50 mL) and extracted with EA (150 mL). The organic phase was washed with brine, dried over $Na_2SO_4$, concentrated and purified by column chromatography (PE/EA=10/1~4/1, Silica-CS 40 g, 20 mL/min, silica gel, UV 254) to afford the product (1.2 g, 63%). ESI-MS m/z calcd for $[C_{18}H_{19}ClFN_3O_7S][M+NH_4]^+$: 493.1; found: 493.2. $^1H$ NMR (400 MHz, Chloroform-d) δ 7.43 (dd, J=6.0, 2.4 Hz, 1H), 7.24-7.17 (m, 1H), 6.97 (t, J=8.8 Hz, 1H), 5.93 (d, J=5.6 Hz, 1H), 5.41 (m, 1H), 5.29-5.17 (m, 1H), 4.62-4.51 (m, 1H), 4.03 (dd, J=11.6, 5.2 Hz, 1H), 3.97-3.86 (m, 2H), 2.13 (s, 3H), 2.09 (s, 3H), 1.92 (s, 3H).

5-Chloro-2-fluorophenyl 3-azido-3-deoxy-1-thio-α-D-galactopyranoside

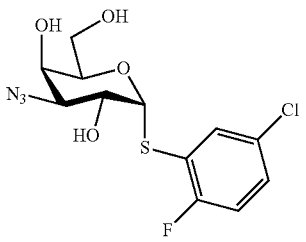

A solution of 5-chloro-2-fluorophenyl 2,4,6-tri-O-acetyl-3-azido-3-deoxy-1-thio-α-D-galactopyranoside (1.2 g, 2.52 mmol) in MeOH (10 mL), $Et_3N$ (6 mL) and water (2 mL) was stirred overnight at rt. The mixture was evaporated to give the product (880 mg, 99%). ESI-MS m/z calcd for $[Cl_2H_{13}ClFN_3O_4S]$ $[M+NH_4]^+$: 367.0; found: 367.2. $^1H$ NMR (400 MHz, DMSO-$d_6$) δ 7.69 (dd, J=6.4, 2.4 Hz, 1H), 7.42-7.35 (m, 1H), 7.28 (t, J=8.8 Hz, 1H), 6.03 (d, J=4.8 Hz, 1H), 5.78 (d, J=5.2 Hz, 1H), 5.30 (d, J=6.4 Hz, 1H), 4.64 (t, J=5.6 Hz, 1H), 4.32-4.22 (m, 1H), 4.00-3.89 (m, 2H), 3.51-3.43 (m, 2H), 3.30-3.20 (m, 1H).

5-Chloro-2-fluorophenyl 3-azido-4,6-O-benzylidene-3-deoxy-1-thio-α-D-galactopyranoside

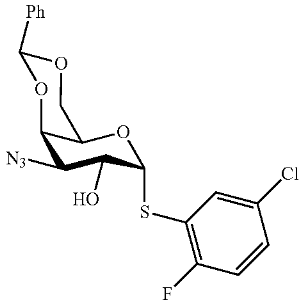

To a solution of 5-chloro-2-fluorophenyl 3-azido-3-deoxy-1-thio-α-D-galactopyranoside (880 mg, 2.52 mmol) in DMF (10 mL) benzaldehyde dimethyl acetal (766 mg, 5.03 mmol) and D(+)-10-camphorsulfonic acid (117 mg, 0.50 mmol) were added and the mixture was stirred 2 h at 50° C. The mixture was neutralized with $Et_3N$, evaporated and purified by column chromatography (PE/EA=5/1~1/5, Silica-CS 20 g, 20 mL/min, silica gel, UV 254) to afford the product (1.0 g, 91%). ESI-MS m/z calcd for $[C_{19}H_{17}ClFN_3O_4S]$ $[M+H]^+$: 438.1; found: 438.0. $^1H$ NMR (400 MHz, Chloroform-d) δ 7.50 (dd, J=6.0, 2.4 Hz, 1H), 7.46-7.40 (m, 2H), 7.33-7.25 (m, 3H), 7.18-7.13 (m, 1H), 6.96 (t, J=8.8 Hz, 1H), 5.77 (d, J=5.2 Hz, 1H), 5.55 (s, 1H), 4.58-4.49 (m, 1H), 4.32 (dd, J=3.2, 1.2 Hz, 1H), 4.19-4.02 (m, 3H), 3.57 (dd, J=10.4, 3.2 Hz, 1H), 2.35 (d, J=6.8 Hz, 1H).

5-Chloro-2-fluorophenyl 3-azido-4,6-O-benzylidene-3-deoxy-2-O-methyl-1-thio-α-D-galactopyranoside

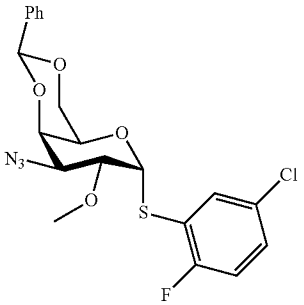

To a solution of 5-chloro-2-fluorophenyl 3-azido-4,6-O-benzylidene-3-deoxy-1-thio-α-D-galactopyranoside (310 mg, 0.81 mmol) in DMF (10 mL) $Cs_2CO_3$ (461 mg, 1.42 mmol) and iodomethane (502 mg, 3.54 mmol) were added and the mixture was stirred overnight at rt. The mixture was poured into water (30 mL) and extracted with EA (2×20 mL). The organic phases were washed with water (20 mL) and brine (20 mL), dried over $Na_2SO_4$, concentrated and purified by column chromatography (PE/EA=10/1~5/1, Silica-CS 12 g, 12 mL/min, silica gel, UV 254) to give the product (210 mg, 66%). ESI-MS m/z calcd for $[C_{20}H_{19}ClFN_3O_4S]$ $[M+H]^+$: 452.1; found: 452.2. $^1H$ NMR (400 MHz, Chloroform-d) δ 7.47 (dd, J=6.0, 2.4 Hz, 1H), 7.46-7.41 (m, 2H), 7.33-7.24 (m, 3H), 7.18-7.13 (m, 1H), 6.96 (t, J=8.8 Hz, 1H), 5.98 (d, J=5.2 Hz, 1H), 5.53 (s, 1H), 4.25 (d, J=3.2 Hz, 1H), 4.16 (dd, J=10.4, 5.2 Hz, 1H), 4.11-3.99 (m, 3H), 3.71 (dd, J=10.4, 3.2 Hz, 1H), 3.51 (s, 3H).

5-Chloro-2-fluorophenyl 4,6-O-benzylidene-3-deoxy-2-O-methyl-3-[4-(2-thiazolyl)-1H-1,2,3-triazol-1-yl]-1-thio-α-D-galactopyranoside

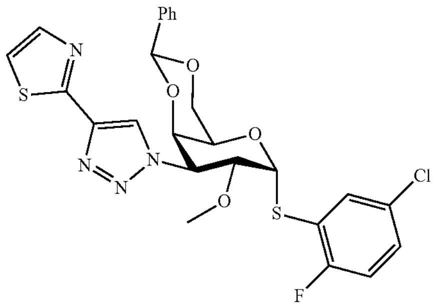

To a solution of 5-chloro-2-fluorophenyl 3-azido-4,6-O-benzylidene-3-deoxy-2-O-methyl-1-thio-α-D-galactopyranoside (210 mg, 0.47 mmol) and trimethyl(2-thiazol-2-ylethynyl)silane (101 mg, 0.56 mmol) in DMF (4 mL) (+)-sodium L-ascorbate (138 mg, 0.70 mmol) and copper (II) sulfate pentahydrate (58 mg, 0.23 mmol) were added and the mixture was stirred 4 h at rt. The mixture was concentrated and purified by column chromatography (PE/EA=2/1~1/2, Silica-CS 20 g, 30 mL/min, silica gel, UV 254) to afford the product (180 mg, 69%). ESI-MS m/z calcd for $[C_{25}H_{22}ClFN_4O_4S_2][M+H]^+$: 561.0; found: 561.0. $^1H$ NMR (400 MHz, $CDCl_3$) δ 8.22 (s, 1H), 7.78 (d, J=3.2 Hz, 1H), 7.51 (dd, J=6.0, 2.4 Hz, 1H), 7.35-7.26 (m, 6H), 7.24-7.20 (m, 1H), 7.00 (t, J=8.8 Hz, 1H), 6.13 (d, J=5.2 Hz, 1H), 5.43 (s, 1H), 5.31 (dd, J=11.2, 3.2 Hz, 1H), 4.55-4.44 (m, 2H), 4.29 (s, 1H), 4.16-4.02 (m, 2H), 3.33 (s, 3H).

Intermediate 69

O-5-Bromo-2-fluorophenyl N,N-dimethylcarbamothioate

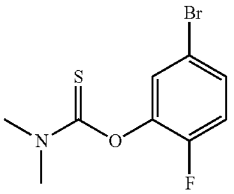

To a solution of 5-bromo-2-fluorophenol (1.05 g, 5.50 mmol) in THF (20 mL) 1,4-diazabicyclo [2.2.2]octane (1.21 mL, 112.0 mmol) and N,N-dimethylcarbamothioyl chloride (1.02 g, 8.25 mmol) were added and the mixture was stirred overnight at rt. The mixture was concentrated, dissolved in EtOAc and washed with water and brine. The organic phase was dried over $Na_2SO_4$, concentrated and purified by column chromatography (PE/EA=1/0~5/1, Silica-CS 20 g, 25 mL/min, silica gel, UV 254) to give the product (1.2 g, 79%). ESI-MS m/z calcd for $[C_9H_9BrFNOS]$ $[M+H]^+$: 278.0; found: 278.0. $^1H$ NMR (400 MHz, Chloroform-d) δ 7.37-7.32 (m, 1H), 7.31-7.27 (m, 1H), 7.09-7.01 (m, 1H), 3.46 (s, 3H), 3.35 (s, 3H).

S-(5-Bromo-2-fluorophenyl) N,N-dimethylcarbamothioate

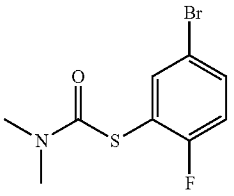

A solution of O-5-bromo-2-fluorophenyl N,N-dimethylcarbamothioate (1.2 g, 4.31 mmol) in diphenyl ether (10 mL) was stirred 4 h at 220° C. The mixture was cooled to rt and purified by column chromatography (PE/EA=10/1~1/1, Silica-CS 20 g, 25 mL/min, silica gel, UV 254) to give the product (960 mg, 80%). ESI-MS m/z calcd for $[C_9H_9ClFNOS]$ $[M+H]^+$: 278.0; found: 278.0. $^1H$ NMR (400 MHz, Chloroform-d) δ 7.62 (dd, J=6.0, 2.4 Hz, 1H), 7.55-7.47 (m, 1H), 7.05 (t, J=8.4 Hz, 1H), 3.23-2.90 (m, 6H).

5-Bromo-2-fluorobenzenethiol

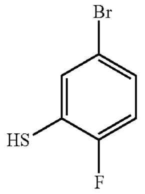

To a solution of S-(5-bromo-2-fluorophenyl) N,N-dimethylcarbamothioate (960 mg, 3.45 mmol) in MeOH (25 mL) a solution of NaOH (276 mg, 6.90 mmol) in water (1 mL) was added and the mixture was stirred 2 h at 60° C. The mixture was concentrated, water (60 mL) was added and the pH was adjusted to ~2 using aq $KHSO_4$. The mixture was extracted with EA (2×50 mL) and the combined organic layers were washed with brine, dried over $Na_2SO_4$ and concentrated to afford the product (650 mg, 91%). ESI-MS m/z calcd for $[C_6H_4BrFS]$. $^1H$ NMR (400 MHz, Chloroform-d) δ 7.42 (dd, J=6.8, 2.4 Hz, 1H), 7.25-7.20 (m, 1H), 6.94 (t, J=8.8 Hz, 1H), 3.64 (d, J=1.6 Hz, 1H).

5-Bromo-2-fluorophenyl 2,4,6-tri-O-acetyl-3-azido-3-deoxy-1-thio-α-D-galactopyranoside

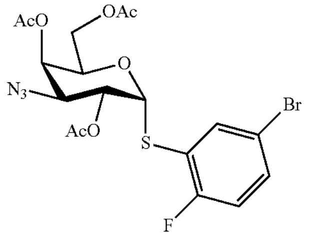

To a solution of 5-bromo-2-fluorobenzenethiol (355 mg, 1.72 mmol) in DMF (5 mL) NaH (60% in oil, 143 mg, 3.57 mmol) was added at 0° C. and the mixture was stirred 5 min at rt. To the solution 2,4,6-tri-O-acetyl-3-azido-3-deoxy-β-D-galactopyranosyl chloride (500 mg, 1.43 mmol) was added and the mixture was stirred 2 h at rt. The mixture was poured into water (60 mL) and extracted with EA (60 mL). The organic phase was washed with brine (50 mL), dried over $Na_2SO_4$, concentrated and purified by column chromatography (PE/EA=10/1~1/1, Silica-CS 12 g, 20 mL/min, silica gel, UV 254) to afford the product (440 mg, 60%). ESI-MS m/z calcd for $[C_{18}H_{19}BrFN_3O_7S]$ $[M+NH_4]^+$: 537.0; found: 537.0. $^1H$ NMR (400 MHz, Chloroform-d) δ 7.64 (dd, J=6.4, 2.4 Hz, 1H), 7.46-7.37 (m, 1H), 6.99 (t, J=8.8 Hz, 1H), 6.00 (d, J=5.6 Hz, 1H), 5.51-5.46 (m, 1H), 5.33-5.25 (m, 1H), 4.65-4.57 (m, 1H), 4.12-4.07 (m, 1H), 4.07-3.92 (m, 2H), 2.20 (s, 3H), 2.16 (s, 3H), 2.00 (s, 3H).

5-Bromo-2-fluorophenyl 3-azido-3-deoxy-1-thio-α-D-galactopyranoside

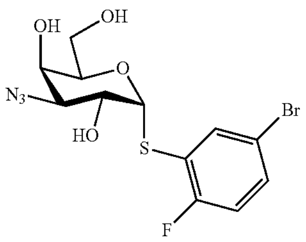

To a solution of 5-bromo-2-fluorophenyl 2,4,6-tri-O-acetyl-3-azido-3-deoxy-1-thio-α-D-galactopyranoside (450 mg, 0.87 mmol) in MeOH (10 mL) NaOMe (46.7 mg, 0.87 mmol) was added and the mixture was stirred 1 h at rt. Acetic acid was added until pH=6. The mixture was evaporated and purified by column chromatography (PE/EA=10/1~1/1, Silica-CS 4 g, 10 mL/min, silica gel, UV 254) to give the product (330 mg, 97%). ESI-MS m/z calcd for $[Cl_2H_{13}BrFN_3O_4S]$ $[M+NH_4]^+$: 411.0; found: 411.0. $^1H$ NMR (400 MHz, Chloroform-d) δ 7.70 (dd, J=6.4, 2.4 Hz, 1H), 7.47-7.39 (m, 1H), 7.00 (t, J=8.8 Hz, 1H), 5.74 (d, J=5.2 Hz, 1H), 4.49 (dd, J=10.4, 5.2 Hz, 1H), 4.31-4.24 (m, 1H), 4.24-4.19 (m, 1H), 3.98-3.90 (m, 1H), 3.89-3.80 (m, 1H), 3.66 (dd, J=10.4, 3.2 Hz, 1H).

5-Bromo-2-fluorophenyl 3-azido-4,6-O-benzylidene-3-deoxy-1-thio-α-D-galactopyranoside

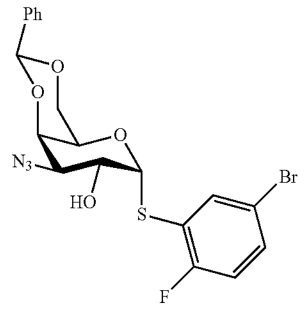

To a solution of 5-bromo-2-fluorophenyl 3-azido-3-deoxy-1-thio-α-D-galactopyranoside (330 mg, 0.84 mmol) in DMF (4 mL) benzaldehyde dimethyl acetal (191 mg, 1.26 mmol) and D(+)-10-camphorsulfonic acid (58.3 mg, 0.25 mmol) were added and the mixture was stirred 1 h at 50° C. The mixture was poured into water and the solids were filtered off to afford the product (350 mg, 87%). ESI-MS m/z calcd for $[C_{19}H_{17}BrFN_3O_4S]$ $[M+H]^+$: 482.0; found: 482.0. $^1H$ NMR (400 MHz, Chloroform-d) δ 7.72 (dd, J=6.4, 2.4 Hz, 1H), 7.54-7.47 (m, 2H), 7.43-7.34 (m, 4H), 6.98 (t, J=8.8 Hz, 1H), 5.85 (d, J=5.2 Hz, 1H), 5.63 (s, 1H), 4.67-4.57 (m, 1H), 4.43-4.38 (m, 1H), 4.27-4.07 (m, 3H), 3.64 (dd, J=10.8, 3.2 Hz, 1H), 2.35 (d, J=6.8 Hz, 1H).

5-Bromo-2-fluorophenyl 3-azido-4,6-O-benzylidene-3-deoxy-2-O-methyl-1-thio-α-D-galactopyranoside

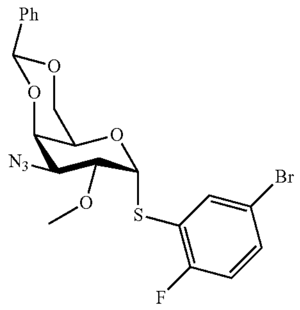

To a solution of 5-bromo-2-fluorophenyl 3-azido-4,6-O-benzylidene-3-deoxy-1-thio-α-D-galactopyranoside (350 mg, 0.73 mmol) in DMF (5 mL) $Cs_2CO_3$ (473 mg, 1.45 mmol) and iodomethane (0.264 mL, 3.63 mmol) were added and the mixture was stirred overnight at rt. The mixture was poured into water (50 mL) and extracted with EA (50 mL). The organic layer was washed with brine (50 mL), dried over $Na_2SO_4$, concentrated and purified by column chromatography (PE/EA=10/1~1/1, Silica-CS 12 g, 20 mL/min, silica gel, UV 254) to give the product (250 mg, 69%). $^1H$ NMR (400 MHz, Chloroform-d) δ 7.68 (dd, J=6.4, 2.4 Hz, 1H), 7.54-7.48 (m, 2H), 7.41-7.34 (m, 4H), 6.98 (t, J=8.8 Hz, 1H), 6.05 (d, J=5.2 Hz, 1H), 5.61 (s, 1H), 4.32 (d, J=3.2 Hz, 1H), 4.23 (dd, J=10.8, 5.2 Hz, 1H), 4.18-4.06 (m, 3H), 3.78 (dd, J=10.8, 3.2 Hz, 1H), 3.58 (s, 3H).

5-Bromo-2-fluorophenyl 4,6-O-benzylidene-3-deoxy-3-[4-(4-methylthiazol-2-yl)-1H-1,2,3-triazol-1-yl]-2-O-methyl-1-thio-α-D-galactopyranoside

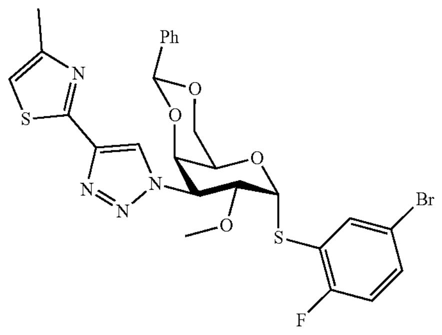

To a solution of 5-bromo-2-fluorophenyl 3-azido-4,6-O-benzylidene-3-deoxy-2-O-methyl-1-thio-α-D-galactopyranoside (130 mg, 0.26 mmol) in DMF (4 mL) trimethyl[2-(4-methylthiazol-2-yl)ethynyl]silane (101 mg, 0.52 mmol), (+)-sodium L-ascorbate (51.2 mg, 0.26 mmol) and copper (II) sulfate pentahydrate (64.5 mg, 0.26 mmol) were added and the mixture was stirred overnight at rt. The mixture was poured into water (50 mL) and extracted with EA (60 mL). The organic phase was washed with brine (50 mL), dried over $Na_2SO_4$, concentrated and purified by column chromatography (PE/EtOAc=10/1~1/1, Silica-CS 4 g, 10 mL/min, silica gel, UV 254) to afford the product (110 mg, 68%).

ESI-MS m/z calcd for $[C_{26}H_{24}BrFN_4O_4S_2][M+H]^+$: 619.0; found: 619.0. $^1$H NMR (400 MHz, Chloroform-d) δ 8.27 (s, 1H), 7.75-7.67 (m, 1H), 7.47-7.32 (m, 6H), 7.06-6.93 (m, 1H), 6.91 (d, J=1.2 Hz, 1H), 6.19 (d, J=5.2 Hz, 1H), 5.50 (s, 1H), 5.42-5.33 (m, 1H), 4.59-4.51 (m, 2H), 4.35 (s, 1H), 4.22-4.09 (m, 2H), 3.40 (s, 3H), 2.49 (s, 3H).

Intermediate 70

5-Chloro-2-cyanopyridin-3-yl 2,4,6-tri-O-acetyl-3-azido-3-deoxy-1-thio-α-D-galactopyranoside

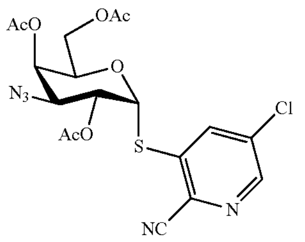

To a solution of acetyl 2,4,6-tri-O-acetyl-3-azido-3-deoxy-1-thio-D-galactopyranoside (4.50 g, 11.5 mmol) in DMF (30 mL) 5-chloro-3-fluoro-pyridine-2-carbonitrile (1.81 g, 11.5 mmol) and diethylamine (1.69 g, 23.0 mmol) were added at 0° C. and the mixture was stirred overnight at rt. The mixture was poured into water (150 mL) and extracted with EtOAc (2×200 mL). The organic layers were washed with brine, dried over $Na_2SO_4$, concentrated and purified by column chromatography (PE/EA=10/1~1/1, Silica-CS 80 g, 50 mL/min, silica gel, UV 254) to give the product (3.30 g, 59%). ESI-MS m/z calcd for $[C_{18}H_{18}ClN_5O_7S]$ $[M+H]^+$: 484.1; found: 484.0. $^1$H NMR (400 MHz, Methanol-$d_4$) δ 8.64 (d, J=2.4 Hz, 1H), 8.28 (d, J=2.4 Hz, 1H), 6.17 (d, J=5.6 Hz, 1H), 5.54 (d, J=2.8 Hz, 1H), 5.29 (dd, J=11.2, 5.2 Hz, 1H), 4.68 (dd, J=7.6, 4.0 Hz, 1H), 4.27 (dd, J=10.8, 3.2 Hz, 1H), 4.15 (dd, J=7.6, 4.0 Hz, 1H), 3.98 (dd, J=11.6, 8.0 Hz, 1H), 2.18 (s, 3H), 2.14 (s, 3H), 2.14 (s, 3H).

5-Chloro-2-cyanopyridin-3-yl 2,4,6-tri-O-acetyl-3-[4-(2-chlorothiazol-4-yl)-1H-1,2,3-triazol-1-yl]-3-deoxy-1-thio-α-D-galactopyranoside

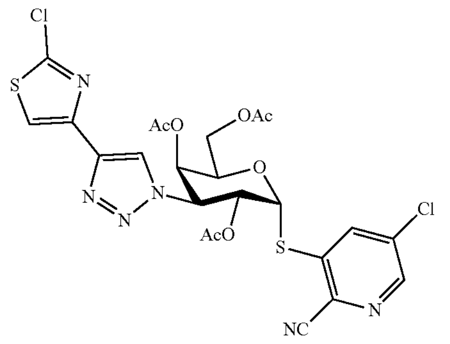

To a solution of 5-chloro-2-cyanopyridin-3-yl 2,4,6-tri-O-acetyl-3-azido-3-deoxy-1-thio-α-D-galactopyranoside (80 mg, 0.17 mmol) and 2-(2-chlorothiazol-4-yl)ethynyl-trimethylsilane (46.4 mg, 0.22 mmol) in DMF (2 mL) (+)-sodium L-ascorbate (65.5 mg, 0.33 mmol) and copper (II) sulfate pentahydrate (20.6 mg, 0.083 mmol) were added and the mixture was stirred overnight at rt. The mixture was concentrated and purified by prep HPLC [MeCN/$H_2O$ (10 mmol/L $NH_4HCO_3$), X-Select 10 μm 19*250 mm, 20 mL/min, UV 254] to give the product (90 mg, 77%). ESI-MS m/z calcd for $[C_{23}H_{20}Cl_2N_6O_7S_2]$ $[M+H]^+$: 627.0; found: 627.0. $^1$H NMR (400 MHz, Chloroform-d) δ 8.53 (s, 1H), 8.01 (d, J=2.0 Hz, 1H), 7.95 (s, 1H), 7.73 (s, 1H), 6.22 (d, J=5.6 Hz, 1H), 5.99 (dd, J=11.6, 5.6 Hz, 1H), 5.58 (d, J=2.0 Hz, 1H), 5.19 (dd, J=9.6 Hz, 2.0 Hz, 1H), 4.84-4.74 (m, 1H), 4.11 (dd, J=11.6, 4.8 Hz, 1H), 4.01 (dd, J=11.6, 7.6 Hz, 1H), 2.02 (s, 3H), 1.96 (s, 3H), 1.95 (s, 3H).

Intermediate 71

2-Bromo-5-chloropyridin-3-yl 3-azido-4,6-O-benzylidene-3-deoxy-2-O-ethyl-1-thio-α-D-galactopyranoside

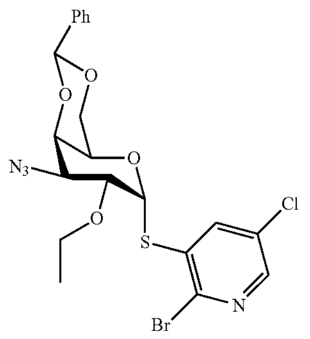

To a solution of 2-bromo-5-chloropyridin-3-yl 3-azido-4,6-O-benzylidene-3-deoxy-1-thio-α-D-galactopyranoside (1.0 g, 2.0 mmol) in DMF (18 mL) $Cs_2CO_3$ (1.3 g, 4.0 mmol) was added followed by iodoethane (936 mg, 6.0 mmol) and the mixture was stirred 6 h at rt. Water (100 mL) was added and the mixture was extracted with EtOAc (3×50 mL). The organic phases were washed with brine (3×50 mL), dried over $Na_2SO_4$, evaporated and purified by column chromatography (PE/EA=10/1~1/1, Silica-CS 40 g, 40 mL/min, silica gel, UV 254) to give the product (880 mg, 76%). ESI-MS m/z calcd for $[C_{20}H_{20}BrClN_4O_4S]$ $[M+H]^+$: 527.0, found: 527.0. $^1$H NMR (400 MHz, Chloroform-d) δ 8.14 (d, J=2.4 Hz, 1H), 7.87 (d, J=2.4 Hz, 1H), 7.54-7.36 (m, 5H), 6.14 (d, J=5.2 Hz, 1H), 5.62 (s, 1H), 4.41 (dd, J=10.8, 5.6 Hz, 1H), 4.32 (d, J=3.2 Hz, 1H), 4.20-4.08 (m, 2H), 4.02 (s, 1H), 3.88-3.81 (m, 2H), 3.66-3.62 (m, 1H), 1.31-1.25 (m, 3H).

5-Chloro-2-cyanopyridin-3-yl 3-azido-4,6-O-benzylidene-3-deoxy-2-O-ethyl-1-thio-α-D-galactopyranoside

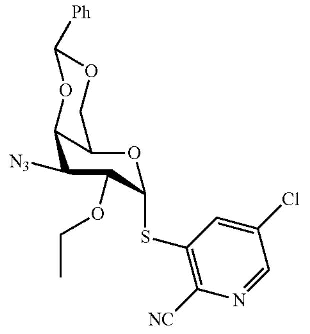

To a solution of 2-bromo-5-chloropyridin-3-yl 3-azido-4,6-O-benzylidene-3-deoxy-2-O-ethyl-1-thio-α-D-galactopyranoside (570 mg, 0.98 mmol) in DMF (15 mL) Zn (64.1 mg, 0.98 mmol), $Zn(CN)_2$ (345 mg, 2.94 mmol), 1,1'-bis (diphenylphosphino)ferrocene (55.3 mg, 0.098 mmol) and tris(dibenzylideneacetone)dipalladium(0) (68.7 mg, 0.098 mmol) were added and the mixture was stirred 3 h at 100° C. under a nitrogen atmosphere. The mixture was concentrated and purified by column chromatography (PE/EA=10/1~2/1, Silica-CS 12 g, 20 mL/min, silica gel, UV 254) to give the product (340 mg, 60%). ESI-MS m/z calcd for $[C_{21}H_{20}ClN_5O_4S]$ $[M+H]^+$: 474.1, found: 474.1. $^1H$ NMR (400 MHz, Chloroform-d) δ 8.50 (d, J=2.0 Hz, 1H), 8.03 (d, J=2.4 Hz, 1H), 7.52-7.35 (m, 5H), 6.14 (d, J=4.8 Hz, 1H), 5.61 (s, 1H), 4.37 (dd, J=10.4, 5.2 Hz, 1H), 4.33 (d, J=3.2 Hz, 1H), 4.15-4.10 (m, 2H), 4.09 (s, 1H), 3.87-3.80 (m, 2H), 3.69-3.63 (m, 1H), 1.32-1.21 (m, 3H).

5-Chloro-2-cyanopyridin-3-yl 4,6-O-benzylidene-3-deoxy-2-O-ethyl-3-[4-(2-thiazolyl)-1H-1,2,3-triazol-1-yl]-1-thio-α-D-galactopyranoside

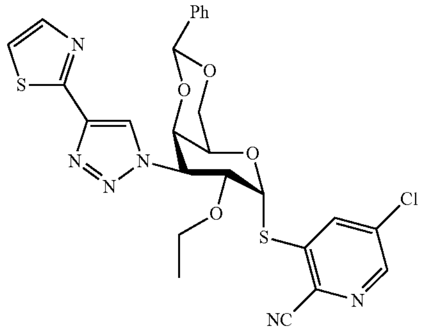

To a solution of 5-chloro-2-cyanopyridin-3-yl 3-azido-4,6-O-benzylidene-3-deoxy-2-O-ethyl-1-thio-α-D-galactopyranoside (180 mg, 0.31 mmol) in DMF (4.0 mL) trimethyl (2-thiazol-2-ylethynyl)silane (130 mg, 0.62 mmol), copper (II) sulfate pentahydrate (38.6 mg, 0.15 mmol) and (+)- sodium L-ascorbate (30.6 mg, 0.15 mmol) were added and the mixture was stirred overnight at rt. The mixture was diluted with water (20 mL) and extracted with EtOAc (3×10 mL). The organic layers were washed with brine, dried over $Na_2SO_4$, concentrated and purified by column chromatography (PE/EA=10/1~1/1, Silica-CS 12 g, 20 mL/min, silica gel, UV 254) to give the product (85 mg, 47%). ESI-MS m/z calcd for $[C_{26}H_{23}ClN_6O_4S_2]$ $[M+H]^+$: 583.1; found: 583.1. $^1H$ NMR (400 MHz, Chloroform-d) δ 8.55 (d, J=2.0 Hz, 1H), 8.29 (s, 1H), 8.06 (d, J=2.0 Hz, 1H), 7.84 (d, J=3.2 Hz, 1H), 7.40-7.35 (m, 6H), 6.26 (d, J=5.2 Hz, 1H), 5.52 (s, 1H), 5.34 (dd, J=11.2, 2.8 Hz, 1H), 4.71 (dd, J=11.2, 5.2 Hz, 1H), 4.58 (d, J=2.8 Hz, 1H), 4.36 (s, 1H), 4.26-4.13 (m, 2H), 3.77-3.73 (m, 1H), 3.40-3.37 (m, 1H), 1.09-1.05 (m, 3H).

Intermediate 72

5-Chloro-2-cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside

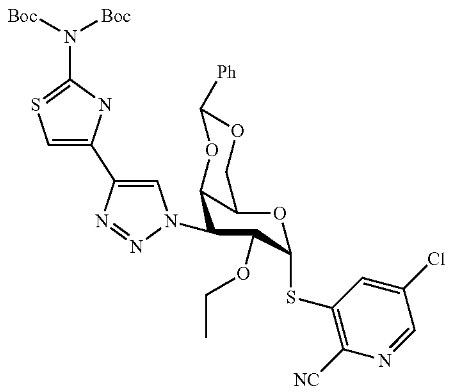

To a solution of 5-chloro-2-cyanopyridin-3-yl 3-azido-4,6-O-benzylidene-3-deoxy-2-O-ethyl-1-thio-α-D-galactopyranoside (160 mg, 0.27 mmol) in DMF (6 mL) tert-butyl N-tert-butoxycarbonyl-N-[4-(2-trimethylsilylethynyl)thiazol-2-yl]carbamate (131 mg, 0.33 mmol), copper (II) sulfate pentahydrate (34.3 mg, 0.14 mmol) and (+)-sodium L-ascorbate (27.2 mg, 0.14 mmol) were added and the mixture was stirred overnight at rt. The mixture was diluted with water (20 mL) and extracted with EtOAc (3×10 mL). The organic layers were washed with brine, dried over $Na_2SO_4$, concentrated and purified by column chromatography (PE/EA=10/1~0/1, Silica-CS 12 g, 20 mL/min, silica gel, UV 254) to give the product (180 mg, 77%). ESI-MS m/z calcd for $[C_{36}H_{40}ClN_7O_8S_2]$ $[M+H]^+$: 798.2; found: 798.1. $^1H$ NMR (400 MHz, Chloroform-d) δ 8.53 (d, J=2.0 Hz, 1H), 8.05 (d, J=2.0 Hz, 1H), 8.00 (s, 1H), 7.72 (s, 1H), 7.39-7.33 (m, 5H), 6.25 (d, J=4.8 Hz, 1H), 5.51 (s, 1H), 5.29 (dd, J=10.8, 2.8 Hz, 1H), 4.72 (dd, J=11.2, 4.8 Hz, 1H), 4.56 (d, J=2.8 Hz, 1H), 4.33 (s, 1H), 4.24-4.10 (m, 2H), 3.75-3.71 (m, 1H), 3.39-3.35 (m, 1H), 1.48 (s, 18H), 1.08-1.04 (m, 3H).

Intermediate 73

5-Chloro-2-cyanophenyl 3-[4-(2-aminothiazol-4-yl)-1H-1,2,3-triazol-1-yl]-4,6-O-benzylidene-3-deoxy-2-O-methyl-1-thio-α-D-galactopyranoside

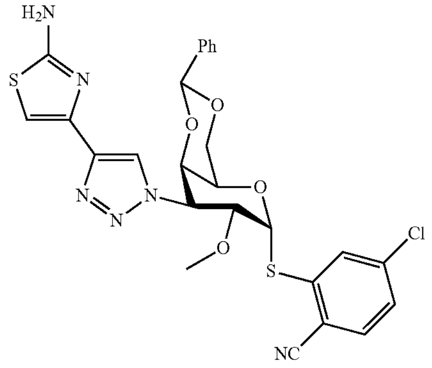

To a solution of 5-chloro-2-cyanophenyl 3-azido-4,6-O-benzylidene-3-deoxy-2-O-methyl-1-thio-α-D-galactopyranoside (69 mg, 0.15 mmol) in DMF (2 mL) 4-(2-trimethylsilylethynyl)thiazol-2-amine (35.4 mg, 0.18 mmol), copper (II) sulfate pentahydrate (18.8 mg, 0.075 mmol) and (+)-sodium L-ascorbate (14.9 mg, 0.075 mmol) were added and the mixture was stirred overnight at rt. The mixture was diluted with water (20 mL) and extracted with EtOAc (3×10 mL). The combined organic layers were washed with brine, dried over $Na_2SO_4$, concentrated and purified by column chromatography (PE/EA=2/1~1/1, Silica-CS 4 g, 12 mL/min, silica gel, UV 254) to give the product (62 mg, 71%). ESI-MS m/z calcd for $[C_{26}H_{23}ClN_6O_4S_2]$ $[M+H]^+$: 594.1; found: 594.1. $^1H$ NMR (400 MHz, Chloroform-d) δ7.99 (s, 1H), 7.74 (d, J=2.0 Hz, 1H), 7.63 (d, J=11.6 Hz, 1H), 7.42-7.35 (m, 6H), 7.11 (s, 1H), 6.22 (d, J=5.2 Hz, 1H), 5.51 (s, 1H), 5.28 (dd, J=11.2, 1.2 Hz, 1H), 4.93 (s, 2H), 4.59-4.52 (m, 2H), 4.41 (s, 1H), 4.26-4.12 (m, 2H), 3.38 (s, 3H).

Intermediate 74

5-Chloro-3-fluoro-2-(1H-imidazol-2-yl)pyridine

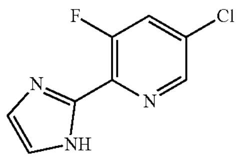 [SMILES: Fc1cc(Cl)cnc1-c1ncc[nH]1]

To a solution of 5-chloro-3-fluoropyridine-2-carbonitrile (4.00 g, 25.6 mmol) in MeOH (20 mL) NaOMe (30.0%, 4.18 g, 23.2 mmol) was added slowly at −10° C. and the mixture was stirred 4 h at −10° C. 2,2-Dimethoxyethanamine (2.69 g, 25.6 mmol) followed by acetic acid (2.93 mL, 51.1 mmol) was added at −10° C. The mixture was stirred 30 min at 65° C. and was then cooled to rt and stirred overnight. $CaCl_2$ (284 mg, 2.56 mmol) was added followed by HCl (5 M, 24 mL) and the suspension was stirred 4 h at 65° C. The mixture was cooled to 0° C. and a 30% NaOH solution was added until pH=12. The mixture was evaporated and purified by column chromatography (EA/PE=0~70%, silica gel column 40 g, 50 mL/min, UV 254) to give the product (780 mg, 15%). ESI-MS m/z calcd for $[C_8H_5ClFN_3]$ $[M+H]^+$: 198.0; found: 198.2. $^1H$ NMR (400 MHz, Chloroform-d) δ 8.58-8.19 (m, 1H), 7.53 (dd, J=10.0, 2.0 Hz, 1H), 7.23 (s, 2H).

5-Chloro-2-(1H-imidazol-2-yl)pyridine-3-thiol

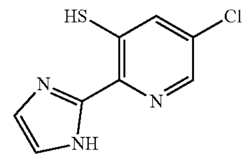 [SMILES: Sc1cc(Cl)cnc1-c1ncc[nH]1]

To a solution of 5-chloro-3-fluoro-2-(1H-imidazol-2-yl)pyridine (800 mg, 4.05 mmol) in DMF (10 mL) $Na_2S$ (474 mg, 6.07 mmol) was added and the mixture was stirred 2 h at 100° C. in a microwave reactor. After cooling to rt, acetic acid (0.348 mL, 6.07 mmol) was added and the mixture was purified by reverse-phase column (MeCN/water (10 mmol/L $NH_4HCO_3$)=0~26%, C18 40 g, 50 mL/min, UV 254) to give the product (700 mg, 82%). ESI-MS m/z calcd for $[C_8H_6ClN_3S]$ $[M+H]^+$: 212.0; found: 212.2. $^1H$ NMR (400 MHz, DMSO-$d_6$) δ 7.90 (d, J=2.4 Hz, 1H), 7.65 (d, J=2.4 Hz, 1H), 7.19 (s, 2H).

5-Chloro-2-(1H-imidazol-2-yl)pyridin-3-yl 2,4,6-tri-O-acetyl-3-azido-3-deoxy-1-thio-α-D-galactopyranoside

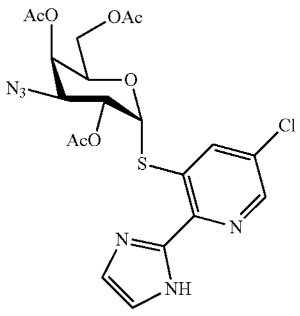

A solution of 5-chloro-2-(1H-imidazol-2-yl)pyridine-3-thiol (700 mg, 3.31 mmol), 2,4,6-tri-O-acetyl-3-azido-3-deoxy-β-D-galactopyranosyl chloride (1.39 g, 3.97 mmol) and $Cs_2CO_3$ (2.16 g, 6.61 mmol) in DMF (12 mL) was stirred 5 days at rt. The mixture was poured into water (200 mL) and extracted with DCM (2×50 mL). The organic layers were washed with water (50 mL) and brine (50 mL), dried and concentrated. The residue was purified by reverse-phase column (MeCN/water (10 mmol/L $NH_4HCO_3$)=0~33%, C18 40 g, 50 mL/min, UV 254) to give the product (650 mg, 37%). ESI-MS m/z calcd for $[C_{20}H_{21}ClN_6O_7S]$ $[M+H]^+$: 525.1; found: 525.2. $^1H$ NMR (400 MHz, DMSO-$d_6$) δ 12.83 (s, 1H), 8.47 (d, J=2.0 Hz, 1H), 8.11 (d, J=2.0 Hz, 1H), 7.27 (s, 1H), 7.18 (s, 1H), 6.30 (d, J=5.6 Hz, 1H), 5.44 (d, J=3.2 Hz, 1H), 5.24 (dd, J=11.2, 5.6 Hz, 1H), 4.50-4.41 (m, 2H), 4.03-3.90 (m, 2H), 2.12 (s, 3H), 2.07 (s, 3H), 1.77 (s, 3H).

5-Chloro-2-(1H-imidazol-2-yl)pyridin-3-yl 2,4,6-tri-O-acetyl-3-[4-(2-aminothiazol-4-yl)-1H-1,2,3-triazol-1-yl]-3-deoxy-1-thio-α-D-galactopyranoside

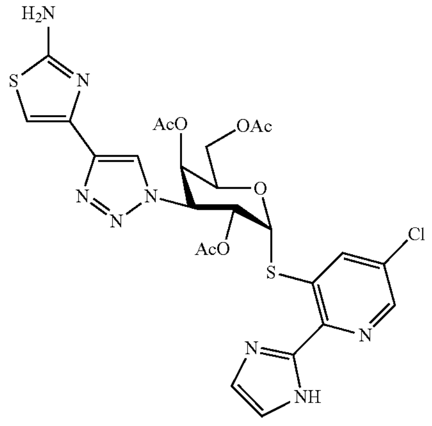

To a solution of 5-chloro-2-(1H-imidazol-2-yl)pyridin-3-yl 2,4,6-tri-O-acetyl-3-azido-3-deoxy-1-thio-α-D-galactopyranoside (80 mg, 0.15 mmol) in DMF (4 mL) 4-(2-trimethylsilylethynyl)thiazol-2-amine (59.8 mg, 0.31 mmol), (+)-sodium L-ascorbate (60.4 mg, 0.31 mmol), copper (II) sulfatepentahydrate (38.1 mg, 0.15 mmol) and CsF (23.2 mg, 0.15 mmol) were added and the mixture was stirred overnight at rt. The mixture was filtered and purified by prep HPLC (MeCN/$H_2O$ (10 mmol/L $NH_4HCO_3$), X-Select 10 μm 19*250 mm, 20 mL/min, UV 254) to afford the product (15 mg, 15%). ESI-MS m/z calcd for [$C_{25}H_{25}ClN_8O_7S_2$] $[M+H]^+$: 649.1; found: 649.1. $^1H$ NMR (400 MHz, Methanol-$d_4$) δ 8.87-7.95 (m, 3H), 7.80-6.83 (m, 2H), 6.38 (s, 1H), 6.23-6.08 (m, 1H), 5.74-5.56 (m, 2H), 4.87-4.71 (m, 2H), 4.18-3.96 (m, 2H), 2.13-1.78 (m, 9H).

Intermediate 75

5-Chloro-2-(1H-imidazol-2-yl)pyridin-3-yl 3-azido-3-deoxy-1-thio-α-D-galactopyranoside

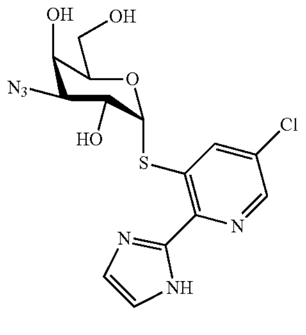

To a solution of 5-chloro-2-(1H-imidazol-2-yl)pyridin-3-yl 2,4,6-tri-O-acetyl-3-azido-3-deoxy-1-thio-α-D-galactopyranoside (300 mg, 0.57 mmol) in MeOH (10 mL) NaOMe (30.9 mg, 0.57 mmol) was added and the mixture was stirred 2 h at rt. The mixture was neutralized with acetic acid, concentrated and purified by reverse-phase column (MeCN/water (10 mmol/L $NH_4HCO_3$)=0~35%, C18 40 g, 50 mL/min, UV 254) to afford the product (150 mg, 66%). ESI-MS m/z calcd for [$C_{14}H_{15}ClN_6O_4S$] $[M+H]^+$: 399.1; found: 399.2. $^1H$ NMR (400 MHz, DMSO-$d_6$) δ 12.74 (s, 1H), 8.40 (d, J=2.0 Hz, 1H), 8.20 (d, J=2.0 Hz, 1H), 7.24 (d, J=2.0 Hz, 1H), 7.14 (d, J=1.2 Hz, 1H), 5.98 (d, J=4.8 Hz, 1H), 5.82 (d, J=5.6 Hz, 1H), 5.27 (d, J=6.0 Hz, 1H), 4.58 (t, J=5.6 Hz, 1H), 4.29 (dt, J=10.4, 5.2 Hz, 1H), 3.89 (t, J=6.4 Hz, 2H), 3.50 (dt, J=11.6, 4.8 Hz, 2H), 3.30 (s, 1H).

Intermediate 76

5-Chloro-2-(pyridin-2-yl)pyridin-3-yl 3-azido-4,6-O-benzylidene-3-deoxy-2-O-methyl-1-thio-α-D-galactopyranoside

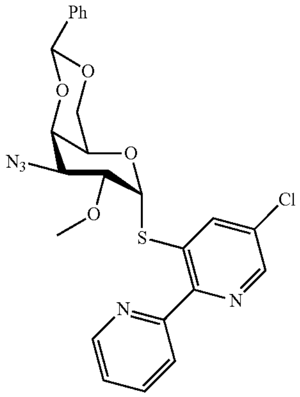

To a solution 2-bromo-5-chloropyridin-3-yl 3-azido-4,6-O-benzylidene-3-deoxy-2-O-methyl-1-thio-α-D-galactopyranoside (200 mg, 0.39 mmol) and tributyl(2-pyridyl)stannane (143 mg, 0.39 mmol) in DMF (3.0 mL) bis(triphenylphosphine)palladium(II) chloride (27.3 mg, 0.039 mmol) was added and the mixture was stirred 6 h at 110° C. under a nitrogen atmosphere. The mixture was purified by prep HPLC (MeCN/$H_2O$ (10 mmol/L $NH_4HCO_3$), X-Select 10 μm 19*250 mm, 20 mL/min, UV 254) to give the product (25 mg, 13%). ESI-MS m/z calcd for [$C_{24}H_{22}ClN_5O_4S$] $[M+H]^+$: 512.1; found: 512.2. $^1H$ NMR (400 MHz, Chloroform-d) δ 8.65 (s, 1H), 8.39 (s, 1H), 8.15 (m, 1H), 7.93 (m, 1H), 7.83-7.69 (m, 1H), 7.54-7.40 (m, 2H), 7.37-7.26 (m, 4H), 5.91 (d, J=5.6 Hz, 1H), 5.55 (s, 1H), 4.29-4.12 (m, 3H), 4.09-3.99 (m, 2H), 3.72 (dd, J=10.8, 3.2 Hz, 1H), 3.39 (s, 3H).

5-Chloro-2-(pyridin-2-yl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

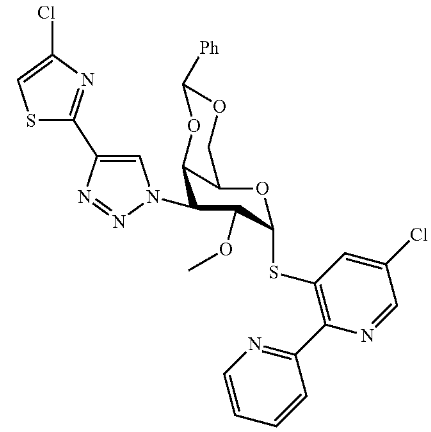

To a solution of 5-chloro-2-(pyridin-2-yl)pyridin-3-yl 3-azido-4,6-O-benzylidene-3-deoxy-2-O-methyl-1-thio-α-D-galactopyranoside (48 mg, 0.094 mmol) and 2-(4-chlorothiazol-2-yl)ethynyl-trimethyl-silane (23.5 mg, 0.11 mmol) in DMF (3 mL) copper (II) sulfate pentahydrate (11.7 mg, 0.047 mmol) and (+)-sodium L-ascorbate (37.1 mg, 0.19 mmol) were added and the mixture was stirred overnight at rt. The mixture was diluted with water (10 mL) and extracted with EtOAc (2×20 mL). The organic layers were washed with brine (10 mL), dried over $Na_2SO_4$, concentrated and purified by column chromatography (PE/EA=10/1~1/1, Silica-CS 4 g, 10 mL/min, silica gel, UV 254) to give the product (36 mg, 59%). ESI-MS m/z calcd for $[C_{29}H_{24}Cl_2N_6O_4S_2]$ $[M+H]^+$: 655.1; found: 655.2 $^1H$ NMR (400 MHz, Chloroform-d) δ 8.30 (s, 1H), 8.23 (s, 1H), 7.88-7.86 (m, 1H), 7.41-7.36 (m, 6H), 7.27-7.25 (m, 3H), 7.10 (s, 1H), 6.14 (d, J=4.8 Hz, 1H), 5.49 (s, 1H), 5.40 (dd, J=11.2, 2.4 Hz, 1H), 4.61 (dd, J=11.2, 5.2 Hz, 1H), 4.49 (d, J=2.0 Hz, 1H), 4.31-4.28 (m, 2H), 4.14-4.12 (m, 1H), 3.24 (s, 3H).

Intermediate 77

3-Fluoro-5-methylpyridine-2-carbonitrile

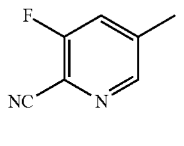

To a solution of 2-bromo-3-fluoro-5-methylpyridine (200 mg, 1.05 mmol) in DMF (5 mL) Zn (34.4 mg, 0.53 mmol), $Zn(CN)_2$ (247 mg, 2.11 mmol), 1,1'-bis(diphenylphosphino) ferrocene (47.5 mg, 0.084 mmol) and tris(dibenzylideneacetone)dipalladium(0) (77.0 mg, 0.084 mmol) were added and the mixture was stirred 2.5 h at 100° C. under a nitrogen atmosphere. The mixture was concentrated and purified by column chromatography (PE/EA=10/1~5/1, Silica-CS 12 g, 20 mL/min, silica gel, UV 254) to give the product (110 mg, 77%). ESI-MS m/z calcd for $[C_7H_5FN_2]$ $[M+H]^+$: 137.0; found: 137.2. $^1H$ NMR (400 MHz, Chloroform-d) δ 8.37 (s, 1H), 7.39 (dd, J=9.2, 0.8 Hz, 1H). 2.47 (s, 3H).

2-Cyano-5-methylpyridin-3-yl 2,4,6-tri-O-acetyl-3-azido-3-deoxy-1-thio-α-D-galactopyranoside

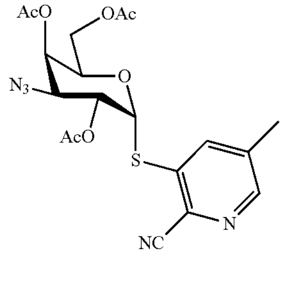

To a mixture of acetyl 2,4,6-tri-O-acetyl-3-azido-3-deoxy-1-thio-α-D-galactopyranoside (170 mg, 0.42 mmol) and 3-fluoro-5-methylpyridine-2-carbonitrile (68.5 mg, 0.50 mmol) in DMF (5 mL) diethylamine (61.3 mg, 0.84 mmol) was added and the mixture was stirred overnight at rt. The mixture was poured into water (20 mL) and extracted with EtOAc (3×20 mL). The combined organic layers were washed with brine (20 mL), dried over $Na_2SO_4$, concentrated and purified by column chromatography (PE/EA=10/1~5/1, Silica-CS 20 g, 20 mL/min, silica gel, UV 254) to afford the product (150 mg, 77%). ESI-MS m/z calcd for $[C_{19}H_{21}N_5O_7S]$ $[M+H]^+$: 464.1; found: 464.1. $^1H$ NMR (400 MHz, Chloroform-d) δ 8.43 (d, J=1.2 Hz, 1H), 7.76 (d, J=0.8 Hz, 1H), 6.03 (d, J=5.2 Hz, 1H), 5.50 (d, J=2.8 Hz, 1H), 5.26 (t, J=5.2 Hz, 1H), 4.64 (t, J=6.0 Hz, 1H), 4.13-4.07 (m, 1H), 4.03-3.95 (m, 2H), 2.42 (s, 3H), 2.22 (s, 3H), 2.15 (s, 3H), 1.97 (s, 3H).

2-Cyano-5-methylpyridin-3-yl 2,4,6-tri-O-acetyl-3-[4-(4-chlorothiazol-2-yl)-1H-1,2,3-triazol-1-yl]-3-deoxy-1-thio-α-D-galactopyranoside

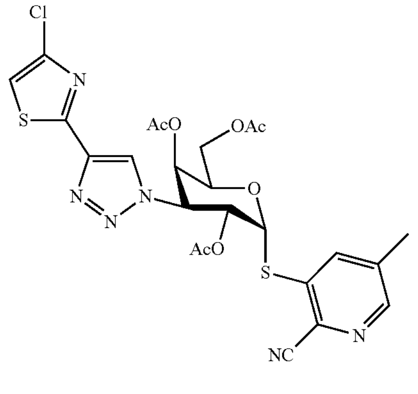

To a solution of 2-cyano-5-methylpyridin-3-yl 2,4,6-tri-O-acetyl-3-azido-3-deoxy-1-thio-α-D-galactopyranoside (55.1 mg, 0.12 mmol) in DMF (3 mL) 2-(4-chlorothiazol-2-yl)ethynyl-trimethyl-silane (51.3 mg, 0.24 mmol), copper (II) sulfate pentahydrate (29.7 mg, 0.12 mmol) and (+)-sodium L-ascorbate (23.6 mg, 0.12 mmol) were added and the mixture was stirred overnight at rt. The mixture was diluted with water (50 mL) and extracted with EtOAc (2×80 mL). The combined organic layers were washed with brine (50 mL), dried over $Na_2SO_4$, concentrated and purified by column chromatography (PE/EA=10/1~1/1, Silica-CS 4 g, 10 mL/min, silica gel, UV 254) to give the product (50 mg, 69%). ESI-MS m/z calcd for $[C_{24}H_{23}ClN_6O_7S_2]$ $[M+H]^+$: 607.1; found: 607.0 $^1$H NMR (400 MHz, Chloroform-d) δ 8.50-8.45 (m, 1H), 8.19-8.14 (m, 1H), 7.84-7.79 (m, 1H), 7.13 (s, 1H), 6.22 (d, J=5.6 Hz, 1H), 6.07-5.98 (m, 1H), 5.67-5.62 (m, 1H), 5.31-5.23 (m, 1H), 4.92-4.85 (m, 1H), 4.17-4.01 (m, 2H), 2.45 (d, J=0.8 Hz, 3H), 2.07 (s, 3H), 2.02 (s, 3H), 1.98 (s, 3H).

Intermediate 78

3,4-Dichlorophenyl 3-azido-4,6-O-benzylidene-3-deoxy-2-O-(2,2,2-trifluoroethyl)-1-thio-α-D-galactopyranoside

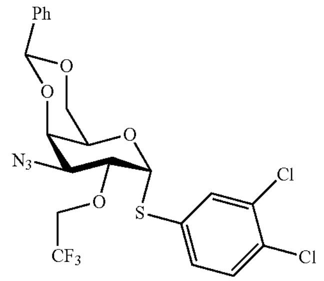

To a solution of 3,4-dichlorophenyl 3-azido-4,6-O-benzylidene-3-deoxy-1-thio-α-D-galactopyranoside (600 mg, 1.32 mmol) in DMF (10 mL) NaH (60% in oil, 78 mg, 1.98 mmol) and 2,2,2-trifluoroethyl trifluoromethanesulfonate (460 mg, 1.98 mmol) were added at 0° C. and the mixture was stirred 1 h at rt. The mixture was diluted with water (10 mL) and extracted with EtOAc (3×20 mL). The combined organic layers were washed with brine (20 mL), dried over $Na_2SO_4$, concentrated and purified by column chromatography (PE/EA=10/1~1/1, Silica-CS 12 g, 20 mL/min, silica gel, UV 254) to give the product (198 mg, 28%). ESI-MS m/z calcd for $[C_{21}H_{18}Cl_2F_3N_3O_4S][M+H]^+$: 536.0, found: 536.0. $^1$H NMR (400 MHz, Chloroform-d) δ 7.59 (d, J=2.0 Hz, 1H), 7.54-7.52 (m, 2H), 7.42-7.38 (m, 4H), 7.33-7.30 (m, 1H), 5.92 (d, J=5.2 Hz, 1H), 5.64 (s, 1H), 4.43-4.38 (m, 2H), 4.27-4.24 (m, 1H), 4.16-4.13 (m, 2H), 4.08 (q, J=16.8, 8.4 Hz, 2H), 5.99 (dd, J=10.4, 3.2 Hz, 1H).

3,4-Dichlorophenyl 3-azido-3-deoxy-2-O-(2,2,2-trifluoroethyl)-1-thio-α-D-galactopyranoside

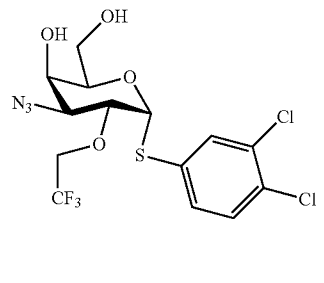

To a solution of 3,4-dichlorophenyl 3-azido-4,6-O-benzylidene-3-deoxy-2-O-(2,2,2-trifluoroethyl)-1-thio-α-D-galactopyranoside (196 mg, 0.37 mmol) in DCM (10 mL) TFA (0.5 mL) and $H_2O$ (0.5 mL) were added and the mixture was stirred 6 h at rt. $Et_3N$ (2 mL) was added dropwise at 0° C. to neutralize the TFA. The mixture was concentrated and purified by preparative TLC (PE/EA=1/2) to give the product (114 mg, 70%). ESI-MS m/z calcd for $[C_{14}H_{14}Cl_2F_3N_3O_4S]$ $[M+NH_4]^+$: 465.0; found: 465.0. $^1$H NMR (400 MHz, Chloroform-d) 7.59 (d, J=2.0 Hz, 1H), 7.39-7.37 (m, 1H), 7.33-7.25 (m, 1H), 5.77 (d, J=5.6 Hz, 1H), 4.30-4.26 (m, 2H), 4.18-4.14 (m, 1H), 4.10-3.92 (m, 3H), 3.85-3.77 (m, 2H).

Intermediate 80

5-Bromopyridin-3-yl 2,4,6-tri-O-acetyl-3-[4-(4-chlorothiazol-2-yl)-1H-1,2,3-triazol-1-yl]-3-deoxy-1-thio-α-D-galactopyranoside

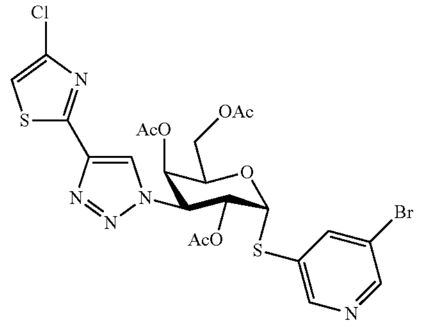

To a solution of 5-bromopyridin-3-yl 2,4,6-tri-O-acetyl-3-azido-3-deoxy-1-thio-α-D-galactopyranoside (500 mg, 0.99 mmol) in DMF (5 mL) 2-(4-chlorothiazol-2-yl)ethynyl-trimethyl-silane (429 mg, 1.99 mmol), copper (II) sulfate pentahydrate (248 mg, 0.99 mmol), (+)-sodium L-ascorbate (197 mg, 0.99 mmol) and CsF (151 mg, 0.99 mmol) were added and the mixture was stirred overnight at rt. The mixture was diluted with water (50 mL) and extracted with EtOAc (2×80 mL). The organic layers were washed with brine (50 mL), dried over $Na_2SO_4$, concentrated and purified by column chromatography (PE/EA=10/1~1/1, Silica-CS 4 g, 10 mL/min, silica gel, UV 254) to give the product (330 mg, 51%). ESI-MS m/z calcd for $[C_{22}H_{21}BrClN_5O_7S_2]$ $[M+H]^+$: 646.0; found: 646.0 $^1$H NMR (400 MHz, Chloroform-d) δ 8.61 (dd, J=7.2, 2.0 Hz, 2H), 8.14 (s, 1H), 8.01 (t, J=2.0 Hz, 1H), 7.14 (s, 1H), 6.16 (d, J=5.6 Hz, 1H), 5.98 (dd, J=11.6, 5.6 Hz, 1H), 5.65-5.60 (m, 1H), 5.27 (dd, J=11.6, 3.2 Hz, 1H), 4.89-4.81 (m, 1H), 4.21-4.03 (m, 2H), 2.09 (s, 3H), 2.04 (s, 3H), 1.99 (s, 3H).

5-(2-Trimethylsilyl-1-ethynyl)pyridin-3-yl 2,4,6-tri-O-acetyl-3-[4-(4-chlorothiazol-2-yl)-1H-1,2,3-triazol-1-yl]-3-deoxy-1-thio-α-D-galactopyranoside

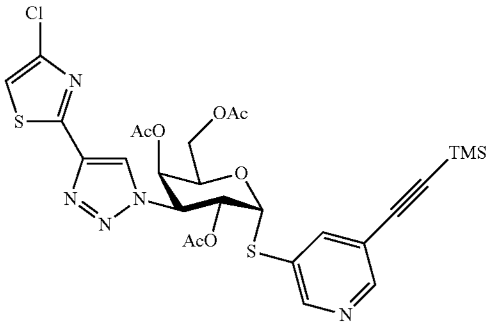

A solution of 5-bromopyridin-3-yl 2,4,6-tri-O-acetyl-3-[4-(4-chlorothiazol-2-yl)-1H-1,2,3-triazol-1-yl]-3-deoxy-1-thio-α-D-galactopyranoside (150 mg, 0.23 mmol), CuI (4.4 mg, 0.023 mmol), bis(triphenylphosphine)palladium(II) chloride (10.2 mg, 0.014 mmol) and ethynyl(trimethyl) silane (114 mg, 1.16 mmol) in DMF (4 mL) and DIPEA (0.397 mL, 2.32 mmol) was stirred 2 h under microwave condition at 100° C. The mixture was poured into water (20 mL) and extracted with EtOAc (2×50 mL). The organic layers were washed with water (50 mL), brine (50 mL), dried over $Na_2SO_4$, concentrated and purified by column chromatography (PE/EA=10/1~2/1, Silica-CS 20 g, 25 mL/min, silica gel, UV 254) to give the product (100 mg, 65%). ESI-MS m/z calcd for $[C_{27}H_{30}ClN_5O_7S_2Si]$ $[M+H]^+$: 664.1; found: 664.0. $^1H$ NMR (400 MHz, Chloroform-d) δ 8.13 (s, 1H), 7.91 (s, 1H), 7.59-7.28 (m, 2H), 7.13 (s, 1H), 6.15 (d, J=5.6 Hz, 1H), 5.97 (dd, J=11.6, 5.6 Hz, 1H), 5.64-5.58 (m, 1H), 5.31-5.23 (m, 1H), 4.89-4.81 (m, 1H), 4.19-4.00 (m, 2H), 2.08 (s, 3H), 2.03 (s, 3H), 1.98 (s, 3H), 0.26 (s, 9H).

Intermediate 81

5-Bromopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside

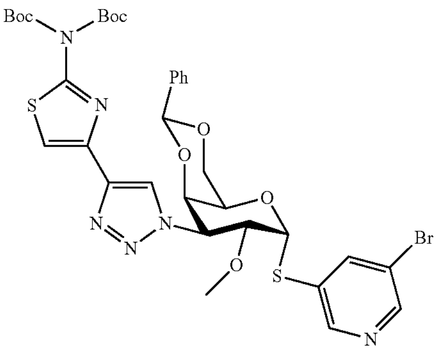

To a solution of 5-bromopyridin-3-yl 3-azido-4,6-O-benzylidene-3-deoxy-2-O-methyl-1-thio-α-D-galactopyranoside (200 mg, 0.42 mmol) in DMF (5 mL) tert-butyl N-tert-butoxycarbonyl-N-[4-(2-trimethylsilylethynyl)thiazol-2-yl] carbamate (199 mg, 0.50 mmol), copper (II) sulfate pentahydrate (104 mg, 0.42 mmol), (+)-sodium L-ascorbate (82.7 mg, 0.42 mmol) and CsF (63.4 mg, 0.42 mmol) were added and the mixture was stirred overnight at rt. The mixture was diluted with water (50 mL) and extracted with EtOAc (2×80 mL). The combined organic layers were washed with brine (50 mL), dried over $Na_2SO_4$, evaporated and purified by column chromatography (PE/EA=10/1~1/1, Silica-CS 4 g, 10 mL/min, silica gel, UV 254) to afford the product (200 mg, 60%). ESI-MS m/z calcd for $[C_{34}H_{39}BrN_6O_8S_2]$ $[M+H]^+$: 803.1, found: 803.0. $^1H$ NMR (400 MHz, Chloroform-d) δ 8.63-8.54 (m, 2H), 8.04-7.98 (m, 2H), 7.71 (s, 1H), 7.42-7.29 (m, 5H), 6.16 (d, J=5.2 Hz, 1H), 5.51 (s, 1H), 5.32-5.24 (m, 1H), 4.60-4.51 (m, 2H), 4.33-4.23 (m, 2H), 4.19-4.10 (m, 1H), 3.33 (s, 3H), 1.47 (s, 18H).

5-(2-Trimethylsilyl-1-ethynyl)pyridin-3-yl 4,6-O-benzylidene-3-{4-[2-(di-tert-butoxycarbonylamino) thiazol-4-yl]-1H-1,2,3-triazol-1-yl}-3-deoxy-2-O-methyl-1-thio-α-D-galactopyranoside

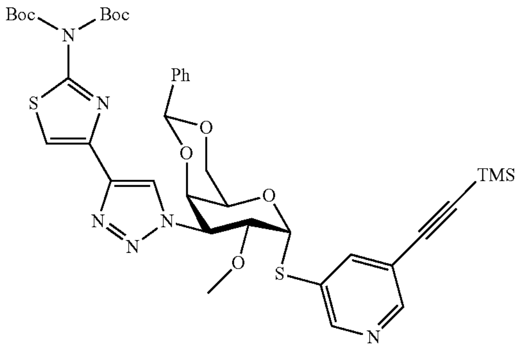

A solution of 5-bromopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside (200 mg, 0.25 mmol), bis(triphenylphosphine) palladium(II) chloride (10.9 mg, 0.015 mmol), CuI (4.7 mg, 0.025 mmol) and ethynyl(trimethyl)silane (122 mg, 1.24 mmol) in DMF (4 mL) and DIPEA (0.426 mL, 2.49 mmol) was stirred 2 h under microwave condition at 100° C. The mixture was poured into water (20 mL) and extracted with EtOAc (2×50 mL). The organic layers were washed with water (50 mL), brine (50 mL), dried over $Na_2SO_4$, concentrated and purified by column chromatography (PE/EA=10/1~1/1, Silica-CS 20 g, 25 mL/min, silica gel, UV 254) to give the product (110 mg, 54%). ESI-MS m/z calcd for $[C_{39}H_{48}N_6O_8S_2Si]$ $[M+H]^+$: 821.3; found: 821.2. $^1H$ NMR (400 MHz, Chloroform-d) δ 8.61-8.54 (m, 2H), 8.01 (s, 1H), 7.94-7.89 (m, 1H), 7.72 (s, 1H), 7.43-7.29 (m, 5H), 6.15 (d, J=5.2 Hz, 1H), 5.51 (s, 1H), 5.34-5.26 (m, 1H), 4.60-4.51 (m, 2H), 4.35-4.24 (m, 2H), 4.18-4.09 (m, 1H), 3.34 (s, 3H), 1.48 (s, 18H), 0.27 (s, 9H).

Intermediate 82

5-Cyanopyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

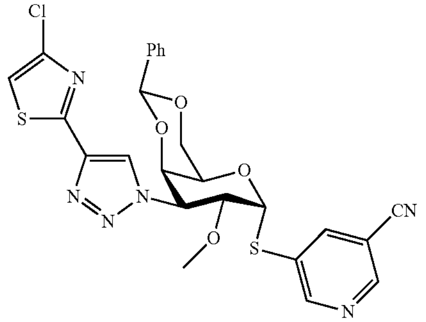

To a solution of 5-cyanopyridin-3-yl 3-azido-4,6-O-benzylidene-3-deoxy-2-O-methyl-1-thio-α-D-galactopyranoside (80 mg, 0.19 mmol) and 2-(4-chlorothiazol-2-yl)ethynyl-trimethyl-silane (60.9 mg, 0.28 mmol) in DMF (4 mL) copper (II) sulfate pentahydrate (23.5 mg, 0.094 mmol) and (+)-sodium L-ascorbate (55.9 mg, 0.28 mmol) were added and the mixture was stirred 4 h at rt. The mixture was diluted with water (20 mL) and extracted with EtOAc (3×20 mL). The organic layers were washed with brine, dried over $Na_2SO_4$, concentrated and purified by column chromatography (PE/EA=10/1~1/1, Silica-CS 12 g, 20 mL/min, silica gel, UV 254) to give the product (90 mg, 84%). ESI-MS m/z calcd for $[C_{25}H_{21}ClN_6O_4S_2]$ $[M+H]^+$: 569.1; found: 569.2 $^1$H NMR (400 MHz, Chloroform-d) δ 9.01-8.67 (m, 2H), 8.30 (s, 1H), 8.14-8.09 (m, 1H), 7.41-7.36 (m, 5H), 7.11 (s, 1H), 6.23 (d, J=5.2 Hz, 1H), 5.52 (s, 1H), 5.36-5.27 (m, 1H), 4.63-4.52 (m, 2H), 4.32-4.24 (m, 2H), 4.19-4.06 (m, 1H), 3.35 (s, 3H).

Intermediate 83

5-Cyanopyridin-3-yl 4,6-O-benzylidene-3-[4-(2-hydroxythiazol-4-yl)-1H-1,2,3-triazol-1-yl]-3-deoxy-2-O-methyl-1-thio-α-D-galactopyranoside

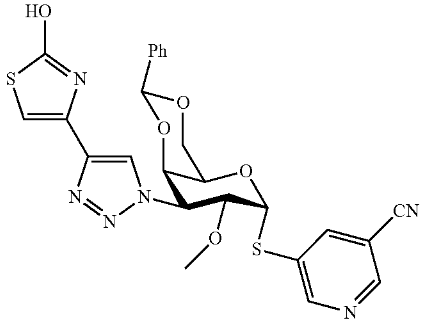

To a solution of 5-cyanopyridin-3-yl 3-azido-4,6-O-benzylidene-3-deoxy-2-O-methyl-1-thio-α-D-galactopyranoside (80 mg, 0.19 mmol) and 4-(2-trimethylsilylethynyl)thiazol-2-ol (44.5 mg, 0.23 mmol) in DMF (4 mL) copper (II) sulfate pentahydrate (23.5 mg, 0.094 mmol) and (+)-sodium L-ascorbate (55.9 mg, 0.28 mmol) were added and the mixture was stirred 4 h at rt. The mixture was diluted with water (20 mL) and extracted with EA (3×10 mL). The organic layers were washed with brine, dried over $Na_2SO_4$, concentrated and purified by prep HPLC ($MeCN/H_2O$ (10 mmol/L $NH_4HCO_3$), X-Select 10 μm 19*250 mm, 20 mL/min, UV 254) to give the product (50 mg, 48%). ESI-MS m/z calcd for $[C_{25}H_{22}N_6O_5S_2]$ $[M+H]^+$: 551.1; found: 551.0 $^1$H NMR (400 MHz, DMSO-$d_6$) δ 8.96 (d, J=2.4 Hz, 1H), 8.93 (d, J=2.0 Hz, 1H), 8.55 (t, J=2.0 Hz, 1H), 8.28 (s, 1H), 7.35 (s, 5H), 6.67 (d, J=5.2 Hz, 1H), 6.51 (s, 1H), 5.58 (s, 1H), 5.14 (dd, J=11.6, 3.2 Hz, 1H), 4.61 (dd, J=11.6, 5.2 Hz, 1H), 4.56 (d, J=3.2 Hz, 1H), 4.25 (s, 1H), 4.08 (dd, J=12.8, 1.6 Hz, 1H), 3.92 (dd, J=12.8, 1.6 Hz, 1H), 3.33 (s, 3H).

Intermediate 84

5-Bromo-2-cyanopyridin-3-yl 2,4,6-tri-O-acetyl-3-{4-[2-(di-tert-butoxycarbonylamino)thiazol-4-yl]-1H-1,2,3-triazol-1-yl}-3-deoxy-1-thio-α-D-galactopyranoside

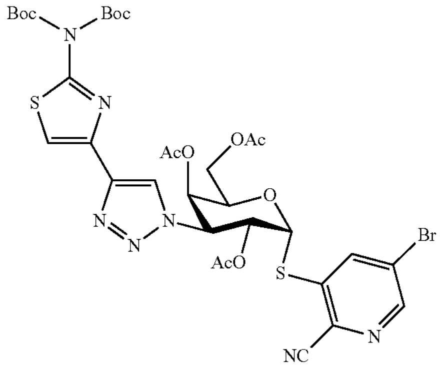

To a solution of 5-bromo-2-cyanopyridin-3-yl 2,4,6-tri-O-acetyl-3-azido-3-deoxy-1-thio-α-D-galactopyranoside (400 mg, 0.76 mmol) and tert-butyl N-tert-butoxycarbonyl-N-[4-(2-trimethylsilylethynyl)thiazol-2-yl]carbamate (360 mg, 0.91 mmol) in DMF (5 mL) copper (II) sulfate pentahydrate (94.5 mg, 0.38 mmol) and (+)-sodium L-ascorbate (225 mg, 1.14 mmol) were added and the mixture was stirred 4 h at rt. The mixture was evaporated and purified by column chromatography (PE/EA=5/1~2/1, Silica-CS 12 g, 20 mL/min, silica gel, UV 254) to afford the product (600 mg, 93%). ESI-MS m/z calcd for $[C_{33}H_{38}BrN_7O_{11}S_2]$ $[M+H]^+$: 852.1, found: 852.0. $^1$H NMR (400 MHz, Chloroform-d) δ 8.68 (d, J=2.0 Hz, 1H), 8.21 (d, J=2.0 Hz, 1H), 7.81 (s, 1H), 7.66 (s, 1H), 6.28 (d, J=5.6 Hz, 1H), 6.07 (dd, J=11.7, 5.6 Hz, 1H), 5.63 (dd, J=3.2, 1.2 Hz, 1H), 5.18 (dd, J=11.8, 3.0 Hz, 1H), 4.84-4.77 (m, 1H), 4.23-3.98 (m, 2H), 2.06 (s, 3H), 2.01 (s, 3H), 2.00 (s, 3H), 1.55 (s, 18H).

2-Cyano-5-(2-trimethylsilyl-1-ethynyl)pyridin-3-yl 2,4,6-tri-O-acetyl-3-{4-[2-(di-tert-butoxycarbonylamino)thiazol-4-yl]-1H-1,2,3-triazol-1-yl}-3-deoxy-1-thio-α-D-galactopyranoside

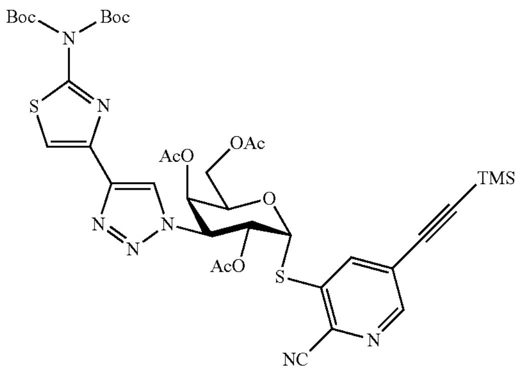

To a solution of 5-bromo-2-cyanopyridin-3-yl 2,4,6-tri-O-acetyl-3-{4-[2-(di-tert-butoxycarbonylamino)thiazol-4-yl]-1H-1,2,3-triazol-1-yl}-3-deoxy-1-thio-α-D-galactopyranoside (200 mg, 0.24 mmol) and ethynyl(trimethyl)silane (115 mg, 1.17 mmol) in DMF (5 mL) bis(triphenylphosphine)palladium(II) chloride (16.5 mg, 0.024 mmol), CuI (4.5 mg, 0.024 mmol) and DIPEA (0.201 mL, 1.17 mmol) were added and the mixture was stirred overnight at rt. The mixture was concentrated and purified by column chromatography (PE/EA=5/1) to give the product (80 mg, 39%). ESI-MS m/z calcd for $[C_{38}H_{47}N_7O_{11}S_2Si]$ $[M+H]^+$: 870.3; found: 870.2. $^1$H NMR (400 MHz, Chloroform-d) δ 8.63 (d, J=2.0 Hz, 1H), 8.03 (d, J=2.0 Hz, 1H), 7.82 (s, 1H), 7.66 (s, 1H), 6.27 (d, J=5.6 Hz, 1H), 6.07 (dd, J=11.6, 5.6 Hz, 1H), 5.65-5.60 (m, 1H), 5.20 (dd, J=11.6, 2.8 Hz, 1H), 4.89-4.81 (m, 1H), 4.15 (dd, J=11.6, 4.8 Hz, 1H), 4.07 (dd, J=11.6, 7.6 Hz, 1H), 2.06 (s, 3H), 2.01 (s, 3H), 2.01 (s, 3H), 1.56 (s, 18H), 0.28 (s, 9H).

Intermediate 85

5-Bromo-2-cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside

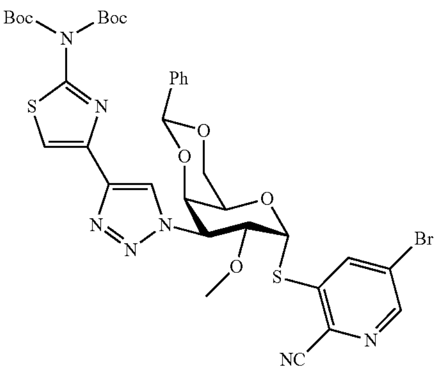

To a solution of 5-bromo-2-cyanopyridin-3-yl 3-azido-4,6-O-benzylidene-3-deoxy-2-O-methyl-1-thio-α-D-galactopyranoside (150 mg, 0.30 mmol) in DMF (5 mL) tert-butyl N-tert-butoxycarbonyl-N-[4-(2-trimethylsilylethynyl)thiazol-2-yl]carbamate (128 mg, 0.32 mmol), copper (II) sulfate pentahydrate (74.3 mg, 0.30 mmol) and (+)-sodium L-ascorbate (58.9 mg, 0.30 mmol) were added and the mixture was stirred overnight at rt. The mixture was diluted with water (50 mL) and extracted with EtOAc (2×80 mL). The combined organic layers were washed with brine (50 mL), dried over $Na_2SO_4$, concentrated and purified by column chromatography (PE/EA=10/1~1/1, Silica-CS 4 g, 10 mL/min, silica gel, UV 254) to afford the product (140 mg, 57%). ESI-MS m/z calcd for $[C_{35}H_{38}BrN_7O_8S_2]$ $[M+H]^+$: 828.1, found: 827.9. $^1$H NMR (400 MHz, Chloroform-d) δ 8.64 (d, J=2.0 Hz, 1H), 8.23 (d, J=2.0 Hz, 1H), 8.01-8.00 (m, 1H), 7.71 (s, 1H), 7.41-7.28 (m, 5H), 6.26 (d, J=5.2 Hz, 1H), 5.51 (s, 1H), 5.27 (dd, J=11.2, 3.2 Hz, 1H), 4.62 (dd, J=11.2, 5.2 Hz, 1H), 4.55 (d, J=3.2 Hz, 1H), 4.35 (s, 1H), 4.27-4.07 (m, 2H), 3.38 (s, 3H), 1.78 (s, 18H).

2-Cyano-5-(2-trimethylsilyl-1-ethynyl)pyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside

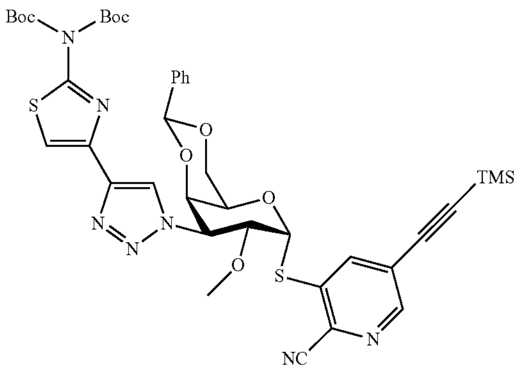

A solution of 5-bromo-2-cyanopyridin-3-yl 4,6-O-benzylidene-3-{4-[2-(di-tert-butoxycarbonylamino)thiazol-4-yl]-1H-1,2,3-triazol-1-yl}-3-deoxy-2-O-methyl-1-thio-α-D-galactopyranoside (140 mg, 0.17 mmol), ethynyl(trimethyl)silane (83 mg, 0.85 mmol), bis(triphenylphosphine)palladium(II) chloride (7.4 mg, 0.010 mmol) and CuI (3.2 mg, 0.017 mmol) in THF (8 mL) and DIPEA (0.289 mL, 1.69 mmol) was stirred 20 h at rt. The mixture was diluted with water (20 mL) and extracted with EtOAc (2×50 mL). The combined organic layers were washed with water (50 mL), brine (50 mL), dried over $Na_2SO_4$, concentrated and purified by column chromatography (PE/EA=10/1~1/1, Silica-CS 20 g, 25 mL/min, silica gel, UV 254) to give the product (110 mg, 77%). $^1$H NMR (400 MHz, Chloroform-d) δ 8.63-8.58 (m, 1H), 8.09-8.04 (m, 1H), 8.04-7.99 (m, 1H), 7.78-7.74 (m, 1H), 7.40-7.31 (m, 5H), 6.26 (d, J=5.2 Hz, 1H), 5.52 (s, 1H), 5.38-5.24 (m, 1H), 4.67-4.55 (m, 2H), 4.39 (s, 1H), 4.28-4.14 (m, 2H), 3.40 (s, 3H), 1.48 (s, 18H), 0.29 (s, 9H).

Intermediate 86

2,5-Dibromopyridin-3-yl 3-azido-4,6-O-benzylidene-3-deoxy-2-O-ethyl-1-thio-α-D-galactopyranoside

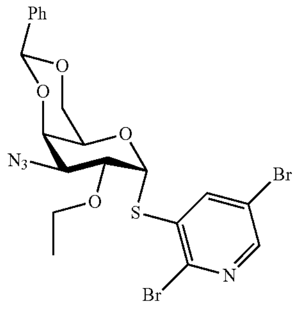

To a solution of 2,5-dibromopyridin-3-yl 3-azido-4,6-O-benzylidene-3-deoxy-1-thio-α-D-galactopyranoside (800 mg, 1.47 mmol) in DMF (10 mL) NaH (60% in oil, 113 mg, 2.94 mmol) was added followed by dropwise addition of iodoethane (1.15 g, 7.35 mmol). The mixture was stirred 1 h at rt before water (30 mL) was added and the aqueous phase was extracted with EtOAc (50 mL). The organic phase was dried and evaporated to afford the product (800 mg, 95%). ESI-MS m/z calcd for $[C_{20}H_{20}Br_2N_4O_4S]$ $[M+H]^+$: 571.0; found: 570.9. $^1H$ NMR (400 MHz, Chloroform-d) δ 8.23 (d, J=2.4 Hz, 1H), 7.98 (d, J=2.4 Hz, 1H), 7.57-7.46 (m, 2H), 7.42-7.32 (m, 3H), 6.14 (d, J=5.2 Hz, 1H), 5.61 (s, 1H), 4.40 (dd, J=10.8, 5.2 Hz, 1H), 4.31 (dd, J=3.2, 1.2 Hz, 1H), 4.23-4.10 (m, 2H), 4.03-3.99 (m, 1H), 3.90-3.76 (m, 2H), 3.64 (dd, J=8.8, 6.8 Hz, 1H), 1.29 (t, J=6.8 Hz, 3H).

5-Bromo-2-cyanopyridin-3-yl 3-azido-4,6-O-benzylidene-3-deoxy-2-O-ethyl-1-thio-α-D-galactopyranoside

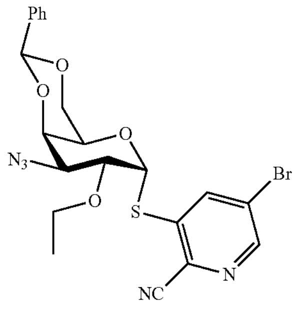

To a solution of 2,5-dibromopyridin-3-yl 3-azido-4,6-O-benzylidene-3-deoxy-2-O-ethyl-1-thio-α-D-galactopyranoside (400 mg, 0.70 mmol) in DMSO (3 mL) copper(I) cyanide (75.1 mg, 0.84 mmol) was added and the mixture was stirred 90 min at 110° C. in a microwave reactor. The mixture was diluted with water (20 mL) and extracted with EtOAc (20 mL). The organic phase was dried over $Na_2SO_4$, concentrated and purified by column chromatography (PE/EtOAc=10/1~5/1, Silica-CS 12 g, 12 mL/min, silica gel, UV 254) to afford the product (105 mg, 29%). ESI-MS m/z calcd for $[C_{21}H_{20}BrN_5O_4S]$ $[M+H]^+$: 518.0; found: 518.0. $^1H$ NMR (400 MHz, Chloroform-d) δ 8.59 (d, J=2.0 Hz, 1H), 8.18 (d, J=2.0 Hz, 1H), 7.57-7.46 (m, 2H), 7.43-7.33 (m, 3H), 6.13 (d, J=5.2 Hz, 1H), 5.61 (s, 1H), 4.37 (dd, J=10.8, 5.2 Hz, 1H), 4.32 (d, J=3.2 Hz, 1H), 4.23-4.07 (m, 3H), 3.91-3.78 (m, 2H), 3.71-3.59 (m, 1H), 1.30 (t, J=6.8 Hz, 3H).

5-Bromo-2-cyanopyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside

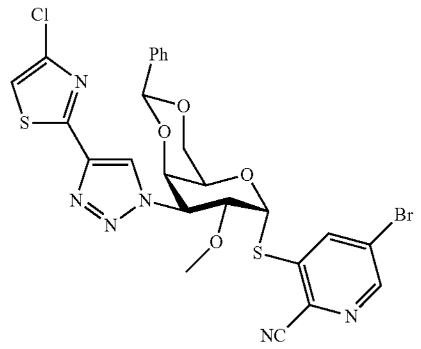

To a solution of 5-bromo-2-cyanopyridin-3-yl 3-azido-4,6-O-benzylidene-3-deoxy-2-O-ethyl-1-thio-α-D-galactopyranoside (105 mg, 0.20 mmol) and 2-(4-chlorothiazol-2-yl)ethynyl-trimethyl-silane (74.9 mg, 0.24 mmol) in DMF (4 mL) copper (II) sulfate pentahydrate (25.3 mg, 0.10 mmol) and (+)-sodium L-ascorbate (60.2 mg, 0.30 mmol) were added and the mixture was stirred 4 h at rt. The mixture was concentrated and purified by prep HPLC [MeCN/$H_2O$ (10 mmol/L $NH_4HCO_3$), X-Select 10 μm 19*250 mm, 20 mL/min, UV 254] to give the product (85 mg, 63%). ESI-MS m/z calcd for $[C_{26}H_{22}BrClN_6O_4S_2]$ $[M+H]^+$: 661.0; found: 661.0 $^1H$ NMR (400 MHz, Chloroform-d) δ 8.65 (d, J=2.0 Hz, 1H), 8.30 (s, 1H), 8.21 (d, J=2.0 Hz, 1H), 7.42-7.33 (m, 5H), 7.11 (s, 1H), 6.25 (d, J=5.2 Hz, 1H), 5.51 (s, 1H), 5.34 (dd, J=11.2, 3.2 Hz, 1H), 4.69 (dd, J=11.2, 5.2 Hz, 1H), 4.56 (dd, J=3.2, 1.2 Hz, 1H), 4.35 (s, 1H), 4.24 (dd, J=12.8, 1.6 Hz, 1H), 4.15 (dd, J=12.8, 1.6 Hz, 1H), 3.84-3.63 (m, 1H), 3.44-3.23 (m, 1H), 1.07 (t, J=6.8 Hz, 3H).

Intermediate 87

3,4-Dichlorophenyl 3-azido-4,6-O-benzylidene-3-deoxy-2-O-ethyl-1-thio-α-D-galactopyranoside

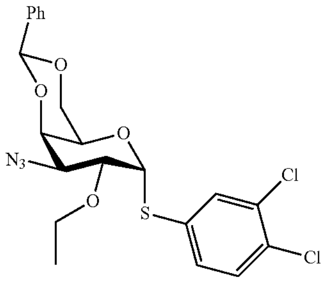

To a solution of 3,4-dichlorophenyl 3-azido-4,6-O-benzylidene-3-deoxy-1-thio-α-D-galactopyranoside (200 mg, 0.44 mmol) in DMF (5.0 mL) $Cs_2CO_3$ (430 mg, 1.32 mmol) followed by iodoethane (343 mg, 2.20 mmol) were added and the mixture was stirred overnight at rt. The mixture was diluted with EtOAc (30 mL) and washed with water (3×30 mL). The organic phase was dried over $Na_2SO_4$, concentrated and purified by column chromatography (PE/EA=5/1, Silica-CS 20 g, 20 mL/min, silica gel, UV 254) to give the product (205 mg, 97%). ESI-MS m/z calcd for $[C_{21}H_{21}Cl_2N_3O_4S][M+H]^+$: 482.1, found: 482.0. $^1H$ NMR (400 MHz, Chloroform-d) δ 7.51 (d, J=2.0 Hz, 1H), 7.48-7.42 (m, 2H), 7.35-7.26 (m, 4H), 7.22 (dd, J=8.4, 2.0 Hz, 1H), 5.94 (d, J=5.2 Hz, 1H), 5.54 (s, 1H), 4.26 (dd, J=10.8, 5.2 Hz, 1H), 4.23 (dd, J=3.2, 1.2 Hz, 1H), 4.14 (dd, J=12.4, 1.6 Hz, 1H), 4.07-3.98 (m, 2H), 3.77-3.64 (m, 2H), 3.59-3.48 (m, 1H), 1.21 (t, J=6.8 Hz, 3H).

3,4-Dichlorophenyl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside

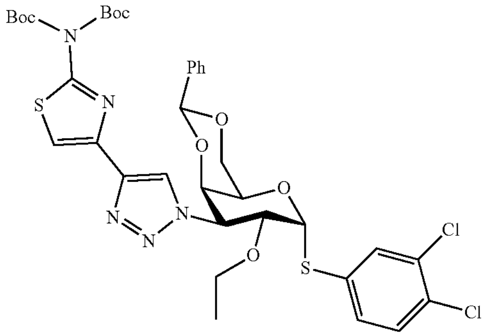

To a solution of 3,4-dichlorophenyl 3-azido-4,6-O-benzylidene-3-deoxy-2-O-ethyl-1-thio-α-D-galactopyranoside (100 mg, 0.21 mmol) and tert-butyl N-tert-butoxycarbonyl-N-[4-(2-trimethylsilylethynyl)thiazol-2-yl]carbamate (98.7 mg, 0.25 mmol) in DMF (5 mL) copper (II) sulfate pentahydrate (25.9 mg, 0.10 mmol) and (+)-sodium L-ascorbate (61.6 mg, 0.31 mmol) were added and the mixture was stirred overnight at rt. The mixture was diluted with water (20 mL) and extracted with EtOAc (3×10 mL). The combined organic layers were washed with brine, dried over $Na_2SO_4$, concentrated and purified by column chromatography (PE/EA=5/1~2/1, Silica-CS 20 g, 20 mL/min, silica gel, UV 254) to afford the product (130 mg, 78%). ESI-MS m/z calcd for $[C_{36}H_{41}Cl_2N_5O_8S_2]$ $[M+H]^+$: 806.2, found: 806.1. $^1H$ NMR (400 MHz, Chloroform-d) δ 8.00 (s, 1H), 7.71 (s, 1H), 7.62 (d, J=2.0 Hz, 1H), 7.41-7.29 (m, 7H), 6.13 (d, J=5.2 Hz, 1H), 5.51 (s, 1H), 5.27 (dd, J=11.2, 3.2 Hz, 1H), 4.64 (dd, J=11.2, 5.2 Hz, 1H), 4.55-4.50 (m, 1H), 4.32-4.21 (m, 2H), 4.17-4.11 (m, 1H), 3.72-3.59 (m, 1H), 3.39-3.27 (m, 1H), 1.48 (s, 18H), 1.03 (t, J=6.8 Hz, 3H).

Intermediate 88

4-Bromo-3-chlorophenyl 2,4,6-tri-O-acetyl-3-azido-3-deoxy-1-thio-α-D-galactopyranoside

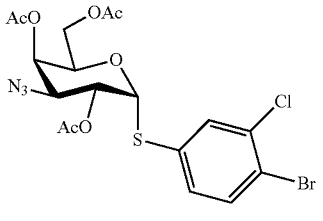

To a solution of 2,4,6-tri-O-acetyl-3-azido-3-deoxy-β-D-galactopyranosyl chloride (1.40 g, 4.0 mmol) and 4-bromo-3-chlorobenzenethiol (823 mg, 3.68 mmol) in DMF (10 mL) $Cs_2CO_3$ (2.61 g, 8.01 mmol) was added and the mixture was stirred overnight at rt. Water (50 mL) was added and the mixture was extracted with EtOAc (100 mL). The organic phase was washed with brine, dried, evaporated and purified by column chromatography (PE/EtOAc=10/1~4/1, Silica-CS 40 g, 20 mL/min, silica gel, UV 254) to afford the product (1.80 g, 84%). ESI-MS m/z calcd for $[C_{18}H_{19}BrClN_3O_7S][M+NH_4]^+$: 553.0; found: 553.0. $^1H$ NMR (400 MHz, Chloroform-d) δ 7.56 (d, J=2.0 Hz, 1H), 7.54 (d, J=8.4 Hz, 1H), 7.20 (dd, J=8.4, 2.0 Hz, 1H), 5.98 (d, J=5.6 Hz, 1H), 5.47 (dd, J=3.2, 1.2 Hz, 1H), 5.27 (dd, J=10.8, 5.6 Hz, 1H), 4.64-4.57 (m, 1H), 4.12 (dd, J=11.6, 4.8 Hz, 1H), 4.01 (dd, J=11.6, 7.6 Hz, 1H), 3.94 (dd, J=10.8, 3.4 Hz, 1H), 2.19 (s, 3H), 2.16 (s, 3H), 1.99 (s, 3H).

4-Bromo-3-chlorophenyl 3-azido-3-deoxy-1-thio-α-D-galactopyranoside

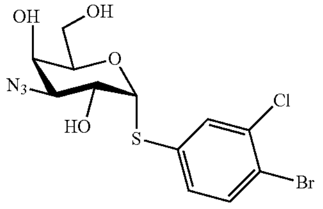

A solution of 4-bromo-3-chlorophenyl 2,4,6-tri-O-acetyl-3-azido-3-deoxy-1-thio-α-D-galactopyranoside (1.80 g, 3.35 mmol) in $MeOH/Et_3N/H_2O$ (9 mL, 5:3:1) was stirred overnight at rt. The mixture was evaporated and purified by reversed-phase chromatography ($MeCN/H_2O$=1/20~3/1, C-18 column, 20 mL/min, UV 254) to give the product (1.20 g, 87%). ESI-MS m/z calcd for $[C_{12}H_{13}BrClN_3O_4S]$ $[M+NH_4]^+$: 426.9; found: 426.7. $^1H$ NMR (400 MHz, DMSO-$d_6$) δ 7.74 (d, J=2.4 Hz, 1H), 7.68 (d, J=8.4 Hz, 1H), 7.37 (dd, J=8.4, 2.4 Hz, 1H), 5.96 (d, J=5.2 Hz, 1H), 5.73 (d, J=5.2 Hz, 1H), 5.31 (d, J=6.4 Hz, 1H), 4.67 (t, J=5.6 Hz, 1H), 4.25 (dt, J=10.8, 5.2 Hz, 1H), 3.98 (t, J=6.4 Hz, 1H), 3.94-3.89 (m, 1H), 3.51 (dt, J=11.6, 6.0 Hz, 1H), 3.41-3.35 (m, 2H).

4-Bromo-3-chlorophenyl 3-azido-4,6-O-benzylidene-3-deoxy-1-thio-α-D-galactopyranoside

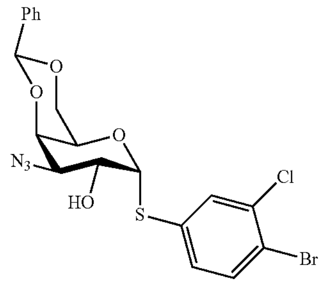

To a solution of 4-bromo-3-chlorophenyl 3-azido-3-deoxy-1-thio-α-D-galactopyranoside (1.20 g, 2.92 mmol) in DMF (20 mL) benzaldehyde dimethylacetal (1.33 g, 8.77 mmol) followed by D(+)-10-camphorsulfonic acid (136 mg, 0.58 mmol) were added and the mixture was stirred 3 h at 50° C. under reduced pressure. The mixture was neutralized with $Et_3N$, concentrated, and purified by column chromatography (PE/EA=5/1~3/1, Silica-CS 12 g, 20 mL/min, silica gel, UV 254) to afford the product (1.30 g, 89%). ESI-MS m/z calcd for $[C_{19}H_{17}BrClN_3O_4S]$ $[M+H]^+$: 498.0; found: 497.6. $^1H$ NMR (400 MHz, DMSO-$d_6$) δ 7.79-7.64 (m, 2H), 7.46-7.21 (m, 6H), 6.14 (d, J=5.2 Hz, 1H), 5.95 (d, J=5.2 Hz, 1H), 5.65 (s, 1H), 4.42-4.38 (m, 1H), 4.29 (dt, J=10.4, 5.2 Hz, 1H), 4.07 (dd, J=12.8, 2.0 Hz, 1H), 3.99 (s, 1H), 3.89 (dd, J=12.8, 2.0 Hz, 1H), 3.63 (dd, J=10.8, 3.2 Hz, 1H).

4-Bromo-3-chlorophenyl 3-azido-4,6-O-benzylidene-3-deoxy-2-O-ethyl-1-thio-α-D-galactopyranoside

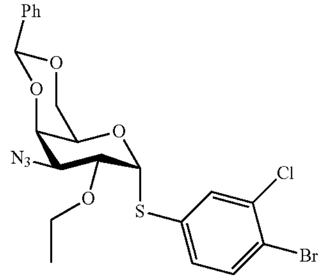

To a solution of 4-bromo-3-chlorophenyl 3-azido-4,6-O-benzylidene-3-deoxy-1-thio-α-D-galactopyranoside (400 mg, 0.80 mmol) in DMF (5.0 mL) $Cs_2CO_3$ (784 mg, 2.41 mmol) followed by iodoethane (1.25 g, 8.02 mmol) were added and the mixture was stirred overnight at rt. The mixture was diluted with EtOAc (30 mL) and washed with water (3×30 mL). The organic phase was dried over $Na_2SO_4$ and concentrated to give the product (410 mg, 97%). ESI-MS m/z calcd for $[C_{21}H_{21}BrClN_3O_4S]$ $[M+H]^+$: 526.0; found: 526.6. $^1H$ NMR (400 MHz, DMSO-$d_6$) δ 7.82-7.70 (m, 2H), 7.47-7.30 (m, 6H), 6.38 (d, J=5.2 Hz, 1H), 5.68 (s, 1H), 4.43-4.38 (m, 1H), 4.17-4.05 (m, 2H), 4.01 (s, 1H), 3.92 (dd, J=12.4, 1.6 Hz, 1H), 3.84-3.72 (m, 2H), 3.61-3.49 (m, 1H), 1.15 (t, J=6.8 Hz, 3H).

3-Chloro-4-cyanophenyl 3-azido-4,6-O-benzylidene-3-deoxy-2-O-ethyl-1-thio-α-D-galactopyranoside

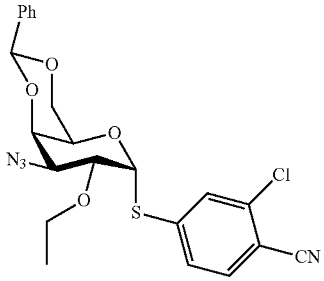

To a solution of 4-bromo-3-chlorophenyl 3-azido-4,6-O-benzylidene-3-deoxy-2-O-ethyl-1-thio-α-D-galactopyranoside (300 mg, 0.57 mmol) in DMF (3 mL) Zn (37.2 mg, 0.57 mmol), $Zn(CN)_2$ (201 mg, 1.71 mmol), 1,1'-bis(diphenylphosphino)ferrocene (25.7 mg, 0.046 mmol) and tris (dibenzylideneacetone)dipalladium(0) (41.7 mg, 0.046 mmol) were added and the mixture was stirred 2.5 h at 100° C. under a nitrogen atmosphere. The mixture was concentrated and purified by column chromatography (PE/EtOAc=10/1~5/1, Silica-CS 12 g, 20 mL/min, silica gel, UV 254) to afford the product (105 mg, 29%). ESI-MS m/z calcd for $[C_{22}H_{21}ClN_4O_4S]$ $[M+H]^+$: 473.1; found: 472.8. $^1H$ NMR (400 MHz, Chloroform-d) δ 7.61 (d, J=1.6 Hz, 1H), 7.56-7.49 (m, 3H), 7.43-7.34 (m, 4H), 6.19 (d, J=5.2 Hz, 1H), 5.61 (s, 1H), 4.37 (dd, J=10.4, 5.2 Hz, 1H), 4.32-4.28 (m, 1H), 4.21 (dd, J=12.8, 1.6 Hz, 1H), 4.10 (dd, J=12.6, 1.6 Hz, 1H), 4.00 (d, J=1.6 Hz, 1H), 3.82-3.71 (m, 2H), 3.67-3.57 (m, 1H), 1.27 (t, J=6.8 Hz, 3H).

3-Chloro-4-cyanophenyl 4,6-O-benzylidene-3-{4-[2-(di-tert-butoxycarbonylamino)thiazol-4-yl]-1H-1,2,3-triazol-1-yl}-3-deoxy-2-O-ethyl-1-thio-α-D-galactopyranoside

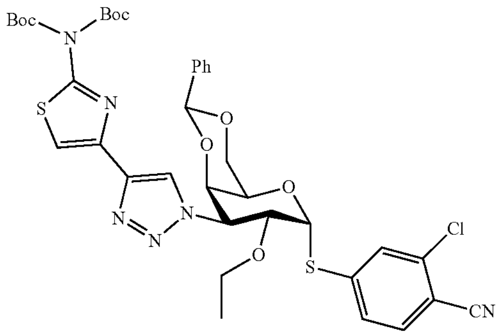

To a solution of 3-chloro-4-cyanophenyl 3-azido-4,6-O-benzylidene-3-deoxy-2-O-ethyl-1-thio-α-D-galactopyranoside (70 mg, 0.15 mmol) and tert-butyl N-tert-butoxycarbonyl-N-[4-(2-trimethylsilylethynyl)thiazol-2-yl]carbamate (70.4 mg, 0.18 mmol) in DMF (4.0 mL) copper (II) sulfate pentahydrate (18.5 mg, 0.074 mmol) and (+)-sodium L-ascorbate (44.0 mg, 0.22 mmol) were added and the mixture was stirred overnight at rt. The mixture was diluted with water (20 mL) and extracted with EtOAc (3×10 mL).

The organic layers were washed with brine, dried over $Na_2SO_4$, concentrated and purified by column chromatography (PE/EA=2/1~1/1, Silica-CS 20 g, 30 mL/min, silica gel, UV 254) to give the product (90 mg, 76%). ESI-MS m/z calcd for $[C_{37}H_{41}ClN_6O_8S_2]$ $[M+H]^+$: 797.2; found: 796.7 $^1H$ NMR (400 MHz, Chloroform-d) δ 8.00 (s, 1H), 7.71 (s, 1H), 7.66 (d, J=1.6 Hz, 1H), 7.56 (d, J=8.4 Hz, 1H), 7.45 (dd, J=8.4, 1.6 Hz, 1H), 7.42-7.29 (m, 5H), 6.31 (d, J=5.2 Hz, 1H), 5.52 (s, 1H), 5.29-5.22 (m, 1H), 4.68 (dd, J=11.2, 5.2 Hz, 1H), 4.53 (d, J=3.2 Hz, 1H), 4.32-4.20 (m, 2H), 4.16-4.06 (m, 1H), 3.70-3.57 (m, 1H), 3.39-3.27 (m, 1H), 1.47 (s, 18H), 1.01 (t, J=6.8 Hz, 3H).

Intermediate 90

5-Bromo-2-cyanopyridin-3-yl 2,4,6-tri-O-acetyl-3-azido-3-deoxy-1-thio-α-D-galactopyranoside

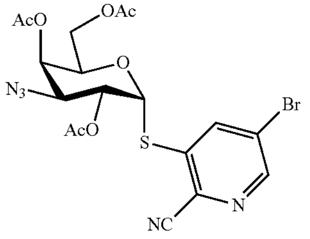

To a solution of acetyl 2,4,6-tri-O-acetyl-3-azido-3-deoxy-1-thio-α-D-galactopyranoside (4.00 g, 10.3 mmol) in DMF (30 mL) 5-bromo-3-fluoropyridine-2-carbonitrile (4.13 g, 20.5 mmol) and diethylamine (1.50 g, 20.5 mmol) were added at 0° C. and the mixture was stirred overnight at rt. The mixture was poured into water (80 mL) and extracted with EtOAc (2×80 mL). The organic phases were washed with brine, dried over $Na_2SO_4$, concentrated and purified by column chromatography (PE/EA=10/1~1/1, Silica-CS 40 g, 50 mL/min, silica gel, UV 254) to afford the product (3.00 g, 55%). ESI-MS m/z calcd for $[C_{18}H_{18}BrN_5O_7S]$ $[M+H]^+$: 528.0; found: 528.1. $^1H$ NMR (400 MHz, Chloroform-d) δ 8.66 (d, J=2.0 Hz, 1H), 8.18 (d, J=2.0 Hz, 1H), 6.11 (d, J=5.6 Hz, 1H), 5.52 (d, J=2.4 Hz, 1H), 5.31 (dd, J=11.2, 5.6 Hz, 1H), 4.60 (dd, J=7.2, 4.8 Hz, 1H), 4.17-4.11 (m, 1H), 4.04-3.98 (m, 2H), 2.24 (s, 3H), 2.18 (s, 3H), 2.02 (s, 3H).

5-Bromo-2-cyanopyridin-3-yl 3-azido-3-deoxy-1-thio-α-D-galactopyranoside

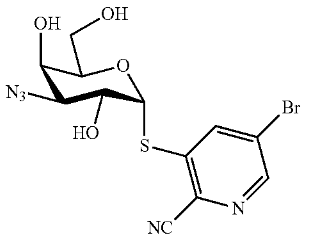

A solution of 5-bromo-2-cyanopyridin-3-yl 2,4,6-tri-O-acetyl-3-azido-3-deoxy-1-thio-α-D-galactopyranoside (3.00 g, 5.68 mmol) in MeOH (50 mL), $Et_3N$ (3.96 mL) and water (2 mL) was stirred 16 h at rt. The mixture was concentrated and DCM (20 mL) was added to the residue. The precipitate was collected and dried in vacuum to give the product (1.8 g, 79%). ESI-MS m/z calcd for $[Cl_2H_{12}BrN_5O_4S]$ $[M+H]^+$: 402.0; found: 402.1. $^1H$ NMR (400 MHz, Methanol-$d_4$) δ 8.62 (d, J=2.0 Hz, 1H), 8.52 (d, J=2.0 Hz, 1H), 6.01 (d, J=5.2 Hz, 1H), 4.43 (dd, J=10.8, 5.2 Hz, 1H), 4.13 (t, J=6.0 Hz, 1H), 4.04 (d, J=2.4 Hz, 1H), 3.65-3.58 (m, 3H).

5-Bromo-2-cyanopyridin-3-yl 3-azido-4,6-O-benzylidene-3-deoxy-1-thio-α-D-galactopyranoside

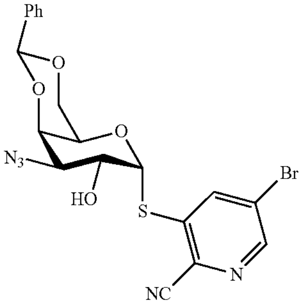

To a solution of 5-bromo-2-cyanopyridin-3-yl 3-azido-3-deoxy-1-thio-α-D-galactopyranoside (1.80 g, 4.48 mmol) in DMF (10 mL) benzaldehyde dimethylacetal (2.04 g, 13.4 mmol) and D(+)-10-camphorsulfonic acid (312 mg, 1.34 mmol) were added and the mixture was stirred 2 h at 50° C. The mixture was cooled to rt and poured into water. The solid was collected and dried in vacuum to afford the product (2.0 g, 91%). ESI-MS m/z calcd for $[C_{19}H_{16}BrN_5O_4S]$ $[M+H]^+$: 490.0; found: 490.0. $^1H$ NMR (400 MHz, Chloroform-d) δ 8.61 (d, J=2.0 Hz, 1H), 8.24 (d, J=2.0 Hz, 1H), 7.52-7.47 (m, 2H), 7.39-7.34 (m, 3H), 5.93 (d, J=5.2 Hz, 1H), 5.64 (s, 1H), 4.67 (dd, J=10.8, 5.2 Hz, 1H), 4.43 (d, J=2.4 Hz, 1H), 4.23-3.89 (m, 3H), 3.67 (dd, J=10.8, 3.2 Hz, 1H).

5-Bromo-2-(ethoxycarbonyl)pyridin-3-yl 3-azido-4,6-O-benzylidene-3-deoxy-2-O-ethyl-1-thio-α-D-galactopyranoside

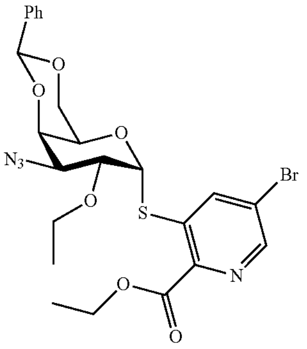

To a solution of 5-bromo-2-cyanopyridin-3-yl 3-azido-4,6-O-benzylidene-3-deoxy-1-thio-α-D-galactopyranoside (500 mg, 1.02 mmol) in EtOH (20 mL) and water (10 mL) NaOH (612 mg, 15.3 mmol) was added and the mixture was stirred overnight at 80° C. The mixture was evaporated to dryness and the residue was dissolved in DMF (6 mL).

$Cs_2CO_3$ (664 mg, 2.04 mmol) and iodoethane (1.59 g, 10.2 mmol) were added and the mixture was stirred 3 h at rt. The mixture was poured into water (200 mL) and extracted with EtOAc (2×100 mL). The organic phases were washed with brine (100 mL), dried over $Na_2SO_4$, concentrated and purified by column chromatography (PE/EA=10/1~1/1, Silica-CS 4 g, 10 mL/min, silica gel, UV 254) to afford the product (140 mg, 24%). ESI-MS m/z calcd for $[C_{23}H_{25}BrN_4O_6S]$ $[M+H]^+$: 565.1; found: 565.0. $^1H$ NMR (400 MHz, Chloroform-d) δ 8.52 (d, J=2.0 Hz, 1H), 8.28 (d, J=2.0 Hz, 1H), 7.55-7.33 (m, 5H), 6.09 (d, J=5.2 Hz, 1H), 5.61 (s, 1H), 4.56-4.01 (m, 7H), 3.91 (dd, J=10.8, 3.2 Hz, 1H), 3.84-3.54 (m, 2H), 1.44 (t, J=7.2 Hz, 3H), 1.26 (t, J=7.2 Hz, 3H).

5-Bromo-2-(ethoxycarbonyl)pyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside

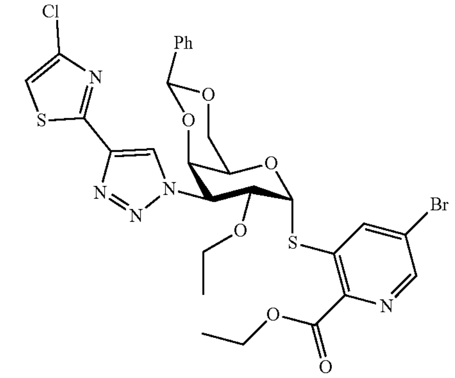

To a solution of 5-bromo-2-(ethoxycarbonyl)pyridin-3-yl 3-azido-4,6-O-benzylidene-3-deoxy-2-O-ethyl-1-thio-α-D-galactopyranoside (140 mg, 0.25 mmol) in DMF (5 mL) 2-(4-chlorothiazol-2-yl)ethynyl-trimethyl-silane (107 mg, 0.50 mmol), (+)-sodium L-ascorbate (49.1 mg, 0.25 mmol) and copper (II) sulfate pentahydrate (61.8 mg, 0.25 mmol) were added and the mixture was stirred overnight at rt. The mixture was diluted with water (50 mL) and extracted with EtOAc (2×80 mL). The organic layers were washed with brine (50 mL), dried over $Na_2SO_4$, concentrated and purified by column chromatography (PE/EA=10/1~1/1, Silica-CS 4 g, 10 mL/min, silica gel, UV 254) to give the product (110 mg, 63%). ESI-MS m/z calcd for $[C_{28}H_{27}BrClN_5O_6S_2]$ $[M+H]^+$: 708.0; found: 708.0 $^1H$ NMR (400 MHz, Chloroform-d) δ 8.57 (d, J=2.0 Hz, 1H), 8.34-8.29 (m, 2H), 7.43-7.35 (m, 5H), 7.12 (s, 1H), 6.24 (d, J=5.2 Hz, 1H), 5.51 (s, 1H), 5.46 (dd, J=11.2, 3.2 Hz, 1H), 4.74 (dd, J=11.2, 5.2 Hz, 1H), 4.55-4.46 (m, 3H), 4.31-4.23 (m, 2H), 4.17-4.10 (m, 1H), 3.76-3.64 (m, 1H), 3.42-3.30 (m, 1H), 1.46 (t, J=7.2 Hz, 3H), 1.03 (t, J=7.2 Hz, 3H).

5-Bromo-2-(ethoxycarbonyl)pyridin-3-yl 3-[4-(4-chlorothiazol-2-yl)-1H-1,2,3-triazol-1-yl]-3-deoxy-2-O-ethyl-1-thio-α-D-galactopyranoside

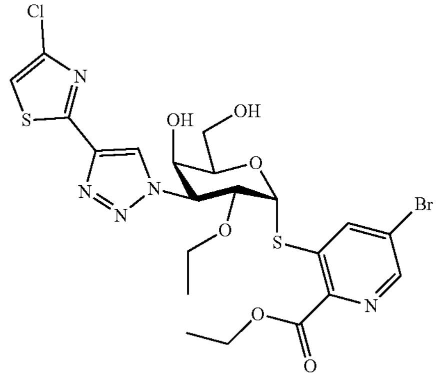

To a solution of 5-bromo-2-(ethoxycarbonyl)pyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside (90 mg, 0.13 mmol) in DCM (6 mL) TFA (0.94 mL) was added and the mixture was stirred overnight at rt. $Et_3N$ (2 mL) was added at 0° C. The mixture was concentrated and purified by prep HPLC [MeCN/$H_2O$ (10 mmol/L $NH_4HCO_3$), X-Select 10 μm 19*250 mm, 20 mL/min, UV 254] to afford the product (40 mg, 51%). ESI-MS m/z calcd for $[C_{21}H_{23}BrClN_5O_6S_2]$ $[M+H]^+$: 620.0; found: 620.1. $^1H$ NMR (400 MHz, Methanol-$d_4$) δ 8.63 (s, 1H), 8.56 (s, 2H), 7.46 (s, 1H), 6.31 (d, J=5.2 Hz, 1H), 5.11 (dd, J=11.2, 2.8 Hz, 1H), 4.76 (dd, J=11.2, 5.2 Hz, 1H), 4.49-4.35 (m, 3H), 4.21-4.17 (m, 1H), 3.83-3.62 (m, 3H), 3.47-3.37 (m, 1H), 1.41 (t, J=7.2 Hz, 3H), 1.01 (t, J=6.8 Hz, 3H).

5-Bromo-2-carboxypyridin-3-yl 3-[4-(4-chlorothiazol-2-yl)-1H-1,2,3-triazol-1-yl]-3-deoxy-2-O-ethyl-1-thio-α-D-galactopyranoside

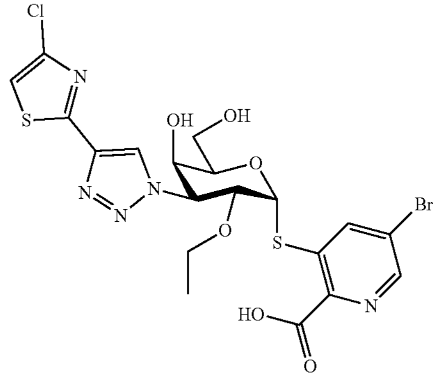

To a solution of 5-bromo-2-(ethoxycarbonyl)pyridin-3-yl 3-[4-(4-chlorothiazol-2-yl)-1H-1,2,3-triazol-1-yl]-3-deoxy-2-O-ethyl-1-thio-α-D-galactopyranoside (40 mg, 0.064 mmol) in MeOH/THF/$H_2O$ (5 mL, 2:2:1) lithium hydroxide monohydrate (8.1 mg, 0.19 mmol) was added and the mixture was stirred overnight at rt. The mixture was concentrated and purified by reverse-phase column (MeCN/water (0.01% TFA)=0~45%, C18 40 g, 50 mL/min, UV 254)

to afford the product (30 mg, 79%). ESI-MS m/z calcd for $[C_{19}H_{19}BrClN_5O_6S_2]$ $[M+H]^+$: 592.0; found: 529.3. $^1H$ NMR (400 MHz, Methanol-$d_4$) δ 8.76-8.28 (m, 3H), 7.46 (s, 1H), 6.38 (d, J=5.6 Hz, 1H), 5.17 (d, J=11.2 Hz, 1H), 4.78 (dd, J=11.2, 5.2 Hz, 1H), 4.35 (t, J=6.0 Hz, 1H), 4.21-4.16 (m, 1H), 3.81-3.59 (m, 3H), 3.48-3.37 (m, 1H), 1.00 (t, J=7.2 Hz, 3H).

Intermediate 91

5-Bromo-2-(methoxycarbonyl)pyridin-3-yl 2,4,6-tri-O-acetyl-3-azido-3-deoxy-1-thio-α-D-galactopyranoside

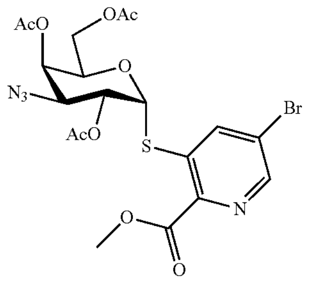

To a solution of acetyl 2,4,6-tri-O-acetyl-3-azido-3-deoxy-1-thio-α-D-galactopyranoside (2.34 g, 6.01 mmol) in DMF (30 mL) methyl 5-bromo-3-fluoro-pyridine-2-carboxylate (1.41 g, 6.01 mmol) and diethylamine (879 mg, 12.0 mmol) were added at 0° C. and the mixture was stirred overnight at rt. The mixture was diluted with water (150 mL) and extracted with EtOAc (2×200 mL). The organic layers were washed with brine, dried over $Na_2SO_4$, concentrated and purified by column chromatography (PE/EA=10/1~1/1, Silica-CS 40 g, 50 mL/min, silica gel, UV 254) to give the product (1.60 g, 47%). ESI-MS m/z calcd for $[C_{19}H_{21}BrN_4O_9S]$ $[M+H]^+$: 561.0; found: 561.1. $^1H$ NMR (400 MHz, Chloroform-d) δ 8.49 (d, J=2.0 Hz, 1H), 8.16 (d, J=2.0 Hz, 1H), 6.06 (d, J=5.6 Hz, 1H), 5.43-5.38 (m, 1H), 5.34-5.25 (m, 1H), 4.51-4.44 (m, 1H), 4.10-3.98 (m, 3H), 3.95 (s, 3H), 2.11-2.09 (m, 6H), 1.86 (s, 3H).

5-Bromo-2-(methoxycarbonyl)pyridin-3-yl 3-azido-4,6-O-benzylidene-3-deoxy-1-thio-α-D-galactopyranoside

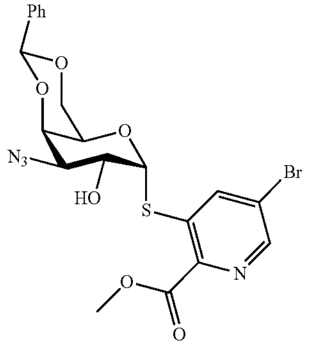

A solution of 5-bromo-2-(methoxycarbonyl)pyridin-3-yl 2,4,6-tri-O-acetyl-3-azido-3-deoxy-1-thio-α-D-galactopyranoside (1.60 g, 2.85 mmol) in MeOH (30 mL), $Et_3N$ (2 mL) and $H_2O$ (1 mL) was stirred overnight at rt. The mixture was concentrated and suspended in DCM. The solid was collected and washed by DCM and diethyl ether. The obtained material was dissolved in DMF (10 mL) and benzaldehyde dimethylacetal (524 mg, 3.45 mmol) and D(+)-10-camphorsulfonic acid (107 mg, 0.46 mmol) were added. The mixture was stirred 2 h at 50° C. before being cooled to rt and neutralized with $Et_3N$ (1 mL). The mixture was concentrated and purified by column chromatography (PE/EA=1/1~1/3, Silica-CS 20 g, 25 mL/min, silica gel, UV 254) to give the product (1.00 g, 67%). ESI-MS m/z calcd for $[C_{20}H_{19}BrN_4O_6S]$ $[M+H]^+$: 523.0; found: 523.0. $^1H$ NMR (400 MHz, DMSO-$d_6$) δ 8.67 (d, J=2.0 Hz, 1H), 8.50 (d, J=2.0 Hz, 1H), 7.53-7.44 (m, 5H), 6.33 (d, J=5.2 Hz, 1H), 6.21 (d, J=5.6 Hz, 1H), 5.74 (s, 1H), 4.53-4.47 (m, 1H), 4.45-4.37 (m, 1H), 4.18-4.11 (m, 1H), 4.05-3.76 (m, 6H).

5-Bromo-2-(methoxycarbonyl)pyridin-3-yl 3-azido-4,6-O-benzylidene-3-deoxy-2-O-methyl-1-thio-α-D-galactopyranoside

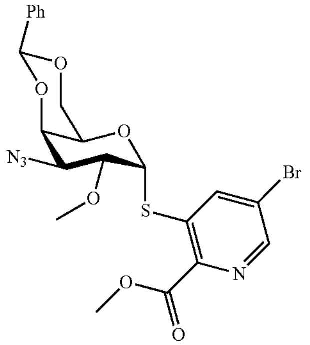

To a solution of 5-bromo-2-(methoxycarbonyl)pyridin-3-yl 3-azido-4,6-O-benzylidene-3-deoxy-1-thio-α-D-galactopyranoside (1.00 g, 1.91 mmol) in DMF (10 mL) $Cs_2CO_3$ (1.25 g, 3.82 mmol) and iodomethane (814 mg, 5.73 mmol) were added and the mixture was stirred overnight at rt. The mixture was poured into water (200 mL) and the precipitate was collected. The solid was dissolved in EtOAc (100 mL) and washed with brine (50 mL). The organic phase was dried over $Na_2SO_4$ and concentrated to yield the product (740 mg, 72%). ESI-MS m/z calcd for $[C_{21}H_{21}BrN_4O_6S]$ $[M+H]^+$: 537.0; found: 537.2. $^1H$ NMR (400 MHz, Chloroform-d) δ 8.52 (d, J=2.0 Hz, 1H), 8.32 (d, J=2.0 Hz, 1H), 7.56-7.49 (m, 2H), 7.41-7.33 (m, 3H), 6.11 (d, J=5.2 Hz, 1H), 5.62 (s, 1H), 4.37-3.79 (m, 9H), 3.53 (s, 3H).

5-Bromo-2-(methoxycarbonyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

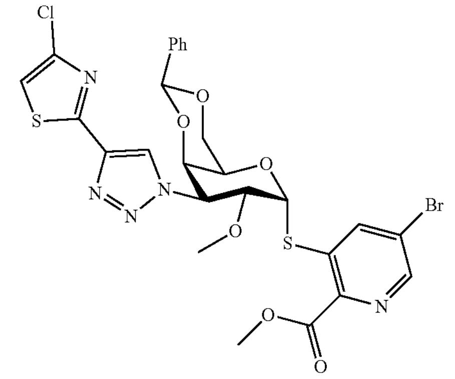

To a solution of 5-bromo-2-(methoxycarbonyl)pyridin-3-yl 3-azido-4,6-O-benzylidene-3-deoxy-2-O-methyl-1-thio-α-D-galactopyranoside (740 mg, 1.38 mmol) in DMF (5 mL) 2-(4-chlorothiazol-2-yl)ethynyl-trimethyl-silane (446 mg, 2.07 mmol), (+)-sodium L-ascorbate (273 mg, 1.38 mmol) and copper (II) sulfate pentahydrate (344 mg, 1.38 mmol) were added and the mixture was stirred overnight at rt. The mixture was diluted with water (50 mL) and extracted with EtOAc (2×80 mL). The organic layers were washed with brine (50 mL), dried over $Na_2SO_4$, concentrated and purified by column chromatography (PE/EA=10/1~1/1, Silica-CS 4 g, 10 mL/min, silica gel, UV 254) to give the product (700 mg, 75%). ESI-MS m/z calcd for $[C_{26}H_{23}BrClN_5O_6S_2]$ $[M+H]^+$: 680.0; found: 680.0 $^1H$ NMR (400 MHz, Chloroform-d) δ 8.56 (d, J=2.0 Hz, 1H), 8.34 (d, J=2.0 Hz, 1H), 7.42-7.34 (m, 6H), 7.11 (s, 1H), 6.27 (d, J=5.2 Hz, 1H), 5.51 (s, 1H), 5.45 (dd, J=11.2, 3.2 Hz, 1H), 4.65 (dd, J=11.2, 5.2 Hz, 1H), 4.53 (d, J=3.2 Hz, 1H), 4.31-4.24 (m, 2H), 4.15-4.09 (m, 1H), 4.02 (s, 3H), 3.34 (s, 3H).

5-(2-Trimethylsilyl-1-ethynyl)-2-(methoxycarbonyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

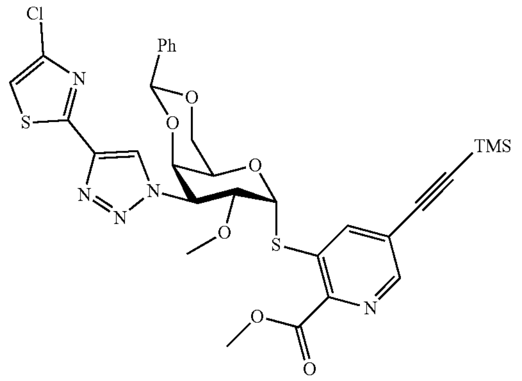

To a solution of 5-bromo-2-(methoxycarbonyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (680 mg, 1.00 mmol) in THF (30 mL) ethynyl (trimethyl)silane (294 mg, 3.00 mmol), bis (triphenylphosphine)palladium(II) chloride (36.4 mg, 0.050 mmol), CuI (57.1 mg, 0.30 mmol) and DIPEA (0.513 mL, 3.00 mmol) were added and the mixture was stirred 1 h at 50° C. The mixture was diluted with water (50 mL) and extracted with EtOAc (2×50 mL). The combined organic layers were washed with water (50 mL) and brine (50 mL), dried over $Na_2SO_4$, concentrated and purified by column chromatography (PE/EA=1/1~0/1, Silica-CS 4 g, 10 mL/min, silica gel, UV 254) to give the product (400 mg, 57%). ESI-MS m/z calcd for $[C_{31}H_{32}ClN_5O_6S_2Si][M+H]^+$: 698.1; found: 698.0 $^1H$ NMR (400 MHz, Chloroform-d) δ 8.53 (d, J=1.6 Hz, 1H), 8.32 (s, 1H), 8.20 (d, J=1.6 Hz, 1H), 7.42-7.34 (m, 5H), 7.11 (s, 1H), 6.29 (d, J=5.2 Hz, 1H), 5.54-5.39 (m, 2H), 4.66 (dd, J=11.2, 5.2 Hz, 1H), 4.56-4.51 (m, 1H), 4.37-4.25 (m, 2H), 4.17-4.06 (m, 1H), 4.02 (s, 3H), 3.34 (s, 3H), 0.28 (s, 9H).

2-Carboxy-5-ethynylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

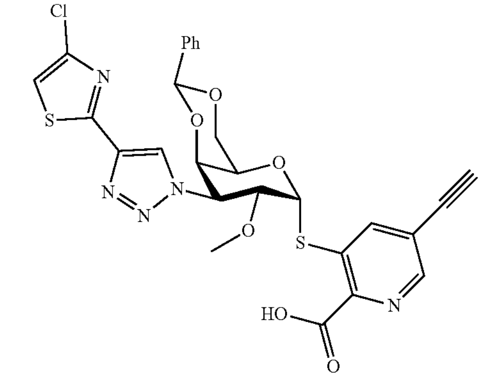

To a solution of 5-(2-trimethylsilyl-1-ethynyl)-2-(methoxycarbonyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (200 mg, 0.29 mmol) in MeOH (3 mL) and water (3 mL) lithium hydroxide monohydrate (36.1 mg, 0.86 mmol) was added and the mixture was stirred overnight at rt. The mixture was filtered and purified by prep HPLC (MeCN/$H_2O$ (10 mmol/L $NH_4HCO_3$), X-Select 10 μm 19*250 mm, 20 mL/min, UV 254) to give the product (80 mg, 46%). $^1H$ NMR (400 MHz, DMSO-$d_6$) δ 8.99 (s, 1H), 8.56 (s, 1H), 8.41-8.21 (m, 1H), 7.80 (s, 1H), 7.46-7.30 (m, 5H), 6.77-6.69 (m, 1H), 5.58 (s, 1H), 5.33-5.21 (m, 1H), 4.96-4.85 (m, 1H), 4.72-4.64 (m, 1H), 4.63-4.50 (m, 1H), 4.23-4.17 (m, 1H), 4.13-4.05 (m, 1H), 3.96-3.88 (m, 1H), 3.32 (s, 3H).

5-Ethynyl-2-(N,N-dimethylcarbamoyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

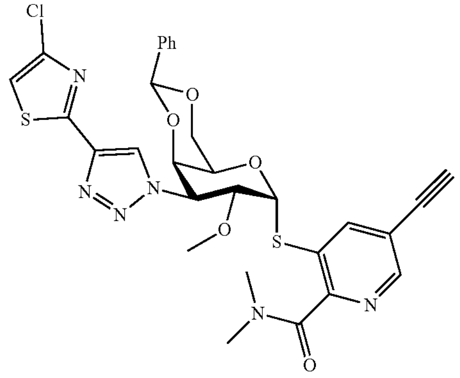

To a solution of 2-carboxy-5-ethynylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (65 mg, 0.11 mmol) in DMF (3 mL) dimethylamine hydrochloride (26 mg, 0.32 mmol), HATU (80.8 mg, 0.21 mmol) and DIPEA (73 μL, 0.43 mmol) were added and the mixture was stirred overnight at rt. The mixture was diluted with water (30 mL) and extracted with EtOAc (2×30 mL). The organic phases were washed with brine (50 mL), dried over $Na_2SO_4$, concentrated and purified by column chromatography (PE/EA=10/1~1/1, Silica-CS 4 g, 10 mL/min, silica gel, UV 254) to afford the product (30 mg, 44%). ESI-MS m/z calcd for $[C_{29}H_{27}ClN_6O_5S_2]$ $[M+H]^+$: 639.1; found: 639.2. $^1H$ NMR (400 MHz, Chloroform-d) δ 8.62 (d, J=2.0 Hz, 1H), 8.29 (s, 1H), 8.02 (d, J=2.0 Hz, 1H), 7.40-7.34 (m, 5H), 7.11 (s, 1H), 6.34 (d, J=5.2 Hz, 1H), 5.49 (s, 1H), 5.34 (dd, J=11.2, 3.2 Hz, 1H), 4.58-4.50 (m, 2H), 4.41 (s, 1H), 4.27-4.10 (m, 2H), 3.38 (s, 3H), 3.30 (s, 1H), 3.17 (s, 3H), 2.87 (s, 3H).

Intermediate 92

2-(N-Azetidinylcarbamoyl)-5-ethynylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

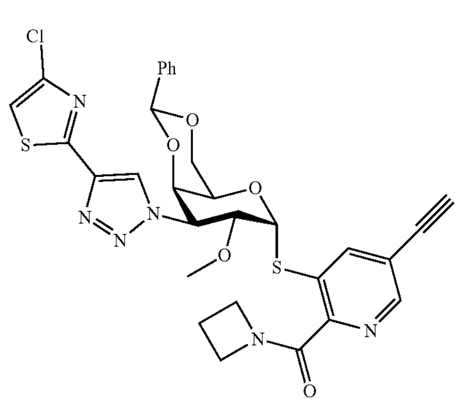

To a solution of 2-carboxy-5-ethynylpyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside (65 mg, 0.11 mmol) in DMF (3 mL) azetidine hydrochloride (19.9 mg, 0.21 mmol), HATU (80.8 mg, 0.21 mmol) and DIPEA (73 μL, 0.43 mmol) were added and the mixture was stirred overnight at rt. The mixture was diluted with water (30 mL) and extracted with EtOAc (2×30 mL). The organic phases were washed with brine (50 mL), dried over $Na_2SO_4$, concentrated and purified by column chromatography (PE/EA=10/1~1/1, Silica-CS 4 g, 10 mL/min, silica gel, UV 254) to afford the product (30 mg, 43%). ESI-MS m/z calcd for $[C_{30}H_{27}ClN_6O_5S_2]$ $[M+H]^+$: 651.1; found: 651.2. $^1H$ NMR (400 MHz, Chloroform-d) δ 8.51 (d, J=1.6 Hz, 1H), 8.31 (s, 1H), 8.16 (d, J=1.6 Hz, 1H), 7.47-7.34 (m, 5H), 7.11 (s, 1H), 6.28 (d, J=5.2 Hz, 1H), 5.50 (s, 1H), 5.45 (dd, J=11.2, 3.2 Hz, 1H), 4.61 (dd, J=11.2, 5.2 Hz, 1H), 4.57-4.48 (m, 2H), 4.43-4.40 (m, 1H), 4.33-4.20 (m, 4H), 4.17-4.11 (m, 1H), 3.36 (s, 3H), 3.30 (s, 1H), 2.42-2.30 (m, 2H).

Intermediate 93

5-Chloro-2-cyanopyridin-3-yl 2,4,6-tri-O-acetyl-3-azido-3-deoxy-1-thio-α-D-galactopyranoside

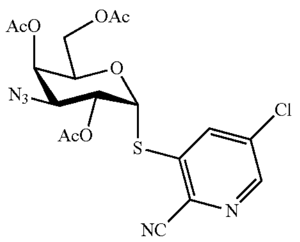

To a solution of acetyl 2,4,6-tri-O-acetyl-3-azido-3-deoxy-1-thio-D-galactopyranoside (4.50 g, 11.5 mmol) in DMF (30 mL) 5-chloro-3-fluoropyridine-2-carbonitrile (1.81 g, 11.5 mmol) and diethylamine (1.69 g, 23.0 mmol) were added at 0° C. and the mixture was stirred overnight at rt. The mixture was poured into water (150 mL) and extracted with EtOAc (2×200 mL). The organic layers were washed with brine, dried over $Na_2SO_4$, concentrated and purified by column chromatography (PE/EA=10/1~1/1, Silica-CS 80 g, 50 mL/min, silica gel, UV 254) to give the product (3.30 g, 59%). ESI-MS m/z calcd for $[C_{18}H_{18}ClN_5O_7S]$ $[M+H]^+$: 484.1; found: 484.0. $^1H$ NMR (400 MHz, Methanol-$d_4$) δ 8.64 (d, J=2.4 Hz, 1H), 8.28 (d, J=2.4 Hz, 1H), 6.17 (d, J=5.6 Hz, 1H), 5.54 (d, J=2.8 Hz, 1H), 5.29 (dd, J=11.2, 5.2 Hz, 1H), 4.68 (dd, J=7.6, 4.0 Hz, 1H), 4.27 (dd, J=10.8, 3.2 Hz, 1H), 4.15 (dd, J=7.6, 4.0 Hz, 1H), 3.98 (dd, J=11.6, 8.0 Hz, 1H), 2.18 (s, 3H), 2.14 (s, 3H), 2.14 (s, 3H).

5-Chloro-2-cyanopyridin-3-yl 3-azido-3-deoxy-1-thio-α-D-galactopyranoside

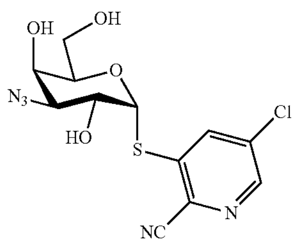

A solution of 5-chloro-2-cyanopyridin-3-yl-2,4,6-tri-O-acetyl-3-azido-3-deoxy-1-thio-α-D-galactopyranoside (3.30 g, 6.83 mmol) in MeOH (30 mL), $Et_3N$ (12 mL) and water (3 mL) was stirred overnight at rt. The mixture was concentrated and DCM (20 mL) was added. The precipitate was isolated to give the product (2.20 g, 90%). ESI-MS m/z calcd for $[C_{12}H_{12}ClN_5O_4S]$ $[M+H]^+$: 358.0; found: 358.0. $^1H$ NMR (400 MHz, Methanol-$d_4$) δ 8.51 (d, J=2.0 Hz, 1H), 8.37 (d, J=2.4 Hz, 1H), 6.03 (d, J=5.2 Hz, 1H), 4.43 (dd, J=6.8, 1.6 Hz, 1H), 4.12 (t, J=6.0 Hz, 1H), 4.04 (d, J=2.4 Hz, 1H), 3.66-3.58 (m, 3H).

5-Chloro-2-cyanopyridin-3-yl 3-azido-4,6-O-benzylidene-3-deoxy-1-thio-α-D-galactopyranoside

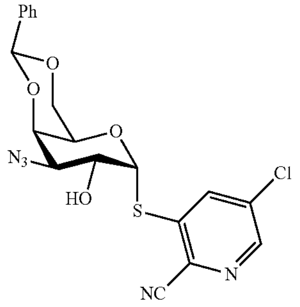

To a solution of 5-chloro-2-cyanopyridin-3-yl-3-azido-3-deoxy-1-thio-α-D-galactopyranoside (2.20 g, 6.15 mmol) in DMF (15 mL) benzaldehyde dimethylacetal (2.81 g, 18.4 mmol) and D(+)-10-camphorsulfonic acid (429 mg, 1.84 mmol) were added and the mixture was stirred 2 h at 50° C. The mixture was cooled to rt and poured into water. The precipitate was isolated to give the product (2.00 g, 70%). ESI-MS m/z calcd for $[C_{19}H_{16}ClN_5O_4S.]$ $[M+H]^+$: 446.1; found: 446.0. $^1H$ NMR (400 MHz, Chloroform-d) δ 8.51 (d, J=2.0 Hz, 1H), 8.08 (d, J=2.4 Hz, 1H), 7.51-7.35 (m, 5H), 5.92 (d, J=5.2 Hz, 1H), 5.64 (s, 1H), 4.66 (dd, J=10.8, 5.2 Hz, 1H), 4.44 (d, J=2.8 Hz, 1H), 4.25-4.13 (m, 3H), 3.67 (dd, J=10.8, 3.2 Hz, 1H).

2-Carboxy-5-chloropyridin-3-yl 3-azido-4,6-O-benzylidene-3-deoxy-1-thio-α-D-galactopyranoside

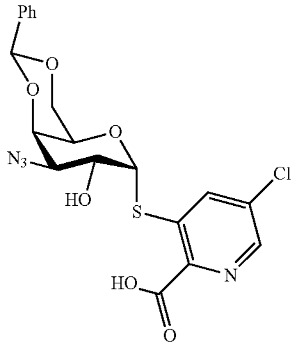

To a solution of 5-chloro-2-cyanopyridin-3-yl 3-azido-4,6-O-benzylidene-3-deoxy-1-thio-α-D-galactopyranoside (2.00 g, 4.33 mmol) in EtOH (50 mL) and water (20 mL) NaOH (2.6 g, 64.9 mmol) was added and the mixture was stirred overnight at 80° C. The EtOH was removed under reduced pressure and the mixture was acidified using HCl (1 M). The precipitate was isolated and dried in vacuum to give the product (1.80 g, 90%). ESI-MS m/z calcd for $[C_{19}H_{17}ClN_4O_6S]$ $[M+H]^+$: 465.1; found: 465.1. $^1H$ NMR (400 MHz, Methanol-$d_4$) δ 8.34-8.28 (m, 2H), 7.49-7.34 (m, 5H), 5.94 (d, J=5.2 Hz, 1H), 5.63 (s, 1H), 4.57 (dd, J=12.0, 4.0 Hz, 1H), 4.41 (s, 1H), 4.14-4.00 (m, 3H), 3.73 (dd, J=8.4, 2.8 Hz, 1H).

5-Chloro-2-(N-methylcarbamoyl)pyridin-3-yl 3-azido-4,6-O-benzylidene-3-deoxy-1-thio-α-D-galactopyranoside

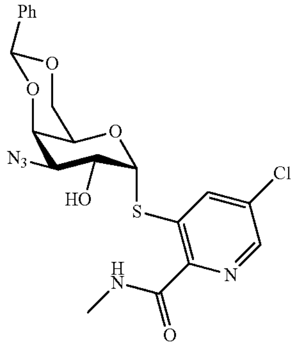

To a solution of 2-carboxy-5-chloropyridin-3-yl 3-azido-4,6-O-benzylidene-3-deoxy-1-thio-α-D-galactopyranoside (200 mg, 0.43 mmol), HATU (327 mg, 0.86 mmol) and DIPEA (221 μL, 1.29 mmol) in DMF (6 mL) methylamine hydrochloride (43.6 mg, 0.65 mmol) was added and the mixture was stirred 2 h at rt. The mixture was purified by reversed-phase chromatography ($MeCN/H_2O$=1/20~3/1, C-18 column, 20 mL/min, UV 254) to afford the product (130 mg, 63%). ESI-MS m/z calcd for $[C_{20}H_{20}ClN_5O_5S]$ $[M+H]^+$: 478.1; found: 478.2. $^1H$ NMR (400 MHz, DMSO-$d_6$) δ 8.67 (d, J=4.8 Hz, 1H), 8.43 (d, J=2.0 Hz, 1H), 8.23 (d, J=2.0 Hz, 1H), 7.51-7.31 (m, 5H), 6.18 (d, J=5.2 Hz, 1H), 6.05 (d, J=5.2 Hz, 1H), 5.67 (s, 1H), 4.42 (d, J=3.2 Hz, 1H), 4.34 (dt, J=10.8, 5.2 Hz, 1H), 4.06 (dd, J=12.4, 1.6 Hz, 1H), 3.97-3.87 (m, 2H), 3.75 (dd, J=10.8, 3.2 Hz, 1H), 2.77 (d, J=4.8 Hz, 3H).

5-Chloro-2-(N-methylcarbamoyl)pyridin-3-yl 3-azido-4,6-O-benzylidene-3-deoxy-2-O-methyl-1-thio-α-D-galactopyranoside

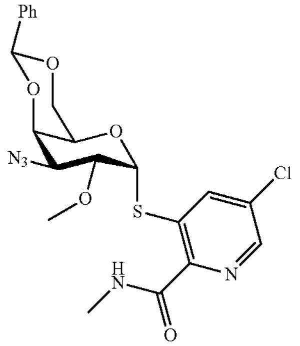

To a solution of 5-chloro-2-(N-methylcarbamoyl)pyridin-3-yl 3-azido-4,6-O-benzylidene-3-deoxy-1-thio-α-D-galactopyranoside (100 mg, 0.21 mmol) and iodomethane (0.13 mL, 2.09 mmol) in DMF (6.0 mL) $Cs_2CO_3$ (205 mg, 0.63 mmol) was added and the mixture was stirred 4 h at rt. The mixture was concentrated and purified by preparative TLC (PE/EA=1/1) to give the product (60 mg, 58%). ESI-MS m/z calcd for $[C_{21}H_{22}ClN_5O_5S]$ $[M+H]^+$: 492.1; found: 492.1. $^1$H NMR (400 MHz, Chloroform-d) δ 8.17 (d, J=2.0 Hz, 1H), 8.12 (d, J=2.0 Hz, 1H), 7.83 (d, J=5.2 Hz, 1H), 7.58-7.42 (m, 2H), 7.38-7.24 (m, 3H), 6.02 (d, J=5.2 Hz, 1H), 5.55 (s, 1H), 4.29-4.20 (m, 2H), 4.13 (dd, J=13.2, 2.0 Hz, 1H), 4.08-3.99 (m, 2H), 3.92 (dd, J=10.8, 3.2 Hz, 1H), 3.45 (s, 3H), 2.93 (d, J=5.2 Hz, 3H).

5-Chloro-2-(N-methylcarbamoyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

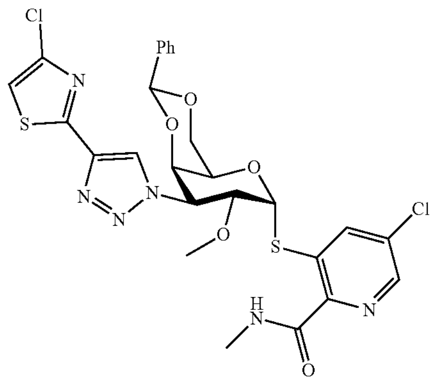

To a solution of 5-chloro-2-(N-methylcarbamoyl)pyridin-3-yl 3-azido-4,6-O-benzylidene-3-deoxy-2-O-methyl-1-thio-α-D-galactopyranoside (60 mg, 0.12 mmol) and 2-(4-chlorothiazol-2-yl)ethynyl-trimethyl-silane (31.6 mg, 0.15 mmol) in DMF (4 mL) (+)-sodium L-ascorbate (36.2 mg, 0.18 mmol) and copper (II) sulfate pentahydrate (15.2 mg, 0.061 mmol) were added and the mixture was stirred 4 h at rt. The mixture was concentrated and purified by column chromatography (PE/EA=2/1~1/2, Silica-CS 20 g, 30 mL/min, silica gel, UV 254) to give the product (40 mg, 52%). ESI-MS m/z calcd for $[C_{26}H_{24}Cl_2N_6O_5S_2]$ $[M+H]^+$: 635.1; found: 635.1 $^1$H NMR (400 MHz, Chloroform-d) δ 8.23 (m, 2H), 8.12 (m, 1H), 7.95 (s, 1H), 7.86 (d, J=4.8 Hz, 1H), 7.32 (m, 5H), 6.18 (d, J=5.2 Hz, 1H), 5.51-5.45 (m, 1H), 5.44 (s, 1H), 4.63 (dd, J=11.2, 5.2 Hz, 1H), 4.47-4.44 (m, 1H), 4.27 (s, 1H), 4.20 (dd, J=12.8, 1.6 Hz, 1H), 4.11-4.03 (m, 1H), 3.27 (s, 3H), 2.95 (d, J=5.2 Hz, 3H).

Intermediate 94

5-Chloro-2-(N-ethylcarbamoyl)pyridin-3-yl 3-azido-4,6-O-benzylidene-3-deoxy-1-thio-α-D-galactopyranoside

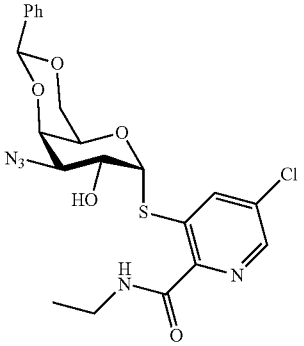

To a solution of 2-carboxy-5-chloropyridin-3-yl 3-azido-4,6-O-benzylidene-3-deoxy-1-thio-α-D-galactopyranoside (200 mg, 0.43 mmol) in DMF (5 mL) HATU (327 mg, 0.86 mmol) and $Et_3N$ (0.60 mL, 4.3 mmol) were added at 0° C. After 10 min ethylamine hydrochloride (70 mg, 0.86 mmol) was added and the mixture was stirred 2 h at rt. The mixture was purified by reversed-phase chromatography (MeCN/$H_2O$=1/20~3/1, C-18 column, 20 mL/min, UV 254) to afford the product (150 mg, 71%). ESI-MS m/z calcd for $[C_{21}H_{22}ClN_5O_5S]$ $[M+H]^+$: 492.1; found: 492.1. $^1$H NMR (400 MHz, Methanol-$d_4$) δ 8.36 (d, 2.0 Hz, 1H), 8.25 (d, J=2.0 Hz, 1H), 7.52-7.34 (m, 5H), 5.96 (d, J=5.1 Hz, 1H), 5.66 (s, 1H), 4.56 (dd, J=11.2, 5.6 Hz, 1H), 4.44 (d, J=2.8 Hz, 1H), 4.16-4.02 (m, 3H), 3.74 (dd, J=10.8, 3.2 Hz, 1H), 3.42-3.37 (m, 2H), 1.25-1.20 (m, 3H).

5-Chloro-2-(N-ethylcarbamoyl)pyridin-3-yl 3-azido-4,6-O-benzylidene-3-deoxy-2-O-methyl-1-thio-α-D-galactopyranoside

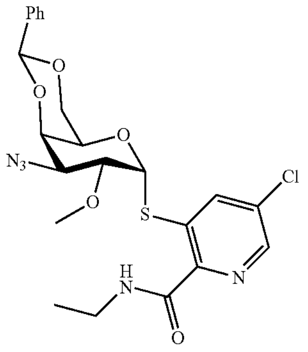

To a solution of 5-chloro-2-(N-ethylcarbamoyl)pyridin-3-yl 3-azido-4,6-O-benzylidene-3-deoxy-1-thio-α-D-galactopyranoside (150 mg, 0.30 mmol) and iodomethane (0.19 mL, 3.0 mmol) in DMF (5.0 mL) $Cs_2CO_3$ (200 mg, 0.61 mmol) was added and the mixture was stirred 2 h at rt. The mixture was concentrated and purified by column chromatography (PE/EA=10/1~1/1, Silica-CS 12 g, 20 mL/min, silica gel, UV 254) to give the product (90 mg, 58%). ESI-MS m/z calcd for $[C_{22}H_{24}ClN_5O_5S][M+H]^+$: 506.1; found: 506.1. $^1H$ NMR (400 MHz, Chloroform-d) δ 8.17 (d, J=2.0 Hz, 1H), 8.12 (d, J=2.1 Hz, 1H), 7.84 (s, 1H), 7.48-7.29 (m, 5H), 6.02 (d, J=5.2 Hz, 1H), 5.55 (s, 1H), 4.27-4.22 (m, 2H), 4.15-3.91 (m, 4H), 3.43-3.38 (m, 2H), 2.93 (d, J=5.1 Hz, 3H), 1.21-1.17 (m, 3H).

5-Chloro-2-(N-ethylcarbamoyl)pyridin-3-yl 4,6-O-benzylidene-3-[4-(4-chlorothiazol-2-yl)-1H-1,2,3-triazol-1-yl]-3-deoxy-2-O-methyl-1-thio-α-D-galactopyranoside

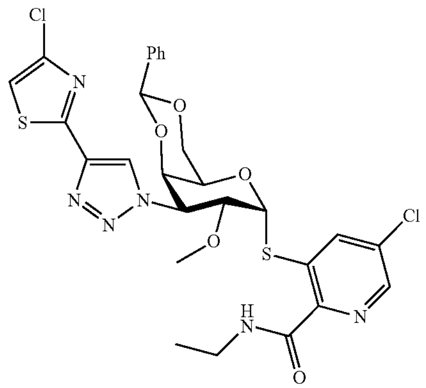

To a solution of 5-chloro-2-(N-ethylcarbamoyl)pyridin-3-yl 3-azido-4,6-O-benzylidene-3-deoxy-2-O-methyl-1-thio-α-D-galactopyranoside (90 mg, 0.18 mmol) and 2-(4-chlorothiazol-2-yl)ethynyl-trimethyl-silane (58 mg, 0.27 mmol) in DMF (5 mL) (+)-sodium L-ascorbate (18 mg, 0.089 mmol) and copper (II) sulfate pentahydrate (22 mg, 0.089 mmol) were added and the mixture was stirred 3 h at rt. The mixture was concentrated and purified by column chromatography (DCM/EA=1/0~4/1, Silica-CS 20 g, 30 mL/min, silica gel, UV 254) to give the product (95 mg, 82%). ESI-MS m/z calcd for $[C_{27}H_{26}Cl_2N_6O_5S_2]$ $[M+H]^+$: 649.1; found: 649.0 $^1H$ NMR (400 MHz, Chloroform-d) δ 8.24 (s, 1H), 8.21 (s, 1H), 8.15 (d, J=2.0 Hz, 1H), 7.84 (s, 1H), 7.34-7.29 (m, 5H), 7.04 (s, 1H), 6.18 (d, J=5.2 Hz, 1H), 5.48 (dd, J=11.2, 3.2 Hz, 1H), 5.44 (s, 1H), 4.62 (dd, J=11.2, 5.2 Hz, 1H), 4.45 (d, J=3.2 Hz, 1H), 4.28 (s, 1H), 4.22-4.04 (m, 2H), 3.46-3.39 (m, 2H), 3.28 (s, 3H), 1.22-1.17 (m, 3H).

Intermediate 95

5-Chloro-2-(N-methylcarbamoyl)pyridin-3-yl 3-azido-4,6-O-benzylidene-3-deoxy-2-O-ethyl-1-thio-α-D-galactopyranoside

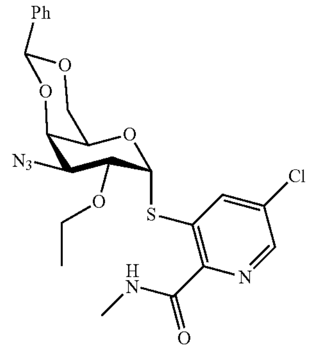

To a solution of 5-chloro-2-(N-methylcarbamoyl)pyridin-3-yl 3-azido-4,6-O-benzylidene-3-deoxy-1-thio-α-D-galactopyranoside (120 mg, 0.25 mmol) and iodoethane (0.156 mL, 2.51 mmol) in DMF (6.0 mL) $Cs_2CO_3$ (245 mg, 0.75 mmol) was added and the mixture was stirred 2 h at rt. The mixture was diluted with water (30 mL) and extracted with EtOAc (30 mL). The organic phase was concentrated and purified by column chromatography (PE/EA=2/1~1/2, Silica-CS 20 g, 30 mL/min, silica gel, UV 254) to give the product (80 mg, 63%). ESI-MS m/z calcd for $[C_{22}H_{24}ClN_5O_5S]$ $[M+H]^+$: 506.1; found: 506.2. $^1H$ NMR (400 MHz, Chloroform-d) δ 8.16 (d, J=2.0 Hz, 1H), 8.10 (d, J=2.0 Hz, 1H), 7.83 (d, J=5.2 Hz, 1H), 7.53-7.43 (m, 2H), 7.37-7.25 (m, 3H), 6.01 (d, J=5.2 Hz, 1H), 5.54 (s, 1H), 4.35 (dd, J=10.8, 5.2 Hz, 1H), 4.20 (d, J=3.4 Hz, 1H), 4.11 (dd, J=13.2, 2.0 Hz, 1H), 4.04-3.92 (m, 3H), 3.80-3.65 (m, 1H), 3.60-3.46 (m, 1H), 2.94 (d, J=5.2 Hz, 3H), 1.18 (t, J=6.8 Hz, 3H).

5-Chloro-2-(N-methylcarbamoyl)pyridin-3-yl 4,6-O-benzylidene-3-[4-(4-chlorothiazol-2-yl)-1H-1,2,3-triazol-1-yl]-3-deoxy-2-O-ethyl-1-thio-α-D-galactopyranoside

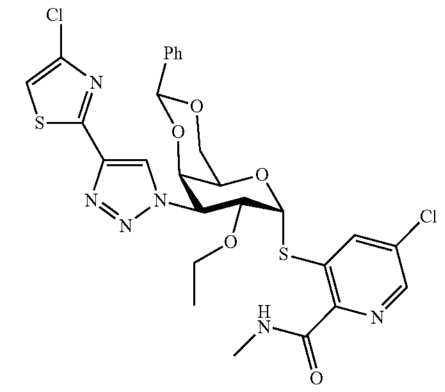

To a solution of 5-chloro-2-(N-methylcarbamoyl)pyridin-3-yl 3-azido-4,6-O-benzylidene-3-deoxy-2-O-ethyl-1-thio-α-D-galactopyranoside (80 mg, 0.16 mmol) and 2-(4-chlorothiazol-2-yl)ethynyl-trimethyl-silane (40.9 mg, 0.19 mmol) in DMF (4 mL) (+)-sodium L-ascorbate (47.0 mg, 0.24 mmol) and copper (II) sulfate pentahydrate (19.7 mg, 0.079 mmol) were added and the mixture was stirred overnight at rt. The mixture was concentrated and purified by column chromatography (PE/EA=2/1~1/2, Silica-CS 20 g, 30 mL/min, silica gel, UV 254) to give the product (80 mg, 78%). ESI-MS m/z calcd for $[C_{27}H_{26}Cl_2N_6O_5S_2]$ $[M+H]^+$: 649.1; found: 649.1 $^1H$ NMR (400 MHz, Chloroform-d) δ 8.24 (s, 1H), 8.20 (s, 1H), 8.13 (d, J=2.0 Hz, 1H), 7.85 (s, 1H), 7.39-7.26 (m, 5H), 7.04 (s, 1H), 6.16 (d, J=5.2 Hz, 1H), 5.49 (dd, J=11.2, 3.2 Hz, 1H), 5.44 (s, 1H), 4.71 (dd, J=11.2, 5.2 Hz, 1H), 4.47-4.43 (m, 1H), 4.26 (s, 1H), 4.18 (dd, J=12.8, 1.6 Hz, 1H), 4.05 (dd, J=12.8, 1.6 Hz, 1H), 3.68-3.57 (m, 1H), 3.36-3.23 (m, 1H), 2.95 (d, J=5.2 Hz, 3H), 0.95 (t, J=6.8 Hz, 3H).

Intermediate 96

5-Chloro-2-cyanophenyl 4,6-di-O-acetyl-3-azido-3-deoxy-2-O-methyl-1-thio-α-D-galactopyranoside

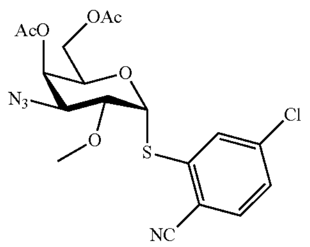

To a solution of triisopropylsilyl 4,6-di-O-acetyl-3-azido-3-deoxy-2-O-methyl-1-thio-α-D-galactopyranoside (100 mg, 0.21 mmol) and 4-chloro-2-fluorobenzonitrile (38 mg, 0.24 mmol) in MeCN (1.5 mL) TBAF (42 μL, 1 M in THF, 0.042 mmol) was added and the mixture was stirred 45 min at rt. The mixture was partitioned between HCl (1 M) and EtOAc. The organic phase was dried, concentrated and purified by chromatography ($SiO_2$, PE/EtOAc) to afford the product (80 mg, 84%). ESI-MS m/z calcd for $[C18H_{19}ClN_4O_6S]$ $[M+NH_4]^+$: 472.1; found: 472.1. $^1H$ NMR (500 MHz, Chloroform-d) δ 7.71 (d, J=2.0 Hz, 1H), 7.62 (d, J=8.3 Hz, 1H), 7.38 (dd, J=8.3, 2.0 Hz, 1H), 6.11 (d, J=5.3 Hz, 1H), 5.41 (d, J=2.4 Hz, 1H), 4.56-4.52 (m, 1H), 4.05 (dd, J=11.7, 5.0 Hz, 1H), 4.02-3.96 (m, 2H), 3.86 (dd, J=10.4, 3.3 Hz, 1H), 3.61 (s, 3H), 2.15 (s, 3H), 1.96 (s, 3H).

Intermediate 97

6-[(2,4-Dimethoxyphenyl)methylsulfanyl]-1,3-benzothiazole

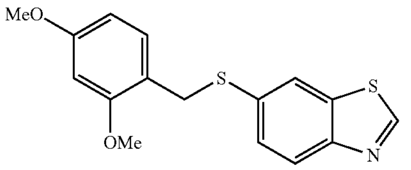 [SMILES: COc1ccc(CSc2ccc3ncsc3c2)c(OC)c1]

To a nitrogen purged solution of 6-bromo-1,3-benzothiazole (1.00 g, 4.67 mmol), bis(dibenzylideneacetone)palladium(0) (161 mg, 0.28 mmol) and 4,5-bis(diphenylphosphino)-9,9-dimethylxanthene (135 mg, 0.23 mmol) in 1,4-dioxane (5 mL) a solution of (2,4-dimethoxyphenyl) methanethiol (947 mg, 5.14 mmol) and DIPEA (1.60 mL, 9.34 mmol) in 1,4-dioxane (15 mL) was added and the mixture was stirred 2 h at 100° C. The mixture was filtered through celite, concentrated and purified by chromatography ($SiO_2$, PE/EtOAc) to afford the product (1.22 g, 82%). ESI-MS m/z calcd for $[C_{16}H_{15}NO_2S]$ $[M+H]^+$: 318.1; found: 318.0. $^1H$ NMR (400 MHz, Chloroform-d) δ 8.95 (s, 1H), 8.01 (d, J=8.5 Hz, 1H), 7.88 (s, 1H), 7.50 (d, J=8.5 Hz, 1H), 7.06 (d, J=8.3 Hz, 1H), 6.46-6.42 (m, 1H), 6.38 (dd, J=8.4, 2.2 Hz, 1H), 4.16 (s, 2H), 3.78 (s, 6H).

1,3-Benzothiazole-6-thiol

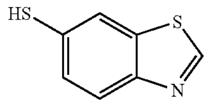

TFA (4 mL) was added to a solution of 6-[(2,4-dimethoxyphenyl)methylsulfanyl]-1,3-benzothiazole (1.22 g, 3.85 mmol) in DCM (10 mL) and triethylsilane (4 mL) and the mixture was stirred 2 h at rt. The mixture was concentrated and purified by chromatography ($SiO_2$, PE/EtOAc) to afford the product (788 mg, quantitative yield). ESI-MS m/z calcd for $[C_7H_5NS]$ $[M+H]^+$: 168.0; found: 168.0.

1,3-Benzothiazol-6-yl 3-azido-3-deoxy-2-O-methyl-1-thio-α-D-galactopyranoside

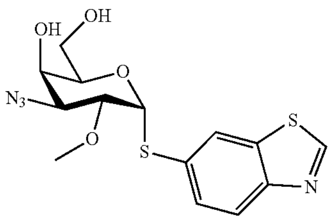

To a solution of acetyl 4,6-di-O-acetyl-3-azido-3-deoxy-2-O-methyl-D-galactopyranoside (1.00 g, 2.90 mmol) and 1,3-benzothiazole-6-thiol (727 mg, 4.34 mmol) in DCM (40 mL) boron trifluoride diethyl etherate (1.07 mL, 8.69 mmol) was added and the mixture was stirred 18 h at rt. More DCM (25 mL) and $BF_3OEt_2$ (1.07 mL, 8.69 mmol) was added and the mixture was stirred an additional 31 h at rt. The mixture was diluted with DCM and washed with saturated aq $NaHCO_3$. The organic phase was dried, evaporated and purified by chromatography ($SiO_2$, PE/EtOAc). The obtained material was stirred 1 h at rt in MeOH (10 mL) and NaOMe (1 mL, 1 M). Acetic acid (0.4 mL) was added and the mixture was concentrated and partitioned between EtOAc and water. The organic phase was dried and evaporated to afford the product as an anomeric mixture (a/p, 3:1, 425 mg, 40%). The product was used without further purification in subsequent steps. ESI-MS m/z calcd for $[C_{14}H_{14}N_4O_4S]$ $[M+H]^+$: 369.1; found: 369.0.

Intermediate 100

5-Bromo-6-fluoro-1,3-benzothiazole

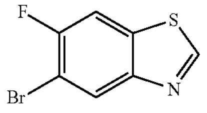 [SMILES: Fc1cc2scnc2cc1Br]

A solution of 5-bromo-2,4-difluoroaniline (2.90 g, 13.9 mmol) and potassium ethyl xanthogenate (2.68 g, 16.7 mmol) in DMF (20 mL) was stirred 5 h at 100° C. The mixture was cooled to rt, diluted with EtOAc (200 mL) and washed with NaCl (10% aq, 3×200 mL) and brine. The organic phase was dried, evaporated and the residue was suspended together with zinc (1.82 g, 27.9 mmol) and nickel (II) chloride hexahydrate (1.66 g, 6.97 mmol) in MeOH (60 mL). The suspension was heated to reflux and HCl (12 M, 10 mL) was added over 10 min. After refluxing 2 h more zinc (912 mg, 13.95 mmol) was added and the suspension was refluxed 1 h. The suspension was cooled to rt and ammonia was added until the suspension was basic. The suspension was diluted with EtOAc (200 mL) and washed with water (200 mL) and brine (200 mL). The organic phase was dried, concentrated and purified by chromatography ($SiO_2$, PE/EtOAc) to yield the product (1.64 g, 51%). ESI-MS m/z calcd for $[C_7H_3BrFNS]$ $[M+H]^+$: 231.9; found: 231.9. $^1H$ NMR (500 MHz, Chloroform-d) δ 9.01 (s, 1H), 8.36 (d, J=6.1 Hz, 1H), 7.72 (d, J=7.7 Hz, 1H).

6-Fluoro-1,3-benzothiazole-5-carbonitrile

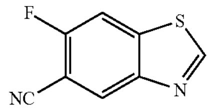 [SMILES: N#Cc1cc2ncsc2cc1F]

A degassed solution of 1,1'-bis(diphenylphosphino)ferrocene (19.5 mg, 0.035 mmol) and tris(dibenzylideneacetone) dipalladium(0) (15.8 mg, 0.017 mmol) in DMF (0.20 mL) was added to a degassed solution of 5-bromo-6-fluoro-1,3-benzothiazole (100 mg, 0.43 mmol), Zn (14.1 mg, 0.22 mmol) and $Zn(CN)_2$ (50.6 mg, 0.43 mmol) in DMF (1.80 mL). The mixture was stirred 2.5 h at 100° C. under argon. The mixture was cooled to rt, diluted with EtOAc (20 mL) and washed with NaCl (10% aq, 5×20 mL) and brine (20 mL). The organic phase was dried, concentrated and purified by chromatography ($SiO_2$, PE/EtOAc) to give the product (53 mg, 69%). ESI-MS m/z calcd for $[C_8H_3FN_2S]$ $[M+H]^+$: 179.0; found: 179.0. $^1H$ NMR (400 MHz, Chloroform-d) δ 9.10 (s, 1H), 8.42 (d, J=5.5 Hz, 1H), 7.83 (d, J=8.0 Hz, 1H).

5-Cyano-1,3-benzothiazol-6-yl 3-azido-3-deoxy-2-O-methyl-1-thio-α-D-galactopyranoside

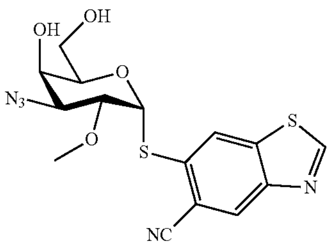

To a solution of triisopropylsilyl 4,6-di-O-acetyl-3-azido-3-deoxy-2-O-methyl-1-thio-α-D-galactopyranoside (177 mg, 0.30 mmol) and 6-fluoro-1,3-benzothiazole-5-carbonitrile (53 mg, 0.30 mmol) in MeCN (2.0 mL) TBAF (30 μL, 1 M in THF, 0.030 mmol) was added and the mixture was stirred 24 h at rt. The mixture was concentrated and purified by chromatography ($SiO_2$, PE/EtOAc). The obtained material was stirred 30 min at rt in MeOH (1.0 mL) and NaOMe (1 M, 12 μL), before being quenched by acetic acid (10 μL). The mixture was concentrated and purified by prep HPLC ($C_{18}$, $H_2O$/MeCN/0.1% TFA) to afford the product (74 mg, 63%). ESI-MS m/z calcd for $[C_{15}H_{15}N_5O_4S_2]$ $[M+H]^+$: 394.1; found: 394.0. $^1H$ NMR (500 MHz, Methanol-$d_4$) δ9.39 (s, 1H), 8.60 (s, 1H), 8.49 (s, 1H), 6.15 (d, J=5.4 Hz, 1H), 4.32 (t, J=6.2 Hz, 1H), 4.13-4.07 (m, 1H), 4.02 (d, J=2.1 Hz, 1H), 3.69 (dd, J=10.6, 3.0 Hz, 1H), 3.66-3.61 (m, 2H), 3.61 (s, 3H).

Intermediate 101

6-[(2,4-Dimethoxyphenyl)methylsulfanyl]thiazolo[4,5-b]pyridine

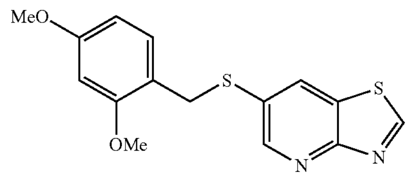 [SMILES: COc1ccc(CSc2cnc3ncsc3c2)c(OC)c1]

An argon purged solution of (2,4-dimethoxyphenyl)methanethiol (942 mg, 5.11 mmol) and DIPEA (1.62 mL, 9.30 mmol) in 1,4-dioxane (14 mL) was added to 6-bromothiazolo[4,5-b]pyridine (1.00 g, 4.65 mmol), bis(dibenzylideneacetone)palladium(0) (128 mg, 0.14 mmol) and 4,5-bis(diphenylphosphino)-9,9-dimethylxanthene (135 mg, 0.23 mmol) and the mixture was stirred 1 h at 100° C. The mixture was cooled to rt, filtered, concentrated and purified by chromatography ($SiO_2$, PE/EtOAc) to afford the product (1.18 g, 80%). ESI-MS m/z calcd for $[C_{15}H_{14}N_2O_2S]$ $[M+H]^+$: 319.0; found: 319.0. $^1H$ NMR (500 MHz, Chloroform-d) δ 9.52 (s, 1H), 8.56 (d, J=2.1 Hz, 1H), 8.48 (d, J=2.1 Hz, 1H), 7.02 (d, J=8.3 Hz, 1H), 6.46 (d, J=2.3 Hz, 1H), 6.41 (dd, J=8.3, 2.4 Hz, 1H), 4.17 (s, 2H), 3.77 (s, 3H), 3.67 (s, 3H).

Thiazolo[4,5-b]pyridin-6-yl 3-azido-3-deoxy-1-thio-α-D-galactopyranoside

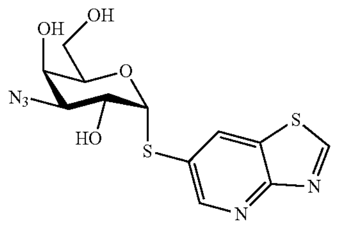

A solution of 6-[(2,4-dimethoxyphenyl)methylsulfanyl]thiazolo[4,5-b]pyridine (966 mg, 3.03 mmol) in TFA (10 mL) was stirred 1 h at 60° C. The mixture was concentrated and co-evaporated using toluene. The residue was dissolved in DMF (15 mL) and 2,4,6-tri-O-acetyl-3-azido-3-deoxy-β-D-galactopyranosyl chloride (1.06 g, 3.03 mmol) and NaH (60% in oil, 581 mg, 15.2 mmol) were added. The mixture was stirred 17 h at rt. The mixture was diluted with EtOAc (150 mL), washed with NaCl (10% aq, 5×150 mL) and brine (150 mL), dried and concentrated. The residue was stirred 3 h at rt in MeOH (10 mL) and NaOMe (1 M, 0.60 mL). Acetic acid (40 μL) and silica were added. The mixture was concentrated and purified by chromatography ($SiO_2$, EtOAc/MeOH) to afford the product (1.10 g, 61%). ESI-MS m/z calcd for $[C_{12}H_{13}N_5O_4S_2]$ $[M+H]^+$: 356.0; found: 356.0. $^1H$ NMR (500 MHz, Chloroform-d) δ 9.54 (s, 1H), 8.84 (d, J=2.1 Hz, 1H), 8.81 (d, J=2.1 Hz, 1H), 5.71 (d, J=5.4 Hz, 1H), 4.41 (dd, J=10.8, 5.4 Hz, 1H), 4.36 (t, J=6.0 Hz, 1H), 4.06 (dd, J=3.0, 1.1 Hz, 1H), 3.73-3.63 (m, 2H), 3.57 (dd, J=10.8, 3.0 Hz, 1H).

Thiazolo[4,5-b]pyridin-6-yl 3-azido-4,6-O-benzylidene-3-deoxy-1-thio-α-D-galactopyranoside

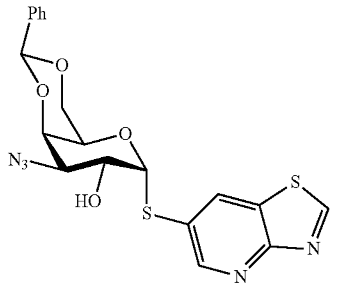

To a suspension of thiazolo[4,5-b]pyridin-6-yl 3-azido-3-deoxy-1-thio-α-D-galactopyranoside (1.10 g, 1.86 mmol) in MeCN (20 mL) benzaldehyde dimethylacetal (0.84 mL, 5.58 mmol) and p-toluenesulfonic acid monohydrate (71 mg, 0.37 mmol) were added and the mixture was stirred 10 h at rt. $Et_3N$ (70 μL) was added and the mixture was concentrated and purified by chromatography ($SiO_2$, PE/EtOAc) to afford the product (695 mg, 68%). ESI-MS m/z calcd for $[C_{19}H_{17}N_5O_4S_2]$ $[M+H]^+$: 444.1; found: 444.0. $^1H$ NMR (500 MHz, Chloroform-d) δ 9.44 (s, 1H), 9.08 (d, J=2.2 Hz, 1H), 8.73 (d, J=2.2 Hz, 1H), 7.57-7.50 (m, 2H), 7.43-7.36 (m, 3H), 6.42 (d, J=3.7 Hz, 1H), 5.65 (s, 1H), 4.48 (dd, J=10.4, 3.7 Hz, 1H), 4.41 (d, J=2.8 Hz, 1H), 4.35 (dd, J=12.8, 1.5 Hz, 1H), 4.20-4.13 (m, 1H), 4.06 (s, 1H), 3.75 (dd, J=10.4, 3.3 Hz, 1H).

Thiazolo[4,5-b]pyridin-6-yl 3-azido-3-deoxy-2-O-methyl-1-thio-α-D-galactopyranoside

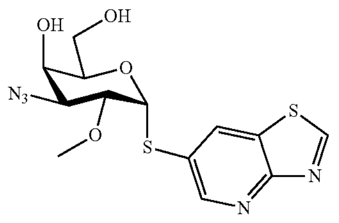

To a solution of thiazolo[4,5-b]pyridin-6-yl 3-azido-4,6-O-benzylidene-3-deoxy-1-thio-α-D-galactopyranoside (695 mg, 1.25 mmol) in DMF (6 mL) NaH (60% in oil, 96 mg, 2.51 mmol) and iodomethane (94 μL, 1.50 mmol) were added and the mixture was stirred 1 h at rt. The mixture was diluted with EtOAc (50 mL), washed with NaCl (10% aq, 5×50 mL) and brine. The organic phase was dried, evaporated and the residue was stirred 30 min at rt in TFA/$H_2O$ (5 mL, 4:1). The mixture was diluted with water (40 mL), made basic using NaOH (5 M) and extracted with EtOAc (2×50 mL). The organic phases were washed with brine, dried, concentrated and purified by chromatography ($SiO_2$, EtOAc/MeOH) to afford the product (224 mg, 48%). ESI-MS m/z calcd for $[C_{13}H_{15}N_5O_4S_2]$ $[M+H]^+$: 370.1; found: 370.0. $^1H$ NMR (500 MHz, Chloroform-d) δ 9.57 (s, 1H), 8.89 (d, J=2.1 Hz, 1H), 8.84 (d, J=2.1 Hz, 1H), 6.04 (d, J=5.3 Hz, 1H), 4.36 (t, J=5.9 Hz, 1H), 4.09 (dd, J=10.6, 5.3 Hz, 1H), 4.04 (d, J=2.4 Hz, 1H), 3.71-3.65 (m, 3H), 3.58 (s, 3H).

Intermediate 103

3-Bromo-5-(trifluoromethylsulfanyl)pyridine

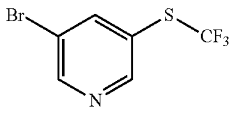

A solution of 5-bromopyridine-3-thiol (228 mg, 1.20 mmol) in DCM (1 mL) was added over 10 min to a cooled (−78° C.) solution of 3,3-dimethyl-1-(trifluoromethyl)-1,2-benziodoxole (330 mg, 1.00 mmol) in DCM (3 mL). The mixture was allowed to reach rt in 2 h. The mixture was concentrated and purified by chromatography ($SiO_2$, PE/EtOAc) to afford the product (218 mg, 85%). ESI-MS m/z calcd for $[C_6H_3BrF_3NS][M+H]^+$: 257.9; found: 257.9. $^1H$ NMR (500 MHz, Chloroform-d) δ 8.80 (d, J=2.1 Hz, 1H), 8.77 (d, J=1.8 Hz, 1H), 8.16 (t, J=1.9 Hz, 1H).

3-[(2,4-Dimethoxyphenyl)methylsulfanyl]-5-(trifluoromethylsulfanyl)pyridine

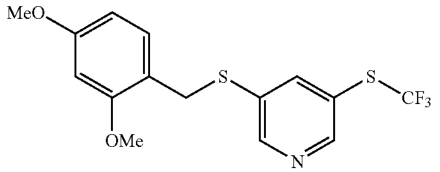

A solution of (2,4-dimethoxyphenyl)methanethiol (171 mg, 0.93 mmol) and DIPEA (0.29 mL, 1.69 mmol) in 1,4-dioxane (2.5 mL) was added to 3-bromo-5-(trifluoromethylsulfanyl)pyridine (218 mg, 0.85 mmol), bis(dibenzylideneacetone)palladium(0) (23 mg, 0.025 mmol) and 4,5-bis(diphenylphosphino)-9,9-dimethylxanthene (24 mg, 0.042 mmol) and the mixture was stirred 1 h at 100° C. The mixture was cooled to rt, filtered, concentrated and purified by chromatography ($SiO_2$, PE/EtOAc) to afford the product (308 mg, quantitative yield). ESI-MS m/z calcd for $[C_{15}H_{14}F_3NO_2S_2]$ $[M+H]^+$: 362.0; found: 362.0. $^1H$ NMR (500 MHz, Chloroform-d) δ 8.71 (d, J=2.1 Hz, 1H), 8.68 (d, J=1.8 Hz, 1H), 8.20 (t, J=2.0 Hz, 1H), 7.18 (d, J=9.0 Hz, 1H), 6.52-6.44 (m, 2H), 4.26 (s, 2H), 3.85 (s, 3H), 3.82 (s, 3H).

5-(Trifluoromethylsulfanyl)pyridine-3-thiol

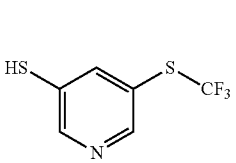 [SMILES: FC(F)(F)Sc1cncc(Br)c1]

To a solution of 3-[(2,4-dimethoxyphenyl)methylsulfanyl]-5-(trifluoromethylsulfanyl)pyridine (277 mg, 0.77 mmol) and anisole (0.83 mL, 7.66 mmol) in DCM (3.0 mL) methanesulfonic acid (0.30 mL, 4.60 mmol) was added and the mixture was stirred 3 h at rt. $Et_3N$ (0.58 mL) was added and the mixture was purified by chromatography ($SiO_2$, PE/EtOAc) to afford the product (146 mg, 90%). ESI-MS m/z calcd for $[C_6H_4F_3NS_2]$ $[M+H]^+$: 212.0; found: 212.0. $^1H$ NMR (500 MHz, Chloroform-d) δ 8.83 (d, J=2.2 Hz, 1H), 8.73 (d, J=1.9 Hz, 1H), 8.32 (t, J=2.0 Hz, 1H).

5-(Trifluoromethylsulfanyl)pyridin-3-yl 2,4,6-tri-O-acetyl-3-azido-3-deoxy-1-thio-α-D-galactopyranoside

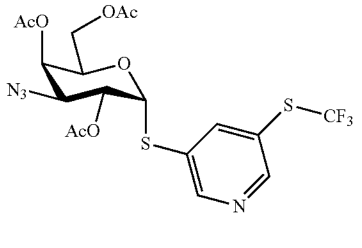

To a solution of 5-(trifluoromethylsulfanyl)pyridine-3-thiol (118 mg, 0.56 mmol) and 2,4,6-tri-O-acetyl-3-azido-3-deoxy-β-D-galactopyranosyl chloride (195 mg, 0.56 mmol) in DMF (2.95 mL) NaH (60% in oil, 54 mg, 1.40 mmol) was added and the mixture was stirred 24 h at rt. The mixture was diluted with EtOAc (50 mL) and washed with NaCl (10% aq, 5×50 mL) and brine (50 mL). The organic phase was dried, concentrated and purified by chromatography ($SiO_2$, PE/EtOAc) to afford the product (67 mg, 23%). ESI-MS m/z calcd for $[C_{18}H_{19}F_3N_4O_7S_2]$ $[M+H]^+$: 525.1; found: 525.1. $^1H$ NMR (500 MHz, Chloroform-d) δ 8.77 (d, J=2.1 Hz, 1H), 8.76 (d, J=1.9 Hz, 1H), 8.11 (t, J=1.9 Hz, 1H), 6.02 (d, J=5.5 Hz, 1H), 5.52 (d, J=2.5 Hz, 1H), 5.32 (dd, J=11.0, 5.5 Hz, 1H), 4.68-4.62 (m, 1H), 4.16 (dd, J=11.7, 4.9 Hz, 1H), 4.04-3.97 (m, 2H), 2.23 (s, 3H), 2.19 (s, 3H), 2.04 (s, 3H).

5-(Trifluoromethylsulfanyl)pyridin-3-yl 3-azido-3-deoxy-2-O-methyl-1-thio-α-D-galactopyranoside

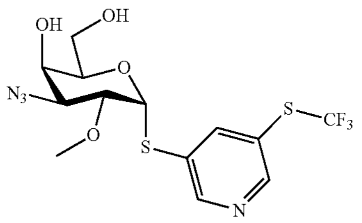

A solution of 5-(trifluoromethylsulfanyl)pyridin-3-yl 2,4,6-tri-O-acetyl-3-azido-3-deoxy-1-thio-α-D-galactopyranoside (67 mg, 0.13 mmol) was stirred 20 h at rt in MeOH (1.0 mL) and NaOMe (13 μL, 1 M, 0.013 mmol). To the mixture p-toluenesulfonic acid monohydrate (7.3 mg, 0.038 mmol) was added and the mixture was concentrated. The residue was suspended in MeCN (1.0 mL), and benzaldehyde dimethyl acetal (38 μL, 0.26 mmol) was added. The mixture was stirred 23 h at rt before $Et_3N$ (10 μL) was added and the mixture was concentrated. The residue was dissolved together with iodomethane (12 μL, 0.19 mmol) in DMF (1.0 mL). NaH (60% in oil, 9.8 mg, 0.26 mmol) was and the mixture was stirred 30 min at rt. The mixture was diluted with EtOAc (20 mL), washed with NaCl (10% aq, 5×20 mL) and brine (20 mL). The organic phase was dried, evaporated and the residue was stirred 20 min at rt in TFA/water (1.0 mL, 4:1). Ice was added and the mixture was made basic using NaOH (1 M aq). The mixture was extracted with EtOAc (2×10 mL) and the organic phases were dried and evaporated. The residue was purified by chromatography ($SiO_2$, PE/EtOAc) to afford the product (39 mg, 70%). ESI-MS m/z calcd for [$C_{13}H_{15}F_3N_4O_4S_2$] $[M+H]^+$: 413.0; found: 413.0. $^1H$ NMR (500 MHz, Methanol-$d_4$) δ 8.86 (d, J=2.1 Hz, 1H), 8.70 (d, J=2.0 Hz, 1H), 8.40 (t, J=2.0 Hz, 1H), 6.13 (d, J=5.3 Hz, 1H), 4.24 (t, J=6.3 Hz, 1H), 4.09 (dd, J=10.6, 5.3 Hz, 1H), 4.03 (d, J=2.0 Hz, 1H), 3.71-3.60 (m, 3H), 3.56 (s, 3H).

REFERENCES

Aits S, Kricker J, Liu B, Ellegaard A M, Hämälistö S, Tvingsholm S, Corcelle-Termeau E, Høgh S, Farkas T, Holm Jonassen A, Gromova I, Mortensen M, Jäättelä M. (2015) Sensitive detection of lysosomal membrane permeabilization by lysosomal galectin puncta assay Autophagy. 2015; 11(8):1408-24.

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

Arthur C M, Baruffi M D, Cummings R D, Stowell S R. (2015) Evolving mechanistic insights into galectin functions. Methods Mol Biol. 1207:1-35.

Helen Blanchard, Khuchtumur Bum-Erdene, Mohammad Hussaini Bohari & Xing Yu (2016) Galectin-1 inhibitors and their potential therapeutic applications: a patent review, Expert Opinion on Therapeutic Patents, 26:5, 537-554, DOI: 10.1517/13543776.2016.1163338

Blidner A G, Méndez-Huergo S P, Cagnoni A J, Rabinovich G A. (2015) Re-wiring regulatory cell networks in immunity by galectin-glycan interactions. FEBS Lett. Sep. 6, 2015. pii: S0014-5793 (15)00807-8.

Chen, W. S., Leffler H., Nilsson, U. J., Panjwani, N. (2012). Targeting Galectin-1 and Galectin-3 Attenuates VEGF-A-induced Angiogenesis; *Mol. Biol. Cell* (suppl), Abstract No. 2695.

Cooper, D. N.; Massa, S. M.; Barondes, S. H. (1991) Endogenous muscle lectin inhibits myoblast adhesion to laminin. The Journal of Cell Biology 115, 1437-1448.

Cumpstey, I., Carlsson, S., Leffler, H. and Nilsson, U. J. (2005) Synthesis of a phenyl thio-ß-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Demotte, N., Wieers, G., van der Smissen, P., Moser, M., Schmidt, C., Thielemans, K., et al., (2010). *Cancer Res.* 70; 7476-7488.

Dings, R. P. M.; Miller, M. C.; Nesmelova, I.; Astorgues-Xerri, L.; Kumar, N.; Serova, M.; Chen, X.; Raymond, E.; Hoye, T. R.; Mayo, K. H. Journal of medicinal . . . 2012, 55, 5121-5129.

Ebrahim A H, Alalawi Z, Mirandola L, Rakhshanda R, Dahlbeck S, Nguyen D, Jenkins M1, Grizzi F, Cobos E, Figueroa J A, Chiriva-Internati M (2014 Galectins in cancer: carcinogenesis, diagnosis and therapy. Ann Transl Med. 2014 September; 2(9):88.

Elola M T, Blidner A G, Ferragut F, Bracalente C, Rabinovich G A. (2015) Assembly, organization and regulation of cell-surface receptors by lectin-glycan complexes. Biochem J. Jul. 1, 2015; 469(1):1-16.

Farkas, I.; Szabó, I. F.; Bognár, R.; Anderle, D. Carbohydr. Res. 1976, 48, 136-138.

Giguère, D.; Bonin, M. A.; Cloutier, P.; Patnam, R.; St-Pierre, C.; Sato, S.; Roy, R. Bioorganic & Medicinal Chemistry 2008, 16, 7811-7823.

Giguère, D.; Andre, S.; Bonin, M. A.; Bellefleur, M. A.; Provencal, A.; Cloutier, P.; Pucci, B.; Roy, R.; Gabius, H. J. Bioorganic & Medicinal Chemistry 2011, 19, 3280-3287.

Giguere, D., Patnam, R., Bellefleur, M. A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

van Hattum, H.; Branderhorst, H. M.; Moret, E. E.; Nilsson, U. J.; Leffler, H.; Pieters, R. J. J. Med. Chem. 2013, 56, 1350-1354.Huflejt, M. E. and Leffler, H. (2004) Galectin-4 in normal tissues and cancer. *Glycoconj. J.* 20: 247-255.

Hockl P F, Wolosiuk A, Pérez-Sáez J M1, Bordoni A V2, Croci D O3, Toum-Terrones Y2, Soler-Illia G J4, Rabinovich G A5. Glyco-nano-oncology: Novel therapeutic opportunities by combining small and sweet. Treatment of cancer Pharmacol Res. Feb. 4, 2016. pii: 51043-6618 (16)00042-6. doi: 10.1016/j.phrs.2016.02.005. [Epub ahead of print]

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast Cancer. *Clin. Cancer Res.* 9: 2374-2383.

Kathiriya, J. J. et al. Galectin-1 inhibition attenuates profibrotic signaling in hypoxia-induced pulmonary fibrosis. Cell Death Discovery 3, 17010-13 (2017).

Kouo, T., Huang, L., Pucsek, A. B., Cao, M., Solt, S., Armstrong, T., Jaffee, E. (2015) *Cancer Immonol. Res.* 3: 412-23

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lepur A, Salomonsson E, Nilsson U J, Leffler H. (2012) Ligand induced galectin-3 protein self-association. J Biol Chem. Jun. 22, 2012; 287(26):21751-6.

Lin, C. I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer,* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perillo, N. L.; Pace, K. E.; Seilhamer, J. J.; Baum, L. G. Nature 1995, 378, 736-739.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Poirier, F. Roles of galectins in vivo. Biochem. Soc. Symp. 2002:95-103.

Ramos-Soriano, J.; Niss, U.; Angulo, J.; Angulo, M.; Moreno-Vargas, A. J.; Carmona, A. T.; Ohlson, S.; Robina, I. Chem. Eur. J. 2013, 19, 17989-18003.

Ruvolo, P. P. *Biochim. Biophys Acta.*Molecular cell research (2015) E-pub ahead of print, title: Galectin-3 as a guardian of the tumor microenvironment, published on-line Apr. 8, 2015: (http://www.sciencedirect.com/science/article/pii/S016748891500270 0), Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P. G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B. G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Tejler, J.; Tullberg, E.; Frejd, T.; Leffler, H.; Nilsson, U. J. *Carbohydrate Research* 2006, 341, 1353-1362.

Tejler, J.; Salameh, B.; Leffler, H.; Nilsson, U. J. Org. Biomol. Chem. 2009, 7, 3982.Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

I claim:

1. A D-galactopyranose compound of formula (1)

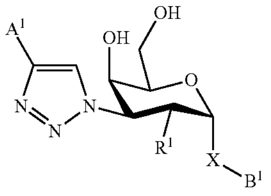

wherein the pyranose ring is α-D-galactopyranose, $A^1$ is selected from the group consisting of

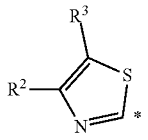

2 and

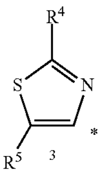

3 wherein the asterix * indicates the carbon atom of the heteroaromatic ring that is covalently attached to the triazole group of formula (1);

wherein $R^2$ is selected from the group consisting of hydrogen, $C_{1-6}$ alkyl, OH and halogen;

$R^3$ is selected from the group consisting of hydrogen, $C_{1-6}$ alkyl and halogen;

$R^4$ is selected from the group consisting of OH, halogen and amino;

$R^5$ is selected from the group consisting of hydrogen, $C_{1-6}$ alkyl and halogen;

X is selected from S, SO, and $SO_2$;

$B^1$ is selected from:

a) a phenyl, optionally substituted with one or more groups selected from:

a halogen;

N-(2-oxa)-6-azaspiro [3.3]heptanyl;

$C_2$-alkynyl;

CN;

—COOH;

$COOC_{1-4}$ alkyl;

—$CONR^6R7$, wherein $R^6$ and $R^7$ are independently selected from H, $C_{1-3}$ alkyl, cyclopropyl, and isopropyl, or $R^6$ and $R^7$ together with the nitrogen form a heterocycloalkyl;

$C_{1-3}$ alkyl, optionally substituted with a F;

cyclopropyl, optionally substituted with a F;

isopropyl, optionally substituted with a F;

$SC_{1-3}$ alkyl, optionally substituted with a F;

$OC_{1-3}$ alkyl, optionally substituted with a F;

O-cyclopropyl, optionally substituted with a F;

O-isopropyl, optionally substituted with a F;

$NR^8R^9$, wherein $R^8$ and $R^9$ are independently selected from H, $C_{1-3}$ alkyl and isopropyl;

OH;

$R^{10}$—CONH— wherein $R^{10}$ is selected from $C_{1-3}$ alkyl and cyclopropyl;

a phenyl; and a heterocycle selected from imidazole, pyridine, tetrahydropyridine, pyrimidin, oxazol and thiazol;

b) a benzothiazolyl, optionally substituted with one or more groups selected from:

a halogen;

N-(2-oxa)-6-azaspiro [3.3]heptanyl;

$C_2$-alkynyl;

CN;

—COOH;

$COOC_{1-4}$ alkyl;

—$CONR^{12}R^{13}$, wherein $R^{12}$ and $R^{13}$ are independently selected from H, $C_{1-3}$ alkyl, cyclopropyl, and isopropyl or $R^{12}$ and $R^{13}$ together with the nitrogen form a heterocycloalkyl;

$C_{1-3}$ alkyl, optionally substituted with a F;

cyclopropyl, optionally substituted with a F;

isopropyl, optionally substituted with a F;

$SC_{1-3}$ alkyl, optionally substituted with a F;

$OC_{1-3}$ alkyl, optionally substituted with a F;

O-cyclopropyl, optionally substituted with a F;

O-isopropyl, optionally substituted with a F;

$SC_{1-3}$ alkyl, optionally substituted with a F;

$NR^{14}R^{15}$, wherein $R^{14}$ and $R^{15}$ are independently selected from H, $C_{1-3}$ alkyl and isopropyl;

OH;

A phenyl;

a heterocycle selected from imidazole, pyridine, tetrahydropyridine, pyrimidin, oxazol and thiazol; and $R^{16}$—CONH— wherein $R^{16}$ is selected from $C_{1-3}$ alkyl and cyclopropyl;

c) thiazolpyridyl, optionally substituted with one or more groups selected from:

a halogen;

N-(2-oxa)-6-azaspiro [3.3]heptanyl;

C2-alkynyl;

CN;

—COOH;

$COOC_{1-4}$ alkyl;

—$CONR^{12}R^{13}$, wherein $R^{12}$ and $R^{13}$ are independently selected from H, $C_{1-3}$ alkyl, cyclopropyl, and isopropyl or $R^{12}$ and $R^{13}$ together with the nitrogen form a heterocycloalkyl;

$C_{1-3}$ alkyl, optionally substituted with a F;

cyclopropyl, optionally substituted with a F;

isopropyl, optionally substituted with a F;

$SC_{1-3}$ alkyl, optionally substituted with a F;

$OC_{1-3}$ alkyl, optionally substituted with a F;

O-cyclopropyl, optionally substituted with a F;

O-isopropyl, optionally substituted with a F;

$SC_{1-3}$ alkyl, optionally substituted with a F;

$NR^{14}R^{15}$, wherein $R^{14}$ and $R^{15}$ are independently selected from H, $C_{1-3}$ alkyl and isopropyl;

OH;

a phenyl;

a heterocycle selected from imidazole, pyridine, tetrahydropyridine, pyrimidin, oxazol and thiazol; and $R^{16}$—CONH— wherein $R^{16}$ is selected from $C_{1-3}$ alkyl and cyclopropyl;

d) a pyridinyl, optionally substituted with one or more groups selected from:

a halogen;

N-(2-oxa)-6-azaspiro [3.3]heptanyl;

$C_2$-alkynyl;

CN;

—COOH;

$COOC_{1-4}$ alkyl;

—$CONR^{12}R^{13}$, wherein $R^{12}$ and $R^{13}$ are independently selected from H, $C_{1-3}$ alkyl, cyclopropyl, and isopropyl or $R^{12}$ and $R^{13}$ together with the nitrogen form a heterocycloalkyl;

$C_{1-3}$ alkyl, optionally substituted with a F;

cyclopropyl, optionally substituted with a F;

isopropyl, optionally substituted with a F;

$SC_{1-3}$ alkyl, optionally substituted with a F;

$OC_{1-3}$ alkyl, optionally substituted with a F;

O-cyclopropyl, optionally substituted with a F;

O-isopropyl, optionally substituted with a F;

$SC_{1-3}$ alkyl, optionally substituted with a F;

$NR^{14}R^{15}$, wherein $R^{14}$ and $R^{15}$ are independently selected from H, $C_{1-3}$ alkyl and isopropyl;

OH;

a phenyl;

a heterocycle selected from imidazole, pyridine, tetrahydropyridine, pyrimidin, oxazol and thiazol; and $R^{16}$—CONH— wherein $R^{16}$ is selected from $C_{1-3}$ alkyl and cyclopropyl;

$R^1$ is H or $OC_{1-6}$ alkyl optionally substituted with one or more halogen, phenyl, and phenyl substituted with one or more groups selected from OH and halogen; or a pharmaceutically acceptable salt or solvate thereof.

2. The compound of claim 1 wherein $A^1$ is

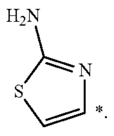

3. The compound of claim 1 wherein $A^1$ is

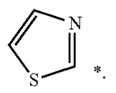

4. The compound of claim 1 wherein $A^1$ is

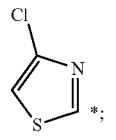

and $R^1$ is selected from the group consisting of a) and c),.

5. The compound of claim 1 wherein $A^1$ is

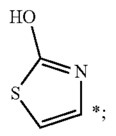

and $R^1$ is selected from the group consisting of a) and c).

6. The compound of claim 1 wherein $A^1$ is

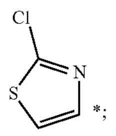

and $R^1$ is selected from the group consisting of a) and c).

7. The compound of claim 1 wherein $A^1$ is

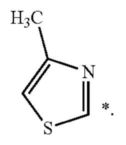

8. The compound of claim 1 wherein $A^1$ is

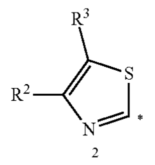

wherein $R^2$ is a halogen; and $R^3$ is selected from the group consisting of $C_{1-6}$ alkyl and halogen.

9. The compound of claim 1 wherein X is selected from S.

10. The compound of claim 1 wherein B1 is selected from a pyridinyl, optionally substituted with a group selected from a Cl; Br; F; ethynyl; N-(2-oxa)-6-azaspiro [3.3]heptanyl; CO-azetidinyl; $CONHCH_3$; $CONHCH_2CH_3$; $CON(CH_3)_2$; CN; methyl; $SCH_3$; $SCF_3$; $CF_3$; imidazole; pyridin; pyrimidin; oxazol; and thiazol.

11. The compound of claim 1 wherein B1 is selected from a benzothiazolyl or a thiazolpyridyl optionally substituted with a group selected from a Cl; Br; F; ethynyl; N-(2-oxa)-6-azaspiro [3.3]heptanyl; CO-azetidinyl; $CONHCH_3$; $CONHCH_2CH_3$; $CON(CH_3)_2$; CN; methyl; $SCH_3$; $SCF_3$; $CF_3$; imidazole; pyridin; pyrimidin; oxazol; and thiazol.

12. The compound of claim 1 wherein B1 is selected from a phenyl, optionally substituted with a group selected from a halogen; CN; —$CONR^6R^7$, wherein R6 and R7 are independently selected from H, $C_{1-3}$ alkyl, cyclopropyl, and iso-propyl; and $C_{1-3}$ alkyl, optionally substituted with a F.

13. The compound of claim 1 wherein B1 is selected from a phenyl, optionally substituted with a group selected from a Cl; F; Br; CN; $CONHCH_3$; and $C_{1-3}$ alkyl, optionally substituted with a F.

14. The compound of claim 1 wherein $R^1$ is selected from H, OH, $OC_{1-4}$ alkyl, $OC_{1-4}$ alkyl substituted with at least one from the group consisting of phenyl and phenyl substituted with one or more groups selected from OH and halogen.

15. The compound of claim 1 wherein $R^1$ is selected from H, OH, $OCH_3$, and $OC_{1-6}$ alkyl optionally substituted with one or more halogen.

16. The compound of claim 1 selected from the group consisting of:

3,5-Dichloro-4-fluorophenyl 3-deoxy-2-O-methyl-3-[4-(2-thiazolyl)-1H-1,2,3-triazol-1-yl]-1-thio-α-D-galactopyranoside, 5-Bromopyridin-3-yl 3-deoxy-2-O-methyl-3-[4-(2-thiazolyl)-1H-1,2,3-triazol-1-yl]-1-thio-α-D-galactopyranoside, 5-Bromo-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 3-deoxy-2-O-methyl-3-[4-(2-thiazolyl)-1H-1,2,3-triazol-1-yl]-1-thio-α-D-galactopyranoside, 5-Chloro-2-cyanopyridin-3-yl 2-O-benzyl-3-deoxy-3-[4-(2-thiazolyl)-1H-1,2,3-triazol-1-yl]-1-thio-α-D-galactopyranoside, 5-Chloro-2-cyanopyridin-3-yl 3-deoxy-2-O-(3,5-difluoro-4-hydroxybenzyl)-3-[4-(2-thiazolyl)-1H-1,2,3-triazol-1-yl]-1-thio-α-D-galactopyranoside, 3,5-Dichloro-4-fluorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 3-deoxy-3-[4-(2-hydroxythiazol-4-yl)-1H-1,2,3-triazol-1-yl]-2-O-isopropyl-1-thio-α-D-galactopyranoside, 3,4-Dichlorophenyl 3-deoxy-3-[4-(2-hydroxythiazol-4-yl)-1H-1,2,3-triazol-1-yl]-2-O-methyl-1-thio-α-D-galactopyranoside, 3,4-Dichlorophenyl 2,3-dideoxy-3-[4-(2-hydroxythiazol-4-yl)-1H-1,2,3-triazol-1-yl]-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Bromo-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(4-chlorothiazol-2-yl)-1H-1,2,3-triazol-1-yl]-3-deoxy-2-O-methyl-1-thio-α-D-galactopyranoside, 3-Chloro-2-cyanopyridin-5-yl 3-[4-(4-chlorothiazol-2-yl)-1H-1,2,3-triazol-1-yl]-3-deoxy-2-O-methyl-1-thio-α-D-galactopyranoside, 5-Chloro-2-cyanopyridin-3-yl 3-[4-(2-chlorothiazol-4-yl)-1H-1,2,3-triazol-1-yl]-3-deoxy-2-O-methyl-1-thio-α-D-galactopyranoside, 3,5-Dichloro-4-fluorophenyl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-2-O-benzyl-3-deoxy-1-thio-α-D-galactopyranoside, 5-Chloro-2-methylpyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-(pyrimidin-5-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-4-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-3-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(1,2,3,6-tetrahydropyridin-4-yl) pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-(3,5-difluoro-4-hydroxybenzyl)-1-thio-α-D-galactopyranoside, 5-Chloro-2-(pyridin-2-yl)-pyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(oxazol-2-yl) pyridin-3-yl 3-[4-(2-aminothiazol-4-yl)-1H-1,2,3-triazol-1-yl]-3-deoxy-2-O-methyl-1-thio-α-D-galactopyranoside, 3,4-Dichlorphenyl 3-[4-(2-aminothiazol-4-yl)-1H-1,2,3-triazol-1-yl]-3-deoxy-2-O-methyl-1-thio-α-D-galactopyranoside, 5-Chloro-2-(thiazol-2-yl) pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-(trifluoromethyl)phenyl 3-[4-(2-aminothiazol-4-yl)-1H-1,2,3-triazol-1-yl]-3-deoxy-2-O-methyl-1-thio-α-D-galactopyranoside, 3-Chlorophenyl 3-[4-(2-aminothiazol-4-yl)-1H-1,2,3-triazol-1-yl]-3-deoxy-2-O-methyl-1-thio-α-D-galactopyranoside, 5-Bromo-2-cyanopyridin-3-yl 3-deoxy-3-[4-(4-methylthiazol-2-yl)-1H-1,2,3-triazol-1-yl]-2-O-methyl-1-thio-α-D-galactopyranoside, 2-Cyano-5-methylpyridin-3-yl 3-deoxy-3-[4-(4-methyltriazol-2-yl)-1H-1,2,3-thiazol-1-yl]-2-O-methyl-1-thio-α-D-galactopyranoside, 2-Cyano-5-methylpyridin-3-yl 3-[4-(4-chlorothiazol-2-yl)-1H-1,2,3-triazol-1-yl]-3-deoxy-2-O-methyl-1-thio-α-D-galactopyranoside, 5-Ethynylpyridin-3-yl 3-[4-(4-chlorothiazol-2-yl)-1H-1,2,3-triazol-1-yl]-3-deoxy-2-O-methyl-1-thio-α-D-galactopyranoside, 5-Chloro-2-{N-(2-oxa)-6-azaspiro [3.3]heptanyl}-pyridin-3-yl 3-[4-(2-aminothiazol-4-yl)-1H-1,2,3-triazol-1-yl]-3-deoxy-2-O-methyl-1-thio-α-D-galactopyranoside, 3-Chloro-4-cyanophenyl 3-[4-(2-aminothiazol-4-yl)-1H-1,2,3-triazol-1-yl]-3-deoxy-2-O-methyl-1-thio-α-D-galactopyranoside, 5-Cyanopyridin-3yl 3-[4-(2-aminothiazol-4-yl)-1H-1,2,3-triazol-1-yl]-3-deoxy-2-O-methyl-1-thio-α-D-galactopyranoside, 3,5-Dichloro-4-fluorophenyl 2,3-dideoxy-3-[4-(2-hydroxythiazol-4-yl)-1H-1,2,3-triazol-1-yl]-1-thio-α-D-galactopyranoside, 3-Chloro-4-cyanophenyl 3-[4-(2-aminothiazol-4-yl)-1H-1,2,3-triazol-1-yl]-2,3-dideoxy-1-thio-α-D-galactopyranoside, 5-Chloro-2-cyanophenyl 3-[4-(4-chlorothiazol-2-yl)-1H-1,2,3-triazol-1-yl]-2,3-dideoxy-1-thio-α-D-galactopyranoside, 3-Cyano-2-(trifluoromethyl) pyridin-5-yl 3-[4-(2-aminothiazol-4-yl)-1H-1,2,3-triazol-1-yl]-3-deoxy-2-O-methyl-1-thio-α-D-galactopyranoside, 5-Chloro-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(pyridin-2-yl)-pyridin-3-yl 3-deoxy-3-[4-(4-methylthiazol-2-yl)-1H-1,2,3-triazol-1-yl]-2-O-methyl-1-thio-α-D-galactopyranoside, 5-Ethynylpyridin-3-yl 3-deoxy-2-O-methyl-3-[4-(2-thiazolyl)-1H-1,2,3-triazol-1-yl]-1-thio-α-D-galactopyranoside, 5-Chloropyridin-3-yl 3-[4-(4-chlorothiazol-2-yl)-1H-1,2,3-triazol-1-yl]-3-deoxy-2-O-methyl-1-thio-α-D-galactopyranoside, 5-Bromopyridin-3-yl 3-[4-(4-chlorothiazol-2-yl)-1H-1,2,3-triazol-1-yl]-3-deoxy-2-O-methyl-1-thio-α-D-galactopyranoside, 5-Bromo-2-cyanopyridin-3-yl 3-[4-(4,5-dichlorothiazol-2-yl)-1H-1,2,3-triazol-1-yl]-3-deoxy-2-O-methyl-1-thio-α-D-galactopyranoside, 5-Bromo-2-cyanophenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-[4-(4-chlorothiazol-2-yl)-1H-1,2,3-triazol-1-yl]-3-deoxy-2-O-methyl-1-thio-α-D-galactopyranoside, 5-Bromo-2-cyanophenyl 3-deoxy-3-[4-(2-hydroxythiazol-4-yl)-1H-1,2,3-triazol-1-yl]-2-O-methyl-1-thio-α-D-galactopyranoside, 5-Bromo-2-cyanophenyl 3-[4-(2-aminothiazol-4-yl)-1H-1,2,3-triazol-1-yl]-3-deoxy-2-O-methyl-1-thio-α-D-galactopyranoside, 5-Bromo-2-(N-methyl-carbonyl)phenyl 3-[4-(4-chlorothiazol-2-yl)-1H-1,2,3-triazol-1-yl]-3-deoxy-2-O-methyl-1-thio-α-D-galactopyranoside, 5-Bromo-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Chloro-2-(N-methyl-carbonyl)phenyl 3-deoxy-2-O-methyl-3-[4-(2-thiazolyl)-1H-1,2,3-triazol-1-yl]-1-thio-α-D-galactopyranoside, 5-Bromo-2-cyanophenyl 3-deoxy-3-[4-(4-methylthiazol-2-yl)-1H-1,2,3-triazol-1-yl]-2-O-methyl-1-thio-α-D-galactopyranoside, 5-Bromo-2-cyanopyridin-3-yl 3-[4-(5-chloro-4-methylthiazol-2-yl)-1H-1,2,3-triazol-1-yl]-3-deoxy-2-O-methyl-1-thio-α-D-galactopyranoside, 5-Bromo-2-cyanophenyl 3-[4-(5-chloro-4-methylthiazol-2-yl)-1H-1,2,3-triazol-1-yl]-3-deoxy-2-O-methyl-1-thio-α-D-galactopyranoside, 2,5-Dichlorophenyl 3-deoxy-2-O-methyl-3-[4-(2-thiazolyl)-1H-1,2,3-triazol-1-yl]-1-thio-α-D-galactopyranoside, 5-Bromo-2-chlorophenyl 3-deoxy-2-O-methyl-3-[4-(2-thiazolyl)-1H-1,2,3-triazol-1-yl]-1-thio-α-D-galactopyranoside, 5-Chloro-2-fluorophenyl 3-deoxy-2-O-methyl-3-[4-(2-thiazolyl)-1H-1,2,3-triazol-1-yl]-1-thio-α-D-galactopyranoside, 5-Bromo-2-fluorophenyl 3-deoxy-3-[4-(4-methylthiazol-2-yl)-1H-1,2,3-triazol-1-yl]-2-O-methyl-1-thio-α-D-galactopyranoside, 5-Chloro-2-cyanopyridin-3-yl 3-deoxy-2-O-ethyl-3-[4-(2-thiazolyl)-1H-1,2,3-triazol-1-yl]-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-ethyl-1-thio-α-D-galactopyranoside, 5-Chloro-2-cyanopyridin-3-yl 3-[4-(2-aminothiazol-4-yl)-1H-1,2,3-triazol-1-yl]-3-deoxy-2-O-methyl-1-thio-α-D-galactopyranoside, 5-Chloro-2-(pyridin-2-yl) pyridin-3-yl 3-[4-(4-chlorothiazol-2-yl)-1H-1,2,3-triazol-1-yl]-3-deoxy-2-O-methyl-1-thio-α-D-galactopyranoside, 3,4-Dichlorophenyl 3-[4-(2-aminothiazol-4-yl)-1H-1,2,3-triazol-1-yl]-3-deoxy-2-O-(2,2,2-trifluoroethyl)-1-thio-α-D-galactopyranoside, 3,4-Dichlorophenyl 3-deoxy-2-O-(2,2,2-trifluoroethyl)-3-[4-(2-hydroxythiazol-4-yl)-1H-1,2,3-triazol-1-yl]-1-thio-α-D-galactopyranoside, 5-Ethynylpyridin-3-yl 3-[4-(4-chlorothiazol-2-yl)-1H-1,2,3-triazol-1-yl]-3-deoxy-1-thio-α-D-galactopyranoside, 5-Ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Cyanopyridin-3-yl 3-[4-(4-chlorothiazol-2-yl)-1H-1,2,3-triazol-1-yl]-3-deoxy-2-O-methyl-1-thio-α-D-galactopyranoside, 5-Cyanopyridin-3-yl 3-deoxy-3-[4-(2-hydroxythiazol-4-yl)-1H-1,2,3-triazol-1-yl]-2-O-methyl-1-thio-α-D-galactopyranoside, 2-Cyano-5-ethynylpyridin-3-yl 3-[4-(2-aminothiazol-4-yl)-1H-1,2,3-triazol-1-yl]-3-deoxy-2-O-methyl-1-thio-α-D-galactopyranoside, 5-Bromo-2-cyanopyridin-3-yl 3-[4-(4-chlorothiazol-2-yl)-1H-1,2,3-triazol-1-yl]-3-deoxy-2-O-ethyl-1-thio-α-D-galactopyranoside, 3,4-Dichlorophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 3-[4-(2-aminothiazol-4-yl)-1H-1,2,3-triazol-1-yl]-3-deoxy-2-O-ethyl-1-thio-α-D-galactopyranoside, 3-Chloro-4-cyanophenyl 2,3-dideoxy-3-[4-(2-hydroxythiazol-4-yl)-1H-1,2,3-triazol-1-yl]-1-thio-α-D-galactopyranoside, 5-Bromo-2-(N,N-dimethylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside, 5-Ethynyl-2-(N,N-dimethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Ethynyl-2-(N-azetidinylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-ethylcarbamoyl)-3-pyridinyl 3-[4-(4-chlorothiazol-2-yl)-1H-1,2,3-triazol-1-yl]-3-deoxy-2-O-methyl-1-thio-α-D-galactopyranoside, 5-Chloro-2-(N-methylcarbamoyl)-3-pyridinyl 3-[4-(4-chlorothiazol-2-yl)-1H-1,2,3-triazol-1-yl]-3-deoxy-2-O-ethyl-1-thio-α-D-galactopyranoside, 1,3-Benzothiazol-6-yl 3-[4-(4-chlorothiazol-2-yl)-1H-1,2,3-triazol-1-yl]-3-deoxy-2-O-methyl-1-thio-α-D-galactopyranoside, 1,3-Benzothiazol-6-yl 3-deoxy-3-[4-(2-hydroxythiazol-4-yl)-1H-1,2,3-triazol-1-yl]-2-O-methyl-1-thio-α-D-galactopyranoside, 1,3-Benzothiazol-6-yl 3-[4-(2-aminothiazol-4-yl)-1H-1,2,3-triazol-1-yl]-3-deoxy-2-O-methyl-1-thio-α-D-galactopyranoside, 5-Cyano-1,3-benzothiazol-6-yl 3-[4-(4-chlorothiazol-2-yl)-1H-1,2,3-triazol-1-yl]-3-deoxy-2-O-methyl-1-thio-α-D-galactopyranoside, Thiazolo [4,5-b]pyridin-6-yl 3-[4-(4-chlorothiazol-2-yl)-1H-1,2,3-triazol-1-yl]-3-deoxy-2-O-methyl-1-thio-α-D-galactopyranoside, 5-Methylsulfanylpyridin-3-yl 3-[4-(4-chlorothiazol-2-yl)-1H-1,2,3-triazol-1-yl]-3-deoxy-2-O-methyl-1-thio-α-D-galactopyranoside, and 5-(Trifluoromethylsulfanyl)pyridin-3-yl 3-[4-(4-chlorothiazol-2-yl)-1H-1,2,3-triazol-1-yl]-3-deoxy-2-O-methyl-1-thio-α-D-galactopyranoside; or a pharmaceutically acceptable salt or solvate thereof.

17. A pharmaceutical composition comprising the compound of claim 1 and optionally a pharmaceutically acceptable additive.

* * * * *